(12) United States Patent
Numata et al.

(10) Patent No.: US 10,537,099 B2
(45) Date of Patent: Jan. 21, 2020

(54) KETONE OR OXIME COMPOUND, AND HERBICIDE

(71) Applicant: NISSAN CHEMICAL CORPORATION, Tokyo (JP)

(72) Inventors: Akira Numata, Funabashi (JP); Yuji Iwawaki, Funabashi (JP); Yuki Furukawa, Funabashi (JP); Yuri Yoshino, Funabashi (JP); Yuuki Miyakado, Shiraoka (JP); Takamasa Furuhashi, Shiraoka (JP); Takao Miyazaki, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/167,884

(22) Filed: Oct. 23, 2018

(65) Prior Publication Data

US 2019/0053488 A1 Feb. 21, 2019

Related U.S. Application Data

(62) Division of application No. 15/537,301, filed as application No. PCT/JP2015/085569 on Dec. 18, 2015, now Pat. No. 10,136,640.

(30) Foreign Application Priority Data

Dec. 18, 2014 (JP) ................. 2014-255973
Feb. 18, 2015 (JP) ................. 2015-029704
Apr. 15, 2015 (JP) ................. 2015-083620
Jul. 8, 2015 (JP) ................. 2015-136991

(51) Int. Cl.
| | | |
|---|---|---|
| *C07C 49/597* | (2006.01) | |
| *C07C 49/707* | (2006.01) | |
| *A01N 35/10* | (2006.01) | |
| *C07F 7/08* | (2006.01) | |
| *A01N 35/06* | (2006.01) | |
| *C07C 251/40* | (2006.01) | |
| *C07C 49/747* | (2006.01) | |
| *A01N 37/42* | (2006.01) | |
| *A01N 41/06* | (2006.01) | |
| *A01N 43/10* | (2006.01) | |
| *A01N 43/40* | (2006.01) | |
| *A01N 43/50* | (2006.01) | |

(Continued)

(52) U.S. Cl.
CPC ............. *A01N 35/10* (2013.01); *A01N 35/06* (2013.01); *A01N 37/42* (2013.01); *A01N 41/06* (2013.01); *A01N 43/10* (2013.01); *A01N 43/40* (2013.01); *A01N 43/50* (2013.01); *A01N 43/56* (2013.01); *A01N 43/84* (2013.01); *A01N 55/00* (2013.01); *C07C 49/747* (2013.01); *C07C 69/78* (2013.01); *C07C 251/40* (2013.01); *C07C 311/29* (2013.01); *C07D 213/53* (2013.01); *C07D 231/12* (2013.01); *C07D 233/61* (2013.01); *C07D 249/08* (2013.01); *C07D 295/135* (2013.01); *C07D 333/22* (2013.01); *C07F 7/081* (2013.01)

(58) Field of Classification Search
CPC ............................ C07C 49/597; C07C 49/707
See application file for complete search history.

(56) References Cited

U.S. PATENT DOCUMENTS 6,894,005 B1   5/2005  Maetzke et al.
8,680,339 B2 * 3/2014  Mathews ............... A01N 35/06
                                                        568/315

(Continued)

FOREIGN PATENT DOCUMENTS

JP      07238045      *  9/1995
JP      H10-503483 A     3/1998

(Continued)

OTHER PUBLICATIONS

Fisher et al., Efficient Synthesis of 4-Hydroxycyclopentenones: Dysprosium(III) Triflate Catalyzed Piancatelli Rearrangement, Tetrahedron, vol. 70, No. 27-28, pp. 4105-4110. (Year: 2014).*
Van Baar et al., Electron Ionization Mass Spectrometry of Curcumin Analogues: an Olefin Metathesis Reaction in the Fragmentation of Radical Cations, Journal of Mass Spectrometry, vol. 33, No. 4, pp. 319-327. (Year: 1998).*
CAPLUS printout of JP 11043461 (Year: 1999).*
CAPLUS printout of Grens et al., Structure and Acidity of 4-Cyclopentene-1,3-diones and 1,3-Indandiones, Zhurnal Organicheskoi Khimii vol. 1, No. 1, pp. 3-7. (Year: 1965).*

(Continued)

*Primary Examiner* — Brenda L Coleman
(74) *Attorney, Agent, or Firm* — Oliff PLC

(57) ABSTRACT

There is provided novel agricultural chemicals, in particular herbicides. A ketone or oxime compound or a salt thereof of Formula (1):

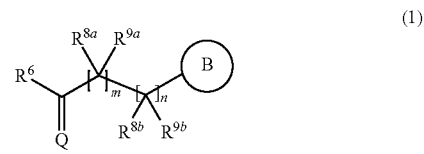

(1)

wherein B is a ring of any one of B-1, B-2, or B-3, Q is an oxygen atom, a sulfur atom, $NOR^7$, etc., $R^6$ is a hydrogen atom, $C_{1-6}$ alkyl, etc., $R^7$ is a hydrogen atom, $C_{1-6}$ alkyl, etc., $R^{8a}$, $R^{8b}$, $R^{9a}$, $R^{9b}$, $R^{10}$, $R^{11}$, $R^{12}$, $R^{13}$, and $R^{14}$ are each independently a hydrogen atom, $C_{1-6}$ alkyl, etc., m is an integer of 1 or 2, n is an integer of 0, 1 or 2; and a herbicide including the compound or salt thereof.

10 Claims, No Drawings

(51) Int. Cl.

| | | |
|---|---|---|
| A01N 43/56 | (2006.01) | |
| A01N 43/653 | (2006.01) | |
| A01N 43/84 | (2006.01) | |
| A01N 55/00 | (2006.01) | |
| C07C 69/78 | (2006.01) | |
| C07C 311/29 | (2006.01) | |
| C07D 213/53 | (2006.01) | |
| C07D 231/12 | (2006.01) | |
| C07D 233/61 | (2006.01) | |
| C07D 249/08 | (2006.01) | |
| C07D 295/135 | (2006.01) | |
| C07D 333/22 | (2006.01) | |

(56) References Cited

U.S. PATENT DOCUMENTS

| | | | | |
|---|---|---|---|---|
| 8,754,242 | B2* | 6/2014 | Tyte | C07D 493/08 549/300 |
| 9,096,560 | B2* | 8/2015 | Jeanmart | A01N 43/08 |
| 9,107,415 | B2* | 8/2015 | Avery | C07C 49/683 |
| 2016/0207934 | A1* | 7/2016 | Black | A01N 43/16 |

FOREIGN PATENT DOCUMENTS

| | | |
|---|---|---|
| JP | 2009-522331 A | 6/2009 |
| JP | 2011-526597 A | 10/2011 |
| JP | 2012-512143 A | 5/2012 |
| JP | 2012-515190 A | 7/2012 |
| JP | 2012-515742 A | 7/2012 |
| JP | 2012-516835 A | 7/2012 |
| JP | 2012-532924 A | 12/2012 |
| WO | 2001/017972 A1 | 3/2001 |
| WO | 2003/062244 A1 | 7/2003 |
| WO | 2010/000773 A1 | 1/2010 |
| WO | 2010/040460 A2 | 4/2010 |
| WO | 2010/069834 A1 | 6/2010 |
| WO | 2013/079708 A1 | 6/2013 |

OTHER PUBLICATIONS

Mar. 15, 2016 International Search Report issued in International Patent Application No. PCT/JP2015/085569.

Mar. 15, 2016 Written Opinion issued in International Patent Application No. PCT/JP2015/085569.

Oct. 16, 2017 Office Action issued in U.S. Appl. No. 15/537,301.

* cited by examiner

KETONE OR OXIME COMPOUND, AND HERBICIDE

TECHNICAL FIELD

The present invention relates to a novel ketone or oxime compound or a salt thereof, and agricultural chemicals, in particular herbicides, containing the ketone or oxime compound or the salt thereof as an active component. The agricultural chemical in the present invention means an insecticide/acaricide, a nematicide, a herbicide, and a bactericide in agricultural and horticultural fields.

BACKGROUND ART

For example, certain types of ketone or oxime compounds have been described in Patent Documents 1 to 4. The ketone or the oxime compound according to the present invention, however, has not been described at all.

PRIOR ART DOCUMENTS

Patent Documents

Patent Document 1: WO2001/017972 Pamphlet
Patent Document 2: WO2003/062244 Pamphlet
Patent Document 3: WO2010/000773 Pamphlet
Patent Document 4: WO2010/069834 Pamphlet

SUMMARY OF THE INVENTION

Problem to be Solved by the Invention

An object of the present invention is to provide a chemical substance that surely shows effect on various weeds in a low application amount of the chemical substance, has reduced land pollution and reduced influence on succeeding crops, and high safety, and is useful as an active component of herbicides.

Means for Solving the Problem

As a result of intensive investigation for solving the problem, the inventors of the present invention have found that a novel ketone or oxime compound of Formula (1) below according to the present invention has excellent herbicidal activity as a herbicide and high safety against target crops as well as has almost no adverse effect on non-target creatures such as mammals, fish, and beneficial insects, and is an extremely useful compound, and thus have accomplished the present invention.

More specifically, the present invention relates to the following [1] to [151].

A ketone or oxime compound or a salt thereof of Formula (1):

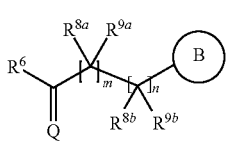

(1)

[wherein B is a ring of any one of B-1, B-2, or B-3,

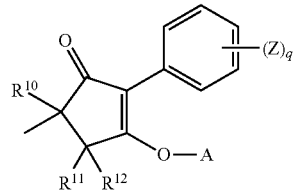

B-1

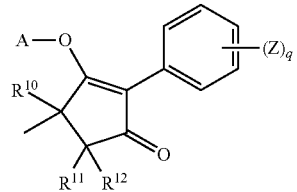

B-2

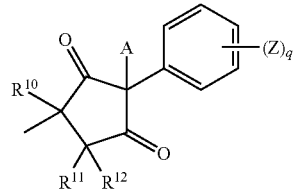

B-3

Q is an oxygen atom, a sulfur atom, or $NOR^7$;

A is a hydrogen atom, $C_{1-6}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $C_{3-8}$ cycloalkenyl, $(C_{3-8})$ cycloalkenyl arbitrarily substituted with $R^5$, $(C_{2-6})$ alkenyl arbitrarily substituted with $R^5$, $C_{2-6}$ alkynyl, $(C_{2-6})$ alkynyl arbitrarily substituted with $R^5$, $-S(O)_{r-2}R^1$, $-C(O)OR^1$, $-C(S)OR^1$, $-C(O)SR^1$, $-C(S)SR^1$, $-C(O)R^2$, $-C(S)R^2$, $-C(O)N(R^4)R^3$, $-C(S)N(R^4)R^3$, $-S(O)_2N(R^4)R^3$, $-P(O)(OR^1)_2$, or $-P(S)(OR^1)_2$;

$R^1$ is $C_{1-s}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $(C_{2-6})$ alkenyl arbitrarily substituted with $R^5$, $C_{3-8}$ cycloalkenyl, $(C_{3-8})$ cycloalkenyl arbitrarily substituted with $R^5$, $C_{2-6}$ alkynyl, $(C_{2-6})$ alkynyl arbitrarily substituted with $R^5$, phenyl, or phenyl substituted with $(Z^2)_{q2}$;

$R^2$ is a hydrogen atom, $C_{1-8}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $(C_{2-6})$ alkenyl arbitrarily substituted with $R^5$, $C_{3-8}$ cycloalkenyl, $(C_{3-8})$ cycloalkenyl arbitrarily substituted with $R^5$, $C_{2-6}$ alkynyl, $(C_{2-6})$ alkynyl arbitrarily substituted with $R^5$, $-C(=NOR^{31})R^{32}$, phenyl, phenyl substituted with $(Z^2)_{q2}$, naphthyl, naphthyl substituted with $(Z^2)_{q2}$, D1-1 to D1-42, D1-81, or D1-84;

$R^3$ and $R^4$ are each independently a hydrogen atom, $C_{1-6}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $(C_{2-6})$ alkenyl arbitrarily substituted with $R^5$, $C_{3-8}$ cycloalkenyl, $(C_{3-8})$ cycloalkenyl arbitrarily substituted with $R^5$, $C_{2-6}$ alkynyl, $(C_{2-6})$ alkynyl arbitrarily substituted with $R^5$, phenyl, phenyl substituted with $(Z^2)_{q2}$, D1-32, D1-33 or D1-34, or $R^3$ optionally forms a 3- to 8-membered ring together with a nitrogen atom to which $R^3$ and $R^4$ are bonded by forming a $C_{2-7}$ alkylene chain or a $C_{2-7}$ alkenylene chain together with $R^4$, and at this time, the alkylene chain or the alkenylene chain optionally contains one oxygen atom, sulfur atom, or nitrogen atom and optionally substituted with $C_{1-6}$ alkyl, oxo, or thioxo;

$R^5$ is a halogen atom, cyano, nitro, $C_{3-8}$ cycloalkyl, $-OR^{31}$, $-S(O)_{r2}R^{31}$, $-C(O)OR^{31}$, $-C(O)R^{32}$, $-N(R^{34})R^{33}$, $-Si(R^{32a})(R^{32b})R^{32c}$, phenyl, phenyl substituted with $(Z^2)_{q2}$, D1-1, D1-32, D1-33, or D1-34, or when two $R^5$s are substituents on a same carbon, the two $R^5$s optionally form oxo, thioxo, imino, $C_{1-6}$ alkylimino, $C_{1-6}$ alkoxyimino, or $C_{1-6}$ alkylidene, together with each other;

$R^6$ is a hydrogen atom, $C_{1-6}$ alkyl, $(C_{1-6})$ alkyl arbitrarily substituted with $R^{15}$, $C_{3-8}$ cycloalkyl, $(C_{3-8})$ cycloalkyl arbitrarily substituted with $R^{15}$, $C_{2-6}$ alkenyl, $(C_{2-6})$ alkenyl arbitrarily substituted with $R^{15}$, $C_{3-8}$ cycloalkenyl, $(C_{3-8})$ cycloalkenyl arbitrarily substituted with $R^{15}$, $C_{2-6}$ alkynyl, $(C_{2-6})$ alkynyl arbitrarily substituted with $R^{15}$, $-C(=NOR^{16})R^{17}$, phenyl, phenyl substituted with $(Z^1)_{q1}$, D1-32, D1-33, D1-34, D1-36, D1-37, or D1-38;

$R^7$ is a hydrogen atom, $C_{1-8}$ alkyl, $(C_{1-6})$ alkyl arbitrarily substituted with $R^{15b}$, $C_{3-8}$ cycloalkyl, $(C_{3-8})$ cycloalkyl arbitrarily substituted with $R^{15b}$, $C_{2-6}$ alkenyl, $(C_{2-6})$ alkenyl arbitrarily substituted with $R^{15b}$, $C_{3-8}$ cycloalkenyl, $(C_{3-8})$ cycloalkenyl arbitrarily substituted with $R^{15b}$, $C_{2-6}$ alkynyl, $(C_{2-6})$ alkynyl arbitrarily substituted with $R^{15b}$, phenyl, or phenyl substituted with $(Z^1)_{q1}$;

$R^{8a}$, $R^{8b}$, $R^{9a}$, and $R^{9b}$ are each independently a hydrogen atom, cyano, nitro, $C_{1-6}$ alkyl, halo $(C_{1-6})$ alkyl, $-OR^{16a}$, $-S(O)_{r1}R^{16a}$, $-C(O)OR^{16a}$, $-C(O)R^{17a}$, $-C(O)N(R^{19a})R^{18a}$, $-C(=NOR^{16a})R^{17a}$, phenyl, or phenyl substituted with $(Z^1)_{q1}$;

$R^{10}$, $R^{11}$ and $R^{12}$ are each independently a hydrogen atom or $C_{1-6}$ alkyl;

$R^{15}$ is a halogen atom, cyano, $C_{3-8}$ cycloalkyl, $-OR^{16}$, $-S(O)_{r1}R^{16}$, phenyl, phenyl substituted with $(Z^1)_{q1}$, D1-7, D1-11, D1-22, D1-32, D1-33, or D1-34; $R^{15b}$ is a halogen atom, cyano, $C_{3-8}$ cycloalkyl, halo $(C_{3-8})$ cycloalkyl, $-OR^{16b}$, $-S(O)_{r1}R^{16b}$, $-C(O)OR^{16b}$, $-C(O)N(R^{18b})R^{19b}$, $-C(=NOR^{16b})R^{17}$, $-N(R^{18b})R^{19b}$, $-Si(R^{32a})(R^{32b})R^{32c}$, phenyl, phenyl substituted with $(Z^1)_{q1}$, D1-32, D1-33, D1-34, D1-36, D1-37, D1-38, D1-81, or D1-84, or when two $R^{15b}$s are substituents on a same carbon, the two $R^{15b}$s optionally form oxo, thioxo, imino, $C_{1-6}$ alkylimino, $C_{1-6}$ alkoxyimino, or $C_{1-6}$ alkylidene, together with each other;

$R^{16}$, $R^{16a}$, $R^{16b}$, $R^{17}$, $R^{17a}$, $R^{17b}$, $R^{18a}$, and $R^{19a}$ are each independently a hydrogen atom or $C_{1-6}$ alkyl;

$R^{18b}$ and $R^{19b}$ are each independently a hydrogen atom, $C_{1-6}$ alkyl, or $(C_{1-6})$ alkyl arbitrarily substituted with $R^{20}$, or $R^{18b}$ optionally forms a 3- to 8-membered ring together with a nitrogen atom to which $R^{18b}$ and $R^{19b}$ are bonded by forming a $C_{2-7}$ alkylene chain or a $C_{2-7}$ alkenylene chain together with $R^{19b}$, and at this time, the alkylene chain or the alkenylene chain optionally contains one oxygen atom, sulfur atom, or nitrogen atom and optionally substituted with oxo or thioxo;

$R^{20}$ is phenyl or phenyl substituted with $(Z^1)_{q1}$; D1-1 to D1-42, D1-81, and D1-84 each are a ring of the following structure;

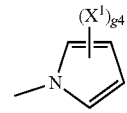

D1-1

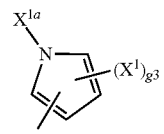

D1-2

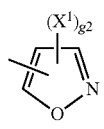

D1-3

D1-4

D1-5

D1-6

D1-7

D1-8

D1-9

D1-10

D1-11

D1-12

D1-13

D1-14

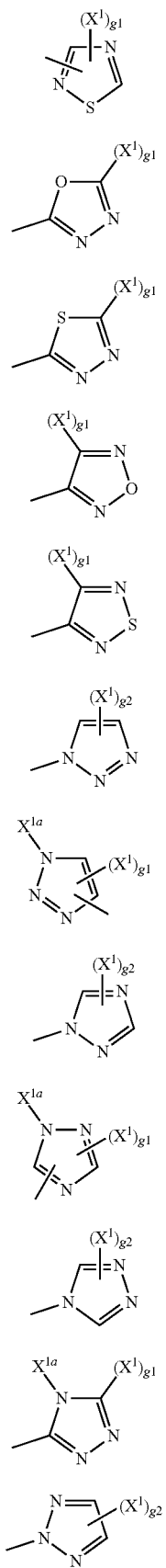
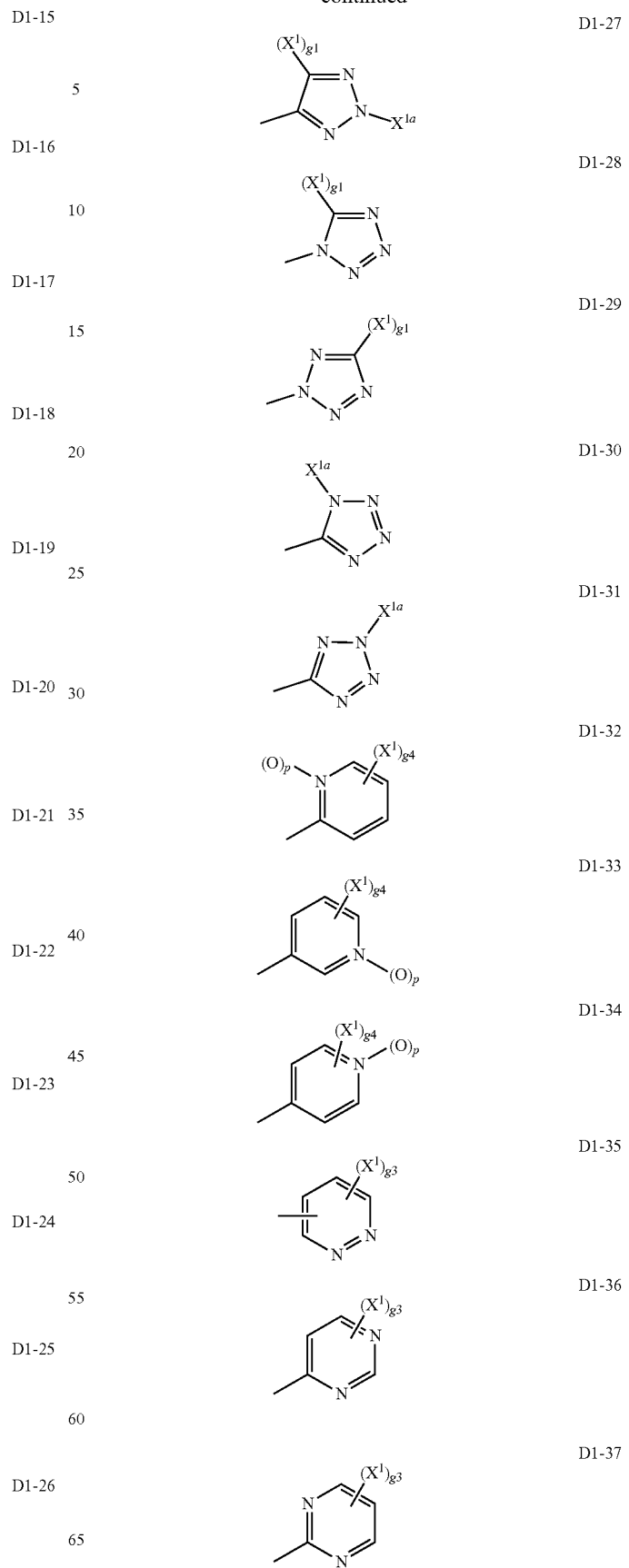

-continued

D1-38
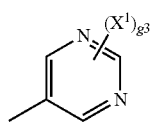

D1-39
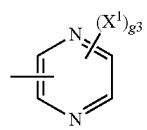

D1-40
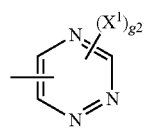

D1-41
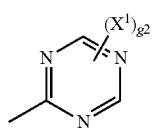

D1-42
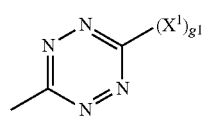

D1-81
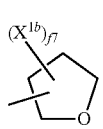

D1-84
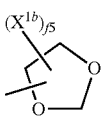

$X^1$ is a halogen atom, cyano, nitro, $C_{1-6}$ alkyl, halo ($C_{1-6}$) alkyl, or $C_{3-8}$ cycloalkyl, when g2, g3, or g4 is an integer of 2 or larger, each $X^1$ is the same as or different from each other, and further when two $X^1$s are adjacent, the two adjacent $X^1$s optionally form a 6-membered ring together with carbon atoms to which each $X^1$ is bonded by forming —CH=CHCH=CH—, and at this time, the hydrogen atom bonded to each carbon atom forming the ring is optionally substituted with a halogen atom, cyano, nitro, $C_{1-6}$ alkyl, halo ($C_{1-6}$) alkyl, $C_{1-6}$ alkoxy, $C_{1-6}$ alkylthio, $C_{1-6}$ alkylsulfinyl, or $C_{1-6}$ alkylsulfonyl;

$X^{1a}$ is a hydrogen atom or $C_{1-6}$ alkyl;

$X^{1b}$ is $C_{1-6}$ alkyl;

Z is a halogen atom, cyano, nitro, $C_{1-6}$ alkyl, ($C_{1-6}$) alkyl arbitrarily substituted with $R^{45}$, $C_{3-8}$ cycloalkyl, ($C_{3-8}$) cycloalkyl arbitrarily substituted with $R^{45}$, $C_{2-6}$ alkenyl, ($C_{2-6}$) alkenyl arbitrarily substituted with $R^{45}$, $C_{3-8}$ cycloalkenyl, ($C_{3-8}$) cycloalkenyl arbitrarily substituted with $R^{45}$, $C_{2-6}$ alkynyl, ($C_{2-6}$) alkynyl arbitrarily substituted with $R^{45}$, —$OR^{41}$, —S(O)$_{r3}R^{41}$, —C(O)$OR^{41}$, —C(O)$R^{42}$, —C(=NOR$^{41}$)R$^{42}$, —N(R$^{44}$)R$^{43}$, phenyl, phenyl substituted with ($Z^3$)$_{q3}$, D1-1, D1-2, D1-7, D1-10, D1-11, D1-22, D1-32, D1-33, D1-34, D1-36, D1-37, or D1-38, and when q is an integer of 2 or larger, each Z is the same as or different from each other; $Z^1$ is a halogen atom, cyano, nitro, $C_{1-6}$ alkyl, halo ($C_{1-6}$) alkyl, $C_{1-6}$ alkoxy, or $C_{1-6}$ alkoxycarbonyl, and when q1 is an integer of 2 or larger, each $Z^1$ is the same as or different from each other;

$Z^2$ is a halogen atom, cyano, nitro, $C_{1-6}$ alkyl, halo ($C_{1-6}$) alkyl, —$OR^{51}$, —S(O)$_{r2}R^{51}$, —C(O)$OR^{51a}$, —C(O)$R^{52}$, —C(O)N(R$^{54}$)R$^{53}$, —C(S)N(R$^{54}$)R$^{53}$, or —N(R$^{54}$)R$^{53}$, when q2 is an integer of 2 or larger, each $Z^2$ is the same as or different from each other, and further when two $Z^2$s are adjacent, the two adjacent $Z^2$s optionally form a 6-membered ring together with carbon atoms to which each $Z^2$ is bonded by forming —N=CHCH=CH—, —CH=NCH=CH—, —N=NCH=CH—, —CH=NN=CH—, —N=CHCH=N—, or —N=CHN=CH—, and at this time, the hydrogen atom bonded to each carbon atom forming the ring is optionally substituted with a halogen atom, cyano, nitro, $C_{1-6}$ alkyl, halo ($C_{1-6}$) alkyl, $C_{1-6}$ alkoxy, $C_{1-6}$ alkylthio, $C_{1-6}$ alkylsulfinyl, or $C_{1-6}$ alkylsulfonyl;

$Z^3$ is a halogen atom, cyano, nitro, $C_{1-6}$ alkyl, halo ($C_{1-6}$) alkyl, $C_{1-6}$ alkoxy, halo ($C_{1-6}$) alkoxy, $C_{1-6}$ alkylthio, $C_{1-6}$ alkylsulfinyl, or $C_{1-6}$ alkylsulfonyl, and when q3 is an integer of 2 or larger, each $Z^3$ is the same as or different from each other;

$R^{31}$ is a hydrogen atom, $C_{1-6}$ alkyl, ($C_{1-6}$) alkyl arbitrarily substituted with $R^{35}$, —C(O)$R^{37}$, phenyl, phenyl substituted with ($Z^2$)$_{q2}$, naphthyl, or naphthyl substituted with ($Z^2$)$_{q2}$;

$R^{32}$ is a hydrogen atom, $C_{1-6}$ alkyl, or ($C_{1-6}$) alkyl arbitrarily substituted with $R^{35}$;

$R^{32a}$, $R^{32b}$, and $R^{32c}$ are each independently $C_{1-6}$ alkyl;

$R^{33}$ and $R^{34}$ are each independently a hydrogen atom, $C_{1-6}$ alkyl, —C(O)$OR^{36}$, or —C(O)$R^{37}$;

$R^{35}$ is a halogen atom, $C_{1-6}$ alkoxy, $C_{1-6}$ alkylthio, $C_{1-6}$ alkylsulfinyl, $C_{1-6}$ alkylsulfonyl, or phenyl;

$R^{36}$ is $C_{1-6}$ alkyl;

$R^{37}$ is a hydrogen atom, $C_{1-6}$ alkyl, phenyl, or phenyl substituted with ($Z^2$)$_{q2}$;

$R^{41}$ is a hydrogen atom, $C_{1-6}$ alkyl, ($C_{1-6}$) alkyl arbitrarily substituted with $R^{45}$, phenyl, phenyl substituted with ($Z^3$)$_{q3}$, D1-32, D1-33, or D1-34;

$R^{42}$ is a hydrogen atom or $C_{1-6}$ alkyl;

$R^{43}$ and $R^{44}$ are each independently a hydrogen atom, $C_{1-6}$ alkyl, $C_{1-6}$ alkoxycarbonyl, or $C_{1-6}$ alkylcarbonyl;

$R^{45}$ is a halogen atom, $C_{3-8}$ cycloalkyl, —OH, $C_{1-6}$ alkoxy, $C_{1-10}$ alkoxycarbonyl, —Si(R$^{32a}$)(R$^{32b}$)R$^{32c}$, phenyl, phenyl substituted with ($Z^3$)$_{q3}$, D1-32, D1-33, or D1-34, or when two $R^{45}$s are substituents on a same carbon, the two $R^{45}$s optionally form oxo, thioxo, imino, $C_{1-6}$ alkylimino, $C_{1-6}$ alkoxyimino, or $C_{1-6}$ alkylidene, together with each other;

$R^{51}$ is a hydrogen atom, $C_{1-6}$ alkyl, halo ($C_{1-6}$) alkyl, phenyl, phenyl arbitrarily substituted with a halogen atom, or D1-39;

$R^{51a}$ and $R^{52}$ are each independently a hydrogen atom or $C_{1-6}$ alkyl;

$R^{53}$ and $R^{54}$ are each independently a hydrogen atom, $C_{1-6}$ alkyl, or $C_{1-6}$ alkylcarbonyl;

f5 is an integer of 0, 1, 2, 3, 4, or 5;

f7 is an integer of 0, 1, 2, 3, 4, 5, 6, or 7;

g1 and p are each independently an integer of 0 or 1;

g2, m, n, r1, r2, and r3 are each independently an integer of 0, 1, or 2;

g3 is an integer of 0, 1, 2, or 3;

g4 is an integer of 0, 1, 2, 3, or 4; and q, q1, q2, and q3 are each independently an integer of 1, 2, 3, 4, or 5].

[2]

The ketone or oxime compound or a salt thereof according to [1], in which B is a ring of either B-1-a or B-2-a; and

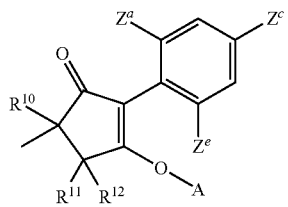

B-1-a

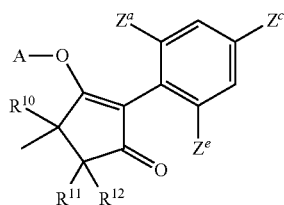

B-2-a $Z^a$, $Z^c$ and $Z^e$ are each independently a hydrogen atom, a halogen atom, cyano, nitro, $C_{1-6}$ alkyl, $(C_{1-6})$ alkyl arbitrarily substituted with $R^{45}$, $C_{3-8}$ cycloalkyl, $(C_{3-8})$ cycloalkyl arbitrarily substituted with $R^{45}$, $C_{2-6}$ alkenyl, $(C_{2-6})$ alkenyl arbitrarily substituted with $R^{45}$, $C_{2-6}$ alkynyl, $(C_{2-6})$ alkynyl arbitrarily substituted with $R^{45}$, —$OR^{41}$, —$S(O)_{r3}R^{41}$, —$C(O)OR^{41}$, —$C(O)R^{42}$, —$C(=NOR^{41})R^{42}$, —$N(R^{44})R^{43}$, phenyl, phenyl substituted with $(Z^3)_{q3}$, D1-1, D1-2, D1-7, D1-10, D1-11, D1-22, D1-32, D1-33, D1-34, D1-36, D1-37, or D1-38.

[3]
The ketone compound or the salt thereof according to [2], in which Q is an oxygen atom.

[4]
The oxime compound or a salt thereof according to [2], in which Q is =$NOR^7$.

[5]
The ketone compound or the salt thereof according to [3], in which A is a hydrogen atom, $C_{1-6}$ alkyl, or —$C(O)R^2$;
$R^2$ is $C_{1-8}$ alkyl;
$R^6$ is $C_{1-6}$ alkyl, $(C_{1-6})$ alkyl arbitrarily substituted with $R^{15}$, $C_{3-8}$ cycloalkyl, $C_{2-6}$ alkenyl, —$C(=NOR^{16})R^{17}$, phenyl, phenyl substituted with $(Z^1)_{q1}$, or D1-32;
$R^{8a}$ is a hydrogen atom, $C_{1-6}$ alkyl, —$C(O)OR^{16a}$, or —$C(O)R^{17a}$;
$R^{9a}$ is a hydrogen atom or $C_{1-6}$ alkyl;
$R^{8b}$ and $R^{9b}$ are hydrogen atoms;
$R^{10}$, $R^{11}$, and $R^{12}$ are hydrogen atoms;
$R^{15}$ is a halogen atom, $C_{3-8}$ cycloalkyl, —$OR^{16}$, or phenyl;
$R^{16}$, $R^{16a}$, $R^{17}$, and $R^{17a}$ are each independently $C_{1-6}$ alkyl;
$X^1$ is halo $(C_{1-6})$ alkyl;
$Z^a$, $Z^c$ and $Z^e$ are each independently a hydrogen atom, a halogen atom, $C_{1-6}$ alkyl, $C_{3-8}$ cycloalkyl, $C_{2-6}$ alkenyl, $(C_{2-6})$ alkenyl arbitrarily substituted with $R^{45}$, $C_{2-6}$ alkynyl, —$OR^{41}$ phenyl, phenyl substituted with $(Z^3)_{q3}$, D1-7, D1-11, D1-22, D1-32, or D1-37;
$Z^1$ is a halogen atom;
$Z^3$ is a halogen atom, $C_{1-6}$ alkyl, halo $(C_{1-6})$ alkyl, $C_{1-6}$ alkoxy, halo $(C_{1-6})$ alkoxy, or $C_{1-6}$ alkylthio;
$R^{41}$ is $C_{1-6}$ alkyl, $(C_{1-6})$ alkyl arbitrarily substituted with $R^{45}$, phenyl, D1-32, or D1-34;
$R^{45}$ is a halogen atom, phenyl, or D1-34;
g2, g3, and p are 0;
q1 and q3 are integers of 1; and
g4, m, and n are each independently an integer of 0 or 1.

[6]
The ketone compound or the salt thereof according to [5], in which B is B-1-a;
$Z^a$ is a halogen atom, $C_{1-6}$ alkyl, or $C_{1-6}$ alkoxy;
$Z^c$ is a halogen atom, $C_{1-6}$ alkyl, $C_{3-8}$ cycloalkyl, $C_{2-6}$ alkenyl, $(C_{2-6})$ alkenyl arbitrarily substituted with $R^{45}$, $C_{2-6}$ alkynyl, —$OR^{41}$, phenyl, phenyl substituted with $(Z^3)_{q3}$, D1-7, D1-11, D1-22, D1-32, or D1-37; and
$Z^e$ is a halogen atom or $C_{1-6}$ alkyl.

[7]
The oxime compound or the salt thereof according to [4], in which A is a hydrogen atom, $C_{1-6}$ alkyl, $(C_{1-6})$ alkyl arbitrarily substituted with $R^5$, $C_{3-8}$ cycloalkyl, $C_{2-6}$ alkenyl, $(C_{2-6})$ alkenyl arbitrarily substituted with $R^5$, $C_{2-6}$ alkynyl, $(C_{2-6})$ alkynyl arbitrarily substituted with $R^5$, —$S(O)_{r2}R^1$, —$C(O)OR^1$, —$C(O)SR^1$, —$C(S)OR^1$, —$C(O)R^2$, —$C(O)N(R^4)R^3$, —$C(S)N(R^4)R^3$, or —$S(O)_2N(R^4)R^3$;
$R^1$ is $C_{1-8}$ alkyl, $(C_{1-6})$ alkyl arbitrarily substituted with $R^5$, $C_{3-8}$ cycloalkyl, $C_{2-6}$ alkenyl, phenyl, or phenyl substituted with $(Z^2)_{q2}$;
$R^2$ is $C_{1-8}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $(C_{2-6})$ alkenyl arbitrarily substituted with $R^5$, $C_{3-8}$ cycloalkenyl, $(C_{3-8})$ cycloalkenyl arbitrarily substituted with $R^5$, $C_{2-6}$ alkynyl, $(C_{2-6})$ alkynyl arbitrarily substituted with $R^5$, —$C(=NOR^{31})R^{32}$, phenyl, phenyl substituted with $(Z^2)_{q2}$, D1-5, D1-6, D1-8, D1-10, or D1-81;
$R^3$ is $C_{1-6}$ alkyl, $(C_{1-6})$ alkyl arbitrarily substituted with $R^5$, $C_{2-6}$ alkenyl, phenyl, or phenyl substituted with $(Z^2)_{q2}$, or $R^3$ forms a 5- to 6-membered ring together with a nitrogen atom to which $R^3$ and $R^4$ are bonded by forming a $C_4$ or $C_5$ alkylene chain together with $R^4$, and at this time, the alkylene chain optionally contains one oxygen atom or nitrogen atom and is optionally substituted with $C_{1-6}$ alkyl;
$R^4$ is $C_{1-6}$ alkyl, $C_{2-6}$ alkenyl, or phenyl;
$R^5$ is a halogen atom, cyano, $C_{3-8}$ cycloalkyl, —$OR^{31}$, —$S(O)_{r2}R^{31}$, —$C(O)OR^{31}$, —$C(O)R^{32}$, —$N(R^{34})R^{33}$, —$Si(R^{32a})(R^{32b})R^{32c}$, phenyl, phenyl substituted with $(Z^2)_{q2}$, or D1-1, or when two $R^5$s are substituents on a same carbon, the two $R^5$s optionally form $C_{1-6}$ alkoxyimino together with each other;
$R^6$ is a hydrogen atom, $C_{1-6}$ alkyl, $(C_{1-6})$ alkyl arbitrarily substituted with $R^{15}$, $C_{3-8}$ cycloalkyl, $C_{2-6}$ alkenyl, —$C(=NOR^{16})R^{17}$, phenyl, phenyl substituted with $(Z^1)_{q1}$ or, D1-32;
$R^7$ is a hydrogen atom, $C_{1-7}$ alkyl, $(C_{1-6})$ alkyl arbitrarily substituted with $R^{15b}$, $C_{3-8}$ cycloalkyl, $C_{2-6}$ alkenyl, $C_{3-8}$ cycloalkenyl, $(C_{2-6})$ alkenyl arbitrarily substituted with $R^{15b}$, $C_{2-6}$ alkynyl, or phenyl;
$R^{8a}$ is a hydrogen atom, $C_{1-6}$ alkyl, halo $(C_{1-6})$ alkyl, —$C(O)OR^{16a}$, —$C(=NOR^{16a})R^{17a}$, or phenyl substituted with $(Z^1)_{q1}$;
$R^{9a}$ is a hydrogen atom or $C_{1-6}$ alkyl;
$R^{8b}$ and $R^{9b}$ are hydrogen atoms;
$R^{12}$ is a hydrogen atom;
$R^{15}$ is a halogen atom, $C_{3-8}$ cycloalkyl, or —$OR^{16}$;
$R^{15b}$ is a halogen atom, cyano, $C_{3-8}$ cycloalkyl, halo $(C_{3-8})$ cycloalkyl, —$OR^{16b}$, —$S(O)_{r1}R^{16b}$, —$C(O)OR^{16b}$, —$C(O)N(R^{18b})R^{19b}$, —$C(=NOR^{16b})R^{17b}$, —$N(R^{18b})R^{19b}$, —$Si(R^{32a})(R^{32b})R^{32c}$, phenyl, phenyl substituted with $(Z^1)_{q1}$, D1-32, or D1-84;
$R^{16}$, $R^{16a}$, $R^{17}$, $R^{17a}$, and $R^{17b}$ are each independently $C_{1-6}$ alkyl;
$R^{18b}$ is a hydrogen atom, $C_{1-6}$ alkyl, or $(C_{1-6})$ alkyl arbitrarily substituted with $R^{20}$, or $R^{18b}$ forms a 6-membered ring together with a nitrogen atom to which $R^{18b}$ and $R^{19b}$ are bonded by forming a $C_5$ alkylene chain together with $R^{19b}$, and at this time, the alkylene chain contains one oxygen atom;

$R^{19b}$ is a hydrogen atom or $C_{1-6}$ alkyl;

$R^{20}$ is phenyl substituted with $(Z^1)_{q1}$;

$X^1$ is a halogen atom, $C_{1-6}$ alkyl, halo $(C_{1-6})$ alkyl, or $C_{3-8}$ cycloalkyl, g3 is an integer of 2, and further the two adjacent $X^1$s form a 6-membered ring together with carbon atoms to which each $X^1$ is bonded by forming —CH=CHCH=CH—, and at this time, one hydrogen atom bonded to each carbon atom forming the ring is arbitrarily substituted with a halogen atom;

$X^{1a}$ is $C_{1-6}$ alkyl;

$Z^a$, $Z^c$, and $Z^e$ are each independently a hydrogen atom, a halogen atom, cyano, nitro, $C_{1-6}$ alkyl, $C_{3-8}$ cycloalkyl, $C_{2-6}$ alkenyl, $(C_{2-6})$ alkenyl arbitrarily substituted with $R^{45}$, $C_{2-6}$ alkynyl, $(C_{2-6})$ alkynyl arbitrarily substituted with $R^{45}$, —$OR^{41}$, —$S(O)_{r3}R^{41}$, —$C(O)OR^{41}$, —$C(O)R^{42}$, —$C(=NOR^{41})R^{42}$, —$N(R^{44})R^{43}$, phenyl, phenyl substituted with $(Z^3)_{q3}$, D1-2, D1-7, D1-11, D1-22, D1-32, D1-33, D1-34, or D1-37, $Z^1$ is a halogen atom, nitro, $C_{1-6}$ alkyl, halo $(C_{1-6})$ alkyl, $C_{1-6}$ alkoxy, or $C_{1-6}$ alkoxycarbonyl, and when q1 is an integer of 2 or larger, each $Z^1$ is the same as or different from each other;

$Z^2$ is a halogen atom, cyano, nitro, $C_{1-6}$ alkyl, halo $(C_{1-6})$ alkyl, —$OR^{51}$, —$S(O)_{r2}R^{51}$, —$C(O)OR^{51a}$, —$C(O)R^{52}$, or —$C(O)N(R^{54})R^{53}$, when q2 is an integer of 2 or larger, each $Z^2$ is the same as or different from each other, and further when the two $Z^2$s are adjacent, the two adjacent $Z^2$s optionally form a 6-membered ring together with carbon atoms to which each $Z^2$ is bonded by forming —N=CHCH=CH—, and at this time, one hydrogen atom bonded to each carbon atom forming the ring is arbitrarily substituted with a halogen atom;

$Z^3$ is a halogen atom, $C_{1-6}$ alkyl, halo $(C_{1-6})$ alkyl, $C_{1-6}$ alkoxy, halo $(C_{1-6})$ alkoxy, or $C_{1-6}$ alkylthio, and when q3 is an integer of 2 or larger, each $Z^3$ is the same as or different from each other;

$R^{31}$ is $C_{1-6}$ alkyl, $(C_{1-6})$ alkyl arbitrarily substituted with $R^{35}$, —$C(O)R^{37}$, phenyl, phenyl substituted with $(Z^2)_{q2}$, or naphthyl;

$R^{32}$ is $C_{1-6}$ alkyl or $(C_{1-6})$ alkyl arbitrarily substituted with $R^{35}$;

$R^{33}$ is —$C(O)R^{37}$;

$R^{34}$ is $C_{1-6}$ alkyl;

$R^{35}$ is a halogen atom, $C_{1-6}$ alkylthio, or phenyl;

$R^{37}$ is $C_{1-6}$ alkyl or phenyl;

$R^{41}$ is a hydrogen atom, $C_{1-6}$ alkyl, $(C_{1-6})$ alkyl arbitrarily substituted with $R^{45}$, phenyl, or D1-32;

$R^{42}$ is $C_{1-6}$ alkyl;

$R^{43}$ is $C_{1-6}$ alkoxycarbonyl;

$R^{44}$ is a hydrogen atom;

$R^{45}$ is a halogen atom, $C_{3-8}$ cycloalkyl, —OH, $C_{1-6}$ alkoxy, $C_{1-10}$ alkoxycarbonyl, —$Si(R^{32a})(R^{32b})R^{32c}$, phenyl, or D1-34;

$R^{51}$ is $C_{1-6}$ alkyl, halo $(C_{1-6})$ alkyl, phenyl arbitrarily substituted with a halogen atom, or D1-39;

$R^{51a}$ is $C_{1-6}$ alkyl;

$R^{53}$ and $R^{54}$ are each independently $C_{1-6}$ alkyl;

g2 is an integer of 0, 1, or 2;

g3 and r1 are each independently an integer of 0, 1, or 2;

g4, m, and n are each independently an integer of 0 or 1;

f7, p, and r3 are 0;

q is an integer of 2 or 3;

q1 is an integer of 1 or 2;

q2 is an integer of 1, 2, or 3;

q3 is an integer of 1, 2, or 3; and r2 is an integer of 0 or 2. [8]

The oxime compound or the salt according to [7], in which B is B-1-a;

$Z^a$ is a halogen atom, $C_{1-6}$ alkyl, $C_{1-6}$ alkoxy, or $C_{1-6}$ alkylthio;

$Z^c$ is a hydrogen atom, a halogen atom, cyano, nitro, $C_{1-6}$ alkyl, $C_{3-8}$ cycloalkyl, $C_{2-6}$ alkenyl, $(C_{2-6})$ alkenyl arbitrarily substituted with $R^{45}$, $C_{2-6}$ alkynyl, $(C_{2-6})$ alkynyl arbitrarily substituted with $R^{45}$, —$OR^{41}$, —$S(O)_{r3}R^{41}$, —$C(O)OR^{41}$, —$C(O)R^{42}$, —$C(=NOR^{41})R^{42}$, —$N(R^{44})R^{43}$, phenyl, phenyl substituted with $(Z^3)_{q3}$, D1-2, D1-7, D1-11, D1-22, D1-32, D1-33, D1-34, or D1-37;

$Z^e$ is a halogen atom, $C_{1-6}$ alkyl, or $C_{1-6}$ alkoxy;

$X^1$ is a halogen atom or halo $(C_{1-6})$ alkyl; and g3 is an integer of 0 or 1.

[9]

The ketone or oxime compound or the salt thereof according to [1], in which B is B-1 or B-2.

[10]

The ketone or oxime compound or the salt thereof according to [1], in which B is B-1.

[11]

The ketone or oxime compound or the salt thereof according to [1], in which B is B-2.

[12]

The ketone or oxime compound or the salt thereof according to [1], in which B is B-3.

[13]

The ketone or oxime compound or the salt thereof according to [2], in which B is B-1-a.

[14]

The ketone or oxime compound or the salt thereof according to [2], in which B is B-1-b.

[15]

The ketone compound or the salt thereof according to [3], in which B is B-1 or B-2.

[16]

The ketone compound or the salt thereof according to [3], in which B is B-1.

[17]

The ketone compound or the salt thereof according to [3], in which B is B-2.

[18]

The ketone compound or the salt thereof according to [3], in which B is B-3.

[19]

The ketone compound or the salt thereof according to [3] and [5], in which B is B-1-a.

[20]

The ketone compound or the salt thereof according to [3] and [5], in which B is B-1-b.

[21]

The oxime compound or the salt thereof according to [4], in which B is B-1 or B-2.

[22]

The oxime compound or the salt thereof according to [4], in which B is B-1.

[23]

The oxime compound or the salt thereof according to [4], in which B is B-2.

[24]

The oxime compound or the salt thereof according to [4], in which B is B-3.

[25]

The oxime compound or the salt thereof according to [4] and [7], in which B is B-1-a.

[26]

The oxime compound or the salt thereof according to [4] and [7], in which B is B-1-b.

[27]

The ketone or oxime compound or the salt thereof according to [1] to [26], in which A is a hydrogen atom, $C_{1-6}$ alkyl, $(C_{1-6})$ alkyl arbitrarily substituted with $R^5$, $C_{3-8}$ cycloalkyl, $C_{2-6}$ alkenyl, $(C_{2-6})$ alkenyl arbitrarily substituted with $R^5$, $C_{2-6}$ alkynyl, or $(C_{2-6})$ alkynyl arbitrarily substituted with $R^5$.

[28]

The ketone or oxime compound or the salt thereof according to [1] to [26], in which A is a hydrogen atom, $C_{1-6}$ alkyl, $(C_{1-6})$ alkyl arbitrarily substituted with $R^5$, $C_{2-6}$ alkenyl, $C_{2-6}$ alkynyl, or $(C_{2-6})$ alkynyl arbitrarily substituted with $R^5$.

[29]

The ketone or oxime compound or the salt thereof according to [1] to [26], in which A is a hydrogen atom, $C_{1-6}$ alkyl, or $(C_{1-6})$ alkyl arbitrarily substituted with $R^5$.

[30]

The ketone or oxime compound or the salt thereof according to [1] to [26], in which A is a hydrogen atom, $—S(O)_{r2}R^1$, $—C(O)OR^1$, $—C(O)SR^1$, $—C(S)OR^1$, $—C(O)R^2$, $—C(O)N(R^4)R^3$, $—C(S)N(R^4)R^3$, or $—S(O)_2N(R^4)R^3$.

[31]

The ketone or oxime compound or the salt thereof according to [1] to [26], in which A is a hydrogen atom, $—C(O)OR^1$, $—C(O)SR^1$, $—C(O)R^2$, $—C(O)N(R^4)R^3$, or $—C(S)N(R^4)R^3$.

[32]

The ketone or oxime compound or the salt thereof according to [1] to [26], in which A is a hydrogen atom, $—C(O)SR^1$, $—C(O)R^2$, or $—C(O)N(R^4)R^3$.

[33]

The ketone or oxime compound or the salt thereof according to [1] to [26], in which A is a hydrogen atom.

[34]

The ketone or oxime compound or the salt thereof according to [1] to [26], in which A is $C_{1-6}$ alkyl or $(C_{1-6})$ alkyl arbitrarily substituted with $R^5$.

[35]

The ketone or oxime compound or the salt thereof according to [1] to [26], in which A is $C_{2-6}$ alkynyl or $(C_{2-6})$ alkynyl arbitrarily substituted with $R^5$.

[36]

The ketone or oxime compound or the salt thereof according to [1] to [26], in which A is $—C(O)SR^1$.

[37]

The ketone or oxime compound or the salt thereof according to [1] to [26], in which A is a $—C(O)R^2$.

[38]

The ketone or oxime compound or the salt thereof according to [1] to [26], in which A is $—C(O)N(R^4)R^3$.

[39]

The ketone or oxime compound or the salt thereof according to [1] to [26], in which A is $—C(S)N(R^4)R^3$.

[40]

The ketone or oxime compound or the salt thereof according to [1] to [39], in which $R^1$ is $C_{1-8}$ alkyl, $(C_{1-6})$ alkyl arbitrarily substituted with $R^5$, $C_{3-8}$ cycloalkyl, or $C_{2-6}$ alkenyl.

[41]

The ketone or oxime compound or the salt thereof according to [1] to [39], in which $R^1$ is $C_{1-8}$ alkyl.

[42]

The ketone or oxime compound or the salt thereof according to [1] to [39], in which $R^1$ is $(C_{1-6})$ alkyl arbitrarily substituted with $R^5$.

[43]

The ketone or oxime compound or the salt thereof according to [1] to [39], in which $R^1$ is $C_{3-8}$ cycloalkyl.

[44]

The ketone or oxime compound or the salt thereof according to [1] to [39], in which $R^1$ is $C_{2-6}$ alkenyl.

[45]

The ketone or oxime compound or the salt thereof according to [1] to [44], in which $R^2$ is $C_{1-8}$ alkyl, $(C_{1-6})$ alkyl arbitrarily substituted with $R^5$, $C_{3-8}$ cycloalkyl, $(C_{3-8})$ cycloalkyl arbitrarily substituted with $R^5$, $C_{2-6}$ alkenyl, $(C_{2-6})$ alkenyl arbitrarily substituted with $R^5$, $C_{3-8}$ cycloalkenyl, $(C_{3-8})$ cycloalkenyl arbitrarily substituted with $R^5$, $C_{2-6}$ alkynyl, $(C_{2-6})$ alkynyl arbitrarily substituted with $R^5$, or $—C(=NOR^{31})R^{32}$

[46]

The ketone or oxime compound or the salt thereof according to [1] to [44], in which $R^2$ is $C_{1-8}$ alkyl or $(C_{1-6})$ alkyl arbitrarily substituted with $R^5$.

[47]

The ketone or oxime compound or the salt thereof according to [1] to [44], in which $R^2$ is $C_{3-8}$ cycloalkyl or $(C_{3-8})$ cycloalkyl arbitrarily substituted with $R^5$.

[48]

The ketone or oxime compound or the salt thereof according to [1] to [44], in which $R^2$ is $C_{2-6}$ alkenyl or $(C_{2-6})$ alkenyl arbitrarily substituted with $R^5$.

[49]

The ketone or oxime compound or the salt thereof according to [1] to [44], in which $R^2$ is $C_{3-8}$ cycloalkenyl or $(C_{3-8})$ cycloalkenyl arbitrarily substituted with $R^5$.

[50]

The ketone or oxime compound or the salt thereof according to [1] to [44], in which $R^2$ is $C_{2-6}$ alkynyl or $(C_{2-6})$ alkynyl arbitrarily substituted with $R^5$.

[51]

The ketone or oxime compound or the salt thereof according to [1] to [44], in which $R^2$ is phenyl, phenyl substituted with $(Z^2)_{q2}$, D1-5, D1-6, D1-8, D1-10, or D1-81.

[52]

The ketone or oxime compound or the salt thereof according to [1] to [44], in which $R^2$ is $C_{1-8}$ alkyl.

[53]

The ketone or oxime compound or the salt thereof according to [1] to [44], in which $R^2$ is $(C_{1-6})$ alkyl arbitrarily substituted with $R^5$.

[54]

The ketone or oxime compound or the salt thereof according to [1] to [53], in which $R^3$ is $C_{1-6}$ alkyl, $(C_{1-6})$ alkyl arbitrarily substituted with $R^5$, $C_{2-6}$ alkenyl, phenyl, or phenyl substituted with $(Z^2)_{q2}$.

[55]

The ketone or oxime compound or the salt thereof according to [1] to [53], in which $R^3$ is $C_{1-6}$ alkyl, $(C_{1-6})$ alkyl arbitrarily substituted with $R^5$, or $C_{2-6}$ alkenyl.

[56]

The ketone or oxime compound or the salt thereof according to [1] to [53], in which $R^3$ is phenyl or phenyl substituted with $(Z^2)_{q2}$.

[57]

The ketone or oxime compound or the salt thereof according to [1] to [53], in which $R^3$ forms a 5- or 6-membered ring together with a nitrogen atom to which $R^3$ and $R^4$ are bonded by forming a $C_4$ or $C_5$ alkylene chain together with $R^4$, and

[58]

The ketone or oxime compound or the salt thereof according to [1] to [57], in which $R^5$ is a halogen atom, cyano, $C_{3-8}$ cycloalkyl, $-OR^{31}$, $-S(O)_r2R^{31}$, $-C(O)OR^{31}$, phenyl, or phenyl substituted with $(Z^2)_{q2}$.

[59]

The ketone or oxime compound or the salt thereof according to [1] to [57], in which $R^5$ is a halogen atom, $-OR^{31}$, or $-S(O)_{r2}R^{31}$

[60]

The ketone or oxime compound or the salt thereof according to [1] to [57], in which $R^5$ is a halogen atom.

[61]

The ketone or oxime compound or the salt thereof according to [1] to [57], in which $R^5$ is $-OR^{31}$

[62]

The ketone or oxime compound or the salt thereof according to [1] to [57], in which $R^5$ is $-S(O)_r2R^{31}$

[63]

The ketone or oxime compound or the salt thereof according to [1] to [57], in which, when two $R^5$s are substituents on a same carbon, the two $R^5$s optionally form $C_{1-6}$ alkoxyimino together with each other.

[64]

The ketone or oxime compound or the salt thereof according to [1] to [63], in which $R^6$ is $C_{1-6}$ alkyl, $(C_{1-6})$ alkyl arbitrarily substituted with $R^{15}$, $C_{3-8}$ cycloalkyl, or $C_{2-6}$ alkenyl.

[65]

The ketone or oxime compound or the salt thereof according to [1] to [63], in which $R^6$ is phenyl, phenyl substituted with $(Z^1)_{q1}$, or D1-32.

[66]

The ketone or oxime compound or the salt thereof according to [1] to [63], in which $R^6$ is $C_{1-6}$ alkyl or $C_{3-8}$ cycloalkyl.

[67]

The ketone or oxime compound or the salt thereof according to [1] to [63], in which $R^6$ is $C_{1-6}$ alkyl.

[68]

The ketone or oxime compound or the salt thereof according to [1] to [63], in which $R^6$ is $C_{3-8}$ cycloalkyl.

[69]

The oxime compound or the salt thereof according to [1], [2], [4], [7] to [14], and [21] to [63], in which $R^7$ is a hydrogen atom, $C_{1-7}$ alkyl, $(C_{1-6})$ alkyl arbitrarily substituted with $R^{15b}$, $C_{3-8}$ cycloalkyl, $C_{2-6}$ alkenyl, $C_{3-8}$ cycloalkenyl, $(C_{2-6})$ alkenyl arbitrarily substituted with $R^{15b}$, or $C_{2-6}$ alkynyl.

[70]

The oxime compound or the salt thereof according to [1], [2], [4], [7] to [14], and [21] to [63], in which $R^7$ is a hydrogen atom, $C_{1-7}$ alkyl, or $(C_{1-6})$ alkyl arbitrarily substituted with $R^{15b}$.

[71]

The oxime compound or the salt thereof according to [1], [2], [4], [7] to [14], and [21] to [63], in which $R^7$ is a hydrogen atom.

[72]

The oxime compound or the salt thereof according to [1], [2], [4], [7] to [14], and [21] to [63], in which $R^7$ is $C_{1-7}$ alkyl.

[73]

The oxime compound or the salt thereof according to [1], [2], [4], [7] to [14], and [21] to [63], in which $R^7$ is $(C_{1-6})$ alkyl arbitrarily substituted with $R^{15b}$.

[74]

The ketone or oxime compound or the salt thereof according to [1] to [73], in which $R^{8a}$ is a hydrogen atom, $C_{1-6}$ alkyl, halo $(C_{1-6})$ alkyl, or $-C(O)OR^{16a}$.

[75]

The ketone or oxime compound or the salt thereof according to [1] to [73], in which $R^{8a}$ is a hydrogen atom or $C_{1-6}$ alkyl.

[76]

The ketone or oxime compound or the salt thereof according to [1] to [73], in which $R^{8a}$ is a hydrogen atom.

[77]

The ketone or oxime compound or the salt thereof according to [1] to [73], in which $R^{8a}$ is $C_{1-6}$ alkyl.

[78]

The ketone or oxime compound or the salt thereof according to [1] to [77], in which $R^{9a}$ is a hydrogen atom.

[79]

The ketone or oxime compound or the salt thereof according to [1] to [79], in which $R^{9a}$ is $C_{1-6}$ alkyl.

[80]

The ketone or oxime compound or the salt thereof according to [1] to [79], in which $R^{15}$ is a halogen atom.

[81]

The ketone or oxime compound or the salt thereof according to [1] to [79], in which $R^{15}$ is $C_{3-8}$ cycloalkyl.

[82]

The ketone or oxime compound or the salt thereof according to [1] to [79], in which $R^{15}$ is $-OR^{16}$.

[83]

The oxime compound or the salt thereof according to [1], [2], [4], [7] to [14], and [21] to [82], in which $R^{15b}$ is a halogen atom, cyano, halo $(C_{3-8})$ cycloalkyl, $-OR^{16b}$, $-S(O)_{r1}R^{16b}$, or $-C(O)N(R^{18b})R^{19b}$.

[84]

The oxime compound or the salt thereof according to [1], [2], [4], [7] to [14], and [21] to [82], in which $R^{15b}$ is a halogen atom, cyano, $-OR^{16b}$, or $-S(O)_{r1}R^{16b}$.

[85]

The oxime compound or the salt thereof according to [1], [2], [4], [7] to [14], and [21] to [82], in which $R^{15b}$ is a halogen atom.

[86]

The oxime compound or the salt thereof according to [1], [2], [4], [7] to [14], and [21] to [82], in which $R^{15b}$ is cyano.

[87]

The oxime compound or the salt thereof according to [1], [2], [4], [7] to [14], and [21] to [82], in which $R^{15b}$ is $-OR^{16b}$.

[88]

The oxime compound or the salt thereof according to [1], [2], [4], [7] to [14], and [21] to [82], in which $R^{15b}$ is $-S(O)_{r1}R^{16b}$

[89]

The oxime compound or the salt thereof according to [1], [2], [4], [7] to [14], and [21] to [82], in which $R^{15b}$ is phenyl, phenyl substituted with $(Z^1)_{q1}$, D1-32, or D1-84.

[90]

The oxime compound or the salt thereof according to [1], [2], [4], [7] to [14], and [21] to [82], in which $R^{15b}$ is phenyl or phenyl substituted with $(Z^1)_{q1}$.

at this time, the alkylene chain optionally contains one oxygen atom or nitrogen atom and is optionally substituted with $C_{1-6}$ alkyl.

[91]
The oxime compound or the salt thereof according to [1], [2], [4], [7] to [14], and [21] to [90], in which $R^{18b}$ is a hydrogen atom or $C_{1-6}$ alkyl.

[92]
The oxime compound or the salt thereof according to [1], [2], [4], [7] to [14], and [21] to [90], in which $R^{18b}$ forms a 6-membered ring together with a nitrogen atom to which $R^{18b}$ and $R^{19b}$ are bonded by forming a $C_5$ alkylene chain together with $R^{19b}$, and at this time, the alkylene chain contains one oxygen atom.

[93]
The ketone or oxime compound or the salt thereof according to [1] to [92], in which $X^1$ is halo $(C_{1-6})$ alkyl or $C_{3-8}$ cycloalkyl.

[94]
The ketone or oxime compound or the salt thereof according to [1] to [92], in which $X^1$ is a halogen atom or $C_{1-6}$ alkyl.

[95]
The ketone or oxime compound or the salt thereof according to [1] to [92], in which $X^1$ is a halogen atom.

[96]
The ketone or oxime compound or the salt thereof according to [1] to [92], in which $X^1$ is $C_{1-6}$ alkyl.

[97]
The ketone or oxime compound or the salt thereof according to [1] to [96], in which $Z^a$ is a halogen atom.

[98]
The ketone or oxime compound or the salt thereof according to [1] to [96], in which $Z^a$ is $C_{1-6}$ alkyl.

[99]
The ketone or oxime compound or the salt thereof according to [1] to [96], in which $Z^a$ is $C_{1-6}$ alkoxy.

[100]
The ketone or oxime compound or the salt thereof according to [1] to [96], in which $Z^a$ is $C_{1-6}$ alkylthio.

The ketone or oxime compound or the salt thereof according to [1] to [100], in which $Z^c$ is a hydrogen atom, a halogen atom, cyano, $C_{1-6}$ alkyl, $C_{2-6}$ alkynyl, $(C_{2-6})$ alkynyl arbitrarily substituted with $R^{45}$, phenyl, phenyl substituted with $(Z^3)_{q3}$, D1-2, D1-7, D1-11, D1-22, D1-32, D1-33, D1-34, or D1-37.

The ketone or oxime compound or the salt thereof according to [1] to [100], in which $Z^c$ is a hydrogen atom, a halogen atom, cyano, $C_{1-6}$ alkyl, $C_{2-6}$ alkynyl, or $(C_{2-6})$ alkynyl arbitrarily substituted with $R^{45}$.

The ketone or oxime compound or the salt thereof according to [1] to [100], in which $Z^c$ is phenyl, phenyl substituted with $(Z^3)_{q3}$, D1-2, D1-7, D1-11, D1-22, D1-32, D1-33, D1-34, or D1-37.

[104]
The ketone or oxime compound or the salt thereof according to [1] to [100], in which $Z^c$ is $C_{1-6}$ alkyl.

The ketone or oxime compound or the salt thereof according to [1] to [100], in which $Z^c$ is $C_{2-6}$ alkynyl or $(C_{2-6})$ alkynyl arbitrarily substituted with $R^{45}$.

The ketone or oxime compound or the salt thereof according to [1] to [100], in which $Z^c$ is phenyl or phenyl substituted with $(Z^3)_{q3}$.

The ketone or oxime compound or the salt thereof according to [1] to [100], in which $Z^c$ is D1-2, D1-7, D1-32, D1-33, D1-34, or D1-37.

The ketone or oxime compound or the salt thereof according to [1] to [100], in which $Z^c$ is D1-32, D1-33, or D1-34.

The ketone or oxime compound or the salt thereof according to [1] to [100], in which $Z^c$ is D1-7.

The ketone or oxime compound or the salt thereof according to [1] to [109], in which $Z^e$ is a halogen atom.

The ketone or oxime compound or the salt thereof according to [1] to [109], in which $Z^e$ is $C_{1-6}$ alkyl.

[112]
The ketone or oxime compound or the salt thereof according to [1] to [109], in which $Z^e$ is $C_{1-6}$ alkoxy.

The ketone or oxime compound or the salt thereof according to [1] to [109], in which $Z^e$ is $C_{1-6}$ alkylthio.

The ketone or oxime compound or the salt thereof according to [1] to [113], in which $Z^2$ is a halogen atom, cyano, nitro, $C_{1-6}$ alkyl, halo $(C_{1-6})$ alkyl, $-OR^{51}$, or $-S(O)_{r2}R^{51}$.

The ketone or oxime compound or the salt thereof according to [1] to [113], in which $Z^2$ is a halogen atom, cyano, nitro, $C_{1-6}$ alkyl, or halo $(C_{1-6})$ alkyl.

The ketone or oxime compound or the salt thereof according to [1] to [113], in which $Z^2$ is a halogen atom or $C_{1-6}$ alkyl.

[117]
The ketone or oxime compound or the salt thereof according to [1] to [113], in which $Z^2$ is $-OR^{51}$ or $-S(O)_{r2}R^{51}$.

The ketone or oxime compound or the salt thereof according to [1] to [113], in which $Z^2$ is a halogen atom.

The ketone or oxime compound or the salt thereof according to [1] to [113], in which $Z^2$ is $C_{1-6}$ alkyl.

[120]
The ketone or oxime compound or the salt thereof according to [1] to [113], in which $Z^2$ is $-OR^{51}$.

The ketone or oxime compound or the salt thereof according to [1] to [113], in which $Z^2$ is $-S(O)_{r2}R^{51}$.

The ketone or oxime compound or the salt thereof according to [1] to [121], in which $Z^3$ is a halogen atom or halo $(C_{1-6})$ alkoxy.

The ketone or oxime compound or the salt thereof according to [1] to [121], in which $Z^3$ is a halogen atom.

The ketone or oxime compound or the salt thereof according to [1] to [121], in which $Z^3$ is halo $(C_{1-6})$ alkoxy.

[125]
The ketone or oxime compound or the salt thereof according to [1] to [124], in which $R^{32}$ is $C_{1-6}$ alkyl.

The ketone or oxime compound or the salt thereof according to [1] to [124], in which $R^{32}$ is $(C_{1-6})$ alkyl arbitrarily substituted with $R^{35}$.

The ketone or oxime compound or the salt thereof according to [1] to [126], in which $R^{35}$ is a halogen atom.

The ketone or oxime compound or the salt thereof according to [1] to [126], in which $R^{35}$ is $C_{1-6}$ alkylthio.

The ketone or oxime compound or the salt thereof according to [1] to [126], in which $R^{35}$ is phenyl.

The ketone or oxime compound or the salt thereof according to [1] to [129], in which $R^{37}$ is $C_{1-6}$ alkyl.

The ketone or oxime compound or the salt thereof according to [1] to [129], in which $R^{37}$ is phenyl.

The ketone or oxime compound or the salt thereof according to [1] to [131], in which $R^{41}$ is a hydrogen atom, $C_{1-6}$ alkyl, or $(C_{1-6})$ alkyl arbitrarily substituted with $R^{45}$.

[133]
The ketone or oxime compound or the salt thereof according to [1] to [131], in which $R^{41}$ is phenyl or D1-32.

The ketone or oxime compound or the salt thereof according to [1] to [131], in which $R^{41}$ is a hydrogen atom.

The ketone or oxime compound or the salt thereof according to [1] to [131], in which $R^{41}$ is $C_{1-6}$ alkyl.

The ketone or oxime compound or the salt thereof according to [1] to [131], in which $R^{41}$ is $(C_{1-6})$ alkyl arbitrarily substituted with $R^{45}$.

The ketone or oxime compound or the salt thereof according to [1] to [136], in which $R^{45}$ is a halogen atom, $C_{3-8}$ cycloalkyl, —OH, or $C_{1-6}$ alkoxy.

The ketone or oxime compound or the salt thereof according to [1] to [136], in which $R^{45}$ is phenyl or D1-34.

[139]

The ketone or oxime compound or the salt thereof according to [1] to [136], in which $R^{45}$ is a halogen atom.

The ketone or oxime compound or the salt thereof according to [1] to [136], in which $R^{45}$ is $C_{3-8}$ cycloalkyl.

[141]

The ketone or oxime compound or the salt thereof according to [1] to [136], in which $R^{45}$ is —OH.

[142]

The ketone or oxime compound or the salt thereof according to [1] to [136], in which $R^{45}$ is $C_{1-6}$ alkoxy.

The ketone or oxime compound or the salt thereof according to [1] to [142], in which $R^{51}$ is $C_{1-6}$ alkyl.

The ketone or oxime compound or the salt thereof according to [1] to [143], in which m is an integer of 0 or 1.

[145]

The ketone or oxime compound or the salt thereof according to [1] to [143], in which m is an integer of 0.

[146]

The ketone or oxime compound or the salt thereof according to [1] to [143], in which m is an integer of 1.

The ketone or oxime compound or the salt thereof according to [1] to [146], in which n is an integer of 0 or 1.

The ketone or oxime compound or the salt thereof according to [1] to [146], in which n is an integer of 0.

[149]

The ketone or oxime compound or the salt thereof according to [1] to [146], in which n is an integer of 1.

An agricultural chemical comprising one or more of compounds selected from the ketone or oxime compound or the salt thereof according to [1] to [149] as an active component.

A herbicide comprising one or more of compounds selected from the ketone or oxime compound or the salt thereof according to [1] to [149] as an active component.

Effects of the Invention

The compound of the present invention has excellent herbicidal activity against various weeds and has high safety to target crops as well as has almost no adverse effect on non-target creatures such as mammals, fish, and beneficial insects and has light environmental burden due to low residual properties.

Accordingly, the present invention can provide a useful herbicide in the agricultural and horticultural fields such as paddy fields, farmlands, and orchards.

MODES FOR CARRYING OUT THE INVENTION

The compound of Formula (1) of the present invention may exist as, for example, keto-enol structural tautomers of the following formula depending on the kind of the substituent and conditions. The present invention includes all of these structures.

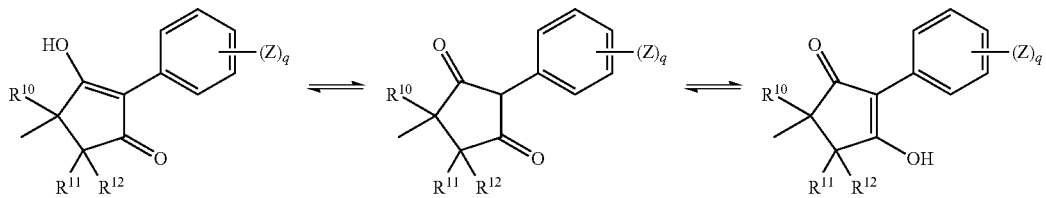

The compounds included in the present invention may include the geometric isomers of an E-form having an E-configuration and a Z-form having a Z-configuration depending on the types of the substituents. The present invention includes the E-form, the Z-form, and a mixture of the E-form and the Z-form in any ratios. In the present specification, these forms are represented as, for example, a bond of wavy lines illustrated below.

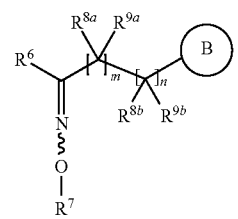

The compounds included in the present invention include optically active isomers due to the existence of one or more of asymmetric carbon atoms. The present invention includes all optically active isomers or racemic forms.

Among the compounds included in the present invention, the compounds that can form an acid-added salt by a conventional method may form, for example, the salts of hydrohalic acids such as hydrofluoric acid, hydrochloric acid, hydrobromic acid, and hydroiodic acid; the salts of inorganic acids such as nitric acid, sulfuric acid, phosphoric acid, chloric acid, and perchloric acid; the salts of sulfonic acids such as methanesulfonic acid, ethanesulfonic acid, trifluoromethanesulfonic acid, benzenesulfonic acid, and p-toluenesulfonic acid; the salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, and citric acid; or the salts of amino acids such as glutamic acid and aspartic acid.

Among the compounds included in the present invention, the compounds that can form a metal salt by a conventional method may form, for example, the salts of alkali metals such as lithium, sodium, and potassium; the salts of alkaline earth metals such as calcium, barium, and magnesium; or the salt of aluminum.

Subsequently, specific examples of each substituent described in the present specification will be described below. Here, n—means normal; i—means iso; s—means secondary; and tert—means tertiary; and Ph means phenyl.

Examples of the halogen atom in the present specification may include a fluorine atom, a chlorine atom, a bromine atom, and an iodine atom. The expression of "halo" in the present specification is also these halogen atoms.

The expression of $C_{a-b}$ alkyl in the present specification is a linear chain or a branched chain hydrocarbon group made of the number of carbon atoms of a to b. Specific examples of the $C_{a-b}$ alkyl may include methyl group, ethyl group, n-propyl group, i-propyl group, n-butyl group, i-butyl group, s-butyl group, tert-butyl group, n-pentyl group, 1,1-dimethylpropyl group, and n-hexyl group and the like. Each of these groups is selected in a range of the specified number of carbon atoms.

The expression of $C_{a-b}$ alkenyl in the present specification is a linear chain or a branched chain unsaturated hydrocarbon group made of the number of carbon atoms of a to b and having one or more double bonds in the molecule. Specific examples of the $C_{a-b}$ alkenyl may include vinyl group, 1-propenyl group, 2-propenyl group, 1-methylethenyl group, 2-butenyl group, 2-methyl-2-propenyl group, 3-methyl-2-butenyl group, and 1,1-dimethyl-2-propenyl group and the like. Each of these groups is selected in a range of the specified number of carbon atoms.

The expression of $C_{a-b}$ alkynyl in the present specification is a linear chain or a branched chain unsaturated hydrocarbon group made of the number of carbon atoms of a to b and having one or more triple bonds in the molecule. Specific examples of the $C_{a-b}$ alkenyl may include ethynyl group, 1-propynyl group, 2-propynyl group, 1-butynyl group, 2-butynyl group, 3-butynyl group, and 1,1-dimethyl-2-propynyl group and the like. Each of these groups is selected in a range of the specified number of carbon atoms.

The expression of halo ($C_{a-b}$) alkyl in the present specification is a linear chain or a branched chain hydrocarbon group made of the number of carbon atoms of a to b in which the hydrogen atoms bonded to the carbon atom are arbitrarily substituted with halogen atoms. When the compound is substituted with two or more halogen atoms, these halogen atoms may be the same as or different from each other. Specific examples of the $C_{a-b}$ haloalkyl may include fluoromethyl group, chloromethyl group, bromomethyl group, iodomethyl group, difluoromethyl group, dichloromethyl group, trifluoromethyl group, chlorodifluoromethyl group, trichloromethyl group, bromodifluoromethyl group, 2-fluoroethyl group, 2-chloroethyl group, 2-bromoethyl group, 2,2-difluoroethyl group, 2,2,2-trifluoroethyl group, 2-chloro-2,2-difluoroethyl group, 2,2,2-trichloroethyl group, 1,1,2,2-tetrafluoroethyl group, 2-chloro-1,1,2-trifluoroethyl group, pentafluoroethyl group, 3,3,3-trifluoropropyl group, 2,2,3,3,3-pentafluoropropyl group, 1,1,2,3,3,3-hexafluoropropyl group, heptafluoropropyl group, 2,2,2-trifluoro-1-(trifluoromethyl)ethyl group, 1,2,2,2-tetrafluoro-1-(trifluoromethyl)ethyl group, 2,2,3,3,4,4,4-heptafluorobutyl group, and nonafluorobutyl group and the like. Each of these groups is selected in a range of the specified number of carbon atoms.

The expression of $C_{a-b}$ cycloalkyl in the present specification is a cyclic hydrocarbon group made of the number of carbon atoms of a to b and can form a monocyclic structure or a fused ring structure of a 3-membered ring to a 6-membered ring. Each ring is optionally substituted with an alkyl group in a range of the specified number of carbon atoms. Specific example of the $C_{a-b}$ cycloalkyl may include cyclopropyl group, 1-methylcyclopropyl group, 2-methylcyclopropyl group, 2,2-dimethylcyclopropyl group, cyclobutyl group, cyclopentyl group, and cyclohexyl group and the like. Each of these groups is selected in a range of the specified number of carbon atoms.

The expression of halo ($C_{a-b}$) cycloalkyl in the present specification is a cyclic hydrocarbon group made of the number of carbon atoms of a to b in which the hydrogen atoms bonded to the carbon atom are arbitrarily substituted with halogen atoms and can form a monocyclic structure or a conjugated-cyclic structure of a 3-membered ring to a 6-membered ring. Each ring can be optionally substituted with an alkyl group in a range of the specified number of carbon atoms. The substitution position with the halogen atom may be at a ring structure part, at a side chain structure part, or at both of them. When the compound is substituted with two or more halogen atoms, these halogen atoms may be the same as or different from each other. Specific examples of the halo ($C_{a-b}$) cycloalkyl may include 2,2-difluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, and 2,2,3,3-tetrafluorocyclobutyl group and the like. Each of these groups is selected in a range of the specified number of carbon atoms.

The expression of $C_{a-b}$ cycloalkenyl in the present specification is a cyclic unsaturated hydrocarbon group made of the number of carbon atoms of a to b and having one or more double bonds and can form a monocyclic structure or a fused ring structure of a 3-membered ring to a 6-membered ring. Each ring can be optionally substituted with an alkyl group in a range of the specified number of carbon atoms. The double bond may be either an endo-form or an exo-form. Specific example of the $C_{a-b}$ cycloalkenyl may include 1-cyclopentene-1-yl group, 2-cyclopentene-1-yl group, 1-cyclohexen-1-yl group, and 2-cyclohexen-1-yl group and the like. Each of these groups is selected in a range of the specified number of carbon atoms.

The expression of $C_{a-b}$ alkoxy in the present specification is an alkyl-O— group in which this alkyl is the above meaning alkyl made of the number of carbon atoms of a to b. Specific examples of the $C_{a-b}$ alkoxy may include methoxy group, ethoxy group, n-propyloxy group, i-propyloxy group, n-butyloxy group, i-butyloxy group, s-butyloxy group, and tert-butyloxy group and the like. Each of these groups is selected in a range of the specified number of carbon atoms.

The expression of halo ($C_{a-b}$) alkoxy in the present specification is a haloalkyl-O— group in which this haloalkyl is the above meaning haloalkyl made of the number of carbon atoms of a to b. Specific examples of the halo ($C_{a-b}$) alkoxy may include difluoromethoxy group, trifluoromethoxy group, chlorodifluoromethoxy group, bromodifluoromethoxy group, 2-fluoroethoxy group, 2-chloroethoxy group, 2,2,2-trifluoroethoxy group, 1,1,2,2-tetrafluoroethoxy group, 2-chloro-1,1,2-trifluoroethoxy group, and 1,1,2,3,3,3-hexafluoropropyloxy group and the like. Each of these groups is selected in a range of the specified number of carbon atoms.

The expression of $C_{a-b}$ alkylthio in the present specification is an alkyl-S— group in which this alkyl is the above meaning alkyl made of the number of carbon atoms of a to b. Specific examples of the $C_{a-b}$ alkylthio may include methylthio group, ethylthio group, n-propylthio group, i-propylthio group, n-butylthio group, i-butylthio group, s-butylthio group, and tert-butylthio group and the like. Each of these groups is selected in a range of the specified number of carbon atoms.

The expression of $C_{a-b}$ alkylsulfinyl in the present specification is an alkyl-S(O)— group in which this alkyl is the above meaning alkyl made of the number of carbon atoms of a to b. Specific examples of the $C_{a-b}$ alkylsulfinyl may include methylsulfinyl group, ethylsulfinyl group, n-propylsulfinyl group, i-propylsulfinyl group, n-butylsulfinyl group, i-butylsulfinyl group, s-butylsulfinyl group, and tert-butylsulfinyl group and the like. Each of these groups is selected in a range of the specified number of carbon atoms.

The expression of $C_{a-b}$ alkylsulfonyl in the present specification is an alkyl-SO$_2$— group in which this alkyl is the above meaning alkyl made of the number of carbon atoms of a to b. Specific examples of the $C_{a-b}$ alkylsulfonyl may include methylsulfonyl group, ethylsulfonyl group, n-propylsulfonyl group, i-propylsulfonyl group, n-butylsulfonyl group, i-butylsulfonyl group, s-butylsulfonyl group, and tert-butylsulfonyl group and the like. Each of these groups is selected in a range of the specified number of carbon atoms.

The expression of $C_{a-b}$ alkoxycarbonyl in the present specification is an alkyl-O—C(O)— group in which this alkyl is the above meaning alkyl made of the number of carbon atoms of a to b. Specific examples of the $C_{a-b}$ alkoxycarbonyl may include methoxycarbonyl group, ethoxycarbonyl group, n-propyloxycarbonyl group, i-propyloxycarbonyl group, n-butoxycarbonyl group, i-butoxycarbonyl group, and tert-butoxycarbonyl group and the like. Each of these groups is selected in a range of the specified number of carbon atoms.

The expression of $C_{a-b}$ alkylcarbonyl in the present specification is an alkyl-C(O)— group in which this alkyl is the above meaning alkyl made of the number of carbon atoms of a to b. Specific examples of the $C_{a-b}$ alkylcarbonyl may include acetyl group, propionyl group, butyryl group, isobutyryl group, valeryl group, isovaleryl group, 2-methylbutanoyl group, pivaloyl group, hexanoyl group, and heptanoyl group and the like. Each of these groups is selected in a range of the specified number of carbon atoms.

The expression of $C_{a-b}$ alkylimino in the present specification is an alkyl-N=group in which this alkyl is the above meaning alkyl made of the number of carbon atoms of a to b. Specific examples of the $C_{a-b}$ alkylimino may include methylimino group, ethylimino group, n-propylimino group, i-propylimino group, n-butylimino group, i-butylimino group, and s-butylimino group and the like. Each of these groups is selected in a range of the specified number of carbon atoms.

The expression of $C_{a-b}$ alkoxyimino in the present specification is an alkoxy-N=group in which this alkoxy is the above meaning alkoxy made of the number of carbon atoms of a to b. Specific examples of the $C_{a-b}$ alkoxyimino may include methoxyimino group, ethoxyimino group, n-propyloxyimino group, i-propyloxyimino group, and n-butyloxyimino group and the like. Each of these groups is selected in a range of the specified number of carbon atoms.

The expression of $C_{a-b}$ alkylidene in the present specification is a linear or branched hydrocarbon group made of the number of carbon atoms of a to b and bonded with a double bond. Specific examples of the $C_{a-b}$ alkylidene may include methylidene group, ethylidene group, propylidene group, and 1-methylethylidene group and the like. Each of these groups is selected in a range of the specified number of carbon atoms.

The expression of "$(C_{a-b})$ alkyl arbitrarily substituted with $R^5$", "$(C_{a-b})$ alkyl arbitrarily substituted with $R^{15}$", "$(C_{a-b})$ alkyl arbitrarily substituted with $R^{15b}$", "$(C_{a-b})$ alkyl arbitrarily substituted with $R^{20}$", "$(C_{a-b})$ alkyl arbitrarily substituted with $R^{35}$", or "$(C_{a-b})$ alkyl arbitrarily substituted with $R^{45}$" in the present specification is the above meaning alkyl group made of the carbon number of a to b in which the hydrogen atoms bonded to the carbon atoms are arbitrarily substituted with any $R^5$, $R^{15}$, $R^{15b}$, $R^{20}$, $R^{35}$, or $R^{45}$. Each of these groups is selected in a range of the specified number of carbon atoms. At this time, when two or more substituents $R^5$s, $R^{15}$s, $R^{15b}$s, $R^{20}$s, $R^{35}$s, or $R^{45}$s are contained in each $(C_{a-b})$ alkyl group, each $R^5$, $R^{15}$, $R^{15b}$, $R^{20}$, $R^{35}$, or $R^{45}$ may be the same as or different from each other.

The expression of "$(C_{a-b})$ cycloalkyl arbitrarily substituted with $R^5$", "$(C_{a-b})$ cycloalkyl arbitrarily substituted with $R^{15}$", "$(C_{a-b})$ cycloalkyl arbitrarily substituted with $R^{15b}$", or "$(C_{a-b})$ cycloalkyl arbitrarily substituted with $R^{45}$" in the present specification is the above meaning cycloalkyl group made of the carbon number of a to b in which the hydrogen atoms bonded to the carbon atoms are arbitrarily substituted with any $R^5$, $R^{15}$, $R^{15b}$, or $R^{45}$. Each of these groups is selected in a range of the specified number of carbon atoms. At this time, when two or more substituents $R^5$s, $R^{15}$s, $R^{15b}$s, or $R^{45}$s are contained in each $(C_{a-b})$ cycloalkyl group, each $R^5$, $R^{15}$, $R^{15b}$, or $R^{45}$ may be the same as or different from each other. The substituted positions may be at a ring structure part, at a side chain structure part, or at both of them.

The expression of "$(C_{a-b})$ alkenyl arbitrarily substituted with $R^5$", "$(C_{a-b})$ alkenyl arbitrarily substituted with $R^{15}$", "$(C_{a-b})$ alkenyl arbitrarily substituted with $R^{15b}$", or "$(C_{a-b})$ alkenyl arbitrarily substituted with $R^{45}$" in the present specification is the above meaning alkenyl group made of the carbon number of a to b in which the hydrogen atoms bonded to the carbon atoms are arbitrarily substituted with any $R^5$, $R^{15}$, $R^{15b}$, or $R^{45}$. Each of these groups is selected in a range of the specified number of carbon atoms. At this time, when two or more substituents $R^5$s, $R^{15}$s, $R^{15b}$s, or $R^{45}$s are contained in each $(C_{a-b})$ alkenyl group, each $R^5$, $R^{15}$, $R^{15b}$, or $R^{45}$ may be the same as or different from each other.

The expression of "$(C_{a-b})$ cycloalkenyl arbitrarily substituted with $R^5$", "$(C_{a-b})$ cycloalkenyl arbitrarily substituted with $R^{15}$", "$(C_{a-b})$ cycloalkenyl arbitrarily substituted with $R^{15b}$", or "$(C_{a-b})$ cycloalkenyl arbitrarily substituted with $R^{45}$" in the present specification is the above meaning cycloalkenyl group made of the carbon number of a to b in which the hydrogen atoms bonded to the carbon atoms are arbitrarily substituted with any $R^5$, $R^{15}$, $R^{15b}$, or $R^{45}$. Each of these groups is selected in a range of the specified number of carbon atoms. At this time, when two or more substituents $R^5$s, $R^{15}$s, $R^{15b}$s, or $R^{45}$s are contained in each $(C_{a-b})$ cycloalkenyl group, each $R^5$, $R^{15}$, $R^{15b}$, or $R^{45}$ may be the same as or different from each other. The substituted positions may be at a ring structure part, at a side chain structure part, or at both of them.

The expression of "$(C_{a-b})$ alkynyl arbitrarily substituted with $R^5$", "$(C_{a-b})$ alkynyl arbitrarily substituted with $R^{15}$", "$(C_{a-b})$ alkynyl arbitrarily substituted with $R^{15b}$", or "$(C_{a-b})$ alkynyl arbitrarily substituted with $R^{45}$" in the present specification is the above meaning alkynyl group made of the carbon number of a to b in which the hydrogen atoms bonded to the carbon atoms are arbitrarily substituted with any $R^5$, $R^{15}$, $R^{15b}$, or $R^{45}$. Each of these groups is selected in a range of the specified number of carbon atoms. At this time, when two or more substituents $R^5$s, $R^{15}$s, $R^{15b}$s, or $R^{45}$s are contained in each $(C_{a-b})$ alkynyl group, each $R^5$, $R^{15}$, $R^{15b}$, or $R^{45}$ may be the same as or different from each other.

Specific examples of the expression of "$R^3$ optionally forms a 3-membered ring to an 8-membered ring together with a nitrogen atom to which $R^3$ and $R^4$ are bonded by forming a $C_{2-7}$ alkylene chain or a $C_{2-7}$ alkenylene chain together with $R^4$, and at this time, the alkylene chain or the alkenylene chain optionally contain one oxygen atom, one sulfur atom, or one nitrogen atom" include aziridine, azetidine, azetidin-2-one, pyrrolidine, pyrrolidin-2-one, oxazolidine, oxazolidin-2-one, oxazolidine-2-thione, thiazolidine, thiazolidin-2-one, thiazolidine-2-thione, imidazolidine, imidazolidin-2-one, imidazolidine-2-thione, piperidine, piperidin-2-one, piperidine-2-thione, 2H-3,4,5,6-tetrahydro-1,3-oxazin-2-one, 2H-3,4,5,6-tetrahydro-1,3-oxazine-2-thione, morpholine, 2H-3,4,5,6-tetrahydro-1,3-thiazin-2-one, 2H-3,4,5,6-tetrahydro-1,3-thiazine-2-thione, thiomorpholine, perhydropyrimidine-2-one, piperazine, homopiperidine, homopiperidin-2-one, heptamethyleneimine, 1,2-dihydropyridine, 1,2-dihydropyrimidine, 1,4-dihydropyridine, 2,3-dihydro-1H-imidazole, 2,3-dihydrothiazole, 2,3-dihydrooxazole, 4,5-dihydro-1H-pyrazole, 2,5-dihydro-1H-pyrrole, 1,2,3,4-tetrahydropyridine, 1,2,3,4-tetrahydropyrimidine, and 1,2,3,4-tetrahydropyridazine and the like. Each of these groups is selected in a range of the specified number of carbon atoms.

Specific examples of the expression of "$R^{18b}$ optionally forms a 3-membered ring to an 8-membered ring together with a nitrogen atom to which $R^{18b}$ and $R^{19b}$ are bonded by forming a $C_{2-7}$ alkylene chain together with $R^{19b}$, and at this time, the alkylene chain contain one oxygen atom, one sulfur atom, or one nitrogen atom" include aziridine, azetidine, azetidin-2-one, pyrrolidin, pyrrolidin-2-one, oxazolidine, oxazolidin-2-one, oxazolidine-2-thione, thiazolidine, thiazolidin-2-one, thiazolidine-2-thione, imidazolidine, imidazolidin-2-one, imidazolidine-2-thione, piperidine, piperidin-2-one, piperidine-2-thione, 2H-3,4,5,6-tetrahydro-1,3-oxazin-2-one, 2H-3,4,5,6-tetrahydro-1,3-oxazine-2-thione, morpholine, 2H-3,4,5,6-tetrahydro-1,3-thiazin-2-one, 2H-3,4,5,6-tetrahydro-1,3-thiazine-2-thione, thiomorpholine, perhydropyrimidin-2-one, piperazine, homopiperidine, homopiperidin-2-one, and heptamethyleneimine and the like. Each of these groups is selected in a range of the specified number of carbon atoms.

Subsequently, the production method of the compound of the present invention will be described below. In Production Method A to Production Method K, $A^1$ in formulas is a hydrogen atom, $C_{1-6}$ alkyl, ($C_{1-6}$) alkyl arbitrarily substituted with $R^5$, $C_{3-8}$ cycloalkyl, ($C_{3-8}$) cycloalkyl arbitrarily substituted with $R^5$, $C_{2-6}$ alkenyl, $C_{3-8}$ cycloalkenyl, ($C_{3-8}$) cycloalkenyl arbitrarily substituted with $R^5$, ($C_{2-6}$) alkenyl arbitrarily substituted with $R^5$, $C_{2-6}$ alkynyl, ($C_{2-6}$) alkynyl arbitrarily substituted with $R^5$, —S(O)$_r$$R^1$, —C(O)OR$^1$, —C(S)OR$^1$, —C(O)SR$^1$, —C(S)SR$^1$, —C(O)R$^2$, —C(S)R$^2$, —C(O)N(R$^4$)R$^3$, —C(S)N(R$^4$)R$^3$, —S(O)$_2$N(R$^4$)R$^3$, —P(O)(OR$^1$)$_2$, or —P(S)(OR$^1$)$_2$ and $R^1$, $R^5$, $R^2$, $R^3$, $R^4$ and r2 have the same meanings as defined above.

Production Method A

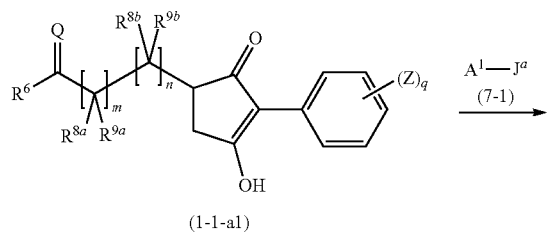

(1-1-a1)

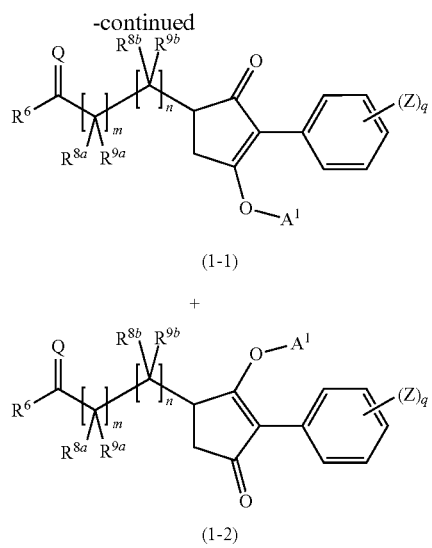

(1-1)

(1-2)

In the compounds of the present invention, the compound of Formula (1-1) of the present invention [wherein Q, $A^1$, $R^6$, $R^{8a}$, $R^{8b}$, $R^{9a}$, $R^{9b}$, Z, m, n, and q have the same meanings as defined above.] and the compound of Formula (1-2) of the present invention [Q, $A^1$, $R^6$, $R^{8a}$, $R^{8b}$, $R^{9a}$, $R^{9b}$, Z, m, n, and q have the same meanings as defined above.] can be produced by reacting the compound of Formula (1-1-a) with a compound of Formula (7-1) [wherein $J^a$ is a leaving group such as a halogen atom, —OSO$_2$Me, and —OSO$_2$CF$_3$ and $A^1$ has the same meaning as defined above.].

Some of the compounds of Formula (7-1) are known compounds and some of the compounds are commercially available. The compounds other than the known compounds or the commercially available compounds can be synthesized in accordance with methods described in documents.

In this reaction, the compound of Formula (7-1) can be used in a range of 0.5 equivalent to 50 equivalents relative to 1 equivalent of the compound of Formula (1-1-a). Bases such as triethylamine, pyridine, 4-(dimethylamino)pyridine, 1,8-diazabicyclo[5.4.0]-7-undecene, n-butyllithium, lithium diisopropylamide, lithium bis(trimethylsilyl)amide, sodium bis(trimethylsilyl)amide, potassium bis(trimethylsilyl)amide, sodium hydride, sodium methoxide, sodium hydroxide, potassium hydroxide, sodium carbonate, and potassium carbonate can be used, if necessary.

This reaction may be carried out in the absence of a solvent or may be carried out using a solvent. Examples of the solvent may include polar solvents such as N,N-dimethylformamide, N,N-dimethylacetamide, acetonitrile, dimethylsulfoxide, and 1,3-dimethyl-2-imidazolinone; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

Production Method B

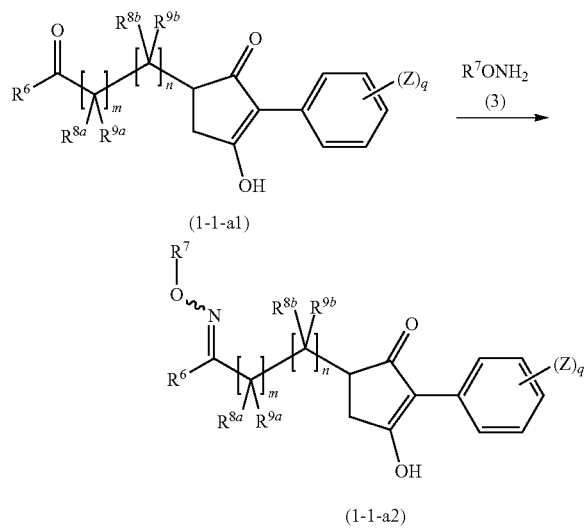

Production Method C

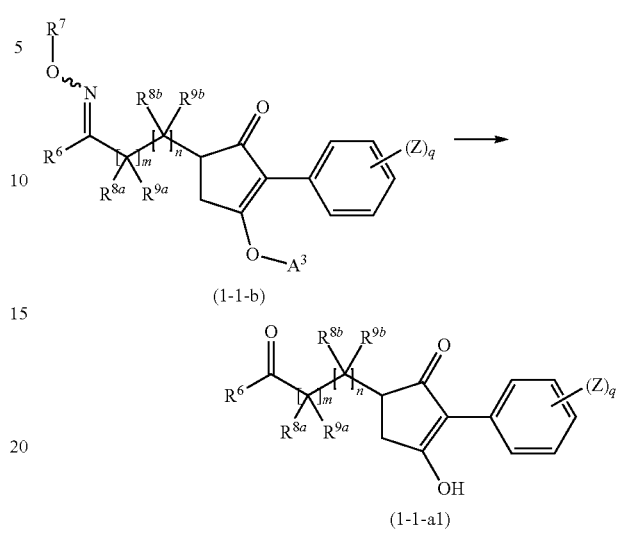

In the compounds of Formula (1-1-a), the compound of Formula (1-1-a2) of the present invention [wherein $R^6$, $R^7$, $R^{8a}$, $R^{8b}$, $R^{9a}$, $R^{9b}$, Z, m, n, and q have the same meanings as defined above.] can be produced by reacting the compound of Formula (1-1-a1) [wherein $R^6$, $R^{8a}$, $R^{8b}$, $R^{9a}$, $R^{9b}$, Z, m, n, and q have the same meanings as defined above.] with a compound of Formula (3) [wherein $R^7$ has the same meaning as defined above.].

Some of the compounds of Formula (3) are known compounds and some of the compounds are commercially available. The compounds other than the known compounds or the commercially available compounds can be synthesized in accordance with methods described in documents.

In this reaction, the compound of Formula (3) can be used in a range of 0.1 equivalent to 100 equivalent relative to 1 equivalent of the compound of Formula (1-1-a1). Bases such as potassium carbonate, triethylamine, pyridine, and 4-(dimethylamino)pyridine can be used, if necessary.

This reaction may be carried out in the absence of a solvent or may be carried out using a solvent. Examples of the solvent may include polar solvents such as N,N-dimethylformamide, N,N-dimethylacetamide, acetonitrile, dimethylsulfoxide, and 1,3-dimethyl-2-imidazolinone; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

In the compounds of Formula (1-1), the compound of Formula (1-1-a1) of the present invention can be obtained by hydrolyzing the compound of Formula (1-1-b) [wherein $R^6$, $R^7$, $R^{8a}$, $R^{8b}$, $R^{9a}$, $R^{9b}$, Z, m, n, and q have the same meanings as defined above, $A^3$ is $C_{1-6}$ alkyl or ($C_{1-6}$) alkyl arbitrarily substituted with $R^5$, and $R^5$ has the same meaning as defined above.].

In this reaction, solvents such as water, methanol, ethanol, dichloromethane, chloroform, diethyl ether, tetrahydrofuran, 1,4-dioxane, acetonitrile, and acetone may be used, if necessary. These solvents may be used singly or in combination of two or more of them.

The reaction can be carried out in the presence of 0.1 equivalent to 20 equivalents of an acid such as hydrochloric acid, sulfuric acid, or p-toluenesulfonic acid relative to 1 equivalent of the compound of Formula (1-1-b), if necessary.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

Production Method D

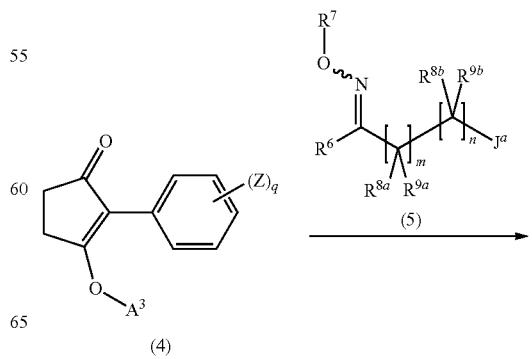

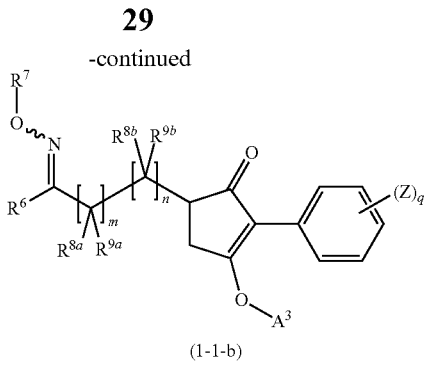

(1-1-b)

In the compounds of Formula (1-1), the compound of Formula (1-1-b) of the present invention [wherein $R^6$, $R^7$, $R^{8a}$, $R^{8b}$, $R^{9a}$, $R^{9b}$, Z, m, n and q have the same meanings as defined above, $A^3$ is $C_{1-6}$ alkyl or $(C_{1-6})$ alkyl arbitrarily substituted with $R^5$, and $R^5$ has the same meaning as defined above.] can be produced by reacting the compound of Formula (4) [wherein Z and q have the same meanings as defined above, $A^3$ is $C_{1-6}$ alkyl or $(C_{1-6})$ alkyl arbitrarily substituted with $R^5$, and $R^5$ has the same meaning as defined above.] with the compound of Formula (5) [wherein $J^a$, $R^6$, $R^7$, $R^{8a}$, $R^{8b}$, $R^{9a}$, $R^{9b}$, m, and n have the same meanings as defined above.].

Some of the compounds of Formula (4) are known compounds. The compounds other than the known compounds can be produced in accordance with the known methods described in, for example, Chemische Berichte, 1983, Vol. 116, P. 119.

Some of the compounds of Formula (5) are known compounds. The compounds other than the known compounds can be produced in accordance with the known methods described in, for example, Synthesis, 1982, P 305.

In this reaction, the compound of Formula (5) can be used in a range of 0.5 equivalent to 50 equivalents relative to 1 equivalent of the compound of Formula (4). Bases such as n-butyllithium, lithium diisopropylamide, lithium bis(trimethylsilyl)amide, sodium bis(trimethylsilyl)amide, potassium bis(trimethylsilyl)amide, sodium hydride, sodium methoxide, and potassium carbonate can be used, if necessary. This reaction may be carried out in the absence of a solvent or may be carried out using a solvent. Examples of the solvent may include polar solvents such as N,N-dimethylformamide, N,N-dimethylacetamide, dimethylsulfoxide, 1-methyl-2-pyrrolidone, and 1,3-dimethyl-2-imidazolinone; alcohols such as methanol, ethanol, propanol, 2-propanol, and ethylene glycol; ethers such as diethyl ether, tetrahydrofuran, and diphenyl ether; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

Production Method E

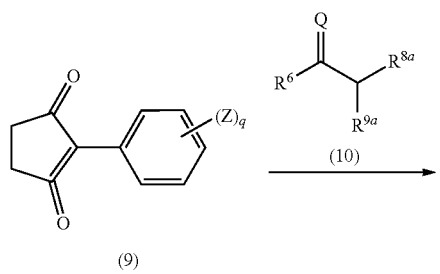

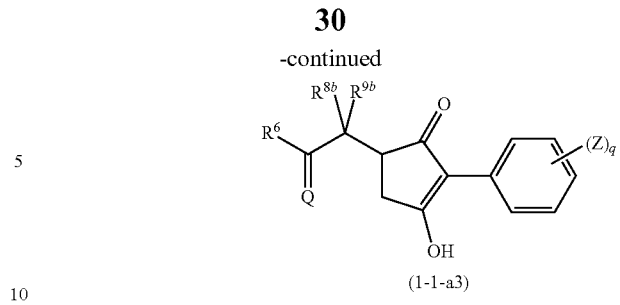

(1-1-a3)

The compound of Formula (1-1-a3) of the present invention [wherein $R^6$, $R^{8a}$, $R^{9a}$, Q, Z, and q have the same meanings as defined above.] can be produced by reacting the compound of Formula (9) [wherein Z and q have the same meanings as defined above.] with the compound of Formula (10) [wherein $R^6$, $R^{8a}$, $R^{9a}$, and Q have the same meanings as defined above.].

Some of the compounds of Formula (9) are known compounds. The compounds other than the known compounds can be produced in accordance with the known methods described in, for example, WO 2009/019005 Pamphlet.

Some of the compounds of Formula (10) are known compounds and some of the compounds are commercially available. The compounds other than the known compound or the commercially available compounds can be synthesized in accordance with methods described in documents.

In this reaction, the compound of Formula (10) can be used in a range of 0.5 equivalent to 50 equivalents relative to 1 equivalent of the compound of Formula (9). Bases such as triethylamine, pyridine, 4-(dimethylamino)pyridine, 1,8-diazabicyclo [5.4.0]-7-undecene, n-butyllithium, lithium diisopropylamide, lithium bis(trimethylsilyl)amide, sodium bis(trimethylsilyl)amide, potassium bis(trimethylsilyl) amide, sodium hydride, sodium methoxide, sodium hydroxide, potassium hydroxide, sodium carbonate, and potassium carbonate can be used, if necessary.

This reaction may be carried out in the absence of a solvent or may be carried out using a solvent. Examples of the solvent may include polar solvents such as N,N-dimethylformamide, N,N-dimethylacetamide, acetonitrile, dimethylsulfoxide, and 1,3-dimethyl-2-imidazolinone; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

Production Method F

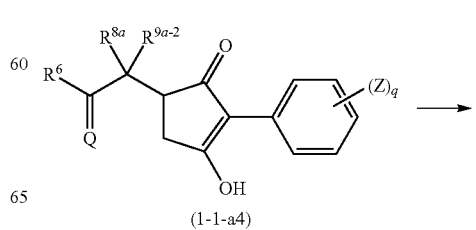

(1-1-a4)

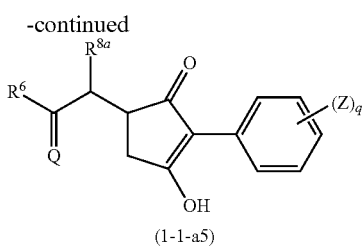

(1-1-a5)

In the compounds of Formula (1-1-a), the compound of Formula (1-1-a5) of the present invention [wherein $R^6$, $R^{8a}$, Q, Z, and q have the same meanings as defined above.] can be obtained by hydrolyzing and then decarboxylating the compound of Formula (1-1-a4) [wherein $R^6$, $R^{8a}$, Q, Z, and q have the same meanings as defined above, $R^{9a\text{-}2}$ is $-\text{C(O)}\text{OR}^{16a}$, and $R^{16a}$ has the same meaning as defined above.].

In this reaction, solvents such as water, methanol, ethanol, dichloromethane, chloroform, diethyl ether, tetrahydrofuran, 1,4-dioxane, acetonitrile, and acetone may be used, if necessary. These solvents may be used singly or in combination of two or more of them.

This reaction can be carried out in the presence of 0.1 equivalent to 20 equivalents of an acid such as hydrochloric acid, sulfuric acid, or p-toluenesulfonic acid or a base such as sodium hydroxide, potassium hydroxide, sodium carbonate, and potassium carbonate relative to 1 equivalent of the compound of Formula (1-1-a4), if necessary.

As the reaction temperature, any temperature from $-80°$ C. to the reflux temperature of the reaction mixture can be set. The reaction time varies depending on the concentration of the reactant and the reaction temperature, and usually the time may be set in a range of 5 minutes to 100 hours.

Production Method G

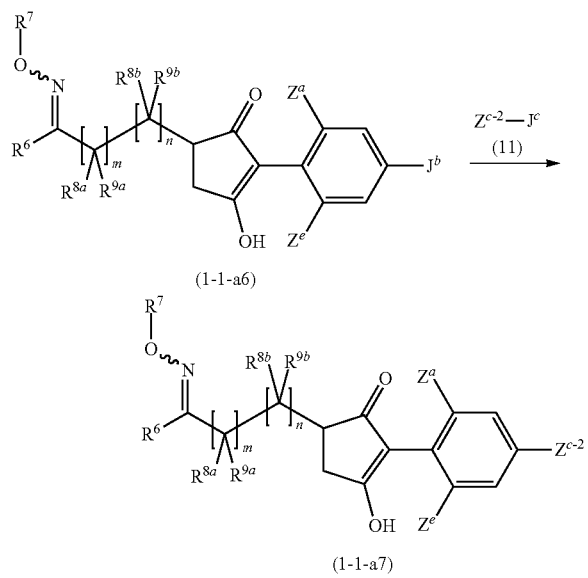

In the compounds of Formula (1-1-a), the compound of Formula (1-1-a7) of the present invention [wherein $R^6$, $R^7$, $R^{8a}$, $R^{8b}$, $R^{9a}$, $R^{9b}$, $Z^a$, $Z^e$, m, and n have the same meanings as defined above and $Z^{c\text{-}2}$ has the same meaning as defined below.] can be produced by reacting the compound of Formula (1-1-a6) [wherein $R^6$, $R^7$, $R^{8a}$, $R^{8b}$, $R^{9a}$, $R^{9b}$, $Z^a$, $Z^e$, m, and n have the same meanings as defined above, and $J^b$ is a leaving group such as a halogen atom, $-\text{OSO}_2\text{Me}$, $-\text{OSO}_2\text{CF}_3$.] with the compound of Formula (11) [wherein $Z^{c\text{-}2}$ is $C_{2\text{-}6}$ alkynyl, $(C_{2\text{-}6})$ alkynyl arbitrarily substituted with $R^{45}$, phenyl, and phenyl substituted with $(Z^3)_{q3}$, $J^c$ is $-\text{C(O)OH}$, $-\text{Sn}(C_{1\text{-}6}\text{ alkyl})_3$, $-\text{B(OH)}_2$, and the like, and $R^{45}$, $Z^3$ and q3 have the same meanings as described above.] in the presence of a catalyst and a base.

The amount of the compound of Formula (11) can be used in a range of 0.5 equivalent to 50 equivalents relative to 1 equivalent of the compound of Formula (1-1-a6).

Some of the compounds of Formula (11) used here are known compounds and some of the compounds are commercially available. The compounds other than the known compound or the commercially available compounds can be synthesized in accordance with methods described in documents.

Examples of the catalyst used in this reaction may include palladium catalysts such as palladium-carbon, palladium chloride, palladium acetate, bis(triphenylphosphine) palladium dichloride, tetrakis(triphenylphosphine) palladium, and [1,1'-bis(diphenylphosphino)ferrocene] palladium (II) dichloride dichloromethane adduct, and copper catalysts such as metal copper, copper acetate (monovalent), copper acetate (divalent), copper oxide (monovalent), copper oxide (divalent), copper iodide, copper bromide, and copper chloride. These catalysts can be used singly or in combination of two or more of them. The amount of the catalyst to be used can be used in a range of 0.001 equivalent to 1.0 equivalent relative to 1 equivalent of the compound of Formula (1-1-a6). Ligands such as 1,4-bis (diphenylphosphino)butane can be used in the range of 0.001 equivalent to 10 equivalents relative to the catalyst.

Examples of the base to be used may include tertiary amine compounds such as pyridine, diisopropylethylamine, and triethylamine and inorganic bases such as sodium hydroxide, potassium hydroxide, sodium carbonate, potassium carbonate, cesium carbonate, sodium hydrogen carbonate, and tripotassium phosphate. The amount of the base to be used can be used in a range of 0.1 equivalent to 10.0 equivalents relative to 1 equivalent of the compound of Formula (11).

This reaction may be carried out in the absence of a solvent or may be carried out using a solvent. Example of usable solvents may include polar solvents such as N,N-dimethylformamide, N,N-dimethylacetamide, acetonitrile, dimethylsulfoxide, 1,3-dimethyl-2-imidazolinone, and water; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from $-80°$ C. to the reflux temperature of the reaction mixture can be set. The reaction time varies depending on the concentration of the reactant and the reaction temperature, and usually the time may be set in a range of 5 minutes to 100 hours.

Production Method H

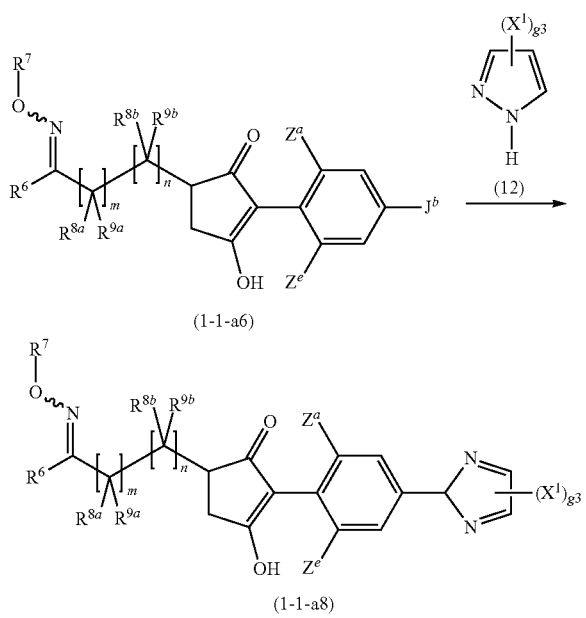

In the compounds of Formula (1-1-a), the compound of Formula (1-1-a8) of the present invention [wherein $R^6$, $R^7$, $R^{8a}$, $R^{8b}$, $R^{9a}$, $R^{9b}$, $Z^a$, $Z^e$, $X^1$, g3, m, and n have the same meanings as defined above.] can be produced by reacting the compound of Formula (1-1-a6) [wherein $R^6$, $R^7$, $R^{8a}$, $R^{8b}$, $R^{9a}$, $R^{9b}$, $Z^a$, $Z^e$, m, and n have the same meanings as defined above, and $J^b$ is a leaving group such as a halogen atom, $-OSO_2Me$, $-OSO_2CF_3$.] with the compound of Formula (12) [wherein $X^1$ and g3 have the same meanings as defined above.] in the presence of a catalyst and a base.

The amount of the compound of Formula (12) can be used in a range of 0.5 equivalent to 50 equivalents relative to 1 equivalent of the compound of Formula (1-1-a6).

Some of the compounds of Formula (12) used here are known compounds and some of the compounds are commercially available. The compounds other than the known compound or the commercially available compounds can be synthesized in accordance with methods described in documents.

Examples of the catalyst used in this reaction may include palladium catalysts such as palladium-carbon, palladium chloride, palladium acetate, bis(triphenylphosphine) palladium dichloride, tetrakis(triphenylphosphine) palladium, and [1,1'-bis(diphenylphosphino)ferrocene] palladium (II) dichloride dichloromethane adduct, and copper catalysts such as metal copper, copper acetate (monovalent), copper acetate (divalent), copper oxide (monovalent), copper oxide (divalent), copper iodide, copper bromide, and copper chloride. These catalysts can be used singly or in combination of two or more of them. The amount of the catalyst to be used can be used in a range of 0.001 equivalent to 1.0 equivalent relative to 1 equivalent of the compound of Formula (1-1-a6). Ligands such as N,N'-dimethylethylenediamine and N,N'-dimethylcyclohexane-1,2-diamine can be used in the range of 0.001 equivalent to 10 equivalents relative to the catalyst.

Examples of the base to be used may include tertiary amine compounds such as pyridine, diisopropylethylamine, and triethylamine and inorganic bases such as sodium hydroxide, potassium hydroxide, sodium carbonate, potassium carbonate, cesium carbonate, sodium hydrogen carbonate, and tripotassium phosphate. The amount of the base to be used can be used in a range of 0.1 equivalent to 10.0 equivalents relative to 1 equivalent of the compound of Formula (12).

This reaction may be carried out in the absence of a solvent or may be carried out using a solvent. Example of usable solvents may include polar solvents such as N,N-dimethylformamide, N,N-dimethylacetamide, acetonitrile, dimethylsulfoxide, 1,3-dimethyl-2-imidazolinone, and water; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

The reaction of Production Method A to Production Method H may be carried out under the atmosphere of inert gas such as nitrogen and argon, if necessary.

In Production Method A to Production Method H, usual post-treatment of the reaction mixture after completion of the reaction such as direct concentration, concentration after dissolving in an organic solvent and washing with water, or concentration after pouring in ice-water and extracting with an organic solvent can give the target compound of the present invention. When purification is required, the compound can be separated and purified by any purification method such as recrystallization and preparative isolation by column chromatography, thin layer chromatography, and liquid chromatography.

Production Method I

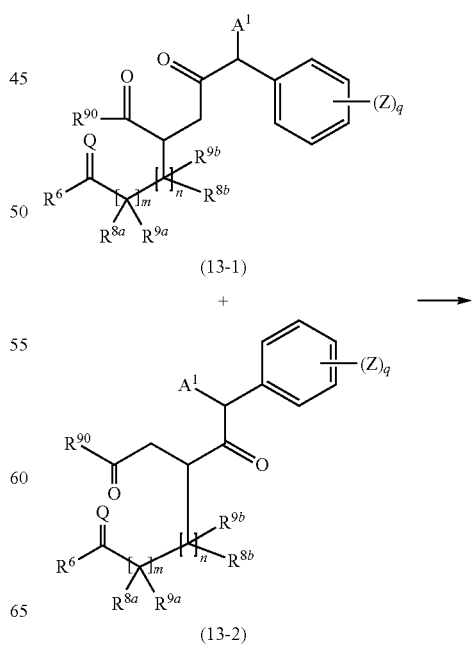

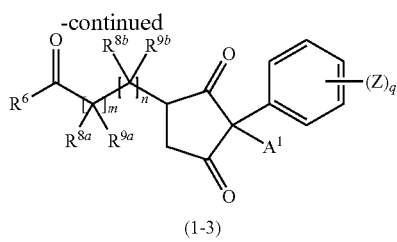

(1-3)

The compounds of Formula (1-3) of the present invention [wherein $A^1$, Q, $R^6$, $R^{8a}$, $R^{8b}$, $R^{9a}$, $R^{9b}$, Z m, n, and q have the same meanings as defined above.] can be produced by reacting the mixture of the compound of Formula (13-1) [wherein $R^{90}$ is a leaving group such as $C_{1-6}$ alkoxy, pyrazol-1-yl, and imidazol-1-yl, and $A^1$, Q, $R^6$, $R^{8a}$, $R^{8b}$, $R^{9a}$, $R^{9b}$, $R^{90}$, Z, m, n, and q have the same meanings as defined above.] and the compound of Formula (13-2) [wherein $R^{90}$ is a leaving group such as $C_{1-6}$ alkoxy, pyrazol-1-yl, and imidazol-1-yl, and $A^1$, Q, $R^6$, $R^{8a}$, $R^{8b}$, $R^{9a}$, $R^{9b}$, $R^{90}$, Z, m, n, and q have the same meanings as defined above.] with a base.

Examples of the base to be used may include n-butyllithium, lithium diisopropylamide, lithium bis(trimethylsilyl)amide, sodium bis(trimethylsilyl)amide, potassium bis(trimethylsilyl)amide, sodium hydride, sodium methoxide, potassium carbonate, triethylamine, pyridine, 4-(dimethylamino)pyridine, and 1,8-diazabicyclo[5.4.0]-7-undecene. The amount of the base to be used can be used in a range of 0.1 equivalent to 10.0 equivalents relative to 1 equivalent of the mixture of the compound of Formula (13-1) and the compound of Formula (13-2).

This reaction may be carried out in the absence of a solvent or may be carried out using a solvent. Example of usable solvents may include polar solvents such as N,N-dimethylformamide, N,N-dimethylacetamide, acetonitrile, dimethylsulfoxide, 1,3-dimethyl-2-imidazolinone, and water; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

A mixture of the compound of Formula (13-1) and the compound of Formula (13-2) used in Production Method I can be produced in accordance with a production route described in Reaction Formula 1, for example.

Reaction Formula 1

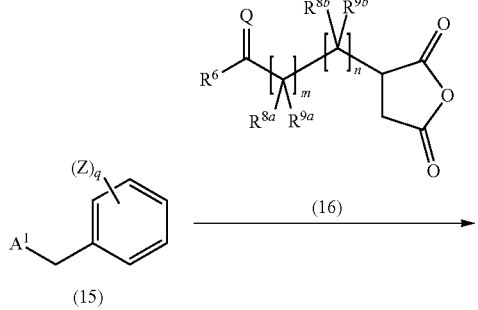

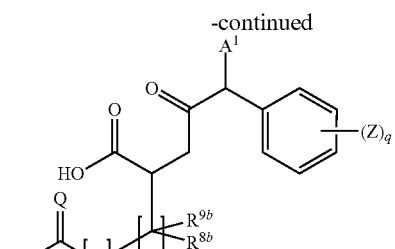

(17-1)

+

$R^{90}$—H (18)

Process 1

The mixture of the compound of Formula (17-1) [wherein $A^1$, Q, $R^6$, $R^{8a}$, $R^{8b}$, $R^{9a}$, $R^{9b}$ Z, m, n, and q have the same meanings as defined above.] and the compound of Formula (17-2) [wherein $A^1$, Q, $R^6$, $R^{8a}$, $R^{8b}$, $R^{9a}$, $R^{9b}$, Z, m, n, and q have the same meanings as defined above.] can be produced by reacting the compound of Formula (15) [wherein $A^1$, Z, and q have the same meanings as defined above.] with the compound of Formula (16) [wherein Q, $R^6$, $R^{8a}$, $R^{8b}$, $R^{9a}$, $R^{9b}$, m, and n have the same meanings as defined above.] in accordance with known methods described in documents, for example, the method described in U.S. Patent No. 1981/4283348.

Some of the compounds of Formula (15) used here are known compounds and some of the compounds are commercially available. The compounds other than the known compounds or the commercially available compounds can be synthesized in accordance with methods described in documents.

Some of the compounds of Formula (16) are known compounds and can be produced in accordance with the known methods described in, for example, J. Chem. Soc., 1965, p. 4355.

Process 2

The mixture of the compound of Formula (13-1) and the compound of Formula (13-2) can be produced by reacting the mixture of the compound of Formula (17-1) and the compound of Formula (17-2) with a halogenating agent such as thionyl chloride or oxalyl chloride in accordance with known methods described in documents, for example, the method described in Jikken Kagaku Kouza 4th edition (The 4th edition of experimental chemistry) (edited by The Chemical Society of Japan) 1992, Vol. 22, P 122, and thereafter reacting the resultant mixture with the compound of Formula (18) [wherein $R^{90}$ is $C_{1-6}$ alkoxy, pyrazol-1-yl, or imidazol-1-yl.] in accordance with known methods described in documents, for example, the method described in Jikken Kagaku Kouza 4th edition (The 4th edition of Experimental Chemistry) (edited by The Chemical Society of Japan) 1992, Vol. 22, P. 50.

Some of the compounds of Formula (18) used here are known compounds and some of the compounds are commercially available. The compounds other than the known compounds or the commercially available compounds can be synthesized in accordance with methods described in documents.

Production Method J

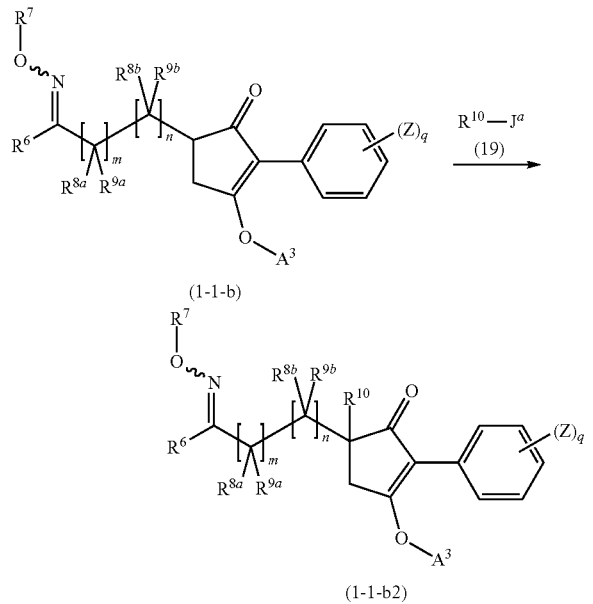

(1-1-b)

(1-1-b2)

In the compounds of formula (1-1), the compound of Formula (1-1-b2) of the present invention [wherein $A^3$, $R^6$, $R^7$, $R^{8a}$, $R^{8b}$, $R^{9a}$, $R^{9b}$, $R^{10}$, Z, m, n, and q have the same meanings as defined above.] can be produced by reacting the compound of Formula (1-1-b) [wherein $A^3$, $R^6$, $R^7$, $R^{8a}$, $R^{8b}$, $R^{9a}$, $R^{9b}$, Z, m, n, and q have the same meanings as defined above.] with the compound of Formula (19) [wherein $R^{10}$ and $J^a$ have the same meanings as defined above.].

Some of the compounds of Formula (19) are known compounds and some of the compounds are commercially available. The compounds other than the known compound or the commercially available compounds can be synthesized in accordance with methods described in documents.

In this reaction, the compound of Formula (19) can be used in a range of 0.5 equivalent to 50 equivalents relative to 1 equivalent of the compound of Formula (1-1-b). Bases such as n-butyllithium, lithium diisopropylamide, lithium bis(trimethylsilyl)amide, sodium bis(trimethylsilyl)amide, potassium bis(trimethylsilyl)amide, sodium hydride, sodium methoxide, and potassium carbonate can be used in a range of 0.5 equivalent to 50.0 equivalents relative to 1 equivalent of the compound of Formula (1-1-b), if necessary.

This reaction may be carried out in the absence of a solvent or may be carried out using a solvent. Examples of the solvent may include polar solvents such as N,N-dimethylformamide, N,N-dimethylacetamide, dimethylsulfoxide, 1-methyl-2-pyrrolidone, and 1,3-dimethyl-2-imidazolinone; alcohols such as methanol, ethanol, propanol, 2-propanol, and ethylene glycol; ethers such as diethyl ether, tetrahydrofuran, and diphenyl ether; and aliphatic hydrocarbons such as pentane and n-hexane. These solvents may be used singly or in combination of two or more of them.

As the reaction temperature, any temperature from −80° C. to the reflux temperature of the reaction mixture can be set. The reaction time varies depending on the concentration of the reactant and the reaction temperature, and usually the time may be set in a range of 5 minutes to 100 hours.

Production Method K

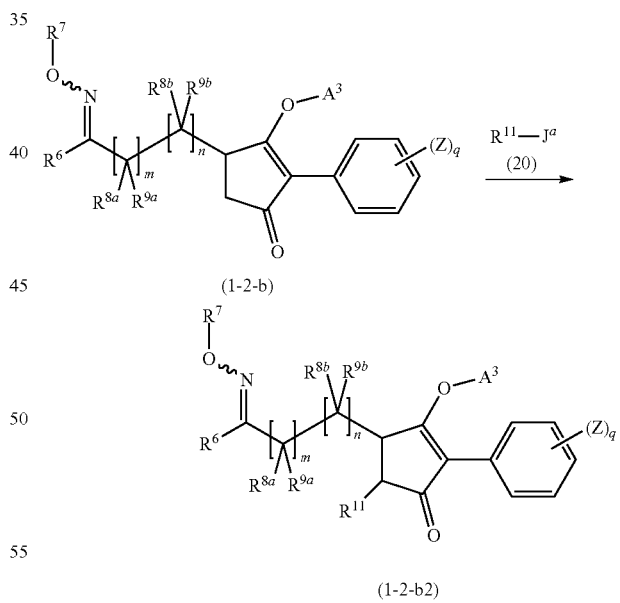

(1-2-b)

(1-2-b2)

In the compounds of Formula (1-2), the compound of Formula (1-2-b2) of the present invention [wherein $A^3$, $R^6$, $R^7$, $R^{8a}$, $R^{8b}$, $R^{9a}$, $R^{9b}$, $R^{11}$, Z, m, n, and q have the same meanings as defined above.] can be produced by reacting the compound of Formula (1-2-b) [wherein $A^3$, $R^6$, $R^7$, $R^{8a}$, $R^{8b}$, $R^{9a}$, $R^{9b}$, Z, m, n, and q have the same meanings as defined above.] with the compound of Formula (20) [wherein $R^{11}$ and $J^a$ have the same meanings as defined above.] in a similar method to Production Method J.

The compound of Formula (1-1-b) used in Production Method J and the compound of Formula (1-2-b) used in Production Method K can be produced as a mixture by Production Method A described above. The compound of Formula (1-1-b2) and the compound of Formula (1-2-b2) can be produced as a mixture by reacting the mixture of the compound of Formula (1-1-b) and the compound of Formula (1-2-b) produced by the method described in Production Method A without separation, the reaction method being the same as that in Production Method J or Production Method K. The compound of Formula (1-1-b2) and the compound of Formula (1-2-b2) can be obtained by separating and purifying the mixture by any purification methods such as recrystallization and column chromatography.

The reaction of Production Method A to Production Method K may be carried out under the atmosphere of inert gas such as nitrogen and argon, if necessary.

In the reactions of Production Method A to Production Method K, usual post-treatment of the reaction mixture after completion of the reaction such as direct concentration, concentration after dissolving in an organic solvent and washing with water, or concentration after pouring in ice-water and extracting with an organic solvent can give the compound of the present invention. When purification is required, the compound can be separated and purified by any purification method such as recrystallization and preparative isolation by column chromatography, thin layer chromatography, and liquid chromatography.

Specific examples of the active compound included in the present invention may include the compounds listed in Table 1 to Table 4. The compounds listed in Table 1 to Table 4, however, are the compounds for exemplification, and thus the present invention is not limited to these compounds. In Tables, the expression of the substituent listed in Me is methyl group. Similarly, the expression of Et is ethyl group, n-Pr and Pr-n being normal-propyl group, i-Pr and Pr-i being iso-propyl group, c-Pr and Pr-c being cyclopropyl group, n-Bu and Bu-n being normal-butyl group, s-Bu and Bu-s being secondary-butyl group, i-Bu and Bu-i being iso-butyl group, t-Bu and Bu-t being tertiary-butyl group, c-Bu and Bu-c being cyclobutyl group, n-Pen and Pen-n being normal-pentyl group, c-Pen and Pen-c being cyclopentyl group, n-Hex and Hex-n being normal-hexyl group, c-Hex and Hex-c being cyclohexyl group, n-Oct and Oct-n being octyl group, and Ph being phenyl group.

In Tables, structures of D1-2a, D1-2c, D1-7a, D1-7b-1, D1-7b-2, D1-7b-3, D1-7b-4, D1-10a, D1-11a, D1-11b-1, D1-11b-2, D1-11b-3, D1-11b-4, D1-22a, D1-22b-1, D1-22b-2, D1-22b-3, D1-22b-4, D1-32a, D1-32b-1, D1-32b-2, D1-32b-3, D1-32b-4, D1-32b-5, D1-33a, D1-33b-1, D1-33b-2, D1-33b-3, D1-33b-4, D1-34a, D1-37a, D1-37b-1, D1-108a, D1-108b-1, D1-108b-2, D1-108b-3, D1-108b-4, D1-108b-5, D1-108b-6, D1-108b-7, D1-108b-8, D1-108b-9, D1-108b-10, D1-108b-11, D1-108b-12, D1-108b-13, D1-108b-14, D1-108b-15, D1-108b-16, D1-108b-17, D1-108b-18, D1-108b-19, D1-103-1, D1-103-2, D1-103-3, D1-103-4, and A1 to A116 are the following structures.

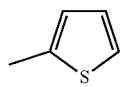

D1-2a

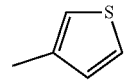

D1-2c

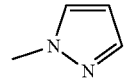

D1-7a

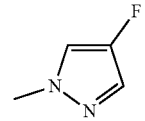

D1-7b-1

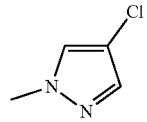

D1-7b-2

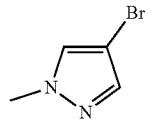

D1-7b-3

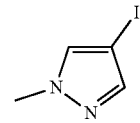

D1-7b-4

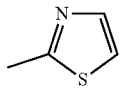

D1-10a

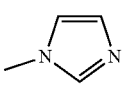

D1-11a

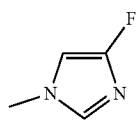

D1-11b-1

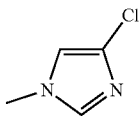

D1-11b-2

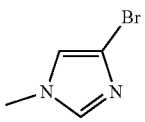

D1-11b-3

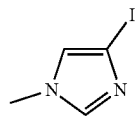

D1-11b-4

D1-22a

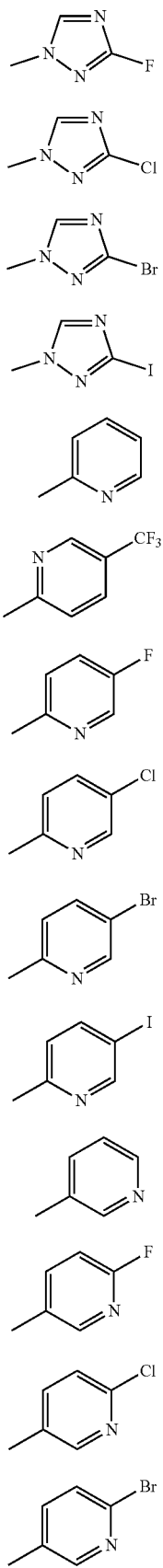
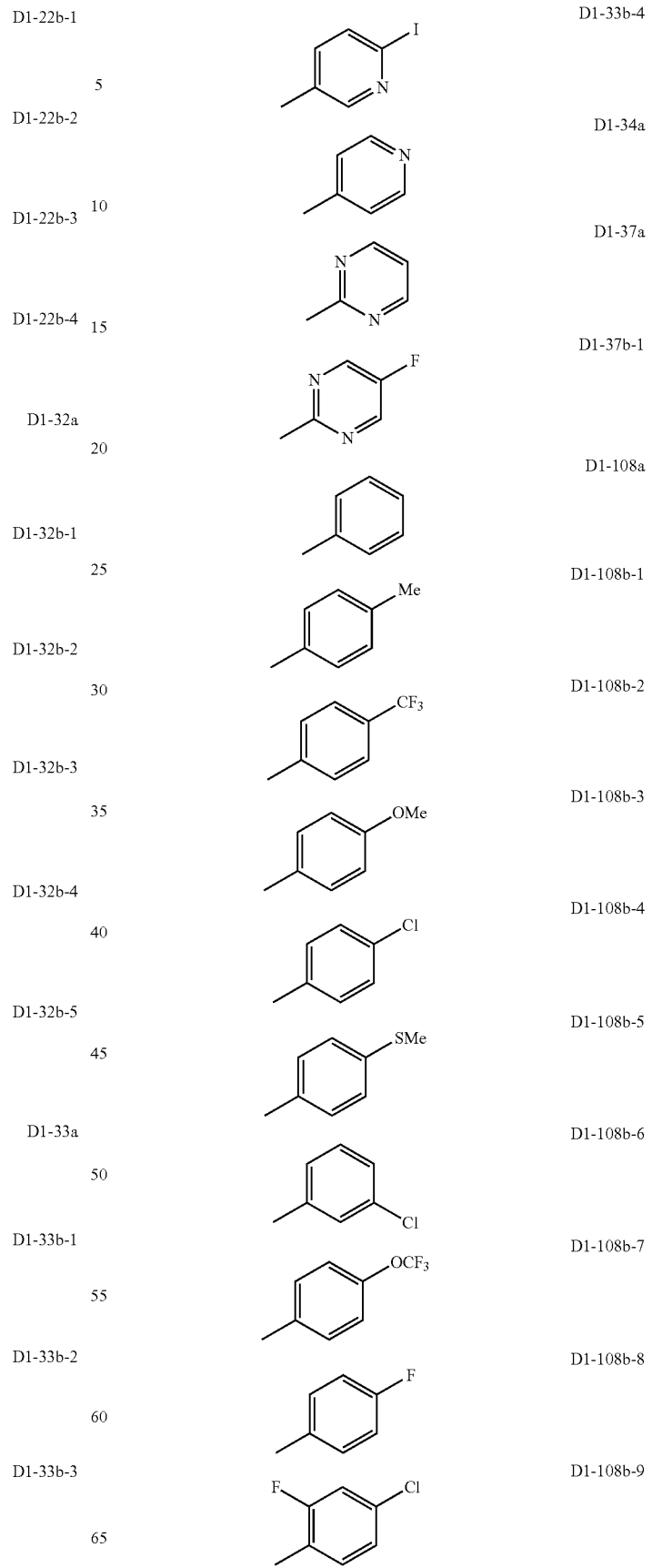
D1-22b-1
D1-22b-2
D1-22b-3
D1-22b-4
D1-32a
D1-32b-1
D1-32b-2
D1-32b-3
D1-32b-4
D1-32b-5
D1-33a
D1-33b-1
D1-33b-2
D1-33b-3
D1-33b-4
D1-34a
D1-37a
D1-37b-1
D1-108a
D1-108b-1
D1-108b-2
D1-108b-3
D1-108b-4
D1-108b-5
D1-108b-6
D1-108b-7
D1-108b-8
D1-108b-9

-continued
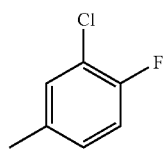 D1-108b-10
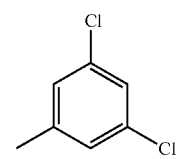 D1-108b-11
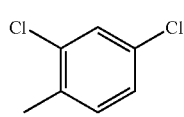 D1-108b-12
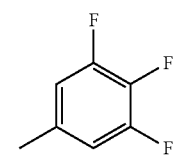 D1-108b-13
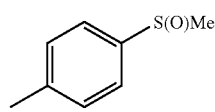 D1-108b-14
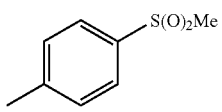 D1-108b-15
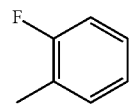 D1-108b-16
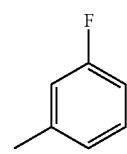 D1-108b-17
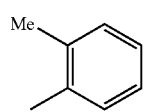 D1-108b-18
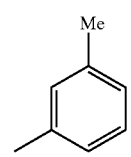 D1-108b-19
 D1-103-1
 D1-103-2
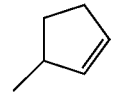 D1-103-3
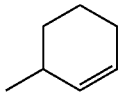 D1-103-4
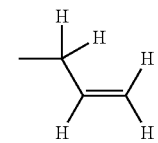 A1
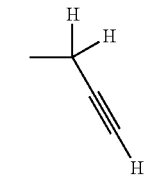 A2
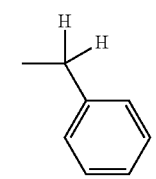 A3
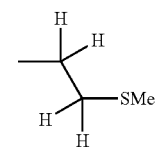 A4
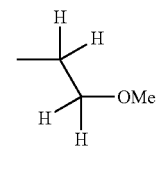 A5
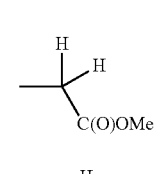 A6
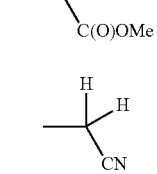 A7
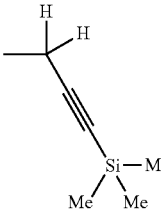 A8
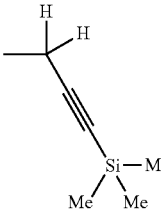 A9

-continued

| | |
|---|---|
| (structure) | A10 |
| (structure) | A11 |
| (structure) | A12 |
| (structure) | A13 |
| (structure) | A14 |
| (structure) | A15 |
| (structure) | A16 |
| (structure) | A17 |
| (structure) | A18 |
| (structure) | A19 |
| (structure) | A20 |

-continued

| | |
|---|---|
| (structure) | A21 |
| (structure) | A22 |
| (structure) | A23 |
| (structure) | A24 |
| (structure) | A25 |
| (structure) | A26 |
| (structure) | A27 |
| (structure) | A28 |
| (structure) | A29 |

-continued
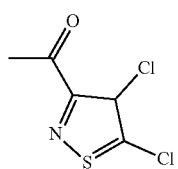 A30
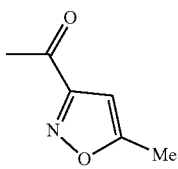 A31
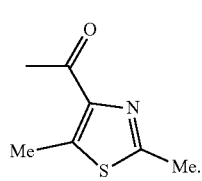 A32
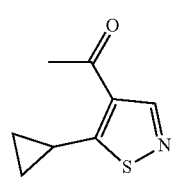 A33
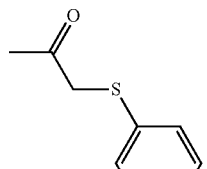 A34
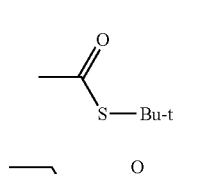 A35
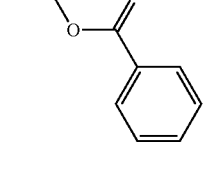 A36
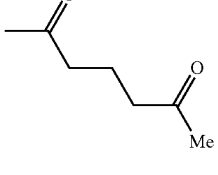 A37
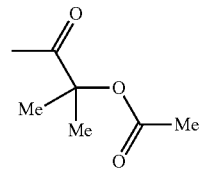 A38
-continued
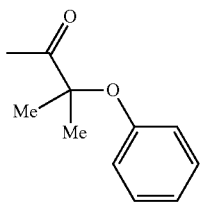 A39
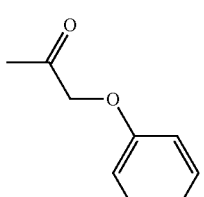 A40
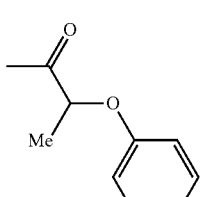 A41
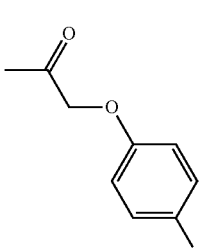 A42
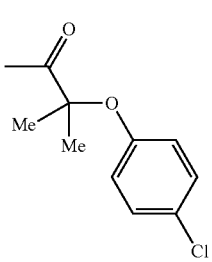 A43
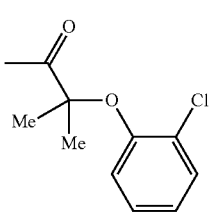 A44
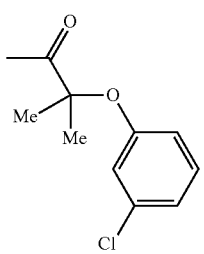 A45

-continued
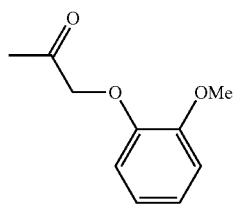
A46
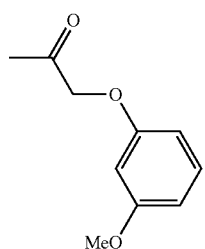
A47
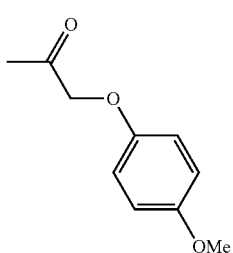
A48
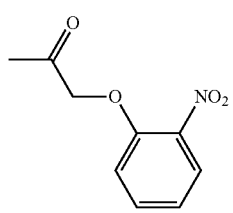
A49
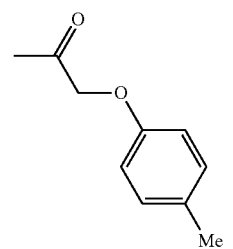
A50
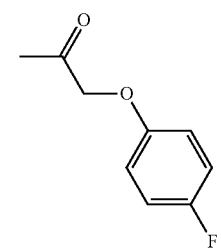
A51
-continued
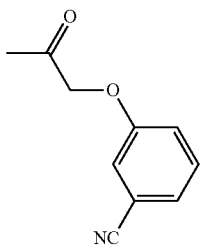
A52
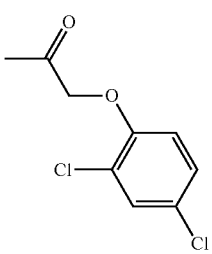
A53
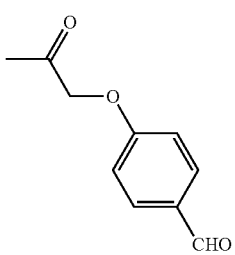
A54
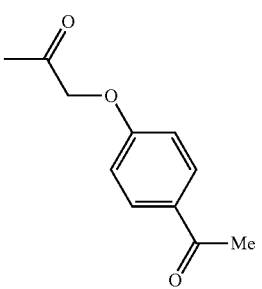
A55
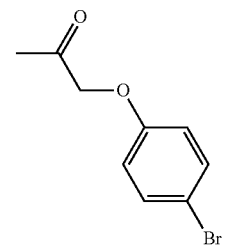
A56
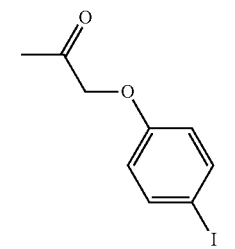
A57

-continued

| Structure | Label |
|---|---|
| CH₃C(O)CH₂-O-(1-naphthyl) | A58 |
| CH₃C(O)CH₂-O-(2-naphthyl) | A59 |
| CH₃C(O)CH₂-OMe | A60 |
| CH₃C(O)CH₂-O-CH₂-Ph | A61 |
| CH₃C(O)CH₂-O-CH₂CF₃ | A62 |
| CH₃C(O)-OMe | A63 |
| CH₃C(O)-O-CH₂-CH=CH₂ | A64 |
| CH₃C(O)-O-CH₂-Ph | A65 |
| CH₃C(O)CH₂-O-CH₂-OMe | A66 |

-continued

| Structure | Label |
|---|---|
| MeS(O)₂-Me | A67 |
| MeS(O)₂-O-n-Oct | A68 |
| MeS(O)₂-cyclopropyl | A69 |
| MeS(O)₂-(4-Me-phenyl) | A70 |
| MeS(O)₂-CH₂CH₂-Si(Me)₃ | A71 |
| MeS(O)₂-CH₂CH₂-Cl | A72 |
| MeS(O)₂-N(Me)₂ | A73 |
| CH₃C(O)-N(morpholine) | A74 |
| CH₃C(O)-N(Me)₂ | A75 |

| | | |
|---|---|---|
| 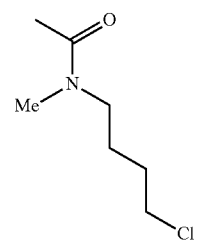 | A76 | 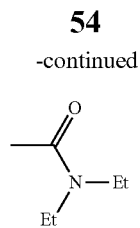 A84 |
| 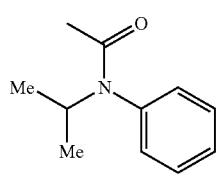 | A77 | 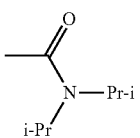 A85 |
| 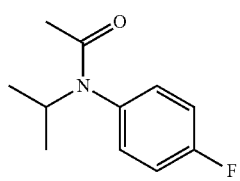 | A78 | 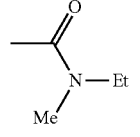 A86 |
| 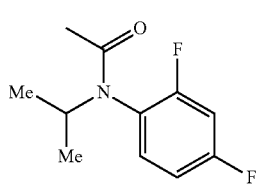 | A79 | A87 |
| 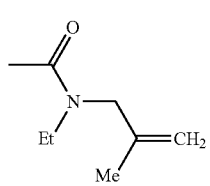 | A80 | 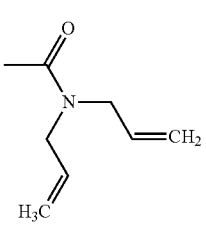 A88 |
| 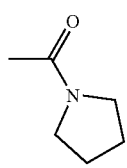 | A81 | 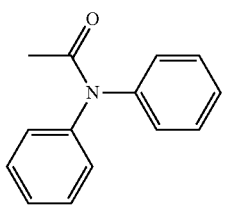 A89 |
| 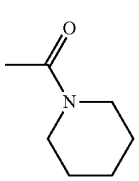 | A82 | 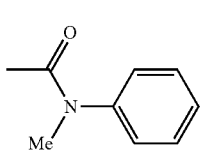 A90 |
| 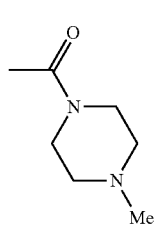 | A83 | 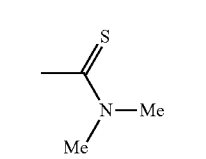 A91 |
| | | 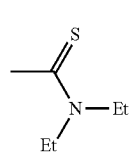 A92 |
| | | 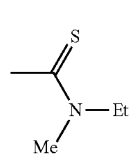 A93 |

-continued
A94 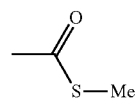
A95 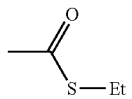
A96 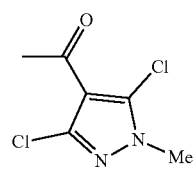
A97 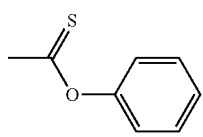
A98 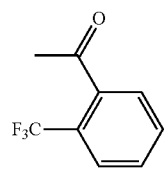
A99 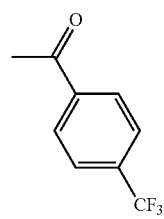
A100 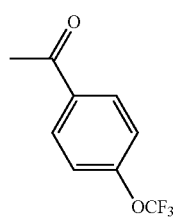
A101 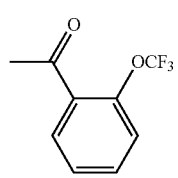
A102 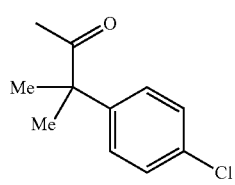
-continued
A103 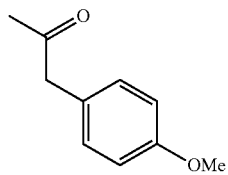
A104 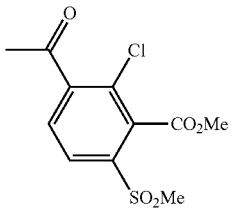
A105 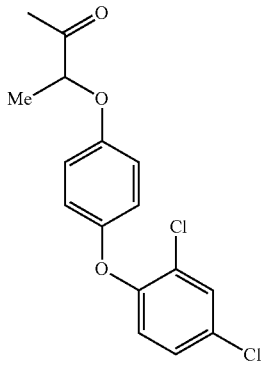
A106 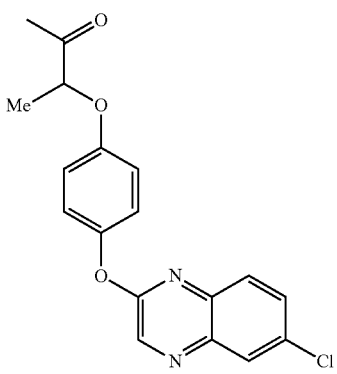
A107 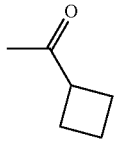
A108 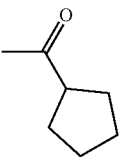
A109 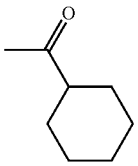

-continued
A110 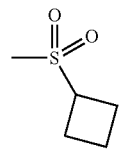
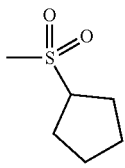
A111
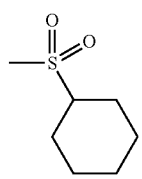
A112
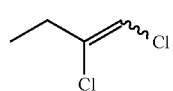
A113
-continued
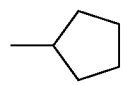
A114
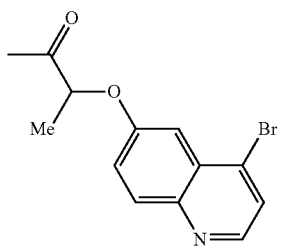
A115
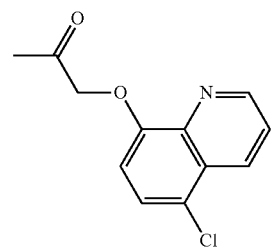
A116
TABLE 1
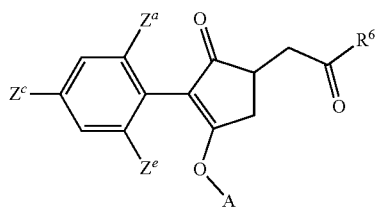
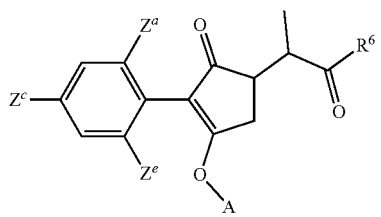
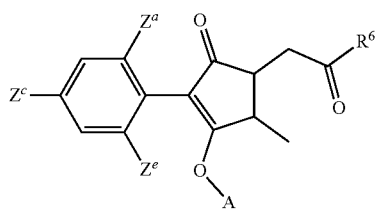
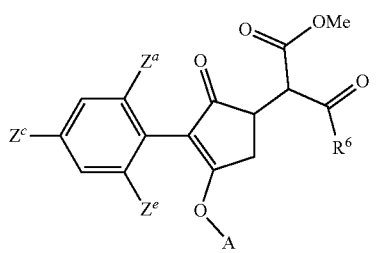

TABLE 1-continued
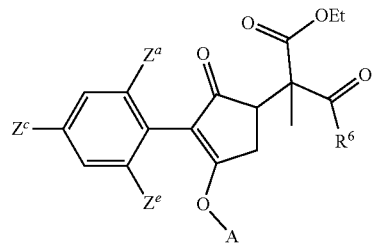
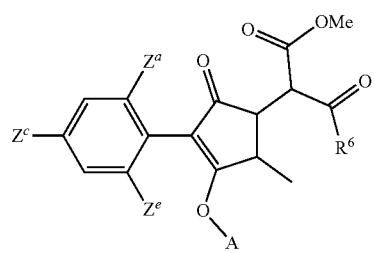
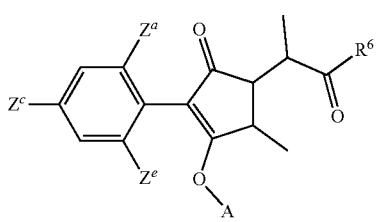
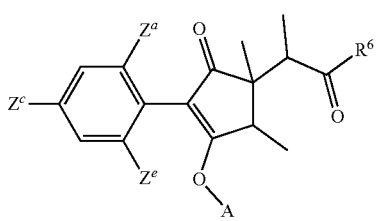
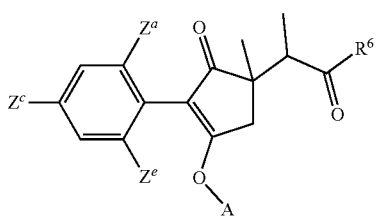
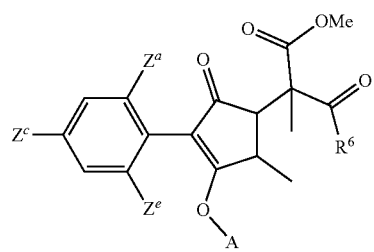

TABLE 1-continued
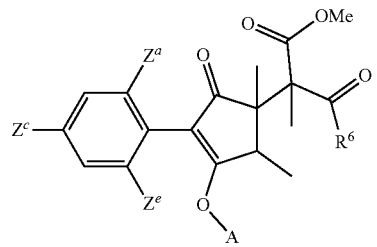
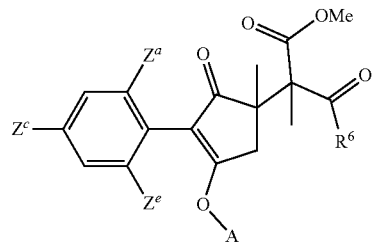
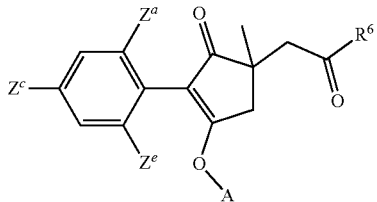
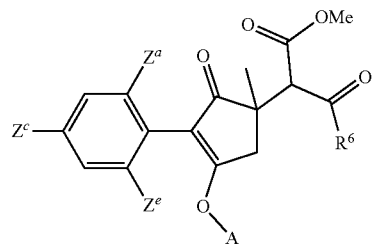
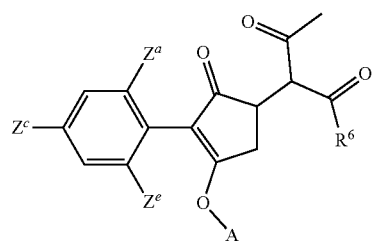
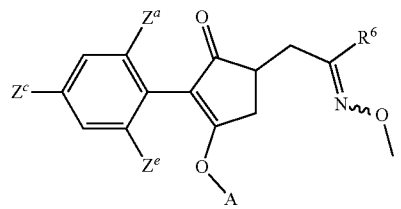
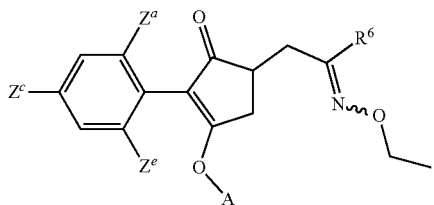

TABLE 1-continued
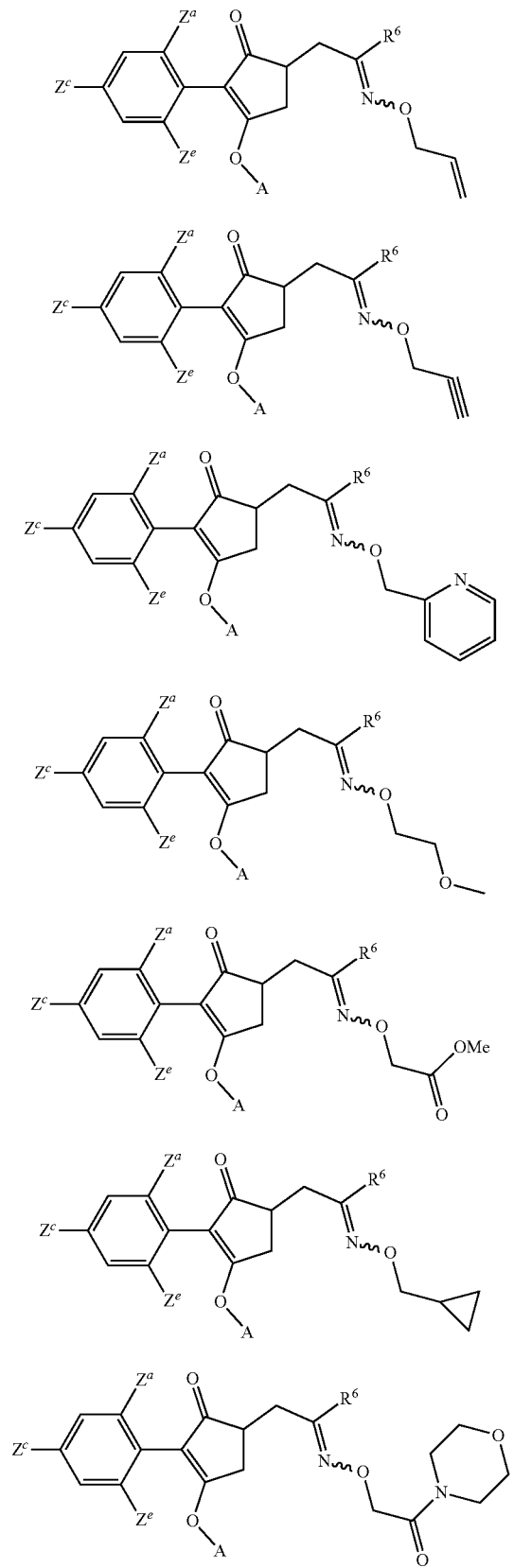

TABLE 1-continued
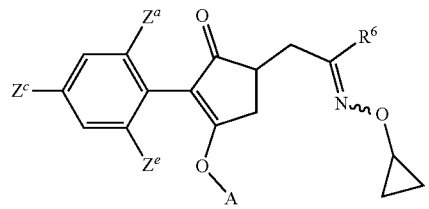
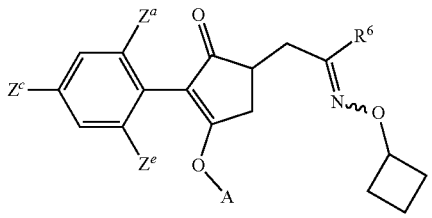
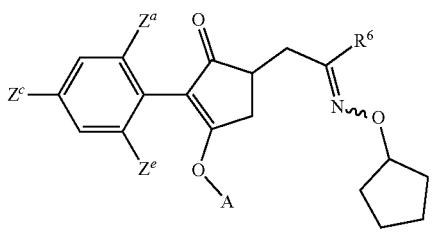
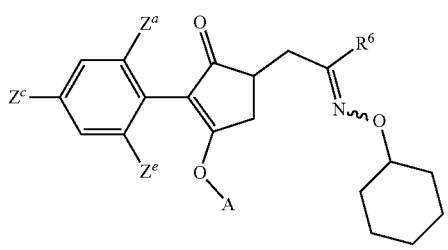
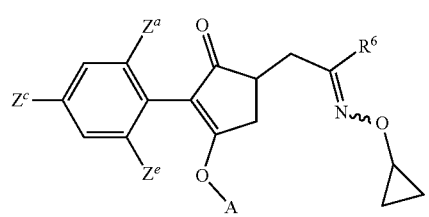
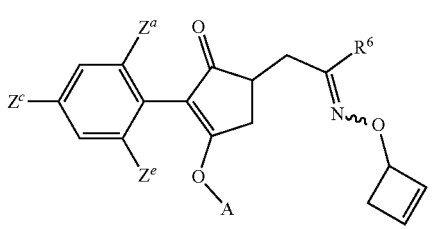
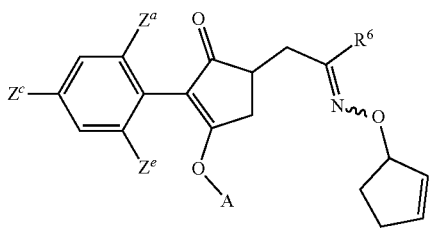

TABLE 1-continued
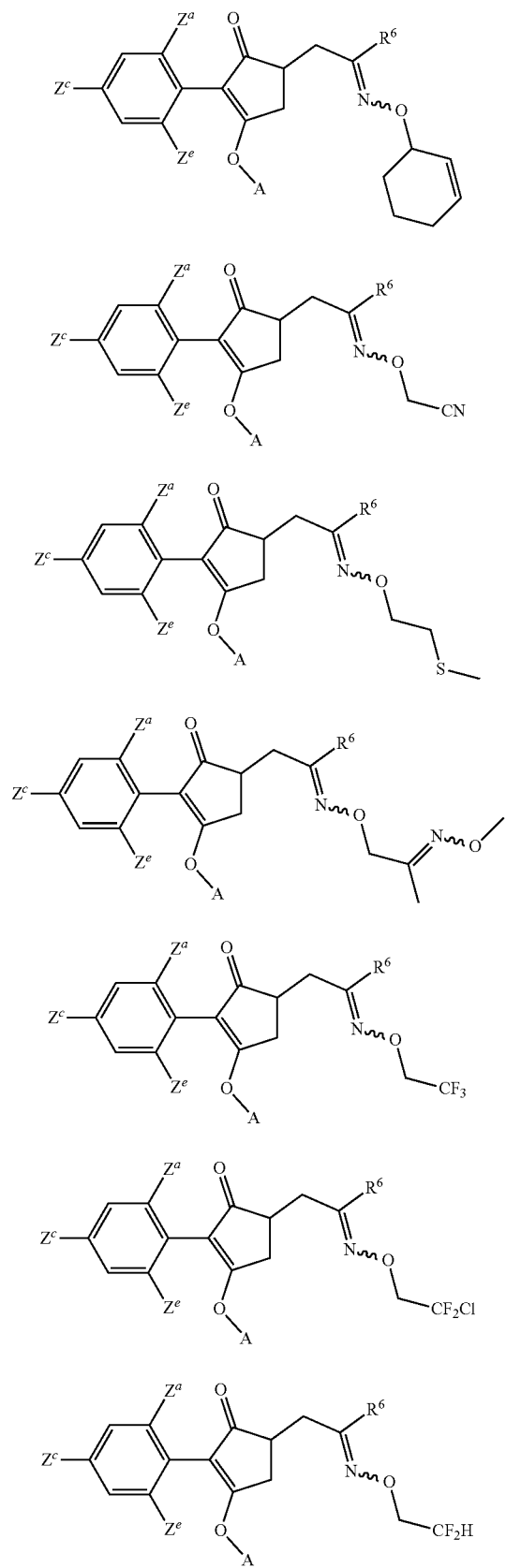

TABLE 1-continued
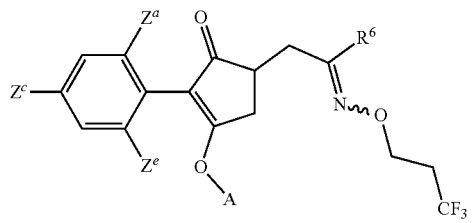
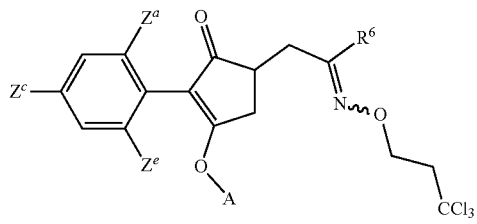
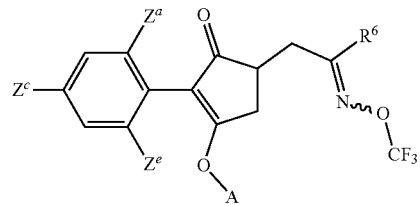
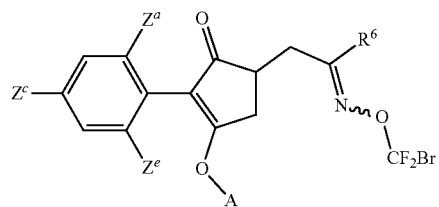
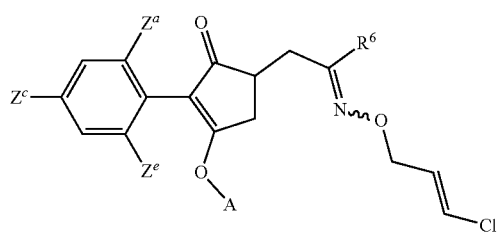
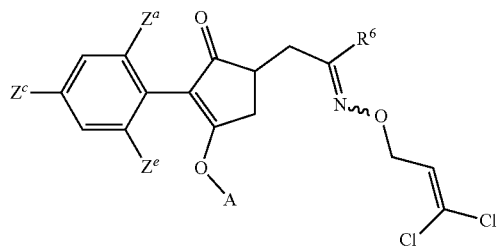
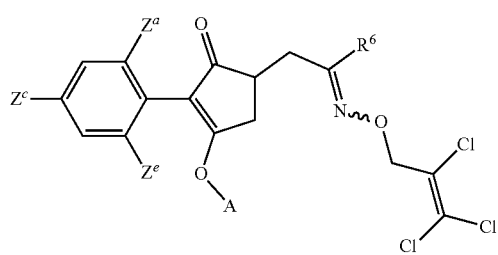

71
TABLE 1-continued
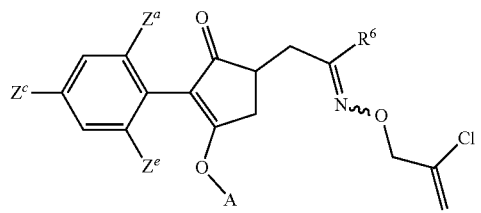
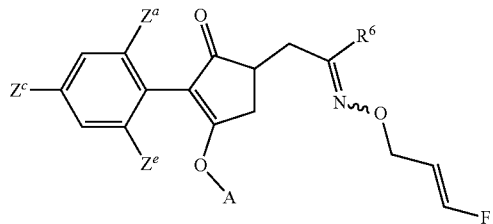
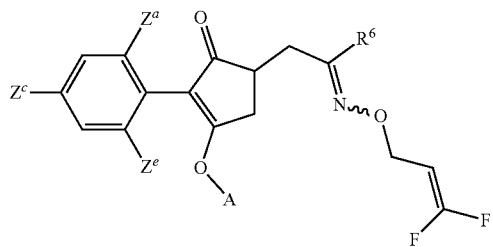
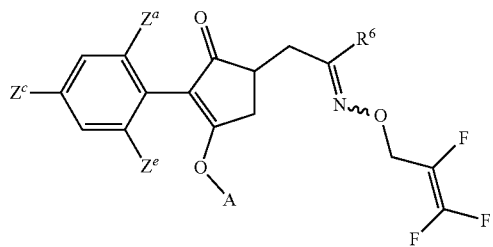
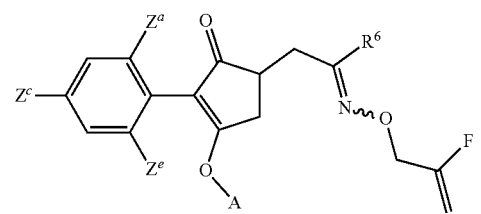
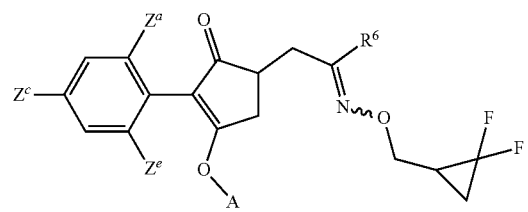
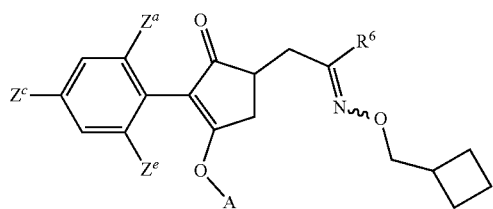

TABLE 1-continued
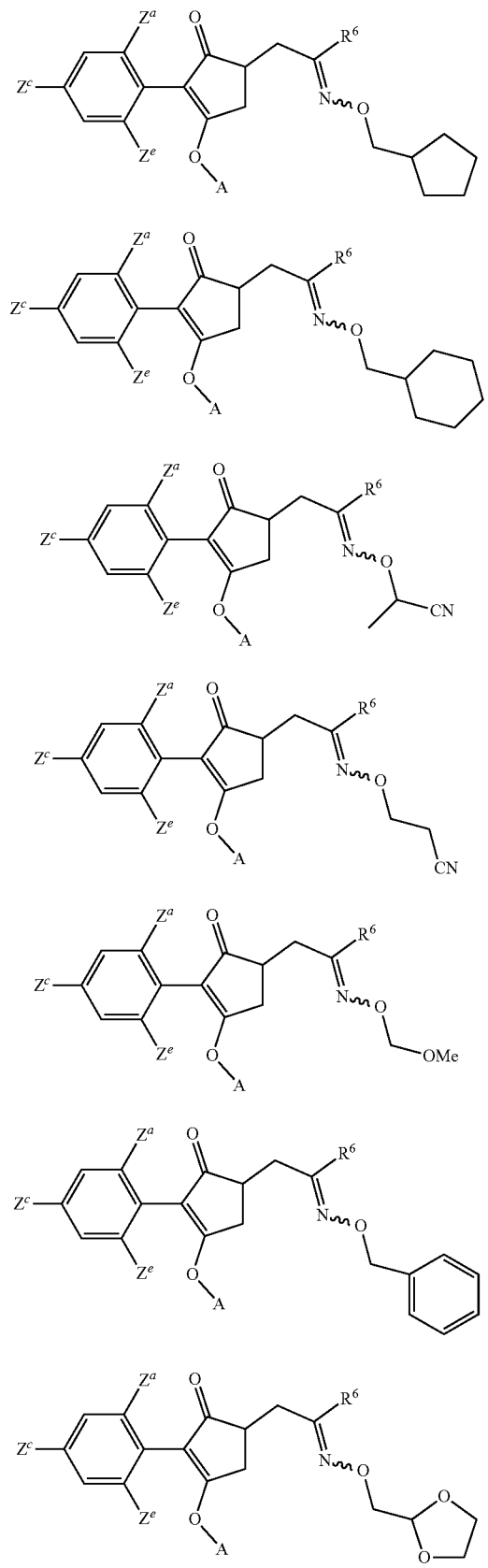

TABLE 1-continued
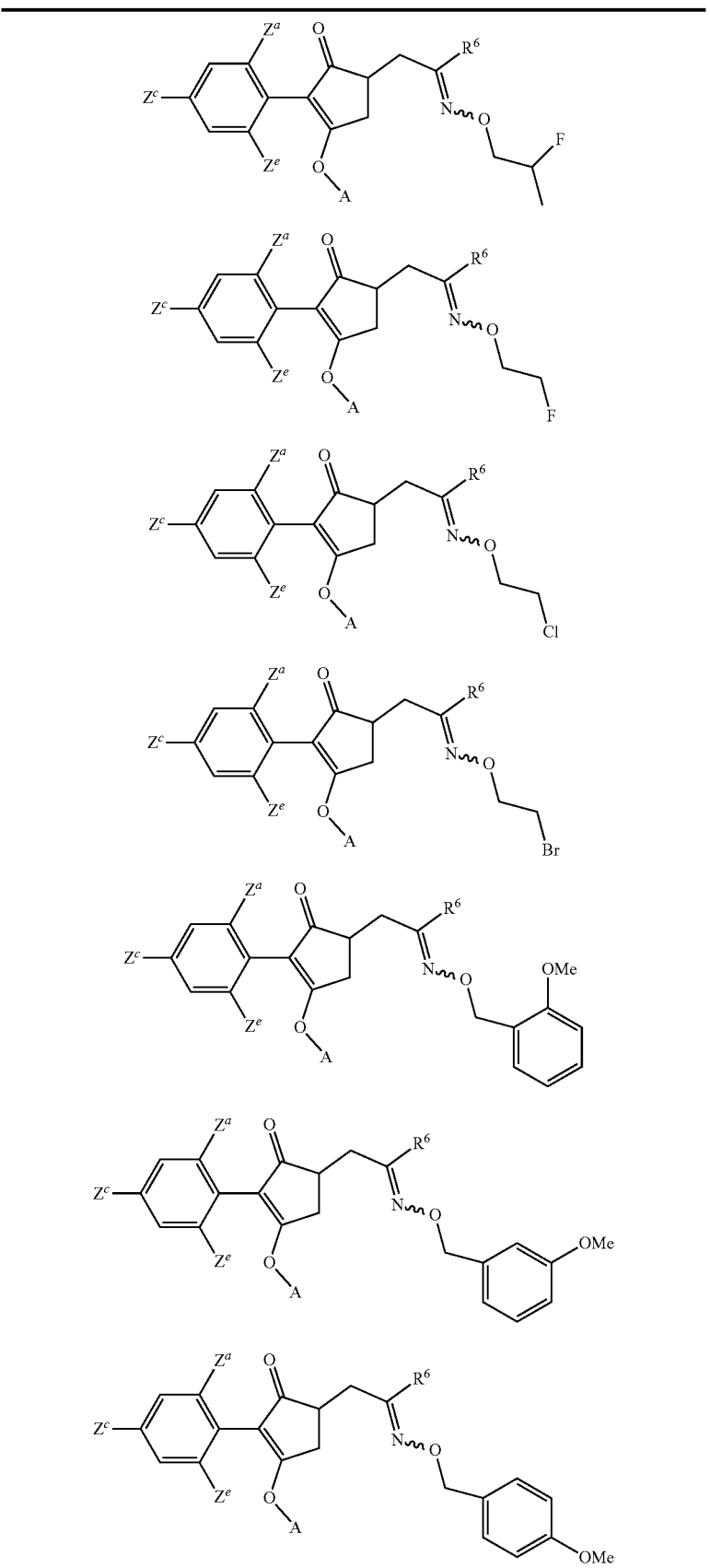

TABLE 1-continued
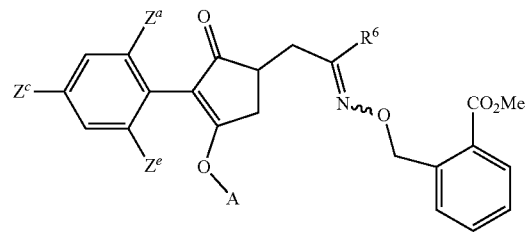
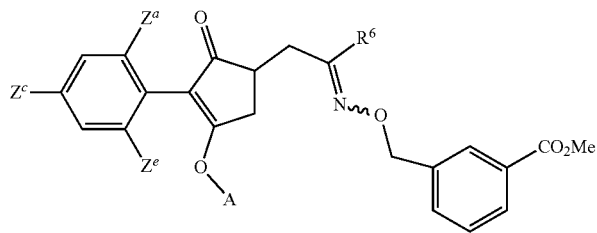
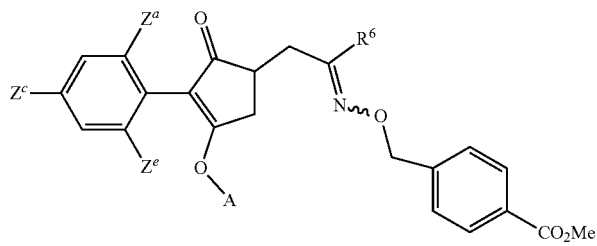
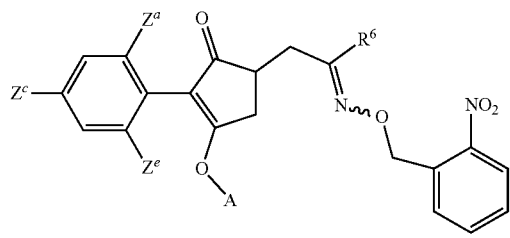
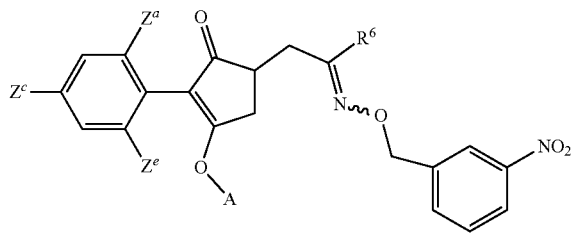
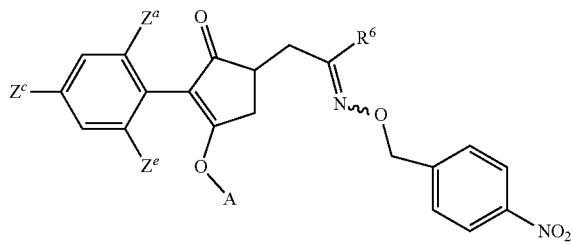

TABLE 1-continued
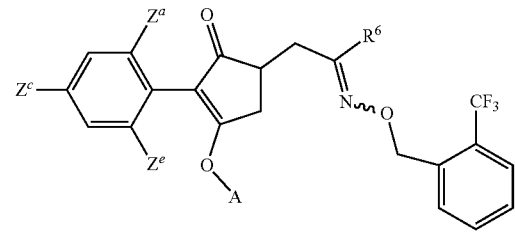
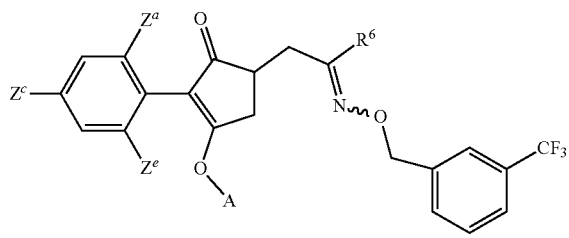
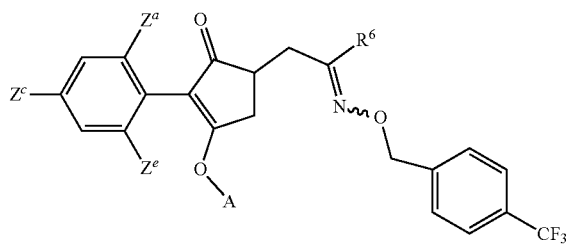
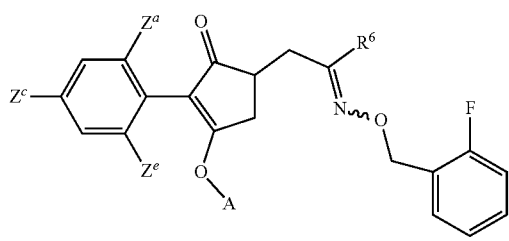
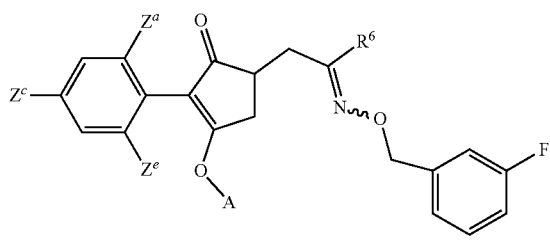
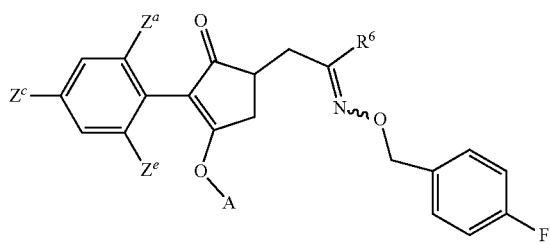

TABLE 1-continued
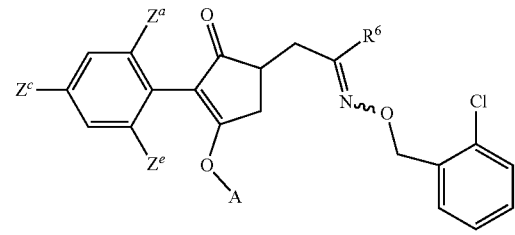
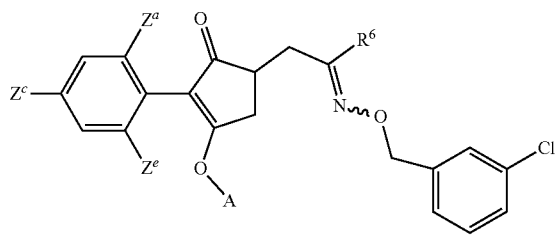
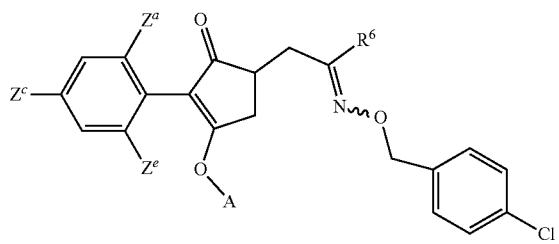
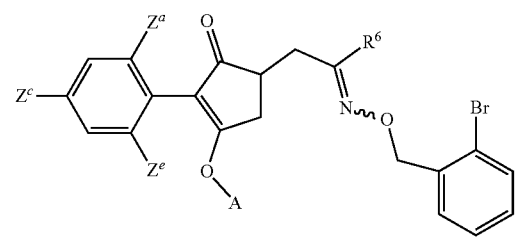
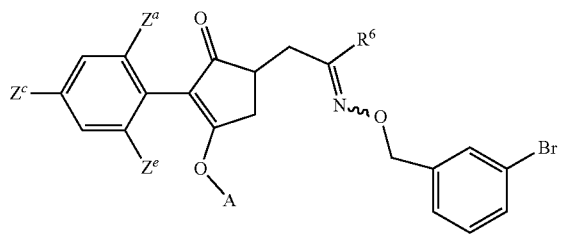
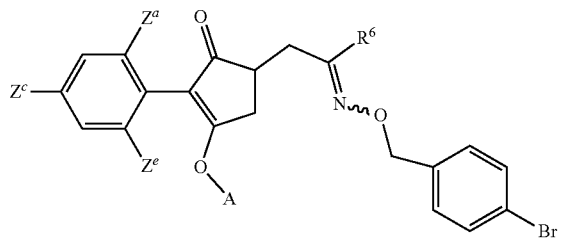

TABLE 1-continued
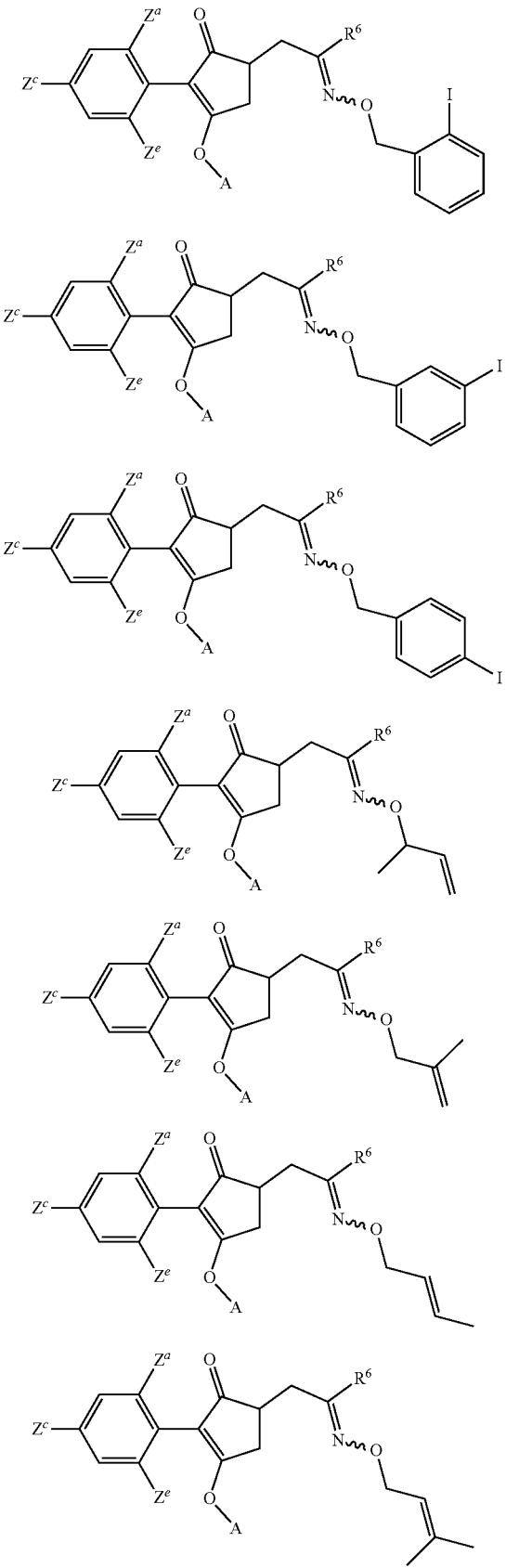

TABLE 1-continued
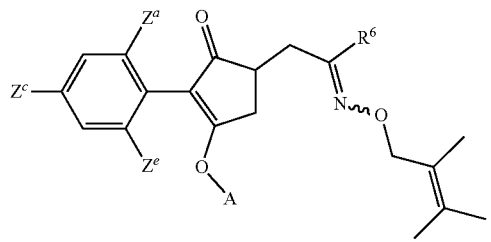
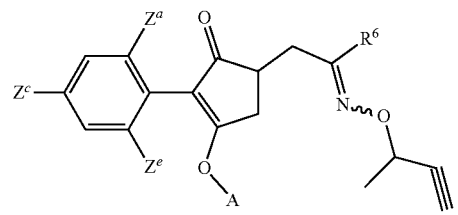
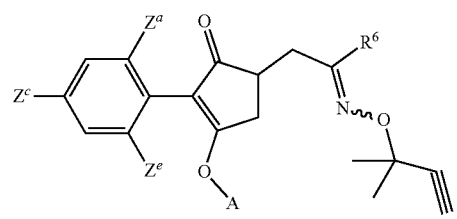
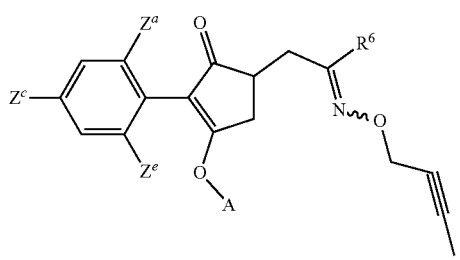
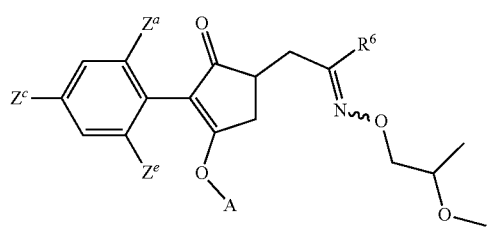
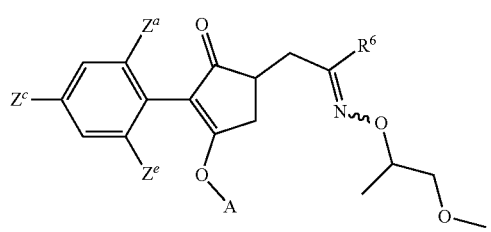
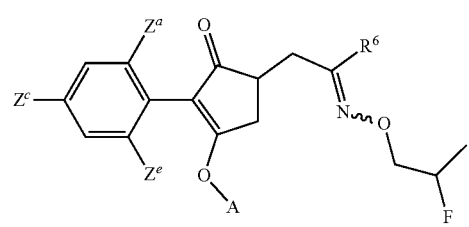

TABLE 1-continued
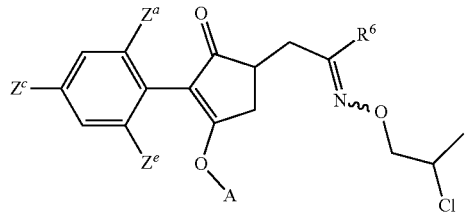
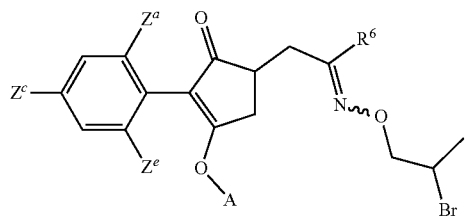
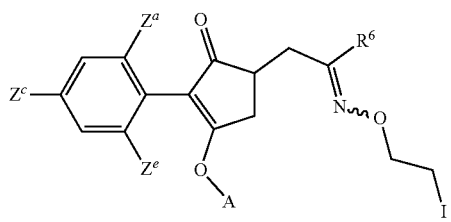
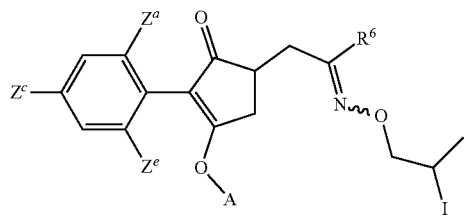
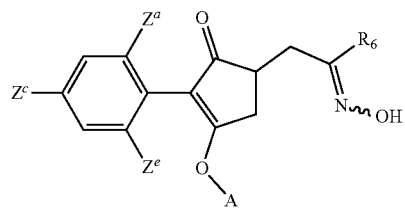
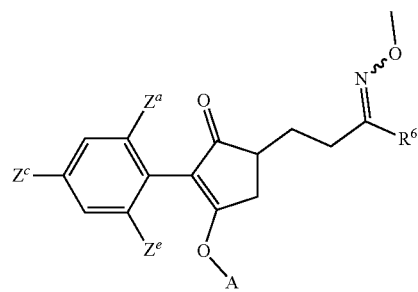

TABLE 1-continued
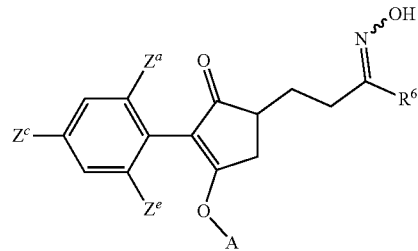
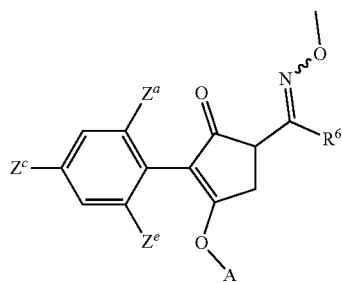
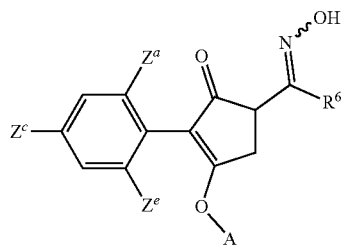
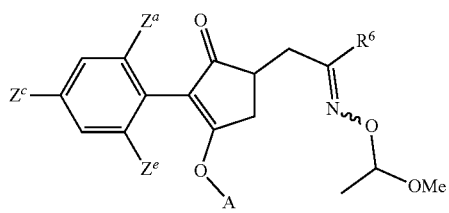
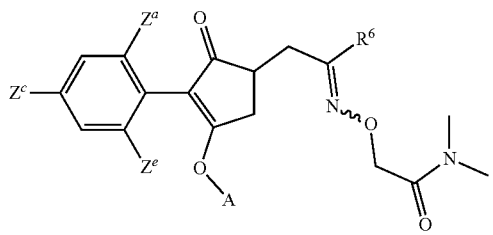
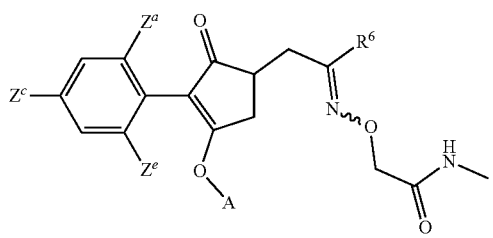

TABLE 1-continued
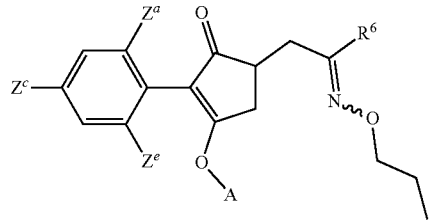
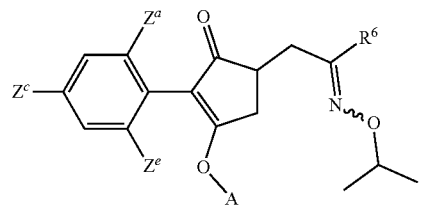
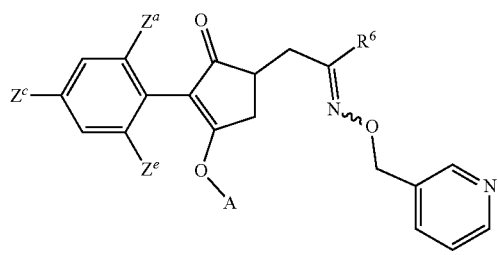
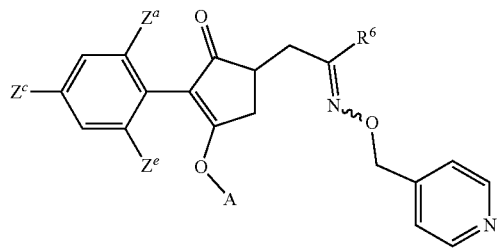
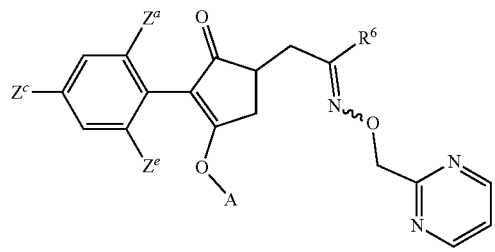
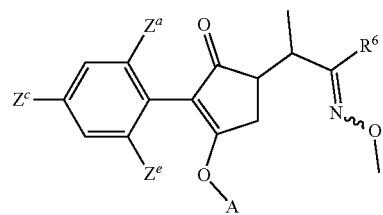

TABLE 1-continued
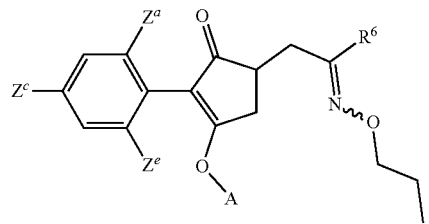
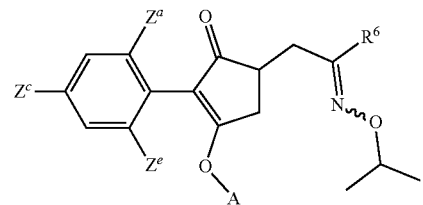
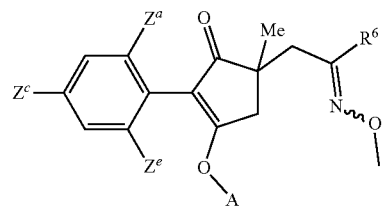
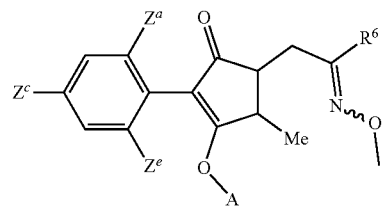
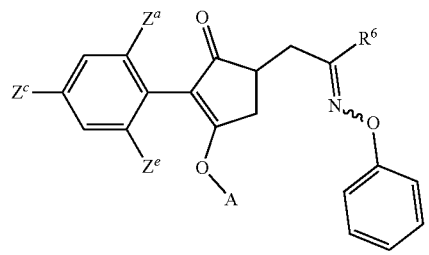
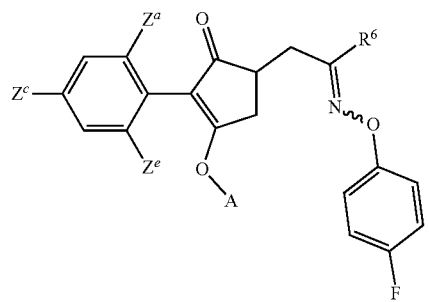

TABLE 1-continued
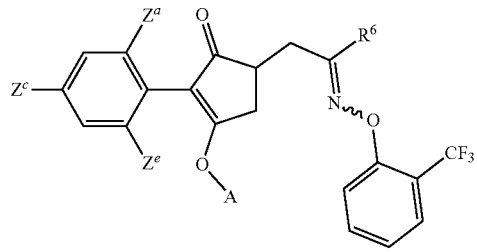
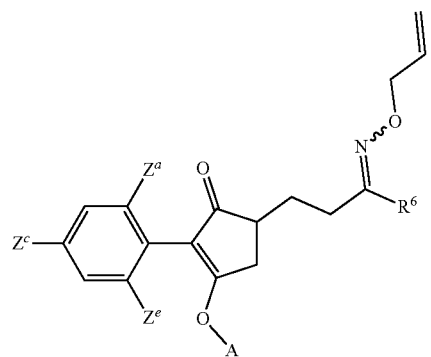
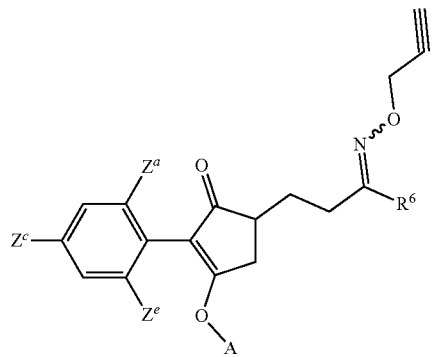
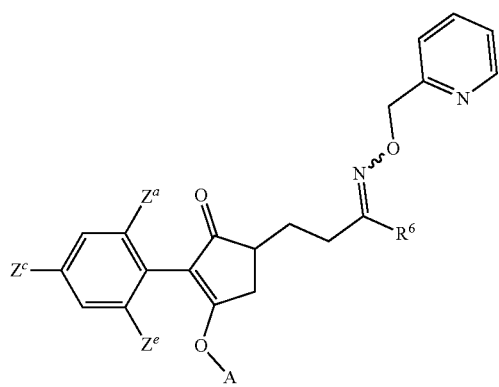

TABLE 1-continued
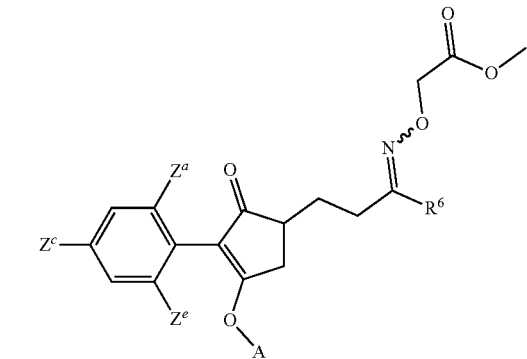
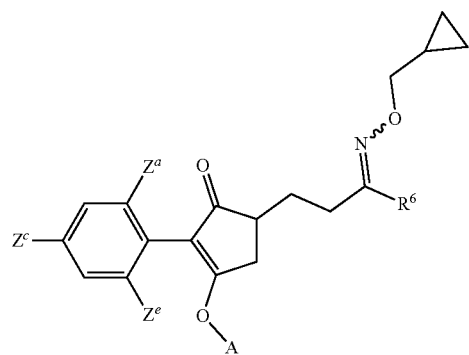
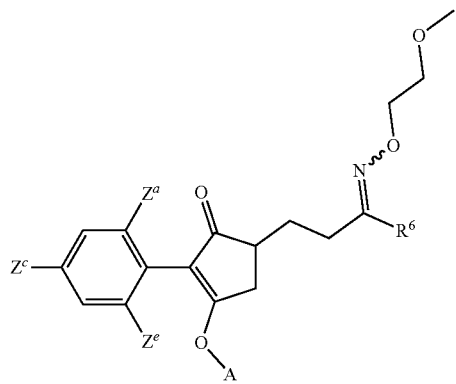
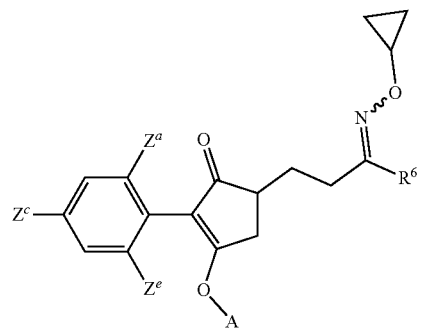

TABLE 1-continued
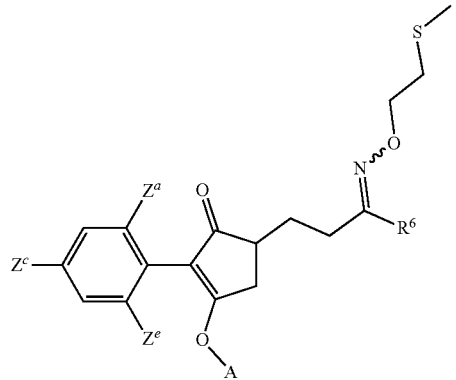
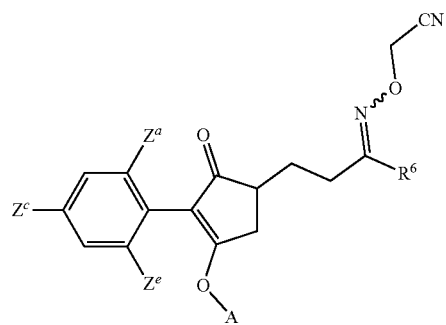
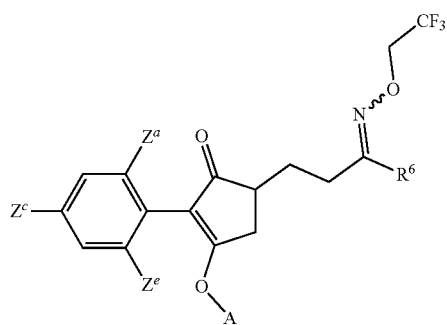
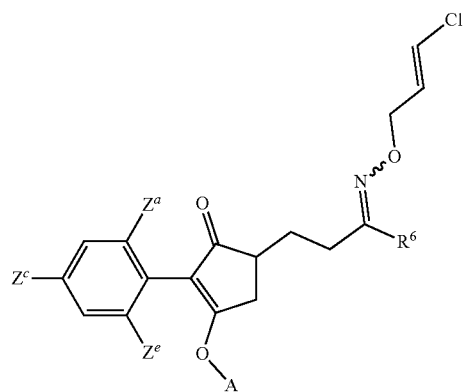

TABLE 1-continued
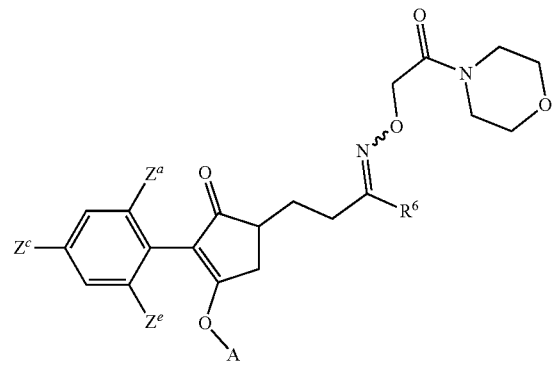
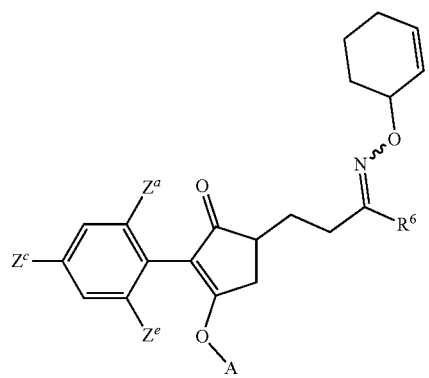
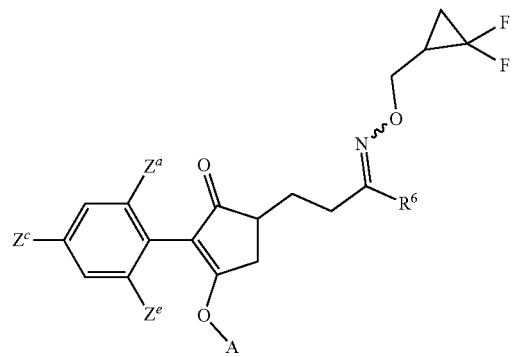
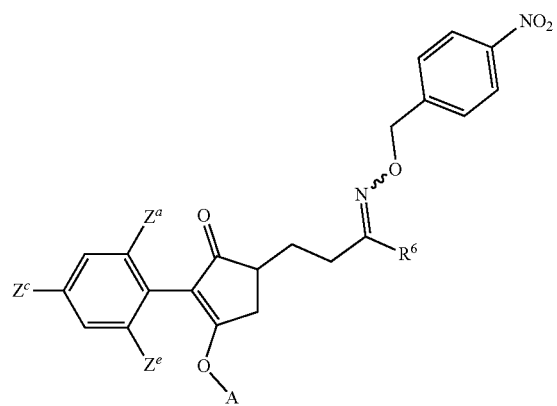

TABLE 1-continued
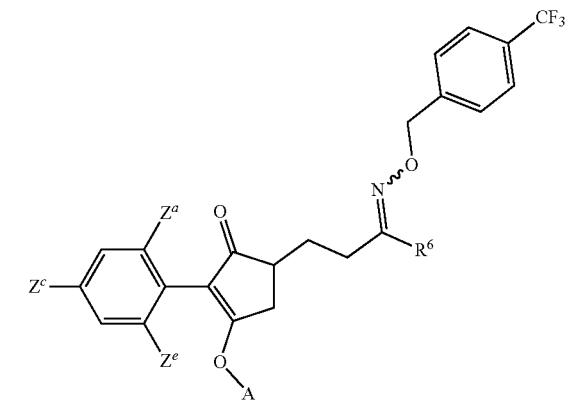
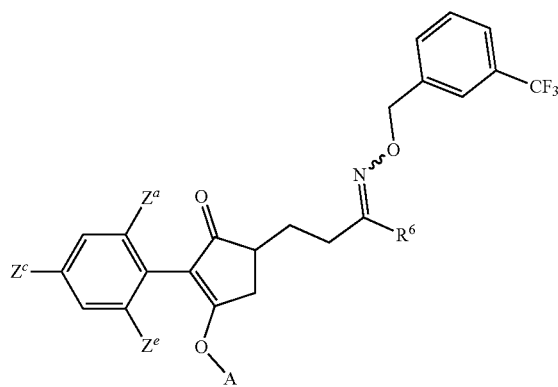
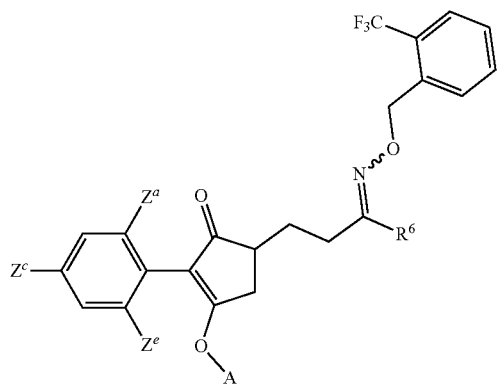
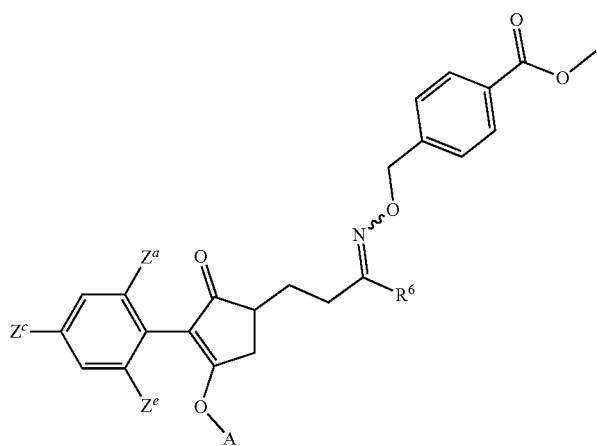

TABLE 1-continued
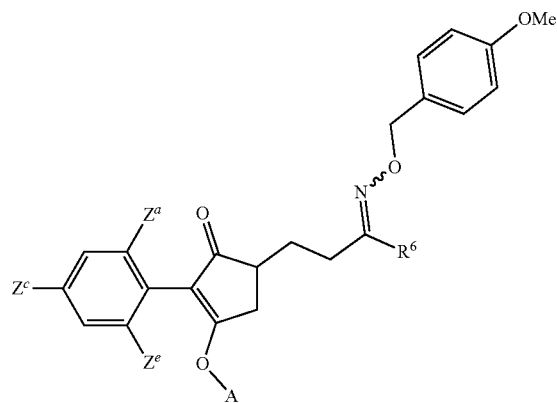
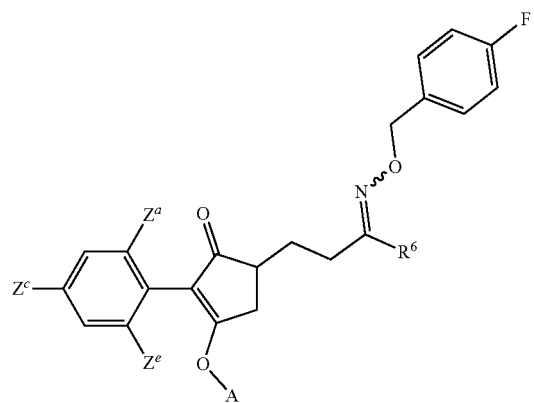
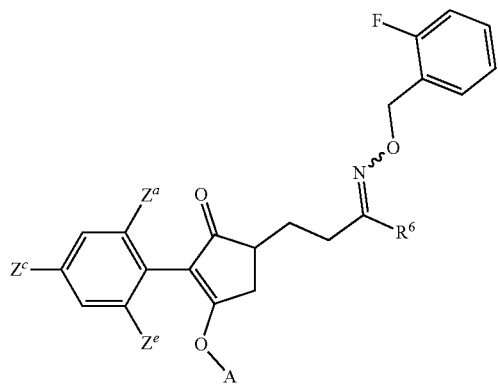
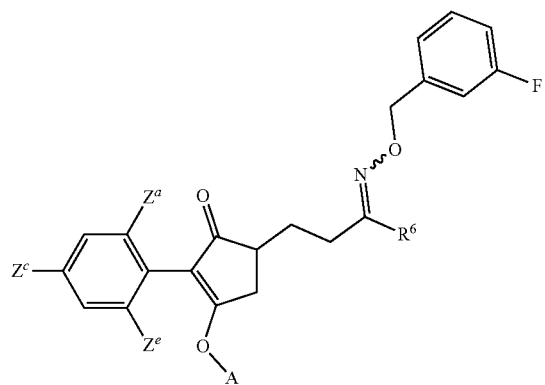

TABLE 1-continued
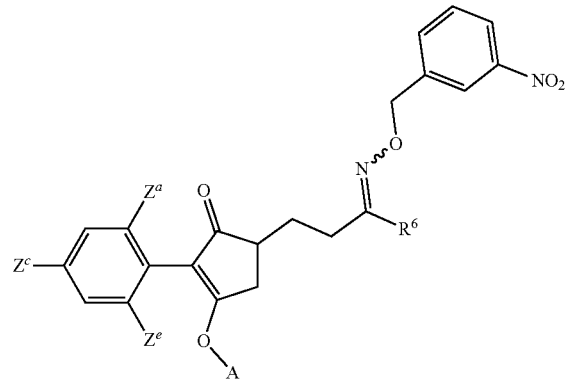
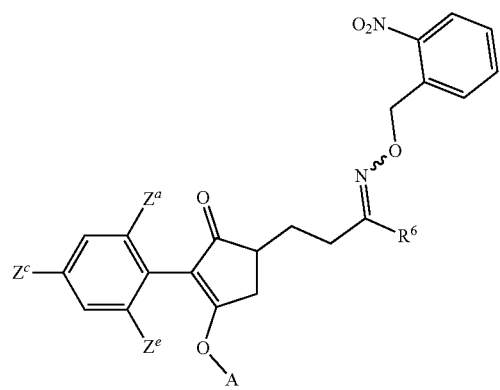
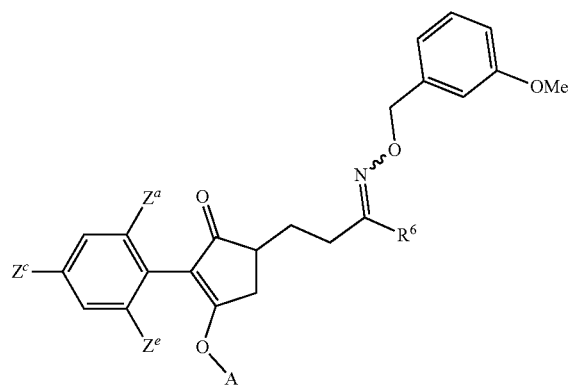
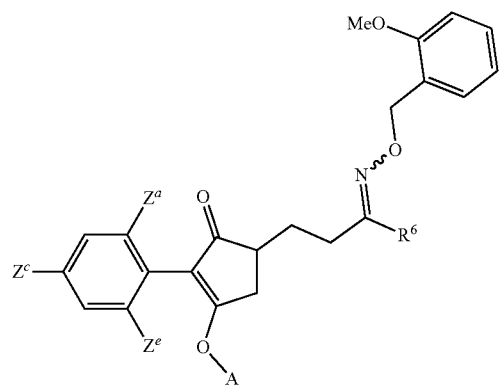

TABLE 1-continued
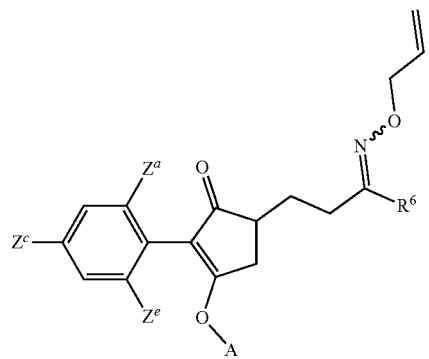
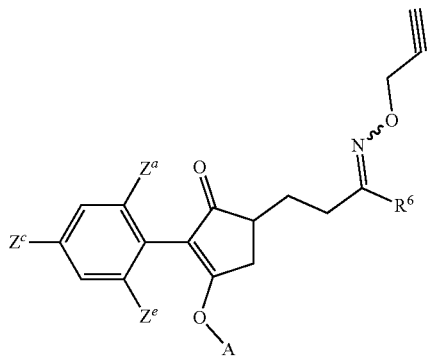
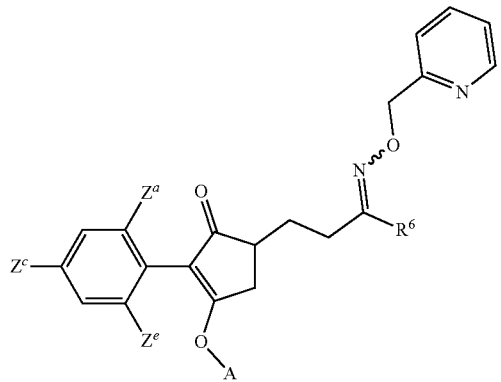
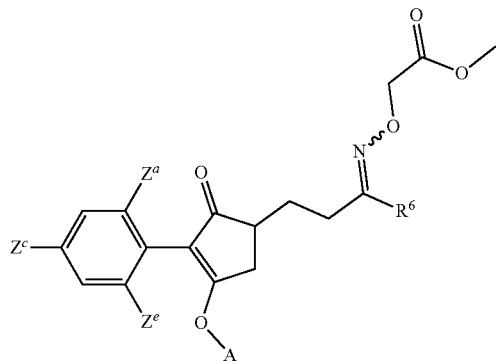

TABLE 1-continued
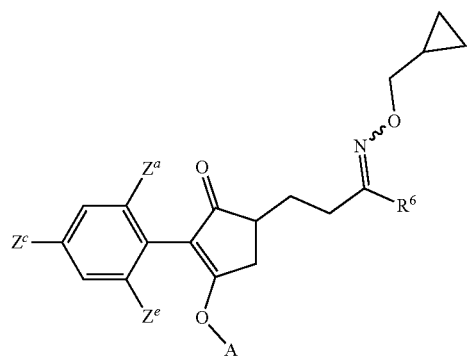
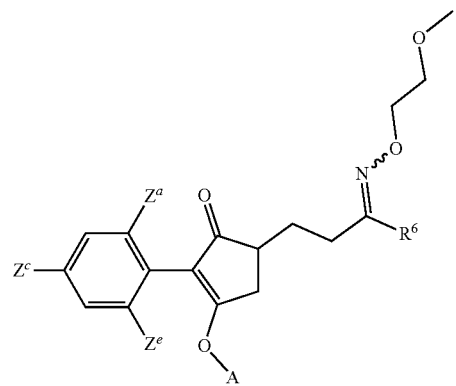
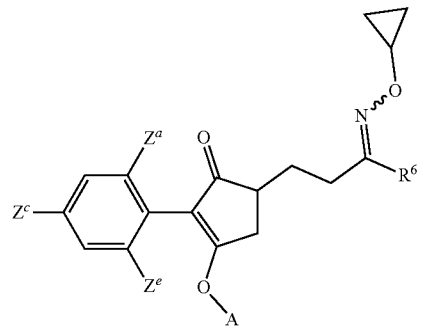
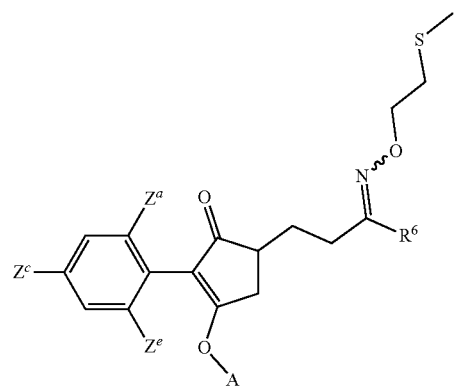

TABLE 1-continued
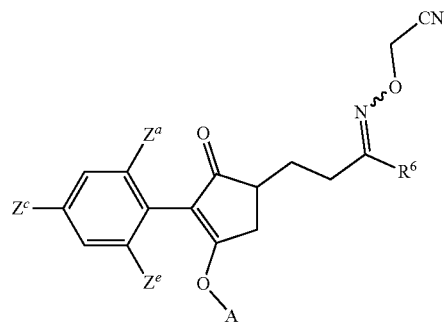
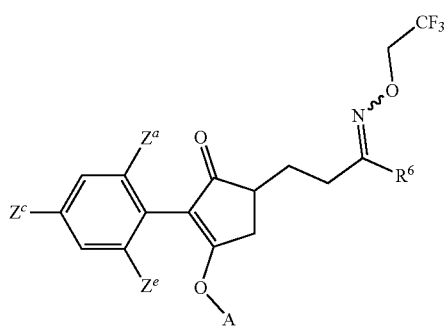
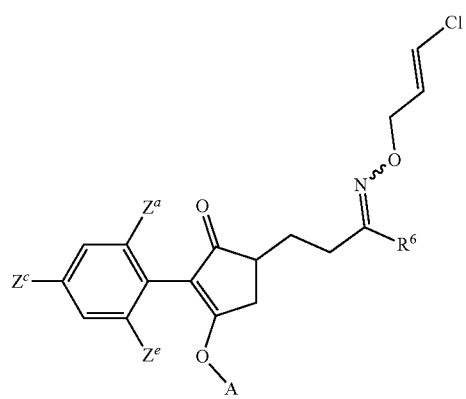
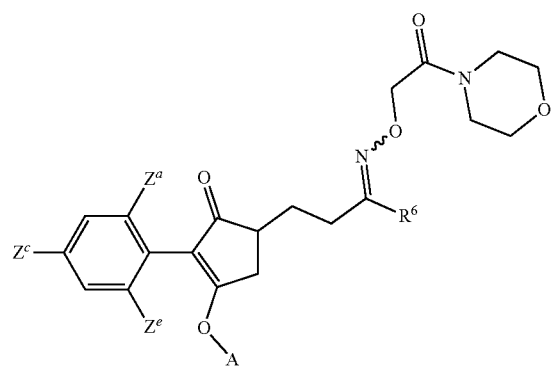

TABLE 1-continued
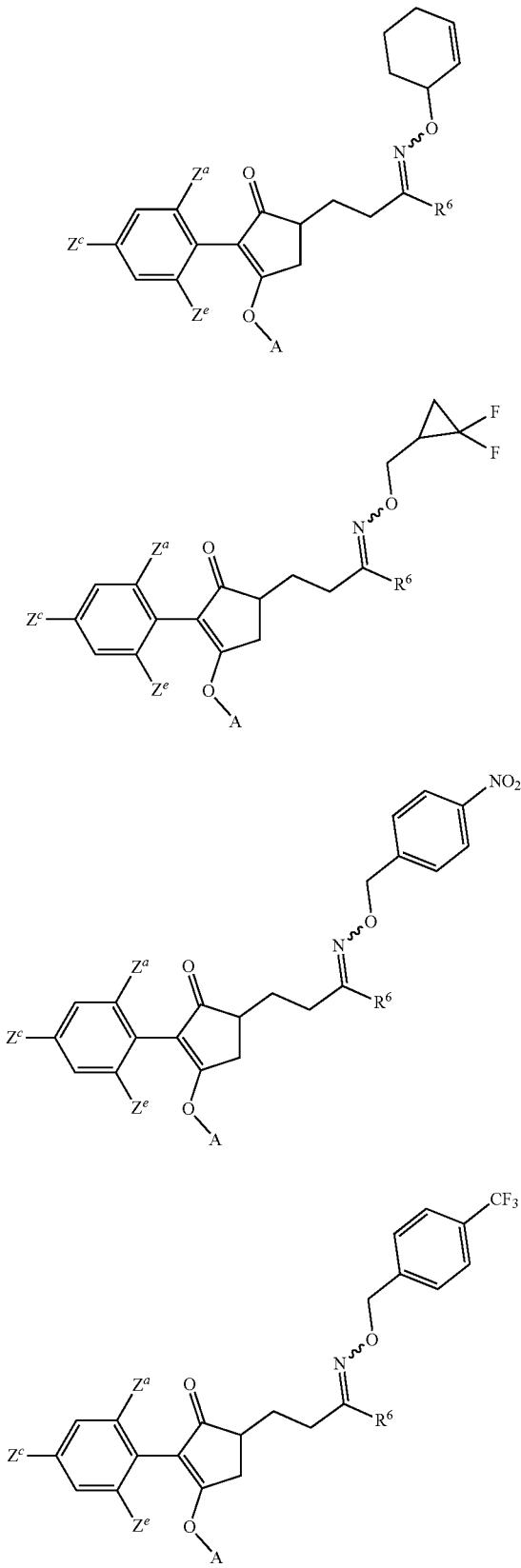

TABLE 1-continued
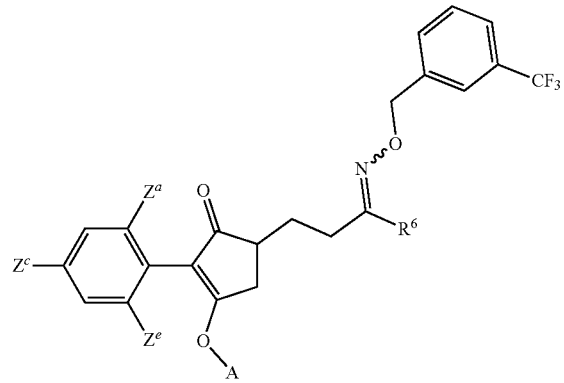
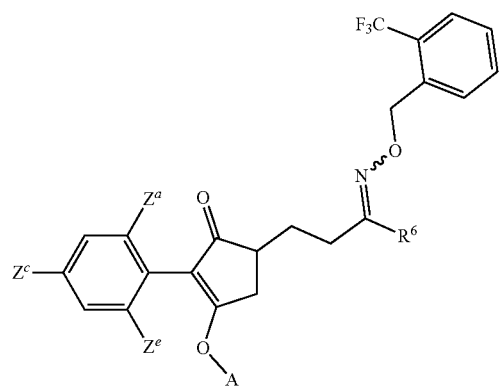
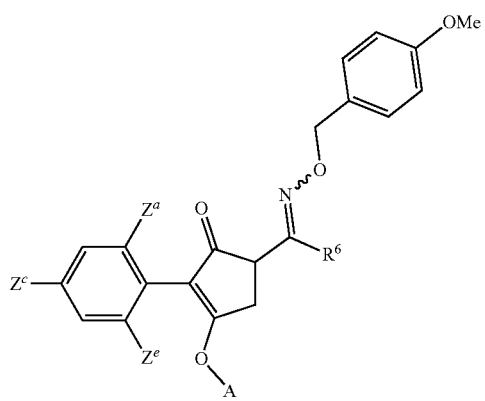
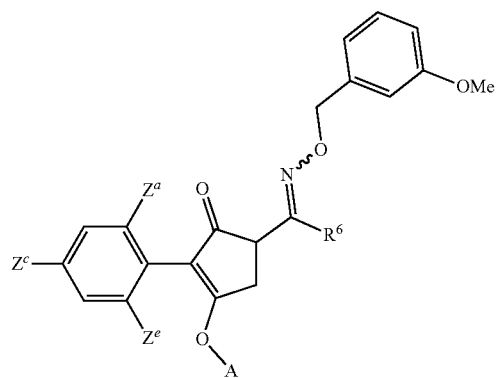

TABLE 1-continued
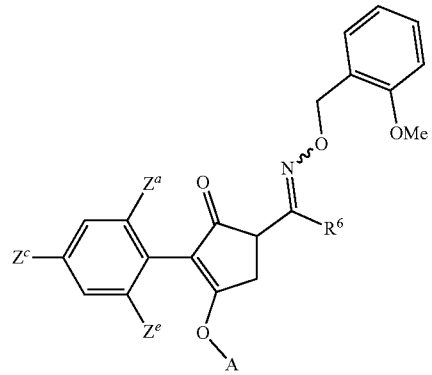
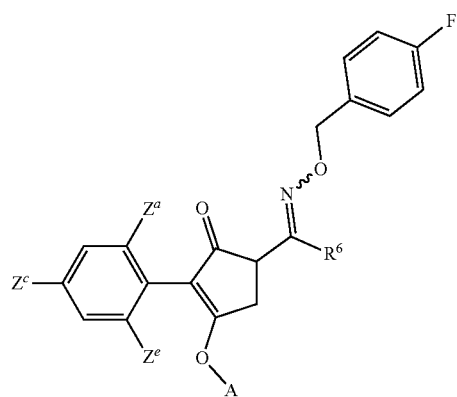
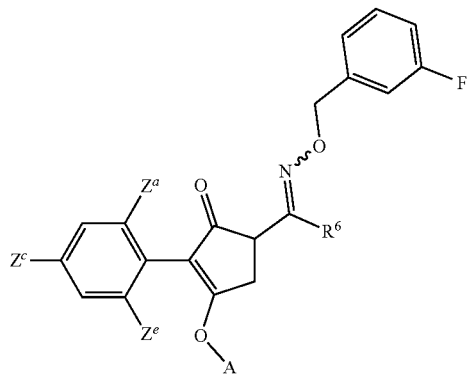
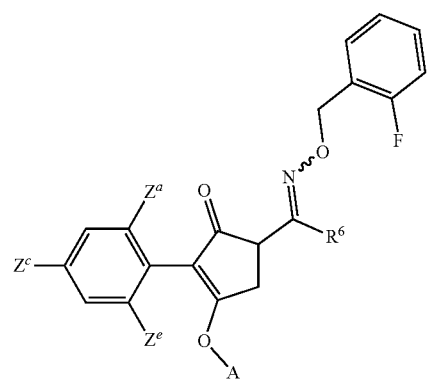

TABLE 1-continued

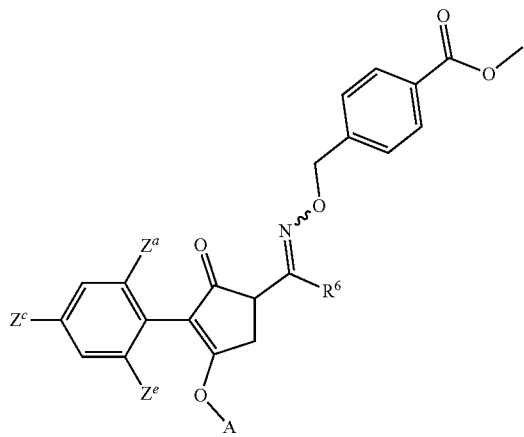

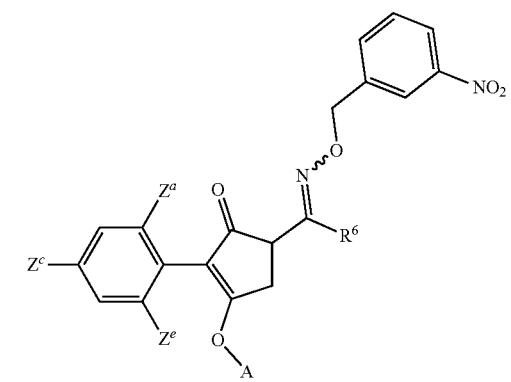

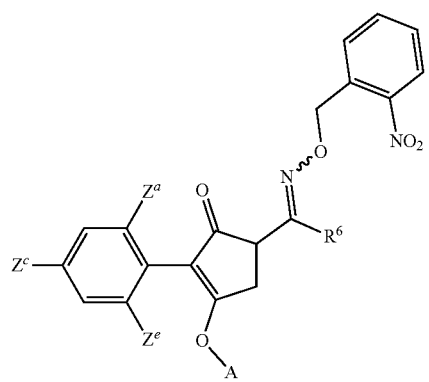

| $R^6$ | $Z^a$ | $Z^e$ | $Z^c$ | A | $R^6$ | $Z^a$ | $Z^e$ | $Z^c$ | A |
|---|---|---|---|---|---|---|---|---|---|
| Me | Me | Me | F | H | Me | Me | Et | F | H |
| Me | Me | Me | Cl | H | Me | Me | Eh | Cl | H |
| Me | Me | Me | Br | H | Me | Me | Et | Br | H |
| Me | Me | Me | I | H | Me | Me | Et | I | H |
| Me | Me | Me | CN | H | Me | Me | Et | CN | H |
| Me | Me | Me | $NO_2$ | H | Me | Me | Et | $NO_2$ | H |
| $CH=CH_2$ | Me | Me | Me | H | $CH=CH_2$ | Me | Et | Me | H |
| c-Bu | Me | Me | Me | H | c-Bu | Me | Et | Me | H |
| c-Pen | Me | Me | Me | H | c-Pen | Me | Et | Me | H |
| c-Hex | Me | Me | Me | H | c-Hex | Me | Et | Me | H |
| Ph | Me | Me | Me | H | Ph | Me | Et | Me | H |
| $CF_3$ | Me | Me | Me | H | $CF_3$ | Me | Et | Me | H |
| $CH_2Cl$ | Me | Me | Me | H | $CH_2Cl$ | Me | Et | Me | H |
| $CH_2OMe$ | Me | Me | Me | H | $CH_2OMe$ | Me | Et | Me | H |
| D1-32a | Me | Me | Me | H | D1-32a | Me | Et | Me | H |
| Me | Me | Me | Me | H | Me | Me | Et | Me | H |
| $CH=CH_2$ | Me | Me | Me | A1 | Me | Me | Et | Me | A1 |
| $CH=CH_2$ | Me | Me | Me | A13 | Me | Me | Et | Me | A2 |
| $CH=CH_2$ | Me | Me | Me | A14 | Me | Me | Et | Me | A3 |

TABLE 1-continued

| | | | | | | | | | |
|---|---|---|---|---|---|---|---|---|---|
| CH=CH$_2$ | Me | Me | Me | A15 | Me | Me | Et | Me | A4 |
| CH=CH$_2$ | Me | Me | Me | A16 | Me | Me | Et | Me | A5 |
| CH=CH$_2$ | Me | Me | Me | A20 | Me | Me | Et | Me | A6 |
| CH=CH$_2$ | Me | Me | Me | A23 | Me | Me | Et | Me | A7 |
| CH=CH$_2$ | Me | Me | Me | A24 | Me | Me | Et | Me | A8 |
| CH=CH$_2$ | Me | Me | Me | A25 | Me | Me | Et | Me | A9 |
| CH=CH$_2$ | Me | Me | Me | A26 | Me | Me | Et | Me | A10 |
| CH=CH$_2$ | Me | Me | Me | A27 | Me | Me | Et | Me | A11 |
| CH=CH$_2$ | Me | Me | Me | A28 | Me | Me | Et | Me | A12 |
| CH=CH$_2$ | Me | Me | Me | A29 | Me | Me | Et | Me | A13 |
| CH=CH$_2$ | Me | Me | Me | A34 | Me | Me | Et | Me | A14 |
| CH=CH$_2$ | Me | Me | Me | A35 | Me | Me | Et | Me | A15 |
| CH=CH$_2$ | Me | Me | Me | A36 | Me | Me | Et | Me | A16 |
| CH=CH$_2$ | Me | Me | Me | A37 | Me | Me | Et | Me | A17 |
| CH=CH$_2$ | Me | Me | Me | A42 | Me | Me | Et | Me | A18 |
| CH=CH$_2$ | Me | Me | Me | A58 | Me | Me | Et | Me | A19 |
| CH=CH$_2$ | Me | Me | Me | A63 | Me | Me | Et | Me | A20 |
| CH=CH$_2$ | Me | Me | Me | A64 | Me | Me | Et | Me | A21 |
| CH=CH$_2$ | Me | Me | Me | A65 | Me | Me | Et | Me | A22 |
| CH=CH$_2$ | Me | Me | Me | A67 | Me | Me | Et | Me | A23 |
| CH=CH$_2$ | Me | Me | Me | A69 | Me | Me | Et | Me | A24 |
| CH=CH$_2$ | Me | Me | Me | A72 | Me | Me | Et | Me | A25 |
| CH=CH$_2$ | Me | Me | Me | A73 | Me | Me | Et | Me | A26 |
| CH=CH$_2$ | Me | Me | Me | A74 | Me | Me | Et | Me | A27 |
| CH=CH$_2$ | Me | Me | Me | A75 | Me | Me | Et | Me | A28 |
| CH=CH$_2$ | Me | Me | Me | A76 | Me | Me | Et | Me | A29 |
| CH=CH$_2$ | Me | Me | Me | A77 | Me | Me | Et | Me | A30 |
| CH=CH$_2$ | Me | Me | Me | A81 | Me | Me | Et | Me | A31 |
| CH=CH$_2$ | Me | Me | Me | A83 | Me | Me | Et | Me | A32 |
| CH=CH$_2$ | Me | Me | Me | A88 | Me | Me | Et | Me | A33 |
| CH=CH$_2$ | Me | Me | Me | A91 | Me | Me | Et | Me | A34 |
| CH=CH$_2$ | Me | Me | Me | A97 | Me | Me | Et | Me | A35 |
| CH=CH$_2$ | Me | Me | Me | A98 | Me | Me | Et | Me | A36 |
| CH=CH$_2$ | Me | Me | Me | A102 | Me | Me | Et | Me | A37 |
| Ph | Me | Me | Me | A1 | Me | Me | Et | Me | A38 |
| Ph | Me | Me | Me | A13 | Me | Me | Et | Me | A39 |
| Ph | Me | Me | Me | A14 | Me | Me | Et | Me | A40 |
| Ph | Me | Me | Me | A15 | Me | Me | Et | Me | A41 |
| Ph | Me | Me | Me | A16 | Me | Me | Et | Me | A42 |
| Ph | Me | Me | Me | A20 | Me | Me | Et | Me | A43 |
| Ph | Me | Me | Me | A23 | Me | Me | Et | Me | A44 |
| Ph | Me | Me | Me | A24 | Me | Me | Et | Me | A45 |
| Ph | Me | Me | Me | A25 | Me | Me | Et | Me | A46 |
| Ph | Me | Me | Me | A26 | Me | Me | Et | Me | A47 |
| Ph | Me | Me | Me | A27 | Me | Me | Et | Me | A48 |
| Ph | Me | Me | Me | A28 | Me | Me | Et | Me | A49 |
| Ph | Me | Me | Me | A29 | Me | Me | Et | Me | A50 |
| Ph | Me | Me | Me | A34 | Me | Me | Et | Me | A51 |
| Ph | Me | Me | Me | A35 | Me | Me | Et | Me | A52 |
| Ph | Me | Me | Me | A36 | Me | Me | Et | Me | A53 |
| Ph | Me | Me | Me | A37 | Me | Me | Et | Me | A54 |
| Ph | Me | Me | Me | A42 | Me | Me | Et | Me | A55 |
| Ph | Me | Me | Me | A58 | Me | Me | Et | Me | A56 |
| Ph | Me | Me | Me | A63 | Me | Me | Et | Me | A57 |
| Ph | Me | Me | Me | A64 | Me | Me | Et | Me | A58 |
| Ph | Me | Me | Me | A65 | Me | Me | Et | Me | A59 |
| Ph | Me | Me | Me | A67 | Me | Me | Et | Me | A60 |
| Ph | Me | Me | Me | A69 | Me | Me | Et | Me | A61 |
| Ph | Me | Me | Me | A72 | Me | Me | Et | Me | A62 |
| Ph | Me | Me | Me | A73 | Me | Me | Et | Me | A63 |
| Ph | Me | Me | Me | A74 | Me | Me | Et | Me | A64 |
| Ph | Me | Me | Me | A75 | Me | Me | Et | Me | A65 |
| Ph | Me | Me | Me | A76 | Me | Me | Et | Me | A66 |
| Ph | Me | Me | Me | A77 | Me | Me | Et | Me | A67 |
| Ph | Me | Me | Me | A81 | Me | Me | Et | Me | A68 |
| Ph | Me | Me | Me | A83 | Me | Me | Et | Me | A69 |
| Ph | Me | Me | Me | A88 | Me | Me | Et | Me | A70 |
| Ph | Me | Me | Me | A91 | Me | Me | Et | Me | A71 |
| Ph | Me | Me | Me | A97 | Me | Me | Et | Me | A72 |
| Ph | Me | Me | Me | A98 | Me | Me | Et | Me | A73 |
| Ph | Me | Me | Me | A102 | Me | Me | Et | Me | A74 |
| Ph | Me | Me | Me | A1 | Me | Me | Et | Me | A75 |
| Ph | Me | Me | Me | A13 | Me | Me | Et | Me | A76 |
| Ph | Me | Me | Me | A14 | Me | Me | Et | Me | A77 |
| Ph | Me | Me | Me | A15 | Me | Me | Et | Me | A78 |
| Ph | Me | Me | Me | A16 | Me | Me | Et | Me | A79 |
| Ph | Me | Me | Me | A20 | Me | Me | Et | Me | A80 |
| Ph | Me | Me | Me | A23 | Me | Me | Et | Me | A81 |
| Ph | Me | Me | Me | A24 | Me | Me | Et | Me | A82 |
| Ph | Me | Me | Me | A25 | Me | Me | Et | Me | A83 |

TABLE 1-continued

| | | | | | | | | | |
|---|---|---|---|---|---|---|---|---|---|
| Ph | Me | Me | Me | A26 | Me | Me | Et | Me | A84 |
| Ph | Me | Me | Me | A27 | Me | Me | Et | Me | A85 |
| Ph | Me | Me | Me | A28 | Me | Me | Et | Me | A86 |
| Ph | Me | Me | Me | A29 | Me | Me | Et | Me | A87 |
| Ph | Me | Me | Me | A34 | Me | Me | Et | Me | A88 |
| Ph | Me | Me | Me | A35 | Me | Me | Et | Me | A89 |
| Ph | Me | Me | Me | A36 | Me | Me | Et | Me | A90 |
| Ph | Me | Me | Me | A37 | Me | Me | Et | Me | A91 |
| Ph | Me | Me | Me | A42 | Me | Me | Et | Me | A92 |
| Ph | Me | Me | Me | A58 | Me | Me | Et | Me | A93 |
| Ph | Me | Me | Me | A63 | Me | Me | Et | Me | A94 |
| Ph | Me | Me | Me | A64 | Me | Me | Et | Me | A95 |
| Ph | Me | Me | Me | A65 | Me | Me | Et | Me | A96 |
| Ph | Me | Me | Me | A67 | Me | Me | Et | Me | A97 |
| Ph | Me | Me | Me | A69 | Me | Me | Et | Me | A98 |
| Ph | Me | Me | Me | A72 | Me | Me | Et | Me | A99 |
| Ph | Me | Me | Me | A73 | Me | Me | Et | Me | A100 |
| Ph | Me | Me | Me | A74 | Me | Me | Et | Me | A101 |
| Ph | Me | Me | Me | A75 | Me | Me | Et | Me | A102 |
| Ph | Me | Me | Me | A76 | Me | Me | Et | Me | A103 |
| Ph | Me | Me | Me | A77 | Me | Me | Et | Me | A104 |
| Ph | Me | Me | Me | A81 | Me | Me | Et | Me | A105 |
| Ph | Me | Me | Me | A83 | Me | Me | Et | Me | A106 |
| Ph | Me | Me | Me | A88 | Me | Me | Et | Me | A107 |
| Ph | Me | Me | Me | A91 | Me | Me | Et | Me | A108 |
| Ph | Me | Me | Me | A97 | Me | Me | Et | Me | A109 |
| Ph | Me | Me | Me | A98 | Me | Me | Et | Me | A110 |
| Ph | Me | Me | Me | A102 | Me | Me | Et | Me | A111 |
| Ph | Me | Me | Me | A112 | Me | Me | Et | Me | A112 |
| Ph | Me | Me | Me | A113 | Me | Me | Et | Me | A113 |
| Ph | Me | Me | Me | A114 | Me | Me | Et | Me | A114 |
| c-Pr | Me | Me | Me | H | c-Pr | Me | Et | Me | H |
| c-Pr | Me | Me | Me | A1 | c-Pr | Me | Et | Me | A1 |
| c-Pr | Me | Me | Me | A2 | c-Pr | Me | Et | Me | A2 |
| c-Pr | Me | Me | Me | A3 | c-Pr | Me | Et | Me | A3 |
| c-Pr | Me | Me | Me | A4 | c-Pr | Me | Et | Me | A4 |
| c-Pr | Me | Me | Me | A5 | c-Pr | Me | Et | Me | A5 |
| c-Pr | Me | Me | Me | A6 | c-Pr | Me | Et | Me | A6 |
| c-Pr | Me | Me | Me | A7 | c-Pr | Me | Et | Me | A7 |
| c-Pr | Me | Me | Me | A8 | c-Pr | Me | Et | Me | A8 |
| c-Pr | Me | Me | Me | A9 | c-Pr | Me | Et | Me | A9 |
| c-Pr | Me | Me | Me | A10 | c-Pr | Me | Et | Me | A10 |
| c-Pr | Me | Me | Me | A11 | c-Pr | Me | Et | Me | A11 |
| c-Pr | Me | Me | Me | A12 | c-Pr | Me | Et | Me | A12 |
| c-Pr | Me | Me | Me | A13 | c-Pr | Me | Et | Me | A13 |
| c-Pr | Me | Me | Me | A14 | c-Pr | Me | Et | Me | A14 |
| c-Pr | Me | Me | Me | A15 | c-Pr | Me | Et | Me | A15 |
| c-Pr | Me | Me | Me | A16 | c-Pr | Me | Et | Me | A16 |
| c-Pr | Me | Me | Me | A17 | c-Pr | Me | Et | Me | A17 |
| c-Pr | Me | Me | Me | A18 | c-Pr | Me | Et | Me | A18 |
| c-Pr | Me | Me | Me | A19 | c-Pr | Me | Et | Me | A19 |
| c-Pr | Me | Me | Me | A20 | c-Pr | Me | Et | Me | A20 |
| c-Pr | Me | Me | Me | A21 | c-Pr | Me | Et | Me | A21 |
| c-Pr | Me | Me | Me | A22 | c-Pr | Me | Et | Me | A22 |
| c-Pr | Me | Me | Me | A23 | c-Pr | Me | Et | Me | A23 |
| c-Pr | Me | Me | Me | A24 | c-Pr | Me | Et | Me | A24 |
| c-Pr | Me | Me | Me | A25 | c-Pr | Me | Et | Me | A25 |
| c-Pr | Me | Me | Me | A26 | c-Pr | Me | Et | Me | A26 |
| c-Pr | Me | Me | Me | A27 | c-Pr | Me | Et | Me | A27 |
| c-Pr | Me | Me | Me | A28 | c-Pr | Me | Et | Me | A28 |
| c-Pr | Me | Me | Me | A29 | c-Pr | Me | Et | Me | A29 |
| c-Pr | Me | Me | Me | A30 | c-Pr | Me | Et | Me | A30 |
| c-Pr | Me | Me | Me | A31 | c-Pr | Me | Et | Me | A31 |
| c-Pr | Me | Me | Me | A32 | c-Pr | Me | Et | Me | A32 |
| c-Pr | Me | Me | Me | A33 | c-Pr | Me | Et | Me | A33 |
| c-Pr | Me | Me | Me | A34 | c-Pr | Me | Et | Me | A34 |
| c-Pr | Me | Me | Me | A35 | c-Pr | Me | Et | Me | A35 |
| c-Pr | Me | Me | Me | A36 | c-Pr | Me | Et | Me | A36 |
| c-Pr | Me | Me | Me | A37 | c-Pr | Me | Et | Me | A37 |
| c-Pr | Me | Me | Me | A38 | c-Pr | Me | Et | Me | A38 |
| c-Pr | Me | Me | Me | A39 | c-Pr | Me | Et | Me | A39 |
| c-Pr | Me | Me | Me | A40 | c-Pr | Me | Et | Me | A40 |
| c-Pr | Me | Me | Me | A41 | c-Pr | Me | Et | Me | A41 |
| c-Pr | Me | Me | Me | A42 | c-Pr | Me | Et | Me | A42 |
| c-Pr | Me | Me | Me | A43 | c-Pr | Me | Et | Me | A43 |
| c-Pr | Me | Me | Me | A44 | c-Pr | Me | Et | Me | A44 |
| c-Pr | Me | Me | Me | A45 | c-Pr | Me | Et | Me | A45 |
| c-Pr | Me | Me | Me | A46 | c-Pr | Me | Et | Me | A46 |
| c-Pr | Me | Me | Me | A47 | c-Pr | Me | Et | Me | A47 |
| c-Pr | Me | Me | Me | A48 | c-Pr | Me | Et | Me | A48 |

TABLE 1-continued

| | | | | | | | | | |
|---|---|---|---|---|---|---|---|---|---|
| c-Pr | Me | Me | Me | A49 | c-Pr | Me | Et | Me | A49 |
| c-Pr | Me | Me | Me | A50 | c-Pr | Me | Et | Me | A50 |
| c-Pr | Me | Me | Me | A51 | c-Pr | Me | Et | Me | A51 |
| c-Pr | Me | Me | Me | A52 | c-Pr | Me | Et | Me | A52 |
| c-Pr | Me | Me | Me | A53 | c-Pr | Me | Et | Me | A53 |
| c-Pr | Me | Me | Me | A54 | c-Pr | Me | Et | Me | A54 |
| c-Pr | Me | Me | Me | A55 | c-Pr | Me | Et | Me | A55 |
| c-Pr | Me | Me | Me | A56 | c-Pr | Me | Et | Me | A56 |
| c-Pr | Me | Me | Me | A57 | c-Pr | Me | Et | Me | A57 |
| c-Pr | Me | Me | Me | A58 | c-Pr | Me | Et | Me | A58 |
| c-Pr | Me | Me | Me | A59 | c-Pr | Me | Et | Me | A59 |
| c-Pr | Me | Me | Me | A60 | c-Pr | Me | Et | Me | A60 |
| c-Pr | Me | Me | Me | A61 | c-Pr | Me | Et | Me | A61 |
| c-Pr | Me | Me | Me | A62 | c-Pr | Me | Et | Me | A62 |
| c-Pr | Me | Me | Me | A63 | c-Pr | Me | Et | Me | A63 |
| c-Pr | Me | Me | Me | A64 | c-Pr | Me | Et | Me | A64 |
| c-Pr | Me | Me | Me | A65 | c-Pr | Me | Et | Me | A65 |
| c-Pr | Me | Me | Me | A66 | c-Pr | Me | Et | Me | A66 |
| c-Pr | Me | Me | Me | A67 | c-Pr | Me | Et | Me | A67 |
| c-Pr | Me | Me | Me | A68 | c-Pr | Me | Et | Me | A68 |
| c-Pr | Me | Me | Me | A69 | c-Pr | Me | Et | Me | A69 |
| c-Pr | Me | Me | Me | A70 | c-Pr | Me | Et | Me | A70 |
| c-Pr | Me | Me | Me | A71 | c-Pr | Me | Et | Me | A71 |
| c-Pr | Me | Me | Me | A72 | c-Pr | Me | Et | Me | A72 |
| c-Pr | Me | Me | Me | A73 | c-Pr | Me | Et | Me | A73 |
| c-Pr | Me | Me | Me | A74 | c-Pr | Me | Et | Me | A74 |
| c-Pr | Me | Me | Me | A75 | c-Pr | Me | Et | Me | A75 |
| c-Pr | Me | Me | Me | A76 | c-Pr | Me | Et | Me | A76 |
| c-Pr | Me | Me | Me | A77 | c-Pr | Me | Et | Me | A77 |
| c-Pr | Me | Me | Me | A78 | c-Pr | Me | Et | Me | A78 |
| c-Pr | Me | Me | Me | A79 | c-Pr | Me | Et | Me | A79 |
| c-Pr | Me | Me | Me | A80 | c-Pr | Me | Et | Me | A80 |
| c-Pr | Me | Me | Me | A81 | c-Pr | Me | Et | Me | A81 |
| c-Pr | Me | Me | Me | A82 | c-Pr | Me | Et | Me | A82 |
| c-Pr | Me | Me | Me | A83 | c-Pr | Me | Et | Me | A83 |
| c-Pr | Me | Me | Me | A84 | c-Pr | Me | Et | Me | A84 |
| c-Pr | Me | Me | Me | A85 | c-Pr | Me | Et | Me | A85 |
| c-Pr | Me | Me | Me | A86 | c-Pr | Me | Et | Me | A86 |
| c-Pr | Me | Me | Me | A87 | c-Pr | Me | Et | Me | A87 |
| c-Pr | Me | Me | Me | A88 | c-Pr | Me | Et | Me | A88 |
| c-Pr | Me | Me | Me | A89 | c-Pr | Me | Et | Me | A89 |
| c-Pr | Me | Me | Me | A90 | c-Pr | Me | Et | Me | A90 |
| c-Pr | Me | Me | Me | A91 | c-Pr | Me | Et | Me | A91 |
| c-Pr | Me | Me | Me | A92 | c-Pr | Me | Et | Me | A92 |
| c-Pr | Me | Me | Me | A93 | c-Pr | Me | Et | Me | A93 |
| c-Pr | Me | Me | Me | A94 | c-Pr | Me | Et | Me | A94 |
| c-Pr | Me | Me | Me | A95 | c-Pr | Me | Et | Me | A95 |
| c-Pr | Me | Me | Me | A96 | c-Pr | Me | H | Me | A96 |
| c-Pr | Me | Me | Me | A97 | c-Pr | Me | Et | Me | A97 |
| c-Pr | Me | Me | Me | A98 | c-Pr | Me | Et | Me | A98 |
| c-Pr | Me | Me | Me | A99 | c-Pr | Me | Et | Me | A99 |
| c-Pr | Me | Me | Me | A100 | c-Pr | Me | Et | Me | A100 |
| c-Pr | Me | Me | Me | A101 | c-Pr | Me | Et | Me | A101 |
| c-Pr | Me | Me | Me | A102 | c-Pr | Me | Et | Me | A102 |
| c-Pr | Me | Me | Me | A103 | c-Pr | Me | Et | Me | A103 |
| c-Pr | Me | Me | Me | A104 | c-Pr | Me | Et | Me | A104 |
| c-Pr | Me | Me | Me | A105 | c-Pr | Me | Et | Me | A105 |
| c-Pr | Me | Me | Me | A106 | c-Pr | Me | Et | Me | A106 |
| c-Pr | Me | Me | Me | A107 | c-Pr | Me | Et | Me | A107 |
| c-Pr | Me | Me | Me | A108 | c-Pr | Me | Et | Me | A108 |
| c-Pr | Me | Me | Me | A109 | c-Pr | Me | Et | Me | A109 |
| c-Pr | Me | Me | Me | A110 | c-Pr | Me | Et | Me | A110 |
| c-Pr | Me | Me | Me | A111 | c-Pr | Me | Et | Me | A111 |
| c-Pr | Me | Me | Me | A112 | c-Pr | Me | Et | Me | A112 |
| c-Pr | Me | Me | Me | A113 | c-Pr | Me | El | Me | A113 |
| c-Pr | Me | Me | Me | A114 | c-Pr | Me | Et | Me | A114 |
| D1-108b-1 | Me | Me | Me | H | D1-108b-1 | Me | Et | Me | H |
| D1-108b-4 | Me | Me | Me | H | D1-108b-4 | Me | Et | Me | H |
| D1-108b-8 | Me | Me | Me | H | D1-108b-8 | Me | Et | Me | H |
| D1-108b-16 | Me | Me | Me | H | D1-108b-16 | Me | Et | Me | H |
| D1-108b-17 | Me | Me | Me | H | D1-108b-17 | Me | Et | Me | H |
| D1-108b-18 | Me | Me | Me | H | D1-108b-18 | Me | Et | Me | II |
| D1-108b-19 | Me | Me | Me | H | D1-108b-19 | Me | Et | Me | H |
| $CH_2Pr$-c | Me | Me | Me | H | $CH_2Pr$-c | Me | Et | Me | H |
| $CH_2Bu$-c | Me | Me | Me | H | $CH_2Bu$-c | Me | Et | Me | H |
| $CH_2Pen$-c | Me | Me | Me | H | $CH_2Pen$-c | Me | Et | Me | H |
| $CH_2Hex$-c | Me | Me | Me | H | $CH_2Hex$-c | Me | Et | Me | H |
| Me | Me | Me | c-Pr | H | Me | Me | Et | c-Pr | H |
| Me | Me | Me | $CH=CH_2$ | H | Me | Me | Et | $CH=CH_2$ | H |
| Me | Me | Me | CH=CHPr-n | H | Me | Me | Et | CH=CHPr-n | H |

TABLE 1-continued

| | | | | | | | | |
|---|---|---|---|---|---|---|---|---|
| Me | Me | Me | CH=CHPh | H | Me | Me | Et | CH=CHPh | H |
| Me | Me | Me | C(O)Me | H | Me | Me | Et | C(O)Me | H |
| Me | Me | Me | C(O)OMe | H | Me | Me | Et | C(O)OMe | H |
| Me | Me | Me | C(=NOMe)Me | H | Me | Me | Et | C(=NOMe)Me | H |
| Me | Me | Me | OH | H | Me | Me | Et | OH | H |
| Me | Me | Me | OMe | H | Me | Me | Et | OMe | H |
| Me | Me | Me | OCH$_2$CH$_2$OMe | H | Me | Me | Et | OCH$_2$CH$_2$OMe | H |
| Me | Me | Me | OCH$_2$Ph | H | Me | Me | Et | OCH$_2$Ph | H |
| Me | Me | Me | OCH$_2$(D1-34a) | H | Me | Me | Et | OCH$_2$(D1-34a) | H |
| Me | Me | Me | OPh | H | Me | Me | Et | OPh | H |
| Me | Me | Me | O(D1-32b-1) | H | Me | Me | Et | O(D1-32b-1) | H |
| Me | Me | Me | Me | A115 | Me | Me | Et | Me | A115 |
| Me | Me | Me | SMe | H | Me | Me | Et | SMe | H |
| Me | Me | Me | S(O)Me | H | Me | Me | Et | S(O)Me | H |
| Me | Me | Me | S(O)$_2$Me | H | Me | Me | Et | S(O)$_2$Me | H |
| Me | Me | Me | NHC(O)OBu-t | H | Me | Me | Et | NHC(O)OBu-t | H |
| Me | Me | Me | H | H | Me | Me | Et | H | H |
| Me | Me | Me | Br | A1 | Me | Me | Et | Br | A1 |
| Me | Me | Me | Br | A2 | Me | Me | Et | Br | A2 |
| Me | Me | Me | Br | A3 | Me | Me | Et | Br | A3 |
| Me | Me | Me | Br | A4 | Me | Me | Et | Br | A4 |
| Me | Me | Me | Br | A5 | Me | Me | Et | Br | A5 |
| Me | Me | Me | Br | A6 | Me | Me | Et | Br | A6 |
| Me | Me | Me | Br | A7 | Me | Me | Et | Br | A7 |
| Me | Me | Me | Br | A8 | Me | Me | Et | Br | A8 |
| Me | Me | Me | Br | A9 | Me | Me | Et | Br | A9 |
| Me | Me | Me | Br | A10 | Me | Me | Et | Br | A10 |
| Me | Me | Me | Br | A11 | Me | Me | Et | Br | A11 |
| Me | Me | Me | Br | A12 | Me | Me | Et | Br | A12 |
| Me | Me | Me | Br | A13 | Me | Me | Et | Br | A13 |
| Me | Me | Me | Br | A14 | Me | Me | Et | Br | A14 |
| Me | Me | Me | Br | A15 | Me | Me | Et | Br | A15 |
| Me | Me | Me | Br | A16 | Me | Me | Et | Br | A16 |
| Me | Me | Me | Br | A17 | Me | Me | Et | Br | A17 |
| Me | Me | Me | Br | A18 | Me | Me | Et | Br | A18 |
| Me | Me | Me | Br | A19 | Me | Me | Et | Br | A19 |
| Me | Me | Me | Br | A20 | Me | Me | Et | Br | A20 |
| Me | Me | Me | Br | A21 | Me | Me | Et | Br | A21 |
| Me | Me | Me | Br | A22 | Me | Me | Et | Br | A22 |
| Me | Me | Me | Br | A23 | Me | Me | Et | Br | A23 |
| Me | Me | Me | Br | A24 | Me | Me | Et | Br | A24 |
| Me | Me | Me | Br | A25 | Me | Me | Et | Br | A25 |
| Me | Me | Me | Br | A26 | Me | Me | Et | Br | A26 |
| Me | Me | Me | Br | A27 | Me | Me | Et | Br | A27 |
| Me | Me | Me | Br | A28 | Me | Me | Et | Br | A28 |
| Me | Me | Me | Br | A29 | Me | Me | Et | Br | A29 |
| Me | Me | Me | Br | A30 | Me | Me | Et | Br | A30 |
| Me | Me | Me | Br | A31 | Me | Me | Et | Br | A31 |
| Me | Me | Me | Br | A32 | Me | Me | Et | Br | A32 |
| Me | Me | Me | Br | A33 | Me | Me | Et | Br | A33 |
| Me | Me | Me | Br | A34 | Me | Me | Et | Br | A34 |
| Me | Me | Me | Br | A35 | Me | Me | Et | Br | A35 |
| Me | Me | Me | Br | A36 | Me | Me | Et | Br | A36 |
| Me | Me | Me | Br | A37 | Me | Me | Et | Br | A37 |
| Me | Me | Me | Br | A38 | Me | Me | Et | Br | A38 |
| Me | Me | Me | Br | A39 | Me | Me | Et | Br | A39 |
| Me | Me | Me | Br | A40 | Me | Me | Et | Br | A40 |
| Me | Me | Me | Br | A41 | Me | Me | Et | Br | A41 |
| Me | Me | Me | Br | A42 | Me | Me | Et | Br | A42 |
| Me | Me | Me | Br | A43 | Me | Me | Et | Br | A43 |
| Me | Me | Me | Br | A44 | Me | Me | Et | Br | A44 |
| Me | Me | Me | Br | A45 | Me | Me | Et | Br | A45 |
| Me | Me | Me | Br | A46 | Me | Me | Et | Br | A46 |
| Me | Me | Me | Br | A47 | Me | Me | Et | Br | A47 |
| Me | Me | Me | Br | A48 | Me | Me | Et | Br | A48 |
| Me | Me | Me | Br | A49 | Me | Me | Et | Br | A49 |
| Me | Me | Me | Br | A50 | Me | Me | Et | Br | A50 |
| Me | Me | Me | Br | A51 | Me | Me | Et | Br | A51 |
| Me | Me | Me | Br | A52 | Me | Me | Et | Br | A52 |
| Me | Me | Me | Br | A53 | Me | Me | Et | Br | A53 |
| Me | Me | Me | Br | A54 | Me | Me | Et | Br | A54 |
| Me | Me | Me | Br | A55 | Me | Me | Et | Br | A55 |
| Me | Me | Me | Br | A56 | Me | Me | Et | Br | A56 |
| Me | Me | Me | Br | A57 | Me | Me | Et | Br | A57 |
| Me | Me | Me | Br | A58 | Me | Me | Et | Br | A58 |
| Me | Me | Me | Br | A59 | Me | Me | Et | Br | A59 |
| Me | Me | Me | Br | A60 | Me | Me | Et | Br | A60 |
| Me | Me | Me | Br | A61 | Me | Me | Et | Br | A61 |
| Me | Me | Me | Br | A62 | Me | Me | Et | Br | A62 |
| Me | Me | Me | Br | A63 | Me | Me | Et | Br | A63 |

TABLE 1-continued

| | | | | | | | | |
|---|---|---|---|---|---|---|---|---|
| Me | Me | Me | Br | A64 | Me | Me | Et | Br | A64 |
| Me | Me | Me | Br | A65 | Me | Me | Et | Br | A65 |
| Me | Me | Me | Br | A66 | Me | Me | Et | Br | A66 |
| Me | Me | Me | Br | A67 | Me | Me | Et | Br | A67 |
| Me | Me | Me | Br | A68 | Me | Me | Et | Br | A68 |
| Me | Me | Me | Br | A69 | Me | Me | Et | Br | A69 |
| Me | Me | Me | Br | A70 | Me | Me | Et | Br | A70 |
| Me | Me | Me | Br | A71 | Me | Me | Et | Br | A71 |
| Me | Me | Me | Br | A72 | Me | Me | Et | Br | A72 |
| Me | Me | Me | Br | A73 | Me | Me | Et | Br | A73 |
| Me | Me | Me | Br | A74 | Me | Me | Et | Br | A74 |
| Me | Me | Me | Br | A75 | Me | Me | Et | Br | A75 |
| Me | Me | Me | Br | A76 | Me | Me | Et | Br | A76 |
| Me | Me | Me | Br | A77 | Me | Me | Et | Br | A77 |
| Me | Me | Me | Br | A78 | Me | Me | Et | Br | A78 |
| Me | Me | Me | Br | A79 | Me | Me | Et | Br | A79 |
| Me | Me | Me | Br | A80 | Me | Me | Et | Br | A80 |
| Me | Me | Me | Br | A81 | Me | Me | Et | Br | A81 |
| Me | Me | Me | Br | A82 | Me | Me | Et | Br | A82 |
| Me | Me | Me | Br | A83 | Me | Me | Et | Br | A83 |
| Me | Me | Me | Br | A84 | Me | Me | Et | Br | A84 |
| Me | Me | Me | Br | A85 | Me | Me | Et | Br | A85 |
| Me | Me | Me | Br | A86 | Me | Me | Et | Br | A86 |
| Me | Me | Me | Br | A87 | Me | Me | Et | Br | A87 |
| Me | Me | Me | Br | A88 | Me | Me | Et | Br | A88 |
| Me | Me | Me | Br | A89 | Me | Me | Et | Br | A89 |
| Me | Me | Me | Br | A90 | Me | Me | Et | Br | A90 |
| Me | Me | Me | Br | A91 | Me | Me | Et | Br | A91 |
| Me | Me | Me | Br | A92 | Me | Me | Et | Br | A92 |
| Me | Me | Me | Br | A93 | Me | Me | Et | Br | A93 |
| Me | Me | Me | Br | A94 | Me | Me | Et | Br | A94 |
| Me | Me | Me | Br | A95 | Me | Me | Et | Br | A95 |
| Me | Me | Me | Br | A96 | Me | Me | Et | Br | A96 |
| Me | Me | Me | Br | A97 | Me | Me | Et | Br | A97 |
| Me | Me | Me | Br | A98 | Me | Me | Et | Br | A98 |
| Me | Me | Me | Br | A99 | Me | Me | Et | Br | A99 |
| Me | Me | Me | Br | A100 | Me | Me | Et | Br | A100 |
| Me | Me | Me | Br | A101 | Me | Me | Et | Br | A101 |
| Me | Me | Me | Br | A102 | Me | Me | Et | Br | A102 |
| Me | Me | Me | Br | A103 | Me | Me | Et | Br | A103 |
| Me | Me | Me | Br | A104 | Me | Me | Et | Br | A104 |
| Me | Me | Me | Br | A105 | Me | Me | Et | Br | A105 |
| Me | Me | Me | Br | A106 | Me | Me | Et | Br | A106 |
| Me | Me | Me | Br | A107 | Me | Me | Et | Br | A107 |
| Me | Me | Me | Br | A108 | Me | Me | Et | Br | A108 |
| Me | Me | Me | Br | A109 | Me | Me | Et | Br | A109 |
| Me | Me | Me | Br | A110 | Me | Me | Et | Br | A110 |
| Me | Me | Me | Br | A111 | Me | Me | Et | Br | A111 |
| Me | Me | Me | Br | A112 | Me | Me | Et | Br | A112 |
| Me | Me | Me | Br | A113 | Me | Me | Et | Br | A113 |
| Me | Me | Me | Br | A114 | Me | Me | Et | Br | A114 |
| Me | Me | Me | Br | A115 | Me | Me | Et | Br | A115 |
| Me | Me | Me | Br | A116 | Me | Me | Et | Br | A116 |
| Me | Et | Et | F | H | Me | Me | n-Pr | F | H |
| Me | Et | Et | Cl | H | Me | Me | n-Pr | Cl | H |
| Me | Et | Et | Br | H | Me | Me | n-Pr | Br | H |
| Me | Et | Et | I | H | Me | Me | n-Pr | I | H |
| Me | Et | Et | CN | H | Me | Me | n-Pr | CN | H |
| Me | Et | Et | $NO_2$ | H | Me | Me | n-Pr | $NO_2$ | H |
| $CH=CH_2$ | Et | Et | Me | H | $CH=CH_2$ | Me | n-Pr | Me | H |
| c-Bu | Et | Et | Me | H | c-Bu | Me | n-Pr | Me | H |
| c-Pen | Et | Et | Me | H | c-Pen | Me | n-Pr | Me | H |
| c-Hex | Et | Et | Me | H | c-Hex | Me | n-Pr | Me | H |
| Ph | Et | Et | Me | H | Ph | Me | n-Pr | Me | H |
| $CF_3$ | Et | Et | Me | H | $CF_3$ | Me | n-Pr | Me | H |
| $CH_2Cl$ | Et | Et | Me | H | $CH_2Cl$ | Me | n-Pr | Me | H |
| $CH_2OMe$ | Et | Et | Me | H | $CH_2OMe$ | Me | n-Pr | Me | H |
| D1-32a | Et | Et | Me | H | D1-32a | Me | n-Pr | Me | H |
| Me | Et | Et | Me | H | Me | Me | n-Pr | Me | H |
| Me | Et | Et | Me | A1 | Me | Me | n-Pr | Me | A1 |
| Me | Et | Et | Me | A2 | Me | Me | n-Pr | Me | A2 |
| Me | Et | Et | Me | A3 | Me | Me | n-Pr | Me | A3 |
| Me | Et | Et | Me | A4 | Me | Me | n-Pr | Me | A4 |
| Me | Et | Et | Me | A5 | Me | Me | n-Pr | Me | A5 |
| Me | Et | Et | Me | A6 | Me | Me | n-Pr | Me | A6 |
| Me | Et | Et | Me | A7 | Me | Me | n-Pr | Me | A7 |
| Me | Et | Et | Me | A8 | Me | Me | n-Pr | Me | A8 |
| Me | Et | Et | Me | A9 | Me | Me | n-Pr | Me | A9 |
| Me | Et | Et | Me | A10 | Me | Me | n-Pr | Me | A10 |
| Me | Et | Et | Me | A11 | Me | Me | n-Pr | Me | A11 |

TABLE 1-continued

| | | | | | | | | | |
|---|---|---|---|---|---|---|---|---|---|
| Me | Et | Et | Me | A12 | Me | Me | n-Pr | Me | A12 |
| Me | Et | Et | Me | A13 | Me | Me | n-Pr | Me | A13 |
| Me | Et | Et | Me | A14 | Me | Me | n-Pr | Me | A14 |
| Me | Et | Et | Me | A15 | Me | Me | n-Pr | Me | A15 |
| Me | Et | Et | Me | A16 | Me | Me | n-Pr | Me | A16 |
| Me | Et | Et | Me | A17 | Me | Me | n-Pr | Me | A17 |
| Me | Et | Et | Me | A18 | Me | Me | n-Pr | Me | A18 |
| Me | Et | Et | Me | A19 | Me | Me | n-Pr | Me | A19 |
| Me | Et | Et | Me | A20 | Me | Me | n-Pr | Me | A20 |
| Me | Et | Et | Me | A21 | Me | Me | n-Pr | Me | A21 |
| Me | Et | Et | Me | A22 | Me | Me | n-Pr | Me | A22 |
| Me | Et | Et | Me | A23 | Me | Me | n-Pr | Me | A23 |
| Me | Et | Et | Me | A24 | Me | Me | n-Pr | Me | A24 |
| Me | Et | Et | Me | A25 | Me | Me | n-Pr | Me | A25 |
| Me | Et | Et | Me | A26 | Me | Me | n-Pr | Me | A26 |
| Me | Et | Et | Me | A27 | Me | Me | n-Pr | Me | A27 |
| Me | Et | Et | Me | A28 | Me | Me | n-Pr | Me | A28 |
| Me | Et | Et | Me | A29 | Me | Me | n-Pr | Me | A29 |
| Me | Et | Et | Me | A30 | Me | Me | n-Pr | Me | A30 |
| Me | Et | Et | Me | A31 | Me | Me | n-Pr | Me | A31 |
| Me | Et | Et | Me | A32 | Me | Me | n-Pr | Me | A32 |
| Me | Et | Et | Me | A33 | Me | Me | n-Pr | Me | A33 |
| Me | Et | Et | Me | A34 | Me | Me | n-Pr | Me | A34 |
| Me | Et | Et | Me | A35 | Me | Me | n-Pr | Me | A35 |
| Me | Et | Et | Me | A36 | Me | Me | n-Pr | Me | A36 |
| Me | Et | Et | Me | A37 | Me | Me | n-Pr | Me | A37 |
| Me | Et | Et | Me | A38 | Me | Me | n-Pr | Me | A38 |
| Me | Et | Et | Me | A39 | Me | Me | n-Pr | Me | A39 |
| Me | Et | Et | Me | A40 | Me | Me | n-Pr | Me | A40 |
| Me | Et | Et | Me | A41 | Me | Me | n-Pr | Me | A41 |
| Me | Et | Et | Me | A42 | Me | Me | n-Pr | Me | A42 |
| Me | Et | Et | Me | A43 | Me | Me | n-Pr | Me | A43 |
| Me | Et | Et | Me | A44 | Me | Me | n-Pr | Me | A44 |
| Me | Et | Et | Me | A45 | Me | Me | n-Pr | Me | A45 |
| Me | Et | Et | Me | A46 | Me | Me | n-Pr | Me | A46 |
| Me | Et | Et | Me | A47 | Me | Me | n-Pr | Me | A47 |
| Me | Et | Et | Me | A48 | Me | Me | n-Pr | Me | A48 |
| Me | Et | Et | Me | A49 | Me | Me | n-Pr | Me | A49 |
| Me | Et | Et | Me | A50 | Me | Me | n-Pr | Me | A50 |
| Me | Et | Et | Me | A51 | Me | Me | n-Pr | Me | A51 |
| Me | Et | Et | Me | A52 | Me | Me | n-Pr | Me | A52 |
| Me | Et | Et | Me | A53 | Me | Me | n-Pr | Me | A53 |
| Me | Et | Et | Me | A54 | Me | Me | n-Pr | Me | A54 |
| Me | Et | Et | Me | A55 | Me | Me | n-Pr | Me | A55 |
| Me | Et | Et | Me | A56 | Me | Me | n-Pr | Me | A56 |
| Me | Et | Et | Me | A57 | Me | Me | n-Pr | Me | A57 |
| Me | Et | Et | Me | A58 | Me | Me | n-Pr | Me | A58 |
| Me | Et | Et | Me | A59 | Me | Me | n-Pr | Me | A59 |
| Me | Et | Et | Me | A60 | Me | Me | n-Pr | Me | A60 |
| Me | Et | Et | Me | A61 | Me | Me | n-Pr | Me | A61 |
| Me | Et | Et | Me | A62 | Me | Me | n-Pr | Me | A62 |
| Me | Et | Et | Me | A63 | Me | Me | n-Pr | Me | A63 |
| Me | Et | Et | Me | A64 | Me | Me | n-Pr | Me | A64 |
| Me | Et | Et | Me | A65 | Me | Me | n-Pr | Me | A65 |
| Me | Et | Et | Me | A66 | Me | Me | n-Pr | Me | A66 |
| Me | Et | Et | Me | A67 | Me | Me | n-Pr | Me | A67 |
| Me | Et | Et | Me | A68 | Me | Me | n-Pr | Me | A68 |
| Me | Et | Et | Me | A69 | Me | Me | n-Pr | Me | A69 |
| Me | Et | Et | Me | A70 | Me | Me | n-Pr | Me | A70 |
| Me | Et | Et | Me | A71 | Me | Me | n-Pr | Me | A71 |
| Me | Et | Et | Me | A72 | Me | Me | n-Pr | Me | A72 |
| Me | Et | Et | Me | A73 | Me | Me | n-Pr | Me | A73 |
| Me | Et | Et | Me | A74 | Me | Me | n-Pr | Me | A74 |
| Me | Et | Et | Me | A75 | Me | Me | n-Pr | Me | A75 |
| Me | Et | Et | Me | A76 | Me | Me | n-Pr | Me | A76 |
| Me | Et | Et | Me | A77 | Me | Me | n-Pr | Me | A77 |
| Me | Et | Et | Me | A78 | Me | Me | n-Pr | Me | A78 |
| Me | Et | Et | Me | A79 | Me | Me | n-Pr | Me | A79 |
| Me | Et | Et | Me | A80 | Me | Me | n-Pr | Me | A80 |
| Me | Et | Et | Me | A81 | Me | Me | n-Pr | Me | A81 |
| Me | Et | Et | Me | A82 | Me | Me | n-Pr | Me | A82 |
| Me | Et | Et | Me | A83 | Me | Me | n-Pr | Me | A83 |
| Me | Et | Et | Me | A84 | Me | Me | n-Pr | Me | A84 |
| Me | Et | Et | Me | A85 | Me | Me | n-Pr | Me | A85 |
| Me | Et | Et | Me | A86 | Me | Me | n-Pr | Me | A86 |
| Me | Et | Et | Me | A87 | Me | Me | n-Pr | Me | A87 |
| Me | Et | Et | Me | A88 | Me | Me | n-Pr | Me | A88 |
| Me | Et | Et | Me | A89 | Me | Me | n-Pr | Me | A89 |
| Me | Et | Et | Me | A90 | Me | Me | n-Pr | Me | A90 |
| Me | Et | Et | Me | A91 | Me | Me | n-Pr | Me | A91 |

TABLE 1-continued

| | | | | | | | | | |
|---|---|---|---|---|---|---|---|---|---|
| Me | Et | Et | Me | A92 | Me | Me | n-Pr | Me | A92 |
| Me | Et | Et | Me | A93 | Me | Me | n-Pr | Me | A93 |
| Me | Et | Et | Me | A94 | Me | Me | n-Pr | Me | A94 |
| Me | Et | Et | Me | A95 | Me | Me | n-Pr | Me | A95 |
| Me | Et | Et | Me | A96 | Me | Me | n-Pr | Me | A96 |
| Me | Et | Et | Me | A97 | Me | Me | n-Pr | Me | A97 |
| Me | Et | El | Me | A98 | Me | Me | n-Pr | Me | A98 |
| Me | Et | Et | Me | A99 | Me | Me | n-Pr | Me | A99 |
| Me | Et | Et | Me | A100 | Me | Me | n-Pr | Me | A100 |
| Me | Et | Et | Me | A101 | Me | Me | n-Pr | Me | A101 |
| Me | Et | Et | Me | A102 | Me | Me | n-Pr | Me | A102 |
| Me | Et | Et | Me | A103 | Me | Me | n-Pr | Me | A103 |
| Me | Et | Et | Me | A104 | Me | Me | n-Pr | Me | A104 |
| Me | Et | Et | Me | A105 | Me | Me | n-Pr | Me | A105 |
| Me | Et | Et | Me | A106 | Me | Me | n-Pr | Me | A106 |
| Me | Et | Et | Me | A107 | Me | Me | n-Pr | Me | A107 |
| Me | Et | Et | Me | A108 | Me | Me | n-Pr | Me | A108 |
| Me | Et | Et | Me | A109 | Me | Me | n-Pr | Me | A109 |
| Me | Et | Et | Me | A110 | Me | Me | n-Pr | Me | A110 |
| Me | Et | Et | Me | A111 | Me | Me | n-Pr | Me | A111 |
| Me | Et | Et | Me | A112 | Me | Me | n-Pr | Me | A112 |
| Me | Et | Et | Me | A113 | Me | Me | n-Pr | Me | A113 |
| Me | Et | Et | Me | A114 | Me | Me | n-Pr | Me | A114 |
| c-Pr | Et | Et | Me | H | c-Pr | Me | n-Pr | Me | H |
| c-Pr | Et | Et | Me | A1 | c-Pr | Me | n-Pr | Me | A1 |
| c-Pr | Et | Et | Me | A2 | c-Pr | Me | n-Pr | Me | A2 |
| c-Pr | Et | Et | Me | A3 | c-Pr | Me | n-Pr | Me | A3 |
| c-Pr | Et | Et | Me | A4 | c-Pr | Me | n-Pr | Me | A4 |
| c-Pr | Et | Et | Me | A5 | c-Pr | Me | n-Pr | Me | A5 |
| c-Pr | Et | Et | Me | A6 | c-Pr | Me | n-Pr | Me | A6 |
| c-Pr | Et | Et | Me | A7 | c-Pr | Me | n-Pr | Me | A7 |
| c-Pr | Et | Et | Me | A8 | c-Pr | Me | n-Pr | Me | A8 |
| c-Pr | Et | Et | Me | A9 | c-Pr | Me | n-Pr | Me | A9 |
| c-Pr | Et | Et | Me | A10 | c-Pr | Me | n-Pr | Me | A10 |
| c-Pr | Et | Et | Me | A11 | c-Pr | Me | n-Pr | Me | A11 |
| c-Pr | Et | Et | Me | A12 | c-Pr | Me | n-Pr | Me | A12 |
| c-Pr | Et | Et | Me | A13 | c-Pr | Me | n-Pr | Me | A13 |
| c-Pr | Et | Et | Me | A14 | c-Pr | Me | n-Pr | Me | A14 |
| c-Pr | Et | Et | Me | A15 | c-Pr | Me | n-Pr | Me | A15 |
| c-Pr | Et | Et | Me | A16 | c-Pr | Me | n-Pr | Me | A16 |
| c-Pr | Et | Et | Me | A17 | c-Pr | Me | n-Pr | Me | A17 |
| c-Pr | Et | Et | Me | A18 | c-Pr | Me | n-Pr | Me | A18 |
| c-Pr | Et | Et | Me | A19 | c-Pr | Me | n-Pr | Me | A19 |
| c-Pr | Et | Et | Me | A20 | c-Pr | Me | n-Pr | Me | A20 |
| c-Pr | Et | Et | Me | A21 | c-Pr | Me | n-Pr | Me | A21 |
| c-Pr | Et | Et | Me | A22 | c-Pr | Me | n-Pr | Me | A22 |
| c-Pr | Et | Et | Me | A23 | c-Pr | Me | n-Pr | Me | A23 |
| c-Pr | Et | Et | Me | A24 | c-Pr | Me | n-Pr | Me | A24 |
| c-Pr | Et | Et | Me | A25 | c-Pr | Me | n-Pr | Me | A25 |
| c-Pr | Et | Et | Me | A26 | c-Pr | Me | n-Pr | Me | A26 |
| c-Pr | Et | Et | Me | A27 | c-Pr | Me | n-Pr | Me | A27 |
| c-Pr | Et | Et | Me | A28 | c-Pr | Me | n-Pr | Me | A28 |
| c-Pr | Et | Et | Me | A29 | c-Pr | Me | n-Pr | Me | A29 |
| c-Pr | Et | Et | Me | A30 | c-Pr | Me | n-Pr | Me | A30 |
| c-Pr | Et | Et | Me | A31 | c-Pr | Me | n-Pr | Me | A31 |
| c-Pr | Et | Et | Me | A32 | c-Pr | Me | n-Pr | Me | A32 |
| c-Pr | Et | Et | Me | A33 | c-Pr | Me | n-Pr | Me | A33 |
| c-Pr | Et | Et | Me | A34 | c-Pr | Me | n-Pr | Me | A34 |
| c-Pr | Et | Et | Me | A35 | c-Pr | Me | n-Pr | Me | A35 |
| c-Pr | Et | Et | Me | A36 | c-Pr | Me | n-Pr | Me | A36 |
| c-Pr | Et | Et | Me | A37 | c-Pr | Me | n-Pr | Me | A37 |
| c-Pr | Et | Et | Me | A38 | c-Pr | Me | n-Pr | Me | A38 |
| c-Pr | Et | Et | Me | A39 | c-Pr | Me | n-Pr | Me | A39 |
| c-Pr | Et | Et | Me | A40 | c-Pr | Me | n-Pr | Me | A40 |
| c-Pr | Et | Et | Me | A41 | c-Pr | Me | n-Pr | Me | A41 |
| c-Pr | Et | Et | Me | A42 | c-Pr | Me | n-Pr | Me | A42 |
| c-Pr | Et | Et | Me | A43 | c-Pr | Me | n-Pr | Me | A43 |
| c-Pr | Et | Et | Me | A44 | c-Pr | Me | n-Pr | Me | A44 |
| c-Pr | Et | Et | Me | A45 | c-Pr | Me | n-Pr | Me | A45 |
| c-Pr | Et | Et | Me | A46 | c-Pr | Me | n-Pr | Me | A46 |
| c-Pr | Et | Et | Me | A47 | c-Pr | Me | n-Pr | Me | A47 |
| c-Pr | Et | Et | Me | A48 | c-Pr | Me | n-Pr | Me | A48 |
| c-Pr | Et | Et | Me | A49 | c-Pr | Me | n-Pr | Me | A49 |
| c-Pr | Et | Et | Me | A50 | c-Pr | Me | n-Pr | Me | A50 |
| c-Pr | Et | Et | Me | A51 | c-pr | Me | n-Pr | Me | A51 |
| c-Pr | Et | Et | Me | A52 | c-Pr | Me | n-Pr | Me | A52 |
| c-Pr | Et | Et | Me | A53 | c-Pr | Me | n-Pr | Me | A53 |
| c-Pr | Et | Et | Me | A54 | c-Pr | Me | n-Pr | Me | A54 |
| c-Pr | Et | Et | Me | A55 | c-Pr | Me | n-Pr | Me | A55 |
| c-Pr | Et | Et | Me | A56 | c-Pr | Me | n-Pr | Me | A56 |

TABLE 1-continued

| | | | | | | | | |
|---|---|---|---|---|---|---|---|---|
| c-Pr | Et | Et | Me | A57 | c-Pr | Me | n-Pr | Me | A57 |
| c-Pr | Et | Et | Me | A58 | c-Pr | Me | n-Pr | Me | A58 |
| c-Pr | Et | Et | Me | A59 | c-Pr | Me | n-Pr | Me | A59 |
| c-Pr | Et | Et | Me | A60 | c-Pr | Me | n-Pr | Me | A60 |
| c-Pr | Et | Et | Me | A61 | c-Pr | Me | n-Pr | Me | A61 |
| c-Pr | Et | Et | Me | A62 | c-Pr | Me | n-Pr | Me | A62 |
| c-Pr | Et | Et | Me | A63 | c-Pr | Me | n-Pr | Me | A63 |
| c-Pr | Et | Et | Me | A64 | c-Pr | Me | n-Pr | Me | A64 |
| c-Pr | Et | Et | Me | A65 | c-Pr | Me | n-Pr | Me | A65 |
| c-Pr | Et | Et | Me | A66 | c-Pr | Me | n-Pr | Me | A66 |
| c-Pr | Et | Et | Me | A67 | c-Pr | Me | n-Pr | Me | A67 |
| c-Pr | Et | Et | Me | A68 | c-Pr | Me | n-Pr | Me | A68 |
| c-Pr | Et | Et | Me | A69 | c-Pr | Me | n-Pr | Me | A69 |
| c-Pr | Et | Et | Me | A70 | c-Pr | Me | n-Pr | Me | A70 |
| c-Pr | Et | Et | Me | A71 | c-Pr | Me | n-Pr | Me | A71 |
| c-Pr | Et | Et | Me | A72 | c-Pr | Me | n-Pr | Me | A72 |
| c-Pr | Et | Et | Me | A73 | c-Pr | Me | n-Pr | Me | A73 |
| c-Pr | Et | Et | Me | A74 | c-Pr | Me | n-Pr | Me | A74 |
| c-Pr | Et | Et | Me | A75 | c-Pr | Me | n-Pr | Me | A75 |
| c-Pr | Et | Et | Me | A76 | c-Pr | Me | n-Pr | Me | A76 |
| c-Pr | Et | Et | Me | A77 | c-Pr | Me | n-Pr | Me | A77 |
| c-Pr | Et | Et | Me | A78 | c-Pr | Me | n-Pr | Me | A78 |
| c-Pr | Et | Et | Me | A79 | c-Pr | Me | n-Pr | Me | A79 |
| c-Pr | Et | Et | Me | A80 | c-Pr | Me | n-Pr | Me | A80 |
| c-Pr | Et | Et | Me | A81 | c-Pr | Me | n-Pr | Me | A81 |
| c-Pr | Et | Et | Me | A82 | c-Pr | Me | n-Pr | Me | A82 |
| c-Pr | Et | Et | Me | A83 | c-Pr | Me | n-Pr | Me | A83 |
| c-Pr | Et | Et | Me | A84 | c-Pr | Me | n-Pr | Me | A84 |
| c-Pr | Et | Et | Me | A85 | c-Pr | Me | n-Pr | Me | A85 |
| c-Pr | Et | Et | Me | A86 | c-Pr | Me | n-Pr | Me | A86 |
| c-Pr | Et | Et | Me | A87 | c-Pr | Me | n-Pr | Me | A87 |
| c-Pr | Et | Et | Me | A88 | c-Pr | Me | n-Pr | Me | A88 |
| c-Pr | Et | Et | Me | A89 | c-Pr | Me | n-Pr | Me | A89 |
| c-Pr | Et | Et | Me | A90 | c-Pr | Me | n-Pr | Me | A90 |
| c-Pr | Et | Et | Me | A91 | c-Pr | Me | n-Pr | Me | A91 |
| c-Pr | Et | Et | Me | A92 | c-Pr | Me | n-Pr | Me | A92 |
| c-Pr | Et | Et | Me | A93 | c-Pr | Me | n-Pr | Me | A93 |
| c-Pr | Et | Et | Me | A94 | c-Pr | Me | n-Pr | Me | A94 |
| c-Pr | Et | Et | Me | A95 | c-Pr | Me | n-Pr | Me | A95 |
| c-Pr | Et | Et | Me | A96 | c-Pr | Me | n-Pr | Me | A96 |
| c-Pr | Et | Et | Me | A97 | c-Pr | Me | n-Pr | Me | A97 |
| c-Pr | Et | Et | Me | A98 | c-Pr | Me | n-Pr | Me | A98 |
| c-Pr | Et | Et | Me | A99 | c-Pr | Me | n-Pr | Me | A99 |
| c-Pr | Et | Et | Me | A100 | c-Pr | Me | n-Pr | Me | A100 |
| c-Pr | Et | Et | Me | A101 | c-Pr | Me | n-Pr | Me | A101 |
| c-Pr | Et | Et | Me | A102 | c-Pr | Me | n-Pr | Me | A102 |
| c-Pr | Et | Et | Me | A103 | c-Pr | Me | n-Pr | Me | A103 |
| c-Pr | Et | Et | Me | A104 | c-Pr | Me | n-Pr | Me | A104 |
| c-Pr | Et | Et | Me | A105 | c-Pr | Me | n-Pr | Me | A105 |
| c-Pr | Et | Et | Me | A106 | c-Pr | Me | n-Pr | Me | A106 |
| c-Pr | Et | Et | Me | A107 | c-Pr | Me | n-Pr | Me | A107 |
| c-Pr | Et | Et | Me | A108 | c-Pr | Me | n-Pr | Me | A108 |
| c-Pr | Et | Et | Me | A109 | c-Pr | Me | n-Pr | Me | A109 |
| c-Pr | Et | Et | Me | A110 | c-Pr | Me | n-Pr | Me | A110 |
| c-Pr | Et | Et | Me | A111 | c-Pr | Me | n-Pr | Me | A111 |
| c-Pr | Et | Et | Me | A112 | c-Pr | Me | n-Pr | Me | A112 |
| c-Pr | Et | Et | Me | A113 | c-Pr | Me | n-Pr | Me | A113 |
| c-Pr | Et | Et | Me | A114 | c-Pr | Me | n-Pr | Me | A114 |
| D1-108b-1 | Et | Et | Me | H | D1-108b-1 | Me | n-Pr | Me | H |
| D1-108b-4 | Et | Et | Me | H | D1-108b-4 | Me | n-Pr | Me | H |
| D1-108b-8 | Et | Et | Me | H | D1-108b-8 | Me | n-Pr | Me | H |
| D1-108b-16 | Et | Et | Me | H | D1-108b-16 | Me | n-Pr | Me | H |
| D1-108b-17 | Et | Et | Me | H | D1-108b-17 | Me | n-Pr | Me | H |
| D1-108b-18 | Et | Et | Me | H | D1-108b-18 | Me | n-Pr | Me | H |
| D1-108b-19 | Et | Et | Me | H | D1-108b-19 | Me | n-Pr | Me | H |
| $CH_2Pr$-c | Et | Et | Me | H | $CH_2Pr$-c | Me | n-Pr | Me | H |
| $CH_2Bu$-c | Et | Et | Me | H | $CH_2Bu$-c | Me | n-Pr | Me | H |
| $CH_2Pen$-c | Et | Et | Me | H | $CH_2Pen$-c | Me | n-Pr | Me | H |
| $CH_2Hex$-c | Et | Et | Me | H | $CH_2Hex$-c | Me | n-Pr | Me | H |
| Me | Et | Et | c-Pr | H | Me | Me | n-Pr | c-Pr | H |
| Me | Et | Et | CH=$CH_2$ | H | Me | Me | n-Pr | CH=$CH_2$ | H |
| Me | Et | Et | CH=CHPr-n | H | Me | Me | n-Pr | CH=CHPr-n | H |
| Me | Et | Et | CH=CHPh | H | Me | Me | n-Pr | CH=CHPh | H |
| Me | Et | Et | C(O)Me | H | Me | Me | n-Pr | C(O)Me | H |
| Me | Et | Et | C(O)OMe | H | Me | Me | n-Pr | C(O)OMe | H |
| Me | Et | Et | C(=NOMe)Me | H | Me | Me | n-Pr | C(=NOMe)Me | H |
| Me | Et | Et | OH | H | Me | Me | n-Pr | OH | H |
| Me | Et | Et | OMe | H | Me | Me | n-Pr | OMe | H |
| Me | Et | Et | $OCH_2CH_2OMe$ | H | Me | Me | n-Pr | $OCH_2CH_2OMe$ | H |
| Me | Et | Et | $OCH_2Ph$ | H | Me | Me | n-Pr | $OCH_2Ph$ | H |

TABLE 1-continued

| Me | Et | Et | OCH$_2$(D1-34a) | H | Me | Me | n-Pr | OCH$_2$(D1-34a) | H |
|---|---|---|---|---|---|---|---|---|---|
| Me | Et | Et | OPh | H | Me | Me | n-Pr | OPh | H |
| Me | Et | Et | O(D1-32b-1) | H | Me | Me | n-Pr | O(D1-32b-1) | H |
| Me | Et | Et | Me | A115 | Me | Me | n-Pr | Me | A115 |
| Me | Et | Et | SMe | H | Me | Me | n-Pr | SMe | H |
| Me | Et | Et | S(O)Me | H | Me | Me | n-Pr | S(O)Me | H |
| Me | Et | Et | S(O)$_2$Me | H | Me | Me | n-Pr | S(O)$_2$Me | H |
| Me | Et | Et | NHC(O)OBu-t | H | Me | Me | n-Pr | NHC(O)OBu-t | H |
| Me | Et | Et | H | H | Me | Me | n-Pr | H | H |
| Me | Et | Et | Br | A1 | Me | Me | n-Pr | Br | A1 |
| Me | Et | Et | Br | A2 | Me | Me | n-Pr | Br | A2 |
| Me | Et | Et | Br | A3 | Me | Me | n-Pr | Br | A3 |
| Me | Et | Et | Br | A4 | Me | Me | n-Pr | Br | A4 |
| Me | Et | Et | Br | A5 | Me | Me | n-Pr | Br | A5 |
| Me | Et | Et | Br | A6 | Me | Me | n-Pr | Br | A6 |
| Me | Et | Et | Br | A7 | Me | Me | n-Pr | Br | A7 |
| Me | Et | Et | Br | A8 | Me | Me | n-Pr | Br | A8 |
| Me | Et | Et | Br | A9 | Me | Me | n-Pr | Br | A9 |
| Me | Et | Et | Br | A10 | Me | Me | n-Pr | Br | A10 |
| Me | Et | Et | Br | A11 | Me | Me | n-Pr | Br | A11 |
| Me | Et | Et | Br | A12 | Me | Me | n-Pr | Br | A12 |
| Me | Et | Et | Br | A13 | Me | Me | n-Pr | Br | A13 |
| Me | Et | Et | Br | A14 | Me | Me | n-Pr | Br | A14 |
| Me | Et | Et | Br | A15 | Me | Me | n-Pr | Br | A15 |
| Me | Et | Et | Br | A16 | Me | Me | n-Pr | Br | A16 |
| Me | Et | Et | Br | A17 | Me | Me | n-Pr | Br | A17 |
| Me | Et | Et | Br | A18 | Me | Me | n-Pr | Br | A18 |
| Me | Et | Et | Br | A19 | Me | Me | n-Pr | Br | A19 |
| Me | Et | Et | Br | A20 | Me | Me | n-Pr | Br | A20 |
| Me | Et | Et | Br | A21 | Me | Me | n-Pr | Br | A21 |
| Me | Et | Et | Br | A22 | Me | Me | n-Pr | Br | A22 |
| Me | Et | Et | Br | A23 | Me | Me | n-Pr | Br | A23 |
| Me | Et | Et | Br | A24 | Me | Me | n-Pr | Br | A24 |
| Me | Et | Et | Br | A25 | Me | Me | n-Pr | Br | A25 |
| Me | Et | Et | Br | A26 | Me | Me | n-Pr | Br | A26 |
| Me | Et | Et | Br | A27 | Me | Me | n-Pr | Br | A27 |
| Me | Et | Et | Br | A28 | Me | Me | n-Pr | Br | A28 |
| Me | Et | Et | Br | A29 | Me | Me | n-Pr | Br | A29 |
| Me | Et | Et | Br | A30 | Me | Me | n-Pr | Br | A30 |
| Me | Et | Et | Br | A31 | Me | Me | n-Pr | Br | A31 |
| Me | Et | Et | Br | A32 | Me | Me | n-Pr | Br | A32 |
| Me | Et | Et | Br | A33 | Me | Me | n-Pr | Br | A33 |
| Me | Et | Et | Br | A34 | Me | Me | n-Pr | Br | A34 |
| Me | Et | Et | Br | A35 | Me | Me | n-Pr | Br | A35 |
| Me | Et | Et | Br | A36 | Me | Me | n-Pr | Br | A36 |
| Me | Et | Et | Br | A37 | Me | Me | n-Pr | Br | A37 |
| Me | Et | Et | Br | A38 | Me | Me | n-Pr | Br | A38 |
| Me | Et | Et | Br | A39 | Me | Me | n-Pr | Br | A39 |
| Me | Et | Et | Br | A40 | Me | Me | n-Pr | Br | A40 |
| Me | Et | Et | Br | A41 | Me | Me | n-Pr | Br | A41 |
| Me | Et | Et | Br | A42 | Me | Me | n-Pr | Br | A42 |
| Me | Et | Et | Br | A43 | Me | Me | n-Pr | Br | A43 |
| Me | Et | Et | Br | A44 | Me | Me | n-Pr | Br | A44 |
| Me | Et | Et | Br | A45 | Me | Me | n-Pr | Br | A45 |
| Me | Et | Et | Br | A46 | Me | Me | n-Pr | Br | A46 |
| Me | Et | Et | Br | A47 | Me | Me | n-Pr | Br | A47 |
| Me | Et | Et | Br | A48 | Me | Me | n-Pr | Br | A48 |
| Me | Et | Et | Br | A49 | Me | Me | n-Pr | Br | A49 |
| Me | Et | Et | Br | A50 | Me | Me | n-Pr | Br | A50 |
| Me | Et | Et | Br | A51 | Me | Me | n-Pr | Br | A51 |
| Me | Et | Et | Br | A52 | Me | Me | n-Pr | Br | A52 |
| Me | Et | Et | Br | A53 | Me | Me | n-Pr | Br | A53 |
| Me | Et | Et | Br | A54 | Me | Me | n-Pr | Br | A54 |
| Me | Et | Et | Br | A55 | Me | Me | n-Pr | Br | A55 |
| Me | Et | Et | Br | A56 | Me | Me | n-Pr | Br | A56 |
| Me | Et | Et | Br | A57 | Me | Me | n-Pr | Br | A57 |
| Me | Et | Et | Br | A58 | Me | Me | n-Pr | Br | A58 |
| Me | Et | Et | Br | A59 | Me | Me | n-Pr | Br | A59 |
| Me | Et | Et | Br | A60 | Me | Me | n-Pr | Br | A60 |
| Me | Et | Et | Br | A61 | Me | Me | n-Pr | Br | A61 |
| Me | Et | Et | Br | A62 | Me | Me | n-Pr | Br | A62 |
| Me | Et | Et | Br | A63 | Me | Me | n-Pr | Br | A63 |
| Me | Et | Et | Br | A64 | Me | Me | n-Pr | Br | A64 |
| Me | Et | Et | Br | A65 | Me | Me | n-Pr | Br | A65 |
| Me | Et | Et | Br | A66 | Me | Me | n-Pr | Br | A66 |
| Me | Et | Et | Br | A67 | Me | Me | n-Pr | Br | A67 |
| Me | Et | Et | Br | A68 | Me | Me | n-Pr | Br | A68 |
| Me | Et | Et | Br | A69 | Me | Me | n-Pr | Br | A69 |
| Me | Et | Et | Br | A70 | Me | Me | n-Pr | Br | A70 |
| Me | Et | Et | Br | A71 | Me | Me | n-Pr | Br | A71 |

TABLE 1-continued

| | | | | | | | | | |
|---|---|---|---|---|---|---|---|---|---|
| Me | Et | Et | Br | A72 | Me | Me | n-Pr | Br | A72 |
| Me | Et | Et | Br | A73 | Me | Me | n-Pr | Br | A73 |
| Me | Et | Et | Br | A74 | Me | Me | n-Pr | Br | A74 |
| Me | Et | Et | Br | A75 | Me | Me | n-Pr | Br | A75 |
| Me | Et | Et | Br | A76 | Me | Me | n-Pr | Br | A76 |
| Me | Et | Et | Br | A77 | Me | Me | n-Pr | Br | A77 |
| Me | Et | Et | Br | A78 | Me | Me | n-Pr | Br | A78 |
| Me | Et | Et | Br | A79 | Me | Me | n-Pr | Br | A79 |
| Me | Et | Et | Br | A80 | Me | Me | n-Pr | Br | A80 |
| Me | Et | Et | Br | A81 | Me | Me | n-Pr | Br | A81 |
| Me | Et | Et | Br | A82 | Me | Me | n-Pr | Br | A82 |
| Me | Et | Et | Br | A83 | Me | Me | n-Pr | Br | A83 |
| Me | Et | Et | Br | A84 | Me | Me | n-Pr | Br | A84 |
| Me | Et | Et | Br | A85 | Me | Me | n-Pr | Br | A85 |
| Me | Et | Et | Br | A86 | Me | Me | n-Pr | Br | A86 |
| Me | Et | Et | Br | A87 | Me | Me | n-Pr | Br | A87 |
| Me | Et | Et | Br | A88 | Me | Me | n-Pr | Br | A88 |
| Me | Et | Et | Br | A89 | Me | Me | n-Pr | Br | A89 |
| Me | Et | Et | Br | A90 | Me | Me | n-Pr | Br | A90 |
| Me | Et | Et | Br | A91 | Me | Me | n-Pr | Br | A91 |
| Me | Et | Et | Br | A92 | Me | Me | n-Pr | Br | A92 |
| Me | Et | Et | Br | A93 | Me | Me | n-Pr | Br | A93 |
| Me | Et | Et | Br | A94 | Me | Me | n-Pr | Br | A94 |
| Me | Et | Et | Br | A95 | Me | Me | n-Pr | Br | A95 |
| Me | Et | Et | Br | A96 | Me | Me | n-Pr | Br | A96 |
| Me | Et | Et | Br | A97 | Me | Me | n-Pr | Br | A97 |
| Me | Et | Et | Br | A98 | Me | Me | n-Pr | Br | A98 |
| Me | Et | Et | Br | A99 | Me | Me | n-Pr | Br | A99 |
| Me | Et | Et | Br | A100 | Me | Me | n-Pr | Br | A100 |
| Me | Et | Et | Br | A101 | Me | Me | n-Pr | Br | A101 |
| Me | Et | Et | Br | A102 | Me | Me | n-Pr | Br | A102 |
| Me | Et | Et | Br | A103 | Me | Me | n-Pr | Br | A103 |
| Me | Et | Et | Br | A104 | Me | Me | n-Pr | Br | A104 |
| Me | Et | Et | Br | A105 | Me | Me | n-Pr | Br | A105 |
| Me | Et | Et | Br | A106 | Me | Me | n-Pr | Br | A106 |
| Me | Et | Et | Br | A107 | Me | Me | n-Pr | Br | A107 |
| Me | Et | Et | Br | A108 | Me | Me | n-Pr | Br | A108 |
| Me | Et | Et | Br | A109 | Me | Me | n-Pr | Br | A109 |
| Me | Et | Et | Br | A110 | Me | Me | n-Pr | Br | A110 |
| Me | Et | Et | Br | A111 | Me | Me | n-Pr | Br | A111 |
| Me | Et | Et | Br | A112 | Me | Me | n-Pr | Br | A112 |
| Me | Et | Et | Br | A113 | Me | Me | n-Pr | Br | A113 |
| Me | Et | Et | Br | A114 | Me | Me | n-Pr | Br | A114 |
| Me | Et | Et | Br | A115 | Me | Me | n-Pr | Br | A115 |
| Me | Et | Et | Br | A116 | Me | Me | n-Pr | Br | A116 |
| H | Me | Me | F | H | H | Et | Et | F | H |
| H | Me | Me | Cl | H | H | Et | Et | Cl | H |
| H | Me | Me | Br | H | H | Et | Et | Br | H |
| H | Me | Me | I | H | H | Et | Et | I | H |
| H | Me | Me | CN | H | H | Et | Et | CN | H |
| H | Me | Me | $NO_2$ | H | H | Et | Et | $NO_2$ | H |
| H | Me | Me | Me | H | H | Et | Et | Me | H |
| H | Me | Me | Me | A1 | H | Et | Et | Me | A1 |
| H | Me | Me | Me | A2 | H | Et | Et | Me | A2 |
| H | Me | Me | Me | A3 | H | Et | Et | Me | A3 |
| H | Me | Me | Me | A4 | H | Et | Et | Me | A4 |
| H | Me | Me | Me | A5 | H | Et | Et | Me | A5 |
| H | Me | Me | Me | A6 | H | Et | Et | Me | A6 |
| H | Me | Me | Me | A7 | H | Et | Et | Me | A7 |
| H | Me | Me | Me | A8 | H | Et | Et | Me | A8 |
| H | Me | Me | Me | A9 | H | Et | Et | Me | A9 |
| H | Me | Me | Me | A10 | H | Et | Et | Me | A10 |
| H | Me | Me | Me | A11 | H | Et | Et | Me | A11 |
| H | Me | Me | Me | A12 | H | Et | Et | Me | A12 |
| H | Me | Me | Me | A13 | H | Et | Et | Me | A13 |
| H | Me | Me | Me | A14 | H | Et | Et | Me | A14 |
| H | Me | Me | Me | A15 | H | Et | Et | Me | A15 |
| H | Me | Me | Me | A16 | H | Et | Et | Me | A16 |
| H | Me | Me | Me | A17 | H | Et | Et | Me | A17 |
| H | Me | Me | Me | A18 | H | Et | Et | Me | A18 |
| H | Me | Me | Me | A19 | H | Et | Et | Me | A19 |
| H | Me | Me | Me | A20 | H | Et | Et | Me | A20 |
| H | Me | Me | Me | A21 | H | Et | Et | Me | A21 |
| H | Me | Me | Me | A22 | H | Et | Et | Me | A22 |
| H | Me | Me | Me | A23 | H | Et | Et | Me | A23 |
| H | Me | Me | Me | A24 | H | Et | Et | Me | A24 |
| H | Me | Me | Me | A25 | H | Et | Et | Me | A25 |
| H | Me | Me | Me | A26 | H | Et | Et | Me | A26 |
| H | Me | Me | Me | A27 | H | Et | Et | Me | A27 |
| H | Me | Me | Me | A28 | H | Et | Et | Me | A28 |

TABLE 1-continued

| | | | | | | | | | |
|---|---|---|---|---|---|---|---|---|---|
| H | Me | Me | Me | A29 | H | Et | Et | Me | A29 |
| H | Me | Me | Me | A30 | H | Et | Et | Me | A30 |
| H | Me | Me | Me | A31 | H | Et | Et | Me | A31 |
| H | Me | Me | Me | A32 | H | Et | Et | Me | A32 |
| H | Me | Me | Me | A33 | H | Et | Et | Me | A33 |
| H | Me | Me | Me | A34 | H | Et | Et | Me | A34 |
| H | Me | Me | Me | A35 | H | Et | Et | Me | A35 |
| H | Me | Me | Me | A36 | H | Et | Et | Me | A36 |
| H | Me | Me | Me | A37 | H | Et | Et | Me | A37 |
| H | Me | Me | Me | A38 | H | Et | Et | Me | A38 |
| H | Me | Me | Me | A39 | H | Et | Et | Me | A39 |
| H | Me | Me | Me | A40 | H | Et | Et | Me | A40 |
| H | Me | Me | Me | A41 | H | Et | Et | Me | A41 |
| H | Me | Me | Me | A42 | H | Et | Et | Me | A42 |
| H | Me | Me | Me | A43 | H | Et | Et | Me | A43 |
| H | Me | Me | Me | A44 | H | Et | Et | Me | A44 |
| H | Me | Me | Me | A45 | H | Et | Et | Me | A45 |
| H | Me | Me | Me | A46 | H | Et | Et | Me | A46 |
| H | Me | Me | Me | A47 | H | Et | Et | Me | A47 |
| H | Me | Me | Me | A48 | H | Et | Et | Me | A48 |
| H | Me | Me | Me | A49 | H | Et | Et | Me | A49 |
| H | Me | Me | Me | A50 | H | Et | Et | Me | A50 |
| H | Me | Me | Me | A51 | H | Et | Et | Me | A51 |
| H | Me | Me | Me | A52 | H | Et | Et | Me | A52 |
| H | Me | Me | Me | A53 | H | Et | Et | Me | A53 |
| H | Me | Me | Me | A54 | H | Et | Et | Me | A54 |
| H | Me | Me | Me | A55 | H | Et | Et | Me | A55 |
| H | Me | Me | Me | A56 | H | Et | Et | Me | A56 |
| H | Me | Me | Me | A57 | H | Et | Et | Me | A57 |
| H | Me | Me | Me | A58 | H | Et | Et | Me | A58 |
| H | Me | Me | Me | A59 | H | Et | Et | Me | A59 |
| H | Me | Me | Me | A60 | H | Et | Et | Me | A60 |
| H | Me | Me | Me | A61 | H | Et | Et | Me | A61 |
| H | Me | Me | Me | A62 | H | Et | Et | Me | A62 |
| H | Me | Me | Me | A63 | H | Et | Et | Me | A63 |
| H | Me | Me | Me | A64 | H | Et | Et | Me | A64 |
| H | Me | Me | Me | A65 | H | Et | Et | Me | A65 |
| H | Me | Me | Me | A66 | H | Et | Et | Me | A66 |
| H | Me | Me | Me | A67 | H | Et | Et | Me | A67 |
| H | Me | Me | Me | A68 | H | Et | Et | Me | A68 |
| H | Me | Me | Me | A69 | H | Et | Et | Me | A69 |
| H | Me | Me | Me | A70 | H | Et | Et | Me | A70 |
| H | Me | Me | Me | A71 | H | Et | Et | Me | A71 |
| H | Me | Me | Me | A72 | H | Et | Et | Me | A72 |
| H | Me | Me | Me | A73 | H | Et | Et | Me | A73 |
| H | Me | Me | Me | A74 | H | Et | Et | Me | A74 |
| H | Me | Me | Me | A75 | H | Et | Et | Me | A75 |
| H | Me | Me | Me | A76 | H | Et | Et | Me | A76 |
| H | Me | Me | Me | A77 | H | Et | Et | Me | A77 |
| H | Me | Me | Me | A78 | H | Et | Et | Me | A78 |
| H | Me | Me | Me | A79 | H | Et | Et | Me | A79 |
| H | Me | Me | Me | A80 | H | Et | Et | Me | A80 |
| H | Me | Me | Me | A81 | H | Et | Et | Me | A81 |
| H | Me | Me | Me | A82 | H | Et | Et | Me | A82 |
| H | Me | Me | Me | A83 | H | Et | Et | Me | A83 |
| H | Me | Me | Me | A84 | H | Et | Et | Me | A84 |
| H | Me | Me | Me | A85 | H | Et | Et | Me | A85 |
| H | Me | Me | Me | A86 | H | Et | Et | Me | A86 |
| H | Me | Me | Me | A87 | H | Et | Et | Me | A87 |
| H | Me | Me | Me | A88 | H | Et | Et | Me | A88 |
| H | Me | Me | Me | A89 | H | Et | Et | Me | A89 |
| H | Me | Me | Me | A90 | H | Et | Et | Me | A90 |
| H | Me | Me | Me | A91 | H | Et | Et | Me | A91 |
| H | Me | Me | Me | A92 | H | Et | Et | Me | A92 |
| H | Me | Me | Me | A93 | H | Et | Et | Me | A93 |
| H | Me | Me | Me | A94 | H | Et | Et | Me | A94 |
| H | Me | Me | Me | A95 | H | Et | Et | Me | A95 |
| H | Me | Me | Me | A96 | H | Et | Et | Me | A96 |
| H | Me | Me | Me | A97 | H | Et | Et | Me | A97 |
| H | Me | Me | Me | A98 | H | Et | Et | Me | A98 |
| H | Me | Me | Me | A99 | H | Et | Et | Me | A99 |
| H | Me | Me | Me | A100 | H | Et | Et | Me | A100 |
| H | Me | Me | Me | A101 | H | Et | Et | Me | A101 |
| H | Me | Me | Me | A102 | H | Et | Et | Me | A102 |
| H | Me | Me | Me | A103 | H | Et | Et | Me | A103 |
| H | Me | Me | Me | A104 | H | Et | Et | Me | A104 |
| H | Me | Me | Me | A105 | H | Et | Et | Me | A105 |
| H | Me | Me | Me | A106 | H | Et | Et | Me | A106 |
| H | Me | Me | c-Pr | H | H | Et | Et | c-Pr | H |
| H | Me | Me | CH=CH$_2$ | H | H | Et | Et | CH=CH$_2$ | H |

TABLE 1-continued

| | | | | | | | | | |
|---|---|---|---|---|---|---|---|---|---|
| H | Me | Me | CH=CHPr-n | H | H | Et | Et | CH=CHPr-n | H |
| H | Me | Me | CH=CHPh | H | H | Et | Et | CH=CHPh | H |
| H | Me | Me | C(O)Me | H | H | Et | Et | C(O)Me | H |
| H | Me | Me | C(O)OMe | H | H | Et | Et | C(O)OMe | H |
| H | Me | Me | C(=NOMe)Me | H | H | Et | Fl | C(=NOMe)Me | H |
| H | Me | Me | OH | H | H | Et | Et | OH | H |
| H | Me | Me | OMe | H | H | Et | Et | OMe | H |
| H | Me | Me | OCH$_2$CH$_2$OMe | H | H | Et | Et | OCH$_2$CH$_2$OMe | H |
| H | Me | Me | OCH$_2$Ph | H | H | Et | Et | OCH$_2$Ph | H |
| H | Me | Me | OCH$_2$(D1-34a) | H | H | Et | Et | OCH$_2$(D1-34a) | H |
| H | Me | Me | OPh | H | H | Et | Et | OPh | H |
| H | Me | Me | O(D1-32b-1) | H | H | El | Et | O(D1-32b-1) | H |
| H | Me | Me | OCH$_2$CF$_3$ | H | H | Et | Et | OCH$_2$CF$_3$ | H |
| H | Me | Me | SMe | H | H | Et | Et | SMe | H |
| H | Me | Me | S(O)Me | H | H | Et | Et | S(O)Me | H |
| H | Me | Me | S(O)$_2$Me | H | H | Et | Et | S(O)$_2$Me | H |
| H | Me | Me | NHC(O)OBu-t | H | H | Et | Et | NHC(O)OBu-t | H |
| Me | Me | Me | Me | A116 | Me | Et | Et | Me | A116 |
| Me | Me | Et | Me | A116 | Me | Me | n-Pr | Me | A116 |
| CF$_3$ | Me | Me | Me | A1 | CH$_2$OMe | Me | Me | Me | A1 |
| CF$_3$ | Me | Me | Me | A13 | CH$_2$OMe | Me | Me | Me | A13 |
| CF$_3$ | Me | Me | Me | A14 | CH$_2$OMe | Me | Me | Me | A14 |
| CF$_3$ | Me | Me | Me | A15 | CH$_2$OMe | Me | Me | Me | A15 |
| CF$_3$ | Me | Me | Me | A16 | CH$_2$OMe | Me | Me | Me | A16 |
| CF$_3$ | Me | Me | Me | A20 | CH$_2$OMe | Me | Me | Me | A20 |
| CF$_3$ | Me | Me | Me | A23 | CH$_2$OMe | Me | Me | Me | A23 |
| CF$_3$ | Me | Me | Me | A24 | CH$_2$OMe | Me | Me | Me | A24 |
| CF$_3$ | Me | Me | Me | A25 | CH$_2$OMe | Me | Me | Me | A25 |
| CF$_3$ | Me | Me | Me | A26 | CH$_2$OMe | Me | Me | Me | A26 |
| CF$_3$ | Me | Me | Me | A27 | CH$_2$OMe | Me | Me | Me | A27 |
| CF$_3$ | Me | Me | Me | A28 | CH$_2$OMe | Me | Me | Me | A28 |
| CF$_3$ | Me | Me | Me | A29 | CH$_2$OMe | Me | Me | Me | A29 |
| CF$_3$ | Me | Me | Me | A34 | CH$_2$OMe | Me | Me | Me | A34 |
| CF$_3$ | Me | Me | Me | A35 | CH$_2$OMe | Me | Me | Me | A35 |
| CF$_3$ | Me | Me | Me | A36 | CH$_2$OMe | Me | Me | Me | A36 |
| CF$_3$ | Me | Me | Me | A37 | CH$_2$OMe | Me | Me | Me | A37 |
| CF$_3$ | Me | Me | Me | A42 | CH$_2$OMe | Me | Me | Me | A42 |
| CF$_3$ | Me | Me | Me | A58 | CH$_2$OMe | Me | Me | Me | A58 |
| CF$_3$ | Me | Me | Me | A63 | CH$_2$OMe | Me | Me | Me | A63 |
| CF$_3$ | Me | Me | Me | A64 | CH$_2$OMe | Me | Me | Me | A64 |
| CF$_3$ | Me | Me | Me | A65 | CH$_2$OMe | Me | Me | Me | A65 |
| CF$_3$ | Me | Me | Me | A67 | CH$_2$OMe | Me | Me | Me | A67 |
| CF$_3$ | Me | Me | Me | A69 | CH$_2$OMe | Me | Me | Me | A69 |
| CF$_3$ | Me | Me | Me | A72 | CH$_2$OMe | Me | Me | Me | A72 |
| CF$_3$ | Me | Me | Me | A73 | CH$_2$OMe | Me | Me | Me | A73 |
| CF$_3$ | Me | Me | Me | A74 | CH$_2$OMe | Me | Me | Me | A74 |
| CF$_3$ | Me | Me | Me | A75 | CH$_2$OMe | Me | Me | Me | A75 |
| CF$_3$ | Me | Me | Me | A76 | CH$_2$OMe | Me | Me | Me | A76 |
| CF$_3$ | Me | Me | Me | A77 | CH$_2$OMe | Me | Me | Me | A77 |
| CF$_3$ | Me | Me | Me | A81 | CH$_2$OMe | Me | Me | Me | A81 |
| CF$_3$ | Me | Me | Me | A83 | CH$_2$OMe | Me | Me | Me | A83 |
| CF$_3$ | Me | Me | Me | A88 | CH$_2$OMe | Me | Me | Me | A88 |
| CF$_3$ | Me | Me | Me | A91 | CH$_2$OMe | Me | Me | Me | A91 |
| CF$_3$ | Me | Me | Me | A97 | CH$_2$OMe | Me | Me | Me | A97 |
| CF$_3$ | Me | Me | Me | A98 | CH$_2$OMe | Me | Me | Me | A98 |
| CF$_3$ | Me | Me | Me | A102 | CH$_2$OMe | Me | Me | Me | A102 |
| D1-32a | Me | Me | Me | A1 | D1-108b-1 | Me | Me | Me | A1 |
| D1-32a | Me | Me | Me | A13 | D1-108b-1 | Me | Me | Me | A13 |
| D1-32a | Me | Me | Me | A14 | D1-108b-1 | Me | Me | Me | A14 |
| D1-32a | Me | Me | Me | A15 | D1-108b-1 | Me | Me | Me | A15 |
| D1-32a | Me | Me | Me | A16 | D1-108b-1 | Me | Me | Me | A16 |
| D1-32a | Me | Me | Me | A20 | D1-108b-1 | Me | Me | Me | A20 |
| D1-32a | Me | Me | Me | A23 | D1-108b-1 | Me | Me | Me | A23 |
| D1-32a | Me | Me | Me | A24 | D1-108b-1 | Me | Me | Me | A24 |
| D1-32a | Me | Me | Me | A25 | D1-108b-1 | Me | Me | Me | A25 |
| D1-32a | Me | Me | Me | A26 | D1-108b-1 | Me | Me | Me | A26 |
| D1-32a | Me | Me | Me | A27 | D1-108b-1 | Me | Me | Me | A27 |
| D1-32a | Me | Me | Me | A28 | D1-108b-1 | Me | Me | Me | A28 |
| D1-32a | Me | Me | Me | A29 | D1-108b-1 | Me | Me | Me | A29 |
| D1-32a | Me | Me | Me | A34 | D1-108b-1 | Me | Me | Me | A34 |
| D1-32a | Me | Me | Me | A35 | D1-108b-1 | Me | Me | Me | A35 |
| D1-32a | Me | Me | Me | A36 | D1-108b-1 | Me | Me | Me | A36 |
| D1-32a | Me | Me | Me | A37 | D1-108b-1 | Me | Me | Me | A37 |
| D1-32a | Me | Me | Me | A42 | D1-108b-1 | Me | Me | Me | A42 |
| D1-32a | Me | Me | Me | A58 | D1-108b-1 | Me | Me | Me | A58 |
| D1-32a | Me | Me | Me | A63 | D1-108b-1 | Me | Me | Me | A63 |
| D1-32a | Me | Me | Me | A64 | D1-108b-1 | Me | Me | Me | A64 |
| D1-32a | Me | Me | Me | A65 | D1-108b-1 | Me | Me | Me | A65 |
| D1-32a | Me | Me | Me | A67 | D1-108b-1 | Me | Me | Me | A67 |
| D1-32a | Me | Me | Me | A69 | D1-108b-1 | Me | Me | Me | A69 |

TABLE 1-continued

| | | | | | | | | | |
|---|---|---|---|---|---|---|---|---|---|
| D1-32a | Me | Me | Me | A72 | D1-108b-1 | Me | Me | Me | A72 |
| D1-32a | Me | Me | Me | A73 | D1-108b-1 | Me | Me | Me | A73 |
| D1-32a | Me | Me | Me | A74 | D1-108b-1 | Me | Me | Me | A74 |
| D1-32a | Me | Me | Me | A75 | D1-108b-1 | Me | Me | Me | A75 |
| D1-32a | Me | Me | Me | A76 | D1-108b-1 | Me | Me | Me | A76 |
| D1-32a | Me | Me | Me | A77 | D1-108b-1 | Me | Me | Me | A77 |
| D1-32a | Me | Me | Me | A81 | D1-108b-1 | Me | Me | Me | A81 |
| D1-32a | Me | Me | Me | A83 | D1-108b-1 | Me | Me | Me | A83 |
| D1-32a | Me | Me | Me | A88 | D1-108b-1 | Me | Me | Me | A88 |
| D1-32a | Me | Me | Me | A91 | D1-108b-1 | Me | Me | Me | A91 |
| D1-32a | Me | Me | Me | A97 | D1-108b-1 | Me | Me | Me | A97 |
| D1-32a | Me | Me | Me | A98 | D1-108b-1 | Me | Me | Me | A98 |
| D1-32a | Me | Me | Me | A102 | D1-108b-1 | Me | Me | Me | A102 |
| CH$_2$Pr-c | Me | Me | Me | A1 | D1-108b-8 | Me | Me | Me | A1 |
| CH$_2$Pr-c | Me | Me | Me | A13 | D1-108b-8 | Me | Me | Me | A13 |
| CH$_2$Pr-c | Me | Me | Me | A14 | D1-108b-8 | Me | Me | Me | A14 |
| CH$_2$Pr-c | Me | Me | Me | A15 | D1-108b-8 | Me | Me | Me | A15 |
| CH$_2$Pr-c | Me | Me | Me | A16 | D1-108b-8 | Me | Me | Me | A16 |
| CH$_2$Pr-c | Me | Me | Me | A20 | D1-108b-8 | Me | Me | Me | A20 |
| CH$_2$Pr-c | Me | Me | Me | A23 | D1-108b-8 | Me | Me | Me | A23 |
| CH$_2$Pr-c | Me | Me | Me | A24 | D1-108b-8 | Me | Me | Me | A24 |
| CH$_2$Pr-c | Me | Me | Me | A25 | D1-108b-8 | Me | Me | Me | A25 |
| CH$_2$Pr-c | Me | Me | Me | A26 | D1-108b-8 | Me | Me | Me | A26 |
| CH$_2$Pr-c | Me | Me | Me | A27 | D1-108b-8 | Me | Me | Me | A27 |
| CH$_2$Pr-c | Me | Me | Me | A28 | D1-108b-8 | Me | Me | Me | A28 |
| CH$_2$Pr-c | Me | Me | Me | A29 | D1-108b-8 | Me | Me | Me | A29 |
| CH$_2$Pr-c | Me | Me | Me | A34 | D1-108b-8 | Me | Me | Me | A34 |
| CH$_2$Pr-c | Me | Me | Me | A35 | D1-108b-8 | Me | Me | Me | A35 |
| CH$_2$Pr-c | Me | Me | Me | A36 | D1-108b-8 | Me | Me | Me | A36 |
| CH$_2$Pr-c | Me | Me | Me | A37 | D1-108b-8 | Me | Me | Me | A37 |
| CH$_2$Pr-c | Me | Me | Me | A42 | D1-108b-8 | Me | Me | Me | A42 |
| CH$_2$Pr-c | Me | Me | Me | A58 | D1-108b-8 | Me | Me | Me | A58 |
| CH$_2$Pr-c | Me | Me | Me | A63 | D1-108b-8 | Me | Me | Me | A63 |
| CH$_2$Pr-c | Me | Me | Me | A64 | D1-108b-8 | Me | Me | Me | A64 |
| CH$_2$Pr-c | Me | Me | Me | A65 | D1-108b-8 | Me | Me | Me | A65 |
| CH$_2$Pr-c | Me | Me | Me | A67 | D1-108b-8 | Me | Me | Me | A67 |
| CH$_2$Pr-c | Me | Me | Me | A69 | D1-108b-8 | Me | Me | Me | A69 |
| CH$_2$Pr-c | Me | Me | Me | A72 | D1-108b-8 | Me | Me | Me | A72 |
| CH$_2$Pr-c | Me | Me | Me | A73 | D1-108b-8 | Me | Me | Me | A73 |
| CH$_2$Pr-c | Me | Me | Me | A74 | D1-108b-8 | Me | Me | Me | A74 |
| CH$_2$Pr-c | Me | Me | Me | A75 | D1-108b-8 | Me | Me | Me | A75 |
| CH$_2$Pr-c | Me | Me | Me | A76 | D1-108b-8 | Me | Me | Me | A76 |
| CH$_2$Pr-c | Me | Me | Me | A77 | D1-108b-8 | Me | Me | Me | A77 |
| CH$_2$Pr-c | Me | Me | Me | A81 | D1-108b-8 | Me | Me | Me | A81 |
| CH$_2$Pr-c | Me | Me | Me | A83 | D1-108b-8 | Me | Me | Me | A83 |
| CH$_2$Pr-c | Me | Me | Me | A88 | D1-108b-8 | Me | Me | Me | A88 |
| CH$_2$Pr-c | Me | Me | Me | A91 | D1-108b-8 | Me | Me | Me | A91 |
| CH$_2$Pr-c | Me | Me | Me | A97 | D1-108b-8 | Me | Me | Me | A97 |
| CH$_2$Pr-c | Me | Me | Me | A98 | D1-108b-8 | Me | Me | Me | A98 |
| CH$_2$Pr-c | Me | Me | Me | A102 | D1-108b-8 | Me | Me | Me | A102 |
| D1-108b-4 | Me | Me | Me | A1 | Me | Me | Me | CN | A1 |
| D1-108b-4 | Me | Me | Me | A13 | Me | Me | Me | CN | A13 |
| D1-108b-4 | Me | Me | Me | A14 | Me | Me | Me | CN | A14 |
| D1-108b-4 | Me | Me | Me | A15 | Me | Me | Me | CN | A15 |
| D1-108b-4 | Me | Me | Me | A16 | Me | Me | Me | CN | A16 |
| D1-108b-4 | Me | Me | Me | A20 | Me | Me | Me | CN | A20 |
| D1-108b-4 | Me | Me | Me | A23 | Me | Me | Me | CN | A23 |
| D1-108b-4 | Me | Me | Me | A24 | Me | Me | Me | CN | A24 |
| D1-108b-4 | Me | Me | Me | A25 | Me | Me | Me | CN | A25 |
| D1-108b-4 | Me | Me | Me | A26 | Me | Me | Me | CN | A26 |
| D1-108b-4 | Me | Me | Me | A27 | Me | Me | Me | CN | A27 |
| D1-108b-4 | Me | Me | Me | A28 | Me | Me | Me | CN | A28 |
| D1-108b-4 | Me | Me | Me | A29 | Me | Me | Me | CN | A29 |
| D1-108b-4 | Me | Me | Me | A34 | Me | Me | Me | CN | A34 |
| D1-108h-4 | Me | Me | Me | A35 | Me | Me | Me | CN | A35 |
| D1-108b-4 | Me | Me | Me | A36 | Me | Me | Me | CN | A36 |
| D1-108b-4 | Me | Me | Me | A37 | Me | Me | Me | CN | A37 |
| D1-108b-4 | Me | Me | Me | A42 | Me | Me | Me | CN | A42 |
| D1-108b-4 | Me | Me | Me | A58 | Me | Me | Me | CN | A58 |
| D1-108b-4 | Me | Me | Me | A63 | Me | Me | Me | CN | A63 |
| D1-108b-4 | Me | Me | Me | A64 | Me | Me | Me | CN | A64 |
| D1-108b-4 | Me | Me | Me | A65 | Me | Me | Me | CN | A65 |
| D1-108b-4 | Me | Me | Me | A67 | Me | Me | Me | CN | A67 |
| D1-108b-4 | Me | Me | Me | A69 | Me | Me | Me | CN | A69 |
| D1-108b-4 | Me | Me | Me | A72 | Me | Me | Me | CN | A72 |
| D1-108b-4 | Me | Me | Me | A73 | Me | Me | Me | CN | A73 |
| D1-108b-4 | Me | Me | Me | A74 | Me | Me | Me | CN | A74 |
| D1-108b-4 | Me | Me | Me | A75 | Me | Me | Me | CN | A75 |
| D1-108b-4 | Me | Me | Me | A76 | D1-108b-8 | Me | Me | CN | A76 |
| D1-108b-4 | Me | Me | Me | A77 | D1-108b-8 | Me | Me | CN | A77 |

TABLE 1-continued

| | | | | | | | | | |
|---|---|---|---|---|---|---|---|---|---|
| D1-108b-4 | Me | Me | Me | A81 | D1-108b-8 | Me | Me | CN | A81 |
| D1-108b-4 | Me | Me | Me | A83 | D1-108b-8 | Me | Me | CN | A83 |
| D1-108b-4 | Me | Me | Me | A88 | D1-108b-8 | Me | Me | CN | A88 |
| D1-108b-4 | Me | Me | Me | A91 | D1-108b-8 | Me | Me | CN | A91 |
| D1-108b-4 | Me | Me | Me | A97 | D1-108b-8 | Me | Me | CN | A97 |
| D1-108b-4 | Me | Me | Me | A98 | D1-108b-8 | Me | Me | CN | A98 |
| D1-108b-4 | Me | Me | Me | A102 | D1-108b-8 | Me | Me | CN | A102 |
| Me | Me | Me | $NO_2$ | A1 | Me | Me | Me | c-Pr | A1 |
| Me | Me | Me | $NO_2$ | A13 | Me | Me | Me | c-Pr | A13 |
| Me | Me | Me | $NO_2$ | A14 | Me | Me | Me | c-Pr | A14 |
| Me | Me | Me | $NO_2$ | A15 | Me | Me | Me | c-Pr | A15 |
| Me | Me | Me | $NO_2$ | A16 | Me | Me | Me | c-Pr | A16 |
| Me | Me | Me | $NO_2$ | A20 | Me | Me | Me | c-Pr | A20 |
| Me | Me | Me | $NO_2$ | A23 | Me | Me | Me | c-Pr | A23 |
| Me | Me | Me | $NO_2$ | A24 | Me | Me | Me | c-Pr | A24 |
| Me | Me | Me | $NO_2$ | A25 | Me | Me | Me | c-Pr | A25 |
| Me | Me | Me | $NO_2$ | A26 | Me | Me | Me | c-Pr | A26 |
| Me | Me | Me | $NO_2$ | A27 | Me | Me | Me | c-Pr | A27 |
| Me | Me | Me | $NO_2$ | A28 | Me | Me | Me | c-Pr | A28 |
| Me | Me | Me | $NO_2$ | A29 | Me | Me | Me | c-Pr | A29 |
| Me | Me | Me | $NO_2$ | A34 | Me | Me | Me | c-Pr | A34 |
| Me | Me | Me | $NO_2$ | A35 | Me | Me | Me | c-Pr | A35 |
| Me | Me | Me | $NO_2$ | A36 | Me | Me | Me | c-Pr | A36 |
| Me | Me | Me | $NO_2$ | A37 | Me | Me | Me | c-Pr | A37 |
| Me | Me | Me | $NO_2$ | A42 | Me | Me | Me | c-Pr | A42 |
| Me | Me | Me | $NO_2$ | A58 | Me | Me | Me | o-Pr | A58 |
| Me | Me | Me | $NO_2$ | A63 | Me | Me | Me | c-Pr | A63 |
| Me | Me | Me | $NO_2$ | A64 | Me | Me | Me | c-Pr | A64 |
| Me | Me | Me | $NO_2$ | A65 | Me | Me | Me | c-Pr | A65 |
| Me | Me | Me | $NO_2$ | A67 | Me | Me | Me | c-Pr | A67 |
| Me | Me | Me | $NO_2$ | A69 | Me | Me | Me | c-Pr | A69 |
| Me | Me | Me | $NO_2$ | A72 | Me | Me | Me | c-Pr | A72 |
| Me | Me | Me | $NO_2$ | A73 | Me | Me | Me | c-Pr | A73 |
| Me | Me | Me | $NO_2$ | A74 | Me | Me | Me | c-Pr | A74 |
| Me | Me | Me | $NO_2$ | A75 | Me | Me | Me | c-Pr | A75 |
| Me | Me | Me | $NO_2$ | A76 | Me | Me | Me | c-Pr | A76 |
| Me | Me | Me | $NO_2$ | A77 | Me | Me | Me | c-Pr | A77 |
| Me | Me | Me | $NO_2$ | A81 | Me | Me | Me | c-Pr | A81 |
| Me | Me | Me | $NO_2$ | A83 | Me | Me | Me | c-Pr | A83 |
| Me | Me | Me | $NO_2$ | A88 | Me | Me | Me | c-Pr | A88 |
| Me | Me | Me | $NO_2$ | A91 | Me | Me | Me | c-Pr | A91 |
| Me | Me | Me | $NO_2$ | A97 | Me | Me | Me | c-Pr | A97 |
| Me | Me | Me | $NO_2$ | A98 | Me | Me | Me | c-Pr | A98 |
| Me | Me | Me | $NO_2$ | A102 | Me | Me | Me | c-Pr | A102 |
| Me | Me | Me | $CH=CH_2$ | A1 | Me | Me | Me | CH=CHPh | A1 |
| Me | Me | Me | $CH=CH_2$ | A13 | Me | Me | Me | CH=CHPh | A13 |
| Me | Me | Me | $CH=CH_2$ | A14 | Me | Me | Me | CH=CHPh | A14 |
| Me | Me | Me | $CH=CH_2$ | A15 | Me | Me | Me | CH=CHPh | A15 |
| Me | Me | Me | $CH=CH_2$ | A16 | Me | Me | Me | CH=CHPh | A16 |
| Me | Me | Me | $CH=CH_2$ | A20 | Me | Me | Me | CH=CHPh | A20 |
| Me | Me | Me | $CH=CH_2$ | A23 | Me | Me | Me | CH=CHPh | A23 |
| Me | Me | Me | $CH=CH_2$ | A24 | Me | Me | Me | CH=CHPh | A24 |
| Me | Me | Me | $CH=CH_2$ | A25 | Me | Me | Me | CH=CHPh | A25 |
| Me | Me | Me | $CH=CH_2$ | A26 | Me | Me | Me | CH=CHPh | A26 |
| Me | Me | Me | $CH=CH_2$ | A27 | Me | Me | Me | CH=CHPh | A27 |
| Me | Me | Me | $CH=CH_2$ | A28 | Me | Me | Me | CH=CHPh | A28 |
| Me | Me | Me | $CH=CH_2$ | A29 | Me | Me | Me | CH=CHPh | A29 |
| Me | Me | Me | $CH=CH_2$ | A34 | Me | Me | Me | CH=CHPh | A34 |
| Me | Me | Me | $CH=CH_2$ | A35 | Me | Me | Me | CH=CHPh | A35 |
| Me | Me | Me | $CH=CH_2$ | A36 | Me | Me | Me | CH=CHPh | A36 |
| Me | Me | Me | $CH=CH_2$ | A37 | Me | Me | Me | CH=CHPh | A37 |
| Me | Me | Me | $CH=CH_2$ | A42 | Me | Me | Me | CH=CHPh | A42 |
| Me | Me | Me | $CH=CH_2$ | A58 | Me | Me | Me | CH=CHPh | A58 |
| Me | Me | Me | $CH=CH_2$ | A63 | Me | Me | Me | CH=CHPh | A63 |
| Me | Me | Me | $CH=CH_2$ | A64 | Me | Me | Me | CH=CHPh | A64 |
| Me | Me | Me | $CH=CH_2$ | A65 | Me | Me | Me | CH=CHPh | A65 |
| Me | Me | Me | $CH=CH_2$ | A67 | Me | Me | Me | CH=CHPh | A67 |
| Me | Me | Me | $CH=CH_2$ | A69 | Me | Me | Me | CH=CHPh | A69 |
| Me | Me | Me | $CH=CH_2$ | A72 | Me | Me | Me | CH=CHPh | A72 |
| Me | Me | Me | $CH=CH_2$ | A73 | Me | Me | Me | CH=CHPh | A73 |
| Me | Me | Me | $CH=CH_2$ | A74 | Me | Me | Me | CH=CHPh | A74 |
| Me | Me | Me | $CH=CH_2$ | A75 | Me | Me | Me | CH=CHPh | A75 |
| Me | Me | Me | $CH=CH_2$ | A76 | Me | Me | Me | CH=CHPh | A76 |
| Me | Me | Me | $CH=CH_2$ | A77 | Me | Me | Me | CH=CHPh | A77 |
| Me | Me | Me | $CH=CH_2$ | A81 | Me | Me | Me | CH=CHPh | A81 |
| Me | Me | Me | $CH=CH_2$ | A83 | Me | Me | Me | CH=CHPh | A83 |
| Me | Me | Me | $CH=CH_2$ | A88 | Me | Me | Me | CH=CHPh | A88 |
| Me | Me | Me | $CH=CH_2$ | A91 | Me | Me | Me | CH=CHPh | A91 |
| Me | Me | Me | $CH=CH_2$ | A97 | Me | Me | Me | CH=CHPh | A97 |
| Me | Me | Me | $CH=CH_2$ | A98 | Me | Me | Me | CH=CHPh | A98 |

TABLE 1-continued

| | | | | | | | | | |
|---|---|---|---|---|---|---|---|---|---|
| Me | Me | Me | CH=CH$_2$ | A102 | Me | Me | Me | CH=CHPh | A102 |
| Me | Me | Me | C(O)Me | A1 | Me | Me | Me | C(O)OMe | A1 |
| Me | Me | Me | C(O)Me | A13 | Me | Me | Me | C(O)OMe | A13 |
| Me | Me | Me | C(O)Me | A14 | Me | Me | Me | C(O)OMe | A14 |
| Me | Me | Me | C(O)Me | A15 | Me | Me | Me | C(O)OMe | A15 |
| Me | Me | Me | C(O)Me | A16 | Me | Me | Me | C(O)OMe | A16 |
| Me | Me | Me | C(O)Me | A20 | Me | Me | Me | C(O)OMe | A20 |
| Me | Me | Me | C(O)Me | A23 | Me | Me | Me | C(O)OMe | A23 |
| Me | Me | Me | C(O)Me | A24 | Me | Me | Me | C(O)OMe | A24 |
| Me | Me | Me | C(O)Me | A25 | Me | Me | Me | C(O)OMe | A25 |
| Me | Me | Me | C(O)Me | A26 | Me | Me | Me | C(O)OMe | A26 |
| Me | Me | Me | C(O)Me | A27 | Me | Me | Me | C(O)OMe | A27 |
| Me | Me | Me | C(O)Me | A28 | Me | Me | Me | C(O)OMe | A28 |
| Me | Me | Me | C(O)Me | A29 | Me | Me | Me | C(O)OMe | A29 |
| Me | Me | Me | C(O)Me | A34 | Me | Me | Me | C(O)OMe | A34 |
| Me | Me | Me | C(O)Me | A35 | Me | Me | Me | C(O)OMe | A35 |
| Me | Me | Me | C(O)Me | A36 | Me | Me | Me | C(O)OMe | A36 |
| Me | Me | Me | C(O)Me | A37 | Me | Me | Me | C(O)OMe | A37 |
| Me | Me | Me | C(O)Me | A42 | Me | Me | Me | C(O)OMe | A42 |
| Me | Me | Me | C(O)Me | A58 | Me | Me | Me | C(O)OMe | A58 |
| Me | Me | Me | C(O)Me | A63 | Me | Me | Me | C(O)OMe | A63 |
| Me | Me | Me | C(O)Me | A64 | Me | Me | Me | C(O)OMe | AM |
| Me | Me | Me | C(O)Me | A65 | Me | Me | Me | C(O)OMe | A65 |
| Me | Me | Me | C(O)Me | A67 | Me | Me | Me | C(O)OMe | A67 |
| Me | Me | Me | C(O)Me | A69 | Me | Me | Me | C(O)OMe | A69 |
| Me | Me | Me | C(O)Me | A72 | Me | Me | Me | C(O)OMe | A72 |
| Me | Me | Me | C(O)Me | A73 | Me | Me | Me | C(O)OMe | A73 |
| Me | Me | Me | C(O)Me | A74 | Me | Me | Me | C(O)OMe | A74 |
| Me | Me | Me | C(O)Me | A75 | Me | Me | Me | C(O)OMe | A75 |
| Me | Me | Me | C(O)Me | A76 | Me | Me | Me | C(O)OMe | A76 |
| Me | Me | Me | C(O)Me | A77 | Me | Me | Me | C(O)OMe | A77 |
| Me | Me | Me | C(O)Me | A81 | Me | Me | Me | C(O)OMe | A81 |
| Me | Me | Me | C(O)Me | A83 | Me | Me | Me | C(O)OMe | A83 |
| Me | Me | Me | C(O)Me | A88 | Me | Me | Me | C(O)OMe | A88 |
| Me | Me | Me | C(O)Me | A91 | Me | Me | Me | C(O)OMe | A91 |
| Me | Me | Me | C(O)Me | A97 | Me | Me | Me | C(O)OMe | A97 |
| Me | Me | Me | C(O)Me | A98 | Me | Me | Me | C(O)OMe | A98 |
| Me | Me | Me | C(=NOMe)Me | A1 | Me | Me | Me | OH | A1 |
| Me | Me | Me | C(=NOMe)Me | A13 | Me | Me | Me | OH | A13 |
| Me | Me | Me | C(=NOMe)Me | A14 | Me | Me | Me | OH | A14 |
| Me | Me | Me | C(=NOMe)Me | A15 | Me | Me | Me | OH | A15 |
| Me | Me | Me | C(=NOMe)Me | A16 | Me | Me | Me | OH | A16 |
| Me | Me | Me | C(=NOMe)Me | A20 | Me | Me | Me | OH | A20 |
| Me | Me | Me | C(=NOMe)Me | A23 | Me | Me | Me | OH | A23 |
| Me | Me | Me | C(=NOMe)Me | A24 | Me | Me | Me | OH | A24 |
| Me | Me | Me | C(=NOMe)Me | A25 | Me | Me | Me | OH | A25 |
| Me | Me | Me | C(=NOMe)Me | A26 | Me | Me | Me | OH | A26 |
| Me | Me | Me | C(=NOMe)Me | A27 | Me | Me | Me | OH | A27 |
| Me | Me | Me | C(=NOMe)Me | A28 | Me | Me | Me | OH | A28 |
| Me | Me | Me | C(=NOMe)Me | A29 | Me | Me | Me | OH | A29 |
| Me | Me | Me | C(=NOMe)Me | A34 | Me | Me | Me | OH | A34 |
| Me | Me | Me | C(=NOMe)Me | A35 | Me | Me | Me | OH | A35 |
| Me | Me | Me | C(=NOMe)Me | A36 | Me | Me | Me | OH | A36 |
| Me | Me | Me | C(=NOMe)Me | A37 | Me | Me | Me | OH | A37 |
| Me | Me | Me | C(=NOMe)Me | A42 | Me | Me | Me | OH | A42 |
| Me | Me | Me | C(=NOMe)Me | A58 | Me | Me | Me | OH | A58 |
| Me | Me | Me | C(=NOMe)Me | A63 | Me | Me | Me | OH | A63 |
| Me | Me | Me | C(=NOMe)Me | A64 | Me | Me | Me | OH | A64 |
| Me | Me | Me | C(=NOMe)Me | A65 | Me | Me | Me | OH | A65 |
| Me | Me | Me | C(=NOMe)Me | A67 | Me | Me | Me | OH | A67 |
| Me | Me | Me | C(=NOMe)Me | A69 | Me | Me | Me | OH | A69 |
| Me | Me | Me | C(=NOMe)Me | A72 | Me | Me | Me | OH | A72 |
| Me | Me | Me | C(=NOMe)Me | A73 | Me | Me | Me | OH | A73 |
| Me | Me | Me | C(=NOMe)Me | A74 | Me | Me | Me | OH | A74 |
| Me | Me | Me | C(=NOMe)Me | A75 | Me | Me | Me | OH | A75 |
| Me | Me | Me | C(=NOMe)Me | A76 | Me | Me | Me | OH | A76 |
| Me | Me | Me | C(=NOMe)Me | A77 | Me | Me | Me | OH | A77 |
| Me | Me | Me | C(=NOMe)Me | A81 | Me | Me | Me | OH | A81 |
| Me | Me | Me | C(=NOMe)Me | A83 | Me | Me | Me | OH | A83 |
| Me | Me | Me | C(=NOMe)Me | A88 | Me | Me | Me | OH | A88 |
| Me | Me | Me | C(=NOMe)Me | A91 | Me | Me | Me | OH | A91 |
| Me | Me | Me | C(=NOMe)Me | A97 | Me | Me | Me | OH | A97 |
| Me | Me | Me | C(=NOMe)Me | A98 | Me | Me | Me | OH | A98 |
| Me | Me | Me | C(=NOMe)Me | A102 | Me | Me | Me | OH | A102 |
| Me | Me | Me | OMe | A1 | Me | Me | Me | OCH$_2$OMe | A1 |
| Me | Me | Me | OMe | A13 | Me | Me | Me | OCH$_2$OMe | A13 |
| Me | Me | Me | OMe | A14 | Me | Me | Me | OCH$_2$OMe | A14 |
| Me | Me | Me | OMe | A15 | Me | Me | Me | OCH$_2$OMe | A15 |
| Me | Me | Me | OMe | A16 | Me | Me | Me | OCH$_2$OMe | A16 |
| Me | Me | Me | OMe | A20 | Me | Me | Me | OCH$_2$OMe | A20 |

TABLE 1-continued

| | | | | | | | | | |
|---|---|---|---|---|---|---|---|---|---|
| Me | Me | Me | OMe | A23 | Me | Me | Me | OCH$_2$OMe | A23 |
| Me | Me | Me | OMe | A24 | Me | Me | Me | OCH$_2$OMe | A24 |
| Me | Me | Me | OMe | A25 | Me | Me | Me | OCH$_2$OMe | A25 |
| Me | Me | Me | OMe | A26 | Me | Me | Me | OCH$_2$OMe | A26 |
| Me | Me | Me | OMe | A27 | Me | Me | Me | OCH$_2$OMe | A27 |
| Me | Me | Me | OMe | A28 | Me | Me | Me | OCH$_2$OMe | A28 |
| Me | Me | Me | OMe | A29 | Me | Me | Me | OCH$_2$OMe | A29 |
| Me | Me | Me | OMe | A34 | Me | Me | Me | OCH$_2$OMe | A34 |
| Me | Me | Me | OMe | A35 | Me | Me | Me | OCH$_2$OMe | A35 |
| Me | Me | Me | OMe | A36 | Me | Me | Me | OCH$_2$OMe | A36 |
| Me | Me | Me | OMe | A37 | Me | Me | Me | OCH$_2$OMe | A37 |
| Me | Me | Me | OMe | A42 | Me | Me | Me | OCH$_2$OMe | A42 |
| Me | Me | Me | OMe | A58 | Me | Me | Me | OCH$_2$OMe | A58 |
| Me | Me | Me | OMe | A63 | Me | Me | Me | OCH$_2$OMe | A63 |
| Me | Me | Me | OMe | A64 | Me | Me | Me | OCH$_2$OMe | A64 |
| Me | Me | Me | OMe | A65 | Me | Me | Me | OCH$_2$OMe | A65 |
| Me | Me | Me | OMe | A67 | Me | Me | Me | OCH$_2$OMe | A67 |
| Me | Me | Me | OMe | A69 | Me | Me | Me | OCH$_2$OMe | A69 |
| Me | Me | Me | OMe | A72 | Me | Me | Me | OCH$_2$OMe | A72 |
| Me | Me | Me | OMe | A73 | Me | Me | Me | OCH$_2$OMe | A73 |
| Me | Me | Me | OMe | A74 | Me | Me | Me | OCH$_2$OMe | A74 |
| Me | Me | Me | OMe | A75 | Me | Me | Me | OCH$_2$OMe | A75 |
| Me | Me | Me | OMe | A76 | Me | Me | Me | OCH$_2$OMe | A76 |
| Me | Me | Me | OMe | A77 | Me | Me | Me | OCH$_2$OMe | A77 |
| Me | Me | Me | OMe | A81 | Me | Me | Me | OCH$_2$OMe | A81 |
| Me | Me | Me | OMe | A83 | Me | Me | Me | OCH$_2$OMe | A83 |
| Me | Me | Me | OMe | A88 | Me | Me | Me | OCH$_2$OMe | A88 |
| Me | Me | Me | OMe | A91 | Me | Me | Me | OCH$_2$OMe | A91 |
| Me | Me | Me | OMe | A97 | Me | Me | Me | OCH$_2$OMe | A97 |
| Me | Me | Me | OMe | A98 | Me | Me | Me | OCH$_2$OMe | A98 |
| Me | Me | Me | OMe | A102 | Me | Me | Me | OCH$_2$OMe | A102 |
| Me | Me | Me | OCH$_2$Ph | A1 | Me | Me | Me | OCH$_2$(D1-34a) | A1 |
| Me | Me | Me | OCH$_2$Ph | A13 | Me | Me | Me | OCH$_2$(D1-34a) | A13 |
| Me | Me | Me | OCH$_2$Ph | A14 | Me | Me | Me | OCH$_2$(D1-34a) | A14 |
| Me | Me | Me | OCH$_2$Ph | A15 | Me | Me | Me | OCH$_2$(D1-34a) | A15 |
| Me | Me | Me | OCH$_2$Ph | A16 | Me | Me | Me | OCH$_2$(D1-34a) | A16 |
| Me | Me | Me | OCH$_2$Ph | A20 | Me | Me | Me | OCH$_2$(D1-34a) | A20 |
| Me | Me | Me | OCH$_2$Ph | A23 | Me | Me | Me | OCH$_2$(D1-34a) | A23 |
| Me | Me | Me | OCH$_2$Ph | A24 | Me | Me | Me | OCH$_2$(D1-34a) | A24 |
| Me | Me | Me | OCH$_2$Ph | A25 | Me | Me | Me | OCH$_2$(D1-34a) | A25 |
| Me | Me | Me | OCH$_2$Ph | A26 | Me | Me | Me | OCH$_2$(D1-34a) | A26 |
| Me | Me | Me | OCH$_2$Ph | A27 | Me | Me | Me | OCH$_2$(D1-34a) | A27 |
| Me | Me | Me | OCH$_2$Ph | A28 | Me | Me | Me | OCH$_2$(D1-34a) | A28 |
| Me | Me | Me | OCH$_2$Ph | A29 | Me | Me | Me | OCH$_2$(D1-34a) | A29 |
| Me | Me | Me | OCH$_2$Ph | A34 | Me | Me | Me | OCH$_2$(D1-34a) | A34 |
| Me | Me | Me | OCH$_2$Ph | A35 | Me | Me | Me | OCH$_2$(D1-34a) | A35 |
| Me | Me | Me | OCH$_2$Ph | A36 | Me | Me | Me | OCH$_2$(D1-34a) | A36 |
| Me | Me | Me | OCH$_2$Ph | A37 | Me | Me | Me | OCH$_2$(D1-34a) | A37 |
| Me | Me | Me | OCH$_2$Ph | A42 | Me | Me | Me | OCH$_2$(D1-34a) | A42 |
| Me | Me | Me | OCH$_2$Ph | A58 | Me | Me | Me | OCH$_2$(D1-34a) | A58 |
| Me | Me | Me | OCH$_2$Ph | A63 | Me | Me | Me | OCH$_2$(D1-34a) | A63 |
| Me | Me | Me | OCH$_2$Ph | A64 | Me | Me | Me | OCH$_2$(D1-34a) | A64 |
| Me | Me | Me | OCH$_2$Ph | A65 | Me | Me | Me | OCH$_2$(D1-34a) | A65 |
| Me | Me | Me | OCH$_2$Ph | A67 | Me | Me | Me | OCH$_2$(D1-34a) | A67 |
| Me | Me | Me | OCH$_2$Ph | A69 | Me | Me | Me | OCH$_2$(D1-34a) | A69 |
| Me | Me | Me | OCH$_2$Ph | A72 | Me | Me | Me | OCH$_2$(D1-34a) | A72 |
| Me | Me | Me | OCH$_2$Ph | A73 | Me | Me | Me | OCH$_2$(D1-34a) | A73 |
| Me | Me | Me | OCH$_2$Ph | A74 | Me | Me | Me | OCH$_2$(D1-34a) | A74 |
| Me | Me | Me | OCH$_2$Ph | A75 | Me | Me | Me | OCH$_2$(D1-34a) | A75 |
| Me | Me | Me | OCH$_2$Ph | A76 | Me | Me | Me | OCH$_2$(D1-34a) | A76 |
| Me | Me | Me | OCH$_2$Ph | A77 | Me | Me | Me | OCH$_2$(D1-34a) | A77 |
| Me | Me | Me | OCH$_2$Ph | A81 | Me | Me | Me | OCH$_2$(D1-34a) | A81 |
| Me | Me | Me | OCH$_2$Ph | A83 | Me | Me | Me | OCH$_2$(D1-34a) | A83 |
| Me | Me | Me | OCH$_2$Ph | A88 | Me | Me | Me | OCH$_2$(D1-34a) | A88 |
| Me | Me | Me | OCH$_2$Ph | A91 | Me | Me | Me | OCH$_2$(D1-34a) | A91 |
| Me | Me | Me | OCH$_2$Ph | A97 | Me | Me | Me | OCH$_2$(D1-34a) | A97 |
| Me | Me | Me | OCH$_2$Ph | A98 | Me | Me | Me | OCH$_2$(D1-34a) | A98 |
| Me | Me | Me | OCH$_2$Ph | A102 | Me | Me | Me | OCH$_2$(D1-34a) | A102 |
| Me | Me | Me | OPh | A1 | Me | Me | Me | O(D1-32b-1) | A1 |
| Me | Me | Me | OPh | A13 | Me | Me | Me | O(D1-32b-1) | A13 |
| Me | Me | Me | OPh | A14 | Me | Me | Me | O(D1-32b-1) | A14 |
| Me | Me | Me | OPh | A15 | Me | Me | Me | O(D1-32b-1) | A15 |
| Me | Me | Me | OPh | A16 | Me | Me | Me | O(D1-32b-1) | A16 |
| Me | Me | Me | OPh | A20 | Me | Me | Me | O(D1-32b-1) | A20 |
| Me | Me | Me | OPh | A23 | Me | Me | Me | O(D1-32b-1) | A23 |
| Me | Me | Me | OPh | A24 | Me | Me | Me | O(D1-32b-1) | A24 |
| Me | Me | Me | OPh | A25 | Me | Me | Me | O(D1-32b-1) | A25 |
| Me | Me | Me | OPh | A26 | Me | Me | Me | O(D1-32b-1) | A26 |
| Me | Me | Me | OPh | A27 | Me | Me | Me | O(D1-32b-1) | A27 |
| Me | Me | Me | OPh | A28 | Me | Me | Me | O(D1-32b-1) | A28 |

TABLE 1-continued

| | | | | | | | | | |
|---|---|---|---|---|---|---|---|---|---|
| Me | Me | Me | OPh | A29 | Me | Me | Me | O(D1-32b-1) | A29 |
| Me | Me | Me | OPh | A34 | Me | Me | Me | O(D1-32b-1) | A34 |
| Me | Me | Me | OPh | A35 | Me | Me | Me | O(D1-32b-1) | A35 |
| Me | Me | Me | OPh | A36 | Me | Me | Me | O(D1-32b-1) | A36 |
| Me | Me | Me | OPh | A37 | Me | Me | Me | O(D1-32b-1) | A37 |
| Me | Me | Me | OPh | A42 | Me | Me | Me | O(D1-32b-1) | A42 |
| Me | Me | Me | OPh | A58 | Me | Me | Me | O(D1-32b-1) | A58 |
| Me | Me | Me | OPh | A63 | Me | Me | Me | O(D1-32b-1) | A63 |
| Me | Me | Me | OPh | A64 | Me | Me | Me | O(D1-32b-1) | A64 |
| Me | Me | Me | OPh | A65 | Me | Me | Me | O(D1-32b-1) | A65 |
| Me | Me | Me | OPh | A67 | Me | Me | Me | O(D1-32b-1) | A67 |
| Me | Me | Me | OPh | A69 | Me | Me | Me | O(D1-32b-1) | A69 |
| Me | Me | Me | OPh | A72 | Me | Me | Me | O(D1-32b-1) | A72 |
| Me | Me | Me | OPh | A73 | Me | Me | Me | O(D1-32b-1) | A73 |
| Me | Me | Me | OPh | A74 | Me | Me | Me | O(D1-32b-1) | A74 |
| Me | Me | Me | OPh | A75 | Me | Me | Me | O(D1-32b-1) | A75 |
| Me | Me | Me | OPh | A76 | Me | Me | Me | O(D1-32b-1) | A76 |
| Me | Me | Me | OPh | A77 | Me | Me | Me | O(D1-32b-1) | A77 |
| Me | Me | Me | OPh | A81 | Me | Me | Me | O(D1-32b-1) | A81 |
| Me | Me | Me | OPh | A83 | Me | Me | Me | O(D1-32b-1) | A83 |
| Me | Me | Me | OPh | A88 | Me | Me | Me | O(D1-32b-1) | A88 |
| Me | Me | Me | OPh | A91 | Me | Me | Me | O(D1-32b-1) | A91 |
| Me | Me | Me | OPh | A97 | Me | Me | Me | O(D1-32b-1) | A97 |
| Me | Me | Me | OPh | A98 | Me | Me | Me | O(D1-32b-1) | A98 |
| Me | Me | Me | OPh | A102 | Me | Me | Me | O(D1-32b-1) | A102 |
| Me | Me | Me | SMe | A1 | Me | Me | Me | NHC(O)OBu-t | A1 |
| Me | Me | Me | SMe | A13 | Me | Me | Me | NHC(O)OBu-t | A13 |
| Me | Me | Me | SMe | A14 | Me | Me | Me | NHC(O)OBu-t | A14 |
| Me | Me | Me | SMe | A15 | Me | Me | Me | NHC(O)OBu-t | A15 |
| Me | Me | Me | SMe | A16 | Me | Me | Me | NHC(O)OBu-t | A16 |
| Me | Me | Me | SMe | A20 | Me | Me | Me | NHC(O)OBu-t | A20 |
| Me | Me | Me | SMe | A23 | Me | Me | Me | NHC(O)OBu-t | A23 |
| Me | Me | Me | SMe | A24 | Me | Me | Me | NHC(O)OBu-t | A24 |
| Me | Me | Me | SMe | A25 | Me | Me | Me | NHC(O)OBu-t | A25 |
| Me | Me | Me | SMe | A26 | Me | Me | Me | NHC(O)OBu-t | A26 |
| Me | Me | Me | SMe | A27 | Me | Me | Me | NHC(O)OBu-t | A27 |
| Me | Me | Me | SMe | A28 | Me | Me | Me | NHC(O)OBu-t | A28 |
| Me | Me | Me | SMe | A29 | Me | Me | Me | NHC(O)OBu-t | A29 |
| Me | Me | Me | SMe | A34 | Me | Me | Me | NHC(O)OBu-t | A34 |
| Me | Me | Me | SMe | A35 | Me | Me | Me | NHC(O)OBu-t | A35 |
| Me | Me | Me | SMe | A36 | Me | Me | Me | NHC(O)OBu-t | A36 |
| Me | Me | Me | SMe | A37 | Me | Me | Me | NHC(O)OBu-t | A37 |
| Me | Me | Me | SMe | A42 | Me | Me | Me | NHC(O)OBu-t | A42 |
| Me | Me | Me | SMe | A58 | Me | Me | Me | NHC(O)OBu-t | A58 |
| Me | Me | Me | SMe | A63 | Me | Me | Me | NHC(O)OBu-t | A63 |
| Me | Me | Me | SMe | A64 | Me | Me | Me | NHC(O)OBu-t | A64 |
| Me | Me | Me | SMe | A65 | Me | Me | Me | NHC(O)OBu-t | A65 |
| Me | Me | Me | SMe | A67 | Me | Me | Me | NHC(O)OBu-t | A67 |
| Me | Me | Me | SMe | A69 | Me | Me | Me | NHC(O)OBu-t | A69 |
| Me | Me | Me | SMe | A72 | Me | Me | Me | NHC(O)OBu-t | A72 |
| Me | Me | Me | SMe | A73 | Me | Me | Me | NHC(O)OBut | A73 |
| Me | Me | Me | SMe | A74 | Me | Me | Me | NHC(O)OBu-t | A74 |
| Me | Me | Me | SMe | A75 | Me | Me | Me | NHC(O)OBu-t | A75 |
| Me | Me | Me | SMe | A76 | Me | Me | Me | NHC(O)OBu-t | A76 |
| Me | Me | Me | SMe | A77 | Me | Me | Me | NHC(O)OBu-t | A77 |
| Me | Me | Me | SMe | A81 | Me | Me | Me | NHC(O)OBu-t | A81 |
| Me | Me | Me | SMe | A83 | Me | Me | Me | NHC(O)OBu-t | A83 |
| Me | Me | Me | SMe | A88 | Me | Me | Me | NHC(O)OBu-t | A88 |
| Me | Me | Me | SMe | A91 | MP | MP | MP | NHC(O)OBu-t | A91 |
| Me | Me | Me | SMe | A97 | Me | Me | Me | NHC(O)OBu-t | A97 |
| Me | Me | Me | SMe | A98 | Me | Me | Me | NHC(O)OBu-t | A98 |
| Me | Me | Me | SMe | A102 | Me | Me | Me | NHC(O)OBu-t | A102 |
| Me | Me | Me | Me | A1 | Me | Me | Me | Me | A11 |
| Me | Me | Me | Me | A2 | Me | Me | Me | Me | A12 |
| Me | Me | Me | Me | A3 | Me | Me | Me | Me | A13 |
| Me | Me | Me | Me | A4 | Me | Me | Me | Me | A14 |
| Me | Me | Me | Me | A5 | Me | Me | Me | Me | A15 |
| Me | Me | Me | Me | A6 | Me | Me | Me | Me | A16 |
| Me | Me | Me | Me | A7 | Me | Me | Me | Me | A17 |
| Me | Me | Me | Me | A8 | Me | Me | Me | Me | A18 |
| Me | Me | Me | Me | A9 | Me | Me | Me | Me | A19 |
| Me | Me | Me | Me | A10 | Me | Me | Me | Me | A20 |
| Me | Me | Me | Me | A21 | Me | Me | Me | Me | A60 |
| Me | Me | Me | Me | A22 | Me | Me | Me | Me | A61 |
| Me | Me | Me | Me | A23 | Me | Me | Me | Me | A62 |
| Me | Me | Me | Me | A24 | Me | Me | Me | Me | A63 |
| Me | Me | Me | Me | A25 | Me | Me | Me | Me | A64 |
| Me | Me | Me | Me | A26 | Me | Me | Me | Me | A65 |
| Me | Me | Me | Me | A27 | Me | Me | Me | Me | A66 |
| Me | Me | Me | Me | A28 | Me | Me | Me | Me | A67 |

TABLE 1-continued

| | | | | | | | | | |
|---|---|---|---|---|---|---|---|---|---|
| Me | Me | Me | Me | A29 | Me | Me | Me | Me | A68 |
| Me | Me | Me | Me | A30 | Me | Me | Me | Me | A69 |
| Me | Me | Me | Me | A31 | Me | Me | Me | Me | A70 |
| Me | Me | Me | Me | A32 | Me | Me | Me | Me | A71 |
| Me | Me | Me | Me | A33 | Me | Me | Me | Me | A72 |
| Me | Me | Me | Me | A34 | Me | Me | Me | Me | A73 |
| Me | Me | Me | Me | A35 | Me | Me | Me | Me | A74 |
| Me | Me | Me | Me | A36 | Me | Me | Me | Me | A75 |
| Me | Me | Me | Me | A37 | Me | Me | Me | Me | A76 |
| Me | Me | Me | Me | A38 | Me | Me | Me | Me | A77 |
| Me | Me | Me | Me | A39 | Me | Me | Me | Me | A78 |
| Me | Me | Me | Me | A40 | Me | Me | Me | Me | A79 |
| Me | Me | Me | Me | A41 | Me | Me | Me | Me | A80 |
| Me | Me | Me | Me | A42 | Me | Me | Me | Me | A81 |
| Me | Me | Me | Me | A43 | Me | Me | Me | Me | A82 |
| Me | Me | Me | Me | A44 | Me | Me | Me | Me | A83 |
| Me | Me | Me | Me | A45 | Me | Me | Me | Me | A84 |
| Me | Me | Me | Me | A46 | Me | Me | Me | Me | A85 |
| Me | Me | Me | Me | A47 | Me | Me | Me | Me | A86 |
| Me | Me | Me | Me | A48 | Me | Me | Me | Me | A87 |
| Me | Me | Me | Me | A49 | Me | Me | Me | Me | A88 |
| Me | Me | Me | Me | A50 | Me | Me | Me | Me | A89 |
| Me | Me | Me | Me | A51 | Me | Me | Me | Me | A90 |
| Me | Me | Me | Me | A52 | Me | Me | Me | Me | A91 |
| Me | Me | Me | Me | A53 | Me | Me | Me | Me | A92 |
| Me | Me | Me | Me | A54 | Me | Me | Me | Me | A93 |
| Me | Me | Me | Me | A55 | Me | Me | Me | Me | A94 |
| Me | Me | Me | Me | A56 | Me | Me | Me | Me | A95 |
| Me | Me | Me | Me | A57 | Me | Me | Me | Me | A96 |
| Me | Me | Me | Me | A58 | Me | Me | Me | Me | A97 |
| Me | Me | Me | Me | A59 | Me | Me | Me | Me | A98 |
| Me | Me | Me | Me | A99 | Me | Me | Me | Me | A108 |
| Me | Me | Me | Me | A100 | Me | Me | Me | Me | A109 |
| Me | Me | Me | Me | A101 | Me | Me | Me | Me | A110 |
| Me | Me | Me | Me | A102 | Me | Me | Me | Me | A111 |
| Me | Me | Me | Me | A103 | Me | Me | Me | Me | A112 |
| Me | Me | Me | Me | A104 | Me | Me | Me | Me | A113 |
| Me | Me | Me | Me | A105 | Me | Me | Me | Me | A114 |
| Me | Me | Me | Me | A106 | Me | Me | Me | Me | A115 |
| Me | Me | Me | Me | A107 | Me | Me | Me | D1-103-3 | H |
| Me | Me | Me | D1-103-1 | H | Me | Me | Me | D1-103-4 | H |
| Me | Me | Me | D1-103-2 | H | Me | Et | Et | D1-103-3 | H. |
| Me | Et | Et | D1-103-1 | H | Me | Et | Et | D1-103-4 | H |
| Me | Et | Et | D1-103-2 | H | | | | | |

TABLE 2

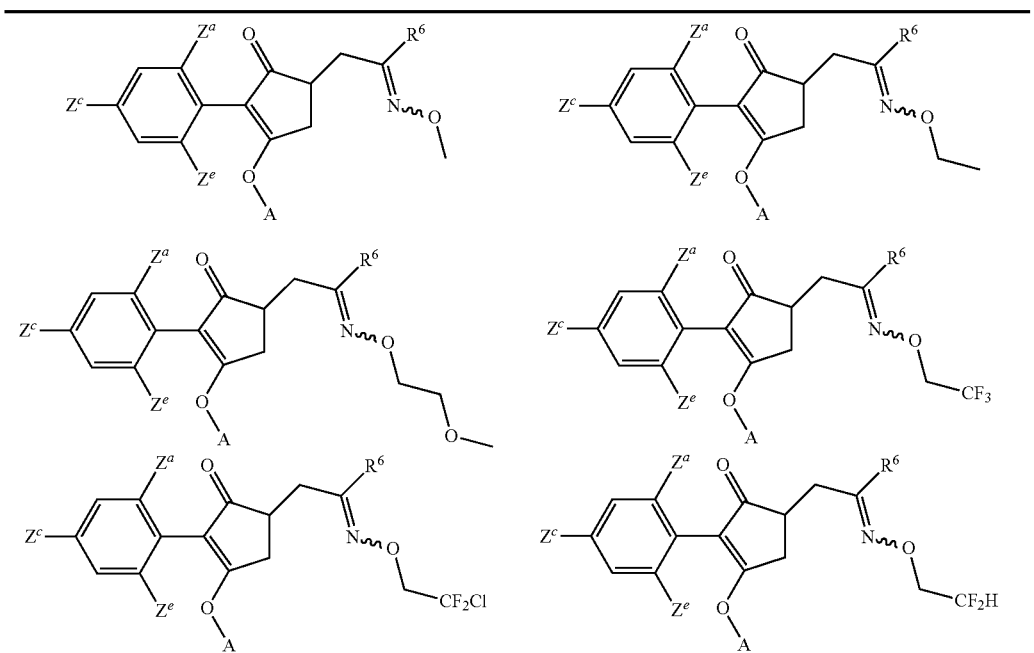

TABLE 2-continued
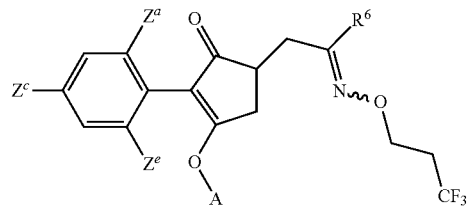 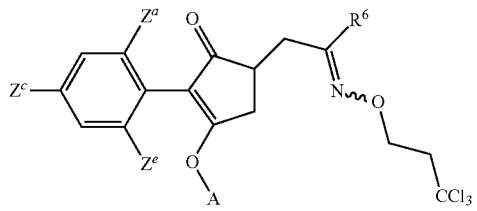
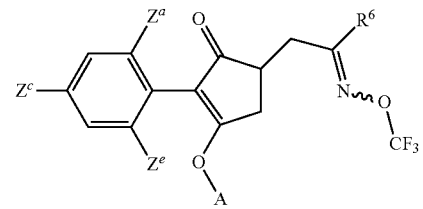 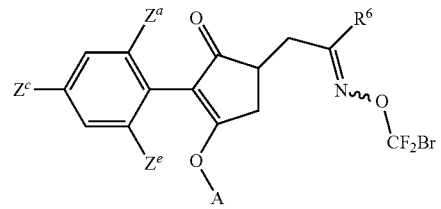
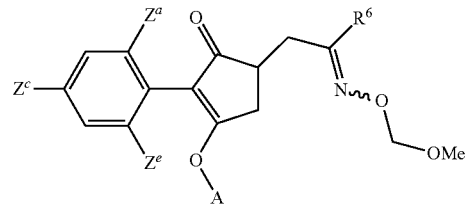 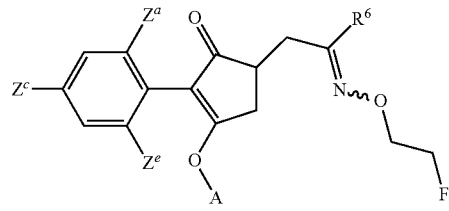
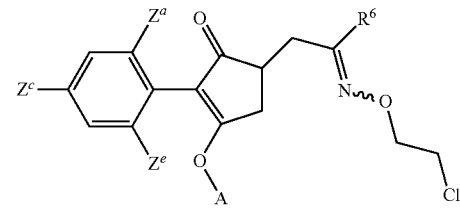 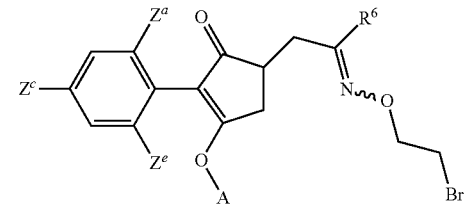
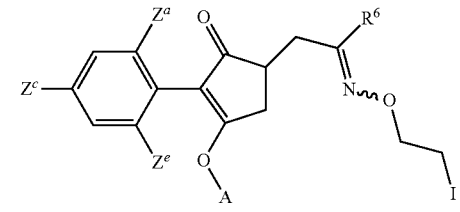 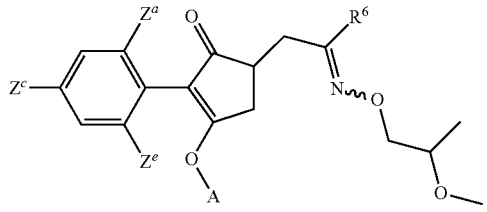
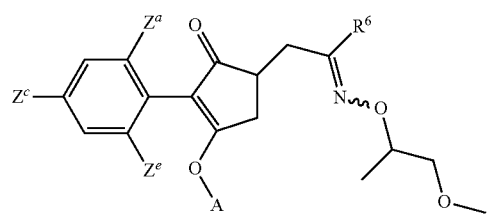 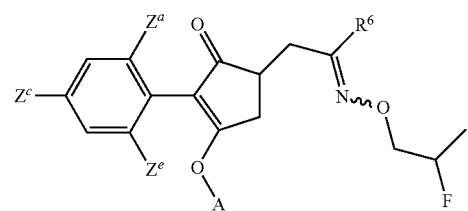
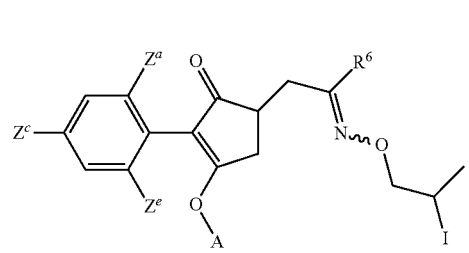 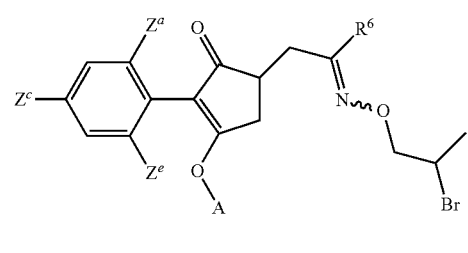

TABLE 2-continued

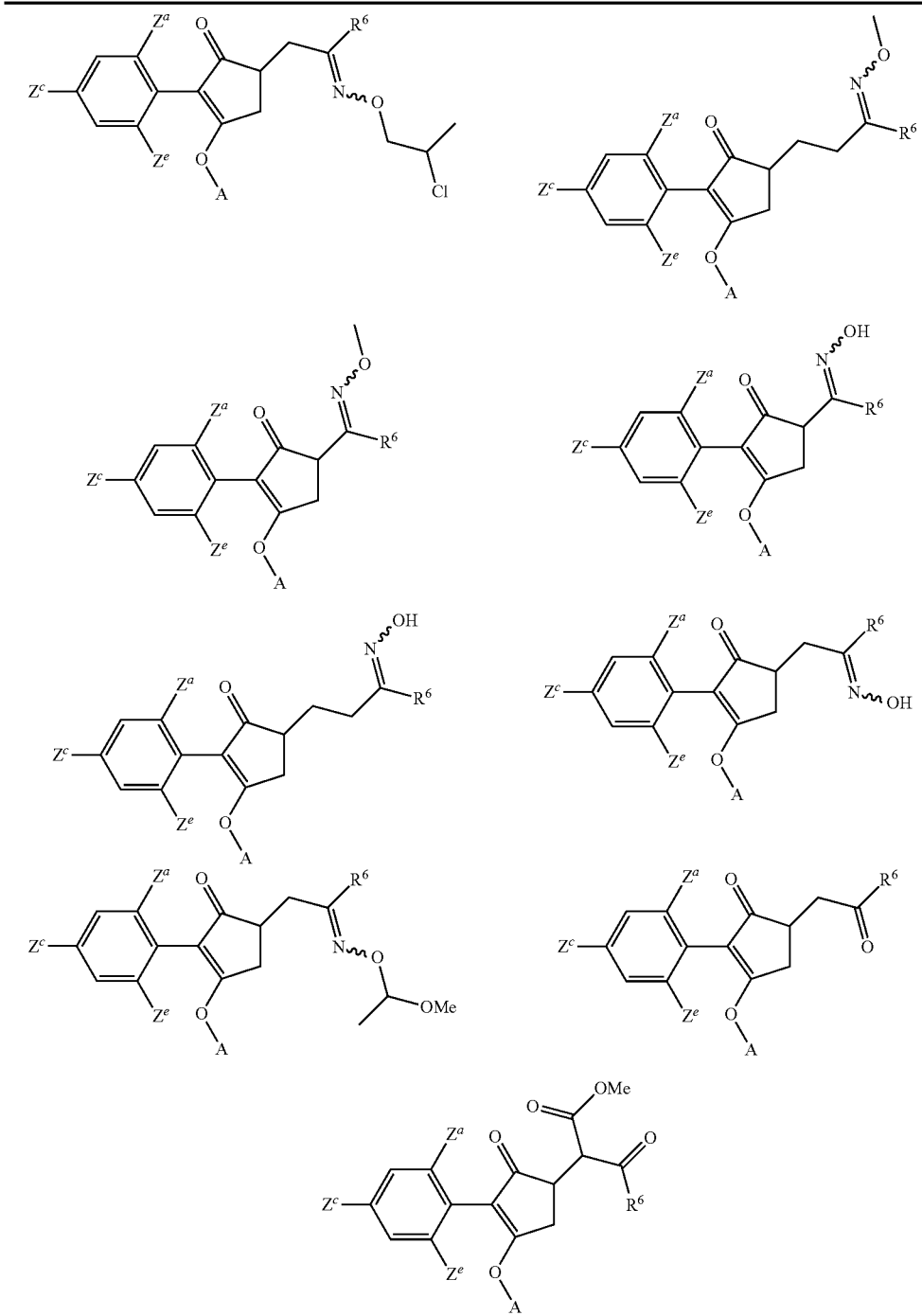

| $R^6$ | $Z^a$ | $Z^e$ | $Z^c$ | A | $R^6$ | $Z^a$ | $Z^e$ | $Z^c$ | A |
|---|---|---|---|---|---|---|---|---|---|
| Me | Me | Me | C≡CMe | H | Me | Me | Et | C≡CMe | H |
| Me | Me | Me | C≡CMe | A39 | Me | Me | Et | C≡CMe | A39 |
| Me | Me | Me | C≡CMe | A40 | Me | Me | Et | C≡CMe | A40 |
| Me | Me | Me | C≡CMe | A41 | Me | Me | Et | C≡CMe | A41 |
| c-Pr | Me | Me | C≡CMe | H | c-Pr | Me | Et | C≡CMe | H |
| c-Pr | Me | Me | C≡CMe | A39 | c-Pr | Me | Et | C≡CMe | A39 |
| c-Pr | Me | Me | C≡CMe | A40 | c-Pr | Me | Et | C≡CMe | A40 |
| c-Pr | Me | Me | C≡CMe | A41 | c-Pr | Me | Et | C≡CMe | A41 |
| c-Bu | Me | Me | C≡CMe | H | c-Bu | Me | Et | C≡CMe | H |
| c-Bu | Me | Me | C≡CMe | A39 | c-Bu | Me | Et | C≡CMe | A39 |
| c-Bu | Me | Me | C≡CMe | A40 | c-Bu | Me | Et | C≡CMe | A40 |
| c-Bu | Me | Me | C≡CMe | A41 | c-Bu | Me | Et | C≡CMe | A41 |

TABLE 2-continued

| | | | | | | | | | |
|---|---|---|---|---|---|---|---|---|---|
| c-Pen | Me | Me | C≡CMe | H | c-Pen | Me | Et | C≡CMe | H |
| c-Pen | Me | Me | C≡CMe | A39 | c-Pen | Me | Et | C≡CMe | A39 |
| c-Pen | Me | Me | C≡CMe | A40 | c-Pen | Me | Et | C≡CMe | A40 |
| c-Pen | Me | Me | C≡CMe | A41 | c-Pen | Me | Et | C≡CMe | A41 |
| c-Hex | Me | Me | C≡CMe | H | c-Hex | Me | Et | C≡CMe | H |
| c-Hex | Me | Me | C≡CMe | A39 | c-Hex | Me | Et | C≡CMe | A39 |
| c-Hex | Me | Me | C≡CMe | A40 | c-Hex | Me | Et | C≡CMe | A40 |
| c-Hex | Me | Me | C≡CMe | A41 | c-Hex | Me | Et | C≡CMe | A41 |
| Me | Me | Me | C≡CSi(Me)$_3$ | H | Me | Me | Et | C≡CSi(Me)$_3$ | H |
| Me | Me | Me | C≡CSi(Me)$_3$ | A39 | Me | Me | Et | C≡CSi(Me)$_3$ | A39 |
| Me | Me | Me | C≡CSi(Me)$_3$ | A40 | Me | Me | Et | C≡CSi(Me)$_3$ | A40 |
| Me | Me | Me | C≡CSi(Me)$_3$ | A41 | Me | Me | Et | C≡CSi(Me)$_3$ | A41 |
| c-Pr | Me | Me | C≡CSi(Me)$_3$ | H | c-Pr | Me | Et | C≡CSi(Me)$_3$ | H |
| c-Pr | Me | Me | C≡CSi(Me)$_3$ | A39 | c-Pr | Me | Et | C≡CSi(Me)$_3$ | A39 |
| c-Pr | Me | Me | C≡CSi(Me)$_3$ | A40 | c-Pr | Me | Et | C≡CSi(Me)$_3$ | A40 |
| c-Pr | Me | Me | C≡CSi(Me)$_3$ | A41 | c-Pr | Me | Et | C≡CSi(Me)$_3$ | A41 |
| c-Bu | Me | Me | C≡CSi(Me)$_3$ | H | c-Bu | Me | Et | C≡CSi(Me)$_3$ | H |
| c-Bu | Me | Me | C≡CSi(Me)$_3$ | A39 | c-Bu | Me | Et | C≡CSi(Me)$_3$ | A39 |
| c-Bu | Me | Me | C≡CSi(Me)$_3$ | A40 | c-Bu | Me | Et | C≡CSi(Me)$_3$ | A40 |
| c-Bu | Me | Me | C≡CSi(Me)$_3$ | A41 | c-Bu | Me | Et | C≡CSi(Me)$_3$ | A41 |
| c-Pen | Me | Me | C≡CSi(Me)$_3$ | H | c-Pen | Me | Et | C≡CSi(Me)$_3$ | H |
| c-Pen | Me | Me | C≡CSi(Me)$_3$ | A39 | c-Pen | Me | Et | C≡CSi(Me)$_3$ | A39 |
| c-Pen | Me | Me | C≡CSi(Me)$_3$ | A40 | c-Pen | Me | Et | C≡CSi(Me)$_3$ | A40 |
| c-Pen | Me | Me | C≡CSi(Me)$_3$ | A41 | c-Pen | Me | Et | C≡CSi(Me)$_3$ | A41 |
| c-Hex | Me | Me | C≡CSi(Me)$_3$ | H | c-Hex | Me | Et | C≡CSi(Me)$_3$ | H |
| c-Hex | Me | Me | C≡CSi(Me)$_3$ | A39 | c-Hex | Me | Et | C≡CSi(Me)$_3$ | A39 |
| c-Hex | Me | Me | C≡CSi(Me)$_3$ | A40 | c-Hex | Me | Et | C≡CSi(Me)$_3$ | A40 |
| c-Hex | Me | Me | C≡CSi(Me)$_3$ | A41 | c-Hex | Me | Et | C≡CSi(Me)$_3$ | A41 |
| Me | Me | Me | C≡CPr-c | H | Me | Me | Et | C≡CPr-c | H |
| Me | Me | Me | C≡CPr-c | A39 | Me | Me | Et | C≡CPr-c | A39 |
| Me | Me | Me | C≡CPr-c | A40 | Me | Me | Et | C≡CPr-c | A40 |
| Me | Me | Me | C≡CPr-c | A41 | Me | Me | Et | C≡CPr-c | A41 |
| c-Pr | Me | Me | C≡CPr-c | H | c-Pr | Me | Et | C≡CPr-c | H |
| c-Pr | Me | Me | C≡CPr-c | A39 | c-Pr | Me | Et | C≡CPr-c | A39 |
| c-Pr | Me | Me | C≡CPr-c | A40 | c-Pr | Me | Et | C≡CPr-c | A40 |
| c-Pr | Me | Me | C≡CPr-c | A41 | c-Pr | Me | Et | C≡CPr-c | A41 |
| c-Bu | Me | Me | C≡CPr-c | H | c-Bu | Me | Et | C≡CPr-c | H |
| c-Bu | Me | Me | C≡CPr-c | A39 | c-Bu | Me | Et | C≡CPr-c | A39 |
| c-Bu | Me | Me | C≡CPr-c | A40 | c-Bu | Me | Et | C≡CPr-c | A40 |
| c-Bu | Me | Me | C≡CPr-c | A41 | c-Bu | Me | Et | C≡CPr-c | A41 |
| c-Pen | Me | Me | C≡CPr-c | H | c-Pen | Me | Et | C≡CPr-c | H |
| c-Pen | Me | Me | C≡CPr-c | A39 | c-Pen | Me | Et | C≡CPr-c | A39 |
| c-Pen | Me | Me | C≡CPr-c | A40 | c-Pen | Me | Et | C≡CPr-c | A40 |
| c-Pen | Me | Me | C≡CPr-c | A41 | c-Pen | Me | Et | C≡CPr-c | A41 |
| c-Hex | Me | Me | C≡CPr-c | H | c-Hex | Me | Et | C≡CPr-c | H |
| c-Hex | Me | Me | C≡CPr-c | A39 | c-Hex | Me | Et | C≡CPr-c | A39 |
| c-Hex | Me | Me | C≡CPr-c | A40 | c-Hex | Me | Et | C≡CPr-c | A40 |
| c-Hex | Me | Me | C≡CPr-c | A41 | c-Hex | Me | Et | C≡CPr-c | A41 |
| Me | Me | Me | C≡CC(Me)$_2$OH | H | Me | Me | Et | C≡CC(Me)$_2$OH | H |
| Me | Me | Me | C≡CC(Me)$_2$OH | A39 | Me | Me | Et | C≡CC(Me)$_2$OH | A39 |
| Me | Me | Me | C≡CC(Me)$_2$OH | A40 | Me | Me | Et | C≡CC(Me)$_2$OH | A40 |
| Me | Me | Me | C≡CC(Me)$_2$OH | A41 | Me | Me | Et | C≡CC(Me)$_2$OH | A41 |
| Me | Me | Me | C≡CCH$_2$OH | H | Me | Me | Et | C≡CCH$_2$OH | H |
| Me | Me | Me | C≡CCH$_2$OH | A39 | Me | Me | Et | C≡CCH$_2$OH | A39 |
| Me | Me | Me | C≡CCH$_2$OH | A40 | Me | Me | Et | C≡CCH$_2$OH | A40 |
| Me | Me | Me | C≡CCH$_2$OH | A41 | Me | Me | Et | C≡CCH$_2$OH | A41 |
| Me | Me | Me | Ph | H | Me | Me | Et | Ph | H |
| Me | Me | Me | Ph | Me | Me | Me | Et | Ph | Me |
| Me | Me | Me | Ph | A11 | Me | Me | Et | Ph | A11 |
| Me | Me | Me | Ph | A34 | Me | Me | Et | Ph | A34 |
| Me | Me | Me | Ph | A35 | Me | Me | Et | Ph | A35 |
| Me | Me | Me | Ph | A37 | Me | Me | Et | Ph | A37 |
| Me | Me | Me | Ph | A39 | Me | Me | Et | Ph | A39 |
| Me | Me | Me | Ph | A40 | Me | Me | Et | Ph | A40 |
| Me | Me | Me | Ph | A41 | Me | Me | Et | Ph | A41 |
| Me | Me | Me | Ph | A73 | Me | Me | Et | Ph | A73 |
| Me | Me | Me | Ph | A75 | Me | Me | Et | Ph | A75 |
| Me | Me | Me | Ph | A83 | Me | Me | Et | Ph | A83 |
| Me | Me | Me | Ph | A84 | Me | Me | Et | Ph | A84 |
| Me | Me | Me | Ph | A85 | Me | Me | Et | Ph | A85 |
| Me | Me | Me | Ph | A91 | Me | Me | Et | Ph | A91 |
| Me | Me | Me | D1-108b-1 | H | Me | Me | Et | D1-108b-1 | H |
| Me | Me | Me | D1-108b-1 | Me | Me | Me | Et | D1-108b-1 | Me |
| Me | Me | Me | D1-108b-1 | A11 | Me | Me | Et | D1-108b-1 | A11 |
| Me | Me | Me | D1-108b-1 | A34 | Me | Me | Et | D1-108b-1 | A34 |
| Me | Me | Me | D1-108b-1 | A35 | Me | Me | Et | D1-108b-1 | A35 |
| Me | Me | Me | D1-108b-1 | A37 | Me | Me | Et | D1-108b-1 | A37 |
| Me | Me | Me | D1-108b-1 | A39 | Me | Me | Et | D1-108b-1 | A39 |
| Me | Me | Me | D1-108b-1 | A40 | Me | Me | Et | D1-108b-1 | A40 |
| Me | Me | Me | D1-108b-1 | A41 | Me | Me | Et | D1-108b-1 | A41 |

TABLE 2-continued

| | | | | | | | | | |
|---|---|---|---|---|---|---|---|---|---|
| Me | Me | Me | D1-108b-1 | A73 | Me | Me | Et | D1-108b-1 | A73 |
| Me | Me | Me | D1-108b-1 | A75 | Me | Me | Et | D1-108b-1 | A75 |
| Me | Me | Me | D1-108b-1 | A83 | Me | Me | Et | D1-108b-1 | A83 |
| Me | Me | Me | D1-108b-1 | A84 | Me | Me | Et | D1-108b-1 | A84 |
| Me | Me | Me | D1-108b-1 | A85 | Me | Me | Et | D1-108b-1 | A85 |
| Me | Me | Me | D1-108b-2 | A91 | Me | Me | Et | D1-108b-2 | A91 |
| Me | Me | Me | D1-108b-3 | H | Me | Me | Et | D1-108b-3 | H |
| Me | Me | Me | D1-108b-4 | H | Me | Me | Et | D1-108b-4 | H |
| Me | Me | Me | D1-108b-4 | Me | Me | Me | Et | D1-108b-4 | Me |
| Me | Me | Me | D1-108b-4 | A11 | Me | Me | Et | D1-108b-4 | A11 |
| Me | Me | Me | D1-108b-4 | A34 | Me | Me | Et | D1-108b-4 | A34 |
| Me | Me | Me | D1-108b-4 | A35 | Me | Me | Et | D1-108b-4 | A35 |
| Me | Me | Me | D1-108b-4 | A37 | Me | Me | Et | D1-108b-4 | A37 |
| Me | Me | Me | D1-108b-4 | A39 | Me | Me | Et | D1-108b-4 | A39 |
| Me | Me | Me | D1-108b-4 | A40 | Me | Me | Et | D1-108b-4 | A40 |
| Me | Me | Me | D1-108b-4 | A41 | Me | Me | Et | D1-108b-4 | A41 |
| Me | Me | Me | D1-108b-4 | A73 | Me | Me | Et | D1-108b-4 | A73 |
| Me | Me | Me | D1-108b-4 | A75 | Me | Me | Et | D1-108b-4 | A75 |
| Me | Me | Me | D1-108b-4 | A83 | Me | Me | Et | D1-108b-4 | A83 |
| Me | Me | Me | D1-108b-4 | A84 | Me | Me | Et | D1-108b-4 | A84 |
| Me | Me | Me | D1-108b-4 | A85 | Me | Me | Et | D1-108b-4 | A85 |
| Me | Me | Me | D1-108b-4 | A91 | Me | Me | Et | D1-108b-4 | A91 |
| Me | Me | Me | D1-108b-5 | H | Me | Me | Et | D1-108b-5 | H |
| Me | Me | Me | D1-108b-6 | H | Me | Me | Et | D1-108b-6 | H |
| Me | Me | Me | D1-108b-7 | H | Me | Me | Et | D1-108b-7 | H |
| Me | Me | Me | D1-108b-8 | H | Me | Me | Et | D1-108b-8 | H |
| Me | Me | Me | D1-108b-8 | Me | Me | Me | Et | D1-108b-8 | Me |
| Me | Me | Me | D1-108b-8 | A11 | Me | Me | Et | D1-108b-8 | A11 |
| Me | Me | Me | D1-108b-8 | A34 | Me | Me | Et | D1-108b-8 | A34 |
| Me | Me | Me | D1-108b-8 | A35 | Me | Me | Et | D1-108b-8 | A35 |
| Me | Me | Me | D1-108b-8 | A37 | Me | Me | Et | D1-108b-8 | A37 |
| Me | Me | Me | D1-108b-8 | A39 | Me | Me | Et | D1-108b-8 | A39 |
| Me | Me | Me | D1-108b-8 | A40 | Me | Me | Et | D1-108b-8 | A40 |
| Me | Me | Me | D1-108b-8 | A41 | Me | Me | Et | D1-108b-8 | A41 |
| Me | Me | Me | D1-108b-8 | A73 | Me | Me | Et | D1-108b-8 | A73 |
| Me | Me | Me | D1-108b-8 | A75 | Me | Me | Et | D1-108b-8 | A75 |
| Me | Me | Me | D1-108b-8 | A83 | Me | Me | Et | D1-108b-8 | A83 |
| Me | Me | Me | D1-108b-8 | A84 | Me | Me | Et | D1-108b-8 | A84 |
| Me | Me | Me | D1-108b-8 | A85 | Me | Me | Et | D1-108b-8 | A85 |
| Me | Me | Me | D1-108b-8 | A91 | Me | Me | Et | D1-108b-8 | A91 |
| Me | Me | Me | D1-108b-9 | H | Me | Me | Et | D1-108b-9 | H |
| Me | Me | Me | D1-108b-9 | Me | Me | Me | Et | D1-108b-9 | Me |
| Me | Me | Me | D1-108b-9 | A11 | Me | Me | Et | D1-108b-9 | A11 |
| Me | Me | Me | D1-108b-9 | A34 | Me | Me | Et | D1-108b-9 | A34 |
| Me | Me | Me | D1-108b-9 | A35 | Me | Me | Et | D1-108b-9 | A35 |
| Me | Me | Me | D1-108b-9 | A37 | Me | Me | Et | D1-108b-9 | A37 |
| Me | Me | Me | D1-108b-9 | A39 | Me | Me | Et | D1-108b-9 | A39 |
| Me | Me | Me | D1-108b-9 | A40 | Me | Me | Et | D1-108b-9 | A40 |
| Me | Me | Me | D1-108b-9 | A41 | Me | Me | Et | D1-108b-9 | A41 |
| Me | Me | Me | D1-108b-9 | A73 | Me | Me | Et | D1-108b-9 | A73 |
| Me | Me | Me | D1-108b-9 | A75 | Me | Me | Et | D1-108b-9 | A75 |
| Me | Me | Me | D1-108b-9 | A83 | Me | Me | Et | D1-108b-9 | A83 |
| Me | Me | Me | D1-108b-9 | A84 | Me | Me | Et | D1-108b-9 | A84 |
| Me | Me | Me | D1-108b-9 | A85 | Me | Me | Et | D1-108b-9 | A85 |
| Me | Me | Me | D1-108b-9 | A91 | Me | Me | Et | D1-108b-9 | A91 |
| Me | Me | Me | D1-108b-10 | H | Me | Me | Et | D1-108b-10 | H |
| Me | Me | Me | D1-108b-10 | Me | Me | Me | Et | D1-108b-10 | Me |
| Me | Me | Me | D1-108b-10 | A11 | Me | Me | Et | D1-108b-10 | A11 |
| Me | Me | Me | D1-108b-10 | A34 | Me | Me | Et | D1-108b-10 | A34 |
| Me | Me | Me | D1-108b-10 | A35 | Me | Me | Et | D1-108b-10 | A35 |
| Me | Me | Me | D1-108b-10 | A37 | Me | Me | Et | D1-108b-10 | A37 |
| Me | Me | Me | D1-108b-10 | A39 | Me | Me | Et | D1-108b-10 | A39 |
| Me | Me | Me | D1-108b-10 | A40 | Me | Me | Et | D1-108b-10 | A40 |
| Me | Me | Me | D1-108b-10 | A41 | Me | Me | Et | D1-108b-10 | A41 |
| Me | Me | Me | D1-108b-10 | A73 | Me | Me | Et | D1-108b-10 | A73 |
| Me | Me | Me | D1-108b-10 | A75 | Me | Me | Et | D1-108b-10 | A75 |
| Me | Me | Me | D1-108b-10 | A83 | Me | Me | Et | D1-108b-10 | A83 |
| Me | Me | Me | D1-108b-10 | A84 | Me | Me | Et | D1-108b-10 | A84 |
| Me | Me | Me | D1-108b-10 | A85 | Me | Me | Et | D1-108b-10 | A85 |
| Me | Me | Me | D1-108b-10 | A91 | Me | Me | Et | D1-108b-10 | A91 |
| Me | Me | Me | D1-108b-11 | H | Me | Me | Et | D1-108b-11 | H |
| Me | Me | Me | D1-108b-12 | H | Me | Me | Et | D1-108b-12 | H |
| Me | Me | Me | D1-108b-12 | Me | Me | Me | Et | D1-108b-12 | Me |
| Me | Me | Me | D1-108b-12 | A11 | Me | Me | Et | D1-108b-12 | A11 |
| Me | Me | Me | D1-108b-12 | A34 | Me | Me | Et | D1-108b-12 | A34 |
| Me | Me | Me | D1-108b-12 | A35 | Me | Me | Et | D1-108b-12 | A35 |
| Me | Me | Me | D1-108b-12 | A37 | Me | Me | Et | D1-108b-12 | A37 |
| Me | Me | Me | D1-108b-12 | A39 | Me | Me | Et | D1-108b-12 | A39 |
| Me | Me | Me | D1-108b-12 | A40 | Me | Me | Et | D1-108b-12 | A40 |
| Me | Me | Me | D1-108b-12 | A41 | Me | Me | Et | D1-108b-12 | A41 |

TABLE 2-continued

| | | | | | | | | | |
|---|---|---|---|---|---|---|---|---|---|
| Me | Me | Me | D1-108b-12 | A73 | Me | Me | Et | D1-108b-12 | A73 |
| Me | Me | Me | D1-108b-12 | A75 | Me | Me | Et | D1-108b-12 | A75 |
| Me | Me | Me | D1-108b-12 | A83 | Me | Me | Et | D1-108b-12 | A83 |
| Me | Me | Me | D1-108b-12 | A84 | Me | Me | Et | D1-108b-12 | A84 |
| Me | Me | Me | D1-108b-12 | A85 | Me | Me | Et | D1-108b-12 | A85 |
| Me | Me | Me | D1-108b-12 | A91 | Me | Me | Et | D1-108b-12 | A91 |
| Me | Me | Me | D1-108b-13 | H | Me | Me | Et | D1-108b-13 | H |
| Me | Me | Me | D1-108b-14 | H | Me | Me | Et | D1-108b-14 | H |
| Me | Me | Me | D1-108b-15 | H | Me | Me | Et | D1-108b-15 | H |
| Me | Me | Me | D1-108b-16 | H | Me | Me | Et | D1-108b-16 | H |
| Me | Me | Me | D1-108b-17 | H | Me | Me | Et | D1-108b-17 | H |
| Me | Me | Me | D1-108b-18 | H | Me | Me | Et | D1-108b-18 | H |
| Me | Me | Me | D1-108b-19 | H | Me | Me | Et | D1-108b-19 | H |
| Me | Me | Me | D1-2a | H | Me | Me | Et | D1-2a | H |
| Me | Me | Me | D1-2b | H | Me | Me | Et | D1-2b | H |
| Me | Me | Me | D1-7a | H | Me | Me | Et | D1-7a | H |
| Me | Me | Me | D1-7b-1 | H | Me | Me | Et | D1-7b-1 | H |
| Me | Me | Me | D1-7b-1 | A39 | Me | Me | Et | D1-7b-1 | A39 |
| Me | Me | Me | D1-7b-1 | A40 | Me | Me | Et | D1-7b-1 | A40 |
| Me | Me | Me | D1-7b-1 | A41 | Me | Me | Et | D1-7b-1 | A41 |
| c-Pr | Me | Me | D1-7b-1 | H | c-Pr | Me | Et | D1-7b-1 | H |
| c-Pr | Me | Me | D1-7b-1 | A39 | c-Pr | Me | Et | D1-7b-1 | A39 |
| c-Pr | Me | Me | D1-7b-1 | A40 | c-Pr | Me | Et | D1-7b-1 | A40 |
| c-Pr | Me | Me | D1-7b-1 | A41 | c-Pr | Me | Et | D1-7b-1 | A41 |
| c-Bu | Me | Me | D1-7b-1 | H | c-Bu | Me | Et | D1-7b-1 | H |
| c-Bu | Me | Me | D1-7b-1 | A39 | c-Bu | Me | Et | D1-7b-1 | A39 |
| c-Bu | Me | Me | D1-7b-1 | A40 | c-Bu | Me | Et | D1-7b-1 | A40 |
| c-Bu | Me | Me | D1-7b-1 | A41 | c-Bu | Me | Et | D1-7b-1 | A41 |
| c-Pen | Me | Me | D1-7b-1 | H | c-Pen | Me | Et | D1-7b-1 | H |
| c-Pen | Me | Me | D1-7b-1 | A39 | c-Pen | Me | Et | D1-7b-1 | A39 |
| c-Pen | Me | Me | D1-7b-1 | A40 | c-Pen | Me | Et | D1-7b-1 | A40 |
| c-Pen | Me | Me | D1-7b-1 | A41 | c-Pen | Me | Et | D1-7b-1 | A41 |
| c-Hex | Me | Me | D1-7b-1 | H | c-Hex | Me | Et | D1-7b-1 | H |
| c-Hex | Me | Me | D1-7b-1 | A39 | c-Hex | Me | Et | D1-7b-1 | A39 |
| c-Hex | Me | Me | D1-7b-1 | A40 | c-Hex | Me | Et | D1-7b-1 | A40 |
| c-Hex | Me | Me | D1-7b-1 | A41 | c-Hex | Me | Et | D1-7b-1 | A41 |
| Me | Me | Me | D1-7b-2 | H | Me | Me | Et | D1-7b-2 | H |
| Me | Me | Me | D1-7b-2 | A39 | Me | Me | Et | D1-7b-2 | A39 |
| Me | Me | Me | D1-7b-2 | A40 | Me | Me | Et | D1-7b-2 | A40 |
| Me | Me | Me | D1-7b-2 | A41 | Me | Me | Et | D1-7b-2 | A41 |
| c-Pr | Me | Me | D1-7b-2 | H | c-Pr | Me | Et | D1-7b-2 | H |
| c-Pr | Me | Me | D1-7b-2 | A39 | c-Pr | Me | Et | D1-7b-2 | A39 |
| c-Pr | Me | Me | D1-7b-2 | A40 | c-Pr | Me | Et | D1-7b-2 | A40 |
| c-Pr | Me | Me | D1-7b-2 | A41 | c-Pr | Me | Et | D1-7b-2 | A41 |
| c-Bu | Me | Me | D1-7b-2 | H | c-Bu | Me | Et | D1-7b-2 | H |
| c-Bu | Me | Me | D1-7b-2 | A39 | c-Bu | Me | Et | D1-7b-2 | A39 |
| c-Bu | Me | Me | D1-7b-2 | A40 | c-Bu | Me | Et | D1-7b-2 | A40 |
| c-Bu | Me | Me | D1-7b-2 | A41 | c-Bu | Me | Et | D1-7b-2 | A41 |
| c-Pen | Me | Me | D1-7b-2 | H | c-Pen | Me | Et | D1-7b-2 | H |
| c-Pen | Me | Me | D1-7b-2 | A39 | c-Pen | Me | Et | D1-7b-2 | A39 |
| c-Pen | Me | Me | D1-7b-2 | A40 | c-Pen | Me | Et | D1-7b-2 | A40 |
| c-Pen | Me | Me | D1-7b-2 | A41 | c-Pen | Me | Et | D1-7b-2 | A41 |
| c-Hex | Me | Me | D1-7b-2 | H | c-Hex | Me | Et | D1-7b-2 | H |
| c-Hex | Me | Me | D1-7b-2 | A39 | c-Hex | Me | Et | D1-7b-2 | A39 |
| c-Hex | Me | Me | D1-7b-2 | A40 | c-Hex | Me | Et | D1-7b-2 | A40 |
| c-Hex | Me | Me | D1-7b-2 | A41 | c-Hex | Me | Et | D1-7b-2 | A41 |
| Me | Me | Me | D1-7b-3 | H | Me | Me | Et | D1-7b-3 | H |
| Me | Me | Me | D1-7b-3 | A39 | Me | Me | Et | D1-7b-3 | A39 |
| Me | Me | Me | D1-7b-3 | A40 | Me | Me | Et | D1-7b-3 | A40 |
| Me | Me | Me | D1-7b-3 | A41 | Me | Me | Et | D1-7b-3 | A41 |
| c-Pr | Me | Me | D1-7b-3 | H | c-Pr | Me | Et | D1-7b-3 | H |
| c-Pr | Me | Me | D1-7b-3 | A39 | c-Pr | Me | Et | D1-7b-3 | A39 |
| c-Pr | Me | Me | D1-7b-3 | A40 | c-Pr | Me | Et | D1-7b-3 | A40 |
| c-Pr | Me | Me | D1-7b-3 | A41 | c-Pr | Me | Et | D1-7b-3 | A41 |
| c-Bu | Me | Me | D1-7b-3 | H | c-Bu | Me | Et | D1-7b-3 | H |
| c-Bu | Me | Me | D1-7b-3 | A39 | c-Bu | Me | Et | D1-7b-3 | A39 |
| c-Bu | Me | Me | D1-7b-3 | A40 | c-Bu | Me | Et | D1-7b-3 | A40 |
| c-Bu | Me | Me | D1-7b-3 | A41 | c-Bu | Me | Et | D1-7b-3 | A41 |
| c-Pen | Me | Me | D1-7b-3 | H | c-Pen | Me | Et | D1-7b-3 | H |
| c-Pen | Me | Me | D1-7b-3 | A39 | c-Pen | Me | Et | D1-7b-3 | A39 |
| c-Pen | Me | Me | D1-7b-3 | A40 | c-Pen | Me | Et | D1-7b-3 | A40 |
| c-Pen | Me | Me | D1-7b-3 | A41 | c-Pen | Me | Et | D1-7b-3 | A41 |
| c-Hex | Me | Me | D1-7b-3 | H | c-Hex | Me | Et | D1-7b-3 | H |
| c-Hex | Me | Me | D1-7b-3 | A39 | c-Hex | Me | Et | D1-7b-3 | A39 |
| c-Hex | Me | Me | D1-7b-3 | A40 | c-Hex | Me | Et | D1-7b-3 | A40 |
| c-Hex | Me | Me | D1-7b-3 | A41 | c-Hex | Me | Et | D1-7b-3 | A41 |
| Me | Me | Me | D1-7b-4 | H | Me | Me | Et | D1-7b-4 | H |
| Me | Me | Me | D1-7b-4 | A39 | Me | Me | Et | D1-7b-4 | A39 |
| Me | Me | Me | D1-7b-4 | A40 | Me | Me | Et | D1-7b-4 | A40 |
| Me | Me | Me | D1-7b-4 | A41 | Me | Me | Et | D1-7b-4 | A41 |

TABLE 2-continued

| | | | | | | | | | |
|---|---|---|---|---|---|---|---|---|---|
| c-Pr | Me | Me | D1-7b-4 | H | c-Pr | Me | Et | D1-7b-4 | H |
| c-Pr | Me | Me | D1-7b-4 | A39 | c-Pr | Me | Et | D1-7b-4 | A39 |
| c-Pr | Me | Me | D1-7b-4 | A40 | c-Pr | Me | Et | D1-7b-4 | A40 |
| c-Pr | Me | Me | D1-7b-4 | A41 | c-Pr | Me | Et | D1-7b-4 | A41 |
| c-Bu | Me | Me | D1-7b-4 | H | c-Bu | Me | Et | D1-7b-4 | H |
| c-Bu | Me | Me | D1-7b-4 | A39 | c-Bu | Me | Et | D1-7b-4 | A39 |
| c-Bu | Me | Me | D1-7b-4 | A40 | c-Bu | Me | Et | D1-7b-4 | A40 |
| c-Bu | Me | Me | D1-7b-4 | A41 | c-Bu | Me | Et | D1-7b-4 | A41 |
| c-Pen | Me | Me | D1-7b-4 | H | c-Pen | Me | Et | D1-7b-4 | H |
| c-Pen | Me | Me | D1-7b-4 | A39 | c-Pen | Me | Et | D1-7b-4 | A39 |
| c-Pen | Me | Me | D1-7b-4 | A40 | c-Pen | Me | Et | D1-7b-4 | A40 |
| c-Pen | Me | Me | D1-7b-4 | A41 | c-Pen | Me | Et | D1-7b-4 | A41 |
| c-Hex | Me | Me | D1-7b-4 | H | c-Hex | Me | Et | D1-7b-4 | H |
| c-Hex | Me | Me | D1-7b-4 | A39 | c-Hex | Me | Et | D1-7b-4 | A39 |
| c-Hex | Me | Me | D1-7b-4 | A40 | c-Hex | Me | Et | D1-7b-4 | A40 |
| c-Hex | Me | Me | D1-7b-4 | A41 | c-Hex | Me | Et | D1-7b-4 | A41 |
| Me | Me | Me | D1-10a | H | Me | Me | Et | D1-10a | H |
| Me | Me | Me | D1-11a | H | Me | Me | Et | D1-11a | H |
| Me | Me | Me | D1-11b-1 | H | Me | Me | Et | D1-11b-1 | H |
| Me | Me | Me | D1-11b-2 | H | Me | Me | Et | D1-11b-2 | H |
| Me | Me | Me | D1-11b-3 | H | Me | Me | Et | D1-11b-3 | H |
| Me | Me | Me | D1-11b-4 | H | Me | Me | Et | D1-11b-4 | H |
| Me | Me | Me | D1-22a | H | Me | Me | Et | D1-22a | H |
| Me | Me | Me | D1-22b-1 | H | Me | Me | Et | D1-22b-1 | H |
| Me | Me | Me | D1-22b-2 | H | Me | Me | Et | D1-22b-2 | H |
| Me | Me | Me | D1-22b-3 | H | Me | Me | Et | D1-22b-3 | H |
| Me | Me | Me | D1-22b-4 | H | Me | Me | Et | D1-22b-4 | H |
| Me | Me | Me | D1-32a | H | Me | Me | Et | D1-32a | H |
| Me | Me | Me | D1-32b-1 | H | Me | Me | Et | D1-32b-1 | H |
| Me | Me | Me | D1-32b-2 | H | Me | Me | Et | D1-32b-2 | H |
| Me | Me | Me | D1-32b-3 | H | Me | Me | Et | D1-32b-3 | H |
| Me | Me | Me | D1-32b-4 | H | Me | Me | Et | D1-32b-4 | H |
| Me | Me | Me | D1-32b-5 | H | Me | Me | Et | D1-32b-5 | H |
| Me | Me | Me | D1-33a | H | Me | Me | Et | D1-33a | H |
| Me | Me | Me | D1-33b-1 | H | Me | Me | Et | D1-33b-1 | H |
| Me | Me | Me | D1-33b-2 | H | Me | Me | Et | D1-33b-2 | H |
| Me | Me | Me | D1-33b-3 | H | Me | Me | Et | D1-33b-3 | H |
| Me | Me | Me | D1-33b-4 | H | Me | Me | Et | D1-33b-4 | H |
| Me | Me | Me | D1-34a | H | Me | Me | Et | D1-34a | H |
| Me | Me | Me | D1-37a | H | Me | Me | Et | D1-37a | H |
| Me | Me | Me | D1-37b-1 | H | Me | Me | Et | D1-37b-1 | H |
| Me | Me | Me | C≡CH | H | Me | Me | Et | C≡CH | H |
| Me | Me | Me | C≡CH | A39 | Me | Me | Et | C≡CH | A39 |
| Me | Me | Me | C≡CH | A40 | Me | Me | Et | C≡CH | A40 |
| Me | Me | Me | C≡CH | A41 | Me | Me | Et | C≡CH | A41 |
| c-Pr | Me | Me | C≡CH | H | c-Pr | Me | Et | C≡CH | H |
| c-Pr | Me | Me | C≡CH | A39 | c-Pr | Me | Et | C≡CH | A39 |
| c-Pr | Me | Me | C≡CH | A40 | c-Pr | Me | Et | C≡CH | A40 |
| c-Pr | Me | Me | C≡CH | A41 | c-Pr | Me | Et | C≡CH | A41 |
| c-Bu | Me | Me | C≡CH | H | c-Bu | Me | Et | C≡CH | H |
| c-Bu | Me | Me | C≡CH | A39 | c-Bu | Me | Et | C≡CH | A39 |
| c-Bu | Me | Me | C≡CH | A40 | c-Bu | Me | Et | C≡CH | A40 |
| c-Bu | Me | Me | C≡CH | A41 | c-Bu | Me | Et | C≡CH | A41 |
| c-Pen | Me | Me | C≡CH | H | c-Pen | Me | Et | C≡CH | H |
| c-Pen | Me | Me | C≡CH | A39 | c-Pen | Me | Et | C≡CH | A39 |
| c-Pen | Me | Me | C≡CH | A40 | c-Pen | Me | Et | C≡CH | A40 |
| c-Pen | Me | Me | C≡CH | A41 | c-Pen | Me | Et | C≡CH | A41 |
| c-Hex | Me | Me | C≡CH | H | c-Hex | Me | Et | C≡CH | H |
| c-Hex | Me | Me | C≡CH | A39 | c-Hex | Me | Et | C≡CH | A39 |
| c-Hex | Me | Me | C≡CH | A40 | c-Hex | Me | Et | C≡CH | A40 |
| c-Hex | Me | Me | C≡CH | A41 | c-Hex | Me | Et | C≡CH | A41 |
| Me | Me | Me | C≡CBu-c | H | Me | Me | Et | C≡CBu-c | H |
| Me | Me | Me | C≡CBu-c | A39 | Me | Me | Et | C≡CBu-c | A39 |
| Me | Me | Me | C≡CBu-c | A40 | Me | Me | Et | C≡CBu-c | A40 |
| Me | Me | Me | C≡CBu-c | A41 | Me | Me | Et | C≡CBu-c | A41 |
| c-Pr | Me | Me | C≡CBu-c | H | c-Pr | Me | Et | C≡CBu-c | H |
| c-Pr | Me | Me | C≡CBu-c | A39 | c-Pr | Me | Et | C≡CBu-c | A39 |
| c-Pr | Me | Me | C≡CBu-c | A40 | c-Pr | Me | Et | C≡CBu-c | A40 |
| c-Pr | Me | Me | C≡CBu-c | A41 | c-Pr | Me | Et | C≡CBu-c | A41 |
| c-Bu | Me | Me | C≡CBu-c | H | c-Bu | Me | Et | C≡CBu-c | H |
| c-Bu | Me | Me | C≡CBu-c | A39 | c-Bu | Me | Et | C≡CBu-c | A39 |
| c-Bu | Me | Me | C≡CBu-c | A40 | c-Bu | Me | Et | C≡CBu-c | A40 |
| c-Bu | Me | Me | C≡CBu-c | A41 | c-Bu | Me | Et | C≡CBu-c | A41 |
| c-Pen | Me | Me | C≡CBu-c | H | c-Pen | Me | Et | C≡CBu-c | H |
| c-Pen | Me | Me | C≡CBu-c | A39 | c-Pen | Me | Et | C≡CBu-c | A39 |
| c-Pen | Me | Me | C≡CBu-c | A40 | c-Pen | Me | Et | C≡CBu-c | A40 |
| c-Pen | Me | Me | C≡CBu-c | A41 | c-Pen | Me | Et | C≡CBu-c | A41 |
| c-Hex | Me | Me | C≡CBu-c | H | c-Hex | Me | Et | C≡CBu-c | H |
| c-Hex | Me | Me | C≡CBu-c | A39 | c-Hex | Me | Et | C≡CBu-c | A39 |
| c-Hex | Me | Me | C≡CBu-c | A40 | c-Hex | Me | Et | C≡CBu-c | A40 |

TABLE 2-continued

| | | | | | | | | | |
|---|---|---|---|---|---|---|---|---|---|
| c-Hex | Me | Me | C≡CBu-c | A41 | c-Hex | Me | Et | C≡CBu-c | A41 |
| Me | Me | Me | C≡CPen-c | H | Me | Me | Et | C≡CPen-c | H |
| Me | Me | Me | C≡CPen-c | A39 | Me | Me | Et | C≡CPen-c | A39 |
| Me | Me | Me | C≡CPen-c | A40 | Me | Me | Et | C≡CPen-c | A40 |
| Me | Me | Me | C≡CPen-c | A41 | Me | Me | Et | C≡CPen-c | A41 |
| c-Pr | Me | Me | C≡CPen-c | H | c-Pr | Me | Et | C≡CPen-c | H |
| c-Pr | Me | Me | C≡CPen-c | A39 | c-Pr | Me | Et | C≡CPen-c | A39 |
| c-Pr | Me | Me | C≡CPen-c | A40 | c-Pr | Me | Et | C≡CPen-c | A40 |
| c-Pr | Me | Me | C≡CPen-c | A41 | c-Pr | Me | Et | C≡CPen-c | A41 |
| c-Bu | Me | Me | C≡CPen-c | H | c-Bu | Me | Et | C≡CPen-c | H |
| c-Bu | Me | Me | C≡CPen-c | A39 | c-Bu | Me | Et | C≡CPen-c | A39 |
| c-Bu | Me | Me | C≡CPen-c | A40 | c-Bu | Me | Et | C≡CPen-c | A40 |
| c-Bu | Me | Me | C≡CPen-c | A41 | c-Bu | Me | Et | C≡CPen-c | A41 |
| c-Pen | Me | Me | C≡CPen-c | H | c-Pen | Me | Et | C≡CPen-c | H |
| c-Pen | Me | Me | C≡CPen-c | A39 | c-Pen | Me | Et | C≡CPen-c | A39 |
| c-Pen | Me | Me | C≡CPen-c | A40 | c-Pen | Me | Et | C≡CPen-c | A40 |
| c-Pen | Me | Me | C≡CPen-c | A41 | c-Pen | Me | Et | C≡CPen-c | A41 |
| c-Hex | Me | Me | C≡CPen-c | H | c-Hex | Me | Et | C≡CPen-c | H |
| c-Hex | Me | Me | C≡CPen-c | A39 | c-Hex | Me | Et | C≡CPen-c | A39 |
| c-Hex | Me | Me | C≡CPen-c | A40 | c-Hex | Me | Et | C≡CPen-c | A40 |
| c-Hex | Me | Me | C≡CPen-c | A41 | c-Hex | Me | Et | C≡CPen-c | A41 |
| Me | Me | Me | C≡CHex-c | H | Me | Me | Et | C≡CHex-c | H |
| Me | Me | Me | C≡CHex-c | A39 | Me | Me | Et | C≡CHex-c | A39 |
| Me | Me | Me | C≡CHex-c | A40 | Me | Me | Et | C≡CHex-c | A40 |
| Me | Me | Me | C≡CHex-c | A41 | Me | Me | Et | C≡CHex-c | A41 |
| c-Pr | Me | Me | C≡CHex-c | H | c-Pr | Me | Et | C≡CHex-c | H |
| c-Pr | Me | Me | C≡CHex-c | A39 | c-Pr | Me | Et | C≡CHex-c | A39 |
| c-Pr | Me | Me | C≡CHex-c | A40 | c-Pr | Me | Et | C≡CHex-c | A40 |
| c-Pr | Me | Me | C≡CHex-c | A41 | c-Pr | Me | Et | C≡CHex-c | A41 |
| c-Bu | Me | Me | C≡CHex-c | H | c-Bu | Me | Et | C≡CHex-c | H |
| c-Bu | Me | Me | C≡CHex-c | A39 | c-Bu | Me | Et | C≡CHex-c | A39 |
| c-Bu | Me | Me | C≡CHex-c | A40 | c-Bu | Me | Et | C≡CHex-c | A40 |
| c-Bu | Me | Me | C≡CHex-c | A41 | c-Bu | Me | Et | C≡CHex-c | A41 |
| c-Pen | Me | Me | C≡CHex-c | H | c-Pen | Me | Et | C≡CHex-c | H |
| c-Pen | Me | Me | C≡CHex-c | A39 | c-Pen | Me | Et | C≡CHex-c | A39 |
| c-Pen | Me | Me | C≡CHex-c | A40 | c-Pen | Me | Et | C≡CHex-c | A40 |
| c-Pen | Me | Me | C≡CHex-c | A41 | c-Pen | Me | Et | C≡CHex-c | A41 |
| c-Hex | Me | Me | C≡CHex-c | H | c-Hex | Me | Et | C≡CHex-c | H |
| c-Hex | Me | Me | C≡CHex-c | A39 | c-Hex | Me | Et | C≡CHex-c | A39 |
| c-Hex | Me | Me | C≡CHex-c | A40 | c-Hex | Me | Et | C≡CHex-c | A40 |
| c-Hex | Me | Me | C≡CHex-c | A41 | c-Hex | Me | Et | C≡CHex-c | A41 |
| Me | Et | Et | C≡CMe | H | Me | Me | n-Pr | C≡CMe | H |
| Me | Et | Et | C≡CMe | A39 | Me | Me | n-Pr | C≡CMe | A39 |
| Me | Et | Et | C≡CMe | A40 | Me | Me | n-Pr | C≡CMe | A40 |
| Me | Et | Et | C≡CMe | A41 | Me | Me | n-Pr | C≡CMe | A41 |
| c-Pr | Et | Et | C≡CMe | H | c-Pr | Me | n-Pr | C≡CMe | H |
| c-Pr | Et | Et | C≡CMe | A39 | c-Pr | Me | n-Pr | C≡CMe | A39 |
| c-Pr | Et | Et | C≡CMe | A40 | c-Pr | Me | n-Pr | C≡CMe | A40 |
| c-Pr | Et | Et | C≡CMe | A41 | c-Pr | Me | n-Pr | C≡CMe | A41 |
| c-Bu | Et | Et | C≡CMe | H | c-Bu | Me | n-Pr | C≡CMe | H |
| c-Bu | Et | Et | C≡CMe | A39 | c-Bu | Me | n-Pr | C≡CMe | A39 |
| c-Bu | Et | Et | C≡CMe | A40 | c-Bu | Me | n-Pr | C≡CMe | A40 |
| c-Bu | Et | Et | C≡CMe | A41 | c-Bu | Me | n-Pr | C≡CMe | A41 |
| c-Pen | Et | Et | C≡CMe | H | c-Pen | Me | n-Pr | C≡CMe | H |
| c-Pen | Et | Et | C≡CMe | A39 | c-Pen | Me | n-Pr | C≡CMe | A39 |
| c-Pen | Et | Et | C≡CMe | A40 | c-Pen | Me | n-Pr | C≡CMe | A40 |
| c-Pen | Et | Et | C≡CMe | A41 | c-Pen | Me | n-Pr | C≡CMe | A41 |
| c-Hex | Et | Et | C≡CMe | H | c-Hex | Me | n-Pr | C≡CMe | H |
| c-Hex | Et | Et | C≡CMe | A39 | c-Hex | Me | n-Pr | C≡CMe | A39 |
| c-Hex | Et | Et | C≡CMe | A40 | c-Hex | Me | n-Pr | C≡CMe | A40 |
| c-Hex | Et | Et | C≡CMe | A41 | c-Hex | Me | n-Pr | C≡CMe | A41 |
| Me | Et | Et | C≡CSi(Me)$_3$ | H | Me | Me | n-Pr | C≡CSi(Me)$_3$ | H |
| Me | Et | Et | C≡CSi(Me)$_3$ | A39 | Me | Me | n-Pr | C≡CSi(Me)$_3$ | A39 |
| Me | Et | Et | C≡CSi(Me)$_3$ | A40 | Me | Me | n-Pr | C≡CSi(Me)$_3$ | A40 |
| Me | Et | Et | C≡CSi(Me)$_3$ | A41 | Me | Me | n-Pr | C≡CSi(Me)$_3$ | A41 |
| c-Pr | Et | Et | C≡CSi(Me)$_3$ | H | c-Pr | Me | n-Pr | C≡CSi(Me)$_3$ | H |
| c-Pr | Et | Et | C≡CSi(Me)$_3$ | A39 | c-Pr | Me | n-Pr | C≡CSi(Me)$_3$ | A39 |
| c-Pr | Et | Et | C≡CSi(Me)$_3$ | A40 | c-Pr | Me | n-Pr | C≡CSi(Me)$_3$ | A40 |
| c-Pr | Et | Et | C≡CSi(Me)$_3$ | A41 | c-Pr | Me | n-Pr | C≡CSi(Me)$_3$ | A41 |
| c-Bu | Et | Et | C≡CSi(Me)$_3$ | H | c-Bu | Me | n-Pr | C≡CSi(Me)$_3$ | H |
| c-Bu | Et | Et | C≡CSi(Me)$_3$ | A39 | c-Bu | Me | n-Pr | C≡CSi(Me)$_3$ | A39 |
| c-Bu | Et | Et | C≡CSi(Me)$_3$ | A40 | c-Bu | Me | n-Pr | C≡CSi(Me)$_3$ | A40 |
| c-Bu | Et | Et | C≡CSi(Me)$_3$ | A41 | c-Bu | Me | n-Pr | C≡CSi(Me)$_3$ | A41 |
| c-Pen | Et | Et | C≡CSi(Me)$_3$ | H | c-Pen | Me | n-Pr | C≡CSi(Me)$_3$ | H |
| c-Pen | Et | Et | C≡CSi(Me)$_3$ | A39 | c-Pen | Me | n-Pr | C≡CSi(Me)$_3$ | A39 |
| c-Pen | Et | Et | C≡CSi(Me)$_3$ | A40 | c-Pen | Me | n-Pr | C≡CSi(Me)$_3$ | A40 |
| c-Pen | Et | Et | C≡CSi(Me)$_3$ | A41 | c-Pen | Me | n-Pr | C≡CSi(Me)$_3$ | A41 |
| c-Hex | Et | Et | C≡CSi(Me)$_3$ | H | c-Hex | Me | n-Pr | C≡CSi(Me)$_3$ | H |
| c-Hex | Et | Et | C≡CSi(Me)$_3$ | A39 | c-Hex | Me | n-Pr | C≡CSi(Me)$_3$ | A39 |
| c-Hex | Et | Et | C≡CSi(Me)$_3$ | A40 | c-Hex | Me | n-Pr | C≡CSi(Me)$_3$ | A40 |

TABLE 2-continued

| | | | | | | | | | |
|---|---|---|---|---|---|---|---|---|---|
| c-Hex | Et | Et | C≡CSi(Me)₃ | A41 | c-Hex | Me | n-Pr | C≡CSi(Me)₃ | A41 |
| Me | Et | Et | C≡CPr-c | H | Me | Me | n-Pr | C≡CPr-c | H |
| Me | Et | Et | C≡CPr-c | A39 | Me | Me | n-Pr | C≡CPr-c | A39 |
| Me | Et | Et | C≡CPr-c | A40 | Me | Me | n-Pr | C≡CPr-c | A40 |
| Me | Et | Et | C≡CPr-c | A41 | Me | Me | n-Pr | C≡CPr-c | A41 |
| c-Pr | Et | Et | C≡CPr-c | H | c-Pr | Me | n-Pr | C≡CPr-c | H |
| c-Pr | Et | Et | C≡CPr-c | A39 | c-Pr | Me | n-Pr | C≡CPr-c | A39 |
| c-Pr | Et | Et | C≡CPr-c | A40 | c-Pr | Me | n-Pr | C≡CPr-c | A40 |
| c-Pr | Et | Et | C≡CPr-c | A41 | c-Pr | Me | n-Pr | C≡CPr-c | A41 |
| c-Bu | Et | Et | C≡CPr-c | H | c-Bu | Me | n-Pr | C≡CPr-c | H |
| c-Bu | Et | Et | C≡CPr-c | A39 | c-Bu | Me | n-Pr | C≡CPr-c | A39 |
| c-Bu | Et | Et | C≡CPr-c | A40 | c-Bu | Me | n-Pr | C≡CPr-c | A40 |
| c-Bu | Et | Et | C≡CPr-c | A41 | c-Bu | Me | n-Pr | C≡CPr-c | A41 |
| c-Pen | Et | Et | C≡CPr-c | H | c-Pen | Me | n-Pr | C≡CPr-c | H |
| c-Pen | Et | Et | C≡CPr-c | A39 | c-Pen | Me | n-Pr | C≡CPr-c | A39 |
| c-Pen | Et | Et | C≡CPr-c | A40 | c-Pen | Me | n-Pr | C≡CPr-c | A40 |
| c-Pen | Et | Et | C≡CPr-c | A41 | c-Pen | Me | n-Pr | C≡CPr-c | A41 |
| c-Hex | Et | Et | C≡CPr-c | H | c-Hex | Me | n-Pr | C≡CPr-c | H |
| c-Hex | Et | Et | C≡CPr-c | A39 | c-Hex | Me | n-Pr | C≡CPr-c | A39 |
| c-Hex | Et | Et | C≡CPr-c | A40 | c-Hex | Me | n-Pr | C≡CPr-c | A40 |
| c-Hex | Et | Et | C≡CPr-c | A41 | c-Hex | Me | n-Pr | C≡CPr-c | A41 |
| Me | Et | Et | C≡CC(Me)₂OH | H | Me | Me | n-Pr | C≡CC(Me)₂OH | H |
| Me | Et | Et | C≡CC(Me)₂OH | A39 | Me | Me | n-Pr | C≡CC(Me)₂OH | A39 |
| Me | Et | Et | C≡CC(Me)₂OH | A40 | Me | Me | n-Pr | C≡CC(Me)₂OH | A40 |
| Me | Et | Et | C≡CC(Me)₂OH | A41 | Me | Me | n-Pr | C≡CC(Me)₂OH | A41 |
| Me | Et | Et | C≡CCH₂OH | H | Me | Me | n-Pr | C≡CCH₂OH | H |
| Me | Et | Et | C≡CCH₂OH | A39 | Me | Me | n-Pr | C≡CCH₂OH | A39 |
| Me | Et | Et | C≡CCH₂OH | A40 | Me | Me | n-Pr | C≡CCH₂OH | A40 |
| Me | Et | Et | C≡CCH₂OH | A41 | Me | Me | n-Pr | C≡CCH₂OH | A41 |
| Me | Et | Et | Ph | H | Me | Me | n-Pr | Ph | H |
| Me | Et | Et | Ph | Me | Me | Me | n-Pr | Ph | Me |
| Me | Et | Et | Ph | A11 | Me | Me | n-Pr | Ph | A11 |
| Me | Et | Et | Ph | A34 | Me | Me | n-Pr | Ph | A34 |
| Me | Et | Et | Ph | A35 | Me | Me | n-Pr | Ph | A35 |
| Me | Et | Et | Ph | A37 | Me | Me | n-Pr | Ph | A37 |
| Me | Et | Et | Ph | A39 | Me | Me | n-Pr | Ph | A39 |
| Me | Et | Et | Ph | A40 | Me | Me | n-Pr | Ph | A40 |
| Me | Et | Et | Ph | A41 | Me | Me | n-Pr | Ph | A41 |
| Me | Et | Et | Ph | A73 | Me | Me | n-Pr | Ph | A73 |
| Me | Et | Et | Ph | A75 | Me | Me | n-Pr | Ph | A75 |
| Me | Et | Et | Ph | A83 | Me | Me | n-Pr | Ph | A83 |
| Me | Et | Et | Ph | A84 | Me | Me | n-Pr | Ph | A84 |
| Me | Et | Et | Ph | A85 | Me | Me | n-Pr | Ph | A85 |
| Me | Et | Et | Ph | A91 | Me | Me | n-Pr | Ph | A91 |
| Me | Et | Et | D1-108b-1 | H | Me | Me | n-Pr | D1-108b-1 | H |
| Me | Et | Et | D1-108b-1 | Me | Me | Me | n-Pr | D1-108b-1 | Me |
| Me | Et | Et | D1-108b-1 | A11 | Me | Me | n-Pr | D1-108b-1 | A11 |
| Me | Et | Et | D1-108b-1 | A34 | Me | Me | n-Pr | D1-108b-1 | A34 |
| Me | Et | Et | D1-108b-1 | A35 | Me | Me | n-Pr | D1-108b-1 | A35 |
| Me | Et | Et | D1-108b-1 | A37 | Me | Me | n-Pr | D1-108b-1 | A37 |
| Me | Et | Et | D1-108b-1 | A39 | Me | Me | n-Pr | D1-108b-1 | A39 |
| Me | Et | Et | D1-108b-1 | A40 | Me | Me | n-Pr | D1-108b-1 | A40 |
| Me | Et | Et | D1-108b-1 | A41 | Me | Me | n-Pr | D1-108b-1 | A41 |
| Me | Et | Et | D1-108b-1 | A73 | Me | Me | n-Pr | D1-108b-1 | A73 |
| Me | Et | Et | D1-108b-1 | A75 | Me | Me | n-Pr | D1-108b-1 | A75 |
| Me | Et | Et | D1-108b-1 | A83 | Me | Me | n-Pr | D1-108b-1 | A83 |
| Me | Et | Et | D1-108b-1 | A84 | Me | Me | n-Pr | D1-108b-1 | A84 |
| Me | Et | Et | D1-108b-1 | A85 | Me | Me | n-Pr | D1-108b-1 | A85 |
| Me | Et | Et | D1-108b-2 | A91 | Me | Me | n-Pr | D1-108b-2 | A91 |
| Me | Et | Et | D1-108b-3 | H | Me | Me | n-Pr | D1-108b-3 | H |
| Me | Et | Et | D1-108b-4 | H | Me | Me | n-Pr | D1-108b-4 | H |
| Me | Et | Et | D1-108b-4 | Me | Me | Me | n-Pr | D1-108b-4 | Me |
| Me | Et | Et | D1-108b-4 | A11 | Me | Me | n-Pr | D1-108b-4 | A11 |
| Me | Et | Et | D1-108b-4 | A34 | Me | Me | n-Pr | D1-108b-4 | A34 |
| Me | Et | Et | D1-108b-4 | A35 | Me | Me | n-Pr | D1-108b-4 | A35 |
| Me | Et | Et | D1-108b-4 | A37 | Me | Me | n-Pr | D1-108b-4 | A37 |
| Me | Et | Et | D1-108b-4 | A39 | Me | Me | n-Pr | D1-108b-4 | A39 |
| Me | Et | Et | D1-108b-4 | A40 | Me | Me | n-Pr | D1-108b-4 | A40 |
| Me | Et | Et | D1-108b-4 | A41 | Me | Me | n-Pr | D1-108b-4 | A41 |
| Me | Et | Et | D1-108b-4 | A73 | Me | Me | n-Pr | D1-108b-4 | A73 |
| Me | Et | Et | D1-108b-4 | A75 | Me | Me | n-Pr | D1-108b-4 | A75 |
| Me | Et | Et | D1-108b-4 | A83 | Me | Me | n-Pr | D1-108b-4 | A83 |
| Me | Et | Et | D1-108b-4 | A84 | Me | Me | n-Pr | D1-108b-4 | A84 |
| Me | Et | Et | D1-108b-4 | A85 | Me | Me | n-Pr | D1-108b-4 | A85 |
| Me | Et | Et | D1-108b-4 | A91 | Me | Me | n-Pr | D1-108b-4 | A91 |
| Me | Et | Et | D1-108b-5 | H | Me | Me | n-Pr | D1-108b-5 | H |
| Me | Et | Et | D1-108b-6 | H | Me | Me | n-Pr | D1-108b-6 | H |
| Me | Et | Et | D1-108b-7 | H | Me | Me | n-Pr | D1-108b-7 | H |
| Me | Et | Et | D1-108b-8 | H | Me | Me | n-Pr | D1-108b-8 | H |
| Me | Et | Et | D1-108b-8 | Me | Me | Me | n-Pr | D1-108b-8 | Me |

TABLE 2-continued

| | | | | | | | | | |
|---|---|---|---|---|---|---|---|---|---|
| Me | Et | Et | D1-108b-8 | A11 | Me | Me | n-Pr | D1-108b-8 | A11 |
| Me | Et | Et | D1-108b-8 | A34 | Me | Me | n-Pr | D1-108b-8 | A34 |
| Me | Et | Et | D1-108b-8 | A35 | Me | Me | n-Pr | D1-108b-8 | A35 |
| Me | Et | Et | D1-108b-8 | A37 | Me | Me | n-Pr | D1-108b-8 | A37 |
| Me | Et | Et | D1-108b-8 | A39 | Me | Me | n-Pr | D1-108b-8 | A39 |
| Me | Et | Et | D1-108b-8 | A40 | Me | Me | n-Pr | D1-108b-8 | A40 |
| Me | Et | Et | D1-108b-8 | A41 | Me | Me | n-Pr | D1-108b-8 | A41 |
| Me | Et | Et | D1-108b-8 | A73 | Me | Me | n-Pr | D1-108b-8 | A73 |
| Me | Et | Et | D1-108b-8 | A75 | Me | Me | n-Pr | D1-108b-8 | A75 |
| Me | Et | Et | D1-108b-8 | A83 | Me | Me | n-Pr | D1-108b-8 | A83 |
| Me | Et | Et | D1-108b-8 | A84 | Me | Me | n-Pr | D1-108b-8 | A84 |
| Me | Et | Et | D1-108b-8 | A85 | Me | Me | n-Pr | D1-108b-8 | A85 |
| Me | Et | Et | D1-108b-8 | A91 | Me | Me | n-Pr | D1-108b-8 | A91 |
| Me | Et | Et | D1-108b-9 | H | Me | Me | n-Pr | D1-108b-9 | H |
| Me | Et | Et | D1-108b-9 | Me | Me | Me | n-Pr | D1-108b-9 | Me |
| Me | Et | Et | D1-108b-9 | A11 | Me | Me | n-Pr | D1-108b-9 | A11 |
| Me | Et | Et | D1-108b-9 | A34 | Me | Me | n-Pr | D1-108b-9 | A34 |
| Me | Et | Et | D1-108b-9 | A35 | Me | Me | n-Pr | D1-108b-9 | A35 |
| Me | Et | Et | D1-108b-9 | A37 | Me | Me | n-Pr | D1-108b-9 | A37 |
| Me | Et | Et | D1-108b-9 | A39 | Me | Me | n-Pr | D1-108b-9 | A39 |
| Me | Et | Et | D1-108b-9 | A40 | Me | Me | n-Pr | D1-108b-9 | A40 |
| Me | Et | Et | D1-108b-9 | A41 | Me | Me | n-Pr | D1-108b-9 | A41 |
| Me | Et | Et | D1-108b-9 | A73 | Me | Me | n-Pr | D1-108b-9 | A73 |
| Me | Et | Et | D1-108b-9 | A75 | Me | Me | n-Pr | D1-108b-9 | A75 |
| Me | Et | Et | D1-108b-9 | A83 | Me | Me | n-Pr | D1-108b-9 | A83 |
| Me | Et | Et | D1-108b-9 | A84 | Me | Me | n-Pr | D1-108b-9 | A84 |
| Me | Et | Et | D1-108b-9 | A85 | Me | Me | n-Pr | D1-108b-9 | A85 |
| Me | Et | Et | D1-108b-9 | A91 | Me | Me | n-Pr | D1-108b-9 | A91 |
| Me | Et | Et | D1-108b-10 | H | Me | Me | n-Pr | D1-108b-10 | H |
| Me | Et | Et | D1-108b-10 | Me | Me | Me | n-Pr | D1-108b-10 | Me |
| Me | Et | Et | D1-108b-10 | A11 | Me | Me | n-Pr | D1-108b-10 | A11 |
| Me | Et | Et | D1-108b-10 | A34 | Me | Me | n-Pr | D1-108b-10 | A34 |
| Me | Et | Et | D1-108b-10 | A35 | Me | Me | n-Pr | D1-108b-10 | A35 |
| Me | Et | Et | D1-108b-10 | A37 | Me | Me | n-Pr | D1-108b-10 | A37 |
| Me | Et | Et | D1-108b-10 | A39 | Me | Me | n-Pr | D1-108b-10 | A39 |
| Me | Et | Et | D1-108b-10 | A40 | Me | Me | n-Pr | D1-108b-10 | A40 |
| Me | Et | Et | D1-108b-10 | A41 | Me | Me | n-Pr | D1-108b-10 | A41 |
| Me | Et | Et | D1-108b-10 | *A73* | Me | Me | n-Pr | D1-108b-10 | A73 |
| Me | Et | Et | D1-108b-10 | A75 | Me | Me | n-Pr | D1-108b-10 | A75 |
| Me | Et | Et | D1-108b-10 | A83 | Me | Me | n-Pr | D1-108b-10 | A83 |
| Me | Et | Et | D1-108b-10 | A84 | Me | Me | n-Pr | D1-108b-10 | A84 |
| Me | Et | Et | D1-108b-10 | A85 | Me | Me | n-Pr | D1-108b-10 | A85 |
| Me | Et | Et | D1-108b-10 | A91 | Me | Me | n-Pr | D1-108b-10 | A91 |
| Me | Et | Et | D1-108b-11 | H | Me | Me | n-Pr | D1-108b-11 | H |
| Me | Et | Et | D1-108b-12 | H | Me | Me | n-Pr | D1-108b-12 | H |
| Me | Et | Et | D1-108b-12 | Me | Me | Me | n-Pr | D1-108b-12 | Me |
| Me | Et | Et | D1-108b-12 | A11 | Me | Me | n-Pr | D1-108b-12 | A11 |
| Me | Et | Et | D1-108b-12 | A34 | Me | Me | n-Pr | D1-108b-12 | A34 |
| Me | Et | Et | D1-108b-12 | A35 | Me | Me | n-Pr | D1-108b-12 | A35 |
| Me | Et | Et | D1-108b-12 | A37 | Me | Me | n-Pr | D1-108b-12 | A37 |
| Me | Et | Et | D1-108b-12 | A39 | Me | Me | n-Pr | D1-108b-12 | A39 |
| Me | Et | Et | D1-108b-12 | A40 | Me | Me | n-Pr | D1-108b-12 | A40 |
| Me | Et | Et | D1-108b-12 | A41 | Me | Me | n-Pr | D1-108b-12 | A41 |
| Me | Et | Et | D1-108b-12 | A73 | Me | Me | n-Pr | D1-108b-12 | A73 |
| Me | Et | Et | D1-108b-12 | A75 | Me | Me | n-Pr | D1-108b-12 | A75 |
| Me | Et | Et | D1-108b-12 | A83 | Me | Me | n-Pr | D1-108b-12 | A83 |
| Me | Et | Et | D1-108b-12 | A84 | Me | Me | n-Pr | D1-108b-12 | A84 |
| Me | Et | Et | D1-108b-12 | A85 | Me | Me | n-Pr | D1-108b-12 | A85 |
| Me | Et | Et | D1-108b-12 | A91 | Me | Me | n-Pr | D1-108b-12 | A91 |
| Me | Et | Et | D1-108b-13 | H | Me | Me | n-Pr | D1-108b-13 | H |
| Me | Et | Et | D1-108b-14 | H | Me | Me | n-Pr | D1-108b-14 | H |
| Me | Et | Et | D1-108b-15 | H | Me | Me | n-Pr | D1-108b-15 | H |
| Me | Et | Et | D1-108b-16 | H | Me | Me | n-Pr | D1-108b-16 | H |
| Me | Et | Et | D1-108b-17 | H | Me | Me | n-Pr | D1-108b-17 | H |
| Me | Et | Et | D1-108b-18 | H | Me | Me | n-Pr | D1-108b-18 | H |
| Me | Et | Et | D1-108b-19 | H | Me | Me | n-Pr | D1-108b-19 | H |
| Me | Et | Et | D1-2a | H | Me | Me | n-Pr | D1-2a | H |
| Me | Et | Et | D1-2b | H | Me | Me | n-Pr | D1-2b | H |
| Me | Et | Et | D1-7a | H | Me | Me | n-Pr | D1-7a | H |
| Me | Et | Et | D1-7b-1 | H | Me | Me | n-Pr | D1-7b-1 | H |
| Me | Et | Et | D1-7b-1 | A39 | Me | Me | n-Pr | D1-7b-1 | A39 |
| Me | Et | Et | D1-7b-1 | A40 | Me | Me | n-Pr | D1-7b-1 | A40 |
| Me | Et | Et | D1-7b-1 | A41 | Me | Me | n-Pr | D1-7b-1 | A41 |
| c-Pr | Et | Et | D1-7b-1 | H | c-Pr | Me | n-Pr | D1-7b-1 | H |
| c-Pr | Et | Et | D1-7b-1 | A39 | c-Pr | Me | n-Pr | D1-7b-1 | A39 |
| c-Pr | Et | Et | D1-7b-1 | A40 | c-Pr | Me | n-Pr | D1-7b-1 | A40 |
| c-Pr | Et | Et | D1-7b-1 | A41 | c-Pr | Me | n-Pr | D1-7b-1 | A41 |
| c-Bu | Et | Et | D1-7b-1 | H | c-Bu | Me | n-Pr | D1-7b-1 | H |
| c-Bu | Et | Et | D1-7b-1 | A39 | c-Bu | Me | n-Pr | D1-7b-1 | A39 |
| c-Bu | Et | Et | D1-7b-1 | A40 | c-Bu | Me | n-Pr | D1-7b-1 | A40 |

TABLE 2-continued

| | | | | | | | | | |
|---|---|---|---|---|---|---|---|---|---|
| c-Bu | Et | Et | D1-7b-1 | A41 | c-Bu | Me | n-Pr | D1-7b-1 | A41 |
| c-Pen | Et | Et | D1-7b-1 | H | c-Pen | Me | n-Pr | D1-7b-1 | H |
| c-Pen | Et | Et | D1-7b-1 | A39 | c-Pen | Me | n-Pr | D1-7b-1 | A39 |
| c-Pen | Et | Et | D1-7b-1 | A40 | c-Pen | Me | n-Pr | D1-7b-1 | A40 |
| c-Pen | Et | Et | D1-7b-1 | A41 | c-Pen | Me | n-Pr | D1-7b-1 | A41 |
| c-Hex | Et | Et | D1-7b-1 | H | c-Hex | Me | n-Pr | D1-7b-1 | H |
| c-Hex | Et | Et | D1-7b-1 | A39 | c-Hex | Me | n-Pr | D1-7b-1 | A39 |
| c-Hex | Et | Et | D1-7b-1 | A40 | c-Hex | Me | n-Pr | D1-7b-1 | A40 |
| c-Hex | Et | Et | D1-7b-1 | A41 | c-Hex | Me | n-Pr | D1-7b-1 | A41 |
| Me | Et | Et | D1-7b-2 | H | Me | Me | n-Pr | D1-7b-2 | H |
| Me | Et | Et | D1-7b-2 | A39 | Me | Me | n-Pr | D1-7b-2 | A39 |
| Me | Et | Et | D1-7b-2 | A40 | Me | Me | n-Pr | D1-7b-2 | A40 |
| Me | Et | Et | D1-7b-2 | A41 | Me | Me | n-Pr | D1-7b-2 | A41 |
| c-Pr | Et | Et | D1-7b-2 | H | c-Pr | Me | n-Pr | D1-7b-2 | H |
| c-Pr | Et | Et | D1-7b-2 | A39 | c-Pr | Me | n-Pr | D1-7b-2 | A39 |
| c-Pr | Et | Et | D1-7b-2 | A40 | c-Pr | Me | n-Pr | D1-7b-2 | A40 |
| c-Pr | Et | Et | D1-7b-2 | A41 | c-Pr | Me | n-Pr | D1-7b-2 | A41 |
| c-Bu | Et | Et | D1-7b-2 | H | c-Bu | Me | n-Pr | D1-7b-2 | H |
| c-Bu | Et | Et | D1-7b-2 | A39 | c-Bu | Me | n-Pr | D1-7b-2 | A39 |
| c-Bu | Et | Et | D1-7b-2 | A40 | c-Bu | Me | n-Pr | D1-7b-2 | A40 |
| c-Bu | Et | Et | D1-7b-2 | A41 | c-Bu | Me | n-Pr | D1-7b-2 | A41 |
| c-Pen | Et | Et | D1-7b-2 | H | c-Pen | Me | n-Pr | D1-7b-2 | H |
| c-Pen | Et | Et | D1-7b-2 | A39 | c-Pen | Me | n-Pr | D1-7b-2 | A39 |
| c-Pen | Et | Et | D1-7b-2 | A40 | c-Pen | Me | n-Pr | D1-7b-2 | A40 |
| c-Pen | Et | Et | D1-7b-2 | A41 | c-Pen | Me | n-Pr | D1-7b-2 | A41 |
| c-Hex | Et | Et | D1-7b-2 | H | c-Hex | Me | n-Pr | D1-7b-2 | H |
| c-Hex | Et | Et | D1-7b-2 | A39 | c-Hex | Me | n-Pr | D1-7b-2 | A39 |
| c-Hex | Et | Et | D1-7b-2 | A40 | c-Hex | Me | n-Pr | D1-7b-2 | A40 |
| c-Hex | Et | Et | D1-7b-2 | A41 | c-Hex | Me | n-Pr | D1-7b-2 | A41 |
| Me | Et | Et | D1-7b-3 | H | Me | Me | n-Pr | D1-7b-3 | H |
| Me | Et | Et | D1-7b-3 | A39 | Me | Me | n-Pr | D1-7b-3 | A39 |
| Me | Et | Et | D1-7b-3 | A40 | Me | Me | n-Pr | D1-7b-3 | A40 |
| Me | Et | Et | D1-7b-3 | A41 | Me | Me | n-Pr | D1-7b-3 | A41 |
| c-Pr | Et | Et | D1-7b-3 | H | c-Pr | Me | n-Pr | D1-7b-3 | H |
| c-Pr | Et | Et | D1-7b-3 | A39 | c-Pr | Me | n-Pr | D1-7b-3 | A39 |
| c-Pr | Et | Et | D1-7b-3 | A40 | c-Pr | Me | n-Pr | D1-7b-3 | A40 |
| c-Pr | Et | Et | D1-7b-3 | A41 | c-Pr | Me | n-Pr | D1-7b-3 | A41 |
| c-Bu | Et | Et | D1-7b-3 | H | c-Bu | Me | n-Pr | D1-7b-3 | H |
| c-Bu | Et | Et | D1-7b-3 | A39 | c-Bu | Me | n-Pr | D1-7b-3 | A39 |
| c-Bu | Et | Et | D1-7b-3 | A40 | c-Bu | Me | n-Pr | D1-7b-3 | A40 |
| c-Bu | Et | Et | D1-7b-3 | A41 | c-Bu | Me | n-Pr | D1-7b-3 | A41 |
| c-Pen | Et | Et | D1-7b-3 | H | c-Pen | Me | n-Pr | D1-7b-3 | H |
| c-Pen | Et | Et | D1-7b-3 | A39 | c-Pen | Me | n-Pr | D1-7b-3 | A39 |
| c-Pen | Et | Et | D1-7b-3 | A40 | c-Pen | Me | n-Pr | D1-7b-3 | A40 |
| c-Pen | Et | Et | D1-7b-3 | A41 | c-Pen | Me | n-Pr | D1-7b-3 | A41 |
| c-Hex | Et | Et | D1-7b-3 | H | c-Hex | Me | n-Pr | D1-7b-3 | H |
| c-Hex | Et | Et | D1-7b-3 | A39 | c-Hex | Me | n-Pr | D1-7b-3 | A39 |
| c-Hex | Et | Et | D1-7b-3 | A40 | c-Hex | Me | n-Pr | D1-7b-3 | A40 |
| c-Hex | Et | Et | D1-7b-3 | A41 | c-Hex | Me | n-Pr | D1-7b-3 | A41 |
| Me | Et | Et | D1-7b-4 | H | Me | Me | n-Pr | D1-7b-4 | H |
| Me | Et | Et | D1-7b-4 | A39 | Me | Me | n-Pr | D1-7b-4 | A39 |
| Me | Et | Et | D1-7b-4 | A40 | Me | Me | n-Pr | D1-7b-4 | A40 |
| Me | Et | Et | D1-7b-4 | A41 | Me | Me | n-Pr | D1-7b-4 | A41 |
| c-Pr | Et | Et | D1-7b-4 | H | c-Pr | Me | n-Pr | D1-7b-4 | H |
| c-Pr | Et | Et | D1-7b-4 | A39 | c-Pr | Me | n-Pr | D1-7b-4 | A39 |
| c-Pr | Et | Et | D1-7b-4 | A40 | c-Pr | Me | n-Pr | D1-7b-4 | A40 |
| c-Pr | Et | Et | D1-7b-4 | A41 | c-Pr | Me | n-Pr | D1-7b-4 | A41 |
| c-Bu | Et | Et | D1-7b-4 | H | c-Bu | Me | n-Pr | D1-7b-4 | H |
| c-Bu | Et | Et | D1-7b-4 | A39 | c-Bu | Me | n-Pr | D1-7b-4 | A39 |
| c-Bu | Et | Et | D1-7b-4 | A40 | c-Bu | Me | n-Pr | D1-7b-4 | A40 |
| c-Bu | Et | Et | D1-7b-4 | A41 | c-Bu | Me | n-Pr | D1-7b-4 | A41 |
| c-Pen | Et | Et | D1-7b-4 | H | c-Pen | Me | n-Pr | D1-7b-4 | H |
| c-Pen | Et | Et | D1-7b-4 | A39 | c-Pen | Me | n-Pr | D1-7b-4 | A39 |
| c-Pen | Et | Et | D1-7b-4 | A40 | c-Pen | Me | n-Pr | D1-7b-4 | A40 |
| c-Pen | Et | Et | D1-7b-4 | A41 | c-Pen | Me | n-Pr | D1-7b-4 | A41 |
| c-Hex | Et | Et | D1-7b-4 | H | c-Hex | Me | n-Pr | D1-7b-4 | H |
| c-Hex | Et | Et | D1-7b-4 | A39 | c-Hex | Me | n-Pr | D1-7b-4 | A39 |
| c-Hex | Et | Et | D1-7b-4 | A40 | c-Hex | Me | n-Pr | D1-7b-4 | A40 |
| c-Hex | Et | Et | D1-7b-4 | A41 | c-Hex | Me | n-Pr | D1-7b-4 | A41 |
| Me | Et | Et | D1-10a | H | Me | Me | n-Pr | D1-10a | H |
| Me | Et | Et | D1-11a | H | Me | Me | n-Pr | D1-11a | H |
| Me | Et | Et | D1-11b-1 | H | Me | Me | n-Pr | D1-11b-1 | H |
| Me | Et | Et | D1-11b-2 | H | Me | Me | n-Pr | D1-11b-2 | H |
| Me | Et | Et | D1-11b-3 | H | Me | Me | n-Pr | D1-11b-3 | H |
| Me | Et | Et | D1-11b-4 | H | Me | Me | n-Pr | D1-11b-4 | H |
| Me | Et | Et | D1-22a | H | Me | Me | n-Pr | D1-22a | H |
| Me | Et | Et | D1-22b-1 | H | Me | Me | n-Pr | D1-22b-1 | H |
| Me | Et | Et | D1-22b-2 | H | Me | Me | n-Pr | D1-22b-2 | H |
| Me | Et | Et | D1-22b-3 | H | Me | Me | n-Pr | D1-22b-3 | H |
| Me | Et | Et | D1-22b-4 | H | Me | Me | n-Pr | D1-22b-4 | H |

TABLE 2-continued

| | | | | | | | | | |
|---|---|---|---|---|---|---|---|---|---|
| Me | Et | Et | D1-32a | H | Me | Me | n-Pr | D1-32a | H |
| Me | Et | Et | D1-32b-1 | H | Me | Me | n-Pr | D1-32b-1 | H |
| Me | Et | Et | D1-32b-2 | H | Me | Me | n-Pr | D1-32b-2 | H |
| Me | Et | Et | D1-32b-3 | H | Me | Me | n-Pr | D1-32b-3 | H |
| Me | Et | Et | D1-32b-4 | H | Me | Me | n-Pr | D1-32b-4 | H |
| Me | Et | Et | D1-32b-5 | H | Me | Me | n-Pr | D1-32b-5 | H |
| Me | Et | Et | D1-33a | H | Me | Me | n-Pr | D1-33a | H |
| Me | Et | Et | D1-33b-1 | H | Me | Me | n-Pr | D1-33b-1 | H |
| Me | Et | Et | D1-33b-2 | H | Me | Me | n-Pr | D1-33b-2 | H |
| Me | Et | Et | D1-33b-3 | H | Me | Me | n-Pr | D1-33b-3 | H |
| Me | Et | Et | D1-33b-4 | H | Me | Me | n-Pr | D1-33b-4 | H |
| Me | Et | Et | D1-34a | H | Me | Me | n-Pr | D1-34a | H |
| Me | Et | Et | D1-37a | H | Me | Me | n-Pr | D1-37a | H |
| Me | Et | Et | D1-37b-1 | H | Me | Me | n-Pr | D1-37b-1 | H |
| Me | Et | Et | C≡CH | H | Me | Me | n-Pr | C≡CH | H |
| Me | Et | Et | C≡CH | A39 | Me | Me | n-Pr | C≡CH | A39 |
| Me | Et | Et | C≡CH | A40 | Me | Me | n-Pr | C≡CH | A40 |
| Me | Et | Et | C≡CH | A41 | Me | Me | n-Pr | C≡CH | A41 |
| c-Pr | Et | Et | C≡CH | H | c-Pr | Me | n-Pr | C≡CH | H |
| c-Pr | Et | Et | C≡CH | A39 | c-Pr | Me | n-Pr | C≡CH | A39 |
| c-Pr | Et | Et | C≡CH | A40 | c-Pr | Me | n-Pr | C≡CH | A40 |
| c-Pr | Et | Et | C≡CH | A41 | c-Pr | Me | n-Pr | C≡CH | A41 |
| c-Bu | Et | Et | C≡CH | H | c-Bu | Me | n-Pr | C≡CH | H |
| c-Bu | Et | Et | C≡CH | A39 | c-Bu | Me | n-Pr | C≡CH | A39 |
| c-Bu | Et | Et | C≡CH | A40 | c-Bu | Me | n-Pr | C≡CH | A40 |
| c-Bu | Et | Et | C≡CH | A41 | c-Bu | Me | n-Pr | C≡CH | A41 |
| c-Pen | Et | Et | C≡CH | H | c-Pen | Me | n-Pr | C≡CH | H |
| c-Pen | Et | Et | C≡CH | A39 | c-Pen | Me | n-Pr | C≡CH | A39 |
| c-Pen | Et | Et | C≡CH | A40 | c-Pen | Me | n-Pr | C≡CH | A40 |
| c-Pen | Et | Et | C≡CH | A41 | c-Pen | Me | n-Pr | C≡CH | A41 |
| c-Hex | Et | Et | C≡CH | H | c-Hex | Me | n-Pr | C≡CH | H |
| c-Hex | Et | Et | C≡CH | A39 | c-Hex | Me | n-Pr | C≡CH | A39 |
| c-Hex | Et | Et | C≡CH | A40 | c-Hex | Me | n-Pr | C≡CH | A40 |
| c-Hex | Et | Et | C≡CH | A41 | c-Hex | Me | n-Pr | C≡CH | A41 |
| Me | Et | Et | C≡CBu-c | H | Me | Me | n-Pr | C≡CBu-c | H |
| Me | Et | Et | C≡CBu-c | A39 | Me | Me | n-Pr | C≡CBu-c | A39 |
| Me | Et | Et | C≡CBu-c | A40 | Me | Me | n-Pr | C≡CBu-c | A40 |
| Me | Et | Et | C≡CBu-c | A41 | Me | Me | n-Pr | C≡CBu-c | A41 |
| c-Pr | Et | Et | C≡CBu-c | H | c-Pr | Me | n-Pr | C≡CBu-c | H |
| c-Pr | Et | Et | C≡CBu-c | A39 | c-Pr | Me | n-Pr | C≡CBu-c | A39 |
| c-Pr | Et | Et | C≡CBu-c | A40 | c-Pr | Me | n-Pr | C≡CBu-c | A40 |
| c-Pr | Et | Et | C≡CBu-c | A41 | c-Pr | Me | n-Pr | C≡CBu-c | A41 |
| c-Bu | Et | Et | C≡CBu-c | H | c-Bu | Me | n-Pr | C≡CBu-c | H |
| c-Bu | Et | Et | C≡CBu-c | A39 | c-Bu | Me | n-Pr | C≡CBu-c | A39 |
| c-Bu | Et | Et | C≡CBu-c | A40 | c-Bu | Me | n-Pr | C≡CBu-c | A40 |
| c-Bu | Et | Et | C≡CBu-c | A41 | c-Bu | Me | n-Pr | C≡CBu-c | A41 |
| c-Pen | Et | Et | C≡CBu-c | H | c-Pen | Me | n-Pr | C≡CBu-c | H |
| c-Pen | Et | Et | C≡CBu-c | A39 | c-Pen | Me | n-Pr | C≡CBu-c | A39 |
| c-Pen | Et | Et | C≡CBu-c | A40 | c-Pen | Me | n-Pr | C≡CBu-c | A40 |
| c-Pen | Et | Et | C≡CBu-c | A41 | c-Pen | Me | n-Pr | C≡CBu-c | A41 |
| c-Hex | Et | Et | C≡CBu-c | H | c-Hex | Me | n-Pr | C≡CBu-c | H |
| c-Hex | Et | Et | C≡CBu-c | A39 | c-Hex | Me | n-Pr | C≡CBu-c | A39 |
| c-Hex | Et | Et | C≡CBu-c | A40 | c-Hex | Me | n-Pr | C≡CBu-c | A40 |
| c-Hex | Et | Et | C≡CBu-c | A41 | c-Hex | Me | n-Pr | C≡CBu-c | A41 |
| Me | Et | Et | C≡CPen-c | H | Me | Me | n-Pr | C≡CPen-c | H |
| Me | Et | Et | C≡CPen-c | A39 | Me | Me | n-Pr | C≡CPen-c | A39 |
| Me | Et | Et | C≡CPen-c | A40 | Me | Me | n-Pr | C≡CPen-c | A40 |
| Me | Et | Et | C≡CPen-c | A41 | Me | Me | n-Pr | C≡CPen-c | A41 |
| c-Pr | Et | Et | C≡CPen-c | H | c-Pr | Me | n-Pr | C≡CPen-c | H |
| c-Pr | Et | Et | C≡CPen-c | A39 | c-Pr | Me | n-Pr | C≡CPen-c | A39 |
| c-Pr | Et | Et | C≡CPen-c | A40 | c-Pr | Me | n-Pr | C≡CPen-c | A40 |
| c-Pr | Et | Et | C≡CPen-c | A41 | c-Pr | Me | n-Pr | C≡CPen-c | A41 |
| c-Bu | Et | Et | C≡CPen-c | H | c-Bu | Me | n-Pr | C≡CPen-c | H |
| c-Bu | Et | Et | C≡CPen-c | A39 | c-Bu | Me | n-Pr | C≡CPen-c | A39 |
| c-Bu | Et | Et | C≡CPen-c | A40 | c-Bu | Me | n-Pr | C≡CPen-c | A40 |
| c-Bu | Et | Et | C≡CPen-c | A41 | c-Bu | Me | n-Pr | C≡CPen-c | A41 |
| c-Pen | Et | Et | C≡CPen-c | H | c-Pen | Me | n-Pr | C≡CPen-c | H |
| c-Pen | Et | Et | C≡CPen-c | A39 | c-Pen | Me | n-Pr | C≡CPen-c | A39 |
| c-Pen | Et | Et | C≡CPen-c | A40 | c-Pen | Me | n-Pr | C≡CPen-c | A40 |
| c-Pen | Et | Et | C≡CPen-c | A41 | c-Pen | Me | n-Pr | C≡CPen-c | A41 |
| c-Hex | Et | Et | C≡CPen-c | H | c-Hex | Me | n-Pr | C≡CPen-c | H |
| c-Hex | Et | Et | C≡CPen-c | A39 | c-Hex | Me | n-Pr | C≡CPen-c | A39 |
| c-Hex | Et | Et | C≡CPen-c | A40 | c-Hex | Me | n-Pr | C≡CPen-c | A40 |
| c-Hex | Et | Et | C≡CPen-c | A41 | c-Hex | Me | n-Pr | C≡CPen-c | A41 |
| Me | Et | Et | C≡CHex-c | H | Me | Me | n-Pr | C≡CHex-c | H |
| Me | Et | Et | C≡CHex-c | A39 | Me | Me | n-Pr | C≡CHex-c | A39 |
| Me | Et | Et | C≡CHex-c | A40 | Me | Me | n-Pr | C≡CHex-c | A40 |
| Me | Et | Et | C≡CHex-c | A41 | Me | Me | n-Pr | C≡CHex-c | A41 |
| c-Pr | Et | Et | C≡CHex-c | H | c-Pr | Me | n-Pr | C≡CHex-c | H |
| c-Pr | Et | Et | C≡CHex-c | A39 | c-Pr | Me | n-Pr | C≡CHex-c | A39 |

TABLE 2-continued

| | | | | | | | | | |
|---|---|---|---|---|---|---|---|---|---|
| c-Pr | Et | Et | C≡CHex-c | A40 | c-Pr | Me | n-Pr | C≡CHex-c | A40 |
| c-Pr | Et | Et | C≡CHex-c | A41 | c-Pr | Me | n-Pr | C≡CHex-c | A41 |
| c-Bu | Et | Et | C≡CHex-c | H | c-Bu | Me | n-Pr | C≡CHex-c | H |
| c-Bu | Et | Et | C≡CHex-c | A39 | c-Bu | Me | n-Pr | C≡CHex-c | A39 |
| c-Bu | Et | Et | C≡CHex-c | A40 | c-Bu | Me | n-Pr | C≡CHex-c | A40 |
| c-Bu | Et | Et | C≡CHex-c | A41 | c-Bu | Me | n-Pr | C≡CHex-c | A41 |
| c-Pen | Et | Et | C≡CHex-c | H | c-Pen | Me | n-Pr | C≡CHex-c | H |
| c-Pen | Et | Et | C≡CHex-c | A39 | c-Pen | Me | n-Pr | C≡CHex-c | A39 |
| c-Pen | Et | Et | C≡CHex-c | A40 | c-Pen | Me | n-Pr | C≡CHex-c | A40 |
| c-Pen | Et | Et | C≡CHex-c | A41 | c-Pen | Me | n-Pr | C≡CHex-c | A41 |
| c-Hex | Et | Et | C≡CHex-c | H | c-Hex | Me | n-Pr | C≡CHex-c | H |
| c-Hex | Et | Et | C≡CHex-c | A39 | c-Hex | Me | n-Pr | C≡CHex-c | A39 |
| c-Hex | Et | Et | C≡CHex-c | A40 | c-Hex | Me | n-Pr | C≡CHex-c | A40 |
| c-Hex | Et | Et | C≡CHex-c | A41 | c-Hex | Me | n-Pr | C≡CHex-c | A41 |

TABLE 3

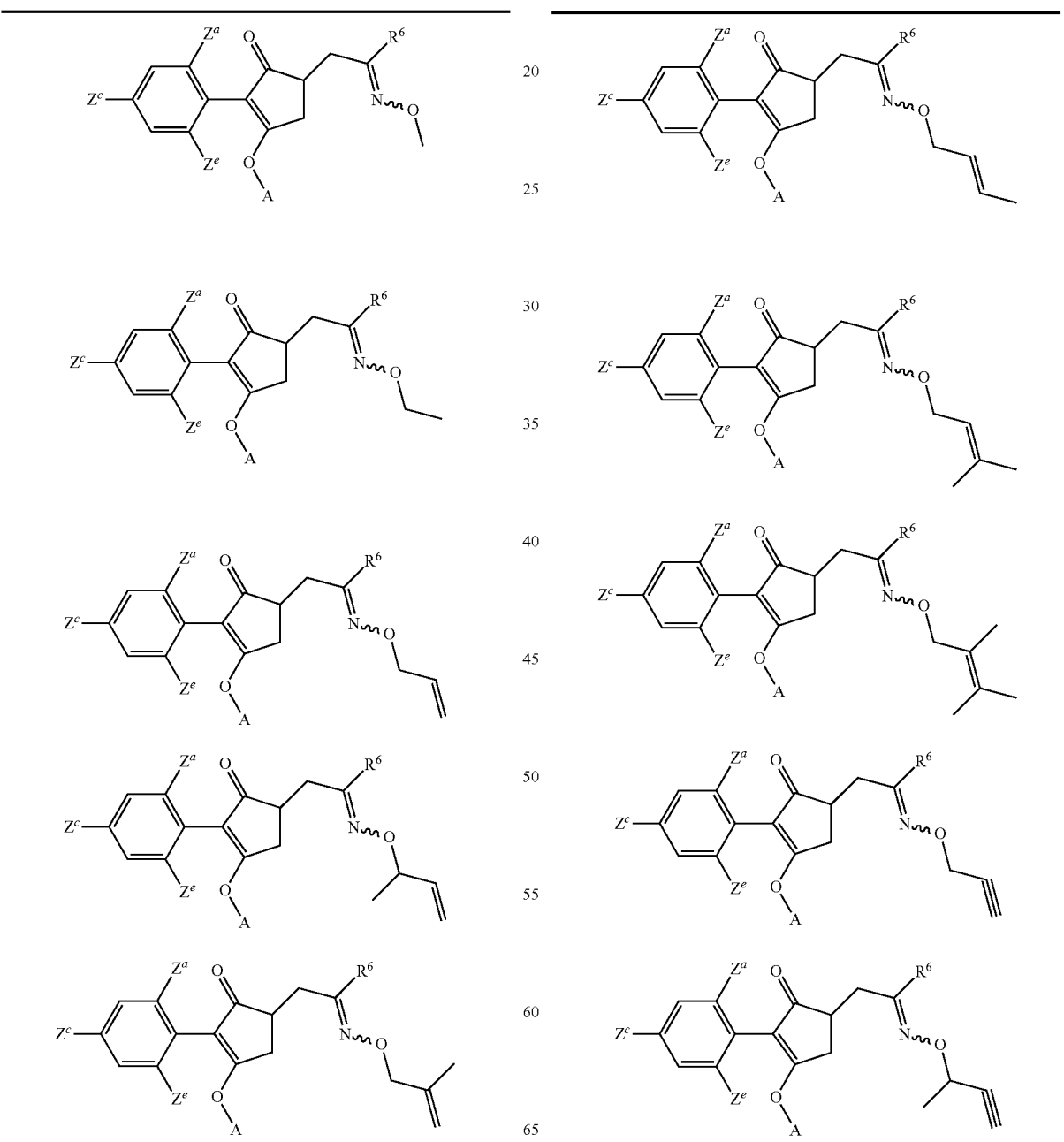

TABLE 3-continued
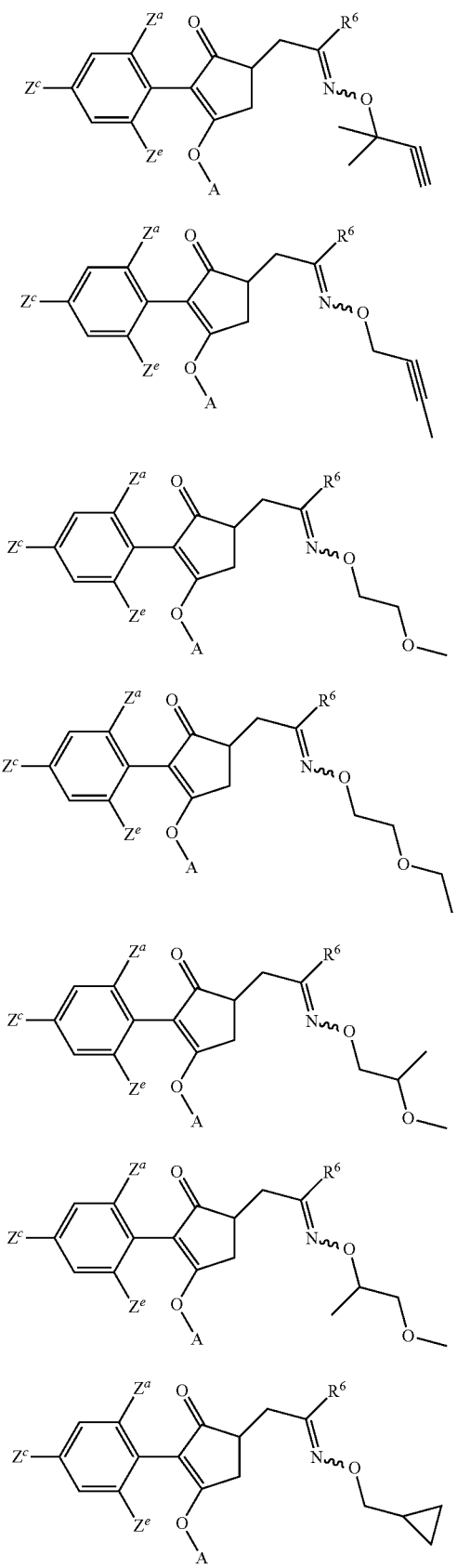
TABLE 3-continued
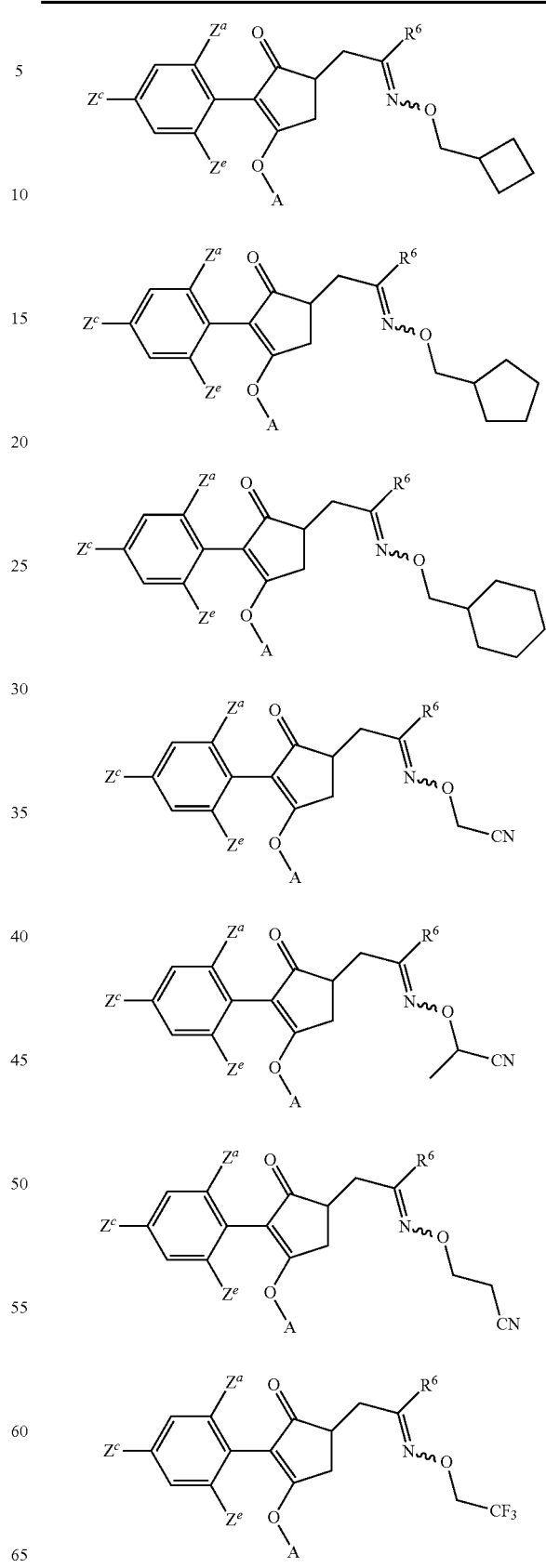

TABLE 3-continued
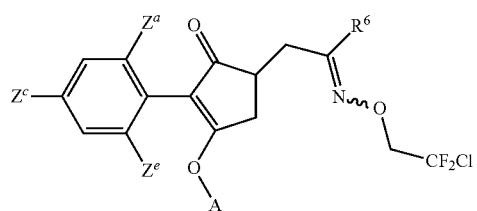
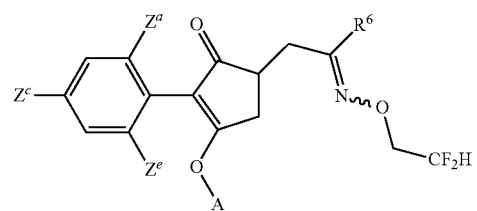
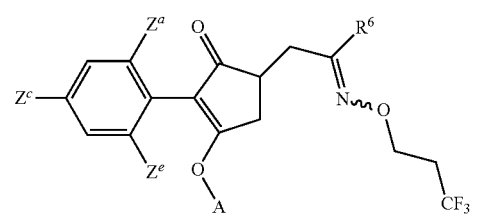
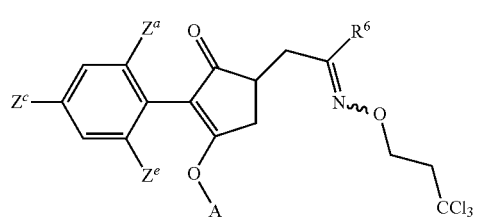
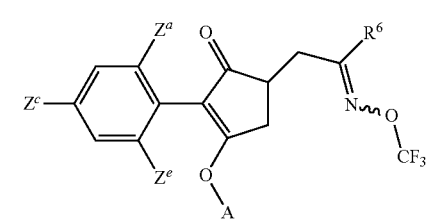
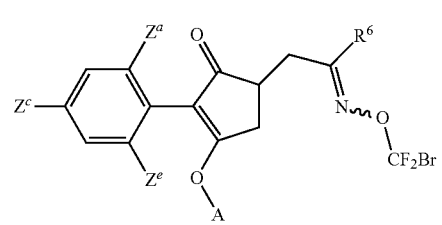
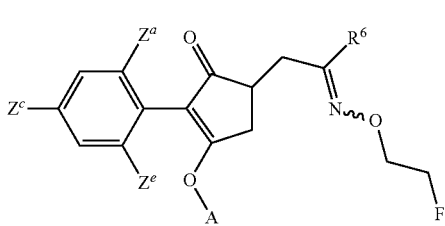
TABLE 3-continued
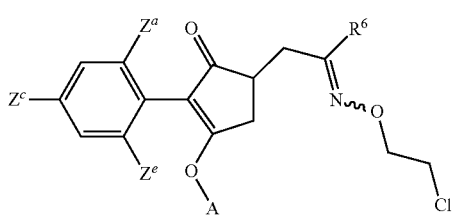
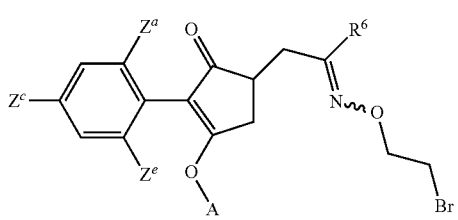
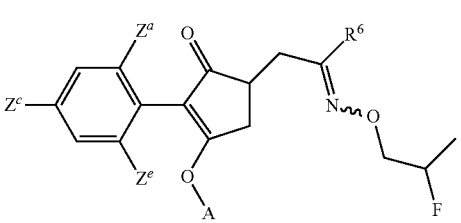
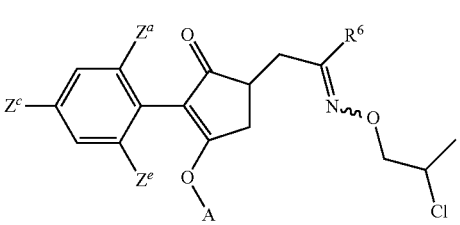
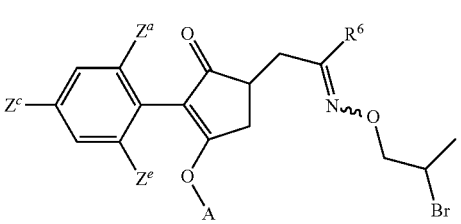
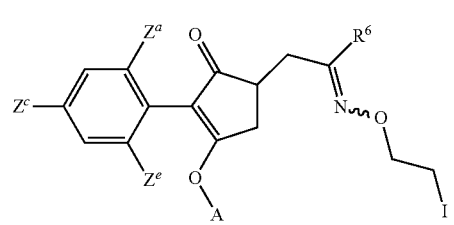
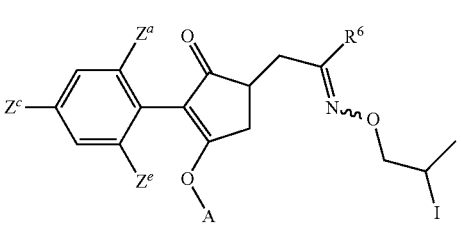

TABLE 3-continued

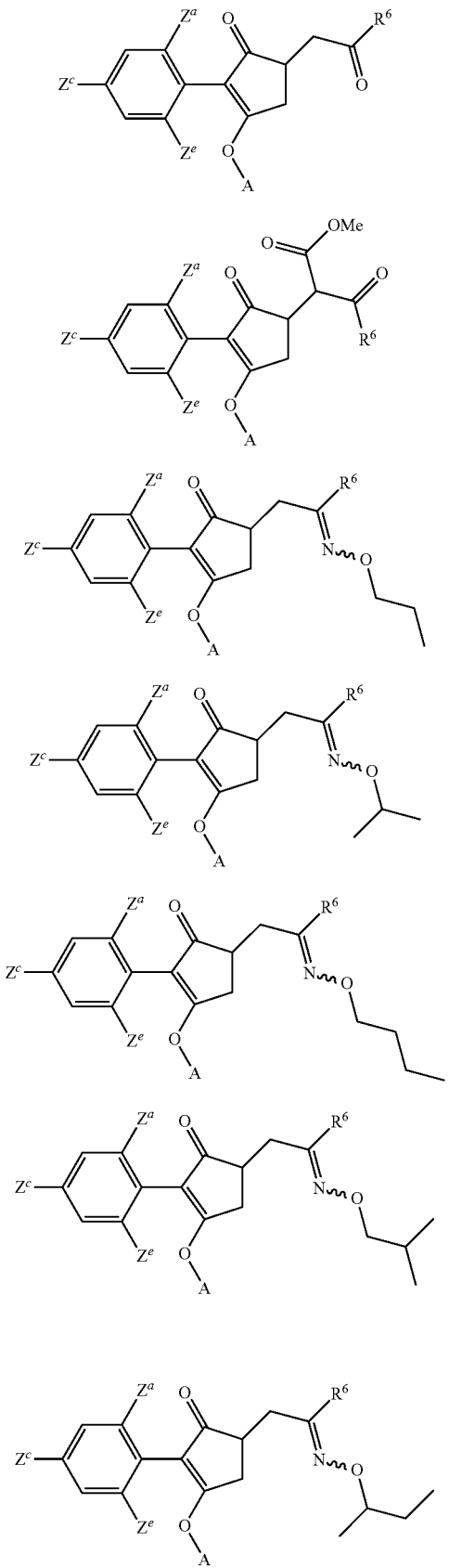

TABLE 3-continued

| R6 | Za | Ze | Zc | A | R6 | Za | Ze | Zc | A |
|---|---|---|---|---|---|---|---|---|---|
| Me | OMe | Me | Me | H | Me | OMe | Et | Me | H |
| Me | OMe | Me | Me | A13 | Me | OMe | Et | Me | A13 |
| Me | OMe | Me | Me | A14 | Me | OMe | Et | Me | A14 |
| Me | OMe | Me | Me | A16 | Me | OMe | Et | Me | A16 |
| Me | OMe | Me | Me | A35 | Me | OMe | Et | Me | A35 |
| Me | OMe | Me | Me | A38 | Me | OMe | Et | Me | A38 |
| Me | OMe | Me | Me | A39 | Me | OMe | Et | Me | A39 |
| Me | OMe | Me | Me | A40 | Me | OMe | Et | Me | A40 |
| Me | OMe | Me | Me | A41 | Me | OMe | Et | Me | A41 |
| Me | OMe | Me | Me | A73 | Me | OMe | Et | Me | A73 |
| Me | OMe | Me | Me | A74 | Me | OMe | Et | Me | A74 |
| Me | OMe | Me | Me | A75 | Me | OMe | Et | Me | A75 |
| Me | OMe | Me | Me | A81 | Me | OMe | Et | Me | A81 |
| Me | OMe | Me | Me | A82 | Me | OMe | Et | Me | A82 |
| Me | OMe | Me | Me | A83 | Me | OMe | Et | Me | A83 |
| Me | OMe | Me | Me | A84 | Me | OMe | Et | Me | A84 |
| Me | OMe | Me | Me | A85 | Me | OMe | Et | Me | A85 |
| Me | OMe | Me | Me | A86 | Me | OMe | Et | Me | A86 |
| Me | OMe | Me | Me | A87 | Me | OMe | Et | Me | A87 |
| Me | OMe | Me | Me | A91 | Me | OMe | Et | Me | A91 |
| Me | OMe | Me | Me | A92 | Me | OMe | Et | Me | A92 |
| Me | OMe | Me | Me | A93 | Me | OMe | Et | Me | A93 |
| Me | OMe | Me | Me | A94 | Me | OMe | Et | Me | A94 |
| Me | OMe | Me | Me | A95 | Me | OMe | Et | Me | A95 |
| Me | OMe | Me | Me | A97 | Me | OMe | Et | Me | A97 |
| Et | OMe | Me | Me | H | Et | OMe | Et | Me | H |
| Et | OMe | Me | Me | A13 | Et | OMe | Et | Me | A13 |
| Et | OMe | Me | Me | A14 | Et | OMe | Et | Me | A14 |
| Et | OMe | Me | Me | A16 | Et | OMe | Et | Me | A16 |
| Et | OMe | Me | Me | A35 | Et | OMe | Et | Me | A35 |
| Et | OMe | Me | Me | A38 | Et | OMe | Et | Me | A38 |
| Et | OMe | Me | Me | A39 | Et | OMe | Et | Me | A39 |
| Et | OMe | Me | Me | A40 | Et | OMe | Et | Me | A40 |
| Et | OMe | Me | Me | A41 | Et | OMe | Et | Me | A41 |
| Et | OMe | Me | Me | A73 | Et | OMe | Et | Me | A73 |
| Et | OMe | Me | Me | A74 | Et | OMe | Et | Me | A74 |
| Et | OMe | Me | Me | A75 | Et | OMe | Et | Me | A75 |
| Et | OMe | Me | Me | A81 | Et | OMe | Et | Me | A81 |
| Et | OMe | Me | Me | A82 | Et | OMe | Et | Me | A82 |
| Me | OMe | n-Pr | Me | H | Me | OEt | Me | Me | H |
| Me | OMe | n-Pr | Me | A13 | Me | OEt | Me | Me | A13 |
| Me | OMe | n-Pr | Me | A14 | Me | OEt | Me | Me | A14 |
| Me | OMe | n-Pr | Me | A16 | Me | OEt | Me | Me | A16 |
| Me | OMe | n-Pr | Me | A35 | Me | OEt | Me | Me | A35 |
| Me | OMe | n-Pr | Me | A38 | Me | OEt | Me | Me | A38 |
| Me | OMe | n-Pr | Me | A39 | Me | OEt | Me | Me | A39 |
| Me | OMe | n-Pr | Me | A40 | Me | OEt | Me | Me | A40 |
| Me | OMe | n-Pr | Me | A41 | Me | OEt | Me | Me | A41 |
| Me | OMe | n-Pr | Me | A73 | Me | OEt | Me | Me | A73 |
| Me | OMe | n-Pr | Me | A74 | Me | OEt | Me | Me | A74 |
| Me | OMe | n-Pr | Me | A75 | Me | OEt | Me | Me | A75 |
| Me | OMe | n-Pr | Me | A81 | Me | OEt | Me | Me | A81 |
| Me | OMe | n-Pr | Me | A82 | Me | OEt | Me | Me | A82 |
| Me | OMe | n-Pr | Me | A83 | Me | OEt | Me | Me | A83 |
| Me | OMe | n-Pr | Me | A84 | Me | OEt | Me | Me | A84 |
| Me | OMe | n-Pr | Me | A85 | Me | OEt | Me | Me | A85 |
| Me | OMe | n-Pr | Me | A86 | Me | OEt | Me | Me | A86 |
| Me | OMe | n-Pr | Me | A87 | Me | OEt | Me | Me | A87 |
| Me | OMe | n-Pr | Me | A91 | Me | OEt | Me | Me | A91 |
| Me | OMe | n-Pr | Me | A92 | Me | OEt | Me | Me | A92 |
| Me | OMe | n-Pr | Me | A93 | Me | OEt | Me | Me | A93 |
| Me | OMe | n-Pr | Me | A94 | Me | OEt | Me | Me | A94 |
| Me | OMe | n-Pr | Me | A95 | Me | OEt | Me | Me | A95 |
| Me | OMe | n-Pr | Me | A97 | Me | OEt | Me | Me | A97 |
| Et | OMe | n-Pr | Me | H | Et | OEt | Me | Me | H |
| Et | OMe | n-Pr | Me | A13 | Et | OEt | Me | Me | A13 |
| Et | OMe | n-Pr | Me | A14 | Et | OEt | Me | Me | A14 |
| Et | OMe | n-Pr | Me | A16 | Et | OEt | Me | Me | A16 |
| Et | OMe | n-Pr | Me | A35 | Et | OEt | Me | Me | A35 |
| Et | OMe | n-Pr | Me | A38 | Et | OEt | Me | Me | A38 |
| Et | OMe | n-Pr | Me | A39 | Et | OEt | Me | Me | A39 |
| Et | OMe | n-Pr | Me | A40 | Et | OEt | Me | Me | A40 |
| Et | OMe | n-Pr | Me | A41 | Et | OEt | Me | Me | A41 |
| Et | OMe | n-Pr | Me | A73 | Et | OEt | Me | Me | A73 |
| Et | OMe | n-Pr | Me | A74 | Et | OEt | Me | Me | A74 |
| Et | OMe | n-Pr | Me | A75 | Et | OEt | Me | Me | A75 |
| Et | OMe | n-Pr | Me | A81 | Et | OEt | Me | Me | A81 |

TABLE 3-continued

| | | | | | | | | | |
|---|---|---|---|---|---|---|---|---|---|
| Et | OMe | n-Pr | Me | A82 | Et | OEt | Me | Me | A82 |
| Me | OEt | Et | Me | H | Me | OMe | Me | Et | H |
| Me | OEt | Et | Me | A13 | Me | OMe | Me | Et | A13 |
| Me | OEt | Et | Me | A14 | Me | OMe | Me | Et | A14 |
| Me | OEt | Et | Me | A16 | Me | OMe | Me | Et | A16 |
| Me | OEt | Et | Me | A35 | Me | OMe | Me | Et | A35 |
| Me | OEt | Et | Me | A38 | Me | OMe | Me | Et | A38 |
| Me | OEt | Et | Me | A39 | Me | OMe | Me | Et | A39 |
| Me | OEt | Et | Me | A40 | Me | OMe | Me | Et | A40 |
| Me | OEt | Et | Me | A41 | Me | OMe | Me | Et | A41 |
| Me | OEt | Et | Me | A73 | Me | OMe | Me | Et | A73 |
| Me | OEt | Et | Me | A74 | Me | OMe | Me | Et | A74 |
| Me | OEt | Et | Me | A75 | Me | OMe | Me | Et | A75 |
| Me | OEt | Et | Me | A81 | Me | OMe | Me | Et | A81 |
| Me | OEt | Et | Me | A82 | Me | OMe | Me | Et | A82 |
| Me | OEt | Et | Me | A83 | Me | OMe | Me | Et | A83 |
| Me | OEt | Et | Me | A84 | Me | OMe | Me | Et | A84 |
| Me | OEt | Et | Me | A85 | Me | OMe | Me | Et | A85 |
| Me | OEt | Et | Me | A86 | Me | OMe | Me | Et | A86 |
| Me | OEt | Et | Me | A87 | Me | OMe | Me | Et | A87 |
| Me | OEt | Et | Me | A91 | Me | OMe | Me | Et | A91 |
| Me | OEt | Et | Me | A92 | Me | OMe | Me | Et | A92 |
| Me | OEt | Et | Me | A93 | Me | OMe | Me | Et | A93 |
| Me | OEt | Et | Me | A94 | Me | OMe | Me | Et | A94 |
| Me | OEt | Et | Me | A95 | Me | OMe | Me | Et | A95 |
| Me | OEt | Et | Me | A97 | Me | OMe | Me | Et | A97 |
| Et | OEt | Et | Me | H | Et | OMe | Me | Et | H |
| Et | OEt | Et | Me | A13 | Et | OMe | Me | Et | A13 |
| Et | OEt | Et | Me | A14 | Et | OMe | Me | Et | A14 |
| Et | OEt | Et | Me | A16 | Et | OMe | Me | Et | A16 |
| Et | OEt | Et | Me | A35 | Et | OMe | Me | Et | A35 |
| Et | OEt | Et | Me | A38 | Et | OMe | Me | Et | A38 |
| Et | OEt | Et | Me | A39 | Et | OMe | Me | Et | A39 |
| Et | OEt | Et | Me | A40 | Et | OMe | Me | Et | A40 |
| Et | OEt | Et | Me | A41 | Et | OMe | Me | Et | A41 |
| Et | OEt | Et | Me | A73 | Et | OMe | Me | Et | A73 |
| Et | OEt | Et | Me | A74 | Et | OMe | Me | Et | A74 |
| Et | OEt | Et | Me | A75 | Et | OMe | Me | Et | A75 |
| Et | OEt | Et | Me | A81 | Et | OMe | Me | Et | A81 |
| Et | OEt | Et | Me | A82 | Et | OMe | Me | Et | A82 |
| Et | OMe | Me | Me | A83 | Et | OMe | Me | Et | A83 |
| Et | OMe | Me | Me | A84 | Et | OMe | Et | Me | A84 |
| Et | OMe | Me | Me | A85 | Et | OMe | Et | Me | A85 |
| Et | OMe | Me | Me | A86 | Et | OMe | Et | Me | A86 |
| Et | OMe | Me | Me | A87 | Et | OMe | Et | Me | A87 |
| Et | OMe | Me | Me | A91 | Et | OMe | Et | Me | A91 |
| Et | OMe | Me | Me | A92 | Et | OMe | Et | Me | A92 |
| Et | OMe | Me | Me | A93 | Et | OMe | Et | Me | A93 |
| Et | OMe | Me | Me | A94 | Et | OMe | Et | Me | A94 |
| Et | OMe | Me | Me | A95 | Et | OMe | Et | Me | A95 |
| Et | OMe | Me | Me | A97 | Et | OMe | Et | Me | A97 |
| Et | OMe | n-Pr | Me | A83 | Et | OEt | Me | Me | A83 |
| Et | OMe | n-Pr | Me | A84 | Et | OEt | Me | Me | A84 |
| Et | OMe | n-Pr | Me | A85 | Et | OEt | Me | Me | A85 |
| Et | OMe | n-Pr | Me | A86 | Et | OEt | Me | Me | A86 |
| Et | OMe | n-Pr | Me | A87 | Et | OEt | Me | Me | A87 |
| Et | OMe | n-Pr | Me | A91 | Et | OEt | Me | Me | A91 |
| Et | OMe | n-Pr | Me | A92 | Et | OEt | Me | Me | A92 |
| Et | OMe | n-Pr | Me | A93 | Et | OEt | Me | Me | A93 |
| Et | OMe | n-Pr | Me | A94 | Et | OEt | Me | Me | A94 |
| Et | OMe | n-Pr | Me | A95 | Et | OEt | Me | Me | A95 |
| Et | OMe | n-Pr | Me | A97 | Et | OEt | Me | Me | A97 |
| Et | OEt | Et | Me | A83 | Et | OMe | Me | Et | A83 |
| Et | OEt | Et | Me | A84 | Et | OMe | Me | Et | A84 |
| Et | OEt | Et | Me | A85 | Et | OMe | Me | Et | A85 |
| Et | OEt | Et | Me | A86 | Et | OMe | Me | Et | A86 |
| Et | OEt | Et | Me | A87 | Et | OMe | Me | Et | A87 |
| Et | OEt | Et | Me | A91 | Et | OMe | Me | Et | A91 |
| Et | OEt | Et | Me | A92 | Et | OMe | Me | Et | A92 |
| Et | OEt | Et | Me | A93 | Et | OMe | Me | Et | A93 |
| Et | OEt | Et | Me | A94 | Et | OMe | Me | Et | A94 |
| Et | OEt | Et | Me | A95 | Et | OMe | Me | Et | A95 |
| Et | OEt | Et | Me | A97 | Et | OMe | Me | Et | A97 |

TABLE 4

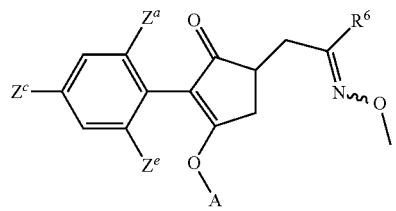

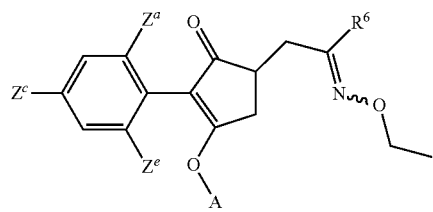

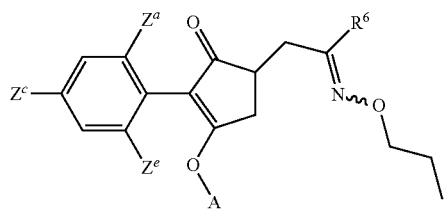

TABLE 4-continued

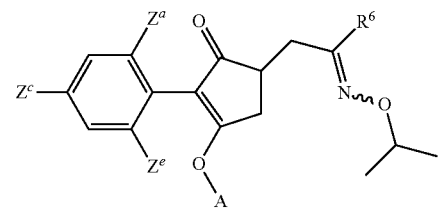

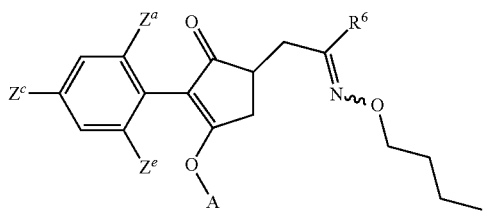

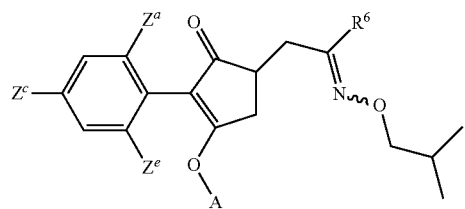

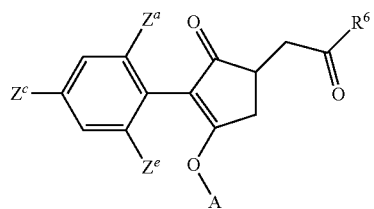

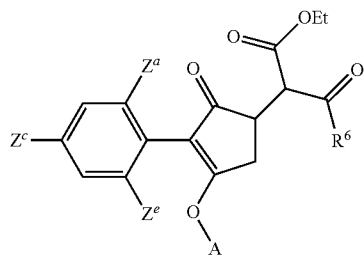

| $R^6$ | $Z^a$ | $Z^e$ | $Z^c$ | A | $R^6$ | $Z^a$ | $Z^e$ | $Z^c$ | A |
|---|---|---|---|---|---|---|---|---|---|
| Me | Me | Me | OCH$_2$CF$_3$ | H | Me | Me | Et | OCH$_2$CF$_3$ | H |
| Me | Et | Et | OCH$_2$CF$_3$ | H | Me | Me | n-Pr | OCH$_2$CF$_3$ | H |
| Me | Me | Me | OCF$_3$ | H | Me | Me | Et | OCF$_3$ | H |
| Me | Et | Et | OCF$_3$ | H | Me | Me | n-Pr | OCF$_3$ | H |
| Me | Me | Me | OCF$_2$H | H | Me | Me | Et | OCF$_2$H | H |
| Me | Et | Et | OCF$_2$H | H | Me | Me | n-Pr | OCF$_2$H | H |
| Me | Me | Me | OCF$_2$Cl | H | Me | Me | Et | OCF$_2$Cl | H |
| Me | Et | Et | OCF$_2$Cl | H | Me | Me | n-Pr | OCF$_2$Cl | H |
| Me | Me | Me | OCF$_2$Br | H | Me | Me | Et | OCF$_2$Br | H |
| Me | Et | Et | OCF$_2$Br | H | Me | Me | n-Pr | OCF$_2$Br | H |
| Me | Me | Me | O(D1-32a) | H | Me | Et | Et | O(D1-32a) | H |
| Me | Me | Me | O(D1-32b-2) | H | Me | Et | Et | O(D1-32b-2) | H |
| Me | Me | Me | O(D1-32b-3) | H | Me | Et | Et | O(D1-32b-3) | H |
| Me | Me | Me | O(D1-32b-4) | H | Me | Et | Et | O(D1-32b-4) | H |
| Me | Me | Me | O(D1-32b-5) | H | Me | Et | Et | O(D1-32b-5) | H |
| Me | Me | Me | O(D1-33a) | H | Me | Me | Me | O(D1-33a) | H |
| Me | Me | Me | O(D1-33b-1) | H | Me | Me | Me | O(D1-33b-1) | H |
| Me | Me | Me | O(D1-33b-2) | H | Me | Me | Me | O(D1-33b-2) | H |
| Me | Me | Me | O(D1-33b-3) | H | Me | Me | Me | O(D1-33b-3) | H |
| Me | Me | Me | O(D1-33b-4) | H | Me | Me | Me | O(D1-33b-4) | H |
| Me | OMe | Me | Ph | H | Me | OMe | Et | Ph | H |
| Me | OMe | Me | Ph | A39 | Me | OMe | Et | Ph | A39 |

TABLE 4-continued

| | | | | | | | | | |
|---|---|---|---|---|---|---|---|---|---|
| Me | OMe | Me | Ph | A40 | Me | OMe | Et | Ph | A40 |
| Me | OMe | Me | Ph | A41 | Me | OMe | Et | Ph | A41 |
| Me | OMe | Me | D1-108b-4 | H | Me | OMe | Et | D1-108b-4 | H |
| Me | OMe | Me | D1-108b-4 | A39 | Me | OMe | Et | D1-108b4 | A39 |
| Me | OMe | Me | D1-108b-4 | A40 | Me | OMe | Et | D1-108b-4 | A40 |
| Me | OMe | Me | D1-108b-4 | A41 | Me | OMe | Et | D1-108b-4 | A41 |
| Me | OMe | Me | D1-108b-4 | A74 | Me | OMe | Et | D1-108b-4 | A74 |
| Me | OMe | Me | D1-108b-4 | A75 | Me | OMe | Et | D1-108b-4 | A75 |
| Me | OMe | Me | D1-108b-4 | A84 | Me | OMe | Et | D1-108b-4 | A84 |
| Me | OMe | Me | D1-108b-4 | A85 | Me | OMe | Et | D1-108b-4 | A85 |
| Me | OMe | Me | D1-108b-4 | A86 | Me | OMe | Et | D1-108b-4 | A86 |
| Me | OMe | Me | D1-108b-4 | A87 | Me | OMe | Et | D1-108b-4 | A87 |
| Me | OMe | Me | D1-108b-8 | H | Me | OMe | Et | D1-108b-8 | H |
| Me | OMe | Me | D1-108b-8 | A39 | Me | OMe | Et | D1-108b-8 | A39 |
| Me | OMe | Me | D1-108b-8 | A40 | Me | OMe | Et | D1-108b-8 | A40 |
| Me | OMe | Me | D1-108b-8 | A41 | Me | OMe | Et | D1-108b-8 | A41 |
| Me | OMe | Me | D1-108b-8 | A74 | Me | OMe | Et | D1-108b-8 | A74 |
| Me | OMe | Me | D1-108b-8 | A75 | Me | OMe | Et | D1-108b-8 | A75 |
| Me | OMe | Me | D1-108b-8 | A84 | Me | OMe | Et | D1-108b-8 | A84 |
| Me | OMe | Me | D1-108b-8 | A85 | Me | OMe | Et | D1-108b-8 | A85 |
| Me | OMe | Me | D1-108b-8 | A86 | Me | OMe | Et | D1-108b-8 | A86 |
| Me | OMe | Me | D1-108b-8 | A87 | Me | OMe | Et | D1-108b-8 | A87 |
| Me | OMe | Me | Br | H | Me | OMe | Et | Br | H |
| Me | SMe | Me | Me | H | Me | SMe | Et | Me | H |
| c-Pr | OMe | Me | Me | H | c-Pr | OMe | Et | Me | H |
| c-Pr | OMe | Me | Me | A12 | c-Pr | OMe | Et | Me | A12 |
| c-Pr | OMe | Me | Me | A13 | c-Pr | OMe | Et | Me | A13 |
| c-Pr | OMe | Me | Me | A74 | c-Pr | OMe | Et | Me | A74 |
| c-Bu | OMe | Me | Me | H | c-Bu | OMe | Et | Me | H |
| c-Bu | OMe | Me | Me | A12 | c-Bu | OMe | Et | Me | A12 |
| c-Bu | OMe | Me | Me | A13 | c-Bu | OMe | Et | Me | A13 |
| c-Bu | OMe | Me | Me | A74 | c-Bu | OMe | Et | Me | A74 |
| c-Pen | OMe | Me | Me | H | c-Pen | OMe | Et | Me | H |
| c-Pen | OMe | Me | Me | A12 | c-Pen | OMe | Et | Me | A12 |
| c-Pen | OMe | Me | Me | A13 | c-Pen | OMe | Et | Me | A13 |
| c-Pen | OMe | Me | Me | A74 | c-Pen | OMe | Et | Me | A74 |
| c-Hex | OMe | Me | Me | H | c-Hex | OMe | Et | Me | H |
| Me | OMe | n-Pr | Ph | H | Me | OEt | Me | Ph | H |
| Me | OMe | n-Pr | Ph | A39 | Me | OEt | Me | Ph | A39 |
| Me | OMe | n-Pr | Ph | A40 | Me | OEt | Me | Ph | A40 |
| Me | OMe | n-Pr | Ph | A41 | Me | OEt | Me | Ph | A41 |
| Me | OMe | n-Pr | D1-108b-4 | H | Me | OEt | Me | D1-108b-4 | H |
| Me | OMe | n-Pr | D1-108b-4 | A39 | Me | OEt | Me | D1-108b-4 | A39 |
| Me | OMe | n-Pr | D1-108b-4 | A40 | Me | OEt | Me | D1-108b-4 | A40 |
| Me | OMe | n-Pr | D1-108b-4 | A41 | Me | OEt | Me | D1-108b-4 | A41 |
| Me | OMe | n-Pr | D1-108b-4 | A74 | Me | OEt | Me | D1-108b-4 | A74 |
| Me | OMe | n-Pr | D1-108b-4 | A75 | Me | OEt | Me | D1-108b-4 | A75 |
| Me | OMe | n-Pr | D1-108b-4 | A84 | Me | OEt | Me | D1-108b-4 | A84 |
| Me | OMe | n-Pr | D1-108b-4 | A85 | Me | OEt | Me | D1-108b-4 | A85 |
| Me | OMe | n-Pr | D1-108b-4 | A86 | Me | OEt | Me | D1-108b-4 | A86 |
| Me | OMe | n-Pr | D1-108b-4 | A87 | Me | OEt | Me | D1-108b-4 | A87 |
| Me | OMe | n-Pr | D1-108b-8 | H | Me | OEt | Me | D1-108b-8 | H |
| Me | OMe | n-Pr | D1-108b-8 | A39 | Me | OEt | Me | D1-108b-8 | A39 |
| Me | OMe | n-Pr | D1-108b-8 | A40 | Me | OEt | Me | D1-108b-8 | A40 |
| Me | OMe | n-Pr | D1-108b-8 | A41 | Me | OEt | Me | D1-108b-8 | A41 |
| Me | OMe | n-Pr | D1-108b-8 | A74 | Me | OEt | Me | D1-108b-8 | A74 |
| Me | OMe | n-Pr | D1-108b-8 | A75 | Me | OEt | Me | D1-108b-8 | A75 |
| Me | OMe | n-Pr | D1-108b-8 | A84 | Me | OEt | Me | D1-108b-8 | A84 |
| Me | OMe | n-Pr | D1-108b-8 | A85 | Me | OEt | Me | D1-108b-8 | A85 |
| Me | OMe | n-Pr | D1-108b-8 | A86 | Me | OEt | Me | D1-108b-8 | A86 |
| Me | OMe | n-Pr | D1-108b-8 | A87 | Me | OEt | Me | D1-108b-8 | A87 |
| Me | OMe | n-Pr | Br | H | Me | OEt | Me | Br | H |
| Me | SMe | n-Pr | Me | H | Me | SEt | Me | Me | H |
| c-Pr | OMe | n-Pr | Me | H | c-Pr | OEt | Me | Me | H |
| c-Pr | OMe | n-Pr | Me | A12 | c-Pr | OEt | Me | Me | A12 |
| c-Pr | OMe | n-Pr | Me | A13 | c-Pr | OEt | Me | Me | A13 |
| c-Pr | OMe | n-Pr | Me | A74 | c-Pr | OEt | Me | Me | A74 |
| c-Bu | OMe | n-Pr | Me | H | c-Bu | OEt | Me | Me | H |
| c-Bu | OMe | n-Pr | Me | A12 | c-Bu | OEt | Me | Me | A12 |
| c-Bu | OMe | n-Pr | Me | A13 | c-Bu | OEt | Me | Me | A13 |
| c-Bu | OMe | n-Pr | Me | A74 | c-Bu | OEt | Me | Me | A74 |
| c-Pen | OMe | n-Pr | Me | H | c-Pr | OEt | Me | Me | H |
| c-Pen | OMe | n-Pr | Me | A12 | c-Pen | OEt | Me | Me | A12 |
| c-Pen | OMe | n-Pr | Me | A13 | c-Pen | OEt | Me | Me | A13 |
| c-Pen | OMe | n-Pr | Me | A74 | c-Pen | OEt | Me | Me | A74 |
| c-Hex | OMe | n-Pr | Me | H | c-Hex | OEt | Me | Me | H |
| Me | OEt | Et | Ph | H | c-Hex | OMe | Me | Me | A12 |
| Me | OEt | Et | Ph | A39 | c-Hex | OMe | Me | Me | A13 |
| Me | OEt | Et | Ph | A40 | c-Hex | OMe | Me | Me | A74 |
| Me | OEt | Et | Ph | A41 | Me | OMe | Me | Me | H |

TABLE 4-continued

| Me | OEt | Et | D1-108b-4 | H | Me | OMe | Br | Me | H |
|---|---|---|---|---|---|---|---|---|---|
| Me | OEt | Et | D1-108b-4 | A39 | Me | Me | Me | Me | H |
| Me | OEt | Et | D1-108b-4 | A40 | c-Hcx | OMe | n-Pr | Me | A12 |
| Me | OEt | Et | D1-108b-4 | A41 | c-Hex | OMe | n-Pr | Me | A13 |
| Me | OEt | Et | D1-108b-4 | A74 | c-Hex | OMe | n-Pr | Me | A74 |
| Me | OEt | Et | D1-108b-4 | A75 | Me | OMe | n-Pr | Me | H |
| Mt | OEt | Et | D1-108b-4 | A84 | Me | OMe | n-Pr | Me | H |
| Me | OEt | Et | D1-108b-4 | A85 | Me | Me | n-Pr | Me | H |
| Me | OEt | Et | D1-108b-4 | A86 | Me | OMe | F | Br | H |
| Me | OEt | Et | D1-108b-4 | A87 | Me | OMe | F | Ph | H |
| Me | OEt | Et | D1-108b-8 | H | Me | OMe | F | Me | H |
| Me | OEt | Et | D1-108b-8 | A39 | c-Hex | OMe | Et | Me | A12 |
| Me | OEt | Et | D1-108b-8 | A40 | c-Hex | OMe | Et | Me | A13 |
| Me | OEt | Et | D1-108b-8 | A41 | c-Hex | OMe | Et | Me | A74 |
| Me | OEt | Et | D1-108b-8 | A74 | Me | OMe | Et | Me | H |
| Me | OEt | Et | D1-108б-8 | A75 | Me | OMe | Et | Me | H |
| Me | OEt | Et | D1-108b-8 | A84 | Me | Me | Et | Me | H |
| Me | OEt | Et | D1-108b-8 | A85 | c-Hex | OEt | Me | Me | A12 |
| Me | OEt | Et | D1-108b-8 | A86 | c-Hex | OEt | Me | Me | A13 |
| Me | OEt | Et | D1-108b-8 | A87 | c-Hex | OEt | Me | Me | A74 |
| Me | OEt | Et | Br | H | Me | OMe | Et | Me | H |
| Me | SEt | Et | Me | H | Me | OMe | Et | Me | H |
| c-Pr | OEt | Et | Me | H | Me | Et | Et | Me | H |
| c-Pr | OEt | Et | Me | A12 | Me | OEt | F | Br | H |
| c-Pr | OEt | Et | Me | A13 | Me | OEt | F | Ph | H |
| c-Pr | OEt | Et | Me | A74 | Me | OEt | F | Me | H |
| c-Bu | OEt | Et | Me | H | c-Pen | OEt | Et | Me | A13 |
| c-Bu | OEt | Et | Me | A12 | c-Pen | OEt | Et | Me | A74 |
| c-Bu | OEt | Et | Me | A13 | c-Hex | OEt | Et | Me | H |
| c-Bu | OEt | Et | Me | A74 | c-Hex | OEt | Et | Me | A12 |
| c-Pen | OEt | Et | Me | H | c-Hex | OEt | Et | Me | A13 |
| c-Pen | OEt | Et | Me | A12 | c-Hex | OEt | Et | Me | A74 |
| Me | OMe | F | Br | H | Me | OEt | F | Br | H |
| Me | OMe | F | Ph | H | Me | OEt | F | Ph | H |
| Me | OMe | F | Me | H | Me | OEt | F | Me | H |

The compound of the present invention can be used in both treatment methods of soil application and foliage application under flooding as a herbicide for paddy fields. Examples of paddy field weeds may include Potamogetonaceae weeds represented by *Potamogeton distinctus*; Alismataceae weeds represented by *Alisma canaliculatum*, *Sagittaria pygmaea*, and *Sagittaria trifolia*; Gramineae weeds represented by *Leptochloa chinensis*, *Echinochloa crusgalli*, *Echinochloa oryzicola*, *Homalocenchrus japonocus*, and *Paspalum distichum*; Cyperaceae weeds represented by *Eleocharis kuroguwai*, *Scirpus juncoides*, *Scirpus nipponicus*, *Cyperus serotinus*, *Cyperus difformis*, and *Cyperus hakonensis*; Lemnaceae weeds represented by *Spirodela polyrhiza* and *Lemna paucicostata*; Commelinaceae weeds represented by *Murdannia keisak*; Pontederiaceae weeds represented by *Monochoria korsakowii* and *Monochoria vaginalis*; Elatinaceae weeds represented by *Elatine triandra*; Lythraceae weeds represented by *Ammannia multiflora* and *Rotala indica*; Oenotheraceae weeds represented by *Lidwigia epilobioides*; Scrophulariaceae weeds represented by *Dopatrium junceum*, *Gratiola japonica*, *Limnophila sessilifolia*, *Lindernia pyxidaria*, and *Lindernia dubia*; Leguminosae weeds such as *Aeschynomene indica*, and Compositae weeds represented by, *Bidensfrondosa* and *Bidens tripartita*.

The compound of the present invention can also be used in any treatment methods of soil treatment, soil incorporation treatment, and foliage treatment as a herbicide for farmlands and orchards. Examples of the farmland weeds may include broad-leaved weeds such as Solanaceae weeds represented by *Solanum nigrum* and *Datura stramonium*; Geraniaceae weeds represented by *Granium carolinianum*; Malvaceae weeds represented by *Abutilon theophrasti* and *Sida spinosa*; Convolvulaceae weeds represented by *Ipomoea* spps such as *Ipomoea purpurea* and *Calystegia* spps; Amaranthaceae weeds represented by *Amaranthus lividus* and *Amaranthus retroflexus*; Compositae weeds represented by *Xanthium pensylvanicum*, *Ambrosia artemisiaefolia*, *Helianthus annuus*, *Galinsoga ciliata*, *Cirsium arvense*, *Senecio vulgaris*, and *Erigeron annus*; Cruciferae weeds represented by *Rorippa indica*, *Sinapis arvensis*, and *Capsella* Bursapastoris; Polygonaceae weeds represented by *Polygonum Blumei* and *Polygonum convolvulus*; Portulacaceae weeds represented by *Portulaca oleracea*; Chenopodiaceae weeds represented by *Chenopodium album*, *Chenopodium ficifolium*, and *Kochia scoparia*; Caryophyllaceae weeds represented by *Stellaria media*; Scrophulariaceae weeds represented by *Veronica persica*; Commelinaceae weeds represented by *Commelina communis*; Labiatae weeds represented by *Lamium amplexicaule* and *Lamium purpureum*; Euphorbiaceae weeds represented by *Euphorbia supina* and *Euphorbia maculata*; Rubiaceae weeds represented by *Galium spurium* and *Rubia akane*; Violaceae weeds represented by *Viola mandshurica*; Leguminosae weeds represented by *Sesbania exalta* and *Cassia obtusifolia*; and Oxsaldaseae represented by *Oxsalis courniculata*; Graminaceous weeds represented by *Sorgham bicolor*, *Panicum dichotomiflorum*, *Sorghum halepense*, *Echinochloa crus-galli* var *Crus-galli*, *Echinochloa crus-galli* var *Praticola*, *Echinochloa utilis*, *Digitaria ciliaris*, *Avena fatua*, *Alopecurus myosuroides*, *Eleusine indica*, *Setaria viridis*, *Setaria faberi*, and *Alopecurus aegualis*; and Cyperaceous weeds represented by *Cyperus rotundus* and *Cyperus esculentus*.

The compound of the present invention can be used in any application methods of soil application, soil incorporation application, and foliage application in non-agricultural lands such as turfs, play grounds, open grounds, side of roads, and line ends other than the agricultural and horticultural fields such as paddy fields, farmlands, and orchards. As weeds in these non-agricultural lands, the following examples of the weeds are exemplified in addition to the weeds described in farmlands and orchards. The examples of the weed may include *Poa annua, Taraxacumofficinale, Conyza sumatrensis, Cardamineflexuosa, Trifoliumrepens, Hydrocotyle sibthorpioides, Plantago asiatica, Cyperus brevifolius, Kyllinga brevifolia*, and *Equisetum arvense*.

The compound of the present invention may be applied in a mixed state with other herbicides, various insecticides, bactericides, plant growth regulators, or synergists at the time of herbicide formulation or spray, if necessary.

In particular, by applying the herbicide in a mixed state with another herbicide, reduction in cost due to reduction in an application amount, expansion in herbicidal spectrum due to synergistic action of mixed herbicides, and a higher herbicidal effect can be expected. At this time, a combination of a plurality of known herbicides at the same time is also possible.

Examples of the preferable herbicide used by mixing with the compound of the present invention may include acetochlor/general name, acifluorfen/general name, aclonifen/general name, alachlor/general name, alloxydim/general name, alloxydim-sodium/general name, ametryn/general name, amicarbazone/general name, amidosulfuron/general name, aminocyclopirachlor/general name, aminocyclopirachlor-salts and esters, aminopyralid/general name, aminopyralid-salts and esters, amiprophos-methyl/general name, amitrol/general name, anilofos/general name, asulam/general name, atrazine/general name, azafenidin/general name, azimsulfuron/general name, beflubutamid/general name, benazolin-ethyl/general name, bencarbazone/general name, benfluralin (benefin)/general name, benfuresate/general name, bensulfuron-methyl/general name, bensulide/general name, bentazone/general name, bentazone-sodium/general name, bentazone-salts, benthiocarb/general name, benzfendizone/general name, benzobicyclon/general name, benzofenap/general name, bialaphos/general name, bialaphos-sodium/general name, bicyclopyrone/general name, bifenox/general name, bispyribac/general name, bispyribac-sodium/general name, bromacil/general name, bromobutide/general name, bromofenoxim/general name, bromoxynil/general name, bromoxynil-salts and esters, butachlor/general name, butafenacil/general name, butamifos/general name, butenachlor/general name, butralin/general name, butroxydim/general name, butylate/general name, cafenstrole/general name, carbetamide/general name, carfentrazone-ethyl, chlomethoxyfen/general name, chlomethoxynil/general name, chloramben/general name, chloramben-salts and esters, chloransulam-methyl/general name, chlorflurenol-methyl/general name, chloridazon/general name, chlorimuron-ethyl/general name, chlorobromuron/general name, chlorotoluron/general name, chloroxuron/general name, chlorphtalim/general name, chlorpropham/general name, chlorpropham/general name, chlorsulfuron/general name, chlorthal-dimethyl/general name, chlorthiamid/general name, cinidon-ethyl/general name, cinmethylin/general name, cinosulfuron/general name, clethodim/general name, clodinafop/general name, clodinafop-propargyl/general name, clomazone/general name, clomeprop/general name, clopyralid/general name, clopyralid-salts and esters, CNP/general name, cumyluron/general name, cyanazin/general name, cycloate/general name, cyclopyrimorate/general name (SW-065/test name), cyclosulfamuron/general name, cycloxydim/general name, cyhalofop-butyl/general name, DAH-500/test name, dalapon/general name, dazomet/general name, desmedipham/general name, desmetryn/general name, dicamba/general name, dicamba-salts and esters, dichlobenil/general name, diclofop/general name, diclofop-methyl/general name, dichlorprop/general name, dichlorprop-salts and esters, dichlorprop-P/general name, dichlorprop-P-salts and esters, diclosulam/general name, difenzoquat/general name, diflufenican/general name, diflufenzopyr/general name, diflufenzopyr-sodium/general name, dimepiperate/general name, dimethametryn/general name, dimethachlor/general name, dimethenamid/general name, dimethenamid-p/general name, dimethipin/general name, dinitramine/general name, dinoseb/general name, dinoterb/general name, DNOC/general name, diphenamid/general name, diquqt/general name, dithiopyl/general name, diuron/general name, DSMA/general name, dymron/general name, endothal/general name, EPTC/general name, esprocarb/general name, ethalfluralin/general name, ethametsulfuron-methyl/general name, ethofumesate/general name, etobenzanid/general name, ethoxysulfuron/general name, flazasulfuron/general name, fenoxaprop/general name, fenoxaprop-ethyl/general name, fenoxasulfone/general name, fenquinotrion/general name, fentrazamide/general name, flamprop/general name, flazasulfuron/general name, florasulam/general name, fluazifop/general name, fluazifop-butyl/general name, fluazolate/general name, flucarbazone-sodium/general name, flucetosulfuron/general name, flucloralin/general name, flufenacet/general name, flufenpyl-ethyl/general name, flumetsulam/general name, flumiclorac-pentyl/general name, flumioxazin/general name, fluometuron/general name, fluoroglycofen-ethyl/general name, flupyrsulfuron/general name, flupoxam/general name, flurenol/general name, fluridone/general name, flurochloridone/general name, fluroxypyr/general name, fluroxypyr-esters, flurprimidol/general name, flurtamone/general name, fluthiacet-methyl/general name, fomesafen/general name, foramsulfuron/general name, fosamine/general name, glufosinate/general name, glufosinate-ammonium/general name, glyphosate/general name, glyphosate-ammonium/general name, glyphosate-iso-propylammonium/general name, glyphosate-potassium/general name, glyphosate-sodium/general name, glyphosate-trimesium/general name, halauxifen/general name, halauxifen-salts and esters, halosafen/general name, halosulfuron/general name, halosulfuron-methyl/general name, haloxyfop/general name, haloxyfop-methyl/general name, hexazinone/general name, imazamethabenz-methyl/general name, imazamox/general name, imazapic/general name, imazapyr/general name, imazethapyr/general name, imazaquin/general name, imazosulfuron/general name, indanofan/general name, indaziflam/general name, iodosulfuron-methyl-sodium/general name, ioxynil octanoate/general name, ioxynil-salts and esters, ipfencarbazone/general name, isoproturon/general name, isouron/general name, isoxaben/general name, isoxaflutole/general name, karbutilate/general name, lactofen/general name, lenacil/general name, linuron/general name, maleic hydrazide/general name, MCPA/general name, MCPA-salts and esters, MCPB/general name, MCPB-salts and esters, mecoprop (MCPP)/general name, mecoprop-salts and esters, mecoprop-P (MCPP-P)/general name, mecoprop-P-salts and esters, mefenacet/general name, mefluidide/general name, mesosulfuron-methyl/general name, mesotrione/general name, metam/general name, metamifop/general name, metamitron/general name, metazachlor/general name, methabenzthiazuron/general name, metazosulfuron/general name, methiozolin/general name, methyl azide/general name, methyl bromide/general name, methyl dymron/general name, methyl iodide/general name, metobenzuron/general name, metolachlor/general name, metolachlor-S/general name, metosulam/general name, metribuzin/general name, metsulfuron-methyl/general name, metoxuron/general name, molinate/general name, monolinuron/general name, monosulfuron/general name, monosulfuron-methyl/general name, MSMA/general name, naproanilide/general name, napropamide/general name, naptalam/general name, naptalam-sodium/general name, neburon/general name, nicosulfuron/general name, norflurazon/general name, OK-701/test name, oleic acid/general name, orbencarb/general name, orthosulfamuron/general name, oryzalin/general name, oxadiargyl/general name, oxadiazon/general name, oxasulfuron/general name, oxaziclomefone/general name, oxyfluorfen/general name, paraquat/general name, pelargonic acid/general name, pendimethalin/general name, penoxsulam/general name, pentanochlor/general name, pentoxazone/general name, pethoxamid/general name, phenmedipham-ethyl/general name, picloram/general name, picloram-salts and esters, picolinafen/general name, pinoxaden/general name, piperophos/general name, pretilachlor/general name, primisulfuron-methyl/general name, prodiamine/general name, profluazol/general name, profoxydim/general name, prometon/general name, prometryn/general name, propachlor/general name, propanil/general name, propaquizafop/general name, propazin/general name, propham/general name, propisochlor/general name, propoxycarbazone-sodium/general name, propyrisulfuron/general name, propyzamide/general name, prosulfocarb/general name, prosulfuron/general name, pyraclonil/general name, pyraflufen-ethyl/general name, pyrasulfotole/general name, pyrazolynate/general name, pyrazosulfuron/general name, pyrazosulfuron-ethyl/general name, pyrazoxyfen/general name, pyribenzoxim/general name, pyributicarb/general name, pyridafol/general name, pyridate/general name, pyriftalid/general name, pyriminobac-methyl/general name, pyrimisulfan/general name, pyrithiobac-sodium/general name, pyroxasulfone/general name, pyroxsulam/general name, quinclorac/general name, quinmerac/general name, quinoclamine/general name, quizalofop/general name, quizalofop-ethyl/general name, quizalofop-tefuryl/general name, quizalofop-P/general name, quizalofop-P-ethyl/general name, quizalofop-P-tefuryl/general name, rimsulfuron/general name, saflufenacil/general name, sethoxydim/general name, siduron/general name, simazine/general name, simetryn/general name, SL-261/test name, sulcotrione/general name, sulfentrazone/general name, sulfometuron-methyl/general name, sulfosulfuron/general name, TCBA (2,3,6-TBA)/general name, 2,3,6-TBA-salts and esters, TCTP (chlorthal-dimethyl, tetrachlorothiophene)/general name, tebutam/general name, tebuthiuron/general name, tefuryltrione/general name, tembotrione/general name, tepraloxydim/general name, terbacil/general name, terbumeton/general name, terbuthylazine/general name, terbutryn/general name, tetrapion (flupropanate)/general name, thenylchlor/general name, thiazafluron/general name, thiazopyr/general name, thidiazimin/general name, thidiazuron/general name, thiencarbazone-methyl/general name, thifensulfuron-methyl/general name, tolpyralate/general name, topramezon/general name, tralkoxydim/general name, triafamone/general name, triallate/general name, triasulfuron/general name, triaziflam/general name, tribenuron-methyl/general name, triclopyr/general name, triclopyr-salts and esters, tridiphane/general name, trietazine/general name, trifludimoxadin/general name, trifloxysulfuron/general name, trifluralin/general name, triflusulfuron-methyl/general name, tritosulfuron/general name, 2,4-PA/general name, 2,4-PA-salts and esters, 2,4-DB/general name, and 2,4-DB-salts and esters. These components may be used singly or in combination of two or more of them. When these components are mixed, the ratio may be freely selected.

Examples of safeners may include AD-67, benoxacor/general name, cloquintocet-mexyl/general name, cyomerinil/general name, dichlormid/general name, dicyclonone/general name, cyprosulfamide/general name, diethorate/general name, DKA-24, dymron/general name, fenclorazole-ethyl/general name, fenclorim/general name, HEXIM/general name, flurazole/general name, fluxofenim/general name, furilazole/general name, isoxadifen/general name, isoxadifen-ethyl/general name, MCPA, mecoprop/general name, mefenpyr/general name, mefenpyr-ethyl/general name, mefenpyr-diethyl/general name, mephenate/general name, MG-191, NA (Naphthalic anhydride), OM (Octamethylene-diamine), oxabetrinil/general name, PPG-1292, and R-29148. These components may be used singly or in combination of two or more of them. When these components are mixed, the ratio may be freely selected.

When the compound of the present invention is applied as the herbicide, the compound is usually mixed with an appropriate solid carrier or liquid carrier. Surfactants, penetrating agents, spreading agents, thickeners, antifreeze agents, binders, anti-caking agents, disintegrating agents and stabilizing agents can be further added, if desired. The herbicide can be applied to practical uses by any herbicide formulation of the herbicide form such as water-dispersible agents, emulsion agents, flowable agents, dry-flowable agents, liquid agents, powder agents, granule agents, or gel agents. From the viewpoint of power saving and improvement in safety, any of the herbicide formulation of the herbicide form can be supplied by encapsulating in a water-soluble package.

Examples of the solid carriers may include natural minerals such as quartz, kaolinite, pyrophyllite, sericite, talc, bentonite, acid clay, attapulgite, zeolite, and diatomaceous earth; inorganic salts such as calcium carbonate, ammonium sulfate, sodium sulfate and potassium chloride; and synthetic silicic acid and synthetic silicates.

Examples of the liquid carriers may include alcohols such as ethylene glycol, propylene glycol, and isopropanol (2-propanol); aromatic hydrocarbons such as xylene, alkylbenzenes, and alkylnaphthalenes; ethers such as butylcellosolve; ketones such as cyclohexanone; esters such as γ-butyrolactone; acid amide such as N-methylpyrrolidone and N-octylpyrrolidone; vegetable oils such as soybean oil, rapeseed oil, cotton seed oil, and castor oil; and water.

These solid carriers and liquid carriers may be used singly or in combination of two or more of them.

Examples of the surfactant may include nonionic surfactants such as polyoxyethylene alkyl ethers, polyoxyethylene alkylaryl ethers, polyoxyethylene styrylphenyl ethers, polyoxyethylene-polyoxypropylene block copolymers, polyoxyethylene fatty acid esters, sorbitan fatty acid esters, and polyoxyethylene sorbitan fatty acid esters; anionic surfactants such as alkyl sulfates, alkylbenzene sulfonates, lignin sulfonates, alkyl sulfosuccinates, naphthalene sulfonate, alkylnaphthalene sulfonates, salts of formalin condensate of naphthalene sulfonic acid, salts of formalin condensate of alkylnaphthalene sulfonic acids, polyoxyethylene alkylaryl ether sulfates and phosphates, polyoxyethylene styrylphenyl ether sulfates and phosphates, polycarboxylates, and polystyrene sulfonates; cationic surfactants such as alkylamine salts and alkyl quaternary ammonium salts; and amphoteric surfactants such as amino acid-type surfactants and betaine-type surfactants.

The content of the surfactants is not particularly limited. Usually, the content is preferably in a range of 0.05 part by mass to 20 parts by mass relative to 100 parts by mass of the herbicide formulation of the present invention. These surfactants may be used singly or in combination of two or more of them.

The compound of the present invention may be applied in a mixed state with other herbicides, various insecticides, bactericides, plant growth regulators, or synergists at the time of herbicide formulation or spray, if necessary.

In particular, by applying the herbicide in a mixed state with another herbicide, reduction in cost due to reduction in an application amount, expansion in herbicidal spectrum due to synergistic action of mixed herbicides, and a higher herbicidal effect can be expected. At this time, a combination of a plurality of known herbicides at the same time is also possible.

Although the application amount of the compound of the present invention varies depending on an application stage, an application time, an application method, and a cultivated crop, the appropriate application amount is generally 0.005 kg to 50 kg per hectare (ha) as the amount of the active component.

The formulation examples of the herbicide formulations when the compound of the present invention is used will be described. However, the formulation examples of the present invention are not limited to these examples. Hereinafter, the term "part" in the formulation examples means part by mass.

Water-Dispersible Agent

| | |
|---|---|
| Compound of the present invention | 0.1 part to 80 parts |
| Solid carrier | 5 parts to 98.9 parts |
| Surfactant | 1 part to 10 parts |
| Others | 0 part to 5 parts |

Examples of Others may include anti-caking agents and stabilizing agents.

Emulsion Agent

| | |
|---|---|
| Compound of the present invention | 0.1 part to 30 parts |
| Liquid carrier | 45 parts to 95 parts |
| Surfactant | 4.9 parts to 15 parts |
| Others | 0 part to 10 parts |

Examples of Others may include spreading agents and stabilizing agents.

Flowable Agent Compound of the present invention 0.1 part to 70 parts

| | |
|---|---|
| Compound of the present invention | 0.1 part to 70 parts |
| Liquid carrier | 15 parts to 98.89 parts |
| Surfactant | 1 part to 12 parts |
| Others | 0.01 part to 30 parts |

Examples of Others may include antifreeze agents and thickeners.

Dry Flowable Agent

| | |
|---|---|
| Compound of the present invention | 0.1 part to 90 parts |
| Solid carrier | 0 parts to 98.9 parts |
| Surfactant | 1 part to 20 parts |
| Others | 0 part to 10 parts |

Examples of Others may include binders and stabilizing agents.

Liquid Agent

| | |
|---|---|
| Compound of the present invention | 0.01 part to 70 parts |
| Liquid carrier | 20 parts to 99.99 parts |
| Others | 0 part to 10 parts |

Examples of Others may include antifreeze agents and spreading agents.

Granule Agent

| | |
|---|---|
| Compound of the present invention | 0.01 part to 80 parts |
| Solid carrier | 10 parts to 99.99 parts |
| Others | 0 part to 10 parts |

Examples of Others may include binders and stabilizing agents.

Powder Agent

| | |
|---|---|
| Compound of the present invention | 0.01 part to 30 parts |
| Solid carrier | 65 parts to 99.99 parts |
| Others | 0 part to 10 parts |

Examples of Others may include anti-drift agent and stabilizing agents.

When the formulation is used, the formulation is applied as it is or by diluting the formulation to 1 to 10000 times with water.

Herbicide Formulation Example

Examples of agricultural chemical formulation containing the compound of the present invention as the active component will be described. The present invention, however, is not limited to these examples. Hereinafter, the term "part" in the formulation examples means part by mass.

[Formulation Example 1] Water-Dispersible Agent

| | |
|---|---|
| Compound of the present invention No. 1-001 | 20 parts |
| Pyrophyllite | 76 parts |
| Sorpol 5039 | 2 parts |
| (Anionic surfactant: manufactured by TOHO Chemical Industry Co., Ltd., trade name) | |
| CARPLEX #80 | 2 parts |
| (Synthetic hydrated silicic acid: Shionogi & Co., Ltd., trade name) | |

The above components are homogeneously mixed and pulverized to form the water-dispersible agent.

[Formulation Example 2] Emulsion Agent

| | |
|---|---|
| Compound of the present invention No. 1-001 | 5 parts |
| Xylene | 75 parts |
| N-methylpyrrolidone | 15 parts |
| Sorpol 2680 | 5 parts |
| (Anionic surfactant: manufactured by TOHO Chemical Industry Co., Ltd., trade name) | |

The above components are homogeneously mixed to form the emulsion agent.

[Formulation Example 3] Flowable Agent

| | |
|---|---|
| Compound of the present invention No. 1-001 | 25 parts |
| Agrisol S-710 | 10 parts |
| (Nonionic surfactant: Kao Corporation, trade name) | |
| Lunox 1000C | 0.5 part |
| (Anionic surfactant: manufactured by TOHO Chemical Industry Co., Ltd., trade name) | |
| Xanthan gum | 0.02 part |
| Water | 64.48 parts |

The above components are homogeneously mixed and thereafter the mixture was wet-pulverized to form the flowable agent.

[Formulation Example 4] Dry Flowable Agent

| | |
|---|---|
| Compound of the present invention No. 1-001 | 75 parts |
| HITENOL NE-15 | 5 parts |
| (Anionic surfactant: manufactured by DKS Co. Ltd., trade name) | |
| Vanillex N | 10 parts |
| (Anionic surfactant: manufactured by NIPPON PAPER INDUSTRIES CO., LTD., trade name) | |
| CARPLEX #80 | 10 parts |

(Synthetic hydrated silicic acid: Shionogi & Co., Ltd., trade name)

The above components are homogeneously mixed and pulverized. Thereafter, a small amount of water was added to the mixture and the resultant mixture was stirred, mixed, and kneaded. The obtained mixture was granulated with an extruding-type granulator. The resultant granules are dried to form the dry flowable agent.

[Formulation Example 5] Granular Agent

| | |
|---|---|
| Compound of the present invention No. 1-001 | 1 part |
| Bentonite | 55 parts |
| Talc | 44 parts |

The above components are homogeneously mixed and pulverized. Thereafter, a small amount of water was added to the mixture and the resultant mixture was stirred, mixed, and kneaded. The obtained mixture was granulated with an extruding-type granulator. The resultant granules are dried to form the granular agent.

EXAMPLES

Hereinafter, in the herbicide of the present invention, the present invention will be further described in detail by specifically describing Synthesis Examples and Test Examples of the ketone or oxime compound of Formula (1) used as the active component as Examples. The present invention, however, is not limited to these Examples.

As a medium pressure preparative liquid chromatography described in Synthesis Examples, medium pressure preparative apparatus; YFLC-Wprep (flow rate: 18 ml/min, 40 μm silica gel packed column) manufactured by Yamazen Corporation was used.

Discaver manufactured by CEM Co., Ltd. was used as a microwave synthesizing apparatus, and a sealed container dedicated for the apparatus was used as a reaction container.

10AVP System manufactured by Shimadzu Corporation was used as a high performance liquid chromatography.

The chemical shift values of proton nuclear magnetic resonance in Examples were measured at 300 MHz using $Me_4Si$ (tetramethylsilane) as a reference substance. Solvents used in measurement are described in Synthesis Examples below. The symbols of the chemical shift values of proton nuclear magnetic resonance in Examples have the following meanings.

s: singlet, brs: broad singlet, d: doublet, t: triplet, and m: multiplet

SYNTHESIS EXAMPLES

Synthesis Example 1: Production of 2-mesityl-3-methoxy-5-{2-(methoxyimino)propyl}cyclopent-2-enone (Compound No. 1-001)

The mixed solution of 0.5 g of 2-mesityl-3-methoxycyclopent-2-enone synthesized by the method described in WO 2010/000773 Pamphlet and 10 ml of tetrahydrofuran was cooled to −78° C. under a nitrogen atmosphere, and thereafter 2.3 ml of lithium diisopropylamide (the mixed solution of about 1.5 mol/L of n-hexane and tetrahydrofuran, manufactured by KANTO CHEMICAL CO., INC.) was added dropwise. After completion of the dropwise addition, the reaction mixture was stirred at the same temperature for 30 minutes. After completion of the stirring, 0.34 g of 1-chloropropan-2-one O-methyl oxime was added to the reaction mixture. After completion of the addition, the reaction solution was stirred at −78° C. for 20 minutes. Thereafter the temperature of the reaction solution was raised to room temperature and the reaction solution was stirred at the same temperature for 15 hours. After completion of the reaction, the reaction mixture was added to ice water and the resultant mixture was extracted with 20 ml of ethyl acetate. The obtained organic phase was washed with water and dehydrated and dried with anhydrous sodium sulfate. Thereafter, the solvent was distilled away under reduced pressure. The obtained residue was purified with medium pressure preparative liquid chromatography eluting the residue with n-hexane-ethyl acetate [1:1 (volume ratio, the same applies hereinafter)] to give 76 mg of the target compound as a white solid.

Melting point 92° C. to 98° C.

Synthesis Example 2: Production of 3-hydroxy-2-mesityl-5-(2-oxopropyl)cyclopent-2-enone (Compound No. 2-001)

To the mixed solution of 60 mg of 2-mesityl-3-methoxy-5-{2-(methoxyimino)propyl}cyclopent-2-enone and 1 ml of acetone, 1 ml of 2 M hydrochloric acid aqueous solution was added. After completion of the addition, the reaction mixture was stirred at 50° C. for 4 hours. After completion of the reaction, 5 ml of ethyl acetate was added to the reaction mixture to take out the organic phase. The obtained organic phase was washed with water and dehydrated and dried with anhydrous sodium sulfate. Thereafter, the solvent was distilled away under reduced pressure to give 56 mg of the target compound as a white solid.

Melting point; 183° C. to 185° C.

Synthesis Example 3: Production of 3-hydroxy-2-mesityl-5-{2-(methoxyimino)propyl}cyclopent-2-enone (Compound No. 1-002)

To the mixed solution of 50 mg of 3-hydroxy-2-mesityl-5-(2-oxopropyl)cyclopent-2-enone, 2 ml of methanol, and 1 ml of water, 24 mg of O-methylhydroxylamine hydrochloride was added. After completion of the addition, the reaction mixture was stirred at 50° C. for 1 hour. After completion of the reaction, the solvent was distilled away from the reaction mixture under reduced pressure. After 10 ml of ethyl acetate was added to the obtained residue, the mixture was washed with water. The obtained organic phase was dehydrated and dried with saturated sodium chloride aqueous solution and then anhydrous sodium sulfate in this order and the solvent was distilled away under reduced pressure to give 31 mg of the target compound as a white solid.
Melting point; 170° C. to 173° C.

Synthesis Example 4: Production of 2-mesityl-4-{2-(methoxyimino)propyl}-3-oxocyclopent-1-en-1-yl pivalate (Compound No. 1-004)

To the mixed solution of 150 mg of 3-hydroxy-2-mesityl-5-{2-(methoxyimino)propyl}cyclopent-2-enone and 5 ml of dichloromethane, 139 mg of triethylamine, 6 mg of 4-dimethylaminopyridine, and 186 mg of pivalic anhydride were sequentially added. After completion of the addition, the reaction mixture was stirred at room temperature for 15 hours. After completion of the reaction, 5 ml of water was added to the reaction mixture and the resultant mixture was extracted with 10 ml of chloroform. The obtained organic phase was dehydrated and dried with anhydrous sodium sulfate, and thereafter the solvent was distilled away under reduced pressure. After the solvent was distilled away, the obtained residue was purified with medium pressure preparative liquid chromatography eluting the residue with hexane-ethyl acetate (2:1) to give 150 mg of the target compound as a colorless oily product.
$^1$H NMR (CDCl$_3$, Me$_4$Si, 300 MHz) δ 6.85-6.81 (m, 2H), 3.87-3.82 (m, 3H), 3.70-2.18 (m, 8H), 2.15-1.78 (m, 9H), 1.08 and 1.06 (s, 9H).

Synthesis Example 5: Production of 2-(4-bromo-2-methoxy-6-methylphenyl)-3-hydroxy-5-(2-oxopropyl)cyclopent-2-enone (Compound No. 7-027)

Process 1: Production of 5-bromo-2-iodo-1-methoxy-3-methylbenzene

The mixed solution of 15.7 g of 4-bromo-2-methoxy-6-methylaniline synthesized by the method described in WO 2005/028479 Pamphlet, 130 ml of concentrated hydrochloric acid, and 130 ml of water was cooled to 0° C. To the mixed solution, 5.5 g of sodium nitrite was added, while maintaining the temperature at 5° C. or lower and the resultant reaction solution was further stirred for 30 minutes. Subsequently, the mixed solution of 13.3 g of potassium iodide and 65 ml of water was added to the reaction solution while maintaining the temperature at 5° C. or lower and thereafter the resultant reaction solution was stirred at room temperature for 15 hours. After completion of the reaction, the reaction solution was extracted with 200 ml of 1,2-dichloroethane. The obtained organic phase was washed with 200 ml of 1 mol/L of a sodium hydroxide aqueous solution, 200 ml of 1 mol/L of a sodium sulfite aqueous solution, 200 ml of 1 mol/L of a hydrochloric acid aqueous solution, and 200 ml of a saturated sodium hydrogencarbonate solution in this order. Subsequently, the obtained organic phase was dehydrated and dried with saturated sodium chloride aqueous solution and then anhydrous sodium sulfate in this order and the solvent was distilled away under reduced pressure. The obtained residue was purified with medium pressure preparative liquid chromatography eluting the residue with n-hexane-ethyl acetate (10:1) to give 10.3 g of the target compound as a brown solid.
Melting point; 72° C. to 75° C.

Process 2: Production of (4-bromo-2-methoxy-6-methylphenyl)(furan-2-yl)methanol The mixed solution of 5 g of 5-bromo-2-iodo-1-methoxy-3-methylbenzene and 50 ml of tetrahydrofuran was cooled to −70° C. under a nitrogen atmosphere. To the mixed solution, 8.1 ml of an isopropylmagnesium chloride-lithium chloride complex (about 1 mol/L of a tetrahydrofuran solution, manufactured by Tokyo Chemical Industry Co., Ltd.) and then 4.6 ml of isopropyl magnesium chloride (about 1 mol/L of a tetrahydrofuran solution, manufactured by Tokyo Chemical Industry Co., Ltd.) were sequentially added and the resultant mixture was stirred for 30 minutes. Thereafter, the mixed solution of 2.2 g of furfural and 20 ml of tetrahydrofuran was added to the mixture. After completion of the addition, the temperature of the resultant reaction solution was raised to room temperature and the reaction solution was stirred at the same temperature for 15 hours. After completion of the reaction, 50 ml of saturated ammonium chloride aqueous solution was added to the reaction solution and the solvent was distilled away under reduced pressure until the amount of the solvent reached to a half amount. The obtained residue was extracted with 30 ml of ethyl acetate, dehydrated and dried with saturated sodium chloride aqueous solution and then anhydrous sodium sulfate in this order, followed by distilling away the solvent under reduced pressure. The obtained residue was purified with medium pressure preparative liquid chromatography eluting the residue with n-hexane-ethyl acetate (gradient from 20:1 to 10:1) to give 4.6 g of the target compound as a yellow oily product.
$^1$H NMR (CDCl$_3$, Me$_4$Si, 300 MHz) δ 7.38-7.34 (m, 1H), 7.00 (brs, 1H), 6.97 (brs, 1H), 6.37-6.20 (m, 1H), 6.03-5.92 (m, 2H), 3.83 (s, 3H), 4.21 (d, J=10.8 Hz, 1H), 2.31 (s, 3H).

Process 3: Production of 5-(4-bromo-2-methoxy-6-methylphenyl)-4-hydroxycyclopent-2-enone The mixed solution of 2.6 g of polyphosphoric acid, 10 ml of acetone, and 4 ml of water was added to the mixed solution of 4.6 g of (4-bromo-2-methoxy-6-methylphenyl)(furan-2-yl)methanol, 35 ml of acetone, and 10 ml of water and the resultant reaction mixture was stirred at 55° C. for 1 hour. After completion of the reaction, the solvent was distilled away under reduced pressure until the volume of the reaction mixture reached a half volume. To the obtained residue, 30 ml of water was added and the resultant mixture was extracted with 30 ml of ethyl acetate. The obtained organic phase was dehydrated and dried with saturated sodium chloride aqueous solution and then anhydrous sodium sulfate in this order and the solvent was distilled away under reduced pressure. The obtained residue was purified with medium pressure preparative liquid chromatography eluting the residue with n-hexane-ethyl acetate (gradient from 4:1 to 1:2) to give 3.1 g of the target compound as a brown oily product.

$^1$H NMR (CDCl$_3$, Me$_4$Si, 300 MHz) δ 7.52-7.46 (m, 1H), 7.02 (brs, 1H), 6.84 (brs, 1H), 6.36-6.28 (m, 1H), 5.09-5.01 (m, 1H), 3.86-3.52 (m, 5H), 2.36 (s, 3H).

Process 4: Production of 2-(4-bromo-2-methoxy-6-methylphenyl)cyclopent-4-ene-1,3-dione To the mixed solution of 1.6 g of chromium oxide (trivalent) and 8.6 ml of water, 1.1 ml of concentrated sulfuric acid was added under cooling with ice. The reaction solution was added to a separately prepared mixed solution of 3.1 g of 5-(4-bromo-2-methoxy-6-methylphenyl)-4-hydroxycyclopent-2-enone and 28 ml of acetone under cooling with ice and the resultant reaction solution was stirred for 25 minutes. After completion of the reaction, 30 ml of isopropyl alcohol was added to the reaction solution and the solvent was distilled away under reduced pressure. To the obtained residue, 30 ml of ethyl acetate was added and the resultant mixture was dehydrated and dried with saturated sodium chloride aqueous solution and then anhydrous sodium sulfate in this order, followed by distilling away the solvent under reduced pressure. The obtained solid was washed with diisopropyl ether to give 1.8 g of the target compound as a yellow solid.

Melting point; 104° C. to 107° C.

Process 5: Production of 2-(4-bromo-2-methoxy-6-methylphenyl)-3-hydroxy-5-(2-oxopropyl)cyclopent-2-enone To the mixed solution of 1.8 g of 2-(4-bromo-2-methoxy-6-methylphenyl)cyclopent-4-ene-1,3-dione and 30 ml of N,N-dimethylformamide, 1.7 g of potassium carbonate and 0.85 g of methyl acetoacetate were sequentially added, and the resultant reaction solution was stirred at room temperature for 15 hours. After completion of the reaction, 1 mol/L of a hydrochloric acid aqueous solution was added to the reaction solution to adjust the pH to 3 and the mixture was extracted with 30 ml of ethyl acetate. The obtained organic phase was dehydrated and dried with saturated sodium chloride aqueous solution and then anhydrous sodium sulfate in this order and the solvent was distilled away under reduced pressure. To the obtained residue, 20 ml of methanol and 5 ml of water were added, and 1 g of potassium hydroxide was further added to the resultant mixture, followed by stirring the obtained mixture at room temperature for 15 hours. After completion of the reaction, the solvent was distilled away under reduced pressure. To the obtained residue, 20 ml of 1 mol/L of a hydrochloric acid aqueous solution was added and the resultant mixture was extracted with 20 ml of ethyl acetate. The obtained organic phase was dehydrated and dried with saturated sodium chloride aqueous solution and then anhydrous sodium sulfate in this order and the solvent was distilled away under reduced pressure to give 1.8 g of the target compound as a brown viscous product.

$^1$H NMR (CDCl$_3$, Me$_4$Si, 300 MHz) δ 7.02 (brs, 1H), 6.88 (brs, 1H), 3.91-3.62 (m, 3H), 3.51-1.97 (m, 12H).

Synthesis Example 6: Production of 2-(4-bromo-2-methoxy-6-methylphenyl)-3-hydroxy-5-{2-(methoxyimino)propyl}cyclopent-2-enone (Compound No. 6-076)

This compound was produced from 2-(4-bromo-2-methoxy-6-methylphenyl)-3-hydroxy-5-(2-oxopropyl)cyclopent-2-enone by a similar method to the method in Synthesis Example 3.

Melting point; 150° C. to 153° C.

Synthesis Example 7: Production of 2-(4'-chloro-3-methoxy-5-methyl-[1,1'-biphenyl]-4-yl)-3-hydroxy-5-{2-(methoxyimino)prop yl}cyclopent-2-enone (Compound No. 6-077)

To the mixed solution of 1.1 g of 2-(4-bromo-2-methoxy-6-methylphenyl)-3-hydroxy-5-{2-(methoxyimino)propyl}cyclopent-2-enone, 540 mg of 4-chlorophenylboronic acid, 8 ml of 1,4-dioxane, and 2.5 ml of water, 2.2 g of tripotassium phosphate and 237 mg of [1,1'-bis(diphenylphosphino)ferrocene] palladium (II) dichloride dichloromethane adducts were sequentially added. After completion of the addition, the reaction container was purged with nitrogen gas and thereafter the resultant mixture was stirred at 100° C. for 2 hours. After completion of the reaction, 1 mol/L of a hydrochloric acid aqueous solution was added to the reaction mixture to adjust the pH to 3 and the obtained mixture was extracted with 10 ml of ethyl acetate. The obtained organic phase was dehydrated and dried with saturated sodium chloride aqueous solution and then anhydrous sodium sulfate in this order and thereafter the solvent was distilled away under reduced pressure. The obtained residue was purified with medium pressure preparative liquid chromatography eluting the residue with n-hexane-ethyl acetate (gradient from 8:1 to 1:1) to give 1.1 g of the target compound as an orange viscous product.

$^1$H NMR (CDCl$_3$, Me$_4$Si, 300 MHz) δ 11.36 (brs, 1H), 7.59-7.34 (m, 4H), 7.09-6.87 (m, 2H), 4.00-3.78 (m, 6H), 3.54-3.32 (m, 1H), 3.09-2.50 and 2.38-1.81 (m, 10H).

Synthesis Example 8: Production of 2-(4'-chloro-3-methoxy-5-methyl-[1,1'-biphenyl]-4-yl)-4-{2-(methoxyimino)propyl}-3-oxocyclopent-1-ene-1-yl morpholine-4-carboxylate (Compound No. 6-078)

To the mixed solution of 70 mg of 2-(4'-chloro-3-methoxy-5-methyl-[1,1'-biphenyl]-4-yl)-3-hydroxy-5-{2-(methoxyimino)prop yl}cyclopent-2-enone and 3 ml of N,N-dimethylformamide, 35 mg of potassium carbonate and then 31 mg of 4-morpholinylcarbonyl chloride were sequentially added, and the resultant reaction solution was stirred at room temperature for 3 hours. After completion of the reaction, 5 ml of water was added to the reaction solution and the resultant mixture was extracted with 5 ml of ethyl acetate. The obtained organic phase was dehydrated and dried with saturated sodium chloride aqueous solution and then anhydrous sodium sulfate in this order and thereafter the solvent was distilled away under reduced pressure. The obtained residue was purified with medium pressure preparative liquid chromatography eluting the residue with n-hexane-ethyl acetate (gradient from 3:1 to 1:1) to give 77 mg of the target compound as a colorless oily product.

$^1$H NMR (CDCl$_3$, Me$_4$Si, 300 MHz) δ 7.58-7.34 (m, 4H), 7.03 (s, 1H), 6.90-6.86 (m, 1H), 3.92-3.22 (m, 15H), 3.09-2.68 (m, 3H), 2.40-2.13 (m, 4H), 1.88 (s, 3H).

Synthesis Example 9: Production of 3-hydroxy-2-(2-methoxy-4,6-dimethylphenyl)-5-{2-(methoxyimino)propyl}cyclopent-2-enone (Compound No. 6-037)

To the mixed solution of 1 g of 2-(4-bromo-2-methoxy-6-methylphenyl)-3-hydroxy-5-{2-(methoxyimino)propyl}cyclopent-2-enone, 326 mg of trimethylboroxine, and 25 ml of 1,4-dioxane, 1.1 g of potassium carbonate and 424 mg of [1,1'-bis(diphenylphosphino)ferrocene] palladium (II) dichloride dichloromethane adduct were sequentially added. After completion of the addition, the reaction container was purged with nitrogen gas and thereafter the resultant reaction mixture was stirred at 90° C. for 3 hours. After completion of the reaction, 1 mol/L of a hydrochloric acid aqueous solution was added to the reaction mixture to adjust the pH to 3 and the obtained mixture was extracted with 25 ml of ethyl acetate. The obtained organic phase was dehydrated and dried with saturated sodium chloride aqueous solution and then anhydrous sodium sulfate in this order and thereafter the solvent was distilled away under reduced pressure. The obtained residue was purified with medium pressure preparative liquid chromatography eluting the residue with n-hexane-ethyl acetate (1:1) to give 496 mg of the target compound as an orange viscous product.

$^1$H NMR (CDCl$_3$, Me$_4$Si, 300 MHz) δ 11.00 (brs, 1H), 6.78-6.53 (m, 2H), 4.05-3.70 (m, 6H), 3.50-3.28 (m, 1H), 3.00-2.55 (m, 3H), 2.40-1.80 (m, 10H).

Synthesis Example 10: Production of mixture of 3-(benzyloxy)-2-mesityl-5-{2-(methoxyimino)propyl}cyclopent-2-enone and 3-(benzyloxy)-2-mesityl-4-{2-(methoxyimino)propyl}cyclopent-2-enone (Compound No. 1-009)

To the mixed solution of 500 mg of 3-hydroxy-2-mesityl-5-{2-(methoxyimino)propyl}cyclopent-2-enone and 6 ml of acetone, 458 mg of potassium carbonate and then 341 mg of benzyl bromide were sequentially added, and the resultant reaction solution was stirred at room temperature for 18 hours. After completion of the reaction, 20 ml of water was added to the reaction solution and the resultant mixture was extracted with 20 ml of ethyl acetate. The obtained organic phase was washed with water, dehydrated and dried with saturated sodium chloride aqueous solution and then anhydrous sodium sulfate in this order and thereafter the solvent was distilled away under reduced pressure. The obtained residue was purified with medium pressure preparative liquid chromatography eluting the residue with n-hexane-ethyl acetate (gradient from 5:1 to 1:1) to give 680 mg of the target compound as a colorless oily product.

$^1$H NMR (CDCl$_3$, Me$_4$Si, 300 MHz) δ 7.28-7.03 (m, 5H), 6.92-6.80 (m, 2H), 4.97-4.92 and 4.73-4.68 (m, 2H), 3.86-3.77 (m, 3H), 3.31-1.80 (m, 17H).

The obtained target compound was a mixture of 1-009a-1, 1-009a-2, 1-009b-1, and 1-009b-2 and the mixing ratio thereof was 16:3:8:1. The mixing ratio was determined by qualitative analysis with high performance liquid chromatography [mobile phase; {(acetonitrile:water=4:1)+acetic acid of a volume ratio of 1%}, measurement wavelength: 254 nm]. The structures of 1-009a-1, 1-009a-2, 1-009b-1 and 1-009b-2 are as follows.

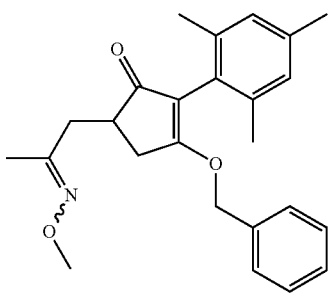

1-009a-1

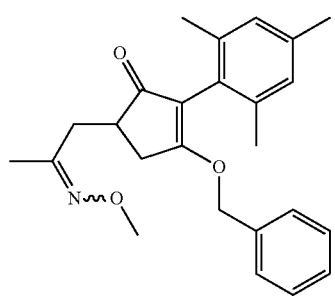

1-009a-2

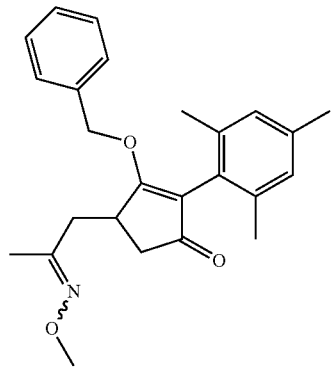

1-009b-1

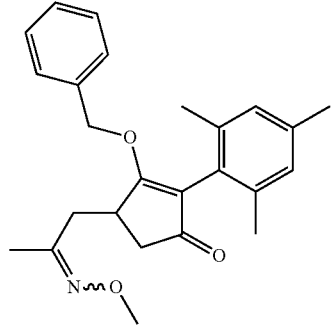

1-009b-2

Synthesis Example 11: Production of 3-(benzyloxy)-2-mesityl-5-{2-(methoxyimino)propyl}-5-methylcyclopent-2-enone (Compound No. 11-001) and 3-(benzyloxy)-2-mesityl-4-{2-(methoxyimino)propyl}-5-methylcyclopent-2-enone (Compound No. 12-001)

The mixed solution of the mixture of 611 mg of 3-(benzyloxy)-2-mesityl-5-{2-(methoxyimino)propyl}cyclopent-2-enone and 3-(benzyloxy)-2-mesityl-4-{2-(methoxyimino)propyl}cyclopent-2-enone (Compound No. 1-009) and 7 ml of tetrahydrofuran was cooled to −78° C. under a nitrogen atmosphere and thereafter 1.7 ml of lithium diisopropylamide (mixed solution of about 1.5 mol/L of n-hexane and tetrahydrofuran, manufactured by KANTO CHEMICAL CO., INC.) was added dropwise to the mixed solution. After completion of the dropwise addition, the reaction mixture was stirred at the same temperature for 30 minutes. After completion of the stirring, 244 mg of iodomethane was added to the reaction mixture. After completion of the addition, the reaction mixture was warmed to room temperature and stirred at the same temperature for 30 minutes. After completion of the reaction, the reaction mixture was added to 30 ml of ice water and the resultant mixture was extracted with 20 ml of ethyl acetate. The obtained organic phase was washed with water, dehydrated and dried with anhydrous sodium sulfate and thereafter the solvent was distilled away under reduced pressure. The obtained residue was purified by high performance liquid chromatography eluting the residue with acetonitrile-water [4:1 (volume ratio)] to give 173 mg of Compound No. 11-001 as a colorless oily product and 86 mg of Compound No. 12-001 as a colorless oily product.

Compound No. 11-001: $^1$H NMR (CDCl$_3$, Me$_4$Si, 300 MHz) δ 7.39-7.12 (m, 5H), 6.86 (brs, 2H), 4.96 (s, 2H), 3.81 (s, 3H), 3.27-3.13 (m, 1H), 2.61-2.22 (m, 6H), 2.06 (brs, 6H), 1.87-1.77 (m, 3H), 1.26 (s, 3H).

Compound No. 12-001: $^1$H NMR (CDCl$_3$, Me$_4$Si, 300 MHz) δ 7.37-7.25 (m, 3H), 7.14-7.04 (m, 2H), 6.86 (brs, 2H), 4.71 (s, 2H), 3.83 (s, 3H), 2.88-2.77 (m, 2H), 2.47-2.23 (m, 5H), 2.15-2.02 (m, 6H), 1.88 (s, 3H), 1.37-1.22 (m, 3H).

The synthesis examples of production intermediates for producing the compounds of the present invention will be specifically described as Reaction Example 1 and Reaction Example 2 below. The production intermediates of the present invention, however, are not limited to only these Reaction Examples.

Reaction Example 1: Production of 2-(2,6-dimethoxy-4-methylphenyl)cyclopent-4-ene-1,3-dione Process 1: Production of (2,6-dimethoxy-4-methylphenyl)(furan-2-yl)methanol The mixed solution of 0.69 g of furan and 10 ml of tetrahydrofuran was cooled to −10° C. under a nitrogen atmosphere. To the mixed solution, 6.9 ml of n-butyllithium (1.6 M of a tetrahydrofuran solution) was added, and the resultant reaction solution was stirred at the same temperature for 1 hour and 30 minutes. The mixed solution of 2.0 g of 2,6-dimethoxy-4-methylbenzaldehyde and 10 ml of tetrahydrofuran was added at −10° C. to the reaction solution and then the temperature of the resultant reaction solution was raised to room temperature, followed by stirring the resultant reaction solution for 12 hours. After completion of the reaction, the reaction solution was poured to ice water and the resultant mixture was extracted with 20 ml of ethyl acetate. The obtained organic phase was dehydrated and dried with saturated sodium chloride aqueous solution and then anhydrous sodium sulfate in this order and the solvent was distilled away under reduced pressure. The obtained residue was purified with medium pressure preparative liquid chromatography eluting the residue with n-hexane-ethyl acetate (3:1) to give 1.89 g of the target compound as a pale yellow solid.

Melting point; 75° C. to 85° C.

Process 2: Production of 2-(2,6-dimethoxy-4-methylphenyl)cyclopent-4-ene-1,3-dione The mixed solution of 100 mg of (2,6-dimethoxy-4-methylphenyl)(furan-2-yl)methanol and 1 ml of water was irradiated with microwaves (200 W) using the microwave synthesizing apparatus and the resultant reaction solution was stirred at 200° C. for 30 minutes. After completion of the reaction, the reaction solution was extracted with 3 ml of ethyl acetate. The obtained organic phase was dried with anhydrous sodium sulfate and the solvent was distilled away under reduced pressure. To the obtained residue, 5 ml of dichloromethane and 0.13 g of pyridinium chlorochromate were sequentially added and, after completion of the addition, the resultant reaction solution was stirred at room temperature for 2 hours. After completion of the reaction, 5 ml of isopropyl alcohol was added to the reaction solution and the solvent was distilled away under reduced pressure. To the obtained residue, 10 ml of water was added and the resultant mixture was extracted with 10 ml of ethyl acetate. The obtained organic phase was dehydrated and dried with saturated sodium chloride aqueous solution and then anhydrous sodium sulfate in this order and the solvent was distilled away under reduced pressure. The obtained residue was purified with medium pressure preparative liquid chromatography eluting the residue with n-hexane-ethyl acetate (2:1) to give 20 mg of the target compound as a yellow solid.

Melting point: 122° C. to 126° C.

Reaction Example 2: Production of 2-(2-methoxy-4,6-dimethylphenyl)cyclopent-4-ene-1,3-dione As a yellow solid 0.2 g of 2-(2-methoxy-4,6-dimethylphenyl)cyclopent-4-ene-1,3-dione was obtained by the similar method to Process 1 to Process 4 of Synthesis Example 5 using 10.0 g of 2-methoxy-4,6-dimethylaniline synthesized by the method described in J. Am. Chem. Soc. 2000, Vol. 122, P 5043 as a raw material.

Melting point; 123° C. to 125° C.

The compound of the present invention can be synthesized in accordance with the above production examples. Examples of the compounds of the present invention produced in a similar manner to Synthesis Examples 1 to 11 are listed in Table 5 to Table 20. The present invention, however, is not limited to these examples. In Tables, the expression of Me is methyl group. Similarly, the expression of Et is ethyl group, n-Pr and Pr-n are normal-propyl group, i-Pr and Pr-i are iso-propyl group, c-Pr and Pr-c are cyclopropyl group, n-Bu and Bu-n are normal-butyl group, s-Bu and Bu-s are secondary-butyl group, i-Bu and Bu-i are iso-butyl group, t-Bu and Bu-t are tertiary-butyl group, c-Bu and Bu-c are cyclobutyl group, n-Pen and Pen-n are normal-pentyl group, c-Pen and Pen-c are cyclopentyl group, n-Hex and Hex-n are normal-hexyl group, c-Hex and Hex-c are cyclohexyl group, Hept is heptyl group, Oct is octyl group, and Ph is phenyl group. The structures of D1-1a, D1-2c, D1-5d, D1-5e, D1-6d, D1-7a, D1-7b, D1-8b, D1-10d, D1-11a, D1-22a, D1-32a, D1-32b, D1-33b, D1-34a, D1-37a, D1-81a, D1-84a, D1-103a, D1-103b, D1-103c, D1-103d, D1-103e, D1-103f, D1-103g, D1-103h, D1-103i, D1-103j, D1-103k, D1-103l, D1-103m, D1-103n, D1-108b, D1-108c, D1-108d, and D1-108e are the following structures. The numbers shown in the structural formulas of D1-5d, D1-5e, D1-6d, D1-7b, D1-10d, D1-32b, and D1-33b are the substitution positions of $X^1$. The numbers shown in the structural formula of D1-108b are the substitution positions of $Z^3$. The numbers shown in the structural formula of D1-108c are the substitution positions of $Z^1$. The numbers shown in the structural formula of D1-108d are the substitution positions of $Z^2$.

In Tables, the expression of "m. p." means a "melting point", the expression of "*1" means "resinous", and the expression of "decomp." means decomposition.

D1-1a

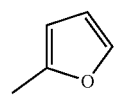

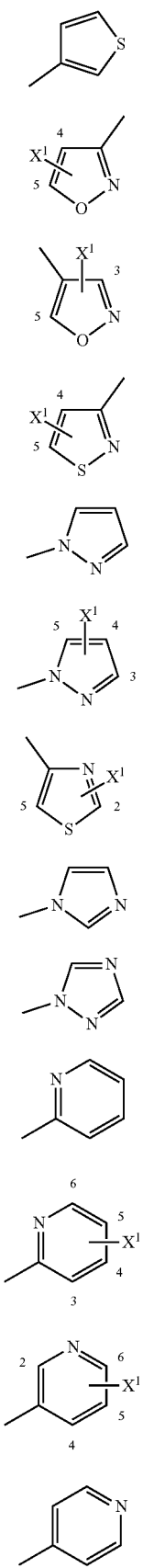
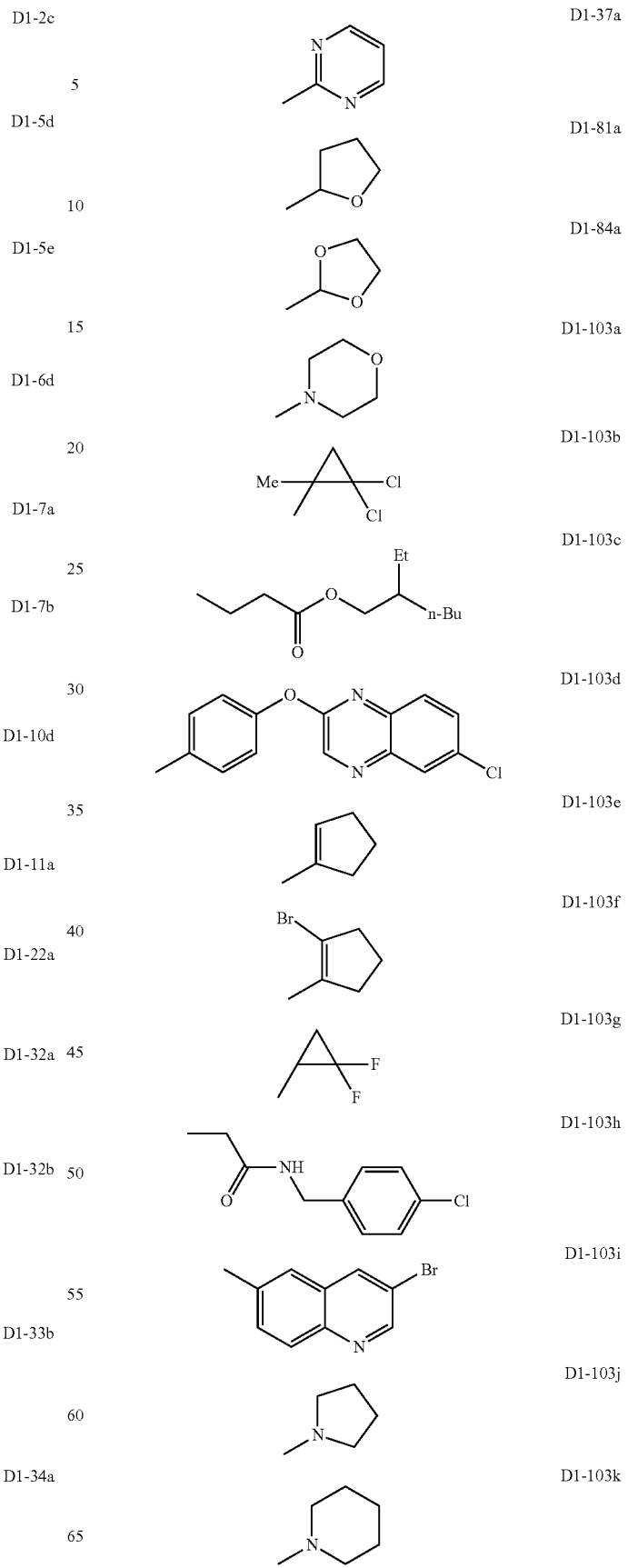

-continued

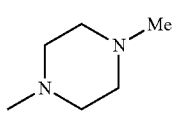 D1-103l

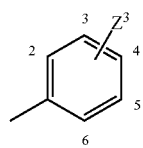 D1-108b

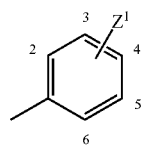 D1-108c

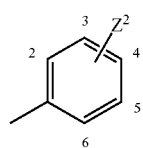 D1-108d

-continued

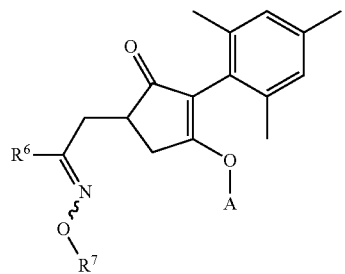

TABLE 5

| No. | $R^6$ | $R^7$ | A | m.p. (° C.) |
|---|---|---|---|---|
| 1-001 | Me | Me | Me | 92-98 |
| 1-002 | Me | Me | H | 170-173 |
| 1-003 | Me | Et | H | 135-140 |
| 1-004 | Me | Me | C(O)Bu-t | *1 |
| 1-005 | Me | Me | C(O)Me | *1 |
| 1-006 | Me | Me | S(O)$_2$Me | *1 |
| 1-007 | Me | Me | CH$_2$CH=CH$_2$ | *1 |
| 1-008 | Me | Me | CH$_2$C≡CH | *1 |
| 1-009 | Me | Me | CH$_2$Ph | *1 |
| 1-010 | Me | Me | C(O)Ph | *1 |
| 1-011 | Me | Me | CH$_2$CH$_2$SMe | *1 |
| 1-012 | Me | Me | CH$_2$C(O)OMe | *1 |
| 1-013 | Me | Me | CH$_2$CN | *1 |
| 1-014 | Me | Me | C(O)OMe | *1 |
| 1-015 | Me | Me | C(O)Pr-c | *1 |
| 1-016 | Me | Me | C(O)C(Me)$_2$CH$_2$Cl | *1 |
| 1-017 | Me | Me | C(O)C(Me)$_2$OPh | *1 |
| 1-018 | Me | CH$_2$CH=CH$_2$ | H | 119-120 |
| 1-019 | Me | CH$_2$C≡CH | H | 113-114 |
| 1-020 | Me | CH$_2$Ph | H | 190-192 |
| 1-022 | Me | CH$_2$(D1-32a) | H | 118-120 |
| 1-023 | Me | CH$_2$C(O)OMe | H | 100-102 |
| 1-024 | Me | CH$_2$Pr-c | H | 138-140 |
| 1-025 | Me | CH$_2$C(O)(D1-103a) | H | 152-156 |
| 1-026 | Me | CH$_2${D1-108c(2-F)} | H | 198-200 |
| 1-027 | Me | CH$_2$CH(OH)Me | H | 143-144 |
| 1-028 | Me | CH$_2$CF$_3$ | H | 172-174 |
| 1-029 | Me | CH$_2$CH$_2$SMe | H | 94-102 |
| 1-031 | Me | Me | CH$_2$C≡CSi(Me)$_3$ | *1 |
| 1-033 | Me | Me | C(O)Oct-n | *1 |

TABLE 5-continued

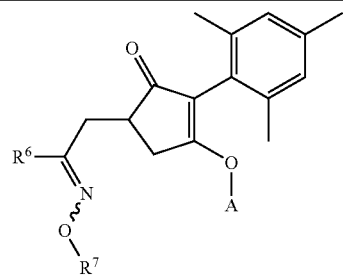

| No. | $R^6$ | $R^7$ | A | m.p. (° C.) |
|---|---|---|---|---|
| 1-034 | Me | Me | C(O)C(Me)$_2$OC(O)Me | *1 |
| 1-035 | Me | Me | C(O)CH$_2$CH$_2$Hex-c | *1 |
| 1-036 | Me | Me | C(O)(D1-103b) | *1 |
| 1-037 | Me | Me | CH$_2$CH$_2$OMe | *1 |
| 1-038 | Et | Me | H | 147-149 |
| 1-039 | Me | Me | C(O)C(Me)$_2$F | *1 |
| 1-040 | CH$_2$OMe | Me | H | 150-153 |
| 1-041 | Me | CH$_2$CH$_2$OMe | H | 129-132 |
| 1-042 | Me | Me | C(O)CH(Me)Cl | *1 |
| 1-043 | Me | Me | C(O)CH$_2$OPh | *1 |
| 1-044 | Me | Me | C(O)CH$_2$O{D1-108d(4-Cl)} | *1 |
| 1-045 | D1-32a | Me | H | *1 |
| 1-046 | c-Pr | Me | H | *1 |
| 1-047 | Ph | Me | H | *1 |
| 1-048 | i-Pr | Me | H | *1 |
| 1-050 | H | Me | H | 96-108 |
| 1-051 | Me | Me | C(O)C(Me)$_2$O{D1-108d(4-Cl)} | *1 |
| 1-052 | Me | i-Pr | H | 93-95 |
| 1-053 | Me | t-Bu | H | 145-147 |
| 1-054 | Me | n-Hept | H | 136-137 |
| 1-055 | Me | CH$_2$CH$_2$Si(Me)$_3$ | H | 133-135 |
| 1-056 | Me | CH$_2$CH=CHCl | H | 100-102 |
| 1-057 | Me | Ph | H | 149-151 |
| 1-058 | Me | H | H | 95-98 |
| 1-059 | t-Bu | Me | H | 163-164 |
| 1-060 | Me | Me | C(O)CH(Me)OPh | *1 |
| 1-062 | n-Pr | Me | H | 134-137 |
| 1-063 | c-Pr | Me | C(O)CH$_2$OPh | *1 |
| 1-064 | Me | Me | C(O)C(Me)$_2$O{D1-108d(2-Cl)} | *1 |
| 1-065 | Me | Me | C(O)C(Me)$_2$O{D1-108d(3-Cl)} | *1 |
| 1-066 | s-Bu | Me | H | 154-156 |
| 1-067 | Me | Me | C(O)CH$_2$O{D1-108d(2-OMe)} | *1 |
| 1-068 | Me | Me | C(O)CH$_2$O{D1-108d(3-OMe)} | *1 |
| 1-069 | Me | Me | C(O)CH$_2$O{D1-108d(4-OMe)} | *1 |
| 1-070 | CH$_2$Pr-c | Me | H | 153-155 |
| 1-071 | Me | Me | C(O)CH$_2$O{D1-108d(2-NO$_2$)} | *1 |
| 1-072 | Me | Me | C(O)CH$_2$O{D1-108d(4-Me)} | *1 |
| 1-073 | Me | Me | C(O)CH$_2$O{D1-108d(4-F)} | *1 |
| 1-074 | Me | Me | C(O)CH$_2$O{D1-108d(3-CN)} | *1 |
| 1-075 | Me | Me | C(O)CH$_2$O{D1-108d[2,4-(Cl)$_2$]} | *1 |
| 1-076 | Me | Me | C(O)(D1-81a) | *1 |
| 1-077 | CH$_2$Cl | Me | Me | *1 |
| 1-078 | c-Pen | Me | H | 161-163 |
| 1-079 | Me | Me | C(O)CH$_2$O{D1-108d(4-CHO)} | *1 |
| 1-080 | Me | Me | C(O)CH$_2$O{D1-108d[4-C(O)Me]} | *1 |
| 1-081 | Me | Me | C(O)CH$_2$O{D1-108d(4-Br)} | *1 |
| 1-082 | Me | Me | C(O)CH$_2$O{D1-108d(4-I)} | *1 |
| 1-083 | Me | Me | C(O)CH$_2$O(D1-108e) | *1 |
| 1-084 | CH$_2$Cl | Me | H | 159-161 |
| 1-085 | c-Hex | Me | H | 149-152 |
| 1-086 | CH=CH$_2$ | Me | H | 115-117 |
| 1-087 | Me | Me | C(O)CH(Me)O(D1-103d) | *1 |
| 1-088 | Me | Me | C(O)(D1-103e) | *1 |
| 1-089 | Me | Me | C(O)(D1-103f) | *1 |
| 1-090 | Me | Me | C(O)CH=CHPr-n | *1 |
| 1-091 | Me | Me | C(O)CH=CH(D1-1a) | *1 |
| 1-092 | Me | Me | C(O)CH$_2$OCH$_2$CF$_3$ | *1 |
| 1-093 | Me | Me | C(O)CH$_2$OMe | *1 |
| 1-094 | Me | Me | C(O)CH$_2$OCH$_2$Ph | *1 |
| 1-095 | Me | Me | C(O)C≡CMe | *1 |
| 1-096 | Me | Me | C(O)C≡CSi(Me)$_3$ | *1 |
| 1-097 | CF$_3$ | Me | H | 115-118 |
| 1-098 | Me | Me | C(O)C(=NOMe)CH$_2$SMe | *1 |
| 1-099 | Me | Me | C(O){D1-6d(4,5-Cl$_2$)} | *1 |

TABLE 5-continued

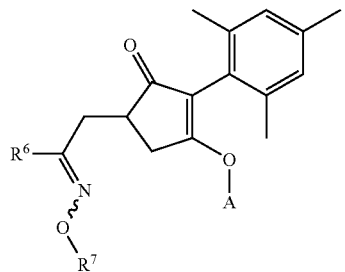

| No. | $R^6$ | $R^7$ | A | m.p. (° C.) |
|---|---|---|---|---|
| 1-100 | Me | Me | C(O){D1-5d(5-Me)} | *1 |
| 1-101 | Me | Me | C(O){D1-10d(2,5-Me$_2$)} | *1 |
| 1-102 | Me | CH$_2$CN | H | 163-166 |
| 1-103 | Me | Me | C(O){D1-5e(5-Pr-c)} | *1 |
| 1-104 | Me | Me | C(O)(D1-103a) | *1 |
| 1-105 | Me | CH$_2$C(=NOMe)Me | H | 118-122 |
| 1-106 | Me | c-Pen | H | 120-122 |
| 1-107 | Me | Me | S(O)$_2$C$_8$H$_{17}$ | *1 |
| 1-108 | Me | Me | C(O)N(Me)$_2$ | *1 |
| 1-109 | Me | CH$_2$(D1-103g) | H | 155-158 |
| 1-110 | Me | CH$_2$CH$_2$S(O)$_2$Me | H | 130-132 |
| 1-111 | Me | CH$_2$(D1-84a) | H | 150-153 |
| 1-112 | Me | CH$_2${D1-108c(4-OMe)} | H | 179-180 |
| 1-113 | Me | CH$_2${D1-108c(2-Cl)} | H | 194-197 |
| 1-114 | Me | CH$_2${D1-108c(3-Cl)} | H | 188-193 |
| 1-115 | Me | CH$_2${D1-108c(2-Cl,6-F)} | H | 225-228 |
| 1-116 | Me | CH$_2${D1-108c(2-CF$_3$)} | H | 147-154 |
| 1-117 | Me | CH$_2${D1-108c(3-CF$_3$)} | H | 143-154 |
| 1-118 | Me | CH$_2${D1-108c[4-C(O)OMe]} | H | 183-189 |
| 1-119 | Me | CH$_2${D1-108c(2-NO$_2$)} | H | 177-179 |
| 1-120 | Me | D1-103h | H | 162-166 |
| 1-121 | Me | CH$_2$CH(Cl)Me | H | 182-185 |
| 1-122 | Me | Me | SO$_2$N(Me)$_2$ | *1 |
| 1-123 | Me | n-Pr | H | 123-126 |
| 1-124 | Me | CH$_2$C(O)NH$_2$ | H | 120-123 |
| 1-125 | Me | CH$_2$CH$_2$S(O)Me | H | *1 |
| 1-126 | Me | Me | C(O)N(Me)(CH$_2$)$_4$Cl | *1 |
| 1-127 | Me | Me | C(O)N(i-Pr)Ph | *1 |
| 1-128 | Me | Me | C(O)N(i-Pr){D1-108d(4-F)} | *1 |
| 1-129 | Me | Me | C(O)N(i-Pr){D1-108d(2,4-F$_2$)} | *1 |
| 1-130 | Me | Me | C(O)N(Et)CH$_2$C(Me)=CH$_2$ | *1 |
| 1-131 | c-Pr | CH$_2$CF$_3$ | H | 137-138 |
| 1-132 | Me | CH$_2$CH$_2$NH$_2$ | H | 209 (decomp.) |
| 1-133 | D1-108c(4-F) | Me | H | 181-183 |
| 1-134 | Me | Me | C(O)CH$_2$SPh | *1 |
| 1-135 | Me | CH$_2$CH(Br)Me | H | 179-181 |
| 1-136 | Me | CH$_2${D1-108c(4-F)} | H | 171-180 |
| 1-137 | Me | CH$_2${D1-108c(4-Cl)} | H | 135-150 |
| 1-138 | Me | CH$_2${D1-108c(4-CF$_3$)} | H | 168-173 |
| 1-139 | Me | Me | C(O)CH$_2$N(Me)C(O)Ph | *1 |
| 1-140 | Me | Me | C(O)CH(Et)O(D1-103i) | *1 |
| 1-141 | Me | Me | C(S)N(Me)$_2$ | *1 |
| 1-142 | Me | Me | SO$_2$(CH$_2$)$_3$Cl | *1 |
| 1-143 | Me | Me | SO$_2$Pr-c | *1 |
| 1-144 | Me | Me | SO$_2$(CH$_2$)$_2$Si(Me)$_3$ | *1 |
| 1-145 | Me | Me | C(O)OCH$_2$Ph | *1 |
| 1-146 | Me | Me | C(O)OCH$_2$CH=CH$_2$ | *1 |
| 1-147 | Me | Me | C(O)O(CH$_2$)$_2$OMe | *1 |
| 1-148 | Me | Me | C(O)C(Me)$_2${D1-108d(4-Cl)} | *1 |
| 1-149 | Me | Me | C(O){D1-108d(4-CF$_3$)} | *1 |
| 1-150 | Me | Me | C(O)(D1-103j) | *1 |
| 1-151 | Me | Me | C(O)(D1-103k) | *1 |
| 1-152 | Me | Me | C(O)(D1-103l) | *1 |
| 1-153 | Me | Me | C(O)N(CH$_2$CH=CH$_2$)$_2$ | *1 |
| 1-154 | Me | Me | C(O){D1-108d(2-CF$_3$)} | 90-92 |
| 1-155 | Me | Me | C(O){D1-108d(2-OCF$_3$)} | *1 |
| 1-156 | Me | Me | C(O)CH$_2${D1-108d(4-OMe)} | *1 |
| 1-157 | Me | Me | C(O)N(Ph)$_2$ | 165-168 |
| 1-158 | Me | Me | C(O)N(i-Pr)$_2$ | 74-75 |
| 1-159 | Me | Me | C(O)N(Me)Ph | *1 |
| 1-160 | Me | Me | C(O)(D1-8b) | *1 |
| 1-161 | Me | Me | SO$_2${D1-108d(4-Me)} | *1 |
| 1-162 | Me | Me | C(O){D1-108d[2-Cl,3-C(O)OMe,4-SO$_2$Me]} | *1 |
| 1-163 | Me | Me | C(O)CH(Me)O(D1-103m) | *1 |

TABLE 5-continued

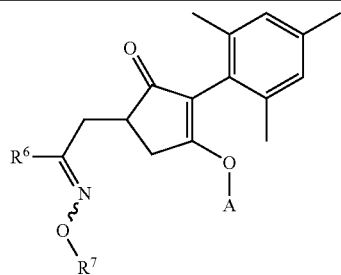

| No. | R⁶ | R⁷ | A | m.p. (° C.) |
|---|---|---|---|---|
| 1-164 | D1-108c(4-Me) | Me | H | *1 |
| 1-165 | Me | Me | c-Pen | *1 |
| 1-166 | Me | Me | CH₂C(Cl)=CHCl | *1 |

Compound No. 1-009 of the present invention is the mixture of Compound Nos. 1-009a-1, 1-009a-2, 1-009b-1, and 1-009b-2 in Synthesis Example 10 described above.

Compound Nos. 1-009a-1 and 1-009a-2 and Compound Nos. 1-009b-1 and 1-009b-2 are respective geometric isomers of the oxime moiety.

TABLE 6

| No. | R⁶ | R⁷ | R⁸ᵃ | R⁹ᵃ | A | m.p. (° C.) |
|---|---|---|---|---|---|---|
| 1-021 | Me | Me | C(=NOMe)Me | H | H | 163-164 |
| 1-030 | H | Me | Me | Me | H | 176-180 |
| 1-032 | Me | Me | Me | H | H | 199-206 |
| 1-049 | Me | Me | D1-108c(4-F) | H | H | 160-168 |
| 1-061 | Me | Me | CF₃ | H | H | 155-158 |

TABLE 7

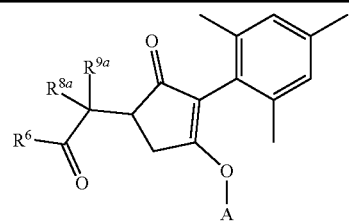

| No. | R⁶ | R⁸ᵃ | R⁹ᵃ | A | m.p. (° C.) |
|---|---|---|---|---|---|
| 2-001 | Me | H | H | H | 183-185 |
| 2-002 | Me | C(O)Me | H | H | 190-193 |
| 2-003 | Me | C(O)OMe | H | H | 155-158 |
| 2-004 | Me | C(O)OEt | Me | H | 154-163 |
| 2-005 | Me | Me | H | H | 153-158 |
| 2-006 | Et | H | H | H | 197-198 |
| 2-007 | CH₂OMe | H | H | H | 143-145 |
| 2-008 | Ph | C(O)OEt | H | H | *1 |
| 2-009 | i-Pr | C(O)OEt | H | H | 150-153 |

TABLE 7-continued

| No. | R⁶ | R⁸ᵃ | R⁹ᵃ | A | m.p. (° C.) |
|---|---|---|---|---|---|
| 2-010 | CF₃ | C(O)OEt | H | H | *1 |
| 2-011 | CH₂Ph | C(O)OEt | H | H | 110-114 |
| 2-012 | Me | C(O)OEt | Et | H | 140-144 |
| 2-013 | D1-32a | C(O)OEt | H | H | 79-88 |
| 2-014 | c-Pr | C(O)OMe | H | H | 204-206 |
| 2-015 | CH₂Ph | H | H | H | *1 |
| 2-016 | i-Pr | H | H | H | 139-144 |
| 2-017 | c-Pr | H | H | H | 191-192 |
| 2-018 | Me | H | H | C(O)Bu-t | *1 |
| 2-019 | t-Bu | C(O)OMe | H | H | 192-194 |
| 2-020 | n-Pr | C(O)OMe | H | H | 164-167 |
| 2-021 | n-Pr | H | H | H | 190-193 |
| 2-022 | t-Bu | H | H | H | 50-54 |
| 2-023 | Me | C(O)OMe | Et | H | 160-163 |
| 2-024 | s-Bu | H | H | H | 112-115 |
| 2-025 | CH₂Pr-c | C(O)OEt | H | H | 132-134 |
| 2-026 | CH₂Pr-c | H | H | H | 195-197 |
| 2-027 | c-Pen | C(O)OEt | H | H | 168-170 |
| 2-028 | c-Pen | H | H | H | 147-149 |
| 2-029 | c-Hex | C(O)OEt | H | H | 154-157 |
| 2-030 | c-Hex | H | H | H | 167-169 |
| 2-031 | CH=CH2 | H | H | H | 123-126 |
| 2-032 | D1-108c(4-F) | H | H | H | 194-196 |

TABLE 8

| No. | R⁶ | R⁷ | A | m.p. (° C.) |
|---|---|---|---|---|
| 3-001 | H | Me | H | *1 |
| 3-002 | Me | Me | H | *1 |

TABLE 9

| No. | R⁶ | R⁷ | R⁸ᵃ | R⁸ᵇ | R⁹ᵃ | R⁹ᵇ | A | m.p. (° C.) |
|---|---|---|---|---|---|---|---|---|
| 4-001 | Et | Me | H | H | H | H | H | *1 |

TABLE 10

| No. | R⁶ | R⁸ᵃ | R⁸ᵇ | R⁹ᵃ | R⁹ᵇ | A | m.p. (° C.) |
|---|---|---|---|---|---|---|---|
| 5-001 | Et | H | H | H | H | H | *1 |
| 5-002 | Et | H | H | H | H | Me | *1 |

TABLE 11

| No. | Zᵃ | Zᶜ | Zᵉ | R⁸ᵃ | A | m.p. (° C.) |
|---|---|---|---|---|---|---|
| 6-001 | Et | Br | Me | H | H | 151-153 |
| 6-002 | Et | Br | Me | C(O)OMe | H | 184-188 |
| 6-003 | Me | Br | Me | H | H | 164-166 |
| 6-004 | Me | D1-7b(X¹=4-Cl) | Me | H | H | *1 |
| 6-005 | Et | D1-7b(X¹=4-Cl) | Me | H | H | *1 |
| 6-006 | Et | C≡CMe | Me | H | H | *1 |
| 6-007 | Et | Me | Me | H | H | 122-125 |
| 6-008 | Et | C≡CSi(Me)₃ | Me | H | H | *1 |
| 6-009 | Me | C≡CMe | Me | H | H | 60-65 |
| 6-010 | Me | C≡CPr-c | Me | H | H | *1 |
| 6-011 | Me | Br | Me | H | Me | *1 |
| 6-012 | Me | Ph | Me | H | Me | *1 |
| 6-013 | Me | D1-108b(4-Me) | Me | H | Me | *1 |
| 6-014 | Me | D1-108b(4-CF₃) | Me | H | Me | *1 |
| 6-015 | Me | Ph | Me | H | H | 167-169 |
| 6-016 | Me | D1-108b(4-CF₃) | Me | H | H | 163-164 |
| 6-017 | Me | D1-108b(4-OMe) | Me | H | H | 155-157 |
| 6-018 | Me | D1-108b(4-Me) | Me | H | H | 137-139 |
| 6-019 | Me | D1-108b(4-Cl) | Me | H | Me | *1 |
| 6-020 | Me | D1-108b(4-OMe) | Me | H | Me | 124-125 |
| 6-021 | Me | D1-108b(4-SMe) | Me | H | Me | 65-66 |
| 6-022 | Me | S(D1-103c) | Me | H | H | *1 |
| 6-023 | Me | C(O)OMe | Me | H | H | *1 |
| 6-024 | Me | SMe | Me | H | H | *1 |
| 6-025 | Me | C≡CCH₂OH | Me | H | H | *1 |
| 6-026 | Me | C(O)Me | Me | H | H | *1 |
| 6-027 | Me | CN | Me | H | H | 181-184 |
| 6-028 | Me | D1-32a | Me | H | Me | 151-154 |
| 6-029 | Me | D1-108b(4-Cl) | Me | H | H | 145-150 |
| 6-030 | Me | D1-108b(4-SMe) | Me | H | H | 167-169 |
| 6-031 | Me | CH=CH₂ | Me | H | H | 166-172 |
| 6-032 | Me | NO₂ | Me | H | H | 181-183 |
| 6-033 | Me | NHC(O)OBu-t | Me | H | H | *1 |
| 6-034 | Me | D1-108b(3-Cl) | Me | H | H | 197-199 |
| 6-035 | Me | D1-33b(6-Cl) | Me | H | H | *1 |
| 6-036 | Me | C≡CC(Me)₂OH | Me | H | H | *1 |
| 6-037 | OMe | Me | Me | H | H | *1 |
| 6-038 | Br | Me | Me | H | H | *1 |
| 6-039 | Me | c-Pr | Me | H | Me | *1 |
| 6-040 | Me | D1-7a | Me | H | Me | 129-132 |
| 6-041 | Me | OPh | Me | H | Me | *1 |
| 6-042 | Me | OCH₂CF₃ | Me | H | Me | 117-119 |
| 6-043 | Me | D1-108b(4-OCF₃) | Me | H | Me | *1 |
| 6-044 | Me | D1-37a | Me | H | Me | 166-169 |

TABLE 11-continued

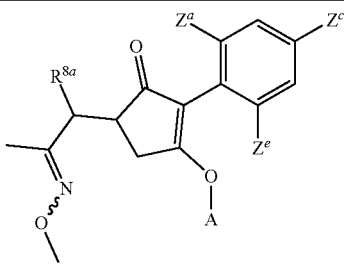

| No. | $Z^a$ | $Z^c$ | $Z^e$ | $R^{8a}$ | A | m.p. (° C.) |
|---|---|---|---|---|---|---|
| 6-045 | Me | OCH₂Ph | Me | H | Me | *1 |
| 6-046 | Me | OCH₂(D1-34a) | Me | H | Me | *1 |
| 6-047 | Me | O{D1-32b(5-CF₃)} | Me | H | Me | *1 |
| 6-048 | Me | OMe | Me | H | Me | 82-85 |
| 6-049 | Me | OCH₂CF₃ | Me | H | H | 165-172 |
| 6-050 | Me | c-Pr | Me | H | H | 170-178 |
| 6-051 | Me | D1-32a | Me | H | H | *1 |
| 6-052 | Me | OPh | Me | H | H | *1 |
| 6-053 | Me | OCH₂(D1-34a) | Me | H | H | 118-122 |
| 6-054 | Me | O{D1-32b(5-CF₃)} | Me | H | H | 169-172 |
| 6-055 | Me | OMe | Me | H | H | 141-143 |
| 6-056 | Me | D1-108b(4-OCF₃) | Me | H | H | 161-163 |
| 6-057 | Me | D1-37a | Me | H | H | 183-188 |
| 6-058 | Me | D1-108b(4-F) | Me | H | H | 159-161 |
| 6-059 | Me | D1-108b(4-F) | Me | H | C(O)(D1-103a) | *1 |
| 6-060 | Me | D1-108b(4-F) | Me | H | S(O)₂N(Me)₂ | *1 |
| 6-061 | Me | D1-108b(4-Cl) | Me | H | C(O)CH₂OPh | *1 |
| 6-062 | Me | D1-108b(4-Cl) | Me | H | C(O)(D1-103a) | *1 |
| 6-063 | Me | D1-108b(4-Cl) | Me | H | C(O)N(Me)₂ | *1 |
| 6-064 | Et | D1-108b(4-Cl) | Me | H | C(O)(D1-103a) | *1 |
| 6-065 | Me | C(=NOMe)Me | Me | H | H | 177-180 |
| 6-066 | Et | D1-108b(4-Cl) | Me | H | H | 165-167 |
| 6-067 | Me | CH=CHPr-n | Me | H | Me | *1 |
| 6-068 | Me | CH=CHPh | Me | H | Me | 125-126 |
| 6-069 | Me | OH | Me | H | Me | 192-195 |
| 6-070 | Me | OCH₂(D1-34a) | Me | H | H | *1 |
| 6-071 | Me | CH=CHPr-n | Me | H | H | 171-177 |
| 6-072 | Me | CH=CHPh | Me | H | H | 150-152 |
| 6-073 | Me | D1-7a | Me | H | H | 200-203 |
| 6-074 | Me | D1-22a | Me | H | H | 164-167 |
| 6-075 | SMe | Me | Me | H | H | *1 |
| 6-076 | OMe | Br | Me | H | H | 150-153 |
| 6-077 | OMe | D1-108b(4-Cl) | Me | H | H | *1 |
| 6-078 | OMe | D1-108b(4-Cl) | Me | H | C(O)(D1-103a) | *1 |
| 6-079 | OMe | D1-108b(4-Cl) | Me | H | C(O)CH₂OPh | *1 |
| 6-080 | Me | D1-108b(4-Cl) | Me | H | C(O)CH₂CH₂CH₂C(O)Me | *1 |
| 6-081 | OMe | D1-108b(4-Cl) | Me | H | C(O)N(Me)₂ | *1 |
| 6-082 | Me | D1-108b(4-Cl) | Me | H | C(O)SBu-t | *1 |
| 6-083 | Me | D1-108b(4-Cl) | Me | H | CH₂OC(O)Ph | *1 |
| 6-084 | Me | D1-108b(2-F, 4-Cl) | Me | H | H | 175-177 |
| 6-085 | Me | D1-108b(3-Cl,4-F) | Me | H | H | 187-190 |
| 6-086 | Me | D1-108b(4-Cl) | Me | H | C(O)CH(Me)CH₂SMe | *1 |
| 6-087 | Me | D1-108b(3,5-Cl₂) | Me | H | H | 205-215 |
| 6-088 | Me | D1-108b(2,4-Cl₂) | Me | H | H | 148-151 |
| 6-089 | Me | D1-108b(2-F, 4-Cl) | Me | H | C(O)(D1-103a) | *1 |
| 6-090 | Me | D1-108b(2,4-Cl₂) | Me | H | C(O)(D1-103a) | *1 |
| 6-091 | OMe | Me | Me | H | C(O)CH₂OPh | *1 |
| 6-092 | Me | D1-108b(2,4-Cl₂) | Me | H | C(O)CH₂OPh | *1 |
| 6-093 | Me | D1-108b(3-Cl, 4-F) | Me | H | C(O)(D1-103a) | *1 |
| 6-094 | OMe | Me | Me | H | C(O)(D1-103a) | *1 |
| 6-095 | OMe | Me | Me | H | S(O)₂N(Me)₂ | *1 |
| 6-096 | OMe | Br | F | H | H | 157-159 |
| 6-097 | Me | OCH₂CH₂O | Me | H | Me | *1 |
| 6-098 | Me | OCH₂CH₂O | Me | H | H | 119-121 |
| 6-099 | OMe | Ph | Me | H | H | 175-177 |
| 6-100 | OMe | Ph | Me | H | C(O)CH₂OPh | *1 |
| 6-101 | Me | D1-11a | Me | H | Me | *1 |
| 6-102 | Me | D1-22a | Me | H | Me | 103-104 |
| 6-103 | OMe | Me | OMe | H | H | 171-175 |
| 6-104 | Me | D1-108b(3,4,5-F3) | Me | H | H | 161-163 |
| 6-105 | Me | D1-34a | Me | H | H | *1 |
| 6-106 | Me | D1-2c | Me | H | H | 204-207 |
| 6-107 | OMe | Ph | F | H | H | 175-177 |
| 6-108 | OMe | Me | F | H | H | *1 |
| 6-109 | OMe | Me | Me | H | C(O)N(Me)₂ | *1 |

TABLE 11-continued

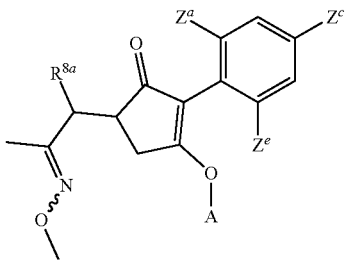

| No. | $Z^a$ | $Z^c$ | $Z^e$ | $R^{8a}$ | A | m.p. (° C.) |
|---|---|---|---|---|---|---|
| 6-110 | OMe | Me | Me | H | C(O)(D1-103j) | *1 |
| 6-111 | OMe | Me | Me | H | C(O)(D1-103k) | *1 |
| 6-112 | Me | H | Me | H | H | 167-170 |
| 6-113 | OMe | Br | Me | Me | H | *1 |
| 6-114 | OMe | Me | Me | Me | H | *1 |
| 6-115 | OMe | Me | Me | H | C(O)N(Et)$_2$ | *1 |
| R-116 | OMe | Me | Me | H | C(S)N(Et)$_2$ | *1 |
| 6-117 | OMe | Me | Me | H | C(O)Bu-t | *1 |
| 6-118 | OMe | Me | Me | H | C(O){D1-108d[4-C(O)N(Me)$_2$]} | *1 |
| 6-119 | OMe | Me | Me | H | C(S)OPh | *1 |
| 6-120 | OMe | Me | Me | H | C(O)CH=CH$_2$ | *1 |
| 6-121 | OMe | Me | Me | H | C(O)Ph | *1 |
| 6-122 | OMe | Me | Me | H | C(O)CH$_2$OC(O)Me | *1 |
| 6-123 | OMe | Me | Me | Me | C(O)Bu-t | *1 |
| 6-124 | OMe | Me | Me | H | C(O)SBu-t | *1 |
| 6-125 | OMe | Me | Me | H | C(S)N(Me)$_2$ | *1 |
| 6-126 | OMe | Me | Me | H | C(O)CH$_2$CH$_2$CH$_2$Cl | *1 |
| 6-127 | OMe | Me | Me | Me | C(O)(D1-103a) | *1 |

TABLE 12

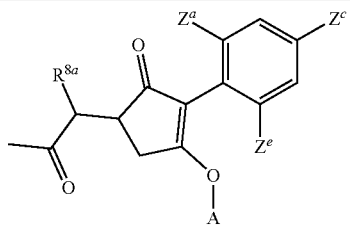

| No. | $Z^a$ | $Z^c$ | $Z^e$ | $R^{8a}$ | A | m.p. (° C.) |
|---|---|---|---|---|---|---|
| 7-001 | Et | Br | Me | C(O)OMe | H | *1 |
| 7-002 | Me | Br | Me | H | H | 203-204 |
| 7-003 | Et | Br | Me | H | H | 170-172 |
| 7-004 | Me | Ph | Me | H | H | 196-200 |
| 7-005 | Me | D1-108b(4-CF$_3$) | Me | H | H | 174-176 |
| 7-006 | Me | D1-108b(4-OMe) | Me | H | H | 170-171 |
| 7-007 | Me | D1-108b(4-Me) | Me | H | H | 90-93 |
| 7-008 | Me | D1-108b(4-Cl) | Me | H | H | 173-175 |
| 7-009 | Me | D1-108b(4-SMe) | Me | H | H | 179-184 |
| 7-010 | Me | C≡CMe | Me | H | H | 207-209 |
| 7-011 | Br | Me | Me | H | H | 182-186 |
| 7-012 | Me | D1-32a | Me | H | H | 118-122 |
| 7-013 | Me | c-Pr | Me | H | H | 176-183 |
| 7-014 | Me | OPh | Me | H | H | 142-148 |
| 7-015 | Me | OCH$_2$CF$_3$ | Me | H | H | 122-125 |
| 7-016 | Me | D1-108b(4-OCF$_3$) | Me | H | H | 169-172 |
| 7-017 | Me | D1-37a | Me | H | H | *1 |
| 7-018 | Me | OCH$_2$Ph | Me | H | H | 156-158 |
| 7-019 | Me | O{D1-32b(5-CF$_3$)} | Me | H | H | 100-102 |
| 7-020 | Me | OMe | Me | H | H | 204-207 |
| 7-021 | Me | OCH$_2$(D1-34a) | Me | H | H | 187(decomp.) |
| 7-022 | Me | CH=CHPr-n | Me | H | H | 106-116 |
| 7-023 | Me | CH=CHPh | Me | H | H | 181-185 |
| 7-024 | Me | D1-7a | Me | H | H | 184-187 |
| 7-025 | Me | D1-11a | Me | H | H | 61-65 |
| 7-026 | Me | D1-22a | Me | H | H | 54-66 |
| 7-027 | OMe | Br | Me | H | H | *1 |
| 7-028 | OMe | Br | F | C(O)OMe | H | 210-213 |

TABLE 12-continued

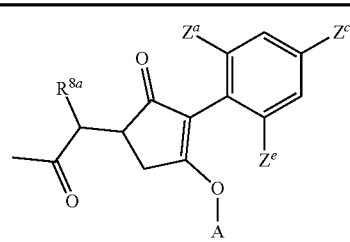

| No. | $Z^a$ | $Z^c$ | $Z^e$ | $R^{8a}$ | A | m.p. (° C.) |
|---|---|---|---|---|---|---|
| 7-029 | OMe | Br | F | H | H | 163-165 |
| 7-030 | OMe | Me | Me | H | H | 147-152 |
| 7-031 | OMe | Br | Me | Me | H | 93-95 |

TABLE 13

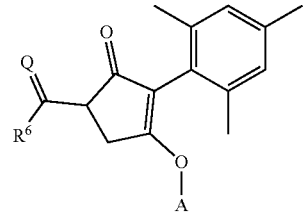

| No. | Q | $R^6$ | A | m.p. (° C.) |
|---|---|---|---|---|
| 8-001 | O | Me | H | 178-182 |
| 8-002 | O | C(=NOMe)Me | H | 50-55 |
| 8-003 | NOMe | C(=NOMe)Me | H | 190(decomp.) |

TABLE 14

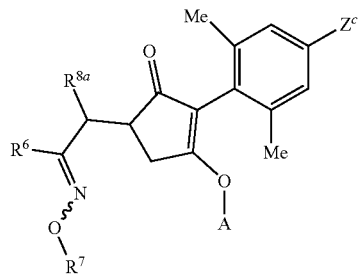

| No. | $R^6$ | $R^7$ | $Z^c$ | A | m.p. (° C.) |
|---|---|---|---|---|---|
| 9-001 | i-Pr | Me | Br | H | 93-96 |
| 9-002 | c-Pr | Me | Br | H | 167-168 |
| 9-003 | i-Pr | Me | C≡CMe | C(O)CH$_2$OPh | *1 |
| 9-004 | i-Pr | Me | D1-7b(X$^1$=4-Cl) | H | *1 |
| 9-005 | i-Pr | Me | C≡CSi(Me)$_3$ | H | *1 |
| 9-006 | i-Pr | Me | C≡CMe | H | 176-178 |
| 9-007 | c-Pr | Me | D1-7b(X$^1$=4-Cl) | H | *1 |
| 9-008 | c-Pr | Me | C≡CMe | H | 170-173 |
| 9-009 | c-Pr | CH$_2$CF$_3$ | Br | H | 128-130 |
| 9-010 | Me | CH$_2$CF$_3$ | D1-7b(X$^1$=4-Cl) | H | 161-184 |
| 9-011 | Me | CH$_2$CF$_3$ | C≡CMe | H | 158-161 |
| 9-012 | Me | CH$_2$CF$_3$ | D1-7b(X$^1$=4-Cl) | C(O)CH$_2$OPh | *1 |
| 9-013 | Me | CH$_2$CF$_3$ | C≡CMe | C(O)CH$_2$OPh | *1 |
| 9-014 | i-Pr | CH$_2$CF$_3$ | D1-7b(X$^1$=4-Cl) | H | *1 |
| 9-015 | i-Pr | CH$_2$CF$_3$ | C≡CMe | H | 189-192 |
| 9-016 | Me | CH$_2$CH$_2$OMe | D1-7b(X$^1$=4-Cl) | H | 119-122 |
| 9-017 | Me | CH$_2$CH$_2$OMe | Br | H | 70-74 |
| 9-018 | i-Pr | CH$_2$CH$_2$OMe | Br | H | *1 |
| 9-019 | c-Pr | CH$_2$CH$_2$OMe | Br | H | *1 |
| 9-020 | c-Pr | CH$_2$CH$_2$OMe | D1-7b(X$^1$=4-Cl) | H | *1 |
| 9-021 | c-Pr | CH$_2$CH$_2$OMe | C≡CMe | H | *1 |
| 9-022 | i-Pr | CH$_2$CH$_2$OMe | D1-7b(X$^1$=4-Cl) | H | *1 |
| 9-023 | i-Pr | CH$_2$CH$_2$OMe | C≡CMe | H | *1 |
| 9-024 | Me | CH$_2$CF$_3$ | D1-108b(4-Cl) | H | 202-204 |
| 9-025 | Me | CH$_2$CF$_3$ | D1-108b(4-Cl) | C(O)(D1-103a) | *1 |
| 9-026 | Me | CH$_2$CF$_3$ | D1-108b(4-Cl) | C(O)N(Me)$_2$ | *1 |
| 9-027 | Me | CH$_2$CF$_3$ | D1-108b(4-Cl) | C(O)CH$_2$OPh | *1 |
| 9-028 | c-Pr | Me | Ph | H | 202-209 |
| 9-029 | Me | CH$_2$C(O)N(Me)$_2$ | Br | H | *1 |
| 9-030 | Me | D1-103n | Br | H | *1 |

TABLE 15

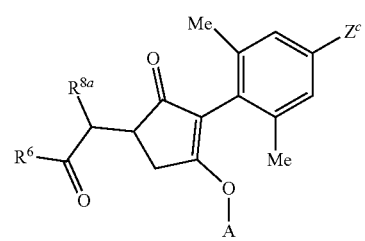

| No. | $R^6$ | $R^{8a}$ | $Z^c$ | A | m.p. (° C.) |
|---|---|---|---|---|---|
| 10-001 | i-Pr | C(O)OEt | Br | H | 143-145 |
| 10-002 | c-Pr | C(O)OMe | Br | H | 171-173 |
| 10-003 | i-Pr | H | Br | H | 151-153 |
| 10-004 | c-Pr | H | Br | H | 171-174 |

TABLE 16

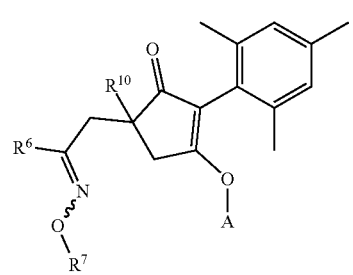

| No. | $R^6$ | $R^7$ | $R^{10}$ | A | m.p. (° C.) |
|---|---|---|---|---|---|
| 11-001 | Me | Me | Me | CH$_2$Ph | *1 |
| 11-002 | Me | Me | Me | H | 165-168 |

TABLE 17

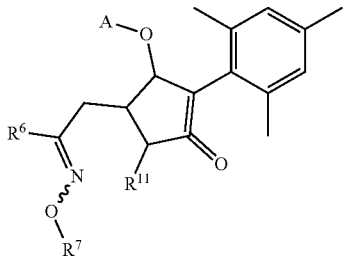

| No. | $R^6$ | $R^7$ | $R^{11}$ | A | m.p. (° C.) |
|---|---|---|---|---|---|
| 12-001 | Me | Me | Me | CH$_2$Ph | *1 |
| 12-002 | Me | Me | Me | H | *1 |

TABLE 18

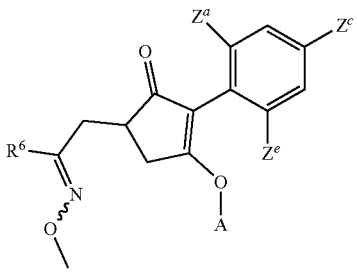

| No. | $Z^a$ | $Z^c$ | $Z^e$ | $R^6$ | A | m.p. (° C.) |
|---|---|---|---|---|---|---|
| 13-001 | OMe | Br | Me | Et | H | *1 |
| 13-002 | OMe | Me | Me | c-Pr | H | 81-84 |
| 13-003 | OMe | Me | Me | Et | H | 81-84 |
| 13-004 | OMe | Ph | Me | Et | H | 178-181 |
| 13-005 | OMe | Me | Me | c-Pr | C(O)(D1-103a) | *1 |
| 13-006 | OMe | Me | Me | c-Pr | C(O)Bu-t | *1 |

TABLE 19

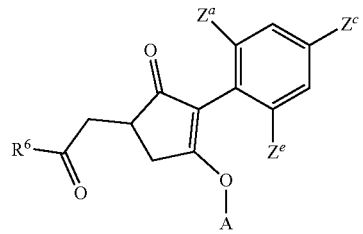

| No. | $Z^a$ | $Z^c$ | $Z^e$ | $R^6$ | A | m.p. (° C.) |
|---|---|---|---|---|---|---|
| 14-001 | OMe | Br | Me | c-Pr | H | *1 |
| 14-002 | OMe | Br | Me | Et | H | *1 |

TABLE 20

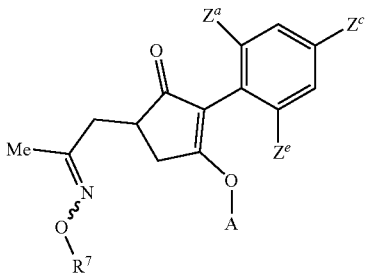

| No. | $Z^a$ | $Z^c$ | $Z^e$ | $R^7$ | A | m.p. (° C.) |
|---|---|---|---|---|---|---|
| 15-001 | OMe | Me | Me | CH$_2$C≡CH | H | *1 |
| 15-002 | OMe | Me | Me | CH$_2$CH=CH$_2$ | H | *1 |
| 15-003 | OMe | Me | Me | CH$_2$Pr-C | H | *1 |
| 15-004 | OMe | Me | Me | CH$_2$CH$_2$OMe | H | *1 |
| 15-005 | OMe | Me | Me | CH$_2$CF$_3$ | H | *1 |
| 15-006 | OMe | Me | Me | CH$_2$CN | H | *1 |
| 15-007 | OMe | Me | Me. | CH$_2$CH$_2$OMe | C(O)(D1-103a) | *1 |
| 15-008 | OMe | Me | Me | CH$_2$CH$_2$OMe | C(S)N(Me)$_2$ | *1 |
| 15-009 | OMe | Me | Me | CH$_2$CF$_3$ | C(O)Bu-t | *1 |
| 15-010 | OMe | Me | Me | CH$_2$CF$_3$ | C(O)N(Me)$_2$ | *1 |
| 15-011 | OMe | Me | Me | CH$_2$CN | S(O)$_2$Me | *1 |
| 15-012 | OMe | Me | Me | CH$_2$CN | C(O)N(Et)$_2$ | *1 |
| 15-013 | OMe | Me | Me | CH$_2$C≡CH | C(O)OMe | *1 |
| 15-014 | OMe | Me | Me | CH$_2$Pr-c | C(O)SBu-t | *1 |
| 15-015 | OMe | Me | Me | CH$_2$CH=CH$_2$ | C(O)CH$_2$OPh | *1 |
| 15-016 | OMe | Me | Me | CH$_2$C≡CH | C(O)(D1-103j) | *1 |
| 15-017 | OMe | Me | Me. | CH$_2$CH=CH$_2$ | C(O)(D1-103l) | *1 |
| 15-018 | OMe | Me | Me | CH$_2$Pr-c | C(O)(D1-103k) | *1 |

In the compounds of the present invention, $^1$H-NMR data of the compounds having no description of the melting point are listed in Table 21.

The chemical shift value of proton nuclear magnetic resonance was measured at 300 MHz in a deuterochloroform solvent using Me$_4$Si (tetramethylsilane) as a reference material. The symbols in Table 21 are the following meanings. s: singlet, brs: broad singlet, d: doublet, t: triplet, and m: multiplet. For the signals that can be analyzed when two or more structural isomers are present, the chemical shift values of each of the signals are marked with "and".

TABLE 21

| No. | $^1$H-NMR (CDCl$_3$, Me$_4$Si, 300 MHz) |
|---|---|
| 1-004; | 6.85-6.81(m, 2H), 3.87-3.82(m, 3H), 3.70-2.18(m, 8H), 2.15-1.78(m, 9H), 1.08 and 1.06(s, 9H) |
| 1-005; | 6.90-6.85(m, 2H), 3.87-3.82(m, 3H), 3.77-2.18(m, 8H), 2.17-1.98(m, 9H), 1.97-1.83(m, 3H) |

TABLE 21-continued

| No. | ¹H-NMR (CDCl₃, Me₄Si, 300 MHz) |
|---|---|
| 1-006; | 6.92-6.87(m, 2H), 3.84(s, 3H), 3.37-2.60(m, 7H), 2.40-2.24 (m, 4H), 2.13-2.02(m, 6H), 1.97-1.83(m, 3H) |
| 1-007; | 6.90-6.85(m, 2H), 5.90-5.67(m, 1H), 5.28-5.07(m, 2H), 4.50-4.40 and 4.23-4.15(m, 2H), 3.88-3.78(m, 3H), 3.00-1.85 (m, 17H) |
| 1-008; | 6.90-6.80(m, 2H), 4.60-4.48 and 4.38-4.30(m, 2H), 3.90-3.75(m, 3H), 3.31-2.35(m, 6H), 2.33-2.00(m, 9H), 1.97-1.85(m, 3H) |
| 1-009; | 7.28-7.03(m, 5H), 6.92-6.80(m, 2H), 4.97-4.92 and 4.73-4.68(m, 2H), 3.86-3.77(m, 3H), 3.31-1.80(m, 17H) |
| 1-009a-1; | 7.35-7.30(m, 3H), 7.20-7.15(m, 2H), 6.90-6.85(m, 2H), 4.95 (s, 2H), 3.84(s, 3H), 3.00-2.80(m, 3H), 2.65-2.55(m, 1H), 2.27(s, 3H), 2.25-2.15(m, 1H), 2.10-2.00(m, 6H), 1.86(s, 3H) |
| 1-009a-2; | 7.35-7.30(m, 3H), 7.20-7.15(m, 2H), 6.90-6.85(m, 2H), 4.95 (s, 2H), 3.80(s, 3H), 2.95-2.80(m, 2H), 2.76-2.70(m, 1H), 2.66-2.57(m, 2H), 2.27(s, 3H), 2.10-2.00(m, 6H), 1.91(s, 3H) |
| 1-009b-1; | 7.31-7.28(m, 3H), 7.10-7.07(m, 2H), 6.87-6.85(m, 2H), 4.72 (s, 2H), 3.84(s, 3H), 3.30-3.20(m, 1H), 2.90-2.80(m, 1H), 2.80-2.70(m, 1H), 2.42-2.37(m, 1H), 2.30-2.23(m, 4H), 2.08-2.05(m, 6H), 1.86(s, 3H) |
| 1-009b-2; | 7.32-7.28(m, 3H), 7.10-7.07(m, 2H), 6.88-6.86(m, 2H), 4.74 (s, 2H), 3.83(s, 3H), 3.29-3.24(m, 1H), 2.82-2.63(m, 3H), 2.39-2.34(m, 1H), 2.28(s, 3H), 2.10(s, 3H), 2.05(s, 3H), 1.92(s, 3H) |
| 1-010; | 7.96-7.15(m, 5H), 6.90-6.87(m, 2H), 3.88-3.75(m, 3H), 3.55-1.83(m, 17H) |
| 1-011; | 6.98-6.75(m, 2H), 4.20-4.77(m, 5H), 3.28-2.60(m, 6H), 2.45-1.80(m, 16H) |
| 1-012; | 6.92-6.80(m, 2H), 4.69 and 4.53 and 4.35and 4.25(s, 2H), 3.88-3.58(m, 3H), 3.38-3.28 and 3.00-1.80(m, 17H) |
| 1-013; | 6.98-6.87(m, 2H), 4.56 and 4.55 and 4.46 and 4.44(s, 2H), 3.92-3.82(m, 3H), 3.36-3.25 and 3.10-2.60(m, 4H), 2.60-1.80(m, 13H) |
| 1-014; | 6.91-6.85(m, 2H), 3.85(s, 3H), 3.77 and 3.70(s, 3H), 3.35-3.18(m, 1H), 3.10-2.65(m, 3H), 2.35-2.22(m, 4H), 2.10-2.02(m, 6H), 1.90-1.83(m, 3H) |
| 1-015; | 6.91-6.82(m, 2H), 3.90-3.80(m, 3H), 3.31-3.20(m, 1H), 3.07-2.78(m, 3H), 2.35-2.20(m, 4H), 2.10-2.00(m, 6H), 1.95-1.83(m, 3H), 1.75-1.50(m, 1H), 1.07-0.80(m, 4H) |
| 1-016; | 6.91-6.77(m, 2H), 3.90-3.77(m, 3H), 3.68-3.42(m, 2H), 3.28-2.48(m, 4H), 2.35-1.80(m, 13H), 1.37(s, 3H), 1.16(s, 3H) |
| 1-017; | 7.17-7.05(m, 2H), 7.00-6.90(m, 1H), 6.87-6.78(m, 2H), 6.65-6.55(m, 2H), 3.87-3.82(m, 3H), 3.56-3.45 and 3.18-2.20 (m, 8H), 2.19-1.70(m, 9H), 1.50-1.38(m, 6H) |
| 1-031; | 6.90-6.85(m, 2H), 4.55 and 4.34(s, 2H), 3.88-3.80(m, 3H), 3.30-2.35(m, 4H), 2.30-1.80(m, 13H), 1.20-1.10(m, 9H) |
| 1-033; | 6.90-6.83(m, 2H), 3.84(s, 3H), 3.28-3.15(m, 1H), 3.07-2.96 (m, 1H), 2.90-2.75(m, 2H), 3.40-3.20(m, 6H), 2.06(s, 3H), 2.04(s, 3H), 1.86(s, 3H), 1.58-1.45(m, 2H), 1.35-1.10(m, 10H), 0.92-0.83(m, 3H) |
| 1-034; | 6.90-6.80(m, 2H), 3.90-3.80(m, 3H), 3.35-3.22(m, 1H), 3.09-2.98(m, 1H), 2.96-2.70(m, 2H), 2.35-2.20(m, 4H), 2.12-2.00(m, 6H), 1.92-1.78(m, 6H), 1.48-1.35(m, 6H) |
| 1-035; | 6.90-6.82(m, 2H), 3.84(s, 3H), 3.28-3.15(m, 1H), 3.08-2.97 (m, 1H), 2.90-2.75(m, 2H), 2.50-2.20(m, 8H), 2.10-2.02(m, 6 H), 1.86(s, 3H), 1.80-0.70(m, 11H) |
| 1-036; | 6.90-6.80(m, 2H), 3.87-3.80(m, 3H), 3.26-3.15(m, 1H), 3.10-3.00(m, 1H), 2.90-2.78(m, 2H), 2.38-2.13(m, 4H), 2.10-2.00(m, 6H), 1.86(s, 3H), 1.58-1.40(m, 5H) |
| 1-037; | 6.90-6.80(m, 2H), 4.07-3.52(m, 14H), 2.45-2.00(m, 10H), 1.90-1.84(m, 3H) |
| 1-039; | 6.90-6.80(m, 2H), 3.84(s, 3H), 3.25-3.13(m, 1H), 3.12-3.01 (m, 1H), 2.90-2.75(m, 2H), 2.38-2.20(m, 4H), 2.06(s, 3H), 2.05(s, 3H), 1.84(s, 3H), 1.48-1.35(m, 6H) |
| 1-042; | 6.88-6.83(m, 2H), 3.87-3.82(m, 3H), 3.32-2.22(m, 9H), 2.15-2.03(m, 6H), 1.89-1.85(m, 3H), 1.59-1.47(m, 3H) |
| 1-043; | 7.28-7.17(m, 2H), 7.02-6.96(m, 1H), 6.89-6.83(m, 2H), 6.74-6.60(m, 2H), 4.65 and 4.62(s, 2H), 3.84(s, 3H), 3.29-3.18(m, 1H), 3.12-3.00(m, 1H), 2.92-2.80(m, 2H), 2.40-2.20(m, 4H), 2.10-2.00(m, 6H), 1.90-1.83(m, 3H) |
| 1-044; | 7.28-7.17(m, 2H), 6.88-6.83(m, 2H), 6.63-6.48(m, 2H), 4.62 and 4.58(s, 2H), 3.84(s, 3H), 3.70-2.22(m, 8H), 2.03-1.95(m, 6H), 1.86(s, 3H) |

TABLE 21-continued

| No. | $^1$H-NMR (CDCl$_3$, Me$_4$Si, 300 MHz) |
|---|---|
| 1-045; | 8.52-8.47(m, 1H), 8.04-7.98(m, 1H), 7.91-7.83(m, 1H), 7.46-7.38(m, 1H), 6.93-6.85(m, 2H), 4.10(s, 3H), 3.43-3.35(m, 1H), 3.15-2.90(m, 3H), 2.58-2.48(m, 1H), 2.26(s, 3H), 2.17(s, 3H), 2.11(s, 3H)<br>(Proton peak corresponding to OH was not observed) |
| 1-046; | 11.85(brs, 1H), 6.95-6.85(m, 2H), 3.95-3.78(m, 3H), 3.40-2.02(m, 14H), 1.08-0.70(m, 5H) |
| 1-047; | 8.14-7.34(m, 5H), 6.95-6.85(m, 2H), 4.05-3.88(m, 3H), 3.35-2.00(m, 14H)<br>(Proton peak corresponding to OH was not observed) |
| 1-048; | 11.78-11.65(m, 1H), 7.00-6.83(m, 2H), 3.97-3.80(m, 3H), 3.55-2.00(m, 15H), 1.25-1.00(m, 6H) |
| 1-051; | 7.06-6.98(m, 2H), 6.87-6.80(m, 2H), 6.52-6.44(m, 2H), 3.87-3.82(m, 3H), 3.62-2.13(m, 8H), 2.08-2.00(m, 6H), 1.87 and 1.82(s, 3H), 1.58-1.40(m, 6H) |
| 1-060; | 7.24-7.22(m, 2H), 7.00-6.90(m, 1H), 6.88-6.78(m, 2H), 6.72-6.60(m, 2H), 4.78-4.65(m, 1H), 3.90-3.76(m, 3H), 3.25-2.96(m, 2H), 2.89-2.69(m, 2H), 2.35-2.20(m, 4H), 2.10-1.94(m, 6H), 1.88-1.80(m, 3H), 1.55-1.45(m, 3H) |
| 1-063; | 7.30-7.15(m, 2H), 7.03-6.94(m, 1H), 6.89-6.82(m, 2H), 6.75-6.60(m, 2H), 4.67-4.60(m, 2H), 3.88-3.77(m, 3H), 3.33-1.80(m, 14H), 0.90-0.65(m, 5H) |
| 1-064; | 7.40-7.30(m, 1H), 7.12-6.77(m, 4H), 6.53-6.27(m, 1H), 4.77-4.59(m, 2H), 3.90-2.80(m, 6H), 2.67-2.17(m, 5H), 2.15-1.80(m, 9H) |
| 1-065; | 7.18-7.05(m, 1H), 7.00-6.95(m, 1H), 6.88-6.72(m, 3H), 6.60-6.42(m, 1H), 4.65-4.53(m, 2H), 3.88-2.45(m, 7H), 2.37-1.85(m, 13H) |
| 1-067; | 7.03-6.68(m, 5H), 6.60-6.38(m, 1H), 4.73-4.65(m, 2H), 3.90-3.80(m, 6H), 3.75-2.15(m, 8H), 2.10-2.00(m, 6H), 1.90-1.82(m, 3H) |
| 1-068; | 7.15-7.07(m, 1H), 6.90-6.80(m, 2H), 6.60-6.52(m, 1H), 6.43-6.37(m, 1H), 6.30-6.22(m, 1H), 4.63(s, 2H), 3.83(s, 3H), 3.76(s, 3H), 3.30-3.20(m, 1H), 3.10-3.00(m, 1H), 2.92-2.80(m, 2H), 2.36-2.23(m, 4H), 2.04(s, 3H), 2.03(s, 3H), 1.54(s, 3H) |
| 1-069; | 6.92-6.53(m, 6H), 4.70-4.52(m, 2H), 3.84(s, 3H), 3.76(s, 3H), 3.30-2.10(m, 8H), 2.09-1.95(m, 6H), 1.93-1.82(m, 3H) |
| 1-071; | 7.88-7.80(m, 1H), 7.40-7.20(m, 1H), 7.14-7.03(m, 1H), 6.90-6.82(m, 2H), 6.57-6.50 and 6.37-6.29(m, 1H), 4.78 and 4.74(s, 2H), 3.87-3.82(m, 3H), 3.70-2.22(m, 8H), 2.14-1.97(m, 6H), 1.90-1.85(m, 3H) |
| 1-072; | 7.05-6.97(m, 2H), 6.92-6.85(m, 2H), 6.65-6.50(m, 2H), 4.65-4.55(m, 2H), 3.90-3.80(m, 3H), 3.29-2.79(m, 4H), 2.38-2.22(m, 7H), 2.10-2.02(m, 6H), 1.88-1.72(m, 3H) |
| 1-073; | 6.93-6.80(m, 4H), 6.67-6.50(m, 2H), 4.65-4.55(m, 2H), 3.84(s, 3H), 3.28-2.45(m, 4H), 2.35-2.20(m, 4H), 2.10-1.95(m, 6H), 1.93-1.80(m, 3H) |
| 1-074; | 7.35-6.70(m, 6H), 4.67 and 4.64(s, 2H), 3.84(s, 3H), 3.30-2.20(m, 8H), 2.15-1.95(m, 6H), 1.92-1.85(m, 3H) |
| 1-075; | 7.37-6.12(m, 5H), 4.73-4.65(m, 2H), 3.88-3.80(m, 3H), 3.72-2.20(m, 8H), 2.10-1.95(m, 6H), 1.90-1.82(m, 3H) |
| 1-076; | 6.87-6.82(m, 2H), 4.50-4.40(m, 1H), 3.90-3.82(m, 3H), 3.80-1.40(m, 23H) |
| 1-077; | 6.87(s, 2H), 4.25-4.20(m, 2H), 3.90(s, 3H), 3.72(s, 3H), 3.15-2.90(m, 2H), 2.85-2.70(m, 2H), 2.60-2.50(m, 1H), 2.26(s, 3H), 2.09(s, 6H) |
| 1-079; | 9.95-9.87(m, 1H), 7.77-7.68(m, 2H), 6.90-6.65(m, 4H), 4.73 and 4.69(s, 2H), 3.88-3.82(m, 3H), 3.70-2.45(m, 5H), 2.37-1.85(m, 12H) |
| 1-080; | 7.88-7.80(m, 2H), 6.86(brs, 2H), 6.75-6.57(m, 2H), 4.70 and 4.67(s, 2H), 3.84(s, 3H), 3.70-3.58and3.30-2.45(m, 7H), 2.40-2.22(m, 4H), 2.15-1.95(m, 6H), 1.86(s, 3H) |
| 1-081; | 7.33-7.20(m, 2H), 6.86(brs, 2H), 6.58-6.42(m, 2H), 4.61(s, 2H), 3.84(s, 3H), 3.27-3.17(m, 1H), 3.12-3.00(m, 1H), 2.90-2.79(m, 2H), 2.37-2.25(m, 4H), 2.02(s, 3H), 2.00(s, 3H), 1.86(s, 3H) |
| 1-082; | 7.52-7.40(m, 2H), 6.86(brs, 2H), 6.48-6.30(m, 2H), 4.61 and 4.57(s, 2H), 3.84(s, 3H), 3.27-3.15(m, 1H), 3.12-3.00(m, 1H), 2.90-2.79(m, 2H), 2.35-2.25(m, 4H), 2.05-1.98(m, 6H), 1.86 (s, 3H) |
| 1-083; | 7.80-7.70(m, 2H), 7.65-7.58(m, 1H), 7.50-7.30(m, 2H) 7.15-7.05(m, 1H), 6.92-6.85(m, 1H), 6.80(brs, 2H), 4.77 and 4.75 (s, 2H), 3.82(s, 3H), 3.32-3.20(m, 1H), 3.12-3.00(m, 1H), 2.95-2.80(m, 2H), 2.35-2.23(m, 4H), 2.08-1.98(m, 6H), 1.86(s, 3H) |
| 1-087; | 8.61(s, 1H), 8.06(s, 1H), 7.70-7.61(m, 2H), 7.10-7.05(m, 2H), 6.87-6.65(m, 4H), 4.75-4.69(m, 1H), 3.84(s, 3H)3.28-2.81(m, 4H)2.40-1.95(m, 10H)1.83(s, 3H), 1.52(m, 3H) |

TABLE 21-continued

| No. | $^1$H-NMR (CDCl$_3$, Me$_4$Si, 300 MHz) |
|---|---|
| 1-088; | 6.86(brs, 2H), 6.81-6.78(m, 1H), 3.84(s, 3H), 3.38-3.27(m, 1H), 3.09-2.98(m, 1H), 2.95-2.80(m, 2H), 2.55-2.45(m, 4H), 2.35-2.21(m, 4H), 2.10-2.01(m, 6H), 2.00-1.90(m, 2H), 1.86(s, 3H) |
| 1-089; | 6.86(brs, 2H), 3.84(s, 3H), 3.40-3.27(m, 1H), 3.10-2.98(m, 1H), 2.97-2.70(m, 4H), 2.58-2.50(m, 2H), 2.35-2.23(m, 4H), 2.10-1.86(m, 11H) |
| 1-090; | 7.08-6.97(m, 1H), 6.87(brs, 2H), 5.83-5.75(m, 1H), 3.84(s, 3H), 3.37-3.26(m, 1H), 3.08-2.98(m, 1H), 2.93-2.80(m, 2H), 2.35-2.10(m, 6H), 2.07(s, 3H), 2.06(s, 3H), 1.86(s, 3H), 1.55-1. |
| 1-091; | 7.52-7.49(m, 1H), 7.40(d, J = 15.6 Hz, 1H), 6.87(brs, 2H), 6.68-6.65(m, 1H), 6.50-6.47(m, 1H), 6.24(d, J = 15.6 Hz, 1H), 3.84(s, 3H), 3.40-3.29(m, 1H), 3.10-2.99(m, 1H), 2.98-2.81(m, 2H), 2.35-2.25(m, 4H), 2.09(s, 3H), 2.07(s, 3H), 1.86(s, 3H) |
| 1-092; | 6.87(brs, 2H), 4.24 and 4.19(brs, 2H), 3.84(s, 3H), 3.75-2.22(m, 10H), 2.15-2.02(m, 6H), 1.90-1.85(m, 3H) |
| 1-093; | 6.86(brs, 2H), 4.05(s, 2H), 3.84(s, 3H), 3.33(s, 3H), 3.32-3.20(m, 1H), 3.10-3.00(m, 1H), 2.92-2.80(m, 2H), 2.35-2.23(m, 4H), 2.10-2.02(m, 6H), 1.87(s, 3H) |
| 1-094; | 7.40-7.15(m, 5H), 6.86(brs, 2H), 4.46and4.38(s, 2H), 4.11 and 4.08(s, 2H), 3.84and3.83(s, 3H), 3.78-2.20(m, 8H), 2.06(s, 3H), 2.04(s, 3H), 1.87(s, 3H) |
| 1-095; | 6.88(brs, 2H), 3.84(s, 3H), 3.30-3.18(m, 1H), 3.08-2.98(m, 1H), 2.92-2.79(m, 2H), 2.35-2.23(m, 4H), 2.10-2.03(m, 6H), 1.98(s, 3H), 1.86(s, 3H) |
| 1-096; | 6.89(brs, 2H), 3.83(s, 3H), 3.28-3.18(m, 1H), 3.08-2.99(m, 1H), 2.90-2.88(m, 2H), 2.35-2.24(m, 4H), 2.07(s, 3H), 2.06(s, 3H), 1.86(s, 3H), 0.23(s, 9H) |
| 1-098; | 6.84(brs, 2H), 4.03(s, 3H), 3.84(s, 3H), 3.39(s, 2H), 3.32-3.20(m, 1H), 3.12-3.00(m, 1H), 2.95-2.80(m, 2H), 2.37-2.22(m, 4H), 2.09(s, 3H), 2.08(s, 3H), 1.92(s, 3H), 1.86(s, 3H) |
| 1-099; | 6.87-6.80(m, 2H), 3.84 and 3.78(s, 3H), 3.40-2.28(m, 5H), 2.26-2.22(m, 3H), 2.15-2.08(m, 6H), 1.88 and 1.86(s, 3H) |
| 1-100; | 6.85(brs, 2H), 6.32-6.28(m, 1H), 3.84(s, 3H), 3.37-3.28(m, 1H), 3.16-3.05(m, 1H), 3.00-2.80(m, 2H), 2.50-2.45(m, 3H), 2.40-2.29(m, 1H), 2.24(s, 3H), 2.11(s, 3H), 2.10(s, 3H), 1.88(s, 3H) |
| 1-101; | 6.87(brs, 2H), 3.84(s, 3H), 3.45-3.33(m, 1H), 3.13-2.80(m, 3H), 2.65(s, 3H), 2.55(s, 3H), 2.37-2.24(m, 4H), 2.10(s, 3H), 2.08(s, 3H), 1.88(s, 3H) |
| 1-103; | 8.31(s, 1H), 6.85(brs, 2H), 3.85(s, 3H), 3.55-3.42(m, 1H), 3.13-3.03(m, 2H), 2.92-2.83(m, 1H), 2.38-2.18(m, 4H), 2.09(s, 3H), 2.07(s, 3H), 1.89(s, 3H), 1.65-1.50(m, 1H), 1.23-1.17(m, 2H), 1.03-0.97(m, 2H) |
| 1-104; | 6.87(brs, 2H), 3.85(s, 3H), 3.70-3.22(m, 10H), 3.08-2.97(m, 1H), 2.96-2.80(m, 2H), 2.32-2.19(m, 3H), 2.08(s, 3H), 2.05(m, 3H), 1.87(s, 3H) |
| 1-107; | 6.86(brs, 2H), 3.84(s, 3H), 3.42-3.31(m, 1H), 3.07-2.72(m, 9H), 2.31-2.19(m, 4H), 2.09(s, 3H), 2.06(s, 3H), 1.86(s, 3H) |
| 1-108; | 7.27(brs, 2H), 3.84(s, 3H), 3.38-3.23(m, 1H), 3.15-2.78(m, 5H), 2.40-2.01(m, 10H), 1.86(s, 3H), 1.69-1.48(m, 3H), 1.38-1.05(m, 10H) |
| 1-122; | 6.86(brs, 2H), 3.85(s, 3H), 3.39-3.28(m, 1H), 3.11-2.59(m, 9H), 2.36-1.98(m, 4H), 2.08(s, 3H), 2.06(s, 3H), 1.54(s, 3H) |
| 1-125; | 10.06(brs, 1H), 6.99-6.81(m, 2H), 4.66-4.42(m, 2H), 3.50-3.32(m, 2H), 3.04-1.42(m, 20H) |
| 1-126; | 6.86(brs, 2H), 3.84(brs, 3H), 3.58-2.72(m, 12H), 2.35-1.20(m, 16H) |
| 1-127; | 7.32-6.62(m, 7H), 4.55-4.28(m, 1H), 3.89-3.79(m, 3H), 3.38-3.20(m, 1H), 3.02-2.65(m, 3H), 2.29-1.44(m, 13H), 1.13-0.87(m, 6H) |
| 1-128; | 6.97-6.66(m, 6H), 4.57-4.31(m, 1H), 3.84(s, 3H), 3.38-3.23(m, 1H), 3.04-2.71(m, 3H), 2.30-1.40(m, 13H), 1.17-0.79(m, 6H) |
| 1-129; | 6.98-6.43(m, 5H), 4.59-4.40(m, 1H), 3.85(s, 3H), 3.50-3.31(m, 1H), 3.07-2.76(m, 3H), 2.32-1.50(m, 13H), 1.20-0.81(m, 6H) |
| 1-130; | 6.84(brs, 2H), 4.92-4.58(m, 2H), 3.84(s, 3H), 3.82-2.77(m, 9H), 2.37-1.32(m, 15H), 1.12-0.81(m, 3H) |
| 1-134; | 7.50-7.00(m, 5H), 6.85(brs, 2H), 3.85-3.50(m, 5H), 3.20-2.18(m, 8H), 2.10-1.97(m, 6H), 1.85 and 1.78(s, 3H) |
| 1-139; | 7.78-7.57(m, 5H), 6.90-6.82(m, 2H), 4.11(s, 2H), 3.89(s, 3H), 3.85(s, 3H), 3.62-2.20(m, 8H), 2.16-1.85(m, 9H) |
| 1-140; | 6.92-6.82(m, 2H), 3.87-3.82(m, 3H), 3.68-3.30(m, 1H), 3.28-2.00(m, 19H), 1.92-1.84(m, 3H) |

TABLE 21-continued

| No. | $^1$H-NMR (CDCl$_3$, Me$_4$Si, 300 MHz) |
|---|---|
| 1-141; | 6.89(brs, 2H), 3.84(s, 3H), 3.38-2.78(m, 8H), 2.40-2.25(m, 4 H), 2.15-1.82(m, 11H) |
| 1-142; | 6.88(brs, 2H), 3.85(s, 3H), 3.63-2.22(m, 9H), 2.13-2.02(m, 6 H), 1.90-1.82(m, 3H), 1.28-0.70(m, 4H) |
| 1-143; | 6.88(brs, 2H), 3.85(s, 3H), 3.42-2.80(m, 6H), 2.40-1.70(m, 13 H), 0.85-0.72(m, 2H), −0.07(s, 9H) |
| 1-144; | 7.45-7.22(m, 5H), 6.86(brs, 2H), 5.13(s, 2H), 3.84(s, 3H), 3.35-2.22(m, 8H), 2.14-2.00(m, 6H), 1.97-1.80(m, 3H) |
| 1-145; | 6.87(brs, 2H), 5.94-5.75(m, 1H), 5.45-5.20(m, 2H), 4.73-4.48(m, 2H), 3.84(s, 3H), 3.34-3.23(m, 1H), 3.10-2.80(m, 3H), 2.40-2.22(m, 4H), 2.07(s, 3H), 2.05(s, 3H), 1.86(s, 3H) |
| 1-146; | 6.87(brs, 2H), 4.33-4.15(m, 2H), 3.85(s, 3H), 3.62-3.52(m, 2 H), 3.43-3.22(m, 4H), 3.10-2.80(m, 3H), 2.35-2.22(m, 4H), 2.13-2.01(m, 6H), 1.86(s, 3H) |
| 1-147; | 6.87(brs, 2H), 4.33-4.15(m, 2H), 3.85(s, 3H), 3.62-3.52(m, 2 H), 3.43-3.22(m, 4H), 3.10-2.80(m, 3H), 2.35-2.22(m, 4H), 2.13-2.01(m, 6H), 1.86(s, 3H) |
| 1-148; | 7.13-7.08(m, 2H), 6.98-6.92(m, 2H), 6.78(brs, 2H), 3.84(s, 3 H), 3.15-2.96(m, 2H), 2.88-2.67(m, 2H), 2.33-2.19(m, 4H), 1.90(s, 3H), 1.87(s, 3H), 1.85(s, 3H), 1.47(s, 3H), 1.47(s, 3H) |
| 1-149; | 8.10-7.97(m, 2H), 7.75-7.65(m, 2H), 6.86(brs, 2H), 3.85(s, 3 H), 3.45-3.35(m, 1H), 3.18-2.85(m, 3H), 2.42-2.29(m, 1H), 2.25(s, 3H), 2.13(s, 3H), 2.11(s, 3H), 1.89(s, 3H) |
| 1-150; | 6.86(s, 2H), 3.84(s, 3H), 3.47-3.32(m, 3H), 3.29-3.19(m, 2H), 3.07-2.80(m, 3H), 2.32-2.19(m, 4H), 2.09(s, 3H), 2.07(s, 3H), 1.90-1.80(m, 7H) |
| 1-151; | 6.86(s, 2H), 3.85(s, 3H), 3.44-3.20(m, 5H), 3.08-2.80(m, 3H), 2.32-2.19(m, 4H), 2.08(s, 3H), 2.06(s, 3H), 1.87(s, 3H), 1.64-1.37(m, 6H) |
| 1-152; | 6.86(s, 2H), 3.84(s, 3H), 3.51-3.28(m, 5H), 3.08-2.80(m, 3H), 2.40-2.18(m, 11H), 2.08(s, 3H), 2.05(s, 3H), 1.86(s, 3H) |
| 1-153; | 6.85(brs, 2H), 5.90-5.42(m, 2H), 5.33-4.74(m, 4H), 4.00-3.58(m, 7H), 3.44-3.30(m, 1H), 3.09-2.80(m, 3H), 2.37-2.18(m, 4H), 2.07(s, 3H), 2.04(s, 3H), 1.87(s, 3H) |
| 1-155; | 7.83-7.77(m, 1H), 7.65-7.57(m, 1H), 7.39-7.29(m, 2H), 6.85 (brs, 2H), 3.85(s, 3H), 3.40-3.29(m, 1H), 3.18-3.05(m, 1H), 3.03-2.84(m, 2H), 2.41-2.28(m, 1H), 2.25(s, 3H), 2.11(s, 3H), 2.09(s, 3H), 1.88(s, 3H) |
| 1-156; | 7.10-6.92(m, 2H), 6.90-6.72(m, 4H), 3.85(s, 3H), 3.80(s, 3H), 3.68-3.53(m, 2H), 3.24-3.12(m, 1H), 3.07-2.74(m, 3H), 2.51-1.82(m, 13H) |
| 1-159; | 7.30-6.67(m, 7H), 3.84(s, 3H), 3.41-3.18(m, 4H), 3.10-2.77 (m, 3H), 2.30-1.66(m, 13H) |
| 1-160; | 6.84(brs, 2H), 3.84(s, 3H), 3.79(s, 3H), 3.40-2.82(m, 4H), 2.35-2.25(m, 1H), 2.25(s, 3H), 2.09(s, 3H), 2.07(s, 3H), 1.87(s, 3 H) |
| 1-161; | 7.56(d, J = 8.4 Hz, 2H), 7.20(d, J = 8.4 Hz, 2H), 6.86(brs, 2H), 3.84(s, 3H), 3.38-2.75(m, 4H), 2.42(s, 3H), 2.41-2.09(m, 1H), 2.25(s, 3H), 1.92(s, 3H), 1.89(s, 3H), 1.85(s, 3H) |
| 1-162; | 7.97(d, J = 8.1 Hz, 1H), 7.75(d, J = 8.1 Hz, 1H), 6.87(brs, 2H), 4.01(s, 3H), 3.86(s, 3H), 3.42-3.30(m, 1H), 3.20-3.08(m, 4H), 3.05-2.73(m, 2H), 2.43-2.22(m, 4H), 2.14-2.05(m, 6H), 1.98-1.85(m, 3H) |
| 1-163; | 7.50-7.44(m, 1H), 7.21-7.13(m, 1H), 6.92-6.70(m, 5H), 6.68-6.55(m, 2H), 4.72-4.59(m, 1H), 3.84(s, 3H), 3.23-2.67(m, 4 H), 2.38-2.16(m, 4H), 2.12-1.80 and 1.62-1.40(m, 12H) |
| 1-164; | 11.4(brs, 1H), 7.56-7.10(m, 4H), 6.87-6.82(m, 2H), 3.96-3.85(m, 3H)3.40-2.65(m, 3H), 2.51-1.97(m, 14H) |
| 1-165; | 6.85(brs, 2H), 4.85-4.50(m, 1H), 3.90-3.80(m, 3H), 3.20-2.50(m, 4H), 2.38-2.00(m, 10H), 1.90-1.83(m, 3H), 1.75-1.35(m, 8H) |
| 1-166; | 6.87(brs, 2H), 6.37-6.05(m, 1H), 4.72-4.30(m, 2H), 3.90-3.80(m, 3H), 3.35-2.55(m, 4H), 2.45-2.03(m, 10H), 1.92-1.85(m, 3H) |
| 2-008; | 10.05-10.02(m, 1H), 8.08-7.95(m, 2H), 7.80-7.35(m, 3H), 6.95-6.85(m, 2H), 5.23-4.78(m, 1H), 4.25-4.05(m, 2H), 3.90-2.00(m, 12H), 1.30-1.10(m, 3H) |
| 2-010; | 7.00-6.85(m, 2H), 4.40-4.25(m, 2H), 4.00-2.02(m, 13H), 1.40-1.22(m, 3H) <br> (Proton peak corresponding to OH was not observed) |
| 2-015; | 10.20-9.95(m, 1H), 8.20-7.98(m, 2H), 7.75-7.45(m, 3H), 7.05-6.80(m, 2H), 3.97-3.72(m, 1H), 3.60-3.47(m, 1H), 3.32-2.95(m, 2H), 2.55-2.05(m, 10H) |
| 2-018; | 6.84(s, 2H), 3.30-3.20(m, 1H), 3.18-3.07(m, 1H), 3.10-3.00 (m, 1H), 2.82-2.68(m, 2H), 2.25(s, 3H), 2.20(s, 3H), 2.08(s, 3 H), 2.06(s, 3H), 1.08(s, 9H) |
| 3-001; | 7.60-7.48 and 6.95-6.80(m, 3H), 4.07-3.85(m, 4H), 3.85-2.50(m, 3H), 2.35-2.00(m, 9H) |

TABLE 21-continued

| No. | ¹H-NMR (CDCl₃, Me₄Si, 300 MHz) |
|---|---|
| 3-002; | 6.97-6.83(m, 2H), 3.88(s, 3H), 3.00-2.42(m, 3H), 2.27(s, 3H), 2.15-2.05(m, 6H), 1.86(s, 3H) (Proton peak corresponding to OH was not observed) |
| 4-001; | 6.88(s, 2H), 3.84 and 3.82(s, 3H), 2.95-2.71(m, 1H), 2.55-1.96(m, 17H), 1.10(t, J = 7.5 Hz, 3H) (Proton peak corresponding to OH was not observed) |
| 5-001; | 6.88(s, 2H), 2.85-1.99(m, 17H), 1.88-1.78(m, 1H), 1.07(t, J = 7.5 Hz, 3H) (Proton peak corresponding to OH was not observed) |
| 5-002; | 6.86(s, 2H), 3.72(s, 3H), 3.01-2.92(m, 1H), 2.72-1.85(m, 17H), 1.60(t, J = 7.5 Hz, 3H) |
| 6-004; | 11.90-11.60(m, 1H), 8.15-7.55(m, 2H), 7.40-7.25(m, 2H), 4.00-3.80(m, 3H), 3.50-3.35(m, 1H), 3.05-2.55(m, 3H), 2.40-1.90(m, 10H) |
| 6-005; | 11.80-11.60(m, 1H), 8.00-7.00(m, 4H), 4.00-3.80(m, 3H), 3.50-3.30(m, 1H), 3.05-1.95(m, 12H), 1.20-1.00(m, 3H) |
| 6-006; | 11.60-11.45(m, 1H), 7.15-7.05(m, 2H), 3.95-3.85(m, 3H), 3.50-3.35(m, 1H), 3.00-2.50(m, 3H), 2.50-2.30(m, 2H), 2.30-1.80(m, 10H), 1.20-1.00(m, 3H) |
| 6-008; | 11.60-11.40(m, 1H), 7.25-7.15(m, 2H), 3.95-3.85(m, 3H), 3.50-3.35(m, 1H), 3.00-2.85(m, 1H), 2.85-2.70(m, 1H), 2.70-2.30(m, 3H), 2.30-2.18(m, 1H), 2.18-2.05(m, 3H), 2.05-1.95(m, 3H), 1.20-1.00(m, 3H), 0.30-0.10(m, 9H) |
| 6-010; | 11.52(brs, 1H), 7.21(brs, 2H), 3.95-3.85(m, 3H), 3.45-3.30(m, 1H), 3.00-2.50(m, 3H), 2.25-1.90(m, 10H), 1.50-1.35(m, 1H), 0.90-0.70(m, 4H) |
| 6-011; | 7.21(brs, 2H), 3.85(s, 3H), 3.76(s, 3H), 2.95-2.55(m, 5H), 2.11(s, 6H), 1.95(s, 3H) |
| 6-012; | 7.63-7.55(m, 2H), 7.48-7.40(m, 2H), 7.40-7.25(m, 3H), 3.86(m, 3H), 3.79(s, 3H), 3.00-2.55(m, 5H), 2.21(s, 6H), 1.95(s, 3H) |
| 6-013; | 7.55-7.40(m, 2H), 7.35-7.17(m, 4H), 3.86(s, 3H), 3.78(s, 3H), 3.00-2.55(m, 5H), 2.38(s, 3H), 2.19(s, 6H), 1.95(s, 3H) |
| 6-014; | 7.74-7.63(m, 4H), 7.29(brs, 2H), 3.86(s, 3H), 3.81(s, 3H), 3.03-2.57(m, 5H), 2.22(s, 6H), 1.96(s, 3H) |
| 6-019; | 7.50(d, J = 8.4 Hz, 2H), 7.38(d, J = 8.4 Hz, 2H), 7.25(brs, 2H), 3.86(s, 3H), 3.80(s, 3H), 3.03-2.57(m, 5H), 2.20(s, 6H), 1.96(s, 3H) |
| 6-022; | 11.61(brs, 1H), 7.07(brs, 2H), 4.05-4.00(m, 2H), 3.91(s, 3H), 3.50-3.35(m, 1H), 3.20-2.50(m, 7H), 2.30-1.90(m, 10H), 1.60-1.20(m, 9H), 0.95-0.85(m, 6H) |
| 6-023; | 11.74(brs, 1H), 7.73(s, 2H), 3.91(s, 3H), 3.88(s, 3H), 3.55-3.35(m, 1H), 3.05-2.50(m, 3H), 2.20-1.90(m, 10H) |
| 6-024; | 11.58(brs, 1H), 6.97(brs, 2H), 3.90(s, 3H), 3.50-3.30(m, 1H), 3.00-2.50(m, 3H), 2.44(s, 3H), 2.20-1.90(m, 10H) |
| 6-025; | 11.65(brs, 1H), 7.25-7.13(m, 2H), 4.47(s, 2H), 3.91(s, 3H), 3.50-3.31(m, 1H), 3.02-2.50(m, 3H), 2.41-1.79(m, 10H) |
| 6-026; | 11.79(brs, 1H), 7.63(s, 2H), 3.91(s, 3H), 3.53-3.31(m, 1H), 3.02-1.90(m, 16H) |
| 6-033; | 11.38(brs, 1H), 7.20-7.01(m, 2H), 6.34(s, 1H), 3.91(s, 3H), 2.99-2.50(m, 3H), 2.28-1.90(m, 11H), 1.51(s, 9H) |
| 6-035; | 11.63(brs, 1H), 7.57-7.27(m, 5H), 3.92(s, 3H), 3.51-3.38(m, 1H), 3.03-2.54(m, 3H), 2.32-2.14(m, 7H), 2.01(s, 3H) |
| 6-036; | 11.70(brs, 1H), 7.21(brs, 2H), 3.91(s, 3H), 3.47-3.33(m, 1H), 2.99-2.52(m, 3H), 2.35-1.80(m, 14H), 1.71-1.36(m, 3H) |
| 6-037; | 11.00(brs, 1H), 6.78-6.53(m, 2H), 4.05-3.70(m, 6H), 3.50-3.28(m, 1H), 3.00-2.55(m, 3H), 2.40-1.80(m, 10H) |
| 6-038; | 11.61(brs, 1H), 7.32-7.25(m, 1H), 7.03-6.96(m, 1H), 3.91(s, 3H), 3.53-3.30(m, 1H), 3.05-2.10(m, 10H), 1.99(m, 3H) |
| 6-039; | 6.75(brs, 2H), 3.86(s, 3H), 3.74(s, 3H), 2.97-2.83(m, 3H), 2.63-2.52(m, 1H), 2.25-1.75(m, 2H), 2.09(s, 3H), 2.06(s, 3H), 1.88(s, 3H), 0.95-0.85(m, 2H), 0.70-0.60(m, 2H) |
| 6-041; | 7.40-7.30(m, 2H), 7.15-7.00(m, 3H), 6.70(brs, 2H), 3.87(s, 3H), 3.80(s, 3H), 3.02-2.85(m, 3H), 2.65-2.2.55(m, 1H), 2.30-2.15(m, 1H), 2.09(s, 3H), 2.07(s, 3H), 1.89(s, 3H) |
| 6-043; | 7.56(d, J = 8.8 Hz, 2H), 7.30-7.20(m, 4H), 3.87(s, 3H), 3.80(s, 3H), 3.05-2.85(m, 3H), 2.70-2.2.55(m, 1H), 2.25-2.15(m, 1H), 2.22(s, 3H), 2.21(s, 3H), 1.89(s, 3H) |
| 6-045; | 7.45-7.25(m, 5H), 6.69(brs, 2H), 5.01(s, 2H), 3.86(s, 3H), 3.76(s, 3H), 3.00-2.85(m, 3H), 2.65-2.50(m, 1H), 2.25-2.15(m, 1H), 2.10(s, 3H), 2.07(s, 3H), 1.88(s, 3H) |
| 6-046; | 8.65-8.55(m, 2H), 7.40-7.30(m, 2H), 6.64(brs, 2H), 5.03(s, 2H), 3.84(s, 3H), 3.75(s, 3H), 3.00-2.80(m, 3H), 2.65-2.50(m, 1H), 2.25-2.15(m, 1H), 2.16(s, 3H), 2.08(s, 3H), 1.86(s, 3H) |
| 6-047; | 8.46(brs, 1H), 7.90-7.80(m, 1H), 7.00-6.90(m, 1H), 6.84(brs, 2H), 3.86(s, 3H), 3.82(s, 3H), 3.05-2.85(m, 3H), 2.70-2.55(m, 1H), 2.30-2.10(m, 1H), 2.13(s, 3H), 2.10(s, 3H), 1.89(s, 3H) |

TABLE 21-continued

| No. | $^1$H-NMR (CDCl$_3$, Me$_4$Si, 300 MHz) |
|---|---|
| 6-051; | 8.70-8.66(m, 1H), 7.78-7.60(m, 3H), 7.26-7.17(m, 2H), 3.91 (s, 3H), 3.60-3.35(m, 1H), 3.03-2.91(m, 1H), 2.85-2.55(m, 2 H), 2.35-2.18(m, 7H), 2.00(s, 3H) (Proton peak corresponding to OH was not observed) |
| 6-052; | 11.52(brs, 1H), 7.36-7.28(m, 2H), 7.12-7.00(m, 3H), 6.70(brs, 2H), 3.92(s, 3H), 3.46-3.37(m, 1H), 2.95(dd, J = 18.0, 7.5 Hz, 1 H), 2.78(dd, J = 18.0, 2.7 Hz, 1H), 2.61(dd, J = 18.0, 10.8 Hz, 1H), 2.25(dd, J = 18.0, 2.7 Hz, 1H)2.12(s, 3H), 2.10(s, 3H), 1.99(s, 3 H) |
| 6-059; | 7.65-7.50(m, 2H), 7.27-7.20(m, 2H), 7.16-7.08(m, 2H), 3.86 (s, 3H), 3.72-3.31(m, 9H), 3.13-2.83(m, 3H), 2.39-2.15(m, 7 H), 1.90(s, 3H) |
| 6-060; | 7.56-7.50(m, 2H), 7.23(s, 2H), 7.14-7.06(m, 2H), 3.86(s, 3H) 3.48-3.33(m, 1H), 3.17-2.72(m, 9H), 2.39-2.18(m, 7H), 1.91-1.87(m, 3H) |
| 6-061; | 7.53-7.45(m, 2H), 7.43-7.35(m, 2H), 7.25-7.10(m, 4H), 6.97-6.88(m, 1H), 6.74-6.62(m, 2H), 4.67and4.64(s, 2H), 3.84(s, 3 H), 3.75-3.65 and 3.34-2.06(m, 11H), 1.87and1.86(s, 3H) |
| 6-062; | 7.54-7.47(m, 2H), 7.40-7.34(m, 2H), 7.23(brs, 2H), 3.85(s, 3 H), 3.70-3.27(m, 9H), 3.12-3.01(m, 1H), 2.98-2.82(m, 2H), 2.29(dd, J = 15.3, 11.1 Hz, 1H), 2.18(s, 3H), 2.16(s, 3H), 1.88(s, 3 H) |
| 6-063; | 7.54-7.47(m, 2H), 7.40-7.34(m, 2H), 7.23(brs, 2H), 3.84(s, 3 H), 3.40(dd, J = 18.6, 6.9 Hz, 1H), 3.10-2.80(m, 9H), 2.28(dd, J = 15.3, 11.1 Hz, 1H), 2.18(s, 3H), 2.17(s, 3H), 1.88(s, 3H) |
| 6-064; | 7.55-7.24(m, 6H), 3.86(s, 3H), 3.70-2.80(m, 12H), 2.57-2.04 (m, 6H), 1.89(s, 3H), 1.20-1.01(m, 3H) |
| 6-067; | 7.01(brs, 2H), 6.31-6.10(m, 2H), 3.84(s, 3H), 3.71(s, 3H), 2.95-2.80(m, 3H), 2.60-2.50(m, 1H), 2.24-2.05(m, 9H), 1.86(s, 3H), 1.50-1.40(m, 2H), 0.97-0.85(m, 3H) |
| 6-070; | 8.50-7.82(m, 2H), 7.38-7.10(m, 2H), 6.65-6.25(m, 2H), 5.05-4.75(m, 2H), 3.93-3.80(m, 3H), 3.45-1.82(m, 14H) (Proton peak corresponding to OH was not observed) |
| 6-075; | 11.45(brs, 1H), 6.90-6.82(m, 2H), 3.89(s, 3H), 3.69-3.33 and 3.05-1.85(m, 17H) |
| 6-077; | 11.36(brs, 1H), 7.59-7.34(m, 4H), 7.09-6.87(m, 2H), 4.00-3.78(m, 6H), 3.54-3.32(m, 1H), 3.09-2.50 and 2.38-1.81(m, 10H) |
| 6-078; | 7.58-7.34(m, 4H), 7.03(s, 1H), 6.90-6.86(m, 1H), 3.92-3.22 (m, 15H), 3.09-2.68(m, 3H), 2.40-2.13(m, 4H), 1.88(s, 3H) |
| 6-079; | 7.54-7.48(m, 2H), 7.43-7.38(m, 2H), 7.25-7.15(m, 2H), 7.05-6.68(m, 5H), 4.68(s, 2H), 3.87 and 3.84(s, 3H), 3.75 and 3.73(s, 3H), 3.41-2.11(m, 8H), 1.90-1.84(m, 3H) |
| 6-080; | 7.54-7.48(m, 2H), 7.41-7.35(m, 2H), 7.22(brs, 2H), 3.88-3.82(m, 3H), 3.58-3.20 and 3.05-2.78 and 2.68-1.70(m, 23H) |
| 6-081; | 7.58-7.32(m, 4H), 7.02(brs, 1H), 6.92-6.82(m, 1H), 3.98-3.69(m, 6H), 3.51-3.26(m, 1H), 3.11-2.73(m, 9H), 2.45-2.12(m, 4H), 1.87(s, 3H) |
| 6-082; | 7.66-7.12(m, 6H), 4.04-3.79(m, 3H), 3.39-2.79(m, 4H), 2.43-1.82(m, 10H), 1.38(s, 9H) |
| 6-083; | 8.12-7.91(m, 2H), 7.72-7.16(m, 9H), 5.92-5.58(m, 2H), 3.92-3.79(m, 3H), 3.42-2.74(m, 4H), 2.52-1.84(m, 10H) |
| 6-086; | 7.53-7.48(m, 2H), 7.40-7.36(m, 2H), 7.22(brs, 2H), 3.86(s, 3 H), 3.35-2.25(m, 8H), 2.20-2.12(m, 6H), 1.99-1.96(m, 3H), 1.88(s, 3H), 1.18-1.12(m, 3H) |
| 6-089; | 7.42-7.30(m, 1H), 7.25-7.12(m, 4H), 3.86(s, 3H), 3.70-3.26 (m, 9H), 3.15-2.79(m, 3H), 2.40-2.11(m, 7H), 1.88(s, 3H) |
| 6-090; | 7.51-7.45(m, 1H), 7.32-7.19(m, 2H), 7.09(brs, 2H), 3.86(s, 3 H), 3.70-3.26(m, 9H), 3.12-2.82(m, 3H), 2.36-2.23(m, 1H), 2.17(s, 3H), 2.14(s, 3H), 1.89(s, 3H) |
| 6-091; | 7.29-7.19(m, 2H), 7.03-6.93(m, 1H), 6.85-6.70(m, 2H), 6.67 (brs, 1H), 6.54(brs, 1H), 4.65(s, 2H), 3.84 and 3.83(s, 3H), 3.69-3.60(m, 3H), 3.38-2.77(m, 3H), 2.65-2.20 and 2.11-1.99 (m, 8H), 1.89-1.79(m, 3H) |
| 6-092; | 7.50-7.47(m, 1H), 7.31-6.92(m, 7H), 6.80-6.67(m, 2H), 4.69 (s, 2H), 3.85(s, 3H), 3.37-2.78(m, 4H), 2.40-2.28(m, 1H), 2.15-2.02(m, 6H), 1.88(s, 3H) |
| 6-093; | 7.65-7.57(m, 1H), 7.48-7.38(m, 1H), 7.25-7.15(m, 3H), 3.86 (s, 3H), 3.70-3.30(m, 9H), 3.11-2.82(m, 3H), 2.35-2.24(m, 1 H), 2.18(s, 3H), 2.16(s, 3H), 2.05(s, 3H) |
| 6-094; | 6.66(brs, 1H), 6.57-6.52(m, 1H), 3.85and3.84(s, 3H), 3.73-3.27(m, 13H), 3.09-2.77(m, 3H), 2.39-2.20(m, 3H), 2.12-2.04 (m, 3H), 1.86(s, 3H) |
| 6-095; | 6.66(brs, 1H), 6.55(brs, 1H), 3.86and3.84(s, 3H), 3.75-3.65(m, 3H), 3.41-3.18(m, 1H), 3.11-2.02(m, 16H), 1.86(s, 3H) |
| 6-097; | 6.63(brs, 2H), 4.13-4.05(m, 2H), 3.85(s, 3H), 3.75-3.68(m, 5 H), 3.43(s, 3H), 2.97-2.82(m, 3H), 2.62-2.50(m, 1H), 2.25-2.13(m, 1H), 2.09(s, 3H)), 2.06(s, 3H)), 1.88(s, 3H) |

TABLE 21-continued

| No. | ¹H-NMR (CDCl₃, Me₄Si, 300 MHz) |
|---|---|
| 6-100; | 7.67-7.51(m, 2H), 7.50-7.27(m, 5H), 7.14-6.87(m, 5H), 4.64 (s, 2H), 4.00-3.71(m, 6H), 3.52-3.30(m, 1H), 3.07-1.85(m, 10H) |
| 6-101; | 7.82(s, 1H), 7.25(s, 1H), 7.18(s, 1H), 7.09(brs, 2H), 3.87(s, 3H), 3.85(s, 3H), 3.10-2.55(m, 4H), 2.30-2.15(m, 7H), 1.90(s, 3H) |
| 6-105; | 8.49-8.40(m, 1H), 7.57-7.27(m, 5H), 7.14(brs, 1H), 3.76-3.65(m, 3H), 2.80-1.70(m, 14H) |
| 6-108; | 11.32(brs, 1H), 6.69-6.47(m, 2H), 4.00-3.71(m, 6H), 3.49-3.31(m, 1H), 3.00-2.62(m, 3H), 2.41-2.13(m, 4H), 1.97(s, 3H) |
| 6-109; | 6.66(brs, 1H), 6.60-6.50(m, 1H), 3.97-3.81(m, 3H), 3.79-3.66(m, 3H), 3.49-3.22(m, 1H), 3.10-2.68(m, 9H), 2.44-2.19(m, 4H), 2.18-2.02(m, 3H), 1.98-1.80(m, 3H) |
| 6-110; | 6.66(m, 1H), 6.57-6.52(m, 1H), 3.85 and 3.84(s, 3H), 3.70 and 3.68(s, 3H), 3.47-3.20(m, 5H), 3.07-2.78(m, 3H), 2.39-2.17(m, 4H), 2.10 and 2.08(s, 3H), 1.93-1.77(m, 7H) |
| 6-111; | 6.66(m, 1H), 6.57-6.50(m, 1H), 3.85 and 3.84(s, 3H), 3.70 and 3.68(s, 3H), 3.50-3.11(m, 5H), 3.06-2.67(m, 3H), 2.38-2.19(m, 4H), 2.09 and 2.07(s, 3H), 1.97-1.83(m, 3H), 1.67-1.38 (m, 6H) |
| 6-113; | 11.85-11.73 and 10.63-10.52 and 9.65-9.35(m, 1H), 7.07-6.98(m, 1H), 6.92-6.83(m, 1H), 4.33-4.05(m, 1H), 3.93-3.65(m, 6H), 3.57-1.82(m, 9H), 1.38-0.98(m, 3H) |
| 6-114; | 11.60-11.47 and 10.20-10.07 and 7.72-7.37(m, 1H), 6.80-6.53(m, 2H), 4.43-3.65(m, 6H), 3.58-1.77(m, 13H), 1.40-0.97(m, 3H) |
| 6-115; | 6.70-6.45(m, 2H), 3.88-3.77(m, 3H), 3.70-3.60(m, 3H), 3.48-2.62(m, 8H), 2.37-2.13(m, 4H), 2.11-1.99(m, 3H), 1.94-1.78(m, 3H), 1.13-0.82(m, 6H) |
| 6-116; | 6.75-6.47(m, 2H), 3.91-3.78(m, 3H), 3.74-3.64(m, 3H), 3.56-3.19(m, 5H), 3.02-2.41(m, 2H), 2.40-1.81(m, 9H), 1.41-1.00(m, 8H) |
| 6-117; | 6.71-6.48(m, 2H), 3.93-3.62(m, 6H), 3.31-2.70(m, 3H), 2.42-1.81(m, 11H), 1.21-1.05(m, 9H) |
| 6-118; | 8.00-7.94(m, 2H), 7.50-7.41(m, 2H), 6.70-6.63(m, 1H), 6.57-6.49(m, 1H), 3.91-3.60 (m, 6H), 3.50-3.22(m, 1H), 3.18-2.82 and 2.46-2.09(m, 16H), 1.90-1.85(m, 3H) |
| 6-119; | 7.43-7.28(m, 3H), 6.97-6.87(m, 2H), 6.68(brs, 1H), 6.58(brs, 1H), 3.89-3.82(m, 3H), 3.75-3.67(m, 3H), 3.37-2.78(m, 4H), 2.49-2.28(m, 4H), 2.15-2.06(m, 3H), 1.98-1.82(m, 3H) |
| 6-120; | 6.71-6.38(m, 3H), 6.19-5.90(m, 2H), 3.91-3.79(m, 3H), 3.73-3.60(m, 3H), 3.40-3.21(m, 1H), 3.10-2.75 and 2.70-2.20 (m, 7H), 2.17-2.00(m, 3H), 1.97-1.80(m, 3H) |
| 6-121; | 8.00-7.90(m, 2H), 7.67-7.53(m, 1H), 7.50-7.37(m, 2H), 6.69-6.63(m, 1H), 6.57-6.50(m, 1H), 3.91-3.82(m, 3H), 3.69-3.62(m, 3H), 3.49-3.32(m, 1H), 3.15-2.65(m, 3H), 2.46-2.22(m, 4H), 2.20-2.02(m, 3H), 1.97-1.80(m, 3H) |
| 6-122; | 6.67(brs, 1H), 6.55(brs, 1H), 4.72-4.54(m, 2H), 3.91-3.82(m, 3H), 3.78-3.65(m, 3H), 3.40-1.80(m, 17H) |
| 6-123; | 6.70-6.47(m, 2H), 4.22-3.50(m, 6H), 3.30-2.40(m, 4H), 2.29 (s, 3H), 2.15-1.79(m, 6H), 1.40-1.02(m, 12H) |
| 6-124; | 6.72-6.50(m, 2H), 3.96-3.63(m, 6H), 3.38-2.68 and 2.42-1.25(m, 23H) |
| 6-125; | 6.79-6.53(m, 2H), 4.00-3.62(m, 6H), 3.30-2.65 and 2.40-1.81(m, 20H) |
| 6-126; | 6.67(brs, 1H), 6.56(brs, 1H), 3.98-3.80(m, 3H), 3.79-3.64(m, 3H), 3.58-2.71(m, 6H), 2.69-2.52(m, 2H), 2.42-2.20(m, 4H), 2.19-1.80(m, 8H) |
| 6-127; | 6.66(brs, 1H), 6.54(brs, 1H), 3.88-2.83(m, 18H), 2.39-1.77(m, 9H), 1.38-1.02(m, 3H) |
| 7-001; | 7.25-7.15(m, 2H), 4.20-4.05(m, 1H), 3.90-3.65(m, 4H), 3.30-2.00(m, 10H), 1.15-1.00(m, 3H) (Proton peak corresponding to OH was not observed) |
| 7-017; | 8.90-8.80(m, 2H), 8.03(brs, 2H), 7.70-7.60(m, 1H), 3.00-2.80(m, 3H), 2.70-2.60(m, 1H), 2.35-2.25(m, 1H), 2.12(s, 9H) (Proton peak corresponding to OH was not observed) |
| 7-027; | 7.02(brs, 1H), 6.88(brs, 1H), 3.91-3.62(m, 3H), 3.51-1.97(m, 12H) |
| 7-030; | 9.05(brs, 1H), 6.81-6.55(m, 2H), 3.86-3.81(m, 3H), 3.52-2.53(m, 3H), 2.52-2.03(m, 11H) |
| 9-003; | 7.25-7.19(m, 2H), 7.08(s, 2H), 7.02-6.92(m, 1H), 6.73-6.54 (m, 2H), 4.67-4.57(m, 2H), 3.85-3.77(m, 3H), 3.41-2.38(m, 5 H), 2.24-1.95(m, 10H), 1.17-0.99(m, 6H) |
| 9-004; | 11.95(s, 1H), 7.85(s, 1H), 7.59(s, 1H), 7.33(s, 2H), 3.91(s, 3H), 3.50-3.29(m, 3H), 3.03-2.92(m, 1H), 2.87-2.77(m, 1H), 2.50-2.09(m, 8H), 1.17-1.05(m, 6H) |
| 9-005; | 11.79(s, 1H), 7.09(s, 2H), 3.91(s, 3H), 3.50-3.25(m, 2H), 3.10-2.75(m, 2H), 2.48-2.35(m, 1H), 2.33-2.21(m, 1H), 2.19-2.00(m, 9H), 1.19-1.05(m, 6H) |

TABLE 21-continued

| No. | ¹H-NMR (CDCl₃, Me₄Si, 300 MHz) |
|---|---|
| 9-007; | 12.17(s, 1H), 7.85(s, 1H), 7.59(s, 1H), 7.38-7.28(m, 2H), 3.94 (s, 3H), 3.38-3.25(m, 1H), 2.92(dd, J = 17.7, 7.5 Hz, 1H), 2.47-2.35(m, 1H), 2.30-2.07(m, 8H), 1.10-0.82(m, 5H) |
| 9-012; | 7.89(s, 1H), 7.64(s, 1H), 7.32(brs, 2H), 7.23-7.11(m, 2H), 6.99-6.88(m, 1H), 6.75-6.61(m, 2H), 4.70-4.59(m, 2H), 4.47-4.32(m, 2H), 3.72-1.83(m, 14H) |
| 9-013; | 7.28-7.18(m, 2H), 7.07(brs, 2H), 7.03-6.95(m, 1H), 6.70-6.56(m, 2H), 4.70-4.63(m, 2H), 4.48-4.32(m, 2H), 3.70-3.56(m, 1H), 3.30-1.82(m, 16H) |
| 9-014; | 7.82(s, 1H), 7.59(s, 1H), 7.25(brs, 2H), 4.50-4.25(m, 2H), 3.52-3.10(m, 1H), 3.03-1.70(m, 12H), 1.17-0.88(m, 6H) |
| 9-018; | 11.60(brs, 1H), 7.20(s, 2H), 4.25-4.05(m, 2H), 3.70-3.20(m, 6H), 3.00-2.70(m, 1H), 2.50-1.80(m, 10H), 1.20-1.00(m, 6H) |
| 9-019; | 11.90(brs, 1H), 7.20(brs, 2H), 4.30-4.20(m, 2H), 3.70-3.60(m, 2H), 3.38(s, 3H), 3.35-3.20(m, 1H), 2.90-2.85(m, 1H), 2.55-2.40(m, 1H), 2.25-2.00(m, 9H), 1.10-0.75(m, 4H) |
| 9-020; | 11.95(brs, 1H), 7.86(s, 1H), 7.60(s, 1H), 7.32(brs, 2H), 4.36-4.21(m, 2H), 3.71-3.59(m, 2H), 3.45-3.22(m, 4H), 3.00-2.86(m, 1H), 2.56-2.04(m, 10H), 1.15-0.69(m, 4H) |
| 9-021; | 11.79(s, 1H), 7.09(brs, 2H), 4.32-4.21(m, 2H), 3.70-3.55(m, 2H), 3.38(s, 3H), 3.35-3.22(m, 1H), 2.96-2.83(m, 1H), 2.52-2.40(m, 1H), 2.30-2.00(m, 12H), 1.09-0.71(m, 4H) |
| 9-022; | 11.67(brs, 1H), 7.86(s, 1H), 7.60(s, 1H), 7.33(brs, 2H), 4.29-4.20(m, 2H), 3.69-3.40(m, 7H), 3.03-2.75(m, 2H), 2.52-2.08(m, 8H), 1.18-1.01(m, 6H) |
| 9-023; | 11.52(brs, 1H), 7.09(brs, 2H), 4.30-4.12(m, 2H), 3.69-3.17(m, 7H), 3.03-2.73(m, 2H), 2.58-1.91(m, 11H), 1.21-0.99(m, 6H) |
| 9-025; | 7.58-7.19(m, 6H), 4.50-4.32(m, 2H), 3.72-3.22(m, 9H), 3.14-2.71(m, 3H), 2.41-1.82(m, 10H) |
| 9-026; | 7.61-7.21(m, 6H), 4.56-4.32(m, 2H), 3.49-3.30(m, 1H), 3.19-2.67(m, 9H), 2.48-1.87(m, 10H) |
| 9-027; | 7.57-7.11(m, 8H), 7.02-6.87(m, 1H), 6.75-6.60(m, 2H), 4.70-4.59(m, 2H), 4.49-4.34(m, 2H), 3.33-1.87(m, 14H) |
| 9-029; | 7.07(brs, 2H), 4.75-4.50(m, 2H), 3.10-2.90(m, 6H), 2.85-1.85(m, 14H) (Proton peak corresponding to OH was not observed) |
| 9-030; | 12.00-11.76(m, 1H), 7.21(brs, 2H), 6.04-5.95(m, 1H), 5.87-5.70(m, 1H), 4.70-4.57(m, 1H), 3.48-3.33(m, 1H), 3.00-2.53 and 2.30-1.49(m, 19H) |
| 11-001; | 7.39-7.12(m, 5H), 6.86(brs, 2H), 4.96(s, 2H), 3.81(s, 3H), 3.27-3.13(m, 1H), 2.61-2.22(m, 6H), 2.06(brs, 6H), 1.87-1.77(m, 3H), 1.26(s, 3H) |
| 12-001; | 7.37-7.25(m, 3H), 7.14-7.04(m, 2H), 6.86(brs, 2H), 4.71(s, 2H), 3.83(s, 3H), 2.88-2.77(m, 2H), 2.47-2.23(m, 5H), 2.15-2.02(m, 6H), 1.88(s, 3H), 1.37-1.22(m, 3H) |
| 12-002; | 11.31(brs, 1H), 6.87(brs, 2H), 3.89(s, 3H), 2.97-1.20(m, 19H) |
| 13-001; | 11.60 and 11.57(brs, 1H), 7.09-6.85(m, 2H), 3.96-3.69(m, 6H), 3.47-3.25(m, 1H), 3.02-2.07(m, 9H), 1.19-1.02(m, 3H) |
| 13-005; | 6.66(s, 1H), 6.55(s, 1H), 3.91-2.45 and 2.39-2.00 and 1.97-1.40(m, 26H), 0.94-0.64(m, 4H) |
| 13-006; | 6.64(s, 1H), 6.52(s, 1H), 3.95-3.60(m, 6H), 3.36-2.64(m, 3H), 2.60-2.42(m, 1H), 2.38-2.00(m, 7H), 1.97-1.78(m, 1H), 1.13 (s, 9H), 0.94-0.61(m, 4H) |
| 14-001; | 10.53 and 10.48(brs, 1H), 7.10-6.82(m, 2H), 3.82-3.60(m, 3H), 3.50-3.21 and 3.10-2.79(m, 3H), 2.31-2.07 and 1.31-0.82(m, 10H) |
| 14-002; | 10.05 and 9.99(brs, 1H), 7.10-6.83(m, 2H), 3.84-3.59(m, 3H), 3.39-1.02(m, 13H) |
| 15-001; | 10.10-9.96(m, 1H), 6.85-6.52(m, 2H), 4.81-4.60(m, 2H), 3.92-3.61(m, 3H), 3.53-3.28(m, 1H), 3.04-1.86(m, 14H) |
| 15-002; | 10.89-10.70(m, 1H), 6.89-6.51(m, 2H), 6.10-5.84(m, 1H), 5.50-5.11(m, 2H), 4.76-4.50(m, 2H), 3.93-3.60(m, 3H), 3.50-3.23(m, 1H), 3.03-1.84(m, 13H) |
| 15-003; | 11.22(brs, 1H), 6.78-6.52(m, 2H), 4.00-3.61(m, 5H), 3.50-3.23(m, 1H), 3.02-2.49(m, 3H), 2.40-1.83(m, 10H), 1.19-1.03(m, 1H), 0.64-0.47(m, 2H), 0.38-0.18(m, 2H) |
| 15-004; | 10.90-10.60 and 8.10-7.60(m, 1H), 6.80-6.55(m, 2H), 4.40-4.06(m, 2H), 3.90-3.70(m, 3H), 3.70-3.53(m, 2H), 3.37(s, 3H), 3.03-1.85(m, 14H) |
| 15-005; | 6.85-6.50(m, 2H), 4.55-4.32(m, 2H), 3.85-3.67(m, 3H), 3.30-2.25(m, 8H), 2.20-1.85(m, 6H) (Proton peak corresponding to OH was not observed) |
| 15-006; | 8.20-7.95 and 7.15-6.95(m, 1H), 6.80-6.55(m, 2H), 4.69(s, 2H), 3.77(s, 3H), 3.45-2.40(m, 4H), 2.33(s, 3H), 2.20-1.85(m, 7H) |
| 15-007; | 6.70-6.52(m, 2H), 4.25-4.15(m, 2H), 3.80-3.22(m, 16H), 3.10-2.70(m, 4H), 2.40-2.02(m, 7H), 1.95-1.85(m, 3H) |

TABLE 21-continued

| No. | $^1$H-NMR (CDCl$_3$, Me$_4$Si, 300 MHz) |
|---|---|
| 15-008; | 6.70-6.48(m, 2H), 4.25-4.00(m, 2H), 3.75-3.60(m, 5H), 3.57-3.22(m, 6H), 3.20-2.28(m, 11H), 2.20-1.88(m, 6H) |
| 15-009; | 6.70-6.48(m, 2H), 4.50-4.35(m, 2H), 3.80-3.63(m, 3H), 3.35-2.50(m, 4H), 2.48-1.85(m, 10H), 1.15-1.10(m, 9H) |
| 15-010; | 6.70-6.50(m, 2H), 4.50-4.30(m, 2H), 3.75-3.65(m, 3H), 3.45-3.20(m, 1H), 3.10-2.70(m, 9H), 2.45-1.85(m, 10H) |
| 15-011; | 6.72-6.55(m, 2H), 4.72-4.65(m, 2H), 3.73(s, 3H), 3.45-2.70 (m, 7H), 2.55-1.90(m, 10H) |
| 15-012; | 6.65(brs, 1H), 6.53(brs, 1H), 4.72-4.68(m, 2H), 3.72-3.68(m, 3H), 3.45-2.70(m, 8H), 2.45-1.85(m, 10H), 1.15-0.90(m, 6H) |
| 15-013; | 6.66(brs, 1H), 6.55(brs, 1H), 4.69-4.61(m, 2H), 3.84-3.68(m, 6H), 3.40-2.68 and 2.59-2.23 and 2.20-1.88(m, 15H) |
| 15-014; | 6.72-6.47(m, 2H), 3.98-3.80(m, 2H), 3.79-3.63(m, 3H), 3.39-2.60 and 2.41-2.20(m, 7H), 2.17-2.01(m, 4H), 1.98-1.83 (m, 3H), 1.65-1.03(m, 10H), 0.63-0.42(m, 2H), 0.37-0.17(m, 2H) |
| 15-015; | 7.39-7.18 and 7.09-6.49(m, 7H), 6.08-5.89(m, 1H), 5.33-5.15(m, 2H), 4.69-4.48(m, 4H), 3.72-3.61(m, 3H), 3.39-2.72(m, 4H), 2.48-2.21(m, 4H), 2.17-1.80(m, 6H) |
| 15-016; | 6.69-6.62(m, 1H), 6.58-6.51(m, 1H), 4.68-4.61(m, 2H), 3.75-3.66(m, 3H), 3.47-3.18(m, 4H), 3.08-2.72(m, 3H), 2.49-2.21 and 2.13-2.02 and 1.98-1.79(m, 16H) |
| 15-017; | 6.70-6.64(m, 1H), 6.58-6.50(m, 1H), 6.09-5.91(m, 1H), 5.35-5.16(m, 2H), 4.60-4.50(m, 2H), 3.74-3.63(m, 3H), 3.58-3.23(m, 5H), 3.08-2.76(m, 3H), 2.44-2.18(m, 11H), 2.13-2.03(m, 3H), 1.89(s, 3H) |
| 15-018; | 6.70-6.63(m, 1H), 6.58-6.50(m, 1H), 3.92-3.81(m, 2H), 3.78-3.62(m, 3H), 3.54-2.72(m, 11H), 2.40-2.21(m, 4H), 2.17-2.07(m, 3H), 1.98-1.82(m, 3H), 1.70-1.05(m, 4H), 0.61-0.46(m, 2H), 0.32-0.20(m, 2H) |

TEST EXAMPLE

Subsequently, usefulness of the compound of the present invention as a herbicide will be specifically described in the following Test Examples. The present invention, however, is not limited to these Test Examples.

[Test Example 1] Herbicidal Activity Test by Application Before Weed Generation in Submerged Conditions After alluvial soil was placed into 1/10000 are of Wagner pot, water was poured and mixed to form a submerged condition having a water depth of 4 cm. Seeds of *Echinochloa oryzacola* Vasing., *Scirpus juncoides*, and *Monochoria vaginalis* were sowed in a mixed manner in the above pot and thereafter 2.5 leaf stage rice plant seedlings were transplanted thereto. On the day of sowing seeds, the emulsion agent of the compound of the present invention prepared in accordance with Formulation Example 2 was diluted with water so as to be a predetermined herbicide amount and the diluted emulsion agent was applied to the surface of the water. The pot was placed in a greenhouse of 25° C. to 30° C. to grow plant. 3 weeks later from the herbicide application, the effect to each plant was investigated in accordance with the following criteria. The results are listed in Table 22.

CRITERIA

5 Herbicidal ratio of 90% or more (almost completely withered)

4 Herbicidal ratio of 70% or higher and lower than 90%

3 Herbicidal ratio of 40% or higher and lower than 70%

2 Herbicidal ratio of 20% or higher and lower than 40%

1 Herbicidal ratio of 5% or higher and lower than 20%

0 Herbicidal ratio of 5% or lower (almost no effect)

[Test Example 2] Herbicidal Activity Test by Application During Weed Generation in Submerged Conditions After alluvial soil was placed into 1/10000 are of Wagner pot, water was poured and mixed to form a submerged condition having a water depth of 4 cm. Seeds of *Echinochloa oryzacola* Vasing., *Scirpus juncoides*, and *Monochoria vaginalis* were sowed in a mixed manner in the above pot and the pot was placed in the greenhouse of 25° C. to 30° C. to grow the plants. When *Echinochloa oryzacola* Vasing., *Scirpus juncoides*, and *Monochoria vaginalis* were grown to one leaf stage to two leaf stage, the emulsion agent of the compound of the present invention prepared in accordance with Formulation Example 2 was diluted with water so as to be a predetermined herbicide amount and the diluted emulsion agent was applied to the surface of the water. 3 weeks later from the herbicide application, the effect to each plant was investigated in accordance with the criteria of Test Example 1. The results are listed in Table 23.

[Test Example 3] Herbicidal Effect Test by Foliage Application

After alluvial soil was placed into 1/10000 are of Wagner pot, water was poured and mixed to form a submerged condition having a water depth of 0.1 cm to 0.5 cm. Seeds of *Echinochloa crus-galli* var *crus-galli*, *Leptochloa chinensis*, *Cyperus difformis*, and rice were sowed and the pot was placed in the greenhouse of 25° C. to 30° C. to grow the plants. After the plants were grown for 14 days, the emulsion agent of the compound of the present invention prepared in accordance with Formulation Example 2 was diluted with water so as to be a predetermined herbicide amount and the diluted emulsion agent was uniformly applied to a foliage part with a small-size spray. 3 weeks later from the herbicide application, the effect to each plant was investigated in accordance with the criteria of Test Example 1. The results are listed in Table 24.

[Test Example 4] Herbicidal Effect Test by Soil Treatment

Sterilized diluvial soil was placed in a plastic box having a length of 21 cm, a width of 13 cm, and a depth of 7 cm. Each of the seeds of *Digitaria ciliaris, Setaria viridis, Echinochloa crus-galli* var *crus-galli, Avena fatua, Alopecurus myosuroides, Lolium multiflorum* Lam., *Apera spica-venti, Abutilon theophrasti, Amaranthus retroflexus, Chenopodium album, Stellaria media, Galium spurium, Veronica persica*, corn, soybean, rice, wheat, beet, and rapeseed was sowed in a spot-like manner and was covered with the soil of a thickness of about 1.5 cm. Subsequently, the emulsion agent of the compound present invention prepared in accordance with Formulation Example 2 was diluted with water so as to be a predetermined herbicide amount and the diluted emulsion agent was uniformly applied to the surface of the soil with a small-size spray. The plastic box was placed in a greenhouse of 25° C. to 30° C. to grow plant. 3 weeks later from the herbicide application, the effect to each plant was investigated in accordance with the criteria of Test Example 1. The results are listed in Table 25.

[Test Example 5] Herbicidal Effect Test by Foliage Application

Sterilized diluvial soil was placed in a plastic box having a length of 21 cm, a width of 13 cm, and a depth of 7 cm. Each of the seeds of *Digitaria ciliaris, Setaria viridis, Echinochloa crus-galli* var *crus-galli, Avena fatua, Alopecurus myosuroides, Lolium multiflorum* Lam., *Apera spica-venti, Abutilon theophrasti, Amaranthus retroflexus, Chenopodium album, Stellaria media, Galium spurium, Veronica persica*, corn, soybean, rice plant, wheat, beet, and rapeseed was sowed in a spot-like manner and was covered with the soil of a thickness of about 1.5 cm. Thereafter, the plants were grown in the greenhouse of 25° C. to 30° C. After the plants were grown for 14 days, the emulsion agent of the compound of the present invention prepared in accordance with Formulation Example 2 was diluted with water so as to be a predetermined herbicide amount and the diluted emulsion agent was uniformly applied to a foliage part with a small-size spray. 3 weeks later from the herbicide application, the effect to each plant was investigated in accordance with the criteria of Test Example 1. The results are listed in Table 26.

The symbols in Table 22 to Table 26 have the following meanings.

A: *Echinochloa oryzacola* Vasing., B: *Scirpus juncoides*, C: *Monochoria vaginalis*, D: *Leptochloa chinensis*, E: *Cyperus iria*, F: *Digitaria ciliaris*, G: *Setaria viridis*, H: *Echinochloa crus-galli* var *crus-galli*, I: *Avena fatua*, J: *Alopecurus myosuroides*, K: *Lolium multiflorum* Lam., L: *Apera spica-venti*, M: *Abutilon theophrasti*, N: *Amaranthus retroflexus*, O: *Chenopodium album*, P: *Stellaria media*, Q: *Galium spurium*, R: *Veronica persica*, a: transplanted rice plant, b: directly sowed rice plant, c: corn, d: soybean, e: wheat, f: beet, and g: rapeseed The application herbicide amount (g/ha) means an amount that a concentration is adjusted so that, when an application amount is converted into per hectare, the herbicide is applied by the number of grams (g) of the described value.

TABLE 22

| No. | Application herbicide amount (g/ha) | A | B | C | a |
|---|---|---|---|---|---|
| 1-001 | 320 | 0 | 0 | 0 | 0 |
| 1-002 | 320 | 5 | 4 | 4 | 5 |
| 1-003 | 320 | 5 | 4 | 5 | 5 |
| 1-004 | 320 | 5 | 5 | 4 | 5 |
| 1-005 | 320 | 5 | 5 | 5 | 5 |
| 1-006 | 320 | 5 | 3 | 3 | 4 |
| 1-007 | 320 | 0 | 0 | 0 | 0 |
| 1-008 | 320 | 5 | 3 | 0 | 0 |
| 1-009 | 320 | 0 | 0 | 0 | 0 |
| 1-010 | 320 | 5 | 5 | 2 | 5 |
| 1-011 | 320 | 0 | 0 | 0 | 0 |
| 1-012 | 320 | 0 | 0 | 0 | 0 |
| 1-013 | 320 | 0 | 0 | 0 | 0 |
| 1-014 | 320 | 5 | 5 | 2 | 5 |
| 1-015 | 320 | 5 | 5 | 2 | 5 |
| 1-016 | 320 | 5 | 5 | 4 | 5 |
| 1-017 | 320 | 5 | 5 | 2 | 5 |
| 1-018 | 320 | 5 | 5 | 2 | 5 |
| 1-019 | 320 | 5 | 5 | 2 | 5 |
| 1-020 | 320 | 5 | 5 | 4 | 5 |
| 1-021 | 320 | 0 | 0 | 0 | 0 |
| 1-022 | 320 | 5 | 5 | 2 | 5 |
| 1-023 | 320 | 4 | 0 | 0 | 1 |
| 1-024 | 320 | 5 | 5 | 2 | 5 |
| 1-025 | 320 | 4 | 2 | 0 | 3 |
| 1-026 | 320 | 5 | 5 | 5 | 5 |
| 1-027 | 320 | 4 | 3 | 3 | 4 |
| 1-028 | 320 | 5 | 5 | 1 | 5 |
| 1-029 | 320 | 4 | 0 | 0 | 5 |
| 1-030 | 320 | 2 | 0 | 0 | 1 |
| 1-031 | 320 | 5 | 4 | 2 | 0 |
| 1-032 | 320 | 5 | 5 | 3 | 5 |
| 1-033 | 320 | 5 | 4 | 1 | 5 |
| 1-034 | 320 | 5 | 4 | 2 | 5 |
| 1-035 | 320 | 5 | 5 | 2 | 5 |
| 1-036 | 320 | 5 | 4 | 1 | 5 |
| 1-037 | 320 | 0 | 0 | 0 | 0 |
| 1-038 | 320 | 5 | 5 | 3 | 5 |
| 1-039 | 320 | 5 | 5 | 2 | 5 |
| 1-040 | 320 | 3 | 2 | 0 | 4 |
| 1-041 | 320 | 5 | 5 | 0 | 5 |
| 1-042 | 320 | 5 | 5 | 4 | 5 |
| 1-043 | 320 | 5 | 5 | 2 | 5 |
| 1-044 | 320 | 5 | 5 | 4 | 5 |
| 1-045 | 320 | 5 | 2 | 0 | 3 |
| 1-046 | 320 | 5 | 5 | 4 | 5 |
| 1-047 | 320 | 4 | 0 | 0 | 1 |
| 1-048 | 320 | 5 | 4 | 1 | 5 |
| 1-049 | 320 | 0 | 0 | 0 | 0 |
| 1-050 | 320 | 4 | 2 | 3 | 4 |
| 1-051 | 320 | 5 | 5 | 0 | 5 |
| 1-052 | 320 | 5 | 5 | 0 | 5 |
| 1-053 | 320 | 5 | 3 | 0 | 5 |
| 1-054 | 320 | 5 | 0 | 0 | 5 |
| 1-055 | 320 | 5 | 3 | 0 | 5 |
| 1-056 | 320 | 5 | 5 | 4 | 5 |
| 1-057 | 320 | 5 | 3 | 2 | 4 |
| 1-058 | 320 | 5 | 0 | 0 | 5 |
| 1-059 | 320 | 5 | 3 | 2 | 4 |
| 1-060 | 320 | 5 | 4 | 3 | 5 |
| 1-062 | 320 | 5 | 2 | 1 | 5 |
| 1-063 | 320 | 5 | 3 | 0 | 5 |
| 1-064 | 320 | 5 | 5 | 1 | 4 |
| 1-065 | 320 | 5 | 5 | 0 | 5 |
| 1-066 | 320 | 4 | 0 | 0 | 5 |
| 1-067 | 320 | 5 | 5 | 1 | 5 |
| 1-068 | 320 | 5 | 4 | 3 | 5 |
| 1-069 | 320 | 5 | 4 | 2 | 5 |
| 1-070 | 320 | 4 | 0 | 0 | 4 |
| 1-071 | 320 | 5 | 4 | 0 | 5 |
| 1-072 | 320 | 5 | 4 | | 5 |
| 1-073 | 320 | 5 | 5 | 1 | 5 |

TABLE 22-continued

| No. | Application herbicide amount (g/ha) | A | B | C | a |
|---|---|---|---|---|---|
| 1-074 | 320 | 5 | 5 | 4 | 5 |
| 1-075 | 320 | 5 | 4 |   | 5 |
| 1-076 | 192 | 4 | 4 | 0 | 5 |
| 1-077 | 320 | 1 | 2 | 0 | 1 |
| 1-078 | 320 | 5 | 2 | 0 | 5 |
| 1-079 | 320 | 5 | 5 | 3 | 5 |
| 1-080 | 320 | 5 | 5 | 3 | 5 |
| 1-081 | 320 | 5 | 5 | 2 | 5 |
| 1-082 | 320 | 5 | 5 | 2 | 5 |
| 1-083 | 320 | 5 | 4 | 1 | 5 |
| 1-085 | 320 | 4 | 0 | 0 | 3 |
| 1-086 | 320 | 5 | 0 | 0 | 3 |
| 1-087 | 320 | 5 | 5 | 1 | 5 |
| 1-088 | 320 | 5 | 5 | 0 | 5 |
| 1-089 | 320 | 5 | 5 | 3 | 5 |
| 1-090 | 320 | 5 | 5 | 1 | 5 |
| 1-091 | 320 | 5 | 5 | 0 | 4 |
| 1-092 | 320 | 5 | 5 | 0 | 5 |
| 1-093 | 320 | 5 | 5 | 2 | 5 |
| 1-094 | 320 | 5 | 5 | 1 | 5 |
| 1-095 | 320 | 5 | 5 | 2 | 5 |
| 1-096 | 320 | 5 | 5 | 0 | 5 |
| 1-097 | 320 | 3 | 0 | 0 | 3 |
| 1-098 | 320 | 5 | 5 | 4 | 5 |
| 1-099 | 320 | 5 | 4 | 2 | 5 |
| 1-100 | 320 | 5 | 5 | 3 | 5 |
| 1-101 | 320 | 5 | 5 | 2 | 5 |
| 1-102 | 320 | 5 | 3 |   | 5 |
| 1-103 | 320 | 5 | 5 | 1 | 5 |
| 1-104 | 320 | 5 | 4 | 1 | 3 |
| 1-105 | 320 | 5 | 5 | 4 | 5 |
| 1-106 | 320 | 5 | 3 |   | 5 |
| 1-107 | 320 | 5 | 4 | 1 | 3 |
| 1-108 | 320 | 5 | 4 | 3 | 5 |
| 1-109 | 320 | 5 | 5 | 3 | 5 |
| 1-110 | 320 | 3 | 0 | 0 | 5 |
| 1-111 | 320 | 5 | 2 | 1 | 5 |
| 1-112 | 320 | 5 | 5 | 5 | 5 |
| 1-113 | 320 | 5 | 4 | 4 | 3 |
| 1-114 | 320 | 5 | 5 | 5 | 5 |
| 1-115 | 320 | 5 | 3 | 4 | 1 |
| 1-116 | 320 | 5 | 4 | 5 | 3 |
| 1-117 | 320 | 5 | 5 | 5 | 5 |
| 1-118 | 320 | 5 | 1 | 2 | 4 |
| 1-119 | 320 | 1 | 0 | 0 | 3 |
| 1-120 | 320 | 4 | 5 | 3 | 0 |
| 1-121 | 320 | 5 | 5 | 3 | 5 |
| 1-122 | 320 | 5 | 5 | 0 | 5 |
| 1-123 | 320 | 5 | 4 | 3 | 5 |
| 1-124 | 320 | 1 | 0 | 0 | 0 |
| 1-125 | 320 | 3 | 0 | 1 | 5 |
| 1-126 | 320 | 4 | 0 | 0 | 3 |
| 1-130 | 320 | 3 | 0 | 0 | 3 |
| 1-131 | 320 | 5 | 4 | 1 | 4 |
| 1-133 | 320 | 4 | 0 | 0 | 1 |
| 1-134 | 320 | 5 | 5 | 1 | 5 |
| 1-135 | 320 | 5 | 5 | 1 | 5 |
| 1-136 | 320 | 5 | 5 | 5 | 5 |
| 1-137 | 320 | 5 | 5 | 5 | 5 |
| 1-138 | 320 | 5 | 5 | 5 | 5 |
| 1-139 | 320 | 5 | 4 | 1 | 5 |
| 1-140 | 320 | 5 | 5 | 1 | 5 |
| 1-142 | 320 | 5 | 5 | 2 | 5 |
| 1-143 | 320 | 4 | 4 | 1 | 5 |
| 1-144 | 320 | 5 | 5 | 3 | 5 |
| 1-145 | 320 | 5 | 5 | 1 | 5 |
| 1-146 | 320 | 5 | 5 | 1 | 5 |
| 1-147 | 320 | 5 | 5 | 1 | 5 |
| 1-148 | 320 | 5 | 4 | 3 | 5 |
| 1-149 | 320 | 5 | 5 | 1 | 5 |
| 1-150 | 320 | 5 | 3 | 0 | 5 |
| 1-151 | 320 | 5 | 3 | 0 | 4 |
| 1-152 | 320 | 4 | 0 | 0 | 2 |
| 1-153 | 320 | 5 | 3 | 0 | 4 |
| 1-154 | 320 | 5 | 4 | 2 | 5 |
| 1-155 | 320 | 5 | 5 | 1 | 5 |
| 1-156 | 320 | 5 | 5 | 1 | 5 |
| 1-159 | 320 | 5 | 0 | 0 | 1 |
| 1-160 | 320 | 5 | 4 | 2 | 5 |
| 1-161 | 320 | 5 | 4 | 1 | 4 |
| 1-162 | 320 | 5 | 4 | 3 | 5 |
| 1-163 | 320 | 5 | 4 | 0 | 5 |
| 1-166 | 320 | 5 | 0 | 0 | 0 |
| 2-001 | 102 | 4 | 0 | 0 | 4 |
| 2-002 | 320 | 0 | 0 | 0 | 0 |
| 2-003 | 320 | 0 | 0 | 0 | 0 |
| 2-005 | 269 | 3 | 0 | 0 | 4 |
| 2-006 | 320 | 5 | 2 | 3 | 3 |
| 2-007 | 320 | 3 | 2 | 0 | 4 |
| 2-008 | 320 | 0 | 0 | 0 | 0 |
| 2-009 | 320 | 0 | 0 | 0 | 0 |
| 2-010 | 320 | 0 | 0 | 0 | 0 |
| 2-011 | 320 | 0 | 0 | 0 | 0 |
| 2-012 | 320 | 0 | 0 | 0 | 0 |
| 2-013 | 320 | 0 | 0 | 0 | 0 |
| 2-014 | 320 | 4 | 3 | 1 | 1 |
| 2-015 | 320 | 0 | 4 | 0 | 0 |
| 2-016 | 320 | 4 | 0 | 0 | 4 |
| 2-017 | 320 | 5 | 5 | 3 | 5 |
| 2-018 | 320 | 5 | 2 | 1 | 4 |
| 2-020 | 320 | 2 | 0 | 0 | 3 |
| 2-021 | 320 | 4 | 4 | 2 | 5 |
| 2-022 | 320 | 1 | 0 | 0 | 3 |
| 2-024 | 320 | 2 | 0 | 0 | 4 |
| 2-025 | 320 | 3 | 0 | 0 | 2 |
| 2-026 | 320 | 3 | 3 | 0 | 4 |
| 2-028 | 320 | 3 | 0 | 0 | 3 |
| 2-030 | 320 | 4 | 0 | 0 | 3 |
| 2-031 | 320 | 4 | 4 | 2 | 5 |
| 2-032 | 320 | 4 | 4 | 1 | 5 |
| 3-001 | 320 | 0 | 0 | 0 | 0 |
| 3-002 | 320 | 0 | 0 | 0 | 0 |
| 4-001 | 320 | 0 | 0 | 0 | 0 |
| 5-001 | 320 | 0 | 0 | 0 | 0 |
| 5-002 | 320 | 0 | 0 | 0 | 0 |
| 6-001 | 320 | 5 | 0 | 0 | 5 |
| 6-002 | 320 | 3 | 0 | 0 | 3 |
| 6-003 | 320 | 5 | 4 | 1 | 5 |
| 6-004 | 320 | 5 | 5 | 2 | 5 |
| 6-005 | 320 | 5 | 5 | 3 | 5 |
| 6-006 | 320 | 5 | 5 | 1 | 5 |
| 6-007 | 320 | 5 | 5 | 1 | 5 |
| 6-008 | 320 | 5 | 5 | 5 | 5 |
| 6-009 | 320 | 5 | 2 | 0 | 3 |
| 6-010 | 320 | 5 | 4 | 1 | 5 |
| 6-015 | 320 | 5 | 5 | 5 | 5 |
| 6-016 | 320 | 5 | 0 | 0 | 4 |
| 6-017 | 320 | 5 | 1 | 0 | 5 |
| 6-018 | 320 | 5 | 5 | 4 | 5 |
| 6-023 | 320 | 0 | 0 | 0 | 4 |
| 6-024 | 320 | 3 | 2 |   | 3 |
| 6-025 | 320 | 2 | 0 | 0 | 3 |
| 6-026 | 320 | 1 | 0 | 0 | 3 |
| 6-029 | 320 | 5 | 3 | 3 | 5 |
| 6-030 | 320 | 3 | 0 | 0 | 2 |
| 6-031 | 320 | 3 | 0 | 0 | 1 |
| 6-034 | 320 | 5 | 5 | 4 | 5 |
| 6-035 | 320 | 5 | 4 | 1 | 5 |
| 6-037 | 320 | 5 | 5 | 4 | 5 |
| 6-038 | 320 | 5 | 4 | 3 | 5 |
| 6-049 | 320 | 5 | 5 | 4 | 5 |
| 6-050 | 320 | 3 | 1 | 0 | 4 |
| 6-051 | 320 | 4 | 4 | 2 | 5 |
| 6-052 | 320 | 4 | 1 | 0 | 3 |
| 6-053 | 320 | 4 | 2 | 1 | 3 |
| 6-054 | 320 | 1 | 0 | 0 | 2 |
| 6-055 | 320 | 4 | 1 | 0 | 5 |
| 6-056 | 320 | 3 | 0 | 0 | 0 |
| 6-057 | 320 | 3 | 3 | 1 | 5 |
| 6-058 | 320 | 5 | 5 | 5 | 5 |
| 6-059 | 320 | 5 | 5 | 4 | 5 |
| 6-060 | 320 | 5 | 5 | 5 | 5 |

TABLE 22-continued

| No. | Application herbicide amount (g/ha) | A | B | C | a |
|---|---|---|---|---|---|
| 6-061 | 320 | 5 | 1 | 1 | 5 |
| 6-062 | 320 | 5 | 4 | 4 | 5 |
| 6-063 | 320 | 5 | 2 | 3 | 4 |
| 6-064 | 320 | 5 | 0 | 0 | 5 |
| 6-065 | 320 | 4 | 2 | 3 | 4 |
| 6-066 | 320 | 5 | 3 | 2 | 3 |
| 6-071 | 320 | 4 | 0 | 0 | 0 |
| 6-072 | 320 | 4 | 0 | 0 | 0 |
| 6-073 | 320 | 4 | 1 | 1 | 5 |
| 6-074 | 320 | 1 | 0 | 0 | 2 |
| 6-075 | 320 | 4 | 1 | 2 | 3 |
| 6-076 | 320 | 5 | 3 | 2 | 5 |
| 6-077 | 320 | 5 | 3 | 3 | 5 |
| 6-078 | 320 | 5 | 5 | 4 | 5 |
| 6-079 | 320 | 4 | 0 | 2 | 5 |
| 6-080 | 320 | 5 | 1 | 2 | 5 |
| 6-081 | 320 | 5 | 0 | 1 | 3 |
| 6-082 | 320 | 5 | 4 | 4 | 5 |
| 6-083 | 320 | 5 | 4 | 4 | 5 |
| 6-084 | 320 | 5 | 3 | 0 | 5 |
| 6-085 | 320 | 5 | 3 | 0 | 5 |
| 6-086 | 320 | 5 | 2 | 0 | 5 |
| 6-087 | 320 | 5 | 0 | 0 | 2 |
| 6-088 | 320 | 4 | 1 | 0 | 3 |
| 6-089 | 320 | 5 | 3 | 3 | 5 |
| 6-090 | 320 | 5 | 0 | 0 | 0 |
| 6-091 | 320 | 5 | 5 | 4 | 5 |
| 6-092 | 320 | 3 | 0 | 0 | 0 |
| 6-093 | 320 | 5 | 5 | 4 | 5 |
| 6-094 | 320 | 5 | 5 | 3 | 5 |
| 6-095 | 320 | 5 | 4 | 0 | 5 |
| 6-096 | 320 | 1 | 0 | 0 | 5 |
| 6-098 | 320 | 0 | 1 | 0 | 1 |
| 6-099 | 320 | 5 | 5 | 5 | 5 |
| 6-100 | 320 | 5 | 5 | 5 | 5 |
| 6-103 | 320 | 5 | 0 | 0 | 5 |
| 6-104 | 320 | 5 | 5 | 5 | 5 |
| 6-106 | 320 | 5 | 5 | 4 | 5 |
| 6-107 | 320 | 5 | 5 | 5 | 5 |
| 6-108 | 320 | 4 | 3 | 0 | 5 |
| 6-109 | 320 | 5 | 3 | 3 | 5 |
| 6-110 | 320 | 5 | 3 | 0 | 5 |
| 6-111 | 320 | 5 | 5 | 2 | 5 |
| 6-112 | 320 | 5 | 0 | 0 | 4 |
| 6-113 | 320 | 4 | 0 | 0 | 5 |
| 7-001 | 320 | 0 | 0 | 0 | 0 |
| 7-002 | 320 | 0 | 0 | 0 | 2 |
| 7-003 | 320 | 5 | 0 | 0 | 0 |
| 7-004 | 320 | 5 | 3 | 0 | 5 |
| 7-005 | 320 | 3 | 0 | 0 | 1 |
| 7-006 | 320 | 3 | 0 | 0 | 2 |
| 7-007 | 320 | 5 | 1 | 3 | 5 |
| 7-008 | 320 | 4 | 2 | 0 | 5 |
| 7-010 | 320 | 5 | 5 | 1 | 5 |
| 7-011 | 320 | 2 | 1 | 0 | 1 |
| 7-012 | 320 | 3 | 0 | 0 | 1 |
| 7-015 | 320 | 5 | 1 | 2 | 5 |
| 7-018 | 320 | 2 | 0 | 0 | 2 |
| 7-019 | 320 | 1 | 0 | 0 | 0 |
| 7-020 | 320 | 2 | 0 | 0 | 2 |
| 7-022 | 320 | 4 | 2 | 3 | 3 |
| 7-023 | 320 | 2 | 0 | 0 | 1 |
| 7-024 | 320 | 2 | 1 | 2 | 2 |
| 7-026 | 320 | 3 | 0 | 0 | 0 |
| 7-027 | 320 | 4 | 0 | 2 | 3 |
| 7-029 | 320 | 2 | 0 | 0 | 0 |
| 8-001 | 320 | 0 | 0 | 0 | 0 |
| 8-002 | 320 | 0 | 0 | 0 | 0 |
| 8-003 | 320 | 0 | 0 | 0 | 0 |
| 9-001 | 320 | 4 | 0 | 0 | 4 |
| 9-002 | 320 | 5 | 2 | 0 | 5 |
| 9-003 | 320 | 5 | 4 | 1 | 5 |
| 9-004 | 320 | 5 | 2 | 0 | 5 |
| 9-005 | 320 | 4 | 0 | 0 | 4 |
| 9-006 | 320 | 5 | 4 | 0 | 5 |
| 9-007 | 320 | 5 | 4 | 0 | 5 |
| 9-008 | 320 | 5 | 5 | 4 | 5 |
| 9-009 | 320 | 4 | 0 | 0 | 5 |
| 9-010 | 320 | 5 | 5 | 4 | 5 |
| 9-011 | 320 | 5 | 5 | 4 | 5 |
| 9-012 | 320 | 5 | 4 | 2 | 5 |
| 9-013 | 320 | 5 | 5 | 1 | 5 |
| 9-014 | 320 | 5 | 4 | 2 | 5 |
| 9-015 | 320 | 5 | 5 | 1 | 5 |
| 9-016 | 320 | 5 | 5 | 2 | 5 |
| 9-017 | 320 | 4 | 2 | 0 | 4 |
| 9-018 | 320 | 1 | 0 | 0 | 2 |
| 9-019 | 320 | 4 | 0 | 0 | 4 |
| 9-020 | 320 | 5 | 4 | 1 | 5 |
| 9-021 | 320 | 5 | 5 | 2 | 5 |
| 9-022 | 320 | 5 | 3 | 0 | 5 |
| 9-023 | 320 | 5 | 5 | 4 | 5 |
| 9-024 | 320 | 5 | 4 | 2 | 5 |
| 9-025 | 320 | 5 | 1 | 1 | 0 |
| 9-026 | 320 | 4 | 0 | 0 | 0 |
| 9-027 | 320 | 5 | 2 | 1 | 5 |
| 9-028 | 320 | 5 | 5 | 5 | 5 |
| 10-002 | 320 | 1 | 0 | 0 | 1 |
| 10-003 | 320 | 1 | 0 | 0 | 3 |
| 10-004 | 320 | 5 | 0 | 0 | 5 |
| 11-002 | 320 | 2 | 0 | 0 | 2 |
| 12-002 | 320 | 5 | 3 | 2 | 3 |
| 13-001 | 320 | 5 | 2 | 0 | 5 |
| 13-002 | 320 | 5 | 4 | 0 | 5 |
| 13-003 | 320 | 5 | 5 | 0 | 5 |
| 13-004 | 320 | 5 | 5 | 5 | 5 |
| 13-005 | 320 | 5 | 0 | 2 | 5 |
| 13-006 | 320 | 5 | 5 | 4 | 5 |
| 14-001 | 320 | 4 | 3 | 3 | 5 |
| 14-002 | 320 | 4 | 1 | 2 | 2 |

TABLE 23

| No. | Application herbicide amount (g/ha) | A | B | C |
|---|---|---|---|---|
| 1-001 | 320 | 0 | 0 | 0 |
| 1-002 | 320 | 5 | 3 | 3 |
| 1-003 | 320 | 5 | 3 | 3 |
| 1-004 | 320 | 5 | 4 | 4 |
| 1-005 | 320 | 5 | 4 | 4 |
| 1-006 | 320 | 5 | 3 | 3 |
| 1-007 | 320 | 0 | 0 | 0 |
| 1-008 | 320 | 5 | 2 | 0 |
| 1-009 | 320 | 0 | 0 | 0 |
| 1-010 | 320 | 5 | 5 | 2 |
| 1-011 | 320 | 0 | 0 | 0 |
| 1-012 | 320 | 0 | 0 | 0 |
| 1-013 | 320 | 0 | 0 | 0 |
| 1-014 | 320 | 5 | 3 | 3 |
| 1-015 | 320 | 5 | 4 | 4 |
| 1-016 | 320 | 5 | 4 | 3 |
| 1-017 | 320 | 5 | 4 | 3 |
| 1-018 | 320 | 5 | 5 | 3 |
| 1-019 | 320 | 5 | 5 | 2 |
| 1-020 | 320 | 5 | 3 | 2 |
| 1-021 | 320 | 0 | 0 | 0 |
| 1-022 | 320 | 4 | 5 | 3 |
| 1-023 | 320 | 4 | 0 | 0 |
| 1-024 | 320 | 5 | 5 | 3 |
| 1-025 | 320 | 1 | 0 | 0 |
| 1-026 | 320 | 5 | 3 | 3 |
| 1-027 | 320 | 4 | 3 | 0 |
| 1-028 | 320 | 5 | 4 | 0 |
| 1-029 | 320 | 4 | 0 | 0 |
| 1-030 | 320 | 2 | 0 | 0 |
| 1-031 | 320 | 5 | 2 | 0 |
| 1-032 | 320 | 5 | 4 | 3 |

TABLE 23-continued

| No. | Application herbicide amount (g/ha) | A | B | C |
|---|---|---|---|---|
| 1-033 | 320 | 5 | 4 | 2 |
| 1-034 | 320 | 5 | 3 | 3 |
| 1-035 | 320 | 5 | 4 | 4 |
| 1-036 | 320 | 5 | 4 | 2 |
| 1-037 | 320 | 0 | 0 | 0 |
| 1-038 | 320 | 5 | 5 | 4 |
| 1-039 | 320 | 5 | 5 | 3 |
| 1-040 | 320 | 4 | 0 | 0 |
| 1-041 | 320 | 5 | 0 | 0 |
| 1-042 | 320 | 5 | 4 | 3 |
| 1-043 | 320 | 5 | 5 | 3 |
| 1-044 | 320 | 5 | 4 | 3 |
| 1-045 | 320 | 3 | 0 | 0 |
| 1-046 | 320 | 5 | 5 | 3 |
| 1-047 | 320 | 2 | 0 | 0 |
| 1-048 | 320 | 5 | 4 | 2 |
| 1-049 | 320 | 0 | 0 | 0 |
| 1-050 | 320 | 3 | 0 | 0 |
| 1-051 | 320 | 5 | 5 | 3 |
| 1-052 | 320 | 5 | 2 | 0 |
| 1-053 | 320 | 4 | 0 | 0 |
| 1-054 | 320 | 3 | 0 | 0 |
| 1-055 | 320 | 2 | 0 | 0 |
| 1-056 | 320 | 5 | 5 | 4 |
| 1-057 | 320 | 2 | 0 | 0 |
| 1-058 | 320 | 5 | 0 | 0 |
| 1-059 | 320 | 4 | 0 | 0 |
| 1-060 | 320 | 5 | 4 | 0 |
| 1-062 | 320 | 3 | 0 | 0 |
| 1-063 | 320 | 4 | 2 | 0 |
| 1-064 | 320 | 5 | 4 | 1 |
| 1-065 | 320 | 4 | 5 | 0 |
| 1-066 | 320 | 2 | 0 | 0 |
| 1-067 | 320 | 4 | 4 | 2 |
| 1-068 | 320 | 5 | 5 | 3 |
| 1-069 | 320 | 4 | 4 | 3 |
| 1-070 | 320 | 4 | 0 | 0 |
| 1-071 | 320 | 5 | 3 | |
| 1-072 | 320 | 5 | 3 | 0 |
| 1-073 | 320 | 5 | 5 | 2 |
| 1-074 | 320 | 5 | 4 | |
| 1-075 | 320 | 5 | 4 | |
| 1-076 | 192 | 5 | 4 | 0 |
| 1-078 | 320 | 4 | 0 | 0 |
| 1-079 | 320 | 5 | 4 | 3 |
| 1-080 | 320 | 4 | 4 | 2 |
| 1-081 | 320 | 5 | 4 | 3 |
| 1-082 | 320 | 5 | 5 | 3 |
| 1-083 | 320 | 5 | 4 | 3 |
| 1-085 | 320 | 3 | 0 | 0 |
| 1-086 | 320 | 5 | 0 | |
| 1-087 | 320 | 5 | 5 | 1 |
| 1-088 | 320 | 5 | 5 | 3 |
| 1-089 | 320 | 5 | 4 | 3 |
| 1-090 | 320 | 5 | 5 | 3 |
| 1-091 | 320 | 5 | 3 | 0 |
| 1-092 | 320 | 5 | 4 | 0 |
| 1-093 | 320 | 5 | 5 | 3 |
| 1-094 | 320 | 5 | 5 | 4 |
| 1-095 | 320 | 5 | 4 | 1 |
| 1-096 | 320 | 5 | 5 | |
| 1-097 | 320 | 1 | 0 | 0 |
| 1-098 | 320 | 5 | 4 | 3 |
| 1-099 | 320 | 4 | 4 | 2 |
| 1-100 | 320 | 5 | 5 | 3 |
| 1-101 | 320 | 5 | 5 | 2 |
| 1-102 | 320 | 5 | 2 | 2 |
| 1-103 | 320 | 5 | 4 | 0 |
| 1-104 | 320 | 5 | 4 | 0 |
| 1-105 | 320 | 5 | 5 | 3 |
| 1-106 | 320 | 5 | 0 | 0 |
| 1-107 | 320 | 5 | 2 | 0 |
| 1-108 | 320 | 5 | 3 | 1 |
| 1-109 | 320 | 5 | 5 | 2 |
| 1-110 | 320 | 2 | 0 | 0 |
| 1-111 | 320 | 5 | 1 | 0 |
| 1-112 | 320 | 4 | 4 | 4 |
| 1-113 | 320 | 3 | 3 | 0 |
| 1-114 | 320 | 4 | 3 | 4 |
| 1-115 | 320 | 3 | 2 | 0 |
| 1-116 | 320 | 2 | 3 | 2 |
| 1-117 | 320 | 4 | 3 | 3 |
| 1-118 | 320 | 2 | 0 | |
| 1-120 | 320 | 1 | 5 | 3 |
| 1-121 | 320 | 5 | 4 | 1 |
| 1-122 | 320 | 5 | 5 | 0 |
| 1-123 | 320 | 5 | 3 | 2 |
| 1-124 | 320 | 2 | 0 | 0 |
| 1-125 | 320 | 2 | 0 | 0 |
| 1-130 | 320 | 1 | 0 | 0 |
| 1-131 | 320 | 4 | 4 | 0 |
| 1-133 | 320 | 1 | 0 | 0 |
| 1-134 | 320 | 5 | 4 | 3 |
| 1-135 | 320 | 5 | 4 | 0 |
| 1-136 | 320 | 4 | 4 | 5 |
| 1-137 | 320 | 4 | 4 | 3 |
| 1-138 | 320 | 3 | 4 | 2 |
| 1-139 | 320 | 5 | 4 | 1 |
| 1-140 | 320 | 5 | 5 | 3 |
| 1-142 | 320 | 5 | 4 | |
| 1-143 | 320 | 4 | 4 | 3 |
| 1-144 | 320 | 5 | 4 | 2 |
| 1-145 | 320 | 5 | 5 | 3 |
| 1-146 | 320 | 5 | 5 | 4 |
| 1-147 | 320 | 5 | 5 | 3 |
| 1-148 | 320 | 5 | 4 | 4 |
| 1-149 | 320 | 5 | 4 | 3 |
| 1-150 | 320 | 5 | 3 | 1 |
| 1-151 | 320 | 5 | 1 | 2 |
| 1-152 | 320 | 2 | 0 | 0 |
| 1-153 | 320 | 4 | 1 | 0 |
| 1-154 | 320 | 5 | 4 | 4 |
| 1-155 | 320 | 5 | 5 | 3 |
| 1-156 | 320 | 5 | 5 | 3 |
| 1-159 | 320 | 4 | 1 | 3 |
| 1-160 | 320 | 5 | 4 | 4 |
| 1-161 | 320 | 5 | 4 | 3 |
| 1-162 | 320 | 5 | 1 | 2 |
| 1-163 | 320 | 5 | 4 | 3 |
| 1-166 | 320 | 3 | 0 | 0 |
| 2-001 | 102 | 0 | 0 | 0 |
| 2-002 | 320 | 0 | 0 | 0 |
| 2-003 | 320 | 0 | 0 | 0 |
| 2-005 | 269 | 3 | 0 | 0 |
| 2-006 | 320 | 5 | 2 | 2 |
| 2-007 | 320 | 3 | 0 | 0 |
| 2-008 | 320 | 0 | 0 | 0 |
| 2-009 | 320 | 0 | 0 | 0 |
| 2-010 | 320 | 0 | 0 | 0 |
| 2-011 | 320 | 0 | 0 | 0 |
| 2-012 | 320 | 0 | 0 | 0 |
| 2-013 | 320 | 0 | 0 | 0 |
| 2-014 | 320 | 4 | 3 | 0 |
| 2-015 | 320 | 0 | 0 | 0 |
| 2-016 | 320 | 4 | 0 | 0 |
| 2-017 | 320 | 5 | 4 | 4 |
| 2-018 | 320 | 4 | 0 | 0 |
| 2-020 | 320 | 1 | 0 | 0 |
| 2-021 | 320 | 5 | 2 | 1 |
| 2-022 | 320 | 1 | 0 | 0 |
| 2-024 | 320 | 1 | 0 | 0 |
| 2-026 | 320 | 4 | 3 | 0 |
| 2-028 | 320 | 3 | 0 | 0 |
| 2-030 | 320 | 3 | 0 | 0 |
| 2-031 | 320 | 4 | 0 | 0 |
| 2-032 | 320 | 4 | 1 | 0 |
| 3-001 | 320 | 0 | 0 | 0 |
| 3-002 | 320 | 0 | 0 | 0 |
| 4-001 | 320 | 0 | 0 | 0 |
| 5-001 | 320 | 0 | 0 | 0 |
| 5-002 | 320 | 0 | 0 | 0 |
| 6-001 | 320 | 4 | 0 | 0 |

TABLE 23-continued

| No. | Application herbicide amount (g/ha) | A | B | C |
| --- | --- | --- | --- | --- |
| 6-002 | 320 | 0 | 0 | 0 |
| 6-003 | 320 | 4 | 1 | 3 |
| 6-004 | 320 | 5 | 4 | |
| 6-005 | 320 | 5 | 2 | 3 |
| 6-006 | 320 | 5 | 5 | 1 |
| 6-007 | 320 | 5 | 3 | 2 |
| 6-008 | 320 | 5 | 5 | 5 |
| 6-009 | 320 | 3 | 0 | 0 |
| 6-010 | 320 | 5 | 3 | 0 |
| 6-015 | 320 | 5 | 5 | 5 |
| 6-016 | 320 | 3 | 0 | 0 |
| 6-017 | 320 | 4 | 3 | 0 |
| 6-018 | 320 | 5 | 4 | 3 |
| 6-024 | 320 | 1 | 0 | 0 |
| 6-025 | 320 | 2 | 0 | 0 |
| 6-029 | 320 | 5 | 3 | 2 |
| 6-030 | 320 | 2 | 0 | 0 |
| 6-031 | 320 | 4 | 0 | 0 |
| 6-034 | 320 | 5 | 5 | 3 |
| 6-035 | 320 | 5 | 4 | 0 |
| 6-036 | 320 | 3 | 0 | 0 |
| 6-037 | 320 | 5 | 4 | 4 |
| 6-038 | 320 | 4 | 4 | 1 |
| 6-049 | 320 | 5 | 4 | 3 |
| 6-050 | 320 | 3 | 0 | 0 |
| 6-051 | 320 | 5 | 4 | 2 |
| 6-052 | 320 | 3 | 0 | 0 |
| 6-053 | 320 | 3 | 1 | 2 |
| 6-054 | 320 | 2 | 1 | 0 |
| 6-055 | 320 | 5 | 2 | 0 |
| 6-056 | 320 | 1 | 0 | 0 |
| 6-057 | 320 | 3 | 2 | 0 |
| 6-058 | 320 | 5 | 5 | 5 |
| 6-059 | 320 | 5 | 4 | 4 |
| 6-060 | 320 | 5 | 4 | 4 |
| 6-061 | 320 | 5 | 4 | 2 |
| 6-062 | 320 | 5 | 3 | 3 |
| 6-063 | 320 | 2 | 3 | 2 |
| 6-064 | 320 | 4 | 0 | 0 |
| 6-065 | 320 | 5 | 1 | 2 |
| 6-066 | 320 | 5 | 0 | 0 |
| 6-071 | 320 | 2 | 0 | 0 |
| 6-072 | 320 | 1 | 0 | 0 |
| 6-073 | 320 | 4 | 2 | 1 |
| 6-074 | 320 | 1 | 0 | 0 |
| 6-075 | 320 | 1 | 0 | 1 |
| 6-076 | 320 | 5 | 1 | 1 |
| 6-077 | 320 | 5 | 4 | 3 |
| 6-078 | 320 | 4 | 2 | 3 |
| 6-079 | 320 | 3 | 2 | 3 |
| 6-080 | 320 | 5 | 4 | 3 |
| 6-081 | 320 | 1 | 0 | 0 |
| 6-082 | 320 | 4 | 3 | 5 |
| 6-083 | 320 | 5 | 3 | 4 |
| 6-084 | 320 | 4 | 3 | 0 |
| 6-085 | 320 | 5 | 4 | 1 |
| 6-086 | 320 | 4 | 4 | 3 |
| 6-087 | 320 | 2 | 0 | 0 |
| 6-088 | 320 | 4 | 2 | 0 |
| 6-089 | 320 | 5 | 2 | 3 |
| 6-090 | 320 | 3 | 0 | 0 |
| 6-091 | 320 | 5 | 5 | 3 |
| 6-092 | 320 | 1 | 0 | 0 |
| 6-093 | 320 | 5 | 3 | 3 |
| 6-094 | 320 | 5 | 2 | 1 |
| 6-095 | 320 | 5 | 3 | 2 |
| 6-096 | 320 | 4 | 0 | 0 |
| 6-099 | 320 | 5 | 5 | 5 |
| 6-100 | 320 | 5 | 5 | 5 |
| 6-103 | 320 | 5 | 0 | 0 |
| 6-104 | 320 | 5 | 5 | 5 |
| 6-106 | 320 | 5 | 5 | 4 |
| 6-107 | 320 | 5 | 5 | 5 |
| 6-108 | 320 | 4 | 1 | 2 |
| 6-109 | 320 | 5 | 2 | 2 |
| 6-110 | 320 | 5 | 1 | 0 |
| 6-111 | 320 | 5 | 3 | 4 |
| 6-112 | 320 | 3 | 0 | 0 |
| 6-113 | 320 | 5 | 0 | 3 |
| 7-001 | 320 | 0 | 0 | 0 |
| 7-002 | 320 | 0 | 0 | 0 |
| 7-003 | 320 | 2 | 0 | 0 |
| 7-004 | 320 | 4 | 0 | 0 |
| 7-005 | 320 | 1 | 0 | 0 |
| 7-006 | 320 | 2 | 0 | 0 |
| 7-007 | 320 | 5 | 0 | 3 |
| 7-008 | 320 | 4 | 0 | 0 |
| 7-010 | 320 | 5 | 5 | 1 |
| 7-011 | 320 | 3 | 2 | 0 |
| 7-012 | 320 | 3 | 0 | 0 |
| 7-013 | 320 | 2 | 0 | 0 |
| 7-015 | 320 | 5 | 0 | 0 |
| 7-018 | 320 | 1 | 0 | 0 |
| 7-020 | 320 | 1 | 0 | 0 |
| 7-024 | 320 | 1 | 0 | 0 |
| 7-027 | 320 | 3 | 0 | 2 |
| 7-031 | 320 | 0 | 1 | 2 |
| 8-001 | 320 | 0 | 0 | 0 |
| 8-002 | 320 | 0 | 0 | 0 |
| 8-003 | 320 | 0 | 0 | 0 |
| 9-001 | 320 | 4 | 0 | 0 |
| 9-002 | 320 | 5 | 0 | 0 |
| 9-003 | 320 | 5 | 4 | |
| 9-004 | 320 | 5 | 2 | 0 |
| 9-005 | 320 | 3 | 0 | 0 |
| 9-006 | 320 | 5 | 4 | |
| 9-007 | 320 | 5 | 4 | |
| 9-008 | 320 | 5 | 4 | 3 |
| 9-009 | 320 | 2 | 0 | 0 |
| 9-010 | 320 | 4 | 4 | 1 |
| 9-011 | 320 | 5 | 5 | 4 |
| 9-012 | 320 | 5 | 4 | 2 |
| 9-013 | 320 | 5 | 5 | 3 |
| 9-014 | 320 | 2 | 0 | 0 |
| 9-015 | 320 | 5 | 3 | |
| 9-016 | 320 | 5 | 4 | 1 |
| 9-017 | 320 | 1 | 0 | 0 |
| 9-018 | 320 | 1 | 0 | 0 |
| 9-019 | 320 | 3 | 0 | 0 |
| 9-020 | 320 | 4 | 4 | 0 |
| 9-021 | 320 | 5 | 5 | |
| 9-022 | 320 | 4 | 0 | 0 |
| 9-023 | 320 | 5 | 4 | 1 |
| 9-024 | 320 | 3 | 3 | 1 |
| 9-027 | 320 | 3 | 0 | 0 |
| 9-028 | 320 | 5 | 4 | 4 |
| 9-029 | 320 | 0 | 0 | 0 |
| 10-002 | 320 | 1 | 0 | 0 |
| 10-003 | 320 | 3 | 0 | 0 |
| 10-004 | 320 | 5 | 0 | 0 |
| 11-002 | 320 | 2 | 0 | 0 |
| 12-002 | 320 | 5 | 3 | 1 |
| 13-001 | 320 | 5 | 0 | 0 |
| 13-002 | 320 | 5 | 5 | 2 |
| 13-003 | 320 | 5 | 4 | 3 |
| 13-004 | 320 | 5 | 5 | 4 |
| 13-005 | 320 | 5 | 2 | |
| 13-006 | 320 | 5 | 3 | 4 |
| 14-001 | 320 | 5 | 0 | 1 |
| 14-002 | 320 | 5 | 0 | 0 |

TABLE 24

| No. | Application herbicide amount (g/ha) | H | D | E | b |
| --- | --- | --- | --- | --- | --- |
| 1-001 | 320 | 0 | 0 | 0 | 0 |
| 1-002 | 320 | 5 | 5 | 5 | 5 |

TABLE 24-continued

| No. | Application herbicide amount (g/ha) | H | D | E | b |
|---|---|---|---|---|---|
| 1-003 | 320 | 5 | 5 | 5 | 5 |
| 1-004 | 320 | 5 | 5 | 5 | 5 |
| 1-005 | 320 | 5 | 5 | 5 | 5 |
| 1-006 | 320 | 5 | 5 | 5 | 5 |
| 1-007 | 320 | 0 | 5 | 0 | 0 |
| 1-008 | 320 | 5 | 5 | 4 | 5 |
| 1-009 | 320 | 0 | 0 | 0 | 0 |
| 1-010 | 320 | 5 | 5 | 5 | 5 |
| 1-011 | 320 | 0 | 5 | 0 | 0 |
| 1-012 | 320 | 0 | 0 | 0 | 0 |
| 1-013 | 320 | 0 | 2 | 0 | 0 |
| 1-014 | 320 | 5 | 5 | 5 | 5 |
| 1-015 | 320 | 5 | 5 | 5 | 5 |
| 1-016 | 320 | 5 | 5 | 5 | 5 |
| 1-017 | 320 | 5 | 5 | 5 | 5 |
| 1-018 | 320 | 5 | 5 | 3 | 5 |
| 1-019 | 320 | 5 | 5 | 5 | 5 |
| 1-020 | 320 | 5 | 5 | 2 | 5 |
| 1-021 | 320 | 2 | 0 | 0 | 0 |
| 1-022 | 320 | 5 | 5 | 4 | 5 |
| 1-023 | 320 | 5 | 5 | 0 | 4 |
| 1-024 | 320 | 5 | 5 | 5 | 5 |
| 1-025 | 320 | 5 | 5 | 5 | 5 |
| 1-026 | 320 | 5 | 5 | 5 | 5 |
| 1-027 | 320 | 5 | 5 | 5 | 5 |
| 1-028 | 320 | 5 | 5 | 5 | 5 |
| 1-029 | 320 | 5 | 5 | 4 | 5 |
| 1-030 | 320 | 5 | 5 | 3 | 5 |
| 1-031 | 320 | 3 | 4 | 0 | 5 |
| 1-032 | 320 | 5 | 5 | 5 | 5 |
| 1-033 | 320 | 5 | 5 | 5 | 5 |
| 1-034 | 320 | 5 | 5 | 5 | 5 |
| 1-035 | 320 | 5 | 5 | 5 | 5 |
| 1-036 | 320 | 5 | 5 | 5 | 5 |
| 1-037 | 320 | 0 | 0 | 0 | 0 |
| 1-038 | 320 | 5 | 5 | 5 | 5 |
| 1-039 | 320 | 5 | 5 | 5 | 5 |
| 1-040 | 320 | 5 | 4 | 4 | 5 |
| 1-041 | 320 | 5 | 5 | 5 | 5 |
| 1-042 | 320 | 5 | 5 | 5 | 5 |
| 1-043 | 320 | 5 | 5 | 5 | 5 |
| 1-044 | 320 | 5 | 5 | 5 | 5 |
| 1-045 | 320 | 5 | 4 | 0 | 3 |
| 1-046 | 320 | 5 | 5 | 5 | 5 |
| 1-047 | 320 | 1 | 3 | 0 | 2 |
| 1-048 | 320 | 5 | 4 | 5 | 5 |
| 1-049 | 320 | 0 | 0 | 0 | 0 |
| 1-050 | 320 | 5 | 4 | 5 | 5 |
| 1-051 | 320 | 5 | 5 | 5 | 5 |
| 1-052 | 320 | 5 | 5 | 5 | 5 |
| 1-053 | 320 | 5 | 5 | 4 | 5 |
| 1-054 | 320 | 5 | 5 | 0 | 5 |
| 1-055 | 320 | 5 | 5 | 4 | 5 |
| 1-056 | 320 | 5 | 5 | 5 | 5 |
| 1-057 | 320 | 4 | 3 | 3 | 5 |
| 1-058 | 320 | 5 | 5 | 5 | 5 |
| 1-059 | 320 | 4 | 1 | 3 | 5 |
| 1-060 | 320 | 5 | 5 | 5 | 5 |
| 1-062 | 320 | 4 | 3 | 4 | 5 |
| 1-063 | 320 | 5 | 5 | 5 | 5 |
| 1-064 | 320 | 5 | 5 | 5 | 5 |
| 1-065 | 320 | 5 | 5 | 5 | 5 |
| 1-066 | 320 | 5 | 2 | 5 | 5 |
| 1-067 | 320 | 5 | 5 | 5 | 5 |
| 1-068 | 320 | 5 | 5 | 5 | 5 |
| 1-069 | 320 | 5 | 5 | 5 | 5 |
| 1-070 | 320 | 5 | 4 | 4 | 5 |
| 1-071 | 320 | 5 | 5 | 5 | 5 |
| 1-072 | 320 | 4 | 5 | 4 | 5 |
| 1-073 | 320 | 5 | 5 | 5 | 5 |
| 1-074 | 320 | 5 | 5 | 5 | 5 |
| 1-075 | 320 | 5 | 5 | 5 | 5 |
| 1-076 | 192 | 5 | 5 | 5 | 5 |
| 1-078 | 320 | 5 | 4 | 0 | 5 |
| 1-079 | 320 | 5 | 5 | 5 | 5 |
| 1-080 | 320 | 5 | 5 | 5 | 5 |
| 1-081 | 320 | 5 | 5 | 5 | 5 |
| 1-082 | 320 | 5 | 5 | 5 | 5 |
| 1-083 | 320 | 5 | 5 | 5 | 5 |
| 1-084 | 320 | 2 | 0 | 0 | 1 |
| 1-085 | 320 | 5 | 4 | 0 | 5 |
| 1-086 | 320 | 5 | 4 | 4 | 5 |
| 1-087 | 320 | 5 | 5 | 5 | 5 |
| 1-088 | 320 | 5 | 5 | 5 | 5 |
| 1-089 | 320 | 5 | 5 | 5 | 5 |
| 1-090 | 320 | 5 | 5 | 5 | 5 |
| 1-091 | 320 | 5 | 5 | 5 | 5 |
| 1-092 | 320 | 5 | 5 | 5 | 5 |
| 1-093 | 320 | 5 | 5 | 5 | 5 |
| 1-094 | 320 | 5 | 5 | 4 | 5 |
| 1-095 | 320 | 5 | 5 | 5 | 5 |
| 1-096 | 320 | 5 | 5 | 5 | 5 |
| 1-098 | 320 | 5 | 5 | 5 | 5 |
| 1-099 | 320 | 5 | 5 | 5 | 5 |
| 1-100 | 320 | 5 | 5 | 5 | 5 |
| 1-101 | 320 | 5 | 5 | 5 | 5 |
| 1-102 | 320 | 5 | 5 | 5 | 5 |
| 1-103 | 320 | 5 | 5 | 5 | 5 |
| 1-104 | 320 | 5 | 5 | 5 | 5 |
| 1-105 | 320 | 5 | 5 | 5 | 5 |
| 1-106 | 320 | 5 | 5 | 5 | 5 |
| 1-107 | 320 | 5 | 5 | 5 | 5 |
| 1-108 | 320 | 5 | 5 | 5 | 5 |
| 1-109 | 320 | 5 | 5 | 5 | 5 |
| 1-110 | 320 | 5 | 5 | 5 | 5 |
| 1-111 | 320 | 5 | 5 | 5 | 5 |
| 1-112 | 320 | 5 | 5 | 5 | 5 |
| 1-114 | 320 | 5 | 5 | 2 | 5 |
| 1-116 | 320 | 5 | 3 | 4 | 5 |
| 1-117 | 320 | 5 | 4 | 5 | 5 |
| 1-118 | 320 | 4 | 0 | 0 | 5 |
| 1-119 | 320 | 5 | 4 | 0 | 5 |
| 1-120 | 320 | 5 | 0 | 4 | 3 |
| 1-121 | 320 | 5 | 5 | 4 | 5 |
| 1-122 | 320 | 5 | 5 | 5 | 5 |
| 1-123 | 320 | 5 | 5 | 4 | 5 |
| 1-124 | 320 | 5 | 5 | 0 | 5 |
| 1-125 | 320 | 5 | 5 | 2 | 5 |
| 1-126 | 320 | 3 | 5 | 2 | 5 |
| 1-130 | 320 | 4 | 5 | 4 | 5 |
| 1-131 | 320 | 5 | 5 | 5 | 5 |
| 1-132 | 320 | 2 | 1 | 0 | 1 |
| 1-133 | 320 | 3 | 0 | 0 | 0 |
| 1-134 | 320 | 5 | 5 | 5 | 5 |
| 1-135 | 320 | 5 | 4 |   | 5 |
| 1-136 | 320 | 5 | 2 |   | 5 |
| 1-137 | 320 | 5 | 5 |   | 5 |
| 1-138 | 320 | 3 | 2 |   | 5 |
| 1-139 | 320 | 5 | 5 | 5 | 5 |
| 1-140 | 320 | 5 | 5 |   | 5 |
| 1-141 | 320 | 2 | 0 |   | 1 |
| 1-142 | 320 | 5 | 5 |   | 5 |
| 1-143 | 320 | 4 | 4 |   | 5 |
| 1-144 | 320 | 5 | 5 |   | 5 |
| 1-145 | 320 | 5 | 5 |   | 5 |
| 1-146 | 320 | 5 | 5 |   | 5 |
| 1-147 | 320 | 5 | 5 |   | 5 |
| 1-148 | 320 | 5 | 5 | 4 | 5 |
| 1-149 | 320 | 5 | 5 | 5 | 5 |
| 1-150 | 320 | 5 | 4 |   | 5 |
| 1-151 | 320 | 4 | 4 |   | 5 |
| 1-152 | 320 | 5 | 5 | 5 | 5 |
| 1-153 | 320 | 5 | 5 | 4 | 5 |
| 1-154 | 320 | 5 | 5 | 5 | 5 |
| 1-155 | 320 | 5 | 5 | 5 | 5 |
| 1-156 | 320 | 5 | 5 | 5 | 5 |
| 1-157 | 320 | 0 | 4 |   | 0 |
| 1-158 | 320 | 0 | 2 | 0 | 2 |
| 1-159 | 320 | 4 | 5 | 4 | 5 |
| 1-160 | 320 | 5 | 5 | 5 | 5 |
| 1-161 | 320 | 4 | 5 | 4 | 5 |
| 1-162 | 320 | 5 | 5 | 5 | 5 |

TABLE 24-continued

| No. | Application herbicide amount (g/ha) | H | D | E | b |
|---|---|---|---|---|---|
| 1-163 | 320 | 5 | 5 | 5 | 5 |
| 1-164 | 320 | 2 | 3 | 0 | 4 |
| 1-166 | 320 | 4 | 4 |   | 3 |
| 2-001 | 102 | 5 | 5 | 5 | 5 |
| 2-002 | 320 | 0 | 0 | 0 | 0 |
| 2-003 | 320 | 5 | 5 | 4 | 4 |
| 2-005 | 269 | 5 | 5 | 4 | 5 |
| 2-006 | 320 | 5 | 5 | 5 | 5 |
| 2-007 | 320 | 5 | 5 | 5 | 5 |
| 2-008 | 320 | 0 | 0 | 0 | 0 |
| 2-009 | 320 | 3 | 0 | 0 | 1 |
| 2-010 | 320 | 3 | 0 | 0 | 1 |
| 2-011 | 320 | 0 | 0 | 0 | 0 |
| 2-012 | 320 | 0 | 0 | 0 | 0 |
| 2-013 | 320 | 0 | 0 | 0 | 0 |
| 2-014 | 320 | 5 | 4 | 5 | 5 |
| 2-015 | 320 | 1 | 0 | 0 | 4 |
| 2-016 | 320 | 5 | 5 | 4 | 5 |
| 2-017 | 320 | 5 | 5 | 5 | 5 |
| 2-018 | 320 | 5 | 5 | 5 | 5 |
| 2-020 | 320 | 2 | 2 | 0 | 2 |
| 2-021 | 320 | 5 | 3 | 3 | 5 |
| 2-022 | 320 | 1 | 4 | 2 | 5 |
| 2-024 | 320 | 5 | 3 | 0 | 5 |
| 2-025 | 320 | 3 | 1 | 0 | 4 |
| 2-026 | 320 | 5 | 4 | 5 | 5 |
| 2-027 | 320 | 3 | 0 | 0 | 5 |
| 2-028 | 320 | 5 | 5 | 4 | 5 |
| 2-029 | 320 | 0 | 0 | 0 | 4 |
| 2-030 | 320 | 4 | 5 | 0 | 5 |
| 2-031 | 320 | 5 | 5 | 5 | 5 |
| 2-032 | 320 | 5 | 3 | 4 | 5 |
| 3-001 | 320 | 3 | 2 | 0 | 2 |
| 3-002 | 320 | 0 | 0 | 0 | 0 |
| 4-001 | 320 | 2 | 3 | 0 | 4 |
| 5-001 | 320 | 2 | 3 | 0 | 5 |
| 5-002 | 320 | 0 | 0 | 0 | 0 |
| 6-001 | 320 | 5 | 5 | 0 | 5 |
| 6-002 | 320 | 4 | 4 | 0 | 5 |
| 6-003 | 320 | 5 | 5 | 5 | 5 |
| 6-004 | 320 | 5 | 5 | 5 | 5 |
| 6-005 | 320 | 5 | 5 | 3 | 5 |
| 6-006 | 320 | 5 | 5 | 5 | 5 |
| 6-007 | 320 | 5 | 5 | 5 | 5 |
| 6-008 | 320 | 5 | 5 | 5 | 5 |
| 6-009 | 320 | 5 | 5 | 0 | 5 |
| 6-010 | 320 | 5 | 5 | 5 | 5 |
| 6-015 | 320 | 5 | 5 | 5 | 5 |
| 6-016 | 320 | 5 | 5 | 1 | 5 |
| 6-017 | 320 | 5 | 5 | 4 | 5 |
| 6-018 | 320 | 5 | 5 | 5 | 5 |
| 6-023 | 320 | 5 | 5 | 4 | 5 |
| 6-024 | 320 | 3 | 2 | 3 | 3 |
| 6-025 | 320 | 5 | 5 | 4 | 5 |
| 6-026 | 320 | 5 | 5 | 5 | 5 |
| 6-027 | 320 | 2 | 3 | 0 | 0 |
| 6-029 | 320 | 5 | 5 | 5 | 5 |
| 6-030 | 320 | 4 | 5 | 0 | 2 |
| 6-031 | 320 | 3 | 2 | 2 | 4 |
| 6-033 | 320 | 0 | 0 | 3 | 0 |
| 6-034 | 320 | 5 | 5 | 4 | 5 |
| 6-035 | 320 | 5 | 5 | 5 | 5 |
| 6-036 | 320 | 4 | 5 | 3 | 4 |
| 6-037 | 320 | 5 | 5 | 5 | 5 |
| 6-038 | 320 | 5 | 5 | 5 | 5 |
| 6-049 | 320 | 5 | 5 | 5 | 5 |
| 6-050 | 320 | 5 | 5 | 5 | 5 |
| 6-051 | 320 | 5 | 5 | 5 | 5 |
| 6-052 | 320 | 5 | 5 | 3 | 5 |
| 6-053 | 320 | 5 | 5 | 3 | 5 |
| 6-054 | 320 | 5 | 5 | 3 | 5 |
| 6-055 | 320 | 5 | 5 | 5 | 5 |
| 6-056 | 320 | 4 | 5 | 3 | 5 |
| 6-057 | 320 | 5 | 5 | 5 | 5 |
| 6-058 | 320 | 5 | 5 | 5 | 5 |
| 6-059 | 320 | 5 | 5 | 5 | 5 |
| 6-060 | 320 | 5 | 5 | 5 | 5 |
| 6-061 | 320 | 5 | 5 | 5 | 5 |
| 6-062 | 320 | 5 | 5 | 5 | 5 |
| 6-063 | 320 | 4 | 5 | 1 | 5 |
| 6-064 | 320 | 5 | 5 | 0 | 4 |
| 6-065 | 320 | 5 | 5 | 5 | 5 |
| 6-066 | 320 | 5 | 5 | 5 | 5 |
| 6-068 | 320 | 0 | 2 | 0 | 0 |
| 6-070 | 320 | 0 | 4 | 0 | 0 |
| 6-071 | 320 | 4 | 5 | 0 | 1 |
| 6-072 | 320 | 5 | 5 | 0 | 0 |
| 6-073 | 320 | 5 | 5 | 5 | 5 |
| 6-074 | 320 | 4 | 5 | 2 | 1 |
| 6-075 | 320 | 3 | 3 | 3 | 4 |
| 6-076 | 320 | 5 | 5 | 5 | 5 |
| 6-077 | 320 | 5 | 5 | 5 | 5 |
| 6-078 | 320 | 5 | 5 | 0 | 5 |
| 6-079 | 320 | 5 | 5 | 4 | 5 |
| 6-080 | 320 | 5 | 5 | 5 | 5 |
| 6-081 | 320 | 1 | 3 | 0 | 0 |
| 6-082 | 320 | 5 | 5 | 5 | 5 |
| 6-083 | 320 | 5 | 5 | 5 | 5 |
| 6-084 | 320 | 5 | 5 | 5 | 5 |
| 6-085 | 320 | 5 | 5 | 5 | 5 |
| 6-086 | 320 | 5 | 5 | 5 | 5 |
| 6-087 | 320 | 5 | 5 | 0 | 5 |
| 6-088 | 320 | 5 | 5 | 5 | 5 |
| 6-089 | 320 | 5 | 5 | 4 | 5 |
| 6-090 | 320 | 0 | 5 | 0 | 0 |
| 6-091 | 320 | 5 | 5 | 5 | 5 |
| 6-092 | 320 | 5 | 5 | 4 | 5 |
| 6-093 | 320 | 5 | 5 | 4 | 5 |
| 6-094 | 320 | 5 | 5 | 5 | 5 |
| 6-095 | 320 | 5 | 5 | 5 | 5 |
| 6-096 | 320 | 5 | 4 | 5 | 5 |
| 6-098 | 320 | 3 | 5 | 4 | 5 |
| 6-099 | 320 | 5 | 5 | 5 | 5 |
| 6-100 | 320 | 5 | 5 | 5 | 5 |
| 6-103 | 320 | 5 | 5 | 5 | 5 |
| 6-104 | 320 | 5 | 5 |   | 5 |
| 6-105 | 320 | 3 | 4 |   | 4 |
| 6-106 | 320 | 4 | 5 |   | 5 |
| 6-107 | 320 | 5 | 5 |   | 5 |
| 6-108 | 320 | 5 | 5 |   | 5 |
| 6-109 | 320 | 5 | 4 |   | 5 |
| 6-110 | 320 | 5 | 5 |   | 5 |
| 6-111 | 320 | 5 | 5 |   | 5 |
| 6-112 | 320 | 5 | 5 | 4 | 5 |
| 6-113 | 320 | 5 | 5 | 5 | 5 |
| 7-001 | 320 | 4 | 5 | 0 | 2 |
| 7-002 | 320 | 5 | 5 | 3 | 5 |
| 7-003 | 320 | 5 | 5 | 0 | 5 |
| 7-004 | 320 | 5 | 5 | 5 | 5 |
| 7-005 | 320 | 5 | 5 | 0 | 5 |
| 7-006 | 320 | 5 | 5 | 0 | 5 |
| 7-007 | 320 | 5 | 5 | 4 | 5 |
| 7-008 | 320 | 5 | 5 | 5 | 5 |
| 7-010 | 320 | 5 | 5 | 5 | 5 |
| 7-011 | 320 | 5 | 4 | 5 | 5 |
| 7-012 | 320 | 5 | 5 | 4 | 5 |
| 7-014 | 320 | 4 | 5 | 2 | 5 |
| 7-015 | 320 | 5 | 5 | 5 | 5 |
| 7-016 | 320 | 0 | 5 | 0 | 0 |
| 7-017 | 320 | 5 | 5 | 4 | 5 |
| 7-018 | 320 | 3 | 5 | 3 | 3 |
| 7-019 | 320 | 5 | 4 | 2 | 3 |
| 7-020 | 320 | 4 | 5 | 3 | 4 |
| 7-021 | 320 | 2 | 2 | 0 | 0 |
| 7-022 | 320 | 0 | 4 | 0 | 0 |
| 7-023 | 320 | 0 | 5 | 0 | 0 |
| 7-024 | 320 | 5 | 5 | 2 | 3 |
| 7-025 | 320 | 1 | 3 | 0 | 0 |
| 7-026 | 320 | 0 | 3 | 0 | 0 |
| 7-027 | 320 | 5 | 5 | 4 | 5 |
| 7-028 | 320 | 0 | 0 | 0 | 0 |
| 7-029 | 320 | 3 | 4 | 0 | 0 |

TABLE 24-continued

| No. | Application herbicide amount (g/ha) | H | D | E | b |
|---|---|---|---|---|---|
| 7-031 | 320 | 4 | 5 | 3 | 5 |
| 8-001 | 320 | 0 | 0 | 0 | 0 |
| 8-002 | 320 | 0 | 0 | 0 | 0 |
| 8-003 | 320 | 0 | 0 | 0 | 0 |
| 9-001 | 320 | 5 | 4 | 2 | 5 |
| 9-002 | 320 | 5 | 5 | 5 | 5 |
| 9-003 | 320 | 5 | 5 | 5 | 5 |
| 9-004 | 320 | 5 | 5 | 5 | 5 |
| 9-005 | 320 | 5 | 5 | 2 | 4 |
| 9-006 | 320 | 5 | 5 | 5 | 5 |
| 9-007 | 320 | 5 | 5 | 5 | 5 |
| 9-008 | 320 | 5 | 5 | 5 | 5 |
| 9-009 | 320 | 5 | 5 | 4 | 5 |
| 9-010 | 320 | 5 | 5 | 5 | 5 |
| 9-011 | 320 | 5 | 5 | 5 | 5 |
| 9-012 | 320 | 5 | 5 | 5 | 5 |
| 9-013 | 320 | 5 | 5 | 5 | 5 |
| 9-014 | 320 | 5 | 5 | 5 | 5 |
| 9-015 | 320 | 5 | 5 | 5 | 5 |
| 9-016 | 320 | 5 | 5 | 5 | 5 |
| 9-017 | 320 | 5 | 5 | 3 | 5 |
| 9-018 | 320 | 2 | 0 | 0 | 4 |
| 9-019 | 320 | 5 | 5 | 4 | 5 |
| 9-020 | 320 | 5 | 5 | 5 | 5 |
| 9-021 | 320 | 5 | 5 | 5 | 5 |
| 9-022 | 320 | 5 | 5 | 5 | 5 |
| 9-023 | 320 | 5 | 5 | 5 | 5 |
| 9-024 | 320 | 5 | 5 | 5 | 5 |
| 9-025 | 320 | 0 | 5 | 0 | 2 |
| 9-026 | 320 | 0 | 3 | 0 | 0 |
| 9-027 | 320 | 5 | 5 | 5 | 3 |
| 9-028 | 320 | 5 | 5 |   | 5 |
| 9-029 | 320 | 4 | 4 |   | 3 |
| 10-001 | 320 | 5 | 4 | 0 | 3 |
| 10-002 | 320 | 5 | 5 | 3 | 5 |
| 10-003 | 320 | 5 | 4 | 0 | 5 |
| 10-004 | 320 | 5 | 5 | 5 | 5 |
| 11-002 | 320 | 5 | 5 | 4 | 5 |
| 12-002 | 320 | 5 | 5 | 5 | 5 |
| 13-001 | 320 | 5 | 5 | 4 | 5 |
| 13-002 | 320 | 5 | 5 | 5 | 5 |
| 13-003 | 320 | 5 | 5 | 5 | 5 |
| 13-004 | 320 | 5 | 5 | 5 | 5 |
| 13-005 | 320 | 5 | 5 | 5 | 5 |
| 13-006 | 320 | 5 | 5 | 5 | 5 |
| 14-001 | 320 | 5 | 5 | 5 | 5 |
| 14-002 | 320 | 5 | 5 | 5 | 5 |

TABLE 25

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-001 | 320 | 0 | 0 | 0 | 0 | 0 | 0 | 0 | 0 | 0 | 0 | 0 | 0 | 0 | 0 | 0 | 0 | 0 | 0 | 0 |
| 1-002 | 320 | 5 | 5 | 5 | 5 | 5 | 5 | 5 | 5 | 5 | 5 | 3 | 1 | 5 | 5 | 4 | 0 | 4 | 5 | 5 |
| 1-003 | 320 | 5 | 5 | 5 | 4 | 5 | 5 | 5 | 4 | 3 |   | 3 | 0 |   | 5 | 5 | 3 | 5 | 2 | 4 |
| 1-004 | 320 | 5 | 5 | 5 | 5 | 5 | 5 | 5 | 5 | 5 | 0 | 0 | 0 |   | 5 | 4 | 3 | 3 | 4 | 4 |
| 1-005 | 320 | 5 | 5 | 5 | 5 | 5 | 5 | 5 | 5 | 5 | 0 | 0 | 0 |   | 5 | 4 | 2 | 4 | 4 | 4 |
| 1-006 | 320 | 5 | 4 | 5 | 3 | 4 | 5 | 5 | 4 | 4 | 0 | 0 | 0 | 0 | 5 | 1 | 0 | 0 | 0 | 0 |
| 1-007 | 320 | 0 | 0 | 0 | 0 | 0 | 2 | 3 | 0 | 0 |   |   |   |   | 0 | 0 | 0 | 0 |   | 0 |
| 1-008 | 320 | 5 | 4 | 4 | 0 | 5 | 5 | 5 | 0 | 0 |   |   |   |   | 3 | 0 | 0 | 0 |   | 0 |
| 1-009 | 320 | 0 | 0 | 0 | 0 | 0 | 0 | 0 | 0 | 0 |   |   |   |   | 0 | 0 | 0 | 0 | 0 | 0 |
| 1-010 | 320 | 5 | 5 | 5 | 5 | 5 | 5 | 5 | 5 | 5 |   | 4 | 2 | 4 | 5 | 4 | 4 | 4 | 4 | 4 |
| 1-011 | 320 | 0 | 0 | 0 | 0 | 0 | 0 | 0 | 0 | 0 |   |   |   |   | 0 | 0 | 0 | 0 | 0 | 0 |
| 1-012 | 320 | 0 | 0 | 0 | 0 | 0 | 0 | 0 | 0 | 0 |   | 0 |   |   | 0 | 0 | 0 | 0 | 0 | 0 |
| 1-013 | 320 | 0 | 0 | 0 | 0 | 0 | 0 |   | 0 | 0 |   | 0 |   |   | 0 | 0 | 0 | 0 | 0 | 0 |
| 1-014 | 320 | 5 | 3 | 5 | 5 | 5 | 5 | 5 | 4 |   |   |   | 5 |   | 4 | 4 | 4 |   |   |   |
| 1-015 | 320 | 5 | 3 | 5 | 5 | 5 | 5 | 5 | 5 | 5 |   |   | 3 |   | 5 | 4 | 3 | 3 |   | 4 |
| 1-016 | 320 | 5 | 5 | 5 | 5 | 5 | 5 | 5 | 5 | 5 |   |   |   |   | 5 | 4 | 3 | 2 | 0 | 4 |
| 1-017 | 320 | 5 | 3 | 5 | 5 | 5 | 5 | 5 | 5 | 5 |   |   |   |   | 5 | 4 | 2 | 2 | 0 | 4 |
| 1-018 | 320 | 5 | 3 | 5 | 4 | 5 | 5 | 5 | 4 | 2 |   |   |   |   | 5 | 4 | 0 | 4 | 0 | 4 |
| 1-019 | 320 | 5 | 5 | 5 | 5 | 5 | 5 | 5 | 4 | 3 |   |   |   |   | 5 | 4 | 3 | 3 | 0 | 4 |
| 1-020 | 320 | 5 | 3 | 5 | 4 | 5 | 5 | 5 | 3 | 0 |   | 0 | 0 |   | 5 | 1 | 0 | 2 | 0 | 4 |
| 1-021 | 320 | 0 | 0 | 0 | 0 | 0 | 2 | 0 | 0 | 0 |   | 0 | 0 |   | 2 | 0 | 0 | 0 | 0 | 0 |
| 1-022 | 320 | 5 | 3 | 5 | 4 | 5 | 5 | 5 | 0 | 0 |   |   |   |   | 5 | 0 | 0 | 4 | 3 |   |
| 1-023 | 320 | 4 | 3 | 3 | 0 | 0 | 3 | 4 | 0 | 0 | 0 | 0 |   |   | 5 | 0 | 0 | 0 | 0 | 0 |
| 1-024 | 320 | 5 | 5 | 5 | 4 | 5 | 5 | 5 | 3 | 4 |   |   | 0 |   | 5 | 1 | 1 | 4 | 0 | 3 |
| 1-025 | 320 | 5 | 5 | 5 | 3 | 4 | 5 | 5 | 0 | 0 |   | 0 | 0 |   | 5 | 0 | 0 | 0 | 0 | 4 |
| 1-026 | 320 | 5 | 5 | 5 | 3 | 5 | 5 | 5 | 0 | 0 |   |   | 0 |   | 4 | 0 | 0 | 2 |   | 3 |
| 1-027 | 320 | 5 | 3 | 5 | 4 | 5 | 5 | 5 | 0 | 0 |   |   | 0 |   | 5 | 4 | 0 | 3 | 0 | 4 |
| 1-028 | 320 | 5 | 5 | 5 | 4 | 5 | 5 | 5 | 3 | 3 |   |   |   |   | 5 | 0 | 0 | 4 | 0 | 4 |
| 1-029 | 320 | 5 | 5 | 5 | 4 | 3 | 5 | 5 | 0 | 0 |   | 0 |   |   | 5 | 0 | 0 | 0 | 0 | 3 |
| 1-030 | 320 | 3 | 2 | 2 | 0 | 3 | 5 | 3 | 0 | 0 |   |   |   |   | 4 | 0 | 0 | 0 |   | 0 |
| 1-031 | 320 | 0 | 0 | 0 | 0 | 0 | 0 | 0 | 0 | 0 |   | 0 | 0 |   | 0 | 0 | 0 | 0 | 0 | 3 |
| 1-032 | 320 | 5 | 5 | 5 | 5 | 5 | 5 | 5 | 4 | 4 |   |   |   |   | 5 | 4 | 0 | 5 | 4 | 5 |
| 1-033 | 320 | 5 | 5 | 5 | 4 | 5 | 5 | 5 | 5 | 5 |   | 0 | 3 | 4 | 5 | 4 | 0 | 5 | 4 | 5 |
| 1-034 | 320 | 5 | 5 | 5 | 5 | 5 | 5 | 5 | 5 | 5 | 5 |   | 4 |   | 5 | 4 | 0 | 4 | 4 | 5 |
| 1-035 | 320 | 5 | 5 | 5 | 4 | 5 | 5 | 5 | 5 | 5 |   |   | 0 |   | 5 | 4 | 0 | 4 | 3 | 5 |
| 1-036 | 320 | 5 | 5 | 5 | 5 | 5 | 5 | 5 | 5 | 5 |   |   |   |   | 5 | 3 | 0 | 3 | 3 | 5 |
| 1-037 | 320 | 0 | 0 | 0 | 0 | 0 | 0 | 0 | 0 | 0 | 0 |   |   |   | 0 | 0 | 0 | 0 | 0 | 0 |
| 1-038 | 320 | 5 | 5 | 5 | 0 | 5 | 5 | 5 | 4 | 3 | 0 | 0 |   | 0 | 5 | 3 | 1 | 3 | 0 | 4 |
| 1-039 | 320 | 5 | 5 | 5 | 4 | 5 | 5 | 5 | 5 | 5 |   |   |   |   | 5 | 4 | 0 | 4 | 3 | 4 |
| 1-040 | 320 | 4 | 4 | 5 | 3 | 4 | 4 | 5 | 0 | 0 |   |   | 0 |   | 5 | 0 | 0 | 0 | 0 | 3 |
| 1-041 | 320 | 5 | 5 | 5 | 5 | 5 | 5 | 5 | 3 | 3 |   | 0 |   | 3 | 5 | 4 | 1 | 4 |   | 4 |
| 1-042 | 320 | 5 | 5 | 5 | 3 | 5 | 5 | 5 | 5 | 4 | 0 | 0 |   |   | 5 | 3 | 0 | 1 | 0 | 4 |
| 1-043 | 320 | 5 | 5 | 5 | 4 | 5 | 5 | 5 | 4 | 4 |   | 0 |   |   | 5 | 4 | 1 | 4 | 4 | 5 |

TABLE 25-continued

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-044 | 320 | 5 | 5 | 5 | 2 | 5 | 5 | 5 | 5 | 4 | | | | | 5 | 4 | 0 | 2 | | 4 |
| 1-045 | 320 | 0 | 0 | 0 | 0 | 0 | 4 | 0 | 0 | 0 | | 0 | | | 0 | 0 | 0 | 0 | 0 | 0 |
| 1-046 | 320 | 5 | 4 | 5 | 5 | 5 | 3 | 5 | 4 | 2 | | | 0 | | 5 | 4 | 0 | 4 | 0 | 4 |
| 1-047 | 320 | 3 | 0 | 3 | 0 | 0 | 3 | 0 | 0 | 0 | 0 | 0 | 0 | 0 | 4 | 0 | 0 | 0 | 0 | |
| 1-048 | 320 | 5 | 5 | 5 | 1 | 5 | 5 | 5 | 3 | 1 | 0 | 0 | 0 | 0 | 5 | 3 | 0 | 2 | 0 | 0 |
| 1-049 | 320 | 0 | 0 | 0 | 0 | 0 | 0 | 0 | 0 | 0 | | 0 | 0 | | 0 | 0 | 0 | 0 | 0 | 0 |
| 1-050 | 320 | 5 | 4 | 4 | 0 | 0 | 4 | 0 | 1 | 0 | 0 | 0 | | | 5 | 0 | 0 | 0 | 0 | 0 |
| 1-051 | 320 | 5 | 5 | 5 | 3 | 5 | 3 | 5 | 5 | 4 | 0 | 0 | 0 | | 5 | 4 | 3 | 2 | 0 | 4 |
| 1-052 | 320 | 5 | 5 | 5 | 4 | 5 | 3 | 5 | 4 | 3 | 0 | 0 | | 0 | 5 | 3 | 0 | 5 | 0 | 3 |
| 1-053 | 320 | 5 | 4 | 5 | 0 | 3 | 5 | 3 | 1 | 0 | 0 | 0 | | 0 | 5 | 1 | 0 | 0 | 0 | 3 |
| 1-054 | 320 | 5 | 5 | 4 | 0 | 1 | 3 | 1 | 0 | 0 | 0 | 0 | | 0 | 5 | 0 | 0 | 0 | 0 | 1 |
| 1-055 | 320 | 5 | 4 | 4 | 0 | 1 | 3 | 2 | 0 | 0 | 0 | 0 | | 0 | 5 | 0 | 0 | 0 | 0 | 0 |
| 1-056 | 320 | 5 | 5 | 5 | 3 | 5 | 3 | 5 | 4 | 3 | | 0 | | 0 | 5 | 3 | 0 | 5 | 0 | 4 |
| 1-057 | 320 | 4 | 4 | 4 | 0 | 4 | 3 | 4 | 3 | 1 | | 0 | | 0 | 5 | 0 | 0 | 0 | 0 | 4 |
| 1-058 | 320 | 5 | 5 | 5 | 1 | 5 | 3 | 4 | 4 | 2 | 0 | 0 | | 0 | 5 | 4 | 0 | 0 | 0 | 3 |
| 1-059 | 320 | 4 | 4 | 4 | 0 | 3 | 5 | 5 | 1 | 0 | | 0 | | | 4 | 3 | 0 | 0 | 0 | 0 |
| 1-060 | 320 | 5 | 5 | 5 | 3 | 5 | 5 | 5 | 1 | 5 | 0 | 0 | | 0 | 5 | 1 | 0 | 2 | 0 | 3 |
| 1-062 | 320 | 5 | 5 | 5 | 0 | 5 | 5 | 4 | 0 | 0 | 0 | 0 | 0 | 0 | 5 | 4 | 0 | 0 | 0 | 3 |
| 1-063 | 320 | 5 | 5 | 5 | 3 | 5 | 5 | 5 | 2 | 0 | | | | 0 | 5 | 4 | 0 | 3 | | 0 |
| 1-064 | 320 | 5 | 5 | 5 | 3 | 5 | 5 | 5 | 5 | 4 | | 0 | | 0 | 5 | 5 | 2 | 3 | 0 | 4 |
| 1-065 | 320 | 5 | 5 | 5 | 3 | 5 | 5 | 5 | 4 | 5 | | 0 | | 0 | 5 | 5 | 0 | 4 | 0 | 4 |
| 1-066 | 320 | 4 | 4 | 5 | 0 | 5 | 5 | 5 | 0 | 0 | 0 | 0 | 0 | 0 | 5 | 4 | 0 | 0 | 0 | 0 |
| 1-067 | 320 | 5 | 5 | 5 | 3 | 5 | 5 | 5 | 5 | 5 | | 0 | 0 | 0 | 5 | 3 | 0 | 5 | 0 | 4 |
| 1-068 | 320 | 5 | 5 | 5 | 3 | 5 | 5 | 5 | 4 | 4 | | 0 | 0 | 0 | 5 | 5 | 0 | 4 | 0 | 4 |
| 1-069 | 320 | 5 | 5 | 4 | 5 | 3 | 5 | 5 | 4 | 4 | | | 0 | | 5 | 5 | 0 | 4 | 0 | 4 |
| 1-070 | 320 | 4 | 4 | 4 | 0 | 5 | 5 | 5 | 0 | 0 | 0 | 0 | 0 | 0 | 5 | 1 | 0 | 0 | 0 | 0 |
| 1-071 | 320 | 5 | 5 | 5 | 4 | 5 | 5 | 5 | 4 | 4 | | 0 | 0 | 0 | 5 | 4 | 0 | 4 | | 4 |
| 1-072 | 320 | 5 | 5 | 5 | 4 | 5 | 5 | 5 | 4 | 5 | | 0 | 0 | 0 | 5 | 5 | 0 | 4 | 0 | 4 |
| 1-073 | 320 | 5 | 5 | 5 | 4 | 5 | 5 | 5 | 5 | 5 | | | | | 5 | 4 | 0 | 4 | | 4 |
| 1-074 | 320 | 5 | 5 | 5 | 4 | 5 | 5 | 5 | 5 | 5 | 0 | 0 | 0 | 0 | 5 | 4 | 0 | 4 | 0 | 4 |
| 1-075 | 320 | 5 | 5 | 5 | | 5 | 5 | 5 | 5 | 5 | 0 | 0 | | | 5 | 5 | 0 | 4 | | |
| 1-076 | 192 | 5 | 5 | 5 | 4 | 4 | 5 | 5 | 4 | 4 | | 0 | 0 | 0 | 5 | 2 | 0 | 4 | 0 | 4 |
| 1-078 | 320 | 5 | 5 | 5 | 2 | 0 | 3 | 5 | 4 | 0 | 0 | 0 | | 0 | 5 | 4 | 0 | 0 | 0 | 1 |
| 1-079 | 320 | 5 | 5 | 5 | 3 | 5 | 5 | 5 | 5 | 4 | 0 | 0 | | 0 | 5 | 4 | 1 | 4 | 0 | 4 |
| 1-080 | 320 | 5 | 5 | 5 | 3 | 5 | 5 | 5 | 4 | 5 | | 0 | | 0 | 5 | 4 | 1 | 4 | 0 | 4 |
| 1-081 | 320 | 5 | 5 | 5 | 3 | 5 | 5 | 5 | 4 | 4 | 0 | 0 | | 0 | 5 | 4 | 1 | 4 | 0 | 4 |
| 1-082 | 320 | 5 | 5 | 5 | 3 | 5 | 5 | 5 | 5 | 5 | | 0 | | 0 | 5 | 4 | 2 | 3 | 0 | 4 |
| 1-083 | 320 | 5 | 5 | 5 | 3 | 5 | 5 | 5 | 4 | 5 | | 0 | | 0 | 5 | 4 | 1 | 4 | 0 | 4 |
| 1-085 | 320 | 0 | 5 | 1 | 0 | 3 | 3 | 3 | 0 | 0 | 0 | 0 | | 0 | 5 | 0 | 0 | 0 | 0 | 0 |
| 1-086 | 320 | 2 | 4 | 4 | 3 | 3 | 5 | 3 | 0 | 0 | 0 | 0 | | 0 | 5 | 1 | 0 | 0 | 0 | 2 |
| 1-087 | 320 | 5 | 5 | 5 | 3 | 5 | 5 | 5 | 5 | 5 | | 0 | 0 | 0 | 5 | 3 | 2 | 5 | 4 | 5 |
| 1-088 | 320 | 5 | 5 | 5 | 3 | 5 | 5 | 5 | 0 | 1 | 0 | 0 | | 0 | 5 | 4 | 0 | 3 | 0 | 4 |
| 1-089 | 320 | 5 | 5 | 5 | 2 | 5 | 5 | 5 | 2 | 3 | 0 | 0 | | 0 | 5 | 5 | 0 | 4 | 0 | 4 |
| 1-090 | 320 | 5 | 5 | 5 | 3 | 5 | 5 | 5 | 4 | 0 | 0 | 0 | | 0 | 5 | 3 | 0 | 4 | 0 | 4 |
| 1-091 | 320 | 5 | 5 | 5 | 3 | 5 | 5 | 5 | 1 | 0 | | 0 | 0 | 0 | 5 | 5 | 0 | 4 | 0 | 3 |
| 1-092 | 320 | 5 | 5 | 5 | 2 | 4 | 5 | 5 | 3 | 3 | | 0 | | 0 | 5 | 5 | 0 | 4 | 0 | 4 |
| 1-093 | 320 | 5 | 5 | 5 | 3 | 5 | 5 | 5 | 4 | 3 | 0 | 0 | 0 | 0 | 5 | 5 | 0 | 4 | 0 | 4 |
| 1-094 | 320 | 5 | 5 | 5 | 3 | 5 | 5 | 5 | 2 | 4 | 0 | 0 | | 0 | 5 | 4 | 1 | 3 | 0 | 4 |
| 1-095 | 320 | 5 | 5 | 5 | 3 | 5 | 5 | 5 | 4 | 4 | 0 | 0 | 0 | 1 | 5 | 5 | 0 | 4 | 0 | 4 |
| 1-096 | 320 | 5 | 5 | 4 | 3 | 5 | 5 | 5 | 4 | 4 | 0 | 0 | | 0 | 5 | 4 | 1 | 3 | 0 | 3 |
| 1-097 | 320 | 0 | 2 | 2 | 1 | 2 | 2 | 0 | 0 | 0 | 3 | 0 | 0 | 0 | 2 | 1 | 0 | 0 | 0 | 3 |
| 1-098 | 320 | 5 | 5 | 5 | 2 | 5 | 5 | 5 | 4 | 4 | | 0 | 0 | 0 | 5 | 5 | 2 | 3 | 0 | 5 |
| 1-099 | 320 | 5 | 5 | 5 | 2 | 5 | 5 | 5 | 5 | 3 | 0 | 0 | | 0 | 5 | 5 | 3 | 3 | 2 | 5 |
| 1-100 | 320 | 5 | 5 | 5 | 3 | 5 | 5 | 5 | 4 | 2 | | 0 | 0 | 1 | 5 | 5 | 2 | 5 | 0 | 3 |
| 1-101 | 320 | 5 | 5 | 5 | 3 | 5 | 5 | 5 | 5 | 3 | 0 | 0 | | 0 | 5 | 5 | 2 | 3 | 3 | 5 |
| 1-102 | 320 | 4 | 5 | 5 | 0 | 5 | 5 | 5 | 0 | 0 | | 0 | | 0 | 5 | 0 | 0 | 0 | 0 | 0 |
| 1-103 | 320 | 5 | 5 | 5 | 3 | 5 | 5 | 4 | 5 | 5 | 0 | 0 | 0 | 0 | 5 | 5 | 1 | 4 | 0 | 3 |
| 1-104 | 320 | 5 | 5 | 5 | 3 | 5 | 5 | 5 | 4 | 0 | | 0 | 0 | 0 | 5 | 1 | 0 | 1 | 0 | 2 |
| 1-105 | 320 | 5 | 5 | 5 | 1 | 5 | 5 | 5 | 1 | 4 | 0 | 0 | 0 | 0 | 5 | 1 | 0 | 3 | 0 | 3 |
| 1-106 | 320 | 5 | 5 | 5 | 3 | 5 | 5 | 5 | 0 | 0 | 0 | 0 | 0 | 0 | 5 | 1 | 0 | 3 | 0 | 3 |
| 1-107 | 320 | 5 | 3 | 5 | 0 | 5 | 5 | 5 | 0 | 0 | | 0 | | | 5 | 0 | 0 | 0 | 0 | 2 |
| 1-108 | 320 | 5 | 5 | 5 | 3 | 5 | 5 | 5 | 4 | 0 | | 0 | | 0 | 5 | 5 | 0 | 4 | 0 | 4 |
| 1-109 | 320 | 5 | 5 | 5 | 2 | 5 | 5 | 5 | 4 | 3 | 0 | 0 | 0 | 2 | 5 | 1 | 0 | 2 | 0 | 2 |
| 1-110 | 320 | 5 | 5 | 5 | 4 | 5 | 5 | 5 | 0 | 0 | 0 | 0 | | 0 | 5 | 4 | 0 | 5 | 0 | 1 |
| 1-111 | 320 | 5 | 5 | 5 | 3 | 5 | 5 | 5 | 4 | 0 | | 0 | 0 | 0 | 5 | 1 | 1 | 5 | 0 | 4 |
| 1-112 | 320 | 4 | 5 | 4 | 3 | 5 | 6 | 5 | 0 | 0 | 0 | 0 | 0 | 0 | 5 | 1 | 0 | 0 | 0 | 0 |
| 1-113 | 320 | 1 | 0 | 0 | 3 | 3 | 6 | 5 | 0 | 0 | 0 | 0 | 0 | 0 | 2 | 0 | 0 | 0 | 0 | 0 |
| 1-114 | 320 | 5 | 5 | 0 | 3 | 4 | 5 | 5 | 0 | 0 | 0 | 0 | 0 | 0 | 3 | 0 | 0 | 0 | 0 | 1 |
| 1-116 | 320 | 1 | 3 | 3 | 3 | 4 | 4 | 3 | 2 | 5 | 0 | 0 | 0 | 0 | 1 | 0 | 0 | 0 | 0 | 2 |
| 1-117 | 320 | 4 | 5 | 5 | 0 | 4 | 4 | 5 | 0 | 0 | 0 | 0 | 0 | 0 | 5 | 0 | 0 | 0 | 0 | 2 |
| 1-118 | 320 | 3 | 2 | 4 | 0 | 3 | 3 | 3 | 0 | 0 | 0 | 0 | 0 | 0 | 5 | 0 | 0 | 0 | 0 | 1 |
| 1-119 | 320 | 4 | 4 | 5 | 4 | 4 | 5 | 5 | 0 | 0 | 0 | 0 | 0 | 0 | 5 | 0 | 0 | 0 | 0 | 0 |
| 1-120 | 320 | 0 | 0 | 0 | 0 | 0 | 4 | 3 | 0 | 0 | 0 | 0 | 0 | 0 | 0 | 0 | 0 | 0 | 0 | 0 |
| 1-121 | 320 | 5 | 5 | 5 | 4 | 5 | 5 | 5 | 0 | 0 | 0 | 0 | 0 | 0 | 5 | 1 | 0 | 0 | 0 | 3 |
| 1-122 | 320 | 2 | 3 | 4 | 2 | 5 | 5 | 4 | 0 | 0 | 0 | 0 | 0 | 0 | 4 | 2 | 0 | 0 | 0 | 0 |
| 1-123 | 320 | 5 | 5 | 5 | 4 | 5 | 5 | 5 | 3 | 0 | 0 | 0 | 0 | 0 | 5 | 3 | 0 | 0 | 0 | 3 |

TABLE 25-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-124 | 320 | 0 | 3 | 1 | 0 | 2 | 3 | 0 | 0 | 0 | 0 | 0 | 0 | 0 | 1 | 0 | 0 | 0 | 0 | 0 |
| 1-125 | 320 | 5 | 5 | 5 | 3 | 0 | 5 | 5 | 0 | 0 | 0 | 0 | 0 | 0 | 5 | 2 | 0 | 3 | 0 | 0 |
| 1-126 | 320 | 0 | 0 | 0 | 0 | 3 | 4 | 0 | 0 | 0 | 0 | 0 | 0 | 0 | 0 | 0 | 0 | 0 | 0 | 0 |
| 1-130 | 320 | 0 | 0 | 0 | 0 | 3 | 3 | 3 | 0 | 0 | 0 | 0 | 0 | 0 | 0 | 0 | 0 | 0 | 0 | 0 |
| 1-131 | 320 | 4 | 5 | 5 | 3 | 5 | 5 | 5 | 0 | 0 | 0 | 0 |   | 3 | 5 | 0 | 0 | 0 | 0 | 4 |
| 1-133 | 320 | 4 | 4 | 4 | 0 | 5 | 3 |   | 0 | 0 | 0 | 0 |   | 0 | 0 | 0 | 4 | 0 | 0 | 0 |
| 1-134 | 320 | 5 | 5 | 5 | 2 | 5 | 5 |   | 3 | 4 | 0 | 0 | 0 | 0 | 5 | 5 | 0 | 2 | 0 | 0 |
| 1-135 | 320 | 5 | 5 | 5 | 3 | 5 | 5 |   | 0 | 0 | 0 | 0 | 0 | 2 | 5 | 0 | 0 | 0 | 0 | 2 |
| 1-136 | 320 | 5 | 5 | 5 | 3 | 5 | 5 |   |   | 0 | 0 | 0 | 0 | 0 | 2 | 0 | 0 | 3 | 0 | 3 |
| 1-137 | 320 | 5 | 5 | 5 | 2 | 5 | 5 |   | 0 |   | 0 | 0 | 0 | 0 | 5 | 0 | 0 | 0 | 0 | 0 |
| 1-138 | 320 |   | 4 | 5 | 0 | 5 | 5 |   | 0 | 0 | 0 | 0 | 0 | 0 | 5 | 0 | 0 | 0 | 0 | 0 |
| 1-139 | 320 | 5 | 5 | 5 | 4 | 5 | 5 | 5 | 4 | 3 | 0 | 0 | 0 |   | 5 | 5 | 0 | 3 | 0 | 4 |
| 1-140 | 320 | 5 | 5 | 5 | 4 | 5 | 5 | 5 | 5 | 5 | 0 | 0 | 0 | 0 | 5 | 4 | 1 | 5 | 0 | 4 |
| 1-142 | 320 | 5 | 5 | 5 | 3 | 5 | 5 |   | 0 | 0 |   | 0 | 0 | 0 | 5 | 0 | 0 | 3 | 0 | 3 |
| 1-143 | 320 | 1 | 1 | 0 | 2 | 2 | 4 | 5 | 0 | 0 |   | 0 | 0 | 0 | 0 | 0 | 0 | 2 | 0 | 0 |
| 1-144 | 320 | 5 | 5 | 5 | 2 | 4 | 4 |   | 0 | 0 | 0 | 0 | 0 | 0 | 5 | 3 | 0 | 0 | 0 | 2 |
| 1-145 | 320 | 5 | 5 | 5 | 4 | 5 | 5 | 5 | 4 | 4 | 0 | 3 | 0 | 3 | 5 | 5 | 0 | 5 | 0 | 4 |
| 1-146 | 320 | 5 | 5 | 5 | 4 | 5 | 5 | 5 | 5 | 5 | 0 | 1 | 0 | 5 | 5 | 1 | 0 | 5 | 3 | 5 |
| 1-147 | 320 | 5 | 5 | 5 | 5 | 5 | 5 | 5 | 5 | 5 | 0 | 2 | 0 | 3 | 5 | 5 | 0 | 5 | 0 | 4 |
| 1-148 | 320 | 5 | 5 | 5 | 0 | 5 | 5 | 5 | 5 | 2 | 0 | 0 | 0 |   | 5 | 3 | 0 | 0 | 0 | 4 |
| 1-149 | 320 | 5 | 5 | 5 | 0 | 5 | 5 | 5 | 5 | 4 | 0 | 0 |   | 0 | 5 | 2 | 0 | 5 | 0 | 4 |
| 1-150 | 320 | 5 | 0 | 0 | 2 | 5 | 5 |   |   |   | 0 | 0 | 0 | 0 | 0 | 0 | 0 | 1 | 0 | 0 |
| 1-151 | 320 | 5 |   | 0 | 3 | 5 | 5 |   | 0 | 0 | 0 | 0 | 0 | 0 | 1 | 0 | 0 | 0 | 0 | 0 |
| 1-152 | 320 | 0 | 0 | 0 | 0 | 3 | 2 |   | 0 | 0 | 0 | 0 | 0 | 0 | 0 | 0 | 0 | 0 | 0 | 0 |
| 1-153 | 320 | 5 | 1 | 0 | 0 | 3 | 4 |   | 0 | 0 | 0 | 0 | 0 | 0 | 1 | 0 | 0 | 2 | 0 | 0 |
| 1-154 | 320 | 5 | 5 | 5 | 0 | 5 | 5 | 5 | 4 | 4 | 0 | 0 | 0 | 0 | 5 | 0 | 0 | 3 | 0 | 4 |
| 1-155 | 320 | 5 | 5 | 5 | 4 | 5 | 5 |   | 5 | 5 | 0 | 0 | 0 |   | 5 | 3 | 0 | 3 | 0 | 4 |
| 1-156 | 320 | 5 | 5 | 5 | 4 | 5 | 5 |   | 5 | 5 | 0 | 2 |   |   | 5 | 1 | 0 | 5 | 1 | 4 |
| 1-159 | 320 | 4 | 3 | 3 | 0 | 4 | 5 |   | 0 | 0 | 0 | 0 | 0 | 0 | 3 | 0 | 0 | 1 | 0 | 0 |
| 1-160 | 320 | 5 | 5 | 5 | 0 | 5 | 5 |   | 4 | 4 | 0 | 0 | 0 | 0 | 5 | 0 | 0 | 2 | 0 | 4 |
| 1-161 | 320 | 5 | 0 | 0 | 0 | 3 | 3 |   | 0 | 0 | 0 | 0 |   | 0 | 3 | 0 | 0 | 3 | 0 | 2 |
| 1-162 | 320 | 5 | 5 | 5 | 3 | 5 | 5 |   | 5 | 4 | 0 | 0 | 0 | 0 | 5 | 2 | 0 | 4 | 0 | 4 |
| 1-163 | 320 | 5 | 5 | 5 | 3 | 5 | 5 |   |   | 4 | 0 | 0 |   | 0 | 5 | 1 | 0 | 0 | 0 | 4 |
| 2-001 | 102 | 5 | 4 | 5 | 0 | 4 | 5 | 2 | 3 | 1 |   | 0 | 0 | 0 | 5 | 4 | 0 | 0 | 0 | 3 |
| 2-002 | 320 | 0 | 0 | 0 | 0 | 0 | 0 | 0 | 0 | 0 |   | 0 | 0 | 0 | 1 | 0 | 0 | 0 | 0 | 0 |
| 2-003 | 320 | 4 | 0 | 0 | 0 | 4 | 5 | 5 | 0 | 0 | 0 | 0 |   |   | 2 | 0 | 0 | 0 | 0 | 0 |
| 2-005 | 269 | 5 | 4 | 5 | 0 | 4 | 5 | 1 | 0 | 0 |   | 0 | 0 |   | 5 | 0 | 0 | 0 | 0 | 4 |
| 2-006 | 320 | 5 | 5 | 5 | 3 | 5 | 5 | 5 | 4 | 0 | 0 | 0 | 0 | 0 | 5 | 2 | 0 | 0 | 0 | 4 |
| 2-007 | 320 | 5 | 4 | 5 | 0 | 3 | 5 | 3 | 0 | 0 | 0 | 0 | 0 |   | 5 | 0 | 0 | 0 | 0 | 4 |
| 2-008 | 320 | 0 | 0 | 0 | 0 | 0 | 3 | 0 | 0 | 0 | 0 | 0 | 0 | 0 | 0 | 0 | 0 | 0 | 0 | 0 |
| 2-009 | 320 | 2 | 0 | 1 | 0 | 0 | 0 | 0 | 0 | 0 | 0 | 0 | 0 |   | 5 | 0 | 0 | 0 | 0 | 0 |
| 2-010 | 320 | 0 | 0 | 0 | 0 | 0 | 0 | 0 | 0 | 0 | 0 | 0 | 0 | 0 | 0 | 0 | 0 | 0 | 0 | 0 |
| 2-011 | 320 | 0 | 0 | 0 | 0 | 0 | 0 | 0 | 0 | 0 | 0 | 0 | 0 |   | 0 | 0 | 0 | 0 | 0 | 0 |
| 2-012 | 320 | 0 | 0 | 0 | 0 | 0 | 0 | 0 | 0 | 0 | 0 | 0 | 0 |   | 0 | 0 | 0 | 0 | 0 | 0 |
| 2-013 | 320 | 1 | 1 | 1 | 0 | 0 | 1 | 0 | 0 | 0 | 0 | 0 | 0 | 0 | 5 | 0 | 0 | 0 | 0 | 0 |
| 2-014 | 320 | 5 | 5 | 5 | 0 | 2 | 4 | 2 | 0 | 0 | 0 | 0 | 0 |   | 5 | 3 | 0 | 0 | 0 | 0 |
| 2-015 | 320 | 3 | 3 | 1 | 0 | 2 | 5 | 3 | 0 | 0 | 0 | 0 |   |   | 4 | 0 | 0 | 0 | 0 | 0 |
| 2-016 | 320 | 5 | 5 | 5 | 0 | 4 | 5 | 2 | 0 |   |   |   |   |   | 5 | 3 | 0 | 0 |   | 2 |
| 2-017 | 320 | 5 | 5 | 5 | 0 | 3 | 5 | 3 | 4 | 0 | 0 | 0 | 0 |   | 5 | 0 | 0 | 0 | 0 | 5 |
| 2-018 | 320 | 5 | 5 | 5 | 0 | 3 | 5 | 2 | 4 | 3 | 0 | 0 |   |   | 5 | 2 | 0 | 0 | 0 | 3 |
| 2-020 | 320 | 5 | 5 | 4 | 0 | 0 | 4 | 0 | 0 | 1 |   |   |   | 0 | 5 | 3 | 0 | 0 | 0 | 0 |
| 2-021 | 320 | 5 | 5 | 4 | 0 | 5 | 5 | 0 | 1 | 2 | 0 | 0 |   | 0 | 5 | 4 | 0 | 0 | 0 | 1 |
| 2-022 | 320 | 0 | 4 | 0 | 0 | 0 | 4 | 0 | 0 | 0 | 0 | 0 |   | 0 | 4 | 0 | 0 | 0 | 0 | 0 |
| 2-024 | 320 | 5 | 5 | 4 | 0 | 0 | 0 | 0 | 0 | 0 | 0 | 0 | 0 | 0 | 5 | 0 | 0 | 0 | 0 | 0 |
| 2-025 | 320 | 4 | 5 | 4 | 0 | 0 | 4 | 0 | 0 | 0 | 0 | 0 | 0 | 0 | 5 | 0 | 0 | 0 | 0 | 0 |
| 2-026 | 320 | 5 | 5 | 5 | 0 | 3 | 5 | 2 | 0 |   |   | 0 |   | 0 | 5 | 1 | 0 | 0 | 0 | 4 |
| 2-027 | 320 | 3 | 5 | 3 | 0 | 1 | 2 | 0 | 0 | 0 |   | 0 |   | 0 | 4 | 1 | 0 | 0 | 0 | 0 |
| 2-028 | 320 | 4 | 5 | 1 | 0 | 3 | 5 | 2 | 1 | 0 | 0 | 0 | 0 | 0 | 5 | 2 | 0 | 0 | 0 | 0 |
| 2-030 | 320 | 4 | 5 | 1 | 0 | 3 | 4 | 4 | 0 | 0 | 0 | 0 | 0 | 0 | 5 | 1 | 0 | 0 | 0 | 0 |
| 2-031 | 320 | 5 | 5 | 5 | 0 | 3 | 5 | 2 | 1 | 0 | 0 | 0 |   |   | 5 | 5 | 0 | 3 | 0 | 3 |
| 2-032 | 320 | 4 | 5 | 4 | 0 | 5 | 5 |   | 0 | 0 | 0 | 0 | 0 | 0 | 5 | 1 | 0 | 0 | 0 | 1 |
| 3-001 | 320 | 2 | 0 | 0 | 0 | 1 | 4 | 5 | 0 | 0 | 0 | 0 | 0 | 0 | 2 | 0 | 0 | 0 | 0 | 0 |
| 3-002 | 320 | 0 | 0 | 0 | 0 | 0 | 0 | 0 | 0 | 0 | 0 | 0 |   |   | 0 | 0 | 0 | 0 | 0 | 0 |
| 4-001 | 320 | 2 | 0 | 0 | 0 | 3 | 5 | 5 | 0 |   |   |   | 0 |   | 5 | 0 | 0 | 0 | 0 | 1 |
| 5-001 | 320 | 4 | 0 | 1 | 0 | 2 | 5 | 5 | 0 |   |   |   | 0 |   | 5 | 0 | 0 | 0 |   | 0 |
| 5-002 | 320 | 0 | 0 | 0 | 0 | 0 | 0 | 0 | 0 | 0 |   |   |   | 0 | 0 | 0 | 0 | 0 | 0 |   |
| 6-001 | 320 | 5 | 5 | 5 | 5 | 5 | 5 | 5 | 0 | 0 |   | 0 | 0 |   | 5 | 5 | 0 | 5 | 0 | 2 |
| 6-002 | 320 | 2 | 3 | 2 | 0 | 2 | 5 | 4 | 0 | 0 |   | 0 |   |   | 5 | 0 | 0 | 0 | 0 | 0 |
| 6-003 | 320 | 5 | 5 | 5 | 3 | 5 | 5 | 5 | 5 | 3 | 0 | 0 |   |   | 5 | 4 | 0 | 0 | 0 | 4 |
| 6-004 | 320 | 5 | 5 | 5 | 4 | 5 | 5 | 5 | 0 | 4 |   | 0 |   |   | 5 | 2 | 0 | 0 | 4 |   |
| 6-005 | 320 | 5 | 5 | 5 | 4 | 5 | 5 | 5 | 0 | 0 | 0 | 0 | 0 |   | 5 | 3 | 1 | 4 | 0 | 0 |
| 6-006 | 320 | 5 | 5 | 5 | 4 | 5 | 5 | 5 | 4 | 3 | 0 | 0 |   | 2 | 5 | 5 | 0 | 5 | 0 | 4 |
| 6-007 | 320 | 5 | 5 | 5 | 4 | 5 | 5 | 5 | 4 | 3 | 0 | 0 | 0 |   | 5 | 5 | 0 | 5 | 0 |   |
| 6-008 | 320 | 5 | 5 | 5 | 4 | 4 | 5 | 5 | 0 | 0 |   | 0 | 0 | 0 | 5 | 3 | 0 | 4 | 0 | 0 |
| 6-009 | 320 | 5 | 5 | 5 | 4 | 5 | 5 | 5 | 5 | 5 |   | 4 |   |   | 5 | 5 | 0 | 5 | 2 | 4 |
| 6-010 | 320 | 5 | 5 | 5 | 3 | 5 | 5 | 5 | 3 | 1 |   | 0 |   |   | 5 | 4 | 0 | 4 | 0 | 0 |

TABLE 25-continued

| | | Application herbicide amount | | | | | | | | | | | | | | | | | | | |
|---|---|---|---|---|---|---|---|---|---|---|---|---|---|---|---|---|---|---|---|---|---|
| No. | (g/ha) | F | G | H | I | J | K | L | M | N | O | P | Q | R | b | c | d | e | f | g |
| 6-015 | 320 | 5 | 5 | 5 | 0 | 5 | 5 | 5 | 3 | 5 | 3 | 2 | | | 5 | 5 | 0 | 0 | 0 | 4 |
| 6-016 | 320 | 5 | 5 | 4 | 0 | 0 | 0 | 5 | 0 | 2 | 0 | 0 | 0 | 0 | 2 | 0 | 0 | 0 | 0 | 0 |
| 6-017 | 320 | 5 | 5 | 3 | 0 | | 4 | 5 | 0 | 1 | 0 | 0 | 0 | 0 | 3 | 0 | 0 | 0 | 0 | 0 |
| 6-018 | 320 | 5 | 5 | 5 | 0 | 5 | 5 | 5 | 0 | 0 | 0 | 0 | 0 | 0 | 3 | 0 | 0 | 0 | 0 | 0 |
| 6-023 | 320 | 1 | 3 | 0 | 0 | 4 | 5 | 4 | 0 | 0 | | 0 | | 0 | 5 | 1 | 0 | 0 | | 3 |
| 6-025 | 320 | 3 | 4 | 0 | 2 | 2 | 5 | 4 | 0 | 0 | | 0 | 0 | 0 | 5 | 0 | 0 | 0 | 0 | 0 |
| 6-026 | 320 | 4 | 4 | 1 | 0 | 1 | 1 | 0 | 0 | 2 | 0 | 0 | 0 | 0 | 5 | 0 | 0 | 0 | 0 | 0 |
| 6-029 | 320 | 5 | 5 | 5 | 4 | 5 | 5 | 5 | 0 | 0 | 3 | | | 4 | 5 | 2 | 0 | 4 | 0 | 2 |
| 6-031 | 320 | 0 | 0 | 0 | 0 | 0 | 3 | 0 | 0 | 4 | | 0 | | 0 | 0 | 0 | 0 | 0 | 0 | 3 |
| 6-034 | 320 | 5 | 5 | 5 | 4 | 5 | 5 | 5 | 1 | 2 | 0 | 0 | | 4 | 2 | 1 | 0 | 0 | 0 | 1 |
| 6-035 | 320 | 5 | 5 | 5 | 3 | 4 | 5 | 5 | 0 | 0 | | 3 | 0 | 3 | 5 | 2 | 0 | 0 | 0 | 0 |
| 6-037 | 320 | 5 | 5 | 5 | 5 | 5 | 5 | 5 | 5 | 3 | 0 | 0 | 0 | 1 | 5 | 5 | 2 | 5 | 0 | 3 |
| 6-038 | 320 | 5 | 5 | 4 | 5 | 2 | 5 | 5 | 5 | 5 | 4 | 0 | 0 | 1 | 5 | 5 | 1 | 1 | 0 | 5 |
| 6-049 | 320 | 5 | 5 | 5 | 5 | 5 | 5 | 5 | 4 | 4 | 4 | 4 | 3 | 4 | 5 | 5 | 0 | 5 | 3 | 5 |
| 6-050 | 320 | 5 | 4 | 4 | 2 | 4 | 5 | 0 | 0 | 0 | | 3 | | 0 | 5 | 1 | 0 | 0 | 0 | 2 |
| 6-051 | 320 | 5 | 5 | 5 | 1 | 5 | 5 | 5 | 1 | 5 | 0 | 2 | 0 | 0 | 5 | 1 | 1 | 2 | 0 | 4 |
| 6-052 | 320 | 4 | 3 | 4 | 0 | 0 | 0 | 5 | 0 | 0 | 0 | 2 | 0 | 0 | 1 | 0 | 0 | 0 | 0 | 3 |
| 6-053 | 320 | 4 | 3 | 2 | 1 | 0 | 0 | 0 | 0 | 0 | | 0 | | 0 | 2 | 1 | 0 | 0 | 0 | 0 |
| 6-055 | 320 | 5 | 5 | 5 | 0 | 4 | 5 | 5 | 3 | 0 | 0 | 0 | 0 | 0 | 5 | 5 | 0 | 0 | 0 | 0 |
| 6-056 | 320 | 0 | 2 | 0 | 0 | 0 | 0 | 0 | 0 | 0 | | 0 | 0 | 0 | 1 | 0 | 0 | 0 | 0 | 0 |
| 6-057 | 320 | 5 | 5 | 5 | 0 | 3 | 5 | 4 | 0 | 0 | 0 | 0 | 0 | 0 | 5 | 1 | 0 | 1 | 0 | 1 |
| 6-058 | 320 | 5 | 5 | 5 | 5 | 5 | 5 | 5 | 5 | 5 | 5 | 5 | | 5 | 5 | 5 | 0 | 5 | 4 | 5 |
| 6-059 | 320 | 5 | 5 | 2 | 3 | 5 | 1 | 5 | 0 | 0 | 0 | 0 | 3 | 3 | 0 | 0 | 0 | 0 | 0 | 0 |
| 6-060 | 320 | 5 | 5 | 4 | 0 | 3 | 3 | 0 | 0 | 5 | 0 | 0 | 0 | 2 | 3 | 0 | 0 | 0 | 0 | 0 |
| 6-061 | 320 | 5 | 5 | 5 | 4 | 5 | 5 | 5 | 1 | 3 | | 3 | | 4 | 5 | 0 | 0 | 2 | 0 | 3 |
| 6-062 | 320 | 3 | 5 | 5 | 0 | 4 | 0 | 5 | 0 | 0 | | 3 | 0 | 3 | 0 | 0 | 0 | 0 | 0 | 0 |
| 6-063 | 320 | 5 | 1 | 0 | 0 | 0 | 0 | 5 | 0 | 0 | 0 | 0 | 0 | 0 | 0 | 0 | 0 | 0 | 0 | 0 |
| 6-064 | 320 | 5 | 5 | 5 | 0 | 4 | 0 | 5 | 0 | 0 | 0 | 0 | 0 | 0 | 0 | 0 | 0 | 0 | 0 | 0 |
| 6-065 | 320 | 5 | 5 | 5 | 4 | 5 | 5 | 5 | 0 | 4 | 3 | 4 | 4 | 3 | 5 | 5 | 0 | 5 | 2 | 3 |
| 6-066 | 320 | 5 | 5 | 5 | 5 | 5 | 5 | 5 | 0 | 2 | 0 | 0 | 0 | 3 | 5 | 4 | 0 | 4 | 0 | 2 |
| 6-073 | 320 | 5 | 5 | 5 | 3 | 2 | 5 | 0 | 0 | 0 | 0 | 0 | 0 | 0 | 5 | 3 | 0 | 2 | 0 | 3 |
| 6-074 | 320 | 0 | 2 | 0 | 0 | 0 | 0 | 0 | 0 | 0 | 0 | 0 | 0 | 0 | 3 | 0 | 0 | 0 | 0 | 0 |
| 6-075 | 320 | 0 | 0 | 0 | 0 | 4 | 4 | 3 | 0 | 0 | 0 | 0 | 0 | 0 | 0 | 0 | 0 | 0 | 0 | 0 |
| 6-076 | 320 | 5 | 5 | 5 | 3 | 0 | 5 | 5 | 5 | 1 | 0 | 0 | 0 | 0 | 5 | 5 | 0 | 0 | 0 | 2 |
| 6-077 | 320 | 5 | 5 | 5 | 4 | 5 | 5 | 5 | 5 | 5 | 4 | 3 | 4 | 4 | 5 | 0 | 0 | 0 | 1 | 4 |
| 6-078 | 320 | 5 | 5 | 0 | 3 | 0 | 0 | 3 | 1 | 0 | 0 | 0 | | 0 | 1 | 0 | 1 | 0 | 0 | 0 |
| 6-079 | 320 | 5 | 5 | 5 | 0 | 3 | 5 | 5 | 1 | 4 | 0 | 0 | 0 | 3 | 3 | 0 | 0 | 3 | 0 | 0 |
| 6-080 | 320 | 5 | 5 | 5 | 0 | 5 | 5 | 5 | 0 | 1 | 0 | 0 | 0 | 0 | 0 | 0 | 0 | 0 | 0 | 0 |
| 6-082 | 320 | 5 | 5 | 5 | 3 | 5 | 5 | 5 | 2 | | 0 | 0 | 0 | 3 | 1 | 0 | 0 | 0 | 0 | 0 |
| 6-083 | 320 | 5 | 5 | 0 | 0 | 5 | 1 | 5 | 0 | 0 | 0 | 0 | 0 | 3 | 0 | 0 | 0 | 0 | 0 | 0 |
| 6-084 | 320 | 5 | 5 | 5 | 5 | 5 | 5 | | 0 | 4 | 3 | 3 | 3 | 4 | 2 | 0 | 5 | 2 | 0 | 1 |
| 6-085 | 320 | 5 | 5 | 5 | 5 | 5 | 5 | | 4 | 5 | 5 | 5 | 4 | 4 | 1 | 1 | 5 | 3 | 3 | 4 |
| 6-086 | 320 | 5 | 5 | 5 | 4 | 5 | 5 | | 0 | 3 | 3 | 4 | | 4 | 1 | 0 | 5 | 2 | 1 | 4 |
| 6-087 | 320 | 5 | 5 | 5 | 0 | 4 | 3 | | 0 | 0 | 0 | 0 | 0 | 2 | 0 | 0 | 3 | 0 | 0 | 1 |
| 6-088 | 320 | 5 | 5 | 5 | 5 | 5 | 5 | | 3 | 0 | 5 | 5 | 4 | 4 | 0 | 0 | 5 | 0 | 0 | 3 |
| 6-089 | 320 | 5 | 4 | 1 | 0 | 2 | 3 | | 0 | 0 | 0 | 0 | 0 | 0 | 0 | 0 | 0 | 0 | 0 | 0 |
| 6-091 | 320 | 5 | 5 | 5 | 5 | 5 | 5 | | 5 | 4 | 3 | 4 | 0 | 4 | 5 | 5 | 1 | 5 | 1 | 4 |
| 6-092 | 320 | 5 | 5 | 3 | 3 | 3 | 5 | | 0 | 0 | 0 | 0 | | 0 | 4 | 0 | 0 | 0 | 0 | 0 |
| 6-093 | 320 | 5 | 5 | 5 | 0 | 3 | 1 | | 0 | 0 | | 5 | 0 | 4 | 1 | 0 | 0 | 0 | 0 | 0 |
| 6-094 | 320 | 5 | 5 | 5 | 5 | 5 | 5 | | 4 | 0 | 5 | 0 | 0 | 3 | 5 | 1 | 0 | 0 | 0 | 4 |
| 6-095 | 320 | 5 | 5 | 5 | 3 | 5 | 5 | | 5 | 1 | 0 | 0 | 0 | 0 | 5 | 2 | 0 | 2 | 0 | 4 |
| 6-096 | 320 | 4 | 4 | 4 | 3 | 3 | 5 | | 0 | 0 | 0 | 0 | | 0 | 5 | 3 | 0 | 0 | 0 | 0 |
| 6-099 | 320 | 5 | 5 | 5 | 5 | 5 | 5 | 5 | 3 | 5 | 4 | 4 | 3 | 4 | 5 | 5 | 0 | 5 | 2 | 5 |
| 6-100 | 320 | 5 | 5 | 5 | 5 | 5 | 5 | 5 | 4 | 5 | 5 | 4 | 1 | 5 | 5 | 4 | 0 | 3 | 0 | 5 |
| 6-103 | 320 | 5 | 5 | 5 | 5 | 5 | 5 | 5 | 0 | 0 | 0 | 0 | 0 | 0 | 5 | 5 | 0 | 5 | 0 | 0 |
| 6-104 | 320 | 5 | 5 | 5 | 4 | 5 | 1 | 5 | 5 | 5 | 4 | 3 | 4 | 4 | 5 | 5 | 0 | 5 | 4 | 4 |
| 6-106 | 320 | 5 | | 5 | 3 | 3 | 3 | | 0 | 0 | 0 | 0 | 0 | 0 | 1 | 0 | 0 | 0 | 0 | 3 |
| 6-107 | 320 | 5 | 5 | 5 | 3 | 5 | 4 | | 4 | | 4 | 2 | 2 | 4 | 5 | 0 | 0 | 4 | 1 | 4 |
| 6-108 | 320 | 5 | 4 | 5 | 3 | 3 | 5 | | 5 | 4 | 5 | 3 | 3 | 3 | 5 | 1 | 0 | 3 | 0 | 4 |
| 6-109 | 320 | 5 | | 5 | 0 | 5 | 5 | | 0 | 0 | 0 | 0 | 0 | 0 | 1 | 0 | 0 | 0 | 0 | 0 |
| 6-110 | 320 | 0 | 0 | 5 | 0 | 3 | 3 | | 0 | 0 | 0 | 0 | 0 | 0 | 0 | 0 | 0 | 0 | 0 | 0 |
| 6-111 | 320 | 4 | 0 | 4 | 0 | 5 | 5 | | 0 | 0 | 0 | 0 | 0 | 0 | 1 | 0 | 0 | 0 | 0 | 0 |
| 6-112 | 320 | 5 | 5 | 5 | 4 | 5 | 5 | | 1 | 1 | 0 | 0 | 0 | 0 | 5 | 4 | 0 | 3 | 0 | 0 |
| 6-113 | 320 | 5 | 5 | 5 | 0 | 5 | 5 | | | 0 | 0 | 0 | 0 | 0 | 5 | 1 | 0 | 0 | 0 | 1 |
| 7-001 | 320 | 5 | 4 | 4 | 3 | 0 | 5 | 0 | 0 | 0 | | 0 | | | 4 | 0 | 0 | 0 | 0 | 0 |
| 7-002 | 320 | 5 | 4 | 5 | 0 | 3 | 5 | 5 | 0 | 0 | 0 | 0 | 0 | | 5 | 0 | 0 | 0 | 0 | 0 |
| 7-003 | 320 | 5 | 5 | 5 | 4 | 5 | 5 | 5 | 0 | 0 | 0 | 0 | 0 | 0 | 5 | 0 | 0 | 0 | 0 | 0 |
| 7-004 | 320 | 5 | 5 | 5 | 0 | 5 | 5 | 5 | 3 | 2 | 0 | 0 | | 0 | 5 | 4 | 0 | 0 | 0 | 3 |
| 7-005 | 320 | 5 | 0 | 0 | 0 | 0 | 2 | 0 | 0 | 0 | 0 | 0 | 0 | 0 | 1 | 0 | 0 | 0 | 0 | 0 |
| 7-006 | 320 | 0 | 0 | 0 | 0 | 0 | 2 | 0 | 0 | 0 | | 0 | | 0 | 3 | 0 | 1 | 0 | 0 | 0 |
| 7-007 | 320 | 4 | 4 | 5 | 0 | 5 | 5 | 0 | 0 | 0 | 0 | 0 | 0 | 0 | 4 | 3 | 0 | 0 | 0 | 0 |
| 7-008 | 320 | 5 | 5 | 5 | 3 | 5 | 5 | 5 | 0 | 0 | 0 | 0 | | 0 | 5 | 4 | 0 | 1 | 0 | 0 |
| 7-010 | 320 | 5 | 5 | 5 | 2 | 5 | 5 | 5 | 4 | 0 | | 0 | 0 | 3 | 5 | 5 | 2 | 4 | 0 | 3 |
| 7-011 | 320 | 5 | 0 | 4 | 0 | 3 | 4 | 3 | 0 | 0 | | 0 | | 0 | 5 | 3 | 0 | 0 | 0 | 4 |
| 7-012 | 320 | 5 | 5 | 5 | 0 | 2 | 2 | 0 | 0 | 0 | 0 | 0 | 0 | 0 | 5 | 0 | 0 | 0 | 0 | 0 |
| 7-013 | 320 | 3 | 0 | 0 | 0 | 0 | 0 | 0 | 0 | 0 | 0 | 0 | 0 | 0 | 4 | 0 | 0 | 0 | 0 | 0 |

TABLE 25-continued

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 7-014 | 320 | 3 | 2 | 0 | 0 | 0 | 3 | 0 | 0 | 0 |   | 0 | 0 | 0 | 4 | 0 | 0 | 0 | 0 | 0 |
| 7-015 | 320 | 5 | 5 | 5 | 3 | 5 | 5 | 4 | 0 | 0 |   | 0 | 0 | 0 | 5 | 5 | 0 | 4 | 0 | 2 |
| 7-016 | 320 | 3 | 2 | 2 | 0 | 0 | 0 | 0 | 0 | 0 | 0 | 0 |   | 0 | 0 | 0 | 0 | 0 | 0 | 0 |
| 7-017 | 320 | 4 | 0 | 0 | 0 | 0 | 0 | 0 | 0 | 0 | 0 | 0 | 0 | 0 | 0 | 0 | 0 | 0 | 0 | 0 |
| 7-018 | 320 | 3 | 1 | 0 | 0 | 0 | 0 | 0 | 0 | 0 | 0 | 0 | 0 | 0 | 0 | 0 | 0 | 0 | 0 | 0 |
| 7-019 | 320 | 3 | 2 | 0 | 0 | 0 | 0 | 0 | 0 | 0 | 0 | 0 | 0 | 0 | 0 | 0 | 0 | 0 | 0 | 0 |
| 7-020 | 320 | 3 | 2 | 0 | 0 | 3 | 3 | 0 | 0 | 0 | 0 | 0 | 0 | 0 | 5 | 0 | 0 | 0 | 0 | 0 |
| 7-024 | 320 | 4 | 0 | 0 | 0 | 0 | 0 | 0 | 0 | 0 | 0 | 0 | 0 | 0 | 5 | 0 | 0 | 0 | 0 | 0 |
| 7-027 | 320 | 5 | 5 | 5 | 0 | 5 | 5 | 5 | 0 | 0 | 0 | 0 | 0 | 0 | 5 | 3 | 0 | 2 | 0 | 0 |
| 7-029 | 320 | 0 | 4 | 2 | 0 | 1 | 3 |   | 0 | 0 | 0 | 0 | 0 | 0 | 1 | 0 | 0 | 0 | 0 | 0 |
| 8-001 | 320 | 0 | 0 | 0 | 0 | 0 | 0 | 0 | 0 | 0 | 0 | 0 |   | 0 | 0 | 0 | 0 | 0 | 0 | 0 |
| 8-002 | 320 | 3 | 0 | 2 | 0 | 0 | 0 | 0 | 0 | 0 |   | 0 |   |   | 0 | 0 | 0 | 0 | 0 | 0 |
| 8-003 | 320 | 0 | 0 | 0 | 0 | 0 | 0 | 0 | 0 | 0 | 0 | 0 |   |   | 0 | 0 | 0 | 0 | 0 | 0 |
| 9-001 | 320 | 4 | 4 | 5 | 0 | 3 | 5 | 4 | 0 | 1 |   | 0 |   | 0 | 4 | 0 | 0 | 0 | 0 | 0 |
| 9-002 | 320 | 5 | 5 | 5 | 3 | 5 | 5 | 5 | 0 | 0 | 0 | 0 |   | 0 | 5 | 3 | 0 | 0 | 0 | 0 |
| 9-003 | 320 | 5 | 5 | 5 | 3 | 5 | 5 | 5 | 0 | 0 | 0 | 0 | 0 | 0 | 5 | 5 | 0 | 4 | 0 | 5 |
| 9-004 | 320 | 5 | 5 | 5 | 2 | 5 | 4 | 5 | 0 | 0 | 0 | 0 | 0 | 0 | 0 | 0 | 0 | 0 | 0 | 0 |
| 9-005 | 320 | 1 | 0 | 0 | 0 | 1 | 4 | 4 | 0 | 0 |   | 0 |   | 0 | 1 | 0 | 0 | 0 | 0 | 0 |
| 9-006 | 320 | 5 | 5 | 5 | 4 | 5 | 5 | 5 | 0 | 2 | 0 | 0 | 0 | 4 | 5 | 5 | 0 | 5 | 0 | 3 |
| 9-007 | 320 | 5 | 5 | 3 | 3 | 5 | 5 | 5 | 0 | 0 | 0 | 0 | 0 | 0 | 5 | 0 | 0 | 0 | 0 | 0 |
| 9-008 | 320 | 5 | 5 | 5 | 3 | 5 | 5 | 5 | 4 | 4 | 0 | 0 | 0 | 3 | 5 | 4 | 0 | 5 | 0 | 4 |
| 9-009 | 320 | 5 | 4 | 0 | 0 | 4 | 5 | 4 | 0 | 0 |   |   | 0 | 1 | 0 | 0 | 0 | 0 | 0 | 0 |
| 9-010 | 320 | 5 | 5 | 5 | 4 | 5 | 5 | 5 | 0 | 0 | 0 | 0 |   | 0 | 5 | 1 | 0 | 0 | 0 | 0 |
| 9-011 | 320 | 5 | 5 | 5 | 3 | 5 | 5 | 5 | 3 | 0 | 0 | 0 |   | 0 | 5 | 5 | 0 | 4 | 0 | 4 |
| 9-012 | 320 | 5 | 5 | 5 | 0 | 5 | 5 | 5 | 0 | 0 | 0 | 0 |   | 2 | 5 | 2 | 0 | 0 | 0 | 0 |
| 9-013 | 320 | 5 | 5 | 5 | 5 | 5 | 5 | 5 | 3 | 1 |   | 0 |   | 4 | 5 | 5 | 0 | 4 | 5 | 4 |
| 9-014 | 320 | 4 | 3 | 1 | 0 | 0 | 0 | 0 | 0 | 0 | 0 | 0 | 0 | 0 | 1 | 0 | 0 | 0 | 0 | 0 |
| 9-015 | 320 | 5 | 5 | 5 | 1 | 5 | 5 | 5 | 0 | 0 | 0 | 0 |   | 0 | 5 | 0 | 0 | 3 | 0 | 0 |
| 9-016 | 320 | 5 | 5 | 5 | 2 | 5 | 5 | 5 | 4 | 0 | 0 |   | 0 | 0 | 5 | 3 | 0 | 0 | 0 | 0 |
| 9-017 | 320 | 4 | 0 | 0 | 0 | 0 | 0 | 0 | 0 | 0 |   |   |   | 0 | 4 | 0 | 0 | 0 | 0 | 0 |
| 9-019 | 320 | 0 | 5 | 0 | 0 | 5 | 3 | 0 | 0 | 0 |   | 0 |   | 0 | 5 | 0 | 0 | 0 | 0 | 0 |
| 9-020 | 320 | 4 | 5 | 0 | 0 | 3 | 5 | 4 | 3 | 0 |   |   |   | 0 | 3 | 0 | 0 | 0 | 0 | 0 |
| 9-021 | 320 | 5 | 5 | 5 | 1 | 5 | 5 | 5 | 1 | 0 | 0 | 0 | 0 | 3 | 5 | 3 | 0 | 3 | 0 | 2 |
| 9-022 | 320 | 5 | 5 | 5 | 0 | 0 | 0 | 0 | 0 | 0 | 0 | 0 |   | 0 | 4 | 1 | 0 | 0 | 0 | 0 |
| 9-023 | 320 | 5 | 5 | 5 | 2 | 3 | 3 | 5 | 0 | 5 | 0 | 0 | 0 | 0 | 5 | 3 | 0 | 3 | 0 | 4 |
| 9-024 | 320 | 5 | 5 | 5 | 3 | 5 | 5 | 5 | 0 | 3 | 0 | 4 | 0 | 4 | 5 | 0 | 0 | 2 | 0 | 0 |
| 9-025 | 320 | 2 | 0 | 0 | 0 | 0 | 0 | 0 | 0 | 0 | 0 | 0 | 0 | 0 | 0 | 0 | 0 | 0 | 0 | 0 |
| 9-027 | 320 | 5 | 5 | 5 | 4 | 5 | 5 | 5 | 0 | 3 | 3 | 3 | 0 | 3 | 5 | 0 | 0 | 2 | 0 | 1 |
| 9-028 | 320 | 5 | 5 | 5 | 3 | 5 | 5 | 5 | 0 | 0 | 0 | 0 | 0 | 0 | 3 | 1 | 0 | 3 | 0 | 4 |
| 9-029 | 320 | 3 | 4 | 3 | 0 | 3 | 4 |   | 0 | 0 | 0 | 0 | 0 | 0 | 1 | 0 | 0 | 0 | 0 | 0 |
| 10-002 | 320 | 4 | 4 | 4 | 3 | 0 | 4 | 3 | 0 | 0 | 0 | 0 |   | 0 | 4 | 0 | 0 | 0 | 0 | 0 |
| 10-003 | 320 | 0 | 4 | 5 | 0 | 3 | 4 | 3 | 0 | 0 | 0 | 0 | 0 | 0 | 4 | 0 | 0 | 0 | 0 | 0 |
| 10-004 | 320 | 5 | 5 | 5 | 3 | 5 | 5 | 5 | 0 | 0 | 0 | 0 |   | 0 | 5 | 5 | 0 | 0 | 0 | 0 |
| 11-002 | 320 | 0 | 1 | 3 | 3 | 3 | 5 | 4 | 0 | 0 | 0 | 0 |   | 0 | 4 | 1 | 0 | 0 | 0 | 2 |
| 12-002 | 320 | 4 | 5 | 5 | 4 | 4 | 5 | 3 | 0 | 0 | 0 | 0 | 0 | 0 | 4 | 3 | 0 | 0 | 0 | 1 |
| 13-001 | 320 | 5 |   | 5 | 2 | 4 | 5 | 5 | 0 | 0 | 0 | 0 | 0 | 0 | 5 | 5 | 0 | 0 | 0 | 0 |
| 13-002 | 320 | 5 | 5 | 5 | 4 | 4 | 5 |   | 0 | 0 |   | 0 | 0 | 0 | 5 | 5 | 1 | 3 | 0 | 1 |
| 13-003 | 320 | 5 | 5 | 5 | 1 | 5 | 5 |   | 4 | 0 | 0 | 0 | 0 | 0 | 5 | 5 | 0 | 0 | 0 | 3 |
| 13-004 | 320 | 5 | 5 | 5 | 3 | 5 | 5 | 5 | 0 | 4 | 0 | 1 | 0 | 3 | 5 | 5 | 1 | 5 | 0 | 4 |
| 13-005 | 320 | 4 | 0 | 1 | 0 | 4 | 5 |   | 0 | 0 | 0 | 0 |   | 0 | 1 | 0 | 0 | 1 | 0 | 0 |
| 13-006 | 320 | 5 | 5 | 5 | 0 | 5 | 5 |   | 5 | 0 |   | 0 | 0 | 0 | 5 | 1 | 0 | 4 | 0 | 3 |
| 14-001 | 320 | 5 | 5 | 5 | 5 | 5 | 5 | 5 | 0 | 0 | 0 | 0 | 0 | 0 | 5 | 5 | 0 | 0 | 0 | 0 |
| 14-002 | 320 | 5 | 5 | 5 | 0 | 4 | 5 | 5 | 0 | 0 | 0 | 0 | 0 | 0 | 5 | 1 | 0 | 3 | 0 | 0 |

TABLE 26

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-001 | 320 | 0 | 0 | 0 | 0 | 0 | 0 | 0 | 0 | 0 | 0 | 0 | 0 | 0 | 0 | 0 | 0 | 0 | 0 | 0 |
| 1-002 | 320 | 5 | 5 | 5 | 5 | 5 | 5 | 5 | 4 | 5 | 4 | 4 | 4 | 4 | 5 | 5 | 4 | 5 | 5 | 5 |
| 1-003 | 320 | 5 | 5 | 5 | 5 | 5 | 5 | 5 | 4 | 3 | 3 | 2 | 3 | 3 | 5 | 5 | 3 | 5 | 3 | 4 |
| 1-004 | 320 | 5 | 5 | 5 | 5 | 5 | 5 | 5 | 4 | 4 | 3 |   | 3 | 4 | 5 | 5 | 4 | 5 | 3 | 4 |
| 1-005 | 320 | 5 | 5 | 5 | 5 | 5 | 5 | 5 | 4 | 4 | 3 | 4 | 4 | 3 | 5 | 5 | 4 | 5 | 3 | 4 |
| 1-006 | 320 | 5 | 5 | 5 | 5 | 5 | 5 | 5 | 4 | 3 | 0 | 0 | 0 | 2 | 5 | 3 | 4 | 3 | 0 | 3 |
| 1-007 | 320 | 0 | 0 | 0 | 3 | 3 | 5 | 1 | 0 | 0 | 0 | 0 | 0 | 0 | 0 | 0 | 0 | 0 | 0 | 0 |
| 1-008 | 320 | 5 | 5 | 4 | 4 | 5 | 5 | 4 | 2 | 0 | 0 | 0 | 0 | 0 | 4 | 0 | 2 | 0 | 0 | 3 |
| 1-009 | 320 | 0 | 0 | 0 | 0 | 1 | 4 | 0 | 1 | 0 | 0 | 0 | 0 | 0 | 0 | 0 | 0 | 0 | 0 | 0 |
| 1-010 | 320 | 5 | 5 | 5 | 5 | 5 | 5 | 5 | 4 | 4 | 4 | 4 | 4 | 4 | 5 | 5 | 4 | 5 | 4 | 4 |
| 1-011 | 320 | 3 | 0 | 0 | 0 | 4 | 5 | 5 | 0 | 0 | 0 |   |   | 0 | 2 | 0 | 0 | 0 | 0 | 4 |
| 1-012 | 320 | 0 | 0 | 0 | 0 | 0 | 0 | 0 | 0 | 0 | 0 |   | 0 | 0 | 0 | 0 | 0 | 0 | 0 | 0 |
| 1-013 | 320 | 0 | 0 | 0 | 0 | 4 | 5 | 4 | 0 | 0 | 0 | 0 |   | 0 | 2 | 0 | 0 | 0 | 0 | 4 |

TABLE 26-continued

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-014 | 320 | 5 | 5 | 5 | 5 | 5 | 5 | 5 | 5 | 5 | 3 |   |   | 3 | 5 | 5 | 5 | 5 | 3 | 4 |
| 1-015 | 320 | 5 | 5 | 5 | 5 | 5 | 5 | 5 | 4 | 4 | 3 | 4 | 4 | 4 | 5 | 5 | 5 | 5 | 3 | 4 |
| 1-016 | 320 | 5 | 5 | 5 | 5 | 5 | 5 | 5 | 4 | 4 | 2 |   |   | 4 | 5 | 4 | 4 | 5 | 3 | 4 |
| 1-017 | 320 | 5 | 5 | 5 | 5 | 5 | 5 | 5 | 4 | 4 | 2 |   |   | 3 | 5 | 4 | 4 | 5 | 2 | 4 |
| 1-018 | 320 | 5 | 5 | 5 | 5 | 5 | 5 | 5 | 3 | 0 |   | 4 | 4 | 4 | 5 | 5 | 3 | 5 | 4 | 4 |
| 1-019 | 320 | 5 | 5 | 5 | 5 | 5 | 5 | 5 | 4 | 2 |   | 4 | 4 | 4 | 5 | 5 | 3 | 5 | 4 | 4 |
| 1-020 | 320 | 5 | 5 | 5 | 4 | 5 | 5 | 5 | 3 |   |   |   | 4 | 4 | 5 | 1 | 0 | 5 | 3 | 4 |
| 1-021 | 320 | 1 | 1 | 3 | 0 | 3 | 4 | 4 | 0 | 0 |   |   | 0 | 0 | 3 | 0 | 0 | 0 | 0 | 2 |
| 1-022 | 320 | 5 | 5 | 5 | 5 | 5 | 5 | 5 | 1 | 1 | 3 | 3 | 4 | 3 | 5 | 3 | 3 | 5 | 0 | 4 |
| 1-023 | 320 | 2 | 1 | 4 | 1 | 4 | 4 | 4 | 0 | 0 | 0 | 0 | 2 | 0 | 4 | 1 | 0 | 0 | 0 | 2 |
| 1-024 | 320 | 5 | 5 | 5 | 5 | 5 | 5 | 5 | 1 | 0 | 1 | 3 | 3 |   | 5 | 5 | 2 | 5 | 0 | 4 |
| 1-025 | 320 | 5 | 4 | 4 | 5 | 5 | 5 | 5 | 1 | 0 | 4 | 4 | 4 | 3 | 4 | 3 | 3 | 4 | 0 | 4 |
| 1-026 | 320 | 5 | 5 | 5 | 4 | 1 | 5 | 5 | 5 | 0 | 0 | 3 | 1 |   | 5 | 3 | 0 | 2 |   | 4 |
| 1-027 | 320 | 5 | 5 | 5 | 5 | 5 | 5 | 5 | 2 | 0 | 1 | 1 | 3 |   | 5 | 5 | 3 | 4 | 0 | 4 |
| 1-028 | 320 | 5 | 5 | 5 | 4 | 5 | 5 | 5 | 3 | 0 | 3 | 3 | 3 |   | 5 | 4 | 2 | 3 | 0 | 4 |
| 1-029 | 320 | 5 | 5 | 5 | 5 | 5 | 5 | 5 | 1 | 0 | 3 | 3 | 3 | 1 | 5 | 3 | 1 | 5 | 0 | 4 |
| 1-030 | 320 | 4 | 5 | 4 | 3 | 4 | 5 | 4 | 0 | 0 | 0 | 0 | 0 | 0 | 5 | 1 | 0 | 0 | 0 | 3 |
| 1-031 | 320 | 1 | 1 | 1 | 3 | 3 | 4 | 0 | 0 | 0 | 0 | 0 | 0 |   | 3 | 0 | 0 | 0 | 0 | 0 |
| 1-032 | 320 | 5 | 5 | 5 | 5 | 5 | 5 | 5 | 4 | 3 | 3 | 4 | 4 |   | 5 | 5 | 4 | 5 | 3 | 4 |
| 1-033 | 320 | 5 | 5 | 5 | 5 | 5 | 5 | 5 | 4 | 4 |   | 3 | 1 | 2 | 5 | 4 | 4 | 5 | 3 | 4 |
| 1-034 | 320 | 5 | 5 | 5 | 5 | 5 | 5 | 5 | 4 | 3 | 5 |   |   |   | 5 | 4 | 4 | 5 | 4 | 5 |
| 1-035 | 320 | 5 | 5 | 5 | 5 | 5 | 5 | 5 | 4 | 3 |   |   |   |   | 5 | 4 | 4 | 5 | 2 | 4 |
| 1-036 | 320 | 5 | 5 | 5 | 5 | 5 | 5 | 5 | 4 | 4 | 2 |   | 0 |   | 5 | 4 | 4 | 5 | 3 | 4 |
| 1-037 | 320 | 0 | 0 | 0 | 0 | 0 | 0 | 0 | 0 | 0 | 0 |   | 0 |   | 0 | 0 | 0 | 0 | 0 | 0 |
| 1-038 | 320 | 5 | 5 | 5 | 5 | 5 | 5 | 5 | 4 | 2 | 0 | 0 | 0 | 1 | 5 | 4 | 4 | 4 | 1 | 4 |
| 1-039 | 320 | 5 | 5 | 5 | 5 | 5 | 5 | 5 | 4 | 4 |   | 3 |   |   | 5 | 4 | 4 | 5 | 3 | 4 |
| 1-040 | 320 | 4 | 4 | 5 | 4 | 5 | 5 | 5 | 1 | 0 | 0 | 0 |   | 0 | 5 | 3 | 0 | 0 | 0 | 4 |
| 1-041 | 320 | 5 | 5 | 5 | 5 | 5 | 5 | 5 | 4 | 3 | 3 | 3 | 3 | 3 | 5 | 5 | 4 | 5 | 1 | 4 |
| 1-042 | 320 | 5 | 5 | 5 | 5 | 5 | 5 | 5 | 3 | 0 | 0 | 0 | 0 | 1 | 5 | 4 | 3 | 5 | 1 | 4 |
| 1-043 | 320 | 5 | 5 | 5 | 5 | 5 | 5 | 5 | 4 | 3 | 2 | 4 | 3 | 2 | 5 | 5 | 4 | 5 | 3 | 4 |
| 1-044 | 320 | 5 | 5 | 5 | 5 | 5 | 5 | 5 | 4 | 2 |   | 0 | 0 | 0 | 5 | 4 | 4 | 5 | 2 | 4 |
| 1-045 | 320 | 4 | 5 | 5 | 5 | 5 | 5 | 5 | 0 | 0 | 0 | 0 | 0 | 0 | 5 | 3 | 1 | 0 | 0 | 2 |
| 1-046 | 320 | 4 | 5 | 5 | 5 | 5 | 5 | 5 | 3 | 2 | 2 | 2 | 0 | 4 | 5 | 5 | 3 | 4 | 0 | 4 |
| 1-047 | 320 | 1 | 1 | 3 | 0 | 3 | 4 | 1 | 0 | 0 | 0 | 0 | 0 | 0 | 4 | 0 | 0 | 0 | 0 | 0 |
| 1-048 | 320 | 4 | 4 | 5 | 4 | 5 | 5 | 5 | 3 | 1 | 3 | 3 | 1 | 3 | 5 | 4 | 0 | 0 | 1 | 3 |
| 1-049 | 320 | 0 | 0 | 0 | 0 | 0 | 0 | 0 | 0 | 0 | 0 | 0 | 0 | 0 | 0 | 0 | 0 | 0 | 0 | 0 |
| 1-050 | 320 | 3 | 5 | 5 | 3 | 4 | 5 | 3 | 3 | 0 | 0 | 0 | 0 | 0 | 5 | 0 | 0 | 0 | 0 | 4 |
| 1-051 | 320 | 5 | 5 | 5 | 5 | 5 | 5 | 5 | 4 | 1 | 0 | 3 |   | 0 | 5 | 5 | 4 | 5 | 0 | 4 |
| 1-052 | 320 | 5 | 5 | 5 | 5 | 5 | 5 | 5 | 3 | 0 | 1 | 0 |   | 3 | 5 | 4 | 4 | 5 | 0 | 4 |
| 1-053 | 320 | 3 | 3 | 4 | 2 | 4 | 5 | 3 | 0 | 0 | 1 | 0 |   | 2 | 5 | 3 | 3 | 0 | 0 | 4 |
| 1-054 | 320 | 2 | 3 | 4 | 3 | 4 | 5 | 3 | 0 | 0 | 0 | 0 | 0 | 0 | 4 | 0 | 0 | 0 | 0 | 3 |
| 1-055 | 320 | 3 | 3 | 4 | 4 | 4 | 5 | 5 | 0 | 0 | 1 | 0 |   |   | 5 | 3 | 2 | 0 | 0 | 3 |
| 1-056 | 320 | 5 | 5 | 5 | 5 | 5 | 5 | 5 | 4 | 2 | 1 | 0 |   |   | 5 | 4 | 4 | 5 | 0 | 4 |
| 1-057 | 320 | 3 | 3 | 4 | 2 | 3 | 5 | 1 | 1 | 0 | 0 | 0 |   | 0 | 3 | 0 | 3 | 0 | 1 | 4 |
| 1-058 | 320 | 5 | 5 | 5 | 5 | 5 | 5 | 5 | 4 | 1 | 0 | 0 |   |   | 5 | 4 | 3 | 5 | 0 | 4 |
| 1-059 | 320 | 1 | 4 | 4 | 4 | 4 | 5 | 4 | 0 | 0 | 0 | 0 |   | 0 | 4 | 4 | 0 | 0 | 0 | 3 |
| 1-060 | 320 | 5 | 5 | 5 | 5 | 5 | 5 | 5 | 3 | 0 | 3 | 3 |   | 3 | 5 | 4 | 4 | 5 | 0 | 4 |
| 1-062 | 320 | 1 | 4 | 4 | 4 | 5 | 5 | 5 | 0 | 0 | 0 | 0 | 0 | 0 | 5 | 4 | 0 | 0 | 0 | 3 |
| 1-063 | 320 | 1 | 5 | 5 | 5 | 5 | 5 | 5 | 2 | 0 | 0 | 0 |   | 4 | 5 | 5 | 3 | 4 | 0 | 4 |
| 1-064 | 320 | 5 | 5 | 5 | 5 | 5 | 5 | 5 | 4 | 2 | 0 | 1 |   | 3 | 5 | 5 | 4 | 5 | 1 | 4 |
| 1-065 | 320 | 5 | 5 | 5 | 5 | 5 | 5 | 5 | 4 | 2 | 2 | 0 |   | 3 | 5 | 5 | 4 | 5 | 0 | 4 |
| 1-066 | 320 | 4 | 5 | 5 | 4 | 5 | 5 | 4 | 1 | 0 | 1 | 0 |   | 3 | 5 | 4 | 0 | 0 | 0 | 3 |
| 1-067 | 320 | 5 | 5 | 5 | 5 | 5 | 5 | 5 | 5 | 4 | 2 | 3 | 2 | 3 | 5 | 5 | 4 | 5 | 1 | 4 |
| 1-068 | 320 | 5 | 5 | 5 | 5 | 5 | 5 | 5 | 5 | 4 | 1 | 3 |   | 3 | 5 | 5 | 4 | 5 | 3 | 4 |
| 1-069 | 320 | 5 | 5 | 5 | 5 | 5 | 5 | 5 | 5 | 5 | 2 | 3 |   | 3 | 5 | 5 | 4 | 5 | 1 | 4 |
| 1-070 | 320 | 1 | 5 | 3 | 5 | 5 | 5 | 4 | 0 | 0 | 1 | 0 | 2 | 2 | 5 | 4 | 0 | 0 | 0 | 3 |
| 1-071 | 320 | 5 | 5 | 5 | 5 | 5 | 5 | 5 | 4 | 0 | 1 | 0 | 2 | 1 | 5 | 5 | 4 | 5 | 0 | 4 |
| 1-072 | 320 | 5 | 5 | 5 | 5 | 5 | 5 | 5 | 5 | 5 | 1 | 2 | 2 | 3 | 5 | 5 | 2 | 5 | 1 | 4 |
| 1-073 | 320 | 5 | 5 | 5 | 5 | 5 | 5 | 5 | 4 | 2 |   | 2 |   | 3 | 5 | 4 | 3 | 5 | 1 | 4 |
| 1-074 | 320 | 5 | 5 | 5 | 5 | 5 | 5 | 5 | 3 | 0 | 2 | 1 | 1 |   | 5 | 5 | 4 | 5 | 0 | 4 |
| 1-075 | 320 | 5 | 5 | 5 | 5 | 5 | 5 | 5 | 4 | 4 |   | 1 | 0 | 0 | 5 | 4 | 1 | 5 |   |   |
| 1-076 | 192 | 5 | 5 | 5 | 5 | 5 | 5 | 5 | 4 | 0 |   | 3 |   | 3 | 5 | 4 | 4 | 5 | 0 | 4 |
| 1-078 | 320 | 1 | 5 | 5 | 5 | 1 | 4 | 5 | 3 | 0 | 0 |   | 0 | 0 | 5 | 3 | 0 | 0 | 0 | 3 |
| 1-079 | 320 | 5 | 5 | 5 | 5 | 5 | 5 | 5 | 4 | 0 | 0 | 1 |   | 3 | 5 | 5 | 4 | 4 | 0 | 5 |
| 1-080 | 320 | 5 | 5 | 5 | 5 | 5 | 5 | 5 | 4 | 0 | 3 | 0 |   | 1 | 5 | 5 | 4 | 4 | 0 | 4 |
| 1-081 | 320 | 5 | 5 | 5 | 5 | 5 | 5 | 5 | 4 | 5 | 3 | 0 | 0 | 0 | 5 | 5 | 5 | 4 | 0 | 5 |
| 1-082 | 320 | 5 | 5 | 5 | 5 | 5 | 5 | 5 | 4 | 0 | 1 | 0 | 0 | 0 | 5 | 5 | 4 | 5 | 0 | 4 |
| 1-083 | 320 | 5 | 5 | 5 | 5 | 5 | 5 | 5 | 4 | 4 | 0 | 4 | 0 | 0 | 5 | 5 | 4 | 5 | 0 | 4 |
| 1-085 | 320 | 3 | 5 | 5 | 3 | 3 | 3 | 3 | 0 | 0 | 0 | 0 | 0 | 0 | 4 | 5 | 0 | 3 | 0 | 1 |
| 1-086 | 320 | 0 | 3 | 5 | 4 | 4 | 5 | 4 | 0 | 0 | 0 | 0 | 0 | 2 | 4 | 3 | 0 | 0 | 0 | 3 |
| 1-087 | 320 | 5 | 5 | 5 | 5 | 5 | 5 | 5 | 5 | 4 | 0 | 3 | 4 | 3 | 5 | 5 | 3 | 5 | 4 | 4 |
| 1-088 | 320 | 5 | 5 | 5 | 5 | 5 | 5 | 5 | 4 | 1 | 2 | 3 |   | 3 | 5 | 5 | 3 | 5 | 4 | 4 |
| 1-089 | 320 | 5 | 5 | 5 | 5 | 5 | 5 | 5 | 4 | 2 | 1 | 0 |   | 3 | 5 | 5 | 2 | 5 | 0 | 4 |
| 1-090 | 320 | 5 | 5 | 5 | 5 | 5 | 5 | 5 | 4 | 1 | 2 | 3 | 0 | 3 | 5 | 5 | 3 | 5 | 0 | 4 |
| 1-091 | 320 | 5 | 5 | 5 | 5 | 5 | 5 | 5 | 4 | 3 | 0 | 0 |   | 1 | 5 | 5 | 1 | 5 | 0 | 4 |
| 1-092 | 320 | 5 | 5 | 5 | 2 | 4 | 5 | 5 | 3 | 3 | 0 | 0 |   | 0 | 5 | 5 | 0 | 4 | 0 | 4 |

TABLE 26-continued

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-093 | 320 | 5 | 5 | 5 | 5 | 5 | 5 | 5 | 4 | 4 | 0 | 2 | 0 | 3 | 5 | 5 | 3 | 5 | 0 | 4 |
| 1-094 | 320 | 5 | 5 | 5 | 5 | 5 | 5 | 5 | 4 | 2 | 0 | 3 | 0 | 3 | 5 | 5 | 2 | 5 | 0 | 4 |
| 1-095 | 320 | 5 | 5 | 5 | 5 | 5 | 5 | 5 | 4 | 3 | 0 | 2 |   | 3 | 5 | 5 | 2 | 5 | 0 | 4 |
| 1-096 | 320 | 5 | 5 | 5 | 5 | 5 | 5 | 5 | 4 | 2 | 2 | 2 |   | 3 | 5 | 5 | 3 | 5 | 0 | 4 |
| 1-097 | 320 | 5 | 5 | 5 | 3 | 5 | 5 | 4 | 3 |   |   | 1 | 0 | 3 | 5 | 5 | 3 | 2 |   | 3 |
| 1-098 | 320 | 5 | 5 | 5 | 5 | 5 | 5 | 5 | 1 | 0 | 0 | 3 | 0 | 3 | 5 | 5 | 3 | 5 | 1 | 5 |
| 1-099 | 320 | 5 | 5 | 5 | 5 | 5 | 5 | 5 | 4 | 0 | 3 | 3 | 3 | 3 | 5 | 5 | 4 | 5 | 1 | 5 |
| 1-100 | 320 | 5 | 5 | 5 | 5 | 5 | 5 | 5 | 4 | 0 | 1 | 0 |   | 3 | 5 | 5 | 3 | 5 | 0 | 5 |
| 1-101 | 320 | 5 | 5 | 5 | 5 | 5 | 5 | 5 | 5 | 5 | 3 | 3 | 0 | 3 | 5 | 5 | 3 | 5 | 0 | 5 |
| 1-102 | 320 | 5 | 5 | 5 | 5 | 5 | 5 | 5 | 0 | 0 | 3 | 0 | 0 | 2 | 5 | 5 | 0 | 4 | 0 | 2 |
| 1-103 | 320 | 5 | 5 | 5 | 5 | 5 | 5 | 5 | 4 | 0 | 2 | 2 |   | 3 | 5 | 5 | 3 | 5 | 0 | 4 |
| 1-104 | 320 | 5 | 5 | 5 | 5 | 5 | 5 | 5 | 3 | 0 | 2 | 1 |   | 1 | 5 | 4 | 1 | 0 | 0 | 4 |
| 1-105 | 320 | 5 | 5 | 5 | 5 | 5 | 5 | 5 | 1 | 0 | 2 | 1 | 2 | 3 | 5 | 4 | 1 | 5 | 0 | 4 |
| 1-106 | 320 | 5 | 5 | 5 | 5 | 5 | 5 | 5 | 1 | 5 | 2 | 2 | 0 | 1 | 5 | 5 | 0 | 4 | 0 | 3 |
| 1-107 | 320 | 4 | 5 | 5 | 5 | 5 | 5 | 5 | 1 | 0 | 0 | 0 |   | 0 | 5 | 2 | 3 | 2 | 0 | 4 |
| 1-108 | 320 | 5 | 5 | 5 | 5 | 5 | 5 | 5 | 4 | 5 | 0 | 3 |   | 1 | 5 | 5 | 3 | 3 | 1 | 4 |
| 1-109 | 320 | 5 | 5 | 5 | 5 | 5 | 5 | 5 | 3 | 0 | 3 | 3 |   | 3 | 5 | 5 | 0 | 5 | 0 | 4 |
| 1-110 | 320 | 5 | 5 | 5 | 5 | 5 | 5 | 5 | 0 | 0 | 2 | 3 | 3 | 3 | 5 | 5 | 0 | 5 | 0 | 5 |
| 1-111 | 320 | 5 | 5 | 5 | 5 | 5 | 5 | 5 | 1 | 0 | 1 | 3 | 2 | 1 | 5 | 5 | 3 | 5 | 0 | 5 |
| 1-112 | 320 | 5 | 4 | 5 | 5 | 5 | 5 | 5 | 1 | 0 | 3 | 1 | 3 | 3 | 5 | 4 | 0 | 5 | 0 | 4 |
| 1-113 | 320 | 5 | 4 | 4 | 4 | 4 | 5 | 5 | 1 | 0 | 2 | 3 | 0 | 4 | 4 | 0 | 0 | 3 | 0 | 5 |
| 1-114 | 320 | 5 | 5 | 5 | 5 | 4 | 5 | 5 | 1 | 1 | 3 | 3 | 0 | 2 | 5 | 1 | 0 | 4 | 0 | 4 |
| 1-115 | 320 | 2 | 1 | 1 | 2 | 3 | 3 | 4 | 0 | 0 | 0 | 1 | 0 | 1 | 1 | 0 | 0 | 0 | 0 | 5 |
| 1-116 | 320 | 5 | 5 | 5 | 4 | 5 | 5 | 5 | 1 | 0 | 3 | 2 | 1 | 3 | 4 | 5 | 3 | 3 | 0 | 5 |
| 1-117 | 320 | 5 | 5 | 5 | 5 | 5 | 5 | 5 | 1 | 1 | 0 | 3 | 0 | 3 | 5 | 3 | 0 | 5 | 0 | 5 |
| 1-118 | 320 | 0 | 0 | 2 | 3 | 4 | 5 | 3 | 0 | 0 | 3 | 3 | 3 | 3 | 4 | 4 | 0 | 0 | 0 | 4 |
| 1-119 | 320 | 5 | 5 | 5 | 5 | 5 | 5 | 5 | 1 | 0 | 3 | 1 | 0 | 3 | 5 | 2 | 0 | 4 | 0 | 5 |
| 1-120 | 320 | 3 | 4 | 5 | 4 | 3 | 5 | 3 | 0 | 0 | 4 | 4 | 5 | 3 | 1 | 1 | 2 | 0 | 0 | 5 |
| 1-121 | 320 | 5 | 5 | 5 | 5 | 5 | 5 | 5 | 3 | 0 | 3 | 2 | 0 | 3 | 5 | 5 | 2 | 3 | 0 | 5 |
| 1-122 | 320 | 4 | 5 | 5 | 5 | 5 | 5 | 5 | 4 | 1 | 0 | 1 | 0 | 0 | 5 | 5 | 4 | 4 | 0 | 5 |
| 1-123 | 320 | 5 | 5 | 5 | 5 | 5 | 5 | 5 | 4 | 0 | 0 | 3 | 0 | 4 | 5 | 5 | 2 | 5 | 0 | 5 |
| 1-124 | 320 | 0 | 2 | 5 | 2 | 3 | 4 | 3 | 0 | 0 | 3 | 2 | 0 | 0 | 3 | 4 | 0 | 3 | 0 | 4 |
| 1-125 | 320 | 5 | 5 | 5 | 5 | 5 | 5 | 5 | 0 | 0 | 1 | 2 | 3 | 2 | 5 | 3 | 0 | 5 | 0 | 3 |
| 1-126 | 320 | 3 | 4 | 4 | 3 | 5 | 5 | 3 | 0 | 0 |   | 0 | 0 | 0 | 4 | 0 | 0 | 0 | 0 | 4 |
| 1-127 | 320 | 0 | 0 | 0 | 0 | 1 | 1 | 0 | 0 | 0 | 0 | 0 | 0 | 0 | 0 | 0 | 0 | 0 | 0 | 0 |
| 1-130 | 320 | 4 | 5 | 5 | 5 | 5 | 5 | 5 | 0 | 0 |   | 0 | 0 | 0 | 5 | 1 | 1 | 2 | 0 | 5 |
| 1-131 | 320 | 0 | 5 | 4 | 4 | 5 | 5 | 5 | 0 | 0 | 0 | 0 | 0 | 4 | 4 | 3 | 0 | 2 | 0 | 5 |
| 1-132 | 320 | 0 | 0 | 0 | 1 | 2 | 3 | 1 | 0 | 0 | 0 | 0 | 0 | 0 | 1 | 0 | 0 | 0 | 0 | 3 |
| 1-133 | 320 | 0 | 4 | 4 | 3 | 4 | 5 | 2 | 0 | 0 | 0 | 3 | 0 | 3 | 1 | 0 | 3 | 0 | 3 | 4 |
| 1-134 | 320 | 5 | 5 | 5 | 5 | 5 | 5 | 5 | 2 | 1 | 4 | 2 | 4 | 1 | 5 | 5 | 2 | 5 | 0 | 4 |
| 1-135 | 320 | 5 | 5 | 5 | 5 | 5 | 5 | 5 | 3 | 0 | 5 | 1 | 0 | 3 | 5 | 4 | 1 | 2 | 0 | 4 |
| 1-136 | 320 | 5 | 5 | 5 | 4 | 5 | 5 | 5 | 3 |   | 0 | 1 | 4 | 2 | 5 | 3 | 1 | 3 | 0 | 4 |
| 1-137 | 320 | 5 | 5 | 5 | 5 | 5 | 5 | 5 | 4 |   | 3 | 0 | 0 | 2 | 5 | 3 | 0 | 3 | 0 | 4 |
| 1-138 | 320 | 5 | 5 | 5 | 5 | 5 | 5 | 5 | 3 | 0 | 0 | 1 | 3 | 3 | 5 | 2 | 0 | 3 | 0 | 4 |
| 1-139 | 320 | 5 | 5 | 5 | 5 | 5 | 5 | 5 | 2 | 0 | 1 | 3 | 3 | 2 | 5 | 5 | 1 | 5 | 0 | 4 |
| 1-140 | 320 | 5 | 5 | 5 | 5 | 5 | 5 | 5 | 4 | 3 | 2 | 3 | 2 | 3 | 5 | 4 | 3 | 5 | 3 | 5 |
| 1-142 | 320 | 5 | 5 | 5 | 5 | 5 | 5 | 5 | 4 | 0 | 2 | 3 | 3 | 3 | 5 | 5 | 3 | 4 | 3 | 4 |
| 1-143 | 320 | 5 | 5 | 5 | 5 | 5 | 5 | 5 | 1 | 1 | 0 | 0 | 0 | 0 | 2 | 3 | 1 | 3 | 0 | 4 |
| 1-144 | 320 | 5 | 5 | 5 | 5 | 5 | 5 | 5 | 4 | 1 | 0 | 2 | 2 | 3 | 5 | 5 | 3 | 4 | 2 | 4 |
| 1-145 | 320 | 5 | 5 | 5 | 5 | 5 | 5 | 5 | 3 | 0 | 1 | 2 | 2 | 3 | 5 | 5 | 2 | 5 | 2 | 4 |
| 1-146 | 320 | 5 | 5 | 5 | 5 | 5 | 5 | 5 | 5 | 0 | 2 | 3 | 3 | 3 | 5 | 5 | 4 | 5 | 4 | 5 |
| 1-147 | 320 | 5 | 5 | 5 | 5 | 5 | 5 | 5 | 4 | 1 | 1 | 3 | 4 | 4 | 5 | 5 | 3 | 5 | 3 | 4 |
| 1-148 | 320 | 5 | 5 | 5 | 5 | 5 | 5 | 5 | 4 | 2 | 1 | 3 | 3 | 3 | 5 | 4 | 3 | 5 | 3 | 5 |
| 1-149 | 320 | 5 | 5 | 5 | 5 | 5 | 5 | 5 | 4 | 0 | 2 | 3 | 3 | 2 | 5 | 4 | 2 | 5 | 2 | 4 |
| 1-150 | 320 | 5 | 4 | 5 | 5 | 5 | 5 | 5 | 3 | 0 | 0 | 0 | 0 | 0 | 5 | 4 | 0 | 4 | 0 | 4 |
| 1-151 | 320 | 5 | 5 | 5 | 5 | 5 | 5 | 5 | 3 | 0 | 0 | 0 | 0 | 1 | 4 | 4 | 2 | 3 | 2 | 4 |
| 1-152 | 320 | 5 | 5 | 5 | 4 | 5 | 5 | 5 | 4 | 3 | 0 | 0 | 0 | 0 | 5 | 2 | 1 | 3 | 0 | 4 |
| 1-153 | 320 | 5 | 5 | 5 | 5 | 5 | 5 | 5 | 4 | 4 | 0 | 0 | 3 | 0 | 5 | 3 | 1 | 5 | 0 | 4 |
| 1-154 | 320 | 5 | 5 | 5 | 5 | 5 | 5 | 5 | 4 | 3 | 1 | 2 | 3 | 3 | 5 | 3 | 3 | 5 | 1 | 4 |
| 1-155 | 320 | 5 | 5 | 5 | 5 | 5 | 5 | 5 | 4 | 2 | 0 | 2 | 0 | 3 | 5 | 4 | 3 | 5 | 2 | 4 |
| 1-156 | 320 | 5 | 5 | 5 | 5 | 5 | 5 | 5 | 4 | 3 | 2 | 3 | 3 | 4 | 5 | 4 | 3 | 5 | 3 | 4 |
| 1-158 | 320 | 0 | 0 | 1 | 3 | 1 | 4 | 0 | 0 | 0 | 0 | 0 | 0 | 0 | 1 | 0 | 0 | 0 | 0 | 2 |
| 1-159 | 320 | 5 | 1 | 4 | 5 | 5 | 5 | 5 | 4 | 3 | 0 | 0 | 0 | 0 | 3 | 0 | 1 | 2 | 2 | 4 |
| 1-160 | 320 | 5 | 5 | 5 | 5 | 5 | 5 | 5 | 4 | 0 | 2 | 3 | 4 | 3 | 5 | 4 | 2 | 5 | 5 | 5 |
| 1-161 | 320 | 4 | 0 | 4 | 4 | 5 | 5 | 5 | 0 | 0 | 0 | 0 | 0 | 0 | 3 | 1 | 0 | 2 | 0 | 3 |
| 1-162 | 320 | 5 | 5 | 5 | 5 | 5 | 5 | 5 | 4 | 1 | 4 | 4 | 4 | 3 | 5 | 4 | 2 | 5 | 3 | 4 |
| 1-163 | 320 | 5 | 5 | 5 | 5 | 5 | 5 | 5 | 4 | 3 | 3 | 3 | 3 | 3 | 5 | 4 | 2 | 5 | 4 | 5 |
| 1-166 | 320 | 1 | 1 | 4 | 5 | 4 | 5 | 5 | 3 | 0 | 0 | 0 | 0 | 0 | 3 | 1 | 1 | 1 | 0 | 4 |
| 2-001 | 102 | 5 | 4 | 5 | 4 | 5 | 5 | 4 | 1 | 2 | 3 | 3 | 3 | 2 | 4 | 3 | 0 | 0 | 1 | 4 |
| 2-002 | 320 | 4 | 4 | 3 | 1 | 4 | 5 | 2 | 0 | 0 | 3 | 2 | 2 | 1 | 4 | 0 | 0 | 0 | 0 | 3 |
| 2-003 | 320 | 4 | 5 | 5 | 5 | 5 | 5 | 4 | 1 | 0 | 0 | 0 | 0 | 3 | 5 | 0 | 0 | 0 | 0 | 3 |
| 2-005 | 269 | 3 | 4 | 5 | 3 | 5 | 5 | 3 | 0 | 0 | 0 | 0 | 0 | 0 | 5 | 3 | 0 | 0 | 2 | 4 |
| 2-006 | 320 | 3 | 3 | 4 | 3 | 4 | 5 | 3 | 0 | 0 | 0 | 0 | 0 | 0 | 4 | 0 | 0 | 0 | 0 | 0 |
| 2-007 | 320 | 1 | 0 | 1 | 0 | 4 | 4 | 3 | 0 | 0 | 0 | 2 | 0 |   | 3 | 1 | 0 | 0 | 0 | 1 |
| 2-008 | 320 | 2 | 3 | 3 | 0 | 3 | 4 | 0 | 0 | 1 | 0 | 0 | 0 |   | 4 | 1 | 1 | 0 | 0 | 3 |
| 2-009 | 320 | 0 | 0 | 3 | 0 | 1 | 1 | 0 | 0 | 0 | 0 | 0 | 0 | 0 | 4 | 0 | 0 | 0 | 0 | 0 |

TABLE 26-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 2-010 | 320 | 0 | 0 | 0 | 0 | 0 | 0 | 0 | 0 | 0 | 0 | 0 | 0 | 0 | 0 | 0 | 0 | 0 | 0 | 0 |
| 2-011 | 320 | 0 | 0 | 2 | 0 | 1 | 2 | 0 | 0 | 0 | 0 | 0 | 0 | 0 | 3 | 0 | 0 | 0 | 0 | 0 |
| 2-012 | 320 | 0 | 0 | 1 | 0 | 1 | 3 | 0 | 0 | 0 | 0 | 0 | 0 | 0 | 4 | 0 | 0 | 0 | 0 | 0 |
| 2-013 | 320 | 4 | 5 | 5 | 3 | 5 | 5 | 4 | 0 | 0 | 1 | 1 | 1 | 2 | 5 | 4 | 0 | 0 | 0 | 4 |
| 2-014 | 320 | 3 | 5 | 5 | 4 | 5 | 5 | 4 | 3 | 0 | 0 | 0 | 0 | 3 | 5 | 3 | 0 | 0 | 0 | 4 |
| 2-015 | 320 | 5 | 5 | 5 | 4 | 5 | 5 | 3 | 1 | 0 | 0 | 0 | 0 | 0 | 5 | 4 | 1 | 0 | 0 | 4 |
| 2-016 | 320 | 5 | 5 | 5 | 4 | 5 | 5 | 4 | 4 | 3 | 0 | 0 | 0 | 0 | 5 | 4 | 3 | 0 | 0 | 4 |
| 2-017 | 320 | 5 | 5 | 5 | 4 | 4 | 5 | 3 | 1 | 0 |  | 0 |  | 0 | 5 | 2 | 0 | 0 | 0 | 4 |
| 2-018 | 320 | 1 | 1 | 1 | 0 | 1 | 4 | 1 | 0 | 0 |  |  | 0 | 0 | 2 | 0 | 0 | 0 | 0 | 0 |
| 2-020 | 320 | 3 | 5 | 4 | 0 | 4 | 5 | 0 | 0 | 0 | 0 | 0 |  | 0 | 4 | 1 | 0 | 0 | 0 | 0 |
| 2-021 | 320 | 4 | 4 | 4 | 3 | 5 | 5 | 0 | 0 | 0 | 0 | 0 | 0 | 0 | 4 | 3 | 0 | 0 | 0 | 3 |
| 2-022 | 320 | 0 | 0 | 1 | 0 | 3 | 5 | 2 | 0 | 0 | 0 | 0 |  | 0 | 5 | 3 | 0 | 0 | 0 | 1 |
| 2-023 | 320 | 0 | 0 | 1 | 0 | 0 | 1 | 0 | 0 | 0 | 0 | 0 |  | 0 | 3 | 0 | 0 | 0 | 0 | 0 |
| 2-024 | 320 | 4 | 5 | 5 | 2 | 4 | 5 | 2 | 0 | 0 | 0 | 0 |  | 2 | 5 | 3 | 0 | 0 | 0 | 3 |
| 2-025 | 320 | 4 | 5 | 4 | 0 | 4 | 5 | 3 | 0 | 0 | 0 | 0 | 0 | 0 | 4 | 1 | 0 | 0 | 0 | 3 |
| 2-026 | 320 | 4 | 5 | 4 | 4 | 4 | 5 | 3 | 0 | 0 | 0 | 0 | 0 | 0 | 5 | 2 | 0 | 0 | 0 | 3 |
| 2-027 | 320 | 0 | 5 | 3 | 1 | 2 | 4 | 0 | 0 | 0 |  | 0 | 0 | 0 | 4 | 1 | 0 | 0 | 0 | 1 |
| 2-028 | 320 | 2 | 5 | 5 | 0 | 4 | 5 | 1 | 0 | 0 | 0 | 0 | 0 | 0 | 5 | 4 | 0 | 0 | 0 | 3 |
| 2-029 | 320 | 0 | 0 | 0 | 2 | 0 | 1 | 0 | 0 | 0 | 0 | 0 | 0 | 0 | 2 | 0 | 0 | 0 | 0 | 0 |
| 2-030 | 320 | 4 | 5 | 4 | 1 | 3 | 5 | 2 | 0 | 0 | 0 | 0 | 0 | 1 | 5 | 2 | 0 | 0 | 0 | 3 |
| 2-031 | 320 | 5 | 5 | 5 | 5 | 5 | 5 | 4 | 0 | 0 | 0 | 0 | 0 | 4 | 5 | 5 | 0 | 0 | 0 | 4 |
| 2-032 | 320 | 2 | 5 | 5 | 3 | 1 | 5 | 5 | 0 | 0 | 0 | 0 | 0 | 0 | 5 | 1 | 0 | 1 | 0 | 4 |
| 3-001 | 320 | 4 | 3 | 4 | 2 | 3 | 4 | 3 | 0 | 0 | 0 | 0 |  | 0 | 4 | 2 | 0 | 0 | 0 | 0 |
| 3-002 | 320 | 0 | 2 | 1 | 0 | 0 | 1 | 0 | 0 | 0 | 0 | 0 | 0 | 0 | 3 | 0 | 0 | 0 | 0 | 0 |
| 4-001 | 320 | 3 | 1 | 2 | 4 | 5 | 5 | 2 | 0 | 0 | 0 |  | 0 |  | 4 | 1 | 0 | 0 | 0 |  |
| 5-001 | 320 | 4 | 3 | 3 | 4 | 5 | 5 | 4 | 0 | 0 |  | 0 | 0 | 0 | 4 | 2 | 0 | 0 |  | 0 |
| 5-002 | 320 | 0 | 0 | 0 | 0 | 0 | 0 | 0 | 0 | 0 |  | 0 |  |  | 0 | 0 | 0 | 0 | 0 |  |
| 6-001 | 320 | 5 | 5 | 5 | 5 | 5 | 5 | 5 | 0 | 0 | 0 |  | 0 | 0 | 5 | 5 | 0 | 5 | 0 | 2 |
| 6-002 | 320 | 5 | 5 | 5 | 5 | 5 | 5 | 5 | 1 | 0 | 0 |  | 0 | 0 | 5 | 5 | 0 | 0 | 0 | 0 |
| 6-003 | 320 | 5 | 5 | 5 | 5 | 5 | 5 | 5 | 3 | 0 | 1 | 2 | 3 | 0 | 5 | 5 | 3 | 0 | 0 | 4 |
| 6-004 | 320 | 5 | 5 | 5 | 4 | 5 | 5 | 5 | 3 | 2 | 3 |  | 3 | 3 | 5 | 4 | 1 | 0 |  | 4 |
| 6-005 | 320 | 5 | 5 | 5 | 5 | 5 | 5 | 5 | 5 | 4 | 3 |  | 3 |  | 5 | 5 | 4 | 4 | 0 | 0 |
| 6-006 | 320 | 3 | 3 | 4 | 1 | 5 | 4 | 3 | 0 | 0 | 0 |  | 0 |  | 4 | 1 | 0 | 5 |  | 4 |
| 6-007 | 320 | 5 | 5 | 5 | 3 | 5 | 5 | 4 | 1 | 0 | 0 |  | 0 |  | 5 | 5 | 2 | 5 | 0 |  |
| 6-008 | 320 | 0 | 5 | 5 | 0 | 5 | 3 | 3 | 0 | 0 | 0 | 0 |  |  | 3 | 3 | 1 | 4 | 0 | 0 |
| 6-009 | 320 | 5 | 5 | 5 | 4 | 5 | 5 | 5 | 3 | 0 | 2 |  | 0 |  | 5 | 5 | 3 | 5 | 2 | 4 |
| 6-010 | 320 | 5 | 5 | 5 | 3 | 5 | 4 | 5 | 0 | 0 | 3 | 0 | 0 |  | 5 | 4 | 3 | 4 | 0 | 0 |
| 6-015 | 320 | 5 | 5 | 5 | 4 | 5 | 5 | 5 | 2 | 2 | 4 | 3 | 2 |  | 5 | 5 | 3 | 0 | 0 | 4 |
| 6-016 | 320 | 5 | 5 | 5 | 4 | 4 | 5 | 5 | 0 | 0 | 3 | 0 |  | 3 | 5 | 5 | 0 | 0 | 0 | 1 |
| 6-017 | 320 | 5 | 5 | 5 | 5 | 5 | 5 | 5 | 0 | 0 | 4 | 1 | 0 | 3 | 5 | 5 | 0 | 1 | 0 | 3 |
| 6-018 | 320 | 5 | 5 | 5 | 4 | 5 | 5 | 5 | 0 | 0 | 3 | 3 |  | 4 | 5 | 5 | 3 | 2 | 1 | 3 |
| 6-023 | 320 | 5 | 5 | 5 | 5 | 5 | 5 | 4 | 0 | 0 |  | 0 | 0 | 1 | 5 | 3 | 0 | 3 |  | 3 |
| 6-024 | 320 | 0 | 3 | 1 | 1 | 3 | 5 | 1 | 0 | 0 | 0 | 0 | 0 | 0 | 0 | 0 | 0 | 0 | 0 | 3 |
| 6-025 | 320 | 4 | 5 | 5 | 5 | 5 | 5 | 5 | 0 | 0 | 0 | 0 | 0 | 0 | 5 | 4 | 0 | 1 | 0 | 3 |
| 6-026 | 320 | 5 | 5 | 5 | 5 | 5 | 5 | 3 | 0 | 0 | 0 | 0 | 0 | 1 | 5 | 5 | 0 | 3 | 0 | 3 |
| 6-027 | 320 | 3 | 4 | 4 | 1 | 0 | 0 | 0 | 0 | 0 | 0 | 0 | 0 | 0 | 1 | 1 | 0 | 0 | 0 | 0 |
| 6-029 | 320 | 5 | 5 | 5 | 5 | 5 | 5 | 5 | 4 | 5 | 4 | 3 | 5 | 4 | 5 | 5 | 0 | 5 | 0 | 4 |
| 6-030 | 320 | 4 | 4 | 1 | 0 | 1 | 1 | 0 | 0 | 0 | 0 | 0 | 0 | 0 | 1 | 0 | 0 | 0 | 0 | 3 |
| 6-031 | 320 | 5 | 5 | 5 | 5 | 5 | 5 | 4 | 2 | 0 | 3 | 0 |  | 1 | 5 | 4 | 0 | 0 | 0 | 3 |
| 6-032 | 320 | 4 | 3 | 4 | 0 | 0 | 0 | 0 | 0 | 0 | 0 |  | 0 |  | 0 | 0 | 0 | 0 | 0 | 0 |
| 6-033 | 320 | 0 | 0 | 1 | 3 | 0 | 5 | 0 | 0 | 0 | 0 | 0 |  | 0 | 3 | 3 | 0 | 0 | 0 | 1 |
| 6-034 | 320 | 5 | 5 | 5 | 5 | 5 | 4 | 5 | 3 | 3 | 3 | 3 | 5 | 3 | 5 | 5 | 0 | 0 | 0 | 4 |
| 6-035 | 320 | 5 | 5 | 5 | 5 | 5 | 5 | 5 | 4 | 5 | 3 | 3 | 4 | 4 | 5 | 5 | 2 | 4 | 0 | 4 |
| 6-036 | 320 | 4 | 4 | 5 | 3 | 3 | 5 | 3 | 0 | 0 | 0 | 1 | 0 | 3 | 4 | 4 | 0 | 0 | 0 | 3 |
| 6-037 | 320 | 5 | 5 | 5 | 5 | 5 | 5 | 5 | 5 | 5 | 3 | 4 |  | 3 | 5 | 5 | 4 | 5 | 3 | 5 |
| 6-038 | 320 | 5 | 5 | 5 | 5 | 5 | 5 | 5 | 5 | 5 | 3 | 4 | 0 | 3 | 5 | 5 | 4 | 3 | 0 | 5 |
| 6-049 | 320 | 5 | 5 | 5 | 0 | 5 | 5 | 5 | 3 | 4 | 5 | 5 | 5 | 5 | 5 | 5 | 2 | 5 | 4 | 5 |
| 6-050 | 320 | 4 | 2 | 4 | 3 | 5 | 5 | 4 | 0 | 0 | 3 | 3 | 3 | 3 | 5 | 4 | 0 | 0 | 2 | 5 |
| 6-051 | 320 | 5 | 5 | 5 | 4 | 5 | 5 | 5 | 1 | 3 | 5 | 4 | 4 | 4 | 5 | 5 | 1 | 4 | 3 | 5 |
| 6-052 | 320 | 5 | 5 | 5 | 2 | 4 | 5 | 4 | 0 | 0 | 0 | 0 | 0 | 0 | 5 | 3 | 0 | 0 | 0 | 3 |
| 6-053 | 320 | 5 | 5 | 5 | 3 | 3 | 5 | 4 | 0 | 0 | 0 | 0 | 0 | 3 | 3 | 2 | 0 | 0 | 0 | 3 |
| 6-054 | 320 | 4 | 5 | 5 | 3 | 5 | 4 | 5 | 0 | 0 | 4 | 0 | 0 | 3 | 3 | 4 | 0 | 0 | 0 | 1 |
| 6-055 | 320 | 5 | 5 | 5 | 5 | 5 | 5 | 5 | 1 | 0 | 3 | 4 | 3 | 4 | 5 | 5 | 3 | 3 | 0 | 5 |
| 6-056 | 320 | 5 | 5 | 5 | 4 | 3 | 3 | 4 | 3 | 0 | 0 | 3 | 0 | 0 | 2 | 1 | 0 | 0 | 0 | 3 |
| 6-057 | 320 | 5 | 5 | 5 | 5 | 5 | 5 | 5 | 1 | 1 | 4 | 4 | 3 | 4 | 5 | 5 | 3 | 5 | 0 | 5 |
| 6-058 | 320 | 5 | 5 | 5 | 5 | 5 | 5 | 5 | 5 | 5 | 5 | 5 | 5 | 5 | 5 | 5 | 2 | 5 | 5 | 5 |
| 6-059 | 320 | 5 | 5 | 5 | 5 | 5 | 5 | 5 | 5 | 5 | 5 | 4 | 5 | 4 | 5 | 5 | 0 | 5 | 0 | 5 |
| 6-060 | 320 | 5 | 4 | 5 | 5 | 5 | 5 | 5 | 5 | 4 | 4 | 4 | 4 | 4 | 5 | 5 | 1 | 4 | 2 | 5 |
| 6-061 | 320 | 5 | 5 | 5 | 5 | 5 | 5 | 5 | 4 | 1 | 4 | 3 | 3 | 4 | 5 | 5 | 3 | 5 | 3 | 4 |
| 6-062 | 320 | 5 | 5 | 5 | 5 | 5 | 4 | 5 | 3 | 1 |  | 3 | 5 | 5 | 5 | 5 | 0 | 5 | 0 | 4 |
| 6-063 | 320 | 5 | 5 | 5 | 5 | 5 | 3 | 5 | 5 | 2 | 0 |  | 0 | 3 | 3 | 5 | 0 | 4 | 0 | 4 |
| 6-064 | 320 | 5 | 5 | 5 | 5 | 5 | 3 | 5 | 5 | 4 |  | 0 |  | 4 | 5 | 5 | 0 | 5 | 0 | 3 |
| 6-065 | 320 | 5 | 5 | 5 | 5 | 5 | 5 | 5 | 2 | 0 | 1 | 3 | 3 | 3 | 5 | 5 | 1 | 5 | 3 | 4 |
| 6-066 | 320 | 5 | 5 | 5 | 5 | 5 | 5 | 5 | 3 | 3 | 4 | 3 | 4 | 4 | 5 | 5 | 3 | 5 | 0 | 4 |
| 6-068 | 320 | 0 | 3 | 3 | 0 | 0 | 0 | 0 | 0 | 0 | 0 | 2 | 0 | 0 | 1 | 4 | 0 | 0 | 0 | 2 |
| 6-071 | 320 | 0 | 0 | 0 | 0 | 3 | 4 | 2 | 0 | 0 | 0 | 0 | 0 | 0 | 1 | 0 | 0 | 2 | 0 | 0 |

TABLE 26-continued

| | | Application herbicide amount | | | | | | | | | | | | | | | | | |
|---|---|---|---|---|---|---|---|---|---|---|---|---|---|---|---|---|---|---|---|
| No. | (g/ha) | F | G | H | I | J | K | L | M | N | O | P | Q | R | b | c | d | e | f | g |
| 6-072 | 320 | 0 | 4 | 1 | 3 | 0 | 2 | 0 | 0 | 0 | 0 | 0 | 0 | 0 | 2 | 3 | 0 | 0 | 0 | 0 |
| 6-073 | 320 | 5 | 5 | 5 | 5 | 5 | 5 | 3 | 0 | 0 | 3 | 2 | 3 | 3 | 5 | 4 | 0 | 3 | 0 | 4 |
| 6-074 | 320 | 0 | 4 | 3 | 1 | 0 | 2 | 0 | 0 | 0 | 0 | 0 | 0 | 0 | 2 | 0 | 0 | 0 | 0 | 0 |
| 6-075 | 320 | 1 | 0 | 2 | 5 | 5 | 5 | 5 | 0 | 0 | 0 | 0 | 0 | 0 | 4 | 4 | 0 | 2 | 0 | 3 |
| 6-076 | 320 | 5 | 5 | 5 | 5 | 5 | 5 | 5 | 5 | 1 | 2 | 2 | 3 | 2 | 5 | 5 | 1 | 5 | 0 | 4 |
| 6-077 | 320 | 5 | 5 | 5 | 5 | 5 | 5 | 5 | 5 | 1 | 4 | 4 | 4 | 4 | 5 | 5 | 2 | 5 | 4 | 5 |
| 6-078 | 320 | 5 | 5 | 5 | 5 | 5 | 4 | 5 | 4 | 0 | 1 | 3 | | 3 | 5 | 0 | 4 | 0 | 4 | |
| 6-079 | 320 | 5 | 5 | 5 | 5 | 5 | 5 | 5 | 4 | 0 | 3 | 3 | 4 | 3 | 5 | 5 | 1 | 5 | 0 | 4 |
| 6-080 | 320 | 5 | 5 | 5 | 5 | 5 | 5 | 5 | 4 | 0 | 0 | 0 | 4 | 4 | 5 | 5 | 1 | 5 | 0 | 3 |
| 6-081 | 320 | 4 | 0 | 4 | 5 | 3 | 4 | 5 | 0 | 0 | 0 | 0 | 0 | 0 | 0 | 5 | 0 | 3 | 0 | 3 |
| 6-082 | 320 | 5 | 5 | 5 | 5 | 5 | 5 | 5 | 4 | 1 | | 1 | 4 | 4 | 5 | 5 | 0 | 5 | 0 | 4 |
| 6-083 | 320 | 5 | 5 | 5 | 5 | 5 | 4 | 5 | 5 | 3 | 5 | 1 | | 4 | 5 | 5 | 0 | 4 | 3 | 4 |
| 6-084 | 320 | 5 | 5 | 5 | 5 | 5 | 5 | 5 | 3 | 3 | 4 | 3 | 3 | 4 | 5 | 0 | 5 | 4 | 0 | 4 |
| 6-085 | 320 | 5 | 5 | 5 | 5 | 5 | 5 | 5 | 4 | 3 | 5 | 3 | 4 | 4 | 5 | 3 | 5 | 5 | 4 | 5 |
| 6-086 | 320 | 5 | 5 | 5 | 5 | 5 | 5 | 5 | 3 | 0 | 5 | 4 | | 5 | 5 | 3 | 5 | 5 | 3 | 4 |
| 6-087 | 320 | 5 | 5 | 5 | 0 | 4 | 4 | 3 | 0 | 0 | 0 | 1 | | 4 | 1 | 0 | 3 | 1 | 0 | 4 |
| 6-088 | 320 | 5 | 5 | 5 | 5 | 5 | 5 | 5 | 3 | 0 | 5 | 4 | 4 | 5 | 5 | 2 | 5 | 4 | 0 | 4 |
| 6-089 | 320 | | | | 5 | 5 | 4 | 5 | | | 4 | 4 | 3 | 4 | | | 4 | 0 | 4 | |
| 6-090 | 320 | 5 | 5 | 4 | 4 | 3 | 4 | 2 | 0 | 0 | 0 | 0 | 0 | 0 | 1 | 2 | 0 | 0 | 0 | 4 |
| 6-091 | 320 | 5 | 5 | 5 | 5 | 5 | 5 | 5 | 4 | 2 | 3 | 4 | 3 | 4 | 5 | 5 | 4 | 5 | 3 | 5 |
| 6-092 | 320 | 5 | 5 | 5 | 4 | 5 | 5 | 5 | 0 | 0 | 5 | 3 | 4 | 4 | 4 | 2 | 1 | 0 | 0 | 4 |
| 6-093 | 320 | 5 | 5 | 5 | 5 | 5 | 5 | 5 | 3 | 3 | 5 | 4 | 5 | 5 | 4 | 5 | 2 | 5 | 3 | 4 |
| 6-094 | 320 | 5 | 5 | 5 | 5 | 5 | 5 | 5 | 4 | 0 | 5 | 3 | 5 | 4 | 5 | 5 | 4 | 4 | | 4 |
| 6-095 | 320 | 5 | 5 | 5 | 5 | 5 | 5 | 5 | 4 | 0 | 5 | 1 | 0 | 3 | 5 | 5 | 3 | 4 | 0 | 4 |
| 6-096 | 320 | | | | 5 | 4 | 5 | 3 | | | 1 | 1 | 0 | 3 | | | | 3 | 0 | 4 |
| 6-098 | 320 | 3 | 3 | 2 | 1 | 3 | 5 | 4 | 0 | 0 | 0 | 0 | 0 | 0 | 2 | 1 | 0 | 2 | 0 | 0 |
| 6-099 | 320 | 5 | 5 | 5 | 5 | 5 | 5 | 5 | 3 | 4 | 5 | 4 | 5 | 5 | 5 | 5 | 4 | 5 | 4 | 5 |
| 6-100 | 320 | 5 | 5 | 5 | 5 | 5 | 5 | 5 | 3 | 4 | 4 | 3 | 4 | 3 | 5 | 5 | 3 | 5 | 0 | 5 |
| 6-103 | 320 | 5 | 5 | 5 | 5 | 5 | 5 | 5 | 5 | 0 | 0 | 1 | 0 | 2 | 5 | 5 | 0 | 5 | 0 | 4 |
| 6-104 | 320 | 5 | 5 | 5 | 5 | 5 | 5 | 5 | 5 | 5 | 4 | 4 | 4 | 4 | 5 | 5 | 3 | 5 | 4 | 4 |
| 6-105 | 320 | 5 | 5 | 5 | 2 | 2 | 4 | 2 | 0 | 0 | 0 | 0 | 3 | 3 | 3 | 3 | 0 | 0 | 0 | 4 |
| 6-106 | 320 | 5 | 5 | 5 | 3 | 5 | 5 | 5 | 0 | 0 | 0 | 3 | 3 | 3 | 3 | 5 | 1 | 3 | 0 | 5 |
| 6-107 | 320 | 5 | 5 | 5 | 5 | 5 | 5 | 5 | 3 | 2 | 4 | 2 | 5 | 4 | 5 | 5 | 1 | 5 | 2 | 4 |
| 6-108 | 320 | 5 | 5 | 5 | 5 | 5 | 5 | 5 | 5 | 5 | 2 | 3 | 3 | 2 | 5 | 5 | 3 | 3 | 0 | 5 |
| 6-109 | 320 | 5 | 5 | 5 | 5 | 5 | 5 | 5 | 4 | 4 | 0 | 0 | 0 | 1 | 5 | 5 | 2 | 4 | 0 | 4 |
| 6-110 | 320 | 5 | 5 | 5 | 5 | 5 | 5 | 5 | 4 | 0 | 0 | 1 | 3 | 2 | 5 | 5 | 2 | 4 | 0 | 4 |
| 6-111 | 320 | 5 | 5 | 5 | 5 | 5 | 5 | 5 | 2 | 2 | 0 | 1 | 0 | 2 | 5 | 5 | 1 | 4 | 0 | 4 |
| 6-112 | 320 | 5 | 5 | 5 | 5 | 5 | 5 | 5 | 5 | 4 | 1 | 0 | 1 | 1 | 5 | 5 | 3 | 4 | 0 | 4 |
| 6-113 | 320 | 5 | 5 | 5 | 5 | 5 | 5 | 5 | 0 | 0 | 2 | 0 | 0 | 0 | 5 | 5 | 0 | 5 | 0 | 1 |
| 7-001 | 320 | 5 | 3 | 4 | 3 | 3 | 5 | 3 | 0 | 0 | | | | 0 | 1 | 2 | 0 | 0 | 0 | 0 |
| 7-002 | 320 | 5 | 3 | 5 | 4 | 4 | 5 | 3 | 0 | 0 | 0 | 0 | 0 | 0 | 5 | 3 | 0 | 0 | 0 | 0 |
| 7-003 | 320 | 5 | 5 | 5 | 5 | h | 5 | 5 | 0 | 0 | 0 | 0 | 0 | 0 | 5 | 5 | 2 | 0 | 0 | 0 |
| 7-004 | 320 | 5 | 4 | 5 | 2 | 5 | 5 | 5 | 0 | 0 | 2 | 0 | 0 | | 5 | 5 | 4 | 0 | 0 | 3 |
| 7-005 | 320 | 5 | 4 | 5 | 2 | 2 | 5 | 4 | 0 | 0 | 3 | 1 | 0 | 0 | 4 | 4 | 0 | 0 | 0 | 0 |
| 7-006 | 320 | 5 | 5 | 5 | 3 | 3 | 5 | 4 | 0 | 0 | 3 | 0 | 0 | 0 | 5 | 4 | 0 | 0 | 0 | 3 |
| 7-007 | 320 | 5 | 5 | 5 | 4 | 5 | 5 | 5 | 0 | 0 | 2 | 0 | | 0 | 5 | 5 | 0 | 2 | 0 | 0 |
| 7-008 | 320 | 5 | 5 | 5 | 5 | 5 | 5 | 5 | 1 | 0 | 2 | 1 | | 3 | 5 | 5 | 0 | 4 | 0 | 3 |
| 7-010 | 320 | 5 | 5 | 5 | 4 | 5 | 5 | 5 | 3 | 1 | 2 | 0 | 0 | 4 | 5 | 5 | 3 | 5 | 0 | 4 |
| 7-011 | 320 | 4 | 3 | 5 | 3 | 4 | 5 | 3 | 4 | 5 | 3 | 3 | 0 | 1 | 5 | 2 | 0 | 0 | 0 | 4 |
| 7-012 | 320 | 5 | 5 | 5 | 1 | 3 | 5 | 0 | 0 | 0 | 3 | 3 | | 2 | 5 | 3 | 2 | 1 | 0 | 3 |
| 7-013 | 320 | 4 | 2 | 1 | 1 | 3 | 3 | 0 | 0 | 5 | 0 | 0 | 0 | 0 | 1 | 0 | 0 | 0 | 0 | 1 |
| 7-014 | 320 | 5 | 0 | 5 | 1 | 0 | 5 | 0 | 0 | 0 | 0 | 0 | | 0 | 3 | 3 | 0 | 0 | 0 | 1 |
| 7-015 | 320 | 5 | 5 | 5 | 5 | 5 | 5 | 5 | 2 | 0 | 3 | 1 | | 4 | 5 | 5 | 0 | 5 | 0 | 5 |
| 7-016 | 320 | 0 | 1 | 1 | 0 | 0 | 0 | 0 | 0 | 0 | 0 | 0 | | 0 | 0 | 0 | 0 | 0 | 0 | 0 |
| 7-017 | 320 | 5 | 5 | 5 | 0 | 2 | 3 | 3 | 0 | 0 | 0 | 0 | | 0 | 5 | 0 | 0 | 0 | 0 | 0 |
| 7-018 | 320 | 5 | 4 | 4 | 0 | 0 | 2 | 2 | 0 | 0 | 0 | 0 | 0 | 0 | 2 | 1 | 0 | 0 | 0 | 0 |
| 7-019 | 320 | 3 | 3 | 4 | 0 | 2 | 3 | 3 | 0 | 0 | 0 | 0 | | 0 | 1 | 2 | 0 | 0 | 0 | 2 |
| 7-020 | 320 | 5 | 3 | 4 | 0 | 4 | 4 | 3 | 0 | 0 | 0 | 0 | | 0 | 3 | 0 | 0 | 0 | 0 | 2 |
| 7-022 | 320 | 0 | 0 | 1 | 0 | 0 | 2 | 0 | 0 | 0 | 0 | 0 | | 0 | 0 | 0 | 0 | 0 | 0 | 0 |
| 7-024 | 320 | 0 | 0 | 5 | 2 | 2 | 3 | 1 | 0 | 0 | 0 | 0 | | 0 | 3 | 1 | 0 | 0 | 0 | 2 |
| 7-025 | 320 | 3 | 0 | 0 | 0 | 0 | 0 | 0 | 0 | 0 | 0 | 0 | | 0 | 0 | 0 | 0 | 0 | 0 | 0 |
| 7-026 | 320 | 0 | 0 | 1 | 0 | 1 | 1 | 0 | 0 | 0 | 0 | 0 | | 0 | 0 | 0 | 0 | 0 | 0 | 0 |
| 7-027 | 320 | 5 | 5 | 5 | 5 | 4 | 5 | 5 | 0 | 0 | 0 | 0 | | 0 | 3 | 5 | 0 | 0 | 0 | 0 |
| 7-029 | 320 | | | | 3 | 3 | 5 | 3 | | | 0 | 0 | 0 | 0 | | | | 2 | 0 | 1 |
| 7-031 | 320 | 4 | 5 | 5 | 3 | 3 | 5 | 5 | 0 | 0 | 0 | 0 | 0 | 0 | 4 | 1 | 0 | 0 | 0 | 0 |
| 8-001 | 320 | 1 | 1 | 1 | 0 | 0 | 1 | 0 | 0 | 0 | 0 | 0 | 0 | | 2 | 0 | 0 | 0 | 0 | 0 |
| 8-002 | 320 | 0 | 0 | 3 | 3 | 4 | 5 | 3 | 0 | 0 | 0 | 0 | 0 | | 4 | 0 | 0 | 0 | 0 | 1 |
| 8-003 | 320 | 0 | 0 | 0 | 0 | 0 | 2 | 0 | 0 | 0 | 0 | 0 | | | 0 | 0 | 0 | 0 | 0 | 0 |
| 9-001 | 320 | 4 | 4 | 5 | 5 | 3 | 5 | 3 | 0 | 0 | 0 | 0 | | 0 | 3 | 4 | 0 | 0 | 0 | 2 |
| 9-002 | 320 | 5 | 5 | 5 | 5 | 5 | 5 | 5 | 4 | 3 | 0 | 0 | | 1 | 5 | 5 | 0 | 3 | 0 | 4 |
| 9-003 | 320 | 5 | 5 | 5 | 4 | 5 | 5 | 5 | 4 | 0 | 3 | 3 | 0 | 4 | 5 | 5 | 4 | 4 | 1 | 4 |
| 9-004 | 320 | 5 | 5 | 5 | 5 | 5 | 5 | 4 | 0 | | 1 | 2 | | 0 | 5 | 5 | 0 | 3 | 0 | 3 |
| 9-005 | 320 | 4 | 4 | 5 | 5 | 4 | 5 | 5 | 0 | 0 | 0 | 0 | 0 | 0 | 4 | 3 | 0 | 0 | 0 | 3 |
| 9-006 | 320 | 5 | 5 | 5 | 4 | 5 | 5 | 5 | 0 | 0 | 2 | 3 | 0 | 4 | 5 | 5 | 0 | 5 | 0 | 4 |
| 9-007 | 320 | 5 | 5 | 5 | 5 | 5 | 5 | 5 | 0 | 0 | 3 | 3 | 1 | 4 | 5 | 5 | 0 | 4 | 0 | 4 |
| 9-008 | 320 | 5 | 5 | 5 | 4 | 5 | 5 | 5 | 4 | 0 | 3 | 4 | 2 | 4 | 5 | 5 | 3 | 5 | 0 | 4 |

TABLE 26-continued

| No. | (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 9-009 | 320 | 4 | 5 | 5 | 5 | 4 | 5 | 5 | 0 | 0 | 0 | 0 | | 0 | 5 | 3 | 0 | 0 | 0 | 3 |
| 9-010 | 320 | 5 | 5 | 5 | 4 | 5 | 5 | 5 | 0 | 3 | 3 | 3 | 3 | 3 | 5 | 3 | 2 | 0 | 0 | 3 |
| 9-011 | 320 | 5 | 5 | 5 | 5 | 5 | 5 | 5 | 2 | 2 | 1 | 0 | 1 | 3 | 5 | 5 | 2 | 5 | 0 | 4 |
| 9-012 | 320 | 5 | 5 | 5 | 5 | 5 | 5 | 5 | 1 | 4 | 2 | 4 | 4 | 3 | 5 | 5 | 1 | 2 | 0 | 3 |
| 9-013 | 320 | 5 | 5 | 5 | 5 | 5 | 5 | 5 | 4 | 0 | 3 | 2 | | 4 | 5 | 5 | 0 | 4 | 4 | 4 |
| 9-014 | 320 | 5 | 5 | 5 | 4 | 4 | 4 | 3 | 0 | 0 | 0 | 0 | 0 | 2 | 5 | 5 | 0 | 1 | 0 | 2 |
| 9-015 | 320 | 5 | 5 | 5 | 4 | 5 | 5 | 5 | 0 | 0 | 3 | 3 | 2 | 4 | 5 | 5 | 0 | 3 | 0 | 5 |
| 9-016 | 320 | 5 | 5 | 5 | 5 | 5 | 5 | 5 | 0 | 0 | 2 | 3 | 2 | 1 | 5 | 5 | 3 | 3 | 0 | 3 |
| 9-017 | 320 | 4 | 5 | 5 | 4 | 3 | 5 | 3 | 0 | 0 | 0 | 0 | 0 | 0 | 5 | 5 | 0 | 3 | 0 | 3 |
| 9-018 | 320 | 0 | 3 | 3 | 3 | 1 | 1 | 0 | 0 | 0 | 0 | 1 | 0 | 0 | 3 | 3 | 0 | 0 | 0 | 0 |
| 9-019 | 320 | 4 | 5 | 5 | 4 | 4 | 5 | 1 | 0 | 0 | 0 | 0 | 0 | 0 | 3 | 5 | 0 | 0 | 0 | 1 |
| 9-020 | 320 | 5 | 5 | 5 | 5 | 5 | 5 | 4 | 4 | 5 | 3 | 3 | | 3 | 5 | 5 | 1 | 2 | 0 | 4 |
| 9-021 | 320 | 5 | 5 | 5 | 4 | 5 | 5 | 5 | 2 | 2 | 3 | 1 | | 4 | 5 | 5 | 1 | 4 | 0 | 4 |
| 9-022 | 320 | 5 | 5 | 5 | 0 | 2 | 2 | 2 | 0 | 0 | 0 | 0 | 0 | 0 | 5 | 2 | 0 | 0 | 0 | 0 |
| 9-023 | 320 | 5 | 5 | 5 | 4 | 5 | 5 | 5 | 0 | 0 | 3 | 3 | 0 | 3 | 5 | 5 | 0 | 1 | 0 | 5 |
| 9-024 | 320 | 5 | 5 | 5 | 5 | 5 | 5 | 5 | 3 | 1 | 4 | 4 | 4 | 4 | 5 | 5 | 0 | 3 | 0 | 4 |
| 9-025 | 320 | 5 | 4 | 1 | 3 | 0 | 0 | 0 | 0 | 0 | 0 | 0 | 0 | 0 | 0 | 5 | 0 | 0 | 0 | 0 |
| 9-026 | 320 | 5 | 4 | 0 | 3 | 0 | 0 | 0 | 0 | 0 | 0 | 0 | 0 | 0 | 0 | 5 | 0 | 0 | 0 | 0 |
| 9-027 | 320 | 5 | 5 | 5 | 5 | 5 | 5 | 5 | 0 | 0 | 2 | 3 | 3 | 2 | 5 | 5 | 0 | 4 | 0 | 4 |
| 9-028 | 320 | 5 | 5 | 5 | 4 | 5 | 5 | 5 | 1 | 4 | 2 | 3 | 4 | 4 | 5 | 5 | 1 | 4 | 3 | 4 |
| 9-029 | 320 | 3 | 3 | 3 | 5 | 4 | 5 | 4 | 0 | 0 | 0 | 0 | 0 | 0 | 3 | 4 | 0 | 4 | 0 | 4 |
| 10-001 | 320 | 3 | 2 | 4 | 1 | 1 | 3 | 0 | 0 | 0 | 0 | 0 | 0 | 0 | 2 | 1 | 0 | 0 | 0 | 0 |
| 10-002 | 320 | 5 | 5 | 5 | 5 | 4 | 5 | 4 | 0 | 0 | 0 | 0 | | 0 | 4 | 5 | 0 | 0 | 0 | 0 |
| 10-003 | 320 | 3 | 5 | 5 | 3 | 3 | 4 | 3 | 0 | 0 | 0 | 0 | 0 | 0 | 4 | 2 | 0 | 0 | 0 | 0 |
| 10-004 | 320 | 5 | 5 | 5 | 5 | 5 | 5 | 5 | 3 | 0 | 0 | 0 | 0 | 3 | 5 | 5 | 0 | 4 | 0 | 4 |
| 11-002 | 320 | 4 | 4 | 5 | 5 | 5 | 5 | 5 | 0 | 0 | 0 | 0 | 0 | 0 | 5 | 2 | 1 | 2 | 0 | 4 |
| 12-002 | 320 | 5 | 5 | 5 | 5 | 5 | 5 | 5 | 1 | 0 | 2 | 4 | 4 | 4 | 5 | 5 | 1 | 2 | 3 | 5 |
| 13-001 | 320 | 5 | 5 | 5 | 5 | 5 | 5 | 5 | 1 | 0 | 0 | 0 | 0 | 0 | 5 | 5 | 0 | 5 | 0 | 4 |
| 13-002 | 320 | 5 | 5 | 5 | 5 | 5 | 5 | 5 | 2 | 0 | 5 | 3 | 4 | 4 | 5 | 5 | 2 | 5 | 3 | 4 |
| 13-003 | 320 | 5 | 5 | 5 | 5 | 5 | 5 | 5 | 4 | 0 | 0 | 1 | 3 | 1 | 5 | 5 | 3 | 5 | 0 | 4 |
| 13-004 | 320 | 5 | 5 | 5 | 5 | 5 | 5 | 5 | 1 | 0 | 4 | 2 | 4 | 3 | 5 | 5 | 1 | 5 | 0 | 4 |
| 13-005 | 320 | 5 | 5 | 5 | 5 | 5 | 5 | 5 | 0 | 0 | 0 | 0 | 0 | 0 | 5 | 4 | 0 | 5 | 0 | 3 |
| 13-006 | 320 | 5 | 5 | 5 | 5 | 5 | 5 | 5 | 4 | 3 | 2 | 3 | | 2 | 5 | 5 | 2 | 5 | 3 | 4 |
| 14-001 | 320 | 5 | 5 | 5 | 5 | 5 | 5 | 5 | 4 | 0 | 0 | 0 | 0 | 2 | 5 | 5 | 2 | 4 | 0 | 4 |
| 14-002 | 320 | 5 | 5 | 5 | 5 | 5 | 5 | 5 | 4 | 0 | 0 | 0 | 0 | 0 | 4 | 5 | 1 | 3 | 0 | 4 |

INDUSTRIAL APPLICABILITY

The ketone or oxime compound of the present invention is a novel compound and is useful as herbicides for rice, corn, soybean, wheat, beet, and rapeseed.

The invention claimed is:

1. A compound of formula where:
R is —O-A;
A is a hydrogen atom, $C_{1-6}$ alkyl, $C_{3-8}$ cycloalkyl, $C_{2-6}$ alkenyl, $C_{3-8}$ cycloalkenyl, or $C_{2-6}$ alkynyl;
$Z_1$ represents a bromine,
$Z_2$ represents methyl,
$Z_3$ represents —OCH$_3$.

2. The compound according to claim 1, wherein A is a hydrogen atom.

3. The compound according to claim 1, having the formula

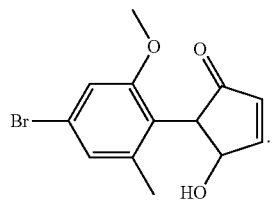 [SMILES: COc1cc(Br)cc(C)c1C1C(=O)C=CC1O]

4. A compound of formula where:
R is =O; and
$Z_1$, $Z_2$, and $Z_3$ satisfy one of:
(i) $Z_1$ represents a bromine, $Z_2$ represents methyl, and $Z_3$ represents —OCH$_3$, or (ii) $Z_1$ represents —$OCH_3$, $Z_2$ represents methyl, and $Z_3$ represents —$OCH_3$, or (iii) $Z_1$ represents methyl, $Z_2$ represents methyl, and $Z_3$ represents —$OCH_3$.

5. The compound according to claim 4, wherein $Z_1$ represents a bromine, $Z_2$ represents methyl, and $Z_3$ represents —$OCH_3$.

6. The compound according to claim 5, having the formula

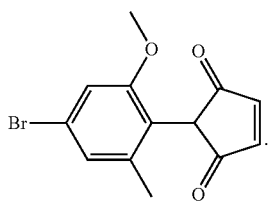 [SMILES: COc1cc(Br)cc(C)c1C1C(=O)C=CC1=O]

7. The compound according to claim 4, wherein $Z_1$ represents —$OCH_3$, $Z_2$ represents methyl, and $Z_3$ represents —$OCH_3$.

8. The compound according to claim 7, having the formula

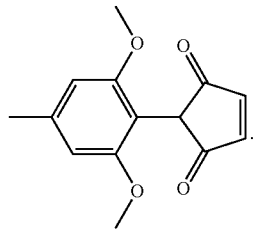 [SMILES: COc1cc(C)cc(OC)c1C1C(=O)C=CC1=O]

9. The compound according to claim 4, wherein $Z_1$ represents methyl, $Z_2$ represents methyl, and $Z_3$ represents —$OCH_3$.

10. The compound according to claim 9, having the formula

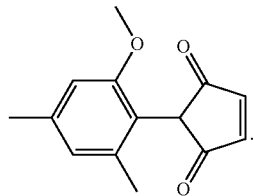 [SMILES: COc1cc(C)cc(C)c1C1C(=O)C=CC1=O]

* * * * *

UNITED STATES PATENT AND TRADEMARK OFFICE
CERTIFICATE OF CORRECTION

PATENT NO. : 10,537,099 B2  Page 1 of 1
APPLICATION NO. : 16/167884
DATED : January 21, 2020
INVENTOR(S) : Akira Numata et al.

It is certified that error appears in the above-identified patent and that said Letters Patent is hereby corrected as shown below:

In the Specification

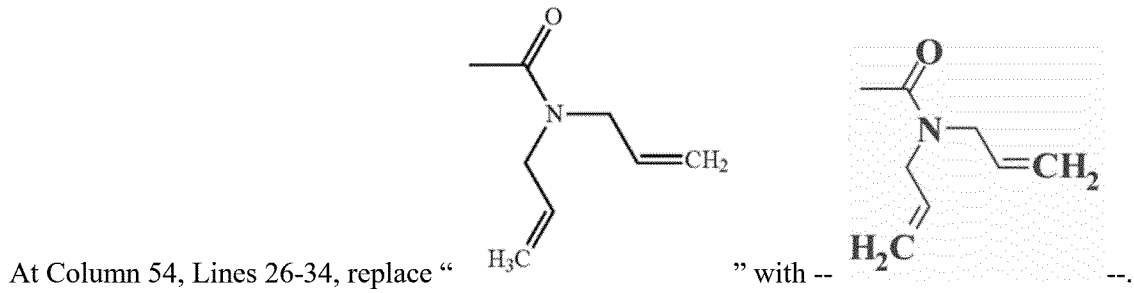

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*